US006780609B1

(12) United States Patent
Carulli et al.

(10) Patent No.: US 6,780,609 B1
(45) Date of Patent: Aug. 24, 2004

(54) HIGH BONE MASS GENE OF 1.1Q13.3

(75) Inventors: John P. Carulli, Southboro, MA (US); Randall D. Little, Newtonville, MA (US); Robert R. Recker, Omaha, NE (US); Mark L. Johnson, Omaha, NE (US)

(73) Assignee: Genome Therapeutics Corporation, Waltham, MA (US)

( * ) Notice: Subject to any disclaimer, the term of this patent is extended or adjusted under 35 U.S.C. 154(b) by 0 days.

(21) Appl. No.: 09/543,771

(22) Filed: Apr. 5, 2000

Related U.S. Application Data

(63) Continuation-in-part of application No. 09/229,319, filed on Jan. 13, 1999, now abandoned.

(60) Provisional application No. 60/105,511, filed on Oct. 23, 1998, and provisional application No. 60/071,449, filed on Jan. 13, 1998.

(51) Int. Cl.$^7$ .......................... C12P 21/06; C12N 5/00; C12N 15/63; C07H 21/04; C07K 1/00

(52) U.S. Cl. .................. 435/69.1; 435/320.1; 435/325; 435/455; 435/252.1; 435/471; 536/23.1; 536/23.5; 530/350; 530/380

(58) Field of Search ............................ 435/69.1, 320.1, 435/325, 455, 252.1, 471; 536/23.1, 23.5; 530/350, 380; 514/2

(56) References Cited

U.S. PATENT DOCUMENTS

| | | | | |
|---|---|---|---|---|
| 5,691,153 A | * 11/1997 | Recker et al. | ................. | 435/6 |
| 6,545,137 B1 | 4/2003 | Todd et al. | | |
| 6,555,654 B1 | 4/2003 | Todd et al. | | |

FOREIGN PATENT DOCUMENTS

| | | |
|---|---|---|
| WO | WO 97/12903 | 4/1997 |
| WO | 9846743 | 10/1998 |
| WO | WO 99/09054 | 2/1999 |
| WO | WO 99/47529 | 9/1999 |

OTHER PUBLICATIONS

Rodan et al., Therapeutic approaches to bone diseases, 2000, Science, vol. 289, pp. 1508–1514.*

Kindu et al., Role of polypeptides in the treatment and diagnosis of osteoporosis, 1999, Peptides, vol. 20, pp. 523–537.*

Ziegler et al., Glucocorticoid–induced osteoporosis: Prevention and treatment, 1998, Steroids, vol. 63, pp. 344–348.*

Kim et al., A new low density lipoprotein receptor related protein, LRP5, is expressed in hepatocytes and adrenal cortex, recognizes apolipoprotein E, 1998, J. Biochem., vol. 124, pp. 1072–1076.*

Bollag et al., Osteoblast–derived cells express functional glucose–dependent insulinotropic peptide receptors, 2000, Endocrinology, vol. 141, pp. 1228–1235.*

Johnson et al., *Journal of Bone and Mineral Research*, 11(Supplement 1):S255, abstract S661, Aug. 1996.

Johnson et al., *American Journal of Human Genetics*, 60: 1326–32 (1997).

Nakagawa et al., *American Journal of Human Genetics*, 63: 547–56 (1998).

Hey et al., *Gene* 216: 103–11 (1998).

Dong et al., *Biochemical and Biophysical Research Communication*, 251: 784–90 (1998).

Kim et al., *Journal of Biochemistry* 124: 1072–76 (1998).

Koller et al., *Journal of Bone and Mineral Research*, 13(12): 1903–8 (1998).

Randall D. Little et al., A Mutation in the LDL Receptor–Related Protein 5 Gene Results in the Autosomal Dominant High–Bone–Mass Trait, The American Journal of Human Genetics, vol. 70, No. 1, pp. 513–523, Jan. 2002, by The University of Chicago Press. Chicago.

Yaoqin Gong, et al., LDL Receptor–Related Protein 5 (LRP5) Affects Bone Accrual and Eye Development, Cell, vol. 107, pp. 513–523, Nov. 16, 2001, by Cell Press.

Dong–Ho Kim et al., A New Low Density Lipoprotein Receptor Related Protein, LRP5, Is Expressed in Hepatocytes and Biochemical Society.

Keiko Tamai et al., LDL–receptor–related proteins in Wnt signal transduction, Nature vol. 407, pp. 530–535, Sep. 28, 2000, by MacMillian Magazines Ltd.

Julian Zielenski, Genotype and Phenotype in Cystic Fibrosis, Respiration, vol. 67, pp. 117–133, 2000, by S. Karger AG, Basel.

Web Page, Abstract for Research News, Researchers Discover "Thermostat" that Regulates Bone Density, Howard Hughes Medical Institute, Nov. 16, 2001, Chevy Chase, Maryland. At http://www. hhmi.org/news/warman.html.

Annex Form PCT/ISA/206 Communication Relating to the Results of the Partial International Search attached to Invitation to Pay Additional Fees dated May 7, 2001 in PCT/US00/16951 filed on Jun. 21, 2000.

(List continued on next page.)

*Primary Examiner*—Jeffrey Fredman
*Assistant Examiner*—Sumesh Kaushal
(74) *Attorney, Agent, or Firm*—Burns, Doane, Swecker & Mathis, L.L.P.

(57) ABSTRACT

The present invention relates to methods and materials used to isolate and detect a high bone mass gene and a corresponding wild-type gene, and mutants thereof. The present invention also relates to the high bone mass gene, the corresponding wild-type gene, and mutants thereof. The genes identified in the present invention are implicated in bone development. The invention also provides nucleic acids, including coding sequences, oligonucleotide primers and probes, proteins, cloning vectors, expression vectors, transformed hosts, methods of developing pharmaceutical compositions, methods of identifying molecules involved in bone development, and methods of diagnosing and treating diseases involved in bone development. In preferred embodiments, the present invention is directed to methods for treating, diagnosing and preventing osteoporosis.

8 Claims, 32 Drawing Sheets

OTHER PUBLICATIONS

A. Courseaux et al., "*Homo Sapiens Chromosome 11 Clone BAC67–M–5 MAP 11q13, * * * Sequencing in Progress * * *, 3 Ordered Pieces*", Database EM_HTG, E.B.I., Hinxton, U.K., Accession No: AC024123, Mar. 2, 2000. XP002165276, Abstract.

D.L. Koller et al., "Linkage of a QTL Contributing to Normal Variation in Bone Mineral Density to Chromosome 11q12–13", J. Bone Miner. Res., vol. 13, No. 12, pp. 1903–1908, Dec. 1998, Blackwall Science, Inc., American Society for Bone and Mineral Research, USA.

Michael P. Whyte, "*Searching for Gene Defects that Cause High Bone Mass*", Am. J. Hum. Genet., vol. 60; No. 6, pp. 1309–1311, Jun. 1997, The American Society of Human Genetics, USA.

Marion Trommsdorff et al., "*Interaction of Cytosolic Adaptor Proteins* with Neuronal Apolipoprotein E Receptors and the Amyloid Precursor Protein", J. Biol. Chem., vol. 273, No. 50, pp. 33556–33560, Dec. 1998, The American Society for Biochemistry and Molecular Biology, Inc., USA.

G. Schneider et al., "*Formation of Focal Adhesions by Osteoblasts Adhering to Different Substrata*", Experimental Cell Research, vol. 214, No. 1, pp. 264–269, Sep. 1994, Academic Press, Inc., USA.

Frederick M. Pavalko et al., "*Fluid Shear–Induced Mechanical Signaling in MC3T3–E1 Osteoblasts Requires Cytoskeleton–Integrin Interactions*", Am. J. Physiol., vol. 275, No. 6 (Pt1), pp. C1591–1601, Dec. 1998, The American Physiological Society, USA.

Mark L. Johnson et al., "*Linkage of a Gene Causing High Bone Mass to Human Chromosome 11*(*11q12–13*)", Am. J. Hum. Genet., vol. 60, No. 6, pp. 1326–1332, Jun. 1997, The American Society of Human Genetics, USA.

Dong–Ho Kim et al., "*A New Low Density Lipoprotein Receptor Related Protein, LRP5, is Expressed in Hepatocytes and Adrenal Cortex, and Recognizes Apolipoprotein E*", J. Biochem., vol. 124, No. 6, pp. 1072–1076, Dec. 1998, The Japanese Biochemical Society, Japan.

* cited by examiner

BAC/STS Map of the HBM Region

BAC/STS Map of the HBM Region

Exon 1
ACTAAAGCGCCGCCGCCGCGCCATGGAGCCCGAGTGAGCGCGGCGCG
GGCCCGTCCGGCCGCCGGACAACATGGAGGCAGCGCCGCCCGGGCCG
CCGTGGCCGCTGCTGCTGCTGCTGCTGCTGCTGCTGGCGCTGTGCGGC
TGCCCGGCCCCCGCCGCGGCC

Exon 2 Coordinates: 527d12_Contig308G 30944-30549
gccccacagCCTCGCCGCTCCTGCTATTTGCCAACCGCCGGGACGTACGGC
TGGTGGACGCCGGCGGAGTCAAGCTGGAGTCCACCATCGTGGTCAGC
GGCCTGGAGGATGCGGCCGCAGTGGACTTCCAGTTTTCCAAGGGAGC
CGTGTACTGGACAGACGTGAGCGAGGAGGCCATCAAGCAGACCTACCT
GAACCAGACGGGGGCCGCCGTGCAGAACGTGGTCATCTCCGGCCTGG
TCTCTCCCGACGGCCTCGCCTGCGACTGGGTGGGCAAGAAGCTGTACT
GGACGGACTCAGAGACCAACCGCATCGAGGTGGCCAACCTCAATGGC
ACATCCCGGAAGGTGCTCTTCTGGCAGGACCTTGACCAGCCGAGGGCC
ATCGCCTTGGACCCCGCTCACGGgtaaaccctgctg ... 9408 nt ...

Exon 3 Coordinates: 527d12_Contig308G 21141-20945
ccccgtcacagGTACATGTACTGGACAGACTGGGGTGAGACGCCCCGGATTG
AGCGGGCAGGGATGGATGGCAGCACCCGGAAGATCATTGTGGACTCG
GACATTTACTGGCCCAATGGACTGACCATCGACCTGGAGGAGCAGAAG
CTCTACTGGGCTGACGCCAAGCTCAGCTTCATCCACCGTGCCAACCTG
GACGGCTCGTTCCGgtaggtacccac ... 6094 nt ...

Exon 4 Coordinates: 527d12_Contig308G 15047-14850
tccctgactgcagGCAGAAGGTGGTGGAGGGCAGCCTGACGCACCCCTTCGCC
CTGACGCTCTCCGGGGACACTCTGTACTGGACAGACTGGCAGACCCGC
TCCATCCATGCCTGCAACAAGCGCACTGGGGGGAAGAGGAAGGAGAT
CCTGAGTGCCCTATACTCACCCATGGACATCCAGGTGCTGAGCCAGGA
GCGGCAGCCTTTCTgtgagtgccgg ... 1827 nt ...

Exon 5 Coordinates: 527d12_Contig308G 13220-13088
tttctcagTCCACACTCGCTGTGAGGAGGACAATGGCGGCTGCTCCCACCTG
TGCCTGCTGTCCCCAAGCGAGCCTTTCTACACATGCGCCTGCCCCACG
GGTGTGCAGCTGCAGGACAACGGCAGGACGTGTAAGGCAGgtgaggcggtgg
gacg

Exon 6 Coordinates: 527d12_Contig309G 7705-8100
ctccacagGAGCCGAGGAGGTGCTGCTGCTGGCCCGGCGGACGGACCTAC
GGAGGATCTCGCTGGACACGCCGGACTTCACCGACATCGTGCTGCAGG
TGGACGACATCCGGCACGCCATTGCCATCGACTACGACCCGCTAGAGG
GCTATGTCTACTGGACAGATGACGAGGTGCGGGCCATCCGCAGGGCG
TACCTGGACGGGTCTGGGGCGCAGACGCTGGTCAACACCGAGATCAA
CGACCCCGATGGCATCGCGGTCGACTGGGTGGCCCGAAACCTCTACTG
GACCGACACGGGCACGGACCGCATCGAGGTGACGCGCCTCAACGGCA
CCTCCCGCAAGATCCTGGTGTCGGAGGACCTGGACGAGCCCCGAGCC
ATCGCACTGCACCCCGTGATGGGgtaagacgggc ..... 3211 nt .....

Exon 7 Coordinates: 527d12_Contig309G 11311-11482
ttcttctccagCCTCATGTACTGGACAGACTGGGGAGAGAACCCTAAAATCGA
GTGTGCCAACTTGGATGGGCAGGAGCGGCGTGTGCTGGTCAATGCCTC
CCTCGGGTGGCCCAACGGCCTGGCCCTGGACCTGCAGGAGGGGAAGC
TCTACTGGGGAGACGCCAAGACAGACAAGATCGAGgtgaggctcctgtgg ...... 13445 nt .....

Exon 8 Coordinates: 527d12_Contig309G 24927-25143
ccgtcctgcagGTGATCAATGTTGATGGGACGAAGAGGCGGACCCTCCTGGA
GGACAAGCTCCCGCACATTTTCGGGTTCACGCTGCTGGGGGACTTCAT
CTACTGGACTGACTGGCAGCGCCGCAGCATCGAGCGGGTGCACAAGG
TCAAGGCCAGCCGGGACGTCATCATTGACCAGCTGCCCGACCTGATGG
GGCTCAAAGCTGTGAATGTGGCCAAGGTCGTCGgtgagtccggggggtc ....2826 nt ......

Exon 9 Coordinates: 527d12_Contig309G 27969-28256
gttcgcttccagGAACCAACCCGTGTGCGGACAGGAACGGGGGGTGCAGCCA
CCTGTGCTTCTTCACACCCCACGCAACCCGGTGTGGCTGCCCCATCGG
CCTGGAGCTGCTGAGTGACATGAAGACCTGCATCGTGCCTGAGGCCTT
CTTGGTCTTCACCAGCAGAGCCGCCATCCACAGGATCTCCCTCGAGAC
CAATAACAACGACGTGGCCATCCCGCTCACGGGCGTCAAGGAGGCCTC
AGCCCTGGACTTTGATGTGTCCAACAACCACATCTACTGGACAGACGT
CAGCCTGAAGgtagcgtgggc

Exon 10 Coordinates: 527d12_Contig309G 31358-31582
cctgctgccagACCATCAGCCGCGCCTTCATGAACGGGAGCTCGGTGGAGCA
CGTGGTGGAGTTTGGCCTTGACTACCCCGAGGGCATGGCCGTTGACTG
GATGGGCAAGAACCTCTACTGGGCCGACACTGGGACCAACAGAATCGA
AGTGGCGCGGCTGGACGGGCAGTTCCGGCAAGTCCTCGTGTGGAGGG
ACTTGGACAACCCGAGGTCGCTGGCCCTGGATCCCACCAAGGGgtaagtgtt
tgcctgtc ......1297 nt......

Exon 11 Coordinates: 527d12_Contig309G 32879-33064
gtgccttccagCTACATCTACTGGACCGAGTGGGGCGGCAAGCCGAGGATCG
TGCGGGCCTTCATGGACGGGACCAACTGCATGACGCTGGTGGACAAG
GTGGGCCGGGCCAACGACCTCACCATTGACTACGCTGACCAGCGCCTC
TACTGGACCGACCTGGACACCAACATGATCGAGTCGTCCAACATGCTG
Ggtgagggccgggct .......2069 nt.....

Exon 12 Coordinates: 527d12_Contig309G 35133-35454
gtgttcatgcagGTCAGGAGCGGGTCGTGATTGCCGACGATCTCCCGCACCCG
TTCGGTCTGACGCAGTACAGCGATTATATCTACTGGACAGACTGGAAT
CTGCACAGCATTGAGCGGGCCGACAAGACTAGCGGCCGGAACCGCAC
CCTCATCCAGGGCCACCTGGACTTCGTGATGGACATCCTGGTGTTCCA
CTCCTCCCGCCAGGATGGCCTCAATGACTGTATGCACAACAACGGGCA
GTGTGGGCAGCTGTGCCTTGCCATCCCCGGCGGCCACCGCTGCGGCT
GCGCCTCACACTACACCCTGGACCCCAGCAGCCGCAACTGCAGCCgtaag
tgcctcatggt .......2006 nt......

Exon 13 Coordinates: 527d12_Contig309G 37460-37659
gcctcctctaCGCCCACCACCTTCTTGCTGTTCAGCCAGAAATCTGCCATCAG
TCGGATGATCCCGGACGACCAGCACAGCCCGGATCTCATCCTGCCCCT
GCATGGACTGAGGAACGTCAAAGCCATCGACTATGACCCACTGGACAA
GTTCATCTACTGGGTGGATGGGCGCCAGAACATCAAGCGAGCCAAGGA
CGACGGGACCCAGgcaggtgccctgtgg ......6965 nt......

FIG. 3C

Exon 14 Coordinates: 527d12_Contig309G 44624-44832
ctttgtcttacagCCCTTTGTTTTGACCTCTCTGAGCCAAGGCCAAAACCCAGAC
AGGCAGCCCCACGACCTCAGCATCGACATCTACAGCCGGACACTGTTC
TGGACGTGCGAGGCCACCAATACCATCAACGTCCACAGGCTGAGCGG
GGAAGCCATGGGGGTGGTGCTGCGTGGGACCGCGACAAGCCCAGGG
CCATCGTCGTCAACGCGGAGCGAGGgtaggaggccaac ......1404 nt.....

Exon 15 Coordinates: 527d12_Contig309G 46236-46427
ccaccctcccgcagGTACCTGTACTTCACCAACATGCAGGACCGGGCAGCCAA
GATCGAACGCGCAGCCCTGGACGGCACCGAGCGCGAGGTCCTCTTCA
CCACCGGCCTCATCCGCCCTGTGGCCCTGGTGGTGGACAACACACTGG
GCAAGCTGTTCTGGGTGGACGCGGACCTGAAGCGCATTGAGAGCTGT
GACCTGTCAGgtacgcgccccgg .....686 nt.....

Exon 16 Coordinates: 527d12_Contig309G 47113-47322
ggctgcttgcagGGGCCAACCGCCTGACCCTGGAGGACGCCAACATCGTGCA
GCCTCTGGGCCTGACCATCCTTGGCAAGCATCTCTACTGGATCGACCG
CCAGCAGCAGATGATCGAGCGTGTGGAGAAGACCACCGGGGACAAGC
GGACTCGCATCCAGGGCCGTGTCGCCCACCTCACTGGCATCCATGCAG
TGGAGGAAGTCAGCCTGGAGGAGTTCTgtacgtgggggc .....3884 nt......

Exon 17 Coordinates: 527d12_Contig309G 51206-51331
ttgtctttgcagCAGCCCACCCATGTGCCCGTGACAATGGTGGCTGCTCCCACA
TCTGTATTGCCAAGGGTGATGGGACACCACGGTGCTCATGCCCAGTCC
ACCTCGTGCTCCTGCAGAACCTGCTGACCTGTGGAGgtaggtgtgacctaggtgc ....3905 nt.......

Exon 18 Coordinates: 527d12_Contig309G 55236-55472
gttctcctctgtccctcccccagAGCCGCCCACCTGCTCCCCGGACCAGTTTGCATGT
GCCACAGGGGAGATCGACTGTATCCCCGGGGCCTGGCGCTGTGACGG
CTTTCCCGAGTGCGATGACCAGAGCGACGAGGAGGGCTGCCCCGTGT
GCTCCGCCGCCCAGTTCCCCTGCGCGCGGGGTCAGTGTGTGGACCTGC
GCCTGCGCTGCGACGGCGAGGCAGACTGTCAGGACCGCTCAGACGAG
GTGGACTGTGACGgtgaggccctcc .......3052 nt.....

FIG. 3D

Exon 19 Coordinates: 527d12_Contig309G 58524-58634
tctccttgcagCCATCTGCCTGCCCAACCAGTTCCGGTGTGCGAGCGGCCAGT
GTGTCCTCATCAAACAGCAGTGCGACTCCTTCCCCGACTGTATCGACG
GCTCCGACGAGCTCATGTGTGgtgagccagctt ........1448 nt......

Exon 20 Coordinates: 527d12_Contig309G 60082-60319
gtttgtctctggcagAAATCACCAAGCCGCCCTCAGACGACAGCCCGGCCCACA
GCAGTGCCATCGGGCCCGTCATTGGCATCATCCTCTCTCTCTTCGTCAT
GGGTGGTGTCTATTTTGTGTGCCAGCGCGTGGTGTGCCAGCGCTATGC
GGGGGCCAACGGGCCCTTCCCGCACGAGTATGTCAGCGGGACCCCGC
ACGTGCCCCTCAATTTCATAGCCCCGGGCGGTTCCCAGCATGGCCCCT
TCACAGgtaaggagcctgagatatggaa ....1095 nt.....

Exon 21 Coordinates: 527d12_Contig309G 61414-61552
cttccctgccagGCATCGCATGCGGAAAGTCCATGATGAGCTCCGTGAGCCTG
ATGGGGGGCCGGGGCGGGGTGCCCCTCTACGACCGGAACCACGTCAC
AGGGGCCTCGTCCAGCAGCTCGTCCAGCACGAAGGCCACGCTGTACCC
GCCGgtgaggggcggg ......6513 nt......

Exon 22 Coordinates: 527d12_Contig309G 68065-68162
ttggctctcctcagATCCTGAACCCGCCGCCCTCCCCGGCCACGGACCCCTCCC
TGTACAACATGGACATGTTCTACTCTTCAAACATTCCGGCCACTGCGA
GACCGTACAGgtaggacatcccctgcag .......2273 nt.....

FIG. 3E

Exon 23 Coordinates: 527d12_Contig309G 70435-70901 tcaaacattccggccactgcgagaccgtacagGCCCTACATCATTCGAGGAATGGCGCCCC
CGACGACGCCCTGCAGCACCGACGTGTGTGACAGCGACTACAGCGCC
AGCCGCTGGAAGGCCAGCAAGTACTACCTGGATTTGAACTCGGACTCA
GACCCCTATCCACCCCCACCCACGCCCCACAGCCAGTACCTGTCGGCG
GAGGACAGCTGCCCGCCCTCGCCCGCCACCGAGAGGAGCTACTTCCAT
CTCTTCCCGCCCCCTCCGTCCCCCTGCACGGACTCATCCTGACCTCGGC
CGGGCCACTCTGGCTTCTCTGTGCCCCTGTAAATAGTTTTAAATATGAACAA
AGAAAAAAATATATTTTATGATTTAAAAAATAAATATAATTGGATTTTAA
AAACATGAGAAATGTGAACTGTGATGGGGTGGGCAGGGCTGGGAGAACTT
TGTACAGTGGAGAAATATTTATAAACTTAATTTTGTAAAACA

```
  1  ACTAAAGCGCCGCCGCCGCGCCATGGAGCCCGAGTGAGCGCGGCGCGGGCCCGTCCGGCC   60
 61  GCCGGACAACATGGAGGCAGCGCCGCCCGGGCCGCCGTGGCCGCTGCTGCTGCTGCTGCT  120
  1              M  E  A  A  P  P  G  P  P  W  P  L  L  L  L  L   17

121  GCTGCTGCTGGCGCTGTGCGGCTGCCCGGCCCCCGCCGCGGCCTCGCCGCTCCTGCTATT  180
 18   L  L  L  A  L  C  G  C  P  A  P  A  A  A  S  P  L  L  L  F   37

181  TGCCAACCGCCGGGACGTACGGCTGGTGGACGCCGGCGGAGTCAAGCTGGAGTCCACCAT  240
 38   A  N  R  R  D  V  R  L  V  D  A  G  G  V  K  L  E  S  T  I   57

241  CGTGGTCAGCGGCCTGGAGGATGCGGCCGCAGTGGACTTCCAGTTTTCCAAGGGAGCCGT  300
 58   V  V  S  G  L  E  D  A  A  A  V  D  F  Q  F  S  K  G  A  V   77

301  GTACTGGACAGACGTGAGCGAGGAGGCCATCAAGCAGACCTACCTGAACCAGACGGGGGC  360
 78   Y  W  T  D  V  S  E  E  A  I  K  Q  T  Y  L  N  Q  T  G  A   97

361  CGCCGTGCAGAACGTGGTCATCTCCGGCCTGGTCTCTCCCGACGGCCTCGCCTGCGACTG  420
 98   A  V  Q  N  V  V  I  S  G  L  V  S  P  D  G  L  A  C  D  W  117

421  GGTGGGCAAGAAGCTGTACTGGACGGACTCAGAGACCAACCGCATCGAGGTGGCCAACCT  480
118   V  G  K  K  L  Y  W  T  D  S  E  T  N  R  I  E  V  A  N  L  137

481  CAATGGCACATCCCGGAAGGTGCTCTTCTGGCAGGACCTTGACCAGCCGAGGGCCATCGC  540
138   N  G  T  S  R  K  V  L  F  W  Q  D  L  D  Q  P  R  A  I  A  157

541  CTTGGACCCCGCTCACGGGTACATGTACTGGACAGACTGGGGTGAGACGCCCCGGATTGA  600
158   L  D  P  A  H  G  Y  M  Y  W  T  D  W  G  E  T  P  R  I  E  177
```

FIG. 6B

```
601  GCGGGCAGGGATGGATGGCAGCACCCGGAAGATCATTGTGGACTCGGACATTTACTGGCC  660
178   R  A  G  M  D  G  S  T  R  K  I  I  V  D  S  D  I  Y  W  P   197

661  CAATGGACTGACCATCGACCTGGAGGAGCAGAAGCTCTACTGGGCTGACGCCAAGCTCAG  720
198   N  G  L  T  I  D  L  E  E  Q  K  L  Y  W  A  D  A  K  L  S   217

721  CTTCATCCACCGTGCCAACCTGGACGGCTCGTTCCGGCAGAAGGTGGTGGAGGGCAGCCT  780
218   F  I  H  R  A  N  L  D  G  S  F  R  Q  K  V  V  E  G  S  L   237

781  GACGCACCCCTTCGCCCTGACGCTCTCCGGGGACACTCTGTACTGGACAGACTGGCAGAC  840
238   T  H  P  F  A  L  T  L  S  G  D  T  L  Y  W  T  D  W  Q  T   257

841  CCGCTCCATCCATGCCTGCAACAAGCGCACTGGGGGGAAGAGGAAGGAGATCCTGAGTGC  900
258   R  S  I  H  A  C  N  K  R  T  G  G  K  R  K  E  I  L  S  A   277

901  CCTCTACTCACCCATGGACATCCAGGTGCTGAGCCAGGAGCGGCAGCCTTTCTTCCACAC  960
278   L  Y  S  P  M  D  I  Q  V  L  S  Q  E  R  Q  P  F  F  H  T   297

961  TCGCTGTGAGGAGGACAATGGCGGCTGCTCCCACCTGTGCCTGCTGTCCCCAAGCGAGCC  1020
298   R  C  E  E  D  N  G  G  C  S  H  L  C  L  L  S  P  S  E  P   317

1021 TTTCTACACATGCGCCTGCCCCACGGGTGTGCAGCTGCAGGACAACGGCAGGACGTGTAA  1080
318   F  Y  T  C  A  C  P  T  G  V  Q  L  Q  D  N  G  R  T  C  K   337

1081 GGCAGGAGCCGAGGAGGTGCTGCTGCTGGCCCGGCGGACGGACCTACGGAGGATCTCGCT  1140
338   A  G  A  E  E  V  L  L  L  A  R  R  T  D  L  R  R  I  S  L   357
```

FIG. 6C

```
1141  GGACACGCCGGACTTCACCGACATCGTGCTGCAGGTGGACGACATCCGGCACGCCATTGC  1200
358    D  T  P  D  F  T  D  I  V  L  Q  V  D  D  I  R  H  A  I  A   377

1201  CATCGACTACGACCCGCTAGAGGGCTATGTCTACTGGACAGATGACGAGGTGCGGGCCAT  1260
378    I  D  Y  D  P  L  E  G  Y  V  Y  W  T  D  D  E  V  R  A  I   397

1261  CCGCAGGGCGTACCTGGACGGGTCTGGGGCGCAGACGCTGGTCAACACCGAGATCAACGA  1320
398    R  R  A  Y  L  D  G  S  G  A  Q  T  L  V  N  T  E  I  N  D   417

1321  CCCCGATGGCATCGCGGTCGACTGGGTGGCCCGAAACCTCTACTGGACCGACACGGGCAC  1380
418    P  D  G  I  A  V  D  W  V  A  R  N  L  Y  W  T  D  T  G  T   437

1381  GGACCGCATCGAGGTGACGCGCCTCAACGGCACCTCCCGCAAGATCCTGGTGTCGGAGGA  1440
438    D  R  I  E  V  T  R  L  N  G  T  S  R  K  I  L  V  S  E  D   457

1441  CCTGGACGAGCCCCGAGCCATCGCACTGCACCCCGTGATGGGCCTCATGTACTGGACAGA  1500
458    L  D  E  P  R  A  I  A  L  H  P  V  M  G  L  M  Y  W  T  D   477

1501  CTGGGGAGAGAACCCTAAAATCGAGTGTGCCAACTTGGATGGGCAGGAGCGGCGTGTGCT  1560
478    W  G  E  N  P  K  I  E  C  A  N  L  D  G  Q  E  R  R  V  L   497

1561  GGTCAATGCCTCCCTCGGGTGGCCCAACGGCCTGGCCCTGGACCTGCAGGAGGGGAAGCT  1620
498    V  N  A  S  L  G  W  P  N  G  L  A  L  D  L  Q  E  G  K  L   517

1621  CTACTGGGGAGACGCCAAGACAGACAAGATCGAGGTGATCAATGTTGATGGGACGAAGAG  1680
518    Y  W  G  D  A  K  T  D  K  I  E  V  I  N  V  D  G  T  K  R   537
```

FIG. 6D

```
1681  GCGGACCCTCCTGGAGGACAAGCTCCCGCACATTTTCGGGTTCACGCTGCTGGGGGACTT  1740
 538   R  T  L  L  E  D  K  L  P  H  I  F  G  F  T  L  L  G  D  F   557

1741  CATCTACTGGACTGACTGGCAGCGCCGCAGCATCGAGCGGGTGCACAAGGTCAAGGCCAG  1800
 558   I  Y  W  T  D  W  Q  R  R  S  I  E  R  V  H  K  V  K  A  S   577

1801  CCGGGACGTCATCATTGACCAGCTGCCCGACCTGATGGGGCTCAAAGCTGTGAATGTGGC  1860
 578   R  D  V  I  I  D  Q  L  P  D  L  M  G  L  K  A  V  N  V  A   597

1861  CAAGGTCGTCGGAACCAACCCGTGTGCGGACAGGAACGGGGGGTGCAGCCACCTGTGCTT  1920
 598   K  V  V  G  T  N  P  C  A  D  R  N  G  G  C  S  H  L  C  F   617

1921  CTTCACACCCCACGCAACCCGGTGTGGCTGCCCCATCGGCCTGGAGCTGCTGAGTGACAT  1980
 618   F  T  P  H  A  T  R  C  G  C  P  I  G  L  E  L  L  S  D  M   637

1981  GAAGACCTGCATCGTGCCTGAGGCCTTCTTGGTCTTCACCAGCAGAGCCGCCATCCACAG  2040
 638   K  T  C  I  V  P  E  A  F  L  V  F  T  S  R  A  A  I  H  R   657

2041  GATCTCCCTCGAGACCAATAACAACGACGTGGCCATCCCGCTCACGGGCGTCAAGGAGGC  2100
 658   I  S  L  E  T  N  N  N  D  V  A  I  P  L  T  G  V  K  E  A   677

2101  CTCAGCCCTGGACTTTGATGTGTCCAACAACCACATCTACTGGACAGACGTCAGCCTGAA  2160
 678   S  A  L  D  F  D  V  S  N  N  H  I  Y  W  T  D  V  S  L  K   697

2161  GACCATCAGCCGCGCCTTCATGAACGGGAGCTCGGTGGAGCACGTGGTGGAGTTTGGCCT  2220
 698   T  I  S  R  A  F  M  N  G  S  S  V  E  H  V  V  E  F  G  L   717
```

FIG. 6E

```
2221  TGACTACCCCGAGGGCATGGCCGTTGACTGGATGGGCAAGAACCTCTACTGGGCCGACAC  2280
718    D  Y  P  E  G  M  A  V  D  W  M  G  K  N  L  Y  W  A  D  T    737

2281  TGGGACCAACAGAATCGAAGTGGCGCGGCTGGACGGGCAGTTCCGGCAAGTCCTCGTGTG  2340
738    G  T  N  R  I  E  V  A  R  L  D  G  Q  F  R  Q  V  L  V  W    757

2341  GAGGGACTTGGACAACCCGAGGTCGCTGGCCCTGGATCCCACCAAGGGCTACATCTACTG  2400
758    R  D  L  D  N  P  R  S  L  A  L  D  P  T  K  G  Y  I  Y  W    777

2401  GACCGAGTGGGGCGGCAAGCCGAGGATCGTGCGGGCCTTCATGGACGGGACCAACTGCAT  2460
778    T  E  W  G  G  K  P  R  I  V  R  A  F  M  D  G  T  N  C  M    797

2461  GACGCTGGTGGACAAGGTGGGCCGGGCCAACGACCTCACCATTGACTACGCTGACCAGCG  2520
798    T  L  V  D  K  V  G  R  A  N  D  L  T  I  D  Y  A  D  Q  R    817

2521  CCTCTACTGGACCGACCTGGACACCAACATGATCGAGTCGTCCAACATGCTGGGTCAGGA  2580
818    L  Y  W  T  D  L  D  T  N  M  I  E  S  S  N  M  L  G  Q  E    837

2581  GCGGGTCGTGATTGCCGACGATCTCCCGCACCCGTTCGGTCTGACGCAGTACAGCGATTA  2640
838    R  V  V  I  A  D  D  L  P  H  P  F  G  L  T  Q  Y  S  D  Y    857

2641  TATCTACTGGACAGACTGGAATCTGCACAGCATTGAGCGGGCCGACAAGACTAGCGGCCG  2700
858    I  Y  W  T  D  W  N  L  H  S  I  E  R  A  D  K  T  S  G  R    877

2701  GAACCGCACCCTCATCCAGGGCCACCTGGACTTCGTGATGGACATCCTGGTGTTCCACTC  2760
878    N  R  T  L  I  Q  G  H  L  D  F  V  M  D  I  L  V  F  H  S    897
```

FIG. 6F

```
2761  CTCCCGCCAGGATGGCCTCAATGACTGTATGCACAACAACGGGCAGTGTGGGCAGCTGTG  2820
 898   S  R  Q  D  G  L  N  D  C  M  H  N  N  G  Q  C  G  Q  L  C   917

2821  CCTTGCCATCCCCGGCGGCCACCGCTGCGGCTGCGCCTCACACTACACCCTGGACCCCAG  2880
 918   L  A  I  P  G  G  H  R  C  G  C  A  S  H  Y  T  L  D  P  S   937

2881  CAGCCGCAACTGCAGCCCGCCCACCACCTTCTTGCTGTTCAGCCAGAAATCTGCCATCAG  2940
 938   S  R  N  C  S  P  P  T  T  F  L  L  F  S  Q  K  S  A  I  S   957

2941  TCGGATGATCCCGGACGACCAGCACAGCCCGGATCTCATCCTGCCCCTGCATGGACTGAG  3000
 958   R  M  I  P  D  D  Q  H  S  P  D  L  I  L  P  L  H  G  L  R   977

3001  GAACGTCAAAGCCATCGACTATGACCCACTGGACAAGTTCATCTACTGGGTGGATGGGCG  3060
 978   N  V  K  A  I  D  Y  D  P  L  D  K  F  I  Y  W  V  D  G  R   997

3061  CCAGAACATCAAGCGAGCCAAGGACGACGGGACCCAGCCCTTTGTTTTGACCTCTCTGAG  3120
 998   Q  N  I  K  R  A  K  D  D  G  T  Q  P  F  V  L  T  S  L  S  1017

3121  CCAAGGCCAAAACCCAGACAGGCAGCCCCACGACCTCAGCATCGACATCTACAGCCGGAC  3180
1018   Q  G  Q  N  P  D  R  Q  P  H  D  L  S  I  D  I  Y  S  R  T  1037

3181  ACTGTTCTGGACGTGCGAGGCCACCAATACCATCAACGTCCACAGGCTGAGCGGGGAAGC  3240
1038   L  F  W  T  C  E  A  T  N  T  I  N  V  H  R  L  S  G  E  A  1057

3241  CATGGGGGTGGTGCTGCGTGGGGACCGCGACAAGCCCAGGGCCATCGTCGTCAACGCGGA  3300
1058   M  G  V  V  L  R  G  D  R  D  K  P  R  A  I  V  V  N  A  E  1077
```

FIG. 6G

```
3301  GCGAGGGTACCTGTACTTCACCAACATGCAGGACCGGGCAGCCAAGATCGAACGCGCAGC  3360
1078   R  G  Y  L  Y  F  T  N  M  Q  D  R  A  A  K  I  E  R  A  A   1097

3361  CCTGGACGGCACCGAGCGCGAGGTCCTCTTCACCACCGGCCTCATCCGCCCTGTGGCCCT  3420
1098   L  D  G  T  E  R  E  V  L  F  T  T  G  L  I  R  P  V  A  L   1117

3421  GGTGGTGGACAACACACTGGGCAAGCTGTTCTGGGTGGACGCGGACCTGAAGCGCATTGA  3480
1118   V  V  D  N  T  L  G  K  L  F  W  V  D  A  D  L  K  R  I  E   1137

3481  GAGCTGTGACCTGTCAGGGGCCAACCGCCTGACCCTGGAGGACGCCAACATCGTGCAGCC  3540
1138   S  C  D  L  S  G  A  N  R  L  T  L  E  D  A  N  I  V  Q  P   1157

3541  TCTGGGCCTGACCATCCTTGGCAAGCATCTCTACTGGATCGACCGCCAGCAGCAGATGAT  3600
1158   L  G  L  T  I  L  G  K  H  L  Y  W  I  D  R  Q  Q  Q  M  I   1177

3601  CGAGCGTGTGGAGAAGACCACCGGGGACAAGCGGACTCGCATCCAGGGCCGTGTCGCCCA  3660
1178   E  R  V  E  K  T  T  G  D  K  R  T  R  I  Q  G  R  V  A  H   1197

3661  CCTCACTGGCATCCATGCAGTGGAGGAAGTCAGCCTGGAGGAGTTCTCAGCCCACCCATG  3720
1198   L  T  G  I  H  A  V  E  E  V  S  L  E  E  F  S  A  H  P  C   1217

3721  TGCCCGTGACAATGGTGGCTGCTCCCACATCTGTATTGCCAAGGGTGATGGGACACCACG  3780
1218   A  R  D  N  G  G  C  S  H  I  C  I  A  K  G  D  G  T  P  R   1237

3781  GTGCTCATGCCCAGTCCACCTCGTGCTCCTGCAGAACCTGCTGACCTGTGGAGAGCCGCC  3840
1238   C  S  C  P  V  H  L  V  L  L  Q  N  L  L  T  C  G  E  P  P   1257
```

FIG. 6H

```
3841  CACCTGCTCCCCGGACCAGTTTGCATGTGCCACAGGGGAGATCGACTGTATCCCCGGGGC  3900
1258   T  C  S  P  D  Q  F  A  C  A  T  G  E  I  D  C  I  P  G  A   1277

3901  CTGGCGCTGTGACGGCTTTCCCGAGTGCGATGACCAGAGCGACGAGGAGGGCTGCCCCGT  3960
1278   W  R  C  D  G  F  P  E  C  D  D  Q  S  D  E  E  G  C  P  V   1297

3961  GTGCTCCGCCGCCCAGTTCCCCTGCGCGCGGGGTCAGTGTGTGGACCTGCGCCTGCGCTG  4020
1298   C  S  A  A  Q  F  P  C  A  R  G  Q  C  V  D  L  R  L  R  C   1317

4021  CGACGGCGAGGCAGACTGTCAGGACCGCTCAGACGAGGTGGACTGTGACGCCATCTGCCT  4080
1318   D  G  E  A  D  C  Q  D  R  S  D  E  V  D  C  D  A  I  C  L   1337

4081  GCCCAACCAGTTCCGGTGTGCGAGCGGCCAGTGTGTCCTCATCAAACAGCAGTGCGACTC  4140
1338   P  N  Q  F  R  C  A  S  G  Q  C  V  L  I  K  Q  Q  C  D  S   1357

4141  CTTCCCCGACTGTATCGACGGCTCCGACGAGCTCATGTGTGAAATCACCAAGCCGCCCTC  4200
1358   F  P  D  C  I  D  G  S  D  E  L  M  C  E  I  T  K  P  P  S   1377

4201  AGACGACAGCCCGGCCCACAGCAGTGCCATCGGGCCCGTCATTGGCATCATCCTCTCTCT  4260
1378   D  D  S  P  A  H  S  S  A  I  G  P  V  I  G  I  I  L  S  L   1397

4261  CTTCGTCATGGGTGGTGTCTATTTTGTGTGCCAGCGCGTGGTGTGCCAGCGCTATGCGGG  4320
1398   F  V  M  G  G  V  Y  F  V  C  Q  R  V  V  C  Q  R  Y  A  G   1417

4321  GGCCAACGGGCCCTTCCCGCACGAGTATGTCAGCGGGACCCCGCACGTGCCCCTCAATTT  4380
1418   A  N  G  P  F  P  H  E  Y  V  S  G  T  P  H  V  P  L  N  F   1437
```

FIG. 6I

```
4381  CATAGCCCCGGGCGGTTCCCAGCATGGCCCCTTCACAGGCATCGCATGCGGAAAGTCCAT  4440
1438   I  A  P  G  G  S  Q  H  G  P  F  T  G  I  A  C  G  K  S  M   1457

4441  GATGAGCTCCGTGAGCCTGATGGGGGGCCGGGGCGGGGTGCCCCTCTACGACCGGAACCA  4500
1458   M  S  S  V  S  L  M  G  G  R  G  G  V  P  L  Y  D  R  N  H   1477

4501  CGTCACAGGGGCCTCGTCCAGCAGCTCGTCCAGCACGAAGGCCACGCTGTACCCGCCGAT  4560
1478   V  T  G  A  S  S  S  S  S  S  S  T  K  A  T  L  Y  P  P  I   1497

4561  CCTGAACCCGCCGCCCTCCCCGGCCACGGACCCCTCCCTGTACAACATGGACATGTTCTA  4620
1498   L  N  P  P  P  S  P  A  T  D  P  S  L  Y  N  M  D  M  F  Y   1517

4621  CTCTTCAAACATTCCGGCCACTGCGAGACCGTACAGGCCCTACATCATTCGAGGAATGGC  4680
1518   S  S  N  I  P  A  T  A  R  P  Y  R  P  Y  I  I  R  G  M  A   1537

4681  GCCCCCGACGACGCCCTGCAGCACCGACGTGTGTGACAGCGACTACAGCGCCAGCCGCTG  4740
1538   P  P  T  T  P  C  S  T  D  V  C  D  S  D  Y  S  A  S  R  W   1557

4741  GAAGGCCAGCAAGTACTACCTGGATTTGAACTCGGACTCAGACCCCTATCCACCCCCACC  4800
1558   K  A  S  K  Y  Y  L  D  L  N  S  D  S  D  P  Y  P  P  P  P   1577

4801  CACGCCCCACAGCCAGTACCTGTCGGCGGAGGACAGCTGCCCGCCCTCGCCCGCCACCGA  4860
1578   T  P  H  S  Q  Y  L  S  A  E  D  S  C  P  P  S  P  A  T  E   1597

4861  GAGGAGCTACTTCCATCTCTTCCCGCCCCCTCCGTCCCCCTGCACGGACTCATCCTGACC  4920
1598   R  S  Y  F  H  L  F  P  P  P  P  S  P  C  T  D  S  S        1615
```

FIG. 6J

```
4921   TCGGCCGGGCCACTCTGGCTTCTCTGTGCCCCTGTAAATAGTTTTAAATATGAACAAAGA   4980
4981   AAAAAATATATTTTATGATTTAAAAAATAAATATAATTGGGATTTTAAAAACATGAGAAA   5040
5041   TGTGAACTGTGATGGGGTGGGCAGGGCTGGGAGAACTTTGTACAGTGGAGAAATATTTAT   5100
5101   AAACTTAATTTTGTAAAACA   5120
```

Mouse Zmax1 In situ hybridization
100X Magnification

Antisense probe

Mouse Zmax1 In situ hybridization
100X Magnification

Sense probe

Mouse Zmax1 In situ hybridization
400X Magnification
Antisense probe

Mouse Zmax1 In situ hybridization
400X Magnification
Sense probe

400X Magnification
Antisense probe

Mouse Zmax1 In situ hybridization
400X Magnification
Sense probe

Antisense Inhibition of Zmax1 Expression

MC-3T3 cells

HIGH BONE MASS GENE OF 1.1Q13.3

RELATED APPLICATIONS

This application is a continuation-in-part of application Ser. No. 09/229,319, filed Jan. 13, 1999 now abandoned, which claims benefit of U.S. Provisional Application No. 60/071,449, filed Jan. 13, 1998, and U.S. Provisional Application No. 60/105,511, filed Oct. 23, 1998, all of which are herein incorporated by reference in their entirety.

FIELD OF THE INVENTION

The present invention relates generally to the field of genetics, genomics and molecular biology. More particularly, the invention relates to methods and materials used to isolate, detect and sequence a high bone mass gene and corresponding wild-type gene, and mutants thereof. The present invention also relates to the high bone mass gene, the corresponding wild-type gene, and mutants thereof. The genes identified in the present invention are implicated in the ontology and physiology of bone development. The invention also provides nucleic acids, proteins, cloning vectors, expression vectors, transformed hosts, methods of developing pharmaceutical compositions, methods of identifying molecules involved in bone development, and methods of diagnosing and treating diseases involved in bone development. In preferred embodiments, the present invention is directed to methods for treating, diagnosing, preventing and screening for normal and abnormal conditions of bone, including metabolic bone diseases such as osteoporosis.

BACKGROUND OF THE INVENTION

Two of the most common types of osteoporosis are postmenopausal and senile osteoporosis. Osteoporosis affects men as well as women, and, taken with other abnormalities of bone, presents an ever-increasing health risk for an aging population. The most common type of osteoporosis is that associated with menopause. Most women lose between 20–60% of the bone mass in the trabecular compartment of the bone within 3–6 years after the cessation of menses. This rapid loss is generally associated with an increase of bone resorption and formation. However, the resorptive cycle is more dominant and the result is a net loss of bone mass. Osteoporosis is a common and serious disease among postmenopausal women. There are an estimated 25 million women in the United States alone who are afflicted with this disease. The results of osteoporosis are both personally harmful, and also account for a large economic loss due to its chronicity and the need for extensive and long-term support (hospitalization and nursing home care) from the disease sequelae. This is especially true in more elderly patients. Additionally, while osteoporosis is generally not thought of as a life-threatening condition, a 20–30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy bone and is particularly concentrated near the ends of the bone near the joints and in the vertebrae of the spine. The trabecular tissue is characterized by small structures which inter-connect with each other as well as the more solid and dense cortical tissue which makes up the outer surface and central shaft of the bone. This criss-cross network of trabeculae gives lateral support to the outer cortical structure and is critical to the biomechanical strength of the overall structure. In postmenopausal osteoporosis, it is primarily the net resorption and loss of the trabeculae which lead to the failure and fracture of the bone. In light of the loss of the trabeculae in postmenopausal women, it is not surprising that the most common fractures are those associated with bones which are highly dependent on trabecular support, e.g., the vertebrae, the neck of the femur, and the forearm. Indeed, hip fracture, Colle's fractures, and vertebral crush fractures are indicative of postmenopausal osteoporosis.

One of the earliest generally accepted methods for treatment of postmenopausal osteoporosis was estrogen replacement therapy. Although this therapy frequently is successful, patient compliance is low, primarily due to the undesirable side-effects of chronic estrogen treatment. Frequently cited side-effects of estrogen replacement therapy include reinitiation of menses, bloating, depression, and fear of breast or uterine cancer. In order to limit the known threat of uterine cancer in those women who have not undergone a hysterectomy, a protocol of estrogen and progestin cyclic therapy is often employed. This protocol is similar to that which is used in birth control regimens, and often is not tolerated by women because of the side-effects characteristic of progestin. More recently, certain antiestrogens, originally developed for the treatment of breast cancer, have been shown in experimental models of postmenopausal osteoporosis to be efficacious. Among these agents is raloxifene (See, U.S. Pat. No. 5,393,763, and Black et al, *J. Clin. Invest.*, 93:63–69 (1994)). In addition, tamoxifene, a widely used clinical agent for the treatment of breast cancer, has been shown to increase bone mineral density in post menopausal women suffering from breast cancer (Love et al, *N. Engl. J. Med.*, 326:852–856 (1992)).

Another therapy for the treatment of postmenopausal osteoporosis is the use of calcitonin. Calcitonin is a naturally occurring peptide which inhibits bone resorption and has been approved for this use in many countries (Overgaard et al, *Br. Med. J.*, 305:556–561 (1992)). The use of calcitonin has been somewhat limited, however. Its effects are very modest in increasing bone mineral density and the treatment is very expensive. Another therapy for the treatment of postmenopausal osteoporosis is the use of bis-phosphonates. These compounds were originally developed for use in Paget's disease and malignant hypercalcemia. They have been shown to inhibit bone resorption. Alendronate, one compound of this class, has been approved for the treatment of postmenopausal osteoporosis. These agents may be helpful in the treatment of osteoporosis, but these agents also have potential liabilities which include osteomalacia, extremely long half-life in bone (greater than 2 years), and possible "frozen bone syndrome," e.g., the cessation of normal bone remodeling.

Senile osteoporosis is similar to postmenopausal osteoporosis in that it is marked by the loss of bone mineral density and resulting increase in fracture rate, morbidity, and associated mortality. Generally, it occurs in later life, i.e., after 70 years of age. Historically, senile osteoporosis has been more common in females, but with the advent of a more elderly male population, this disease is becoming a major factor in the health of both sexes. It is not clear what, if any, role hormones such as testosterone or estrogen have in this disease, and its etiology remains obscure. Treatment of this disease has not been very satisfactory. Hormone therapy, estrogen in women and testosterone in men, has shown equivocal results; calcitonin and bis-phosphonates may be of some utility.

The peak mass of the skeleton at maturity is largely under genetic control. Twin studies have shown that the variance in bone mass between adult monozygotic twins is smaller than between dizygotic twins (Slemenda et al, *J. Bone Miner. Res.*, 6:561–567 (1991); Young et al, *J. Bone Miner. Res.*, 6:561–567 (1995); Pocock et al, *J. Clin. Invest.*, 80:706–710 (1987); Kelly et al, *J. Bone Miner. Res.*, 8:11–17 (1993)), and it has been estimated that up to 60% or more of the variance in skeletal mass is inherited (Krall et al, *J. Bone Miner. Res.*, 10:S367 (1993)). Peak skeletal mass is the most powerful determinant of bone mass in elderly years (Hui et al, *Ann. Int. Med.*, 111:355–361 (1989)), even though the rate of age-related bone loss in adult and later life is also a strong determinant (Hui et al, *Osteoporosis Int.*, 1:30–34 (1995)). Since bone mass is the principal measurable determinant of fracture risk, the inherited peak skeletal mass achieved at maturity is an important determinant of an individual's risk of fracture later in life. Thus, study of the genetic basis of bone mass is of considerable interest in the etiology of fractures due to osteoporosis.

Recently, a strong interest in the genetic control of peak bone mass has developed in the field of osteoporosis. The interest has focused mainly on candidate genes with suitable polymorphisms to test for association with variation in bone mass within the normal range, or has focused on examination of genes and gene loci associated with low bone mass in the range found in patients with osteoporosis. The vitamin D receptor locus (VDR) (Morrison et al, *Nature*, 367:284–287 (1994)), PTH gene (Howard et al, *J. Clin. Endocrinol. Metab.*, 80:2800–2805 (1995); Johnson et al, *J. Bone Miner. Res.*, 8:11–17 (1995); Gong et al, *J. Bone Miner. Res.*, 10:S462 (1995)) and the estrogen receptor gene (Hosoi et al, *J. Bone Miner. Res.*, 10:S170 (1995); Morrison et al, *Nature*, 367:284–287 (1994)) have figured most prominently in this work. These studies are difficult because bone mass (the phenotype) is a continuous, quantitative, polygenic trait, and is confounded by environmental factors such as nutrition, co-morbid disease, age, physical activity, and other factors. Also, this type of study design requires large numbers of subjects. In particular, the results of VDR studies to date have been confusing and contradictory (Garnero et al, *J. Bone Miner. Res.*, 10:1283–1288 (1995); Eisman et al, *J. Bone. Miner. Res.*, 10:1289–1293 (1995); Peacock, *J. Bone Miner. Res.*, 10:1294–1297 (1995)). Furthermore, the work thus far has not shed much light on the mechanism(s) whereby the genetic influences might exert their effect on bone mass.

While it is well known that peak bone mass is largely determined by genetic rather than environmental factors, studies to determine the gene loci (and ultimately the genes) linked to variation in bone mass are difficult and expensive. Study designs which utilize the power of linkage analysis, e.g., sib-pair or extended family, are generally more informative than simple association studies, although the latter do have value. However, genetic linkage studies involving bone mass are hampered by two major problems. The first problem is the phenotype, as discussed briefly above. Bone mass is a continuous, quantitative trait, and establishing a discrete phenotype is difficult. Each anatomical site for measurement may be influenced by several genes, many of which may be different from site to site. The second problem is the age component of the phenotype. By the time an individual can be identified as having low bone mass, there is a high probability that their parents or other members of prior generations will be deceased and therefore unavailable for study, and younger generations may not have even reached peak bone mass, making their phenotyping uncertain for genetic analysis.

Regardless, linkage analysis can be used to find the location of a gene causing a hereditary "disorder" and does not require any knowledge of the biochemical nature of the disorder, i.e., a mutated protein that is believed to cause the disorder does not need to be known. Traditional approaches depend on assumptions concerning the disease process that might implicate a known protein as a candidate to be evaluated. The genetic localization approach using linkage analysis can be used to first find the general chromosomal region in which the defective gene is located and then to gradually reduce the size of the region in order to determine the location of the specific mutated gene as precisely as possible. After the gene itself is discovered within the candidate region, the messenger RNA and the protein are identified and, along with the DNA, are checked for mutations.

The genetic localization approach has practical implications since the location of the disease can be used for prenatal diagnosis even before the altered gene that causes the disease is found. Linkage analysis can enable families, even many of those that do not have a sick child, to know whether they are carriers of a disease gene and to evaluate the condition of an unborn child through molecular diagnosis. The transmission of a disease within families, then, can be used to find the defective gene. As used herein, reference to "high bone mass" (HBM) is analogous to reference to a disease state, although from a practical standpoint high bone mass can actually help a subject avoid the disease known as osteoporosis.

Linkage analysis is possible because of the nature of inheritance of chromosomes from parents to offspring. During meiosis, the two parental homologues pair to guide their proper separation to daughter cells. While they are lined up and paired, the two homologues exchange pieces of the chromosomes, in an event called "crossing over" or "recombination." The resulting chromosomes are chimeric, that is, they contain parts that originate from both parental homologues. The closer together two sequences are on the chromosome, the less likely that a recombination event will occur between them, and the more closely linked they are. In a linkage analysis experiment, two positions on the chromosomes are followed from one generation to the next to determine the frequency of recombination between them. In a study of an inherited disease, one of the chromosomal positions is marked by the disease gene or its normal counterpart, i.e., the inheritance of the chromosomal region can be determined by examining whether the individual displays symptoms of the disorder or not. The other position is marked by a DNA sequence that shows natural variation in the population such that the two homologues can be distinguished based on the copy of the "marker" sequence that they possess. In every family, the inheritance of the genetic marker sequence is compared to the inheritance of the disease state. If, within a family carrying an autosomal dominant disorder such as high bone mass, every affected individual carries the same form of the marker and all the unaffected individuals carry at least one different form of the marker, there is a great probability that the disease gene and the marker are located close to each other. In this way, chromosomes may be systematically checked with known markers and compared to the disease state. The data obtained from the different families is combined, and analyzed together by a computer using statistical methods. The result is information indicating the probability of linkage between the genetic marker and the disease allowing different distances between them. A positive result can mean that the disease is very close to the marker, while a negative result indicates that it is far away on that chromosome, or on an entirely different chromosome.

Linkage analysis is performed by typing all members of the affected family at a given marker locus and evaluating the co-inheritance of a particular disease state with the marker probe, thereby determining how often the two of them are co-inherited. The recombination frequency can be used as a measure of the genetic distance between two gene loci. A recombination frequency of 1% is equivalent to 1 map unit, or 1 centiMorgan (cM), which is roughly equivalent to 1,000 kb of DNA. This relationship holds up to frequencies of about 20% or 20 cM.

The entire human genome is 3,300 cM long. In order to find an unknown disease gene within 5–10 cM of a marker locus, the whole human genome can be searched with roughly 330 informative marker loci spaced at approximately 10 cM intervals (Botstein et al, *Am. J. Hum. Genet.*, 32:314–331 (1980)). The reliability of linkage results is established by using a number of statistical methods. The method most commonly used for the analysis of linkage in humans is the LOD score method (Morton, *Prog. Clin. Biol. Res.*, 147:245–265 (1984), Morton et al, *Am. J. Hum. Genet.*, 38:868–883 (1986)) which was incorporated into the computer program LIPED by Ott, *Am. J. Hum. Genet.*, 28:528–529 (1976). LOD scores are the logarithm of the ratio of the likelihood that two loci are linked at a given distance to that they are not linked (>50 cM apart). The advantage of using logarithmic values is that they can be summed among families with the same disease. This becomes necessary given the relatively small size of human families.

By convention, a total LOD score greater than +3.0 (that is, odds of linkage at the specified recombination frequency being 1000 times greater than odds of no linkage) is considered to be significant evidence for linkage at that particular recombination frequency. A total LOD score of less than −2.0 (that is, odds of no linkage being 100 times greater than odds of linkage at the specified frequency) is considered to be strong evidence that the two loci under consideration are not linked at that particular recombination frequency. Until recently, most linkage analyses have been performed on the basis of two-point data, which is the relationship between the disorder under consideration and a particular genetic marker. However, as a result of the rapid advances in mapping the human genome over the last few years, and concomitant improvements in computer methodology, it has become feasible to carry out linkage analyses using multi-point data. Multi-point analysis provide a simultaneous analysis of linkage between the disease and several linked genetic markers, when the recombination distance among the markers is known.

Multi-point analysis is advantageous for two reasons. First, the informativeness of the pedigree is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows isolation of a small region in which the disease gene resides. Lathrop et al, *Proc. Natl. Acad. Sci. USA*, 81:3443–3446 (1984) have written the most widely used computer package, LINKAGE, for multi-point analysis.

There is a need in the art for identifying the gene associated with a high bone mass phenotype. The present invention is directed to this, as well as other, important ends.

SUMMARY OF THE INVENTION

The present invention describes the Zmax1 gene and the HBM gene on chromosome 11q13.3 by genetic linkage and mutation analysis. The use of additional genetic markers linked to the genes has aided this discovery. By using linkage analysis and mutation analysis, persons predisposed to HBM may be readily identified. Cloning methods using Bacterial Artificial Chromosomes have enabled the inventors to focus on the chromosome region of 11q13.3 and to accelerate the sequencing of the autosomal dominant gene. In addition, the invention identifies the Zmax1 gene and the HBM gene, and identifies the guanine-to-thynine polymorphism mutation at position 582 in the Zmax1 gene that produces the HBM gene and the HBM phenotype.

The present invention identifies the Zmax1 gene and the HBM gene, which can be used to determine if people are predisposed to HBM and, therefore, not susceptible to diseases characterized by reduced bone density, including, for example, osteoporosis, or are predisposed and susceptible to diseases characterized by abnormally high bone density, such as, for example, osteoporosis. Older individuals carrying the HBM gene express the HBM protein, and, therefore, do not develop osteoporosis. In other words, the HBM gene is a suppressor of osteoporosis. This in vivo observation is a strong evidence that treatment of normal individuals with the HBM gene or protein, or fragments thereof, will ameliorate osteoporosis.

Moreover, such treatment will be indicated in the treatment of bone lesions, particularly bone fractures, for bone remodeling in the healing of such lesions. For example, persons predisposed to or suffering from stress fractures (i.e., the accumulation of stress-induced microfractures, eventually resulting in a true fracture through the bone cortex) may be identified and/or treated by means of the invention. Moreover, the methods and compositions of the invention will be of use in the treatment of secondary osteoporosis, where the course of therapy involves bone remodeling, such as endocrine conditions accompanying corticosteroid administration, hyperthyroidism, hypogonadism, hematologic malignancies, malabsorption and alcoholism, as well as disorders associated with vitamin D and/or phosphate metabolism, such as osteomalacia and rickets, and diseases characterized by abnormal or disordered bone remodeling, such as Paget's disease, and in neoplasms of bone, which may be benign or malignant.

In various embodiments, the present invention is directed to nucleic acids, proteins, vectors, and transformed hosts of HBM and Zmax1.

Additionally, the present invention is directed to applications of the above embodiments of the invention including, for example, gene therapy, pharmaceutical development, and diagnostic assays for bone development disorders. In preferred embodiments, the present invention is directed to methods for treating, diagnosing, preventing and screening for osteoporosis.

These and other aspects of the present invention are described in more detail below.

BRIEF DESCRIPTION OF THE FIGURES

FIGS. 3A–3F show the genomic structure of Zmax1 with flanking intron sequences. Translation is initiated by the underlined "ATG" in exon 1. The site of the polymorphism in the HBM gene is in exon 3 and is represented by the underlined "G," whereby this nucleotide is a "T" in the HBM gene. The 3' untranslated region of the mRNA is underlined within exon 23 (exon 1, SEQ ID NO:40; exon 2, SEQ ID NO:41; exon 3, SEQ ID NO:42; exon 4, SEQ ID NO:43; exon 5, SEQ ID NO:44; exon 6, SEQ ID NO:45; exon 7, SEQ ID NO:46; exon 8, SEQ ID NO:47; exon 9, SEQ ID NO:48; exon 10, SEQ ID NO:49; exon 11, SEQ ID NO:50; exon 12, SEQ ID NO:51; exon 13, SEQ ID NO:52; exon 14, SEQ ID NO:53; exon 15, SEQ ID NO:54; exon 16, SEQ ID NO:55; exon 17, SEQ ID NO:56; exon 18, SEQ ID NO:57; exon 19, SEQ ID NO:58; exon 20, SEQ ID NO:59; exon 21, SEQ ID NO:60; exon 22, SEQ ID NO:61; and exon 23; SEQ ID NO:62).

FIG. 4 also shows the site of the glycine to valine change that occurs in the HBM protein. The signal peptide is located at amino acids 1–22, the extracellular domain is located at amino acids 23–1385, the transmembrane segment is located at amino acids 1386–1413, and the cytoplasmic domain is located at amino acids 1414–1615.

FIGS. 6A–6J are the nucleotide and amino acid sequences of the wild-type gene, Zmax1. The location for the base pair substitution at nucleotide 582, a guanine to thymine, is underlined. This allelic variant is the HBM gene. The HBM gene encodes for a protein with an amino acid substitution of glycine to valine at position 171. The 5' untranslated region (UTR) boundaries bases 1 to 70, and the 3' UTR boundaries bases 4916–5120.

DETAILED DESCRIPTION OF THE INVENTION

Figure 1:
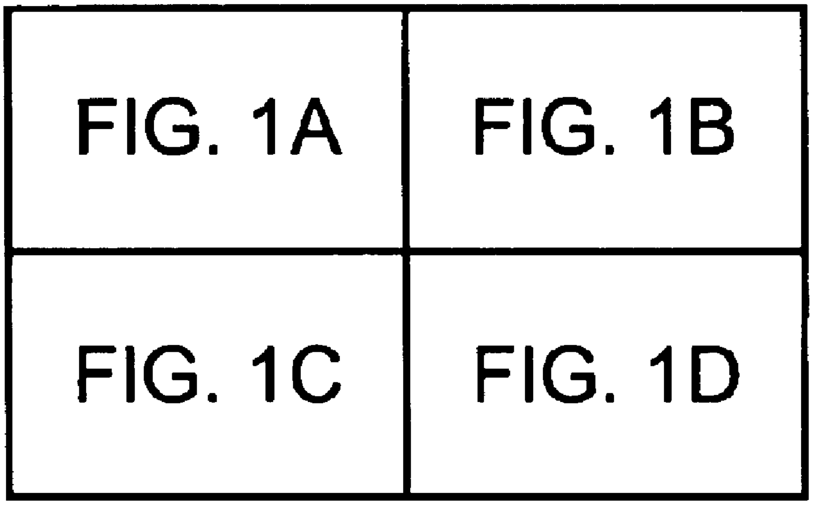
FIGS. 1A–1D show the pedigree of the individuals used in the genetic linkage studies. Under each individual is an ID number, the z-score for spinal BMD, and the allele calls for the critical markers on chromosome 11. Solid symbols represent "affected" individuals. Symbols containing "N" are "unaffected" individuals. DNA from 37 individuals was genotyped. Question marks denote unknown genotypes or individuals who were not genotyped.
Figure 1A:
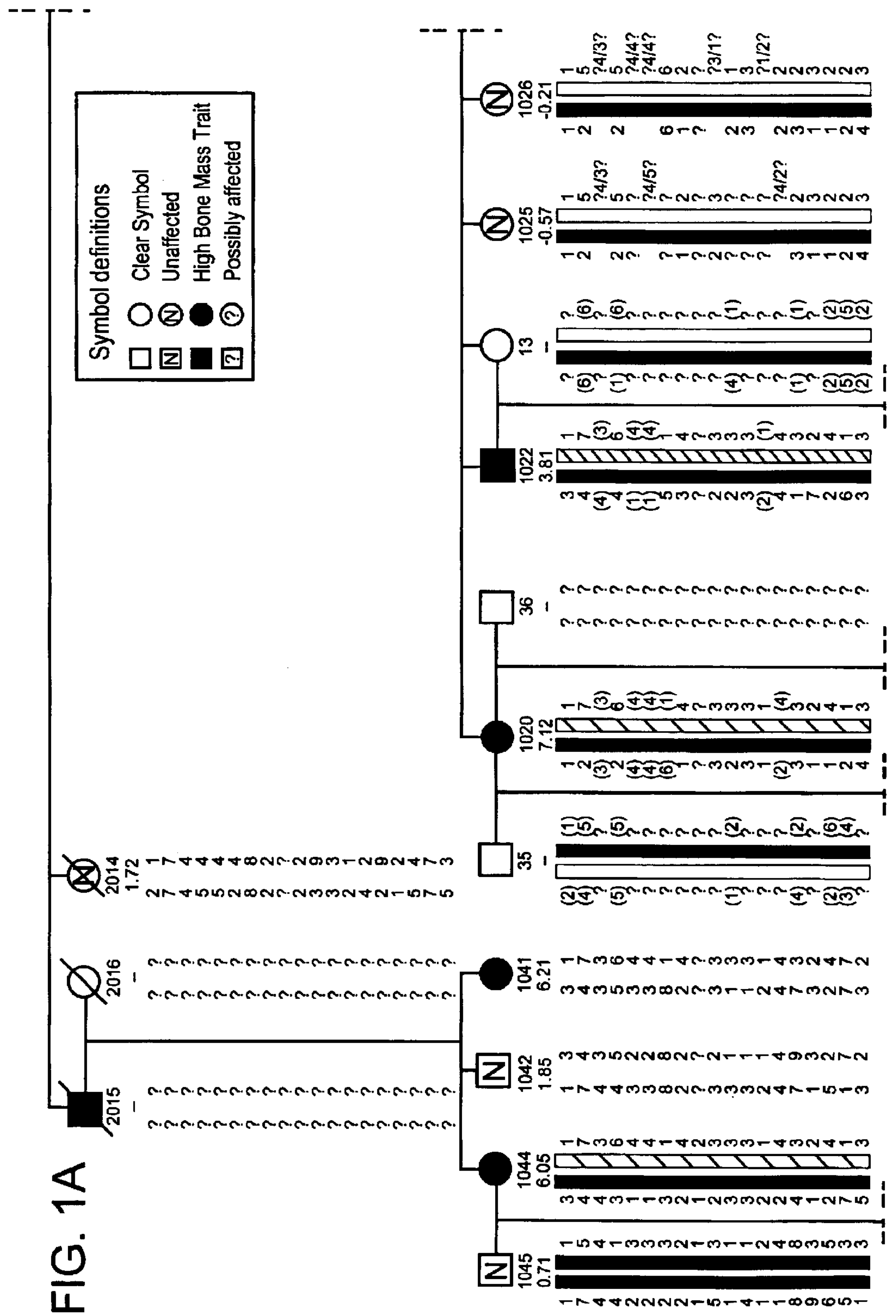
Figure 1B:
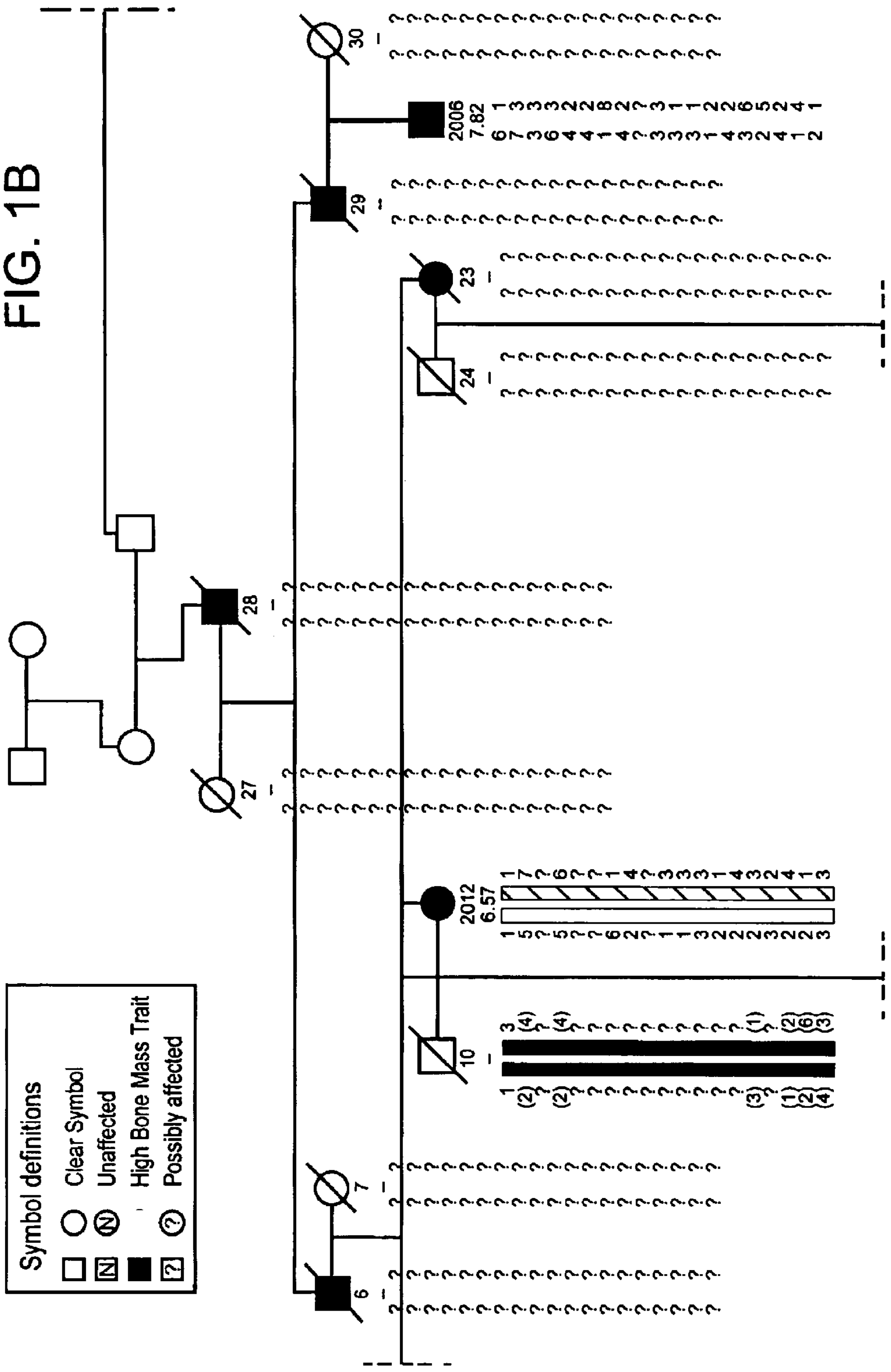
Figure 1C:
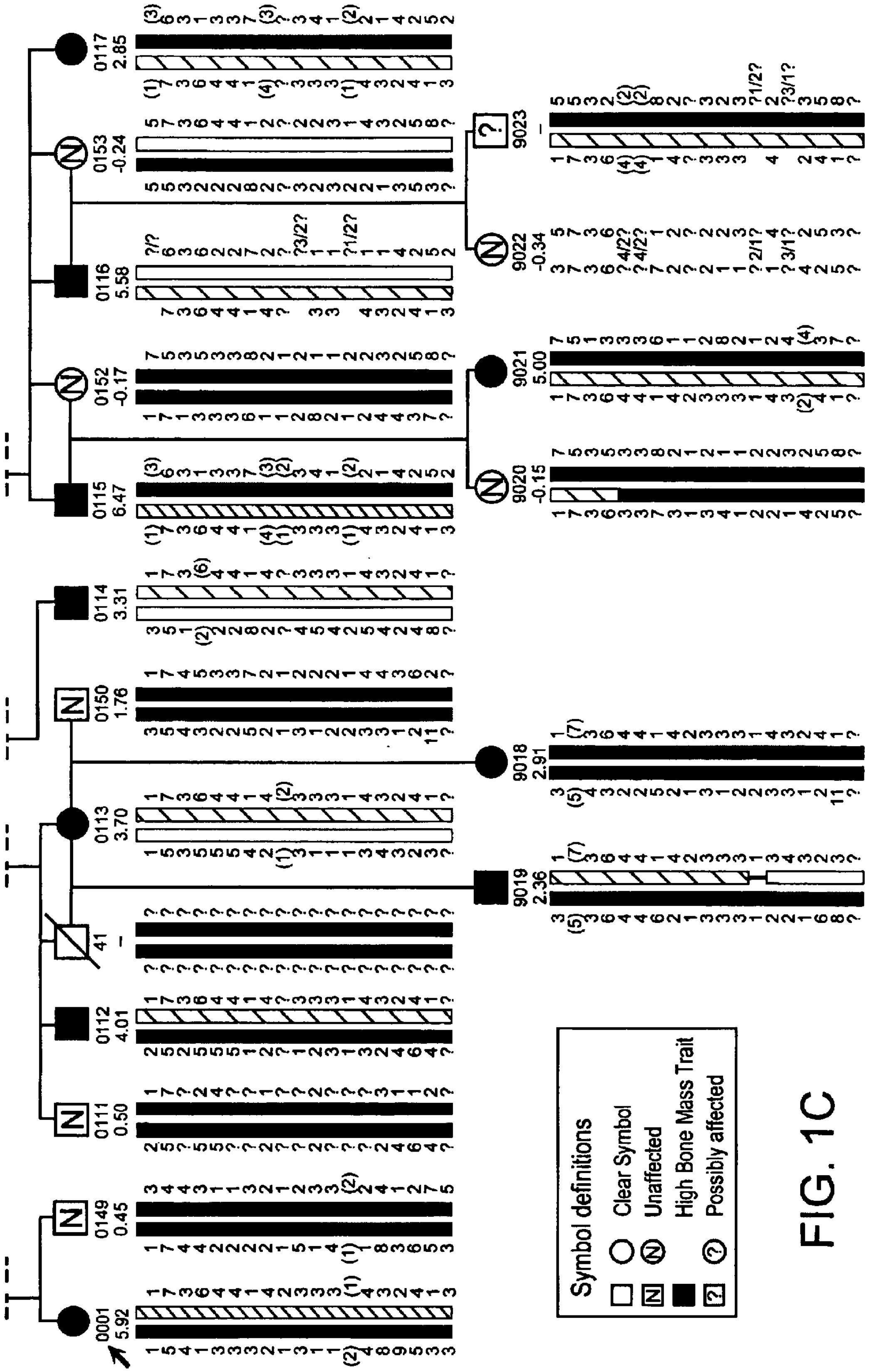
Figure 1D:
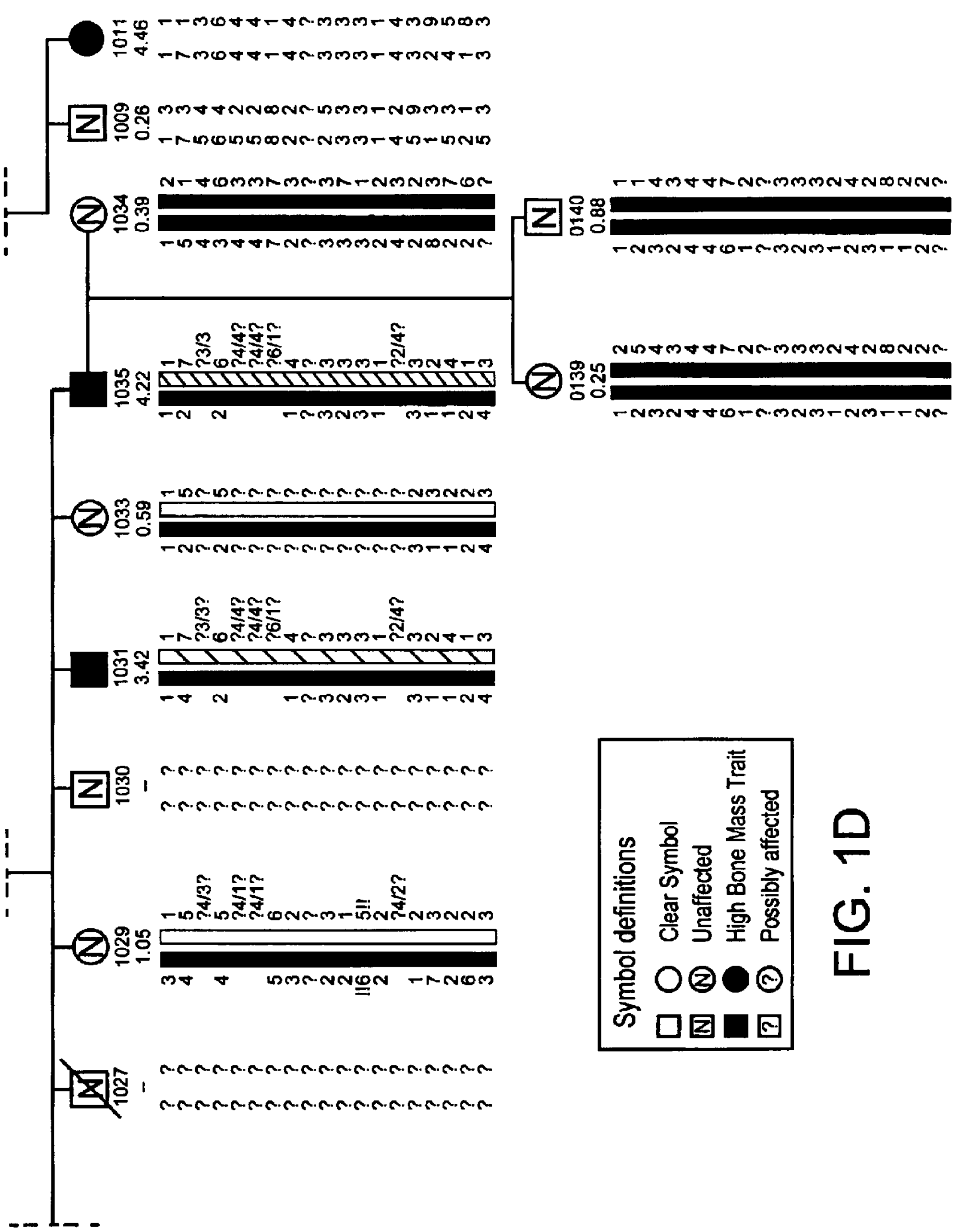

To aid in the understanding of the specification and claims, the following definitions are provided.

"Gene" refers to a DNA sequence that encodes through its template or messenger RNA a sequence of amino acids characteristic of a specific peptide. The term "gene" includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

The sequences of the present invention may be derived from a variety of sources including DNA, cDNA, synthetic DNA, synthetic RNA or combinations thereof. Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"cDNA library" refers to a collection of recombinant DNA molecules containing cDNA inserts which together comprise the entire genome of an organism. Such a cDNA library can be prepared by methods known to one skilled in the art and described by, for example, Cowell and Austin, "cDNA Library Protocols," Methods in Molecular Biology (1997). Generally, RNA is first isolated from the cells of an organism from whose genome it is desired to clone a particular gene.

"Cloning vehicle" refers to a plasmid or phage DNA or other DNA sequence which is able to replicate in a host cell. The cloning vehicle is characterized by one or more endonuclease recognition sites at which such DNA sequences may be cut in a determinable fashion without loss of an essential biological function of the DNA, which may contain a marker suitable for use in the identification of transformed cells.

"Expression control sequence" refers to a sequence of nucleotides that control or regulate expression of structural genes when operably linked to those genes. These include, for example, the lac systems, the trp system, major operator and promoter regions of the phage lambda, the control region of fd coat protein and other sequences known to control the expression of genes in prokaryotic or eukaryotic cells. Expression control sequences will vary depending on whether the vector is designed to express the operably linked gene in a prokaryotic or eukaryotic host, and may contain transcriptional elements such as enhancer elements, termination sequences, tissue-specificity elements and/or translational initiation and termination sites.

"Expression vehicle" refers to a vehicle or vector similar to a cloning vehicle but which is capable of expressing a gene which has been cloned into it, after transformation into a host. The cloned gene is usually placed under the control of (i.e., operably linked to) an expression control sequence.

"Operator" refers to a DNA sequence capable of interacting with the specific repressor, thereby controlling the transcription of adjacent gene(s).

"Promoter" refers to a DNA sequence that can be recognized by an RNA polymerase. The presence of such a sequence permits the RNA polymerase to bind and initiate transcription of operably linked gene sequences.

"Promoter region" is intended to include the promoter as well as other gene sequences which may be necessary for the initiation of transcription. The presence of a promoter region is sufficient to cause the expression of an operably linked gene sequence.

"Operably linked" means that the promoter controls the initiation of expression of the gene. A promoter is operably linked to a sequence of proximal DNA if upon introduction into a host cell the promoter determines the transcription of the proximal DNA sequence(s) into one or more species of RNA. A promoter is operably linked to a DNA sequence if the promoter is capable of initiating transcription of that DNA sequence.

"Prokaryote" refers to all organisms without a true nucleus, including bacteria

"Eukaryote" refers to organisms and cells that have a true nucleus, including mammalian cells.

"Host" includes prokaryotes and eukaryotes, such as yeast and filamentous fungi, as well as plant and animal cells. The term includes an organism or cell that is the recipient of a replicable expression vehicle.

"Fragment" of a gene refers to any variant of the gene that possesses the biological activity of that gene.

"Variant" refers to a gene that is substantially similar in structure and biological activity or immunological characteristics to either the entire gene or to a fragment of the gene. Provided that the two genes possess a similar activity, they are considered variant as that term is used herein even if the sequence of amino acid residues is not identical.

"Amplification of nucleic acids" refers to methods such as polymerase chain reaction (PCR), ligation amplification (or ligase chain reaction, LCR) and amplification methods based on the use of Q-beta replicase. These methods are well known in the art and described, for example, in U.S. Pat. Nos. 4,683,195 and 4,683,202. Reagents and hardware for conducting PCR are commercially available. Primers useful for amplifying sequences from the HBM region are preferably complementary to, and hybridize specifically to sequences in the HBM region or in regions that flank a target region therein. HBM sequences generated by amplification may be sequenced directly. Alternatively, the amplified sequence(s) may be cloned prior to sequence analysis.

"Antibodies" may refer to polyclonal and/or monoclonal antibodies and fragments thereof, and immunologic binding equivalents thereof, that can bind to the HBM proteins and fragments thereof or to nucleic acid sequences from the HBM region, particularly from the HBM locus or a portion thereof. The term antibody is used both to refer to a homogeneous molecular entity, or a mixture such as a serum product made up of a plurality of different molecular entities. Proteins may be prepared synthetically in a protein synthesizer and coupled to a carrier molecule and injected over several months into rabbits. Rabbit sera is tested for immunoreactivity to the HBM protein or fragment. Monoclonal antibodies may be made by injecting mice with the proteins, or fragments thereof. Monoclonal antibodies will be screened by ELISA and tested for specific immunoreactivity with HBM protein or fragments thereof. Harlow et al, *Antibodies: A Laboratory Manual*, Cold Spring Harbor Laboratory, Cold Spring Harbor, N.Y. (1988). These antibodies will be useful in assays as well as pharmaceuticals.

"HBM" refers to high bone mass.

"HBM protein" refers to a protein that is identical to a Zmax1 protein except that it contains an alteration of glycine 171 to valine. An HBM protein is defined for any organism that encodes a Zmax1 true homologue. For example, a mouse HBM protein refers to the mouse Zmax1 protein having the glycine 170 to valine substitution.

"HBM gene" refers to the genomic DNA sequence found in individuals showing the HBM characteristic or phenotype, where the sequence encodes the protein indicated by SEQ ID NO: 4. The HBM gene and the Zmax1 gene are allelic. The protein encoded by the HBM gene has the property of causing elevated bone mass, while the protein encoded by the Zmax1 gene does not. The HBM gene and the Zmax1 gene differ in that the HBM gene has a thymine at position 582, while the Zmax1 gene has a guanine at position 582. The HBM gene comprises the nucleic acid sequence shown as SEQ ID NO: 2. The HBM gene may also be referred to as an "HBM polymorphism."

"Normal," "wild-type," "unaffected" and "Zmax1" all refer to the genomic DNA sequence that encodes the protein indicated by SEQ ID NO: 3. The Zmax1 gene has a guanine at position 582. The Zmax1 gene comprises the nucleic acid sequence shown as SEQ ID NO: 1. "Normal," "wild-type," "unaffected" and "Zmax1" also refer to allelic variants of the genomic sequence that encodes proteins that do not contribute to elevated bone mass. The Zmax1 gene is common in the human population, while the HBM gene is rare.

"SYWT+EGF" refers to a repeat unit found in the Zmax1 protein, consisting of five YWT repeats followed by an EGF repeat.

"Bone development" generally refers to any process involved in the change of bone over time, including, for example, normal development, changes that occur during disease states, and changes that occur during aging. "Bone development disorder" particularly refers to any disorders in bone development including, for example, changes that occur during disease states and changes that occur during aging. Bone development may be progressive or cyclical in nature. Aspects of bone that may change during development include, for example, mineralization, formation of specific anatorical features, and relative or absolute numbers of various cell types.

"Bone modulation" or "modulation of bone formation" refers to the ability to affect any of the physiological processes involved in bone remodeling, as will be appreciated by one skilled in the art, including, for example, bone resorption and appositional bone growth, by, inter alia, osteoclastic and osteoblastic activity, and may comprise some or all of bone formation and development as used herein.

"Normal bone density" refers to a bone density within two standard deviations of a Z score of 0.

A "Zmax1 system" refers to a purified protein, cell extract, cell, animal, human or any other composition of matter in which Zmax1 is present in a normal or mutant form.

A "surrogate marker" refers to a diagnostic indication, symptom, sign or other feature that can be observed in a cell, tissue, human or animal that is correlated with the HBM gene or elevated bone mass or both, but that is easier to measure than bone density. The general concept of a surrogate marker is well accepted in diagnostic medicine.

The present invention encompasses the Zmax1 gene and Zmax1 protein in the forms indicated by SEQ ID NOS: 1 and 3, respectively, and other closely related variants, as well as the adjacent chromosomal regions of Zmax1 necessary for its accurate expression. In a preferred embodiment, the present invention is directed to at least 15 contiguous nucleotides of the nucleic acid sequence of SEQ ID NO: 1.

The present invention also encompasses the HBM gene and HBM protein in the forms indicated by SEQ ID NO: 2 and 4, respectively, and other closely related variants, as well as the adjacent chromosomal regions of the HBM gene necessary for its accurate expression. In a preferred embodiment, the present invention is directed to at least 15 contiguous nucleotides of the nucleic acid sequence of SEQ ID NO: 2. More preferably, the present invention is directed to at least 15 contiguous nucleotides of the nucleic acid sequence of SEQ ID NO: 2, wherein one of the 15 contiguous nucleotides is the thymine at nucleotide 582.

The invention also relates to the nucleotide sequence of the Zmax1 gene region, as well as the nucleotide sequence of the HBM gene region. More particularly, a preferred embodiment are the BAC clones containing segments of the Zmax1 gene region B200E21-H and B527D12-H. A preferred embodiment is the nucleotide sequence of the BAC clones consisting of SEQ ID NOS: 5–12.

The invention also concerns the use of the nucleotide sequence to identify DNA probes for the Zmax1 gene and the HBM gene, PCR primers to amplify the Zmax1 gene and the HBM gene, nucleotide polymorphisms in the Zmax1 gene and the HBM gene, and regulatory elements of the Zmax1 gene and the HBM gene.

This invention describes the further localization of the chromosomal location of the Zmax1 gene and HBM gene on chromosome 11q13.3 between genetic markers D11S987 and SNP_CONTIG033-6, as well as the DNA sequences of the Zmax1 gene and the HBM gene. The chromosomal location was refined by the addition of more genetic markers to the mapping panel used to map the gene, and by the extension of the pedigree to include more individuals. The pedigree extension was critical because the new individuals that have been genotyped harbor critical recombination events that narrow the region. To identify genes in the region on 11q13.3, a set of BAC clones containing this chromosomal region was identified. The BAC clones served as a template for genomic DNA sequencing, and also as a reagent for identifying coding sequences by direct cDNA selection. Genomic sequencing and direct cDNA selection were used to characterize more than 1.5 million base pairs of DNA from 11q13.3. The Zmax1 gene was identified within this region and the HBM gene was then discovered after mutational analysis of affected and unaffected individuals.

When a gene has been genetically localized to a specific chromosomal region, the genes in this region can be characterized at the molecular level by a series of steps that include: cloning of the entire region of DNA in a set of overlapping clones (physical mapping), characterization of genes encoded by these clones by a combination of direct cDNA selection, exon trapping and DNA sequencing (gene identification), and identification of mutations in these genes by comparative DNA sequencing of affected and unaffected members of the HBM kindred (mutation analysis).

Physical mapping is accomplished by screening libraries of human DNA cloned in vectors that are propagated in *E. coli* or *S. cereviseae* using PCR assays designed to amplify unique molecular landmarks in the chromosomal region of interest. To generate a physical map of the HBM candidate region, a library of human DNA cloned in Bacterial Artificial Chromosomes (BACs) was screened with a set of Sequence Tagged Site (STS) markers that had been previously mapped to chromosome 11q12-q13 by the efforts of the Human Genome Project.

STSs are unique molecular landmarks in the human genome that can be assayed by PCR. Through the combined efforts of the Human Genome Project, the location of thousands of STSs on the twenty-two autosomes and two sex chromosomes has been determined. For a positional cloning effort, the physical map is tied to the genetic map because the markers used for genetic mapping can also be used as STSs for physical mapping. By screening a BAC library with a combination of STSs derived from genetic markers, genes, and random DNA fragments, a physical map comprised of overlapping clones representing all of the DNA in a chromosomal region of interest can be assembled.

BACs are cloning vectors for large (80 kilobase to 200 kilobase) segments of human or other DNA that are propagated in *E. coli*. To construct a physical map using BACs, a library of BAC clones is screened so that individual clones harboring the DNA sequence corresponding to a given STS or set of STSs are identified. Throughout most of the human genome, the STS markers are spaced approximately 20 to 50 kilobases apart, so that an individual BAC clone typically contains at least two STS markers. In addition, the BAC libraries that were screened contain enough cloned DNA to cover the human genome six times over. Therefore, an individual STS typically identifies more than one BAC clone. By screening a six-fold coverage BAC library with a series of STS markers spaced approximately 50 kilobases apart, a physical map consisting of a series of overlapping BAC clones, i.e. BAC contigs, can be assembled for any region of the human genome. This map is closely tied to the genetic map because many of the STS markers used to prepare the physical map are also genetic markers.

When constructing a physical map, it often happens that there are gaps in the STS map of the genome that result in the inability to identify BAC clones that are overlapping in a given location. Typically, the physical map is first constructed from a set of STSs that have been identified through the publicly available literature and World Wide Web resources. The initial map consists of several separate BAC contigs that are separated by gaps of unknown molecular distance. To identify BAC clones that fill these gaps, it is necessary to develop new STS markers from the ends of the clones on either side of the gap. This is done by sequencing the terminal 200 to 300 base pairs of the BACs flanking the gap, and developing a PCR assay to amplify a sequence of 100 or more base pairs. If the terminal sequences are demonstrated to be unique within the human genome, then the new STS can be used to screen the BAC library to identify additional BACs that contain the DNA from the gap in the physical map. To assemble a BAC contig that covers a region the size of the HBM candidate region (2,000,000 or more base pairs), it is often necessary to develop new STS markers from the ends of several clones.

After building a BAC contig, this set of overlapping clones serves as a template for identifying the genes encoded in the chromosomal region. Gene identification can be accomplished by many methods. Three methods are commonly used: (1) a set of BACs selected from the BAC contig to represent the entire chromosomal region can be sequenced, and computational methods can be used to identify all of the genes, (2) the BACs from the BAC contig can be used as a reagent to clone cDNAs corresponding to the genes encoded in the region by a method termed direct cDNA selection, or (3) the BACs from the BAC contig can be used to identify coding sequences by selecting for specific DNA sequence motifs in a procedure called exon trapping. The present invention includes genes identified by the first two methods.

To sequence the entire BAC contig representing the HBM candidate region, a set of BACs was chosen for subcloning into plasmid vectors and subsequent DNA sequencing of these subclones. Since the DNA cloned in the BACs represents genomic DNA, this sequencing is referred to as genomic sequencing to distinguish it from cDNA sequencing. To initiate the genomic sequencing for a chromosomal region of interest, several non-overlapping BAC clones are chosen. DNA for each BAC clone is prepared, and the clones are sheared into random small fragments which are subsequently cloned into standard plasmid vectors such as pUC18. The plasmid clones are then grown to propagate the smaller fragments, and these are the templates for sequencing. To ensure adequate coverage and sequence quality for the BAC DNA sequence, sufficient plasmid clones are sequenced to yield six-fold coverage of the BAC clone. For example, if the BAC is 100 kilobases long, then phagemids are sequenced to yield 600 kilobases of sequence. Since the BAC DNA was randomly sheared prior to cloning in the phagemid vector, the 600 kilobases of raw DNA sequence can be assembled by computational methods into overlapping DNA sequences termed sequence contigs. For the purposes of initial gene identification by computational methods, six-fold coverage of each BAC is sufficient to yield ten to twenty sequence contigs of 1000 base pairs to 20,000 base pairs.

The sequencing strategy employed in this invention was to initially sequence "seed" BACs from the BAC contig in the HBM candidate region. The sequence of the "seed" BACs was then used to identify minimally overlapping BACs from the contig, and these were subsequently sequenced. In this manner, the entire candidate region was sequenced, with several small sequence gaps left in each BAC. This sequence served as the template for computational gene identification. One method for computational gene identification is to compare the sequence of BAC contig to publicly available databases of cDNA and genomic sequences, e.g. unigene, dbEST, genbank. These comparisons are typically done using the BLAST family of computer algorithms and programs (Altschul et al, *J. Mol. Biol.*, 215:403–410 (1990)). The BAC sequence can also be translated into protein sequence, and the protein sequence can be used to search publicly available protein databases, using a version of BLAST designed to analyze protein sequences (Altschul et al, *Nucl. Acids Res.*, 25:3389–3402 (1997)). Another method is to use computer algorithms such as MZEF (Zhang, *Proc. Natl. Acad Sci.*, 94:565–568 (1997)) and GRAIL (Uberbacher et al, *Methods Enzymol.*, 266:259–281 (1996)), which predict the location of exons in the sequence based on the presence of specific DNA sequence motifs that are common to all exons, as well as the presence of codon usage typical of human protein encoding sequences.

In addition to identifying genes by computational methods, genes were also identified by direct cDNA selection (Del Mastro et al, *Genome Res.* 5(2):185–194 (1995)). In direct cDNA selection, cDNA pools from tissues of interest are prepared, and the BACs from the candidate region are used in a liquid hybridization assay to capture the cDNAs which base pair to coding regions in the BAC. In the methods described herein, the cDNA pools were created from several different tissues by random priming the first strand cDNA from polyA RNA, synthesizing the second strand cDNA by standard methods, and adding linkers to the ends of the cDNA fragments. The linkers are used to amplify the cDNA pools. The BAC clones are used as a template for in vitro DNA synthesis to create a biotin labelled copy of the BAC DNA. The biotin labelled copy of the BAC DNA is then denatured and incubated with an excess of the PCR amplified, linkered cDNA pools which have also been denatured. The BAC DNA and cDNA are allowed to anneal in solution, and heteroduplexes between the BAC and the cDNA are isolated using streptavidin coated magnetic beads. The cDNAs that are captured by the BAC are then amplified using primers complimentary to the linker sequences, and the hybridization/selection process is repeated for a second round. After two rounds of direct cDNA selection, the cDNA fragments are cloned, and a library of these direct selected fragments is created.

The cDNA clones isolated by direct selection are analyzed by two methods. Since a pool of BACs from the HBM candidate region is used to provide the genomic DNA sequence, the cDNAs must be mapped to individual BACs. This is accomplished by arraying the BACs in microtiter dishes, and replicating their DNA in high density grids. Individual cDNA clones are then hybridized to the grid to confirm that they have sequence identity to an individual BAC from the set used for direct selection, and to determine the specific identity of that BAC. cDNA clones that are confirmed to correspond to individual BACs are sequenced. To determine whether the cDNA clones isolated by direct selection share sequence identity or similarity to previously identified genes, the DNA and protein coding sequences are compared to publicly available databases using the BLAST family of programs.

The combination of genomic DNA sequence and cDNA sequence provided by BAC sequencing and by direct cDNA selection yields an initial list of putative genes in the region. The genes in the region were all candidates for the HBM locus. To further characterize each gene, Northern blots were performed to determine the size of the transcript corresponding to each gene, and to determine which putative exons were transcribed together to make an individual gene. For Northern blot analysis of each gene, probes were prepared from direct selected cDNA clones or by PCR amplifying specific fragments from genomic DNA or from the BAC encoding the putative gene of interest. The Northern blots gave information on the size of the transcript and the tissues in which it was expressed. For transcripts which were not highly expressed, it was sometimes necessary to perform a reverse transcription PCR assay using RNA from the tissues of interest as a template for the reaction.

Gene identification by computational methods and by direct cDNA selection provides unique information about the genes in a region of a chromosome. When genes are identified, then it is possible to examine different individuals for mutations in each gene.

I. Phenotyping Using DXA Measurements

Spinal bone mineral content (BMC) and bone mineral density (BMD) measurements performed at Creighton University (Omaha, Nebr.) were made by DXA using a Norland Instruments densitometer (Norland XR2600 Densitometer, Dual Energy X-ray Absorptiometry, DXA). Spinal BMC and BMD at other locations used the machinery available. There are estimated to be 800 DXA machines currently operating in the U.S. Most larger cities have offices or imaging centers which have DXA capabilities, usually a Lunar or Hologic machine. Each location that provided spine BMC and BMD data included copies of the printouts from their machines to provide verification that the regions of interest for measurement of BMD have been chosen appropriately. Complete clinical histories and skeletal radiographs were obtained.

The HBM phenotype is defined by the following criteria: very high spinal BMD; a clinical history devoid of any known high bone mass syndrome; and skeletal radiographs showing a normal shape of the appendicular skeleton.

II. Genotyping of Microsatellite Markers

Figure 2A:
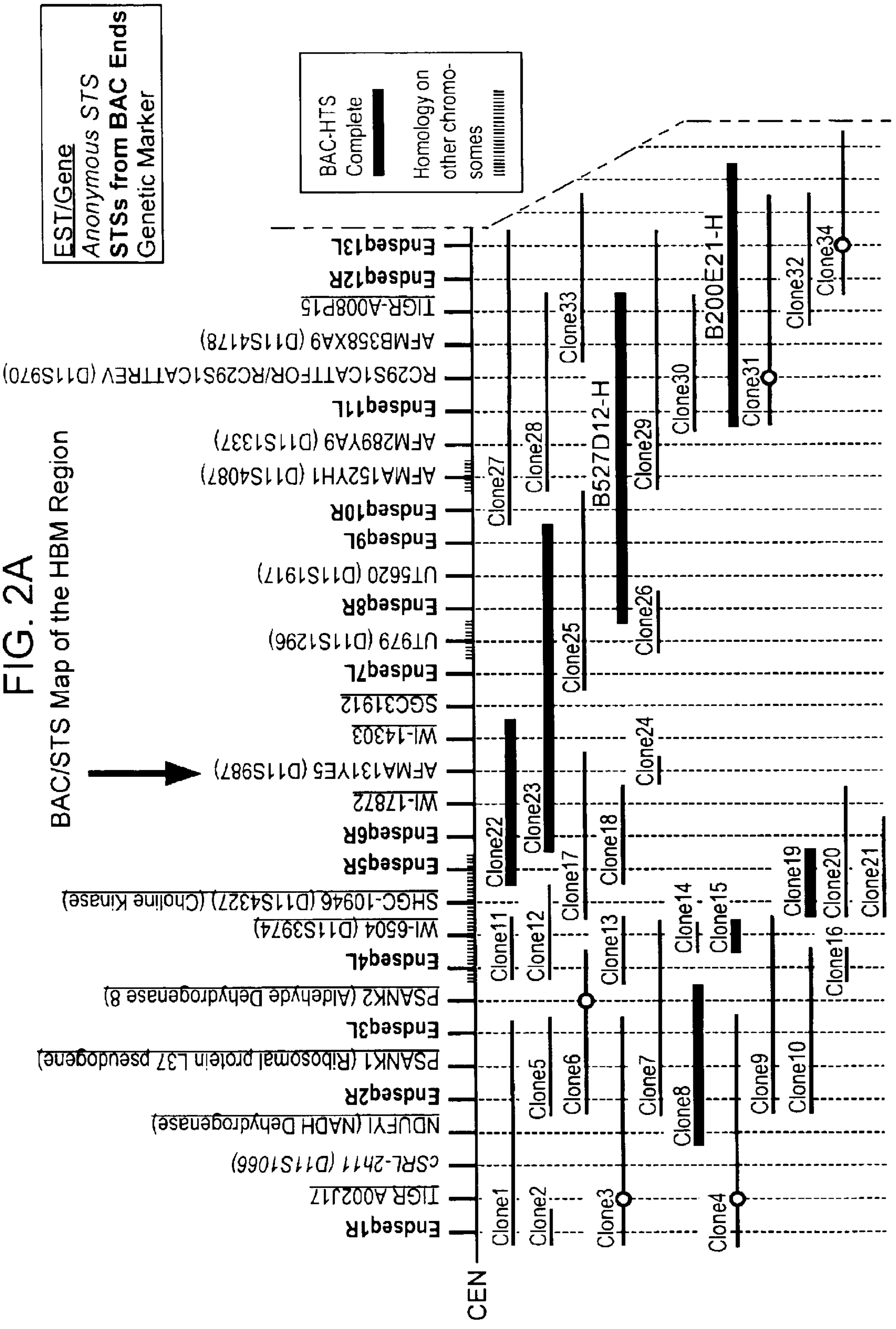
FIGS. 2A–2B depict the BAC/STS content physical map of the HBM region in 11q13.3. STS markers derived from genes, ESTs, microsatellites, random sequences, and BAC endsequences are denoted above the long horizontal line. For markers that are present in GDB the same nomenclature has been used. Locus names (D11S####) are listed in parentheses after the primary name if available. STSs derived from BAC endsequences are listed with the BAC name first followed by L or R for the left and right end of the clone, respectively. The two large arrows indicate the genetic markers that define the HBM critical region. The horizontal lines below the STSs indicate BAC clones identified by PCR-based screening of a nine-fold coverage BAC library. Open circles indicate that the marker did not amplify the corresponding BAC library address during library screening. Clone names use the following convention: B for BAC, the plate, row and column address, followed by -H indicating the HBM project (i.e., B36F16-H).
Figure 2B:
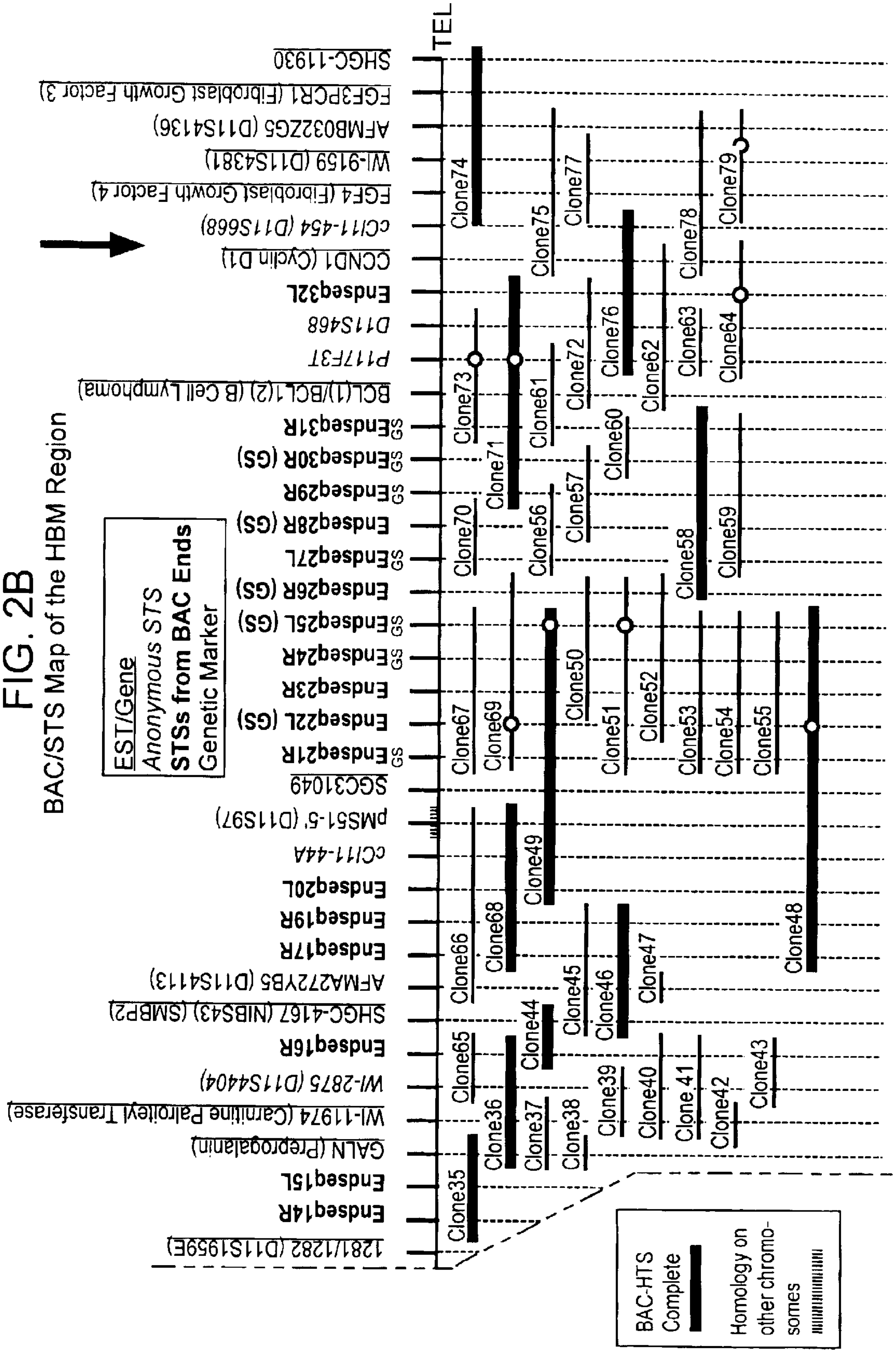
Figure 4:
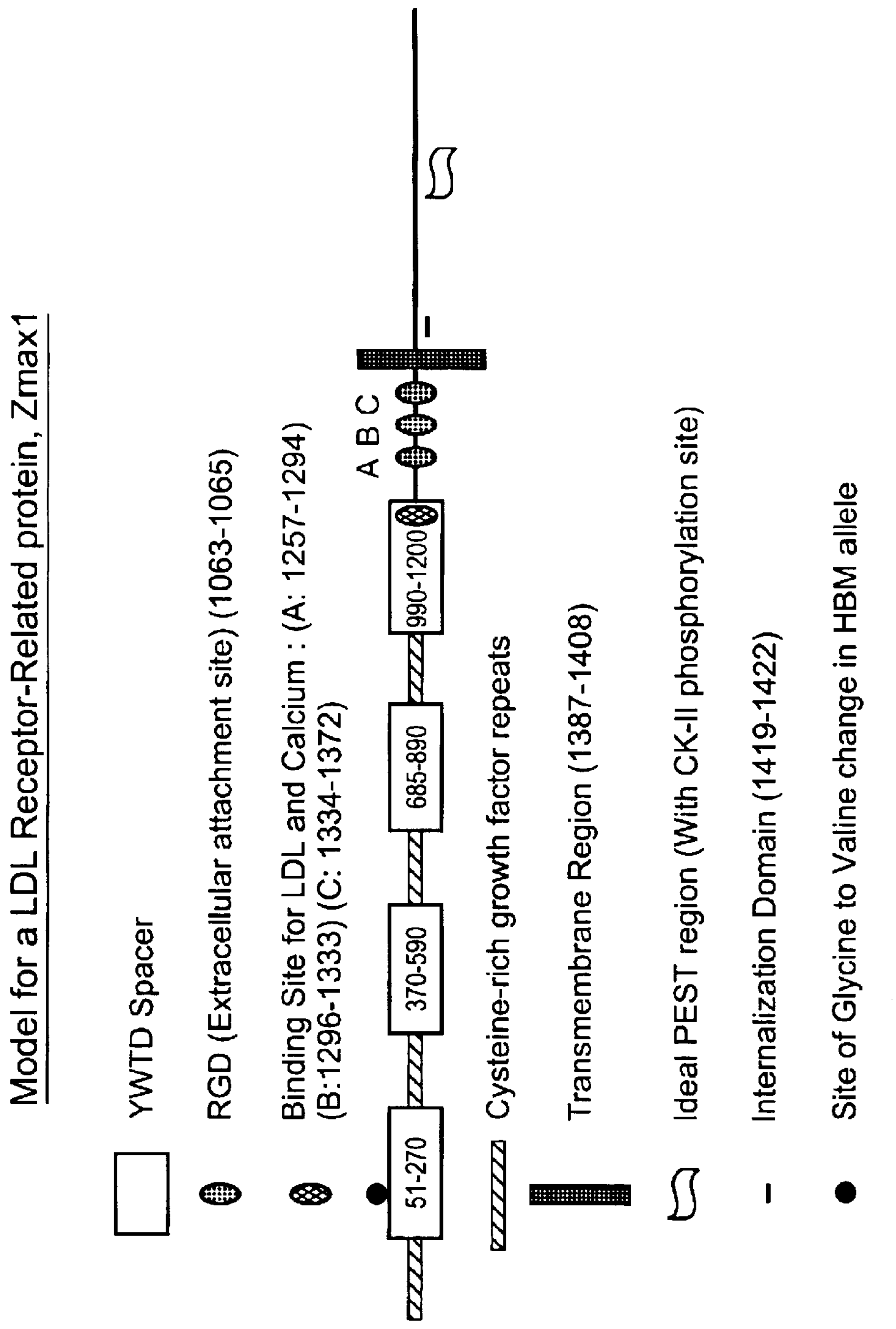
FIG. 4 shows the domain organization of Zmax1, including the YWTD spacers, the extracellular attachment site, the binding site for LDL and calcium, the cysteine-rich growth factor repeats, the transmembrane region, the ideal PEST region with the CK-II phosphorylation site and the internalization domain.

To narrow the genetic interval to a region smaller than that originally reported by Johnson et al, *Am. J. Hum. Genet.*, 60:1326–1332 (1997), additional microsatellite markers on chromosome 11q12-13 were typed. The new markers included: D11S4191, D11S1883, D11S1785, D11S4113, D11S4136, D11S4139, (Dib, et al, *Nature*, 380:152–154 (1996), FGF3 (Polymeropolous, et al, *Nucl. Acid Res.*, 18:7468 (1990)), as well as GTC_HBM_Marker_1, GTC_HBM_Marker_2, GTC_HBM_Marker_3, GTC_HBM_Marker_4, GTC_HBM_Marker_5, GTC_HBM_Marker_6, and GTC_HBM_Marker_7 (See FIG. 2).

Blood (20 ml) was drawn into lavender cap (EDTA containing) tubes by a certified phlebotomist. The blood was stored refrigerated until DNA extraction. DNA has been extracted from blood stored for up to 7 days in the refrigerator without reduction in the quality or quantity of yield. For those subjects that have blood drawn at distant sites, a shipping protocol was successfully used on more than a dozen occasions. Blood samples were shipped by overnight express in a styrofoam container with freezer packs to provide cooling. Lavender cap tubes were placed on individual plastic shipping tubes and then into "zip-lock" biohazard bags. When the samples arrived the next day, they were immediately processed to extract DNA.

The DNA extraction procedure used a kit purchased from Gentra Systems, Inc. (Minneapolis, Minn.). Briefly, the procedure involved adding 3 volumes of a red blood cell lysis buffer to the whole blood. After incubations for 10 minutes at room temperature, the solution was centrifuged in a Beclman tabletop centrifuge at 2,000×g for 10 minutes. The white blood cell pellet was resuspended in Cell Lysis Buffer. Once the pellet was completely resuspended and free of cell clumps, the solution was digested with RNase A for 15 minutes at 37° C. Proteins were precipitated by addition of the provided Protein Precipitation Solution and removed by centrifugation. The DNA was precipitated out of the supernatant by addition of isopropanol. This method was simple and fast, requiring only 1–2 hours, and allowed for the processing of dozens of samples simultaneously. The yield of DNA was routinely >8 mg for a 20 ml sample of whole blood and had a MW of >50 kb. DNA was archived by storing coded 50 $\mu$g aliquots at −80° C. as an ethanol precipitate.

DNA was genotyped using one fluorescently labeled oligonucleotide primer and one unlabeled oligonucleotide primer. Labeled and unlabeled oligonucleotides were obtained from Integrated DNA Technologies, Inc. (Coralville, Iowa). All other reagents for microsatellite genotyping were purchased from Perkin Elmer-Applied Biosystems, Inc. ("PE-ABI") (Norwalk, Conn.). Individual PCR reactions were performed for each marker, as described by PE-ABI using AmpliTag DNA Polymerase. The reactions were added to 3.5 $\mu$l of loading buffer containing deionized formamide, blue dextran and TAMRA 350 size standards (PE-ABI). After heating at 95° C. for 5 minutes to denature the DNA, the samples were loaded and electrophoresed as described in the operator's manual for the Model 377 DNA Sequencer (PE-ABI, Foster City, Calif.). After gel electrophoresis, the data was analyzed using PE-ABI GENESCAN™ and GENOTYPER™ software. First, within the GENESCAN™ software, the lane tracking was manually optimized prior to the first step of analysis. After the gel lane data was extracted, the standard curve profiles of each lane were examined and verified for linearity and size calling. Lanes, which had problems with either of these parameters, were re-tracked and verified. Once all lanes were tracked and the size standards were correctly identified, the data were imported into GENOTYPER™ for allele identification. To expedite allele calling (binning), the program Linkage Designer from the Internet web-site of Dr. Guy Van Camp (http://alt.www.uia.ac.be/u/dnalab/ld.html) was used. This program greatly facilitates the importing of data generated by GENOTYPER™ into the pedigree drawing program Cyrillic (Version 2.0, Cherwell Scientific Publishing Limited, Oxford, Great Britain) and subsequent linkage analysis using the program LINKAGE (Lathrop et al, *Am. J. Hum. Genet.*, 37:482–498 (1985)).

III. Linkage Analysis

FIG. 1 demonstrates the pedigree of the individuals used in the genetic linkage studies for this invention. Specifically, two-point linkage analysis was performed using the MLINK and LINKMAP components of the program LINKAGE (Lathrop et al, *Am. J. Hum. Genet.*, 37:482–498 (1985)). Pedigree/marker data was exported from Cyrillic as a pre-file into the Makeped program and converted into a suitable ped-file for linkage analysis.

The original linkage analysis was performed using three models: (i) an autosomal dominant, fully penetrant model, (ii) an autosomal dominant model with reduced penetrance, and (iii) a quantitative trait model. The HBM locus was mapped to chromosome 11q12-13 by analyzing DNA for linked markers from 22 members of a large, extended kindred. A highly automated technology was used with a panel of 345 fluorescent markers which spanned the 22 autosomes at a spacing interval ranging from 6–22 cM. Only markers from this region of chromosome 11 showed evidence of linkage (LOD score ~3.0). The highest LOD score (5.74) obtained by two-point and multipoint analysis was D11S987 (map position 55 in FIG. 2). The 95% confidence interval placed the HBM locus between markers D11S905 and D11S937 (map position 41–71 in FIG. 2). Haplotype analysis also places the Zmax1 gene in this same region. Further descriptions of the markers D11S987, D11S905, and D11S937 can be found in Gyapay et al, *Nature Genetics*, Vol. 7, (1994).

In this invention, the inventors report the narrowing of the HBM interval to the region between markers D11S987 and GTC_HBM_Marker_5. These two markers lie between the delimiting markers from the original analysis (D11S905 and D11S937) and are approximately 3 cM from one another. The narrowing of the interval was accomplished using genotypic data from the markers D11S4191, D11S1883, D11S1785, D11S4113, D11S4136, D11S4139, (Dib et al, *Nature*, 380:152–154 (1996)), FGF3 (Polymeropolous et al, *Nucl. Acid Res*., 18:7468 (1990)) (information about the genetic markers can be found at the internet site of the Genome Database, http://gdbwww.gdb.org/), as well as the markers GTC_HBM_Marker_1, GTC_HBM_Marker_2, GTC_HBM_Marker_3, GTC_HBM_Marker_4, GTC_HBM_Marker_5, GTC_HBM_Marker_6, and GTC_HBM_Marker_7.

As shown in FIG. 1, haplotype analysis with the above genetic markers identifies recombination events (crossovers) in individuals 9019 and 9020 that significantly refine the interval of chromosome 11 to which the Zmax1 gene is localized. Individual 9019 is an HBM-affected individual that inherits a portion of chromosome 11 from the maternal chromosome with the HBM gene, and a portion from the chromosome 11 homologue. The portion inherited from the HBM gene-carrying chromosome includes markers D11S935, D11S1313, GTC_HBM_Marker_4, D11S987, D11S1296, GTC_HBM_Marker_6, GTC_HBM_Marker_2, D11S970, GTC_HBM_Marker_3, D11S4113, GTC_HBM_Marker_1, GTC_HBM_Marker_7 and GTC_HBM_Marker_5. The portion from D11S4136 and continuing in the telomeric direction is derived from the non-HBM chromosome. This data places the Zmax1 gene in a location centromeric to the marker GTC_HBM_Marker_5. Individual 9020 is an unaffected individual who also exhibits a critical recombination event. This individual inherits a recombinant paternal chromosome 11 that includes markers D11S935, D11S1313, GTC_HBM_Marker_4, D11S987, D11S1296 and GTC_HBM_Marker_6 from her father's (individual 0115) chromosome 11 homologue that carries the HBM gene, and markers GTC_HBM_Marker_2, D11S970, GTC_HBM_Marker_3, GTC_HBM_Marker_1, GTC_HBM_Marker_7, GTC_HBM_Marker_5, D11S4136, D11S4139, D11S1314, and D11S937 from her father's chromosome 11 that does not carry the HBM gene. Marker D11S4113 is uninformative due to its homozygous nature in individual 0115. This recombination event places the centromeric boundary of the HBM region between markers D11S1296 and D11S987.

Two-point linkage analysis was also used to confirm the location of the Zmax1 gene on chromosome 11. The linkage results for two point linkage analysis under a model of full penetrance are presented in Table 1 below. This table lists the genetic markers in the first column and the recombination fractions across the top of the table. Each cell of the column shows the LOD score for an individual marker tested for linkage to the Zmax1 gene at the recombination fraction shown in the first row. For example, the peak LOD score of 7.66 occurs at marker D11S970, which is within the interval defined by haplotype analysis.

TABLE 1

| Marker | 0.0 | 0.05 | 0.1 | 0.15 | 0.2 | 0.25 | 0.3 | 0.35 | 0.4 |
|---|---|---|---|---|---|---|---|---|---|
| D11S935 | −infinity | 0.39 | 0.49 | 0.47 | 0.41 | 0.33 | 0.25 | 0.17 | 0.10 |
| D11S1313 | −infinity | 2.64 | 2.86 | 2.80 | 2.59 | 2.30 | 1.93 | 1.49 | 1.00 |
| D11S987 | −infinity | 5.49 | 5.18 | 4.70 | 4.13 | 3.49 | 2.79 | 2.03 | 1.26 |
| D11S4113 | 4.35 | 3.99 | 3.62 | 3.24 | 2.83 | 2.40 | 1.94 | 1.46 | 0.97 |
| D11S1337 | 2.29 | 2.06 | 1.81 | 1.55 | 1.27 | 0.99 | 0.70 | 0.42 | 0.18 |
| D11S970 | 7.66 | 6.99 | 6.29 | 5.56 | 4.79 | 3.99 | 3.15 | 2.30 | 1.44 |
| D11S4136 | 6.34 | 5.79 | 5.22 | 4.61 | 3.98 | 3.30 | 2.59 | 1.85 | 1.11 |
| D11S4139 | 6.80 | 6.28 | 5.73 | 5.13 | 4.50 | 3.84 | 3.13 | 2.38 | 1.59 |
| FGF3 | 0.59 | 3.23 | 3.15 | 2.91 | 2.61 | 2.25 | 1.84 | 1.40 | 0.92 |
| D11S1314 | 6.96 | 6.49 | 5.94 | 5.34 | 4.69 | 4.01 | 3.27 | 2.49 | 1.67 |
| D11S937 | −infinity | 4.98 | 4.86 | 4.52 | 4.06 | 3.51 | 2.88 | 2.20 | 1.47 |

A single nucleotide polymorphism (SNP) further defines the HBM region. This SNP is termed SNP_Contig033-6 and is located 25 kb centromeric to the genetic marker GTC_HBM_Marker_5. This SNP is telomeric to the genetic marker GTC_HBM_Marker_7. SNP_Contig033-6 is present in HBM-affected individual 0113. However, the HBM-affected individual 9019, who is the son of 0113, does not carry this SNP. Therefore, this indicates that the crossover is centromeric to this SNP. The primer sequence for the genetic markers GTC_HBM_Marker_5 and GTC_HBM_Marker_7 is shown in Table 2 below.

TABLE 2

| Marker | Primer (Forward) | Primer (Reverse) |
| --- | --- | --- |
| GTC_HBM_Marker_5 | TTTTGGGTACACAATTCAGTCG (SEQ. ID. NO.: 63) | AAAACTGTGGGTGCTTCTGG (SEQ. ID. NO.: 64) |
| GTC_HBM_Marker_7 | GTGATTGAGCCAATCCTGAGA (SEQ. ID. NO.: 65) | TGAGCCAAATAAACCCCTTCT (SEQ. ID. NO.: 66) |

The kindred described have several features of great interest, the most important being that their bones, while very dense, have an absolutely normal shape. The outer dimensions of the skeletons of the HBM-affected individuals are normal, and, while medullary cavities are present, there is no interference with hematopoiesis. The HBM-affected members seem to be resistant to fracture, and there are no neurologic symptoms, and no symptoms of impairment of any organ or system function in the members examined. HBM-affected members of the kindred live to advanced age without undue illness or disability. Furthermore, the HBM phenotype matches no other bone disorders such as osteoporosis, osteoporosis pseudoglioma, Engelmann's disease, Ribbing's disease, hyperphosphatasemia, Van Buchem's disease, melorheostosis, osteopetrosis, pycnodysostosis, sclerostenosis, osteopoikilosis, acromegaly, Paget's disease, fibrous dysplasia, tubular stenosis, osteogenesis imperfecta, hypoparathyroidism, pseudohypoparathyroidism, pseudopseudohypoparathyroidism, primary and secondary hyperparathyroidism and associated syndromes, hypercalciuria, medullary carcinoma of the thyroid gland, osteomalacia and other diseases. Clearly, the HBM locus in this family has a very powerful and substantial role in regulating bone density, and its identification is an important step in understanding the pathway(s) that regulate bone density and the pathogenesis of diseases such as osteoporosis.

In addition, older individuals carrying the HBM gene, and therefore expression of the HBM protein, do not show loss of bone mass characteristic of normal individuals. In other words, the HBM gene is a suppressor of osteoporosis. In essence, individuals carrying the HBM gene are dosed with the HBM protein, and, as a result, do not develop osteoporosis. This in vivo observation is strong evidence that treatment of normal individuals with the HBM gene or protein, or a fragment thereof, will ameliorate osteoporosis.

IV. Physical Mapping

To provide reagents for the cloning and characterization of the HBM locus, the genetic mapping data described above were used to construct a physical map of the region containing Zmax1 on chromosome 11q13.3. The physical map consists of an ordered set of molecular landmarks, and a set of BAC clones that contain the Zmax1 gene region from chromosome 11q13.3.

Various publicly available mapping resources were utilized to identify existing STS markers (Olson et al, *Science*, 245:1434–1435 (1989)) in the HBM region. Resources included the GDB, the Whitehead Institute Genome Center, dbSTS and dbEST (NCBI), 11db, the University of Texas Southwestern GESTEC, the Stanford Human Genome Center, and several literature references (Courseaux et al, *Genomics*, 40:13–23 (1997), Courseaux et al, *Genomics*, 37:354–365 (1996), Guru et al, *Genomics*, 42:436–445 (1997), Hosoda et al, *Genes Cells*, 2:345–357 (1997), James et al, *Nat. Genet.*, 8:70–76 (1994), Kitamura et al, *DNA Research*, 4:281–289 (1997), Lemmens et al, *Genomics*, 44:94–100 (1997), Smith et al, *Genome Res.*, 7:835–842 (1997)). Maps were integrated manually to identify markers mapping to the region containing Zmax1.

Primers for existing STSs were obtained from the GDB or literature references are listed in Table 3 below. Thus, Table 3 shows the STS markers used to prepare the physical map of the Zmax1 gene region.

TABLE 3

HBM STS Table

| STS Name | Locus Name | Type | GDB Access. # | Size (kb) | Forward Primer | Reverse Primer | Gene Name |
|---|---|---|---|---|---|---|---|
| ACTN3 | | Gene | GDB:197568 | 0.164 | CTGGACTACGTGGCCTTCTC (SEQ. ID NO.: 67) | TTCGAAGCACTTGGCTGG (SEQ. ID NO.: 68) | Actinin, alpha 3 - skeletal muscle |
| PC-B/YC-Y | | Gene | GDB:197884 | 0.125 | CTCAGTGCCATGAAGATGGA (SEQ. ID NO.: 69) | CAAGATCACTCGATCTCCAGG (SEQ. ID NO.: 70) | Pyruvate Carboxylase |
| | D11S2161E | Gene | | 0.322 | GTTTCAGGAGACTCAGAGTC (SEQ. ID NO.: 71) | TTCTGCAGGTTGCTGTTGAG (SEQ. ID NO.: 72) | AdENOSINE Receptor (A2) Gene |
| ADRBK1 | | Gene | GDB:4590179 | 0.117 | TTATTGTGATTTCCCGTGGC (SEQ. ID NO.: 73) | GCCCTCTGTCCTGACTTCAGG (SEQ. ID NO.: 74) | Beta-adrenergic receptor kinase |
| PSANK3 | | GENE | | 0.259 | GAGAAAGAAATAAGGGGACC (SEQ. ID NO.: 75) | TGCTTTGTAAAGCACTGAGA (SEQ. ID NO.: 76) | sim. to Human endogenous retrovirus mRNA long terminal repeat |
| PP1 (1/2)/PP1 (2/2) | | Gene | GDB:197566 | 0.208 | GAAGTACGGGCAGTTCAGTGGCCT (SEQ. ID NO.: 77) | ATACACCAAGGTCCATGTTCCCCGT (SEQ. ID NO.: 78) | Protein phosphatase 1, catalytic subunit, alpha isoform |
| GSTP1.PCR1 | | Gene | GDB:270066 | 0.19 | AGCCTGGGCCACAGCGTGAGACTACGT (SEQ. ID NO.: 79) | TCCCGGAGCTTGCACACCCGCTTCACA (SEQ. ID NO.: 80) | Glutathione S-transferase pi |
| NDUPV1 | | Gene | | 0.521 | CATGTGCCCACCTCATTCAT (SEQ. ID NO.: 81) | CAAGATTCTGTAGCTTCTGG (SEQ. ID NO.: 82) | NADM dehydrogenase (ubiquinone) flavoprotein 1 (51 kD) |
| PSANK2 | | GENE | | 0.157 | CAGAGAAGTCAAGGGACTTG (SEQ. ID NO.: 83) | ATCCTCTCACATCCCACACT (SEQ. ID NO.: 84) | Aldehyde Dehydrogenase 8 (ALDH8) |
| PSANK1 | | EST | | 0.3 | CAAGGCTAAAAGACGAAAAA (SEQ. ID NO.: 85) | TCAGGAGCATTTCATCTTTT (SEQ. ID NO.: 86) | Human ribosomal protein L37 (PSANK1) pseudogene. |
| UT5620 | D11S1917 | MSAT | GDB:314521 | 0.211 | AAGTCGAGGCTGCAAGGAG (SEQ. ID NO.: 87) | GCCCTGTGTTCCTTTCAGTA (SEQ. ID NO.: 88) | |
| APM289ya9 | D11S1337 | MSAT | GDB:199805 | 0.287 | AAGGTGTGAGGATCACTGG (SEQ. ID NO.: 89) | AGCTCATGGGGGCTATT (SEQ. ID NO.: 90) | |
| GALN | | Gene | | 0.322 | GCTTCTCCGAGTGTATCAAC (SEQ. ID NO.: 91) | ATGGCAGAGGACTTAGAACA (SEQ. ID NO.: 92) | Preprogalanin (GAL1) |
| pM951 | D11S97 | VNTR | GDB:177850 | | GATCAGCGAACTTCCTCTCGGCTC (SEQ. ID NO.: 93) | TCCACATTGAGGACTGTGGGAACG (SEQ. ID NO.: 94) | |
| BCL1 (1)/BCL1 (2) | | Gene | | 0.205 | GCTAATCACAGTCTAACCGA (SEQ. ID NO.: 95) | TTGCACTGTCTTGGATGCA (SEQ. ID NO.: 96) | B-cell CLL/lymphom 1 - Cyclin D1 (PRAD1 gene) |
| CCND1 | | Gene | GDB:4590141 | 0.248 | GCACAGCTGTAGTGGGGTTCTAGGC (SEQ. ID NO.: 97) | CAGGCGCAAAGGACATGCACACGGC (SE0. ID NO.: 98) | Cyclin D1 |
| PGF4 | | Gene | GDB:4590113 | 0.549 | CACCGATGAGTGCACGTTCAAGGAG (SEQ. ID NO.: 99) | CAGACAGAGATGCTCCACGCCATA (SEQ. ID NO.: 100) | Fibroblast growth factor 4 |
| PGP3.PCR | | Gene | GDB:188627 | 0.161 | TTTCTGGGTGTGTCTGAAT (SEQ. ID NO.: 101) | ACACAGTTGCTCTAAAGGGT (SEQ. ID NO.: 102) | Fibroblast growth factor 3 |
| AFM164ZF12 | D11S913 | MSAT | GDB:188151 | 0.22 | CATTTGGGAAATCCAGAAGA (SEQ. ID NO.: 103) | TAGGTGTCTTATTTTTTGTTGCTTC (SEQ. ID NO.: 104) | |
| AFMA190YD5 | | MSAT | GDB:1222329 | 0.275 | GACATACCATGAACACTATAAGAGG (SEQ. ID NO.: 105) | CAACCCATACCAGGGATAAG (SEQ. ID NO.: 106) | |
| SHGC-15295 | D11S4689 | STS | GDB:740600 | 0.147 | GAACAAGAGGGGTAAGTTGGC (SEQ. ID NO.: 107) | TGAGGACACAGATACTGATGGG (SEQ. ID NO.: 108) | |
| SHGC-3084 | D11S4540 | STS | GDB:740102 | 0.167 | GAAGTGTTCCCTCTTAAATTCTTTG (SEQ. ID NO.: 109) | GAACTATATTGTAGTTAGTGAGGAG (SEQ. ID NO.: 110) | |
| SHGC-14407 | D11S4664 | STS | GDB:740516 | 0.158 | CCTGTAACCCCCAGTCCC (SEQ. ID NO.: 111) | TCTTGCTTCCTAAGTTTCTCGG (SEQ. ID NO.: 112) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SHGC-10946 | D11S4327 | Gene | GDB:674522 | 0.311 | ACTCCATCCACCTCATCACTG (SEQ. ID NO.: 113) | TGCTGTTTGCCTCATCTGAC (SEQ. ID NO.: 114) | Choline Kinase |
| S515 | D11S703 | STS | GDB:196290 | 0.166 | GTGGACAGGCATAGCTGAGG (SEQ. ID NO.: 115) | TGTTCACTCTTCTGCCTGCAG (SEQ. ID NO.: 116) | |
| AFM147XD10 | D11S1889 | MSAT | GDB:307895 | 0.183 | AGCTGGACTCTCACAGAATG (SEQ. ID NO.: 117) | CAAGAGGCTGGTAGAAGGTG (SEQ. ID NO.: 118) | |
| AFMA131YES | D11S987 | MSAT | GDB:195002 | 0.082 | GACTCCAGTCTGGGCAATAAAAGC (SEQ. ID NO.: 119) | GGTGGCAGCATGACCTCTAAAG (SEQ. ID NO.: 120) | |
| AFMb358xa9 | D11S4178 | MSAT | GDB:611922 | 0.237 | CAGGCCCAGTCTCTTG (SEQ. ID NO.: 121) | CGTGTCCAGATGAAAGTG (SEQ. ID NO.: 122) | |
| AFMa272yb5 | D11S4113 | MSAT | GDB:608115 | 0.218 | ACCTCACGGTGTAATCCC (SEQ. ID NO.: 123) | CTTGAAGCCCATCTTTGC (SEQ. ID NO.: 124) | |
| WI-17803 | | EST | GDB:4581644 | 0.15 | TATTTGCAAAGCTTGAGACTTCT (SEQ. ID NO.: 125) | AATCACTGTGCTTTGTTGCC (SEQ. ID NO.: 126) | |
| SGC31923 | | EST | GDB:4578606 | 0.126 | ACTTTATTGTCAGCGTGGGC (SEQ. ID NO.: 127) | ACTCCCTCGATGGCTTCC (SEQ. ID NO.: 128) | |
| WI-7741 | D11S4364 | GENE | GDB:677652 | 0.324 | GAGCAGGGGAGAGAAGGC (SEQ. ID NO.: 129) | CCCAACTGGCTTGTTTTATTG (SEQ. ID NO.: 130) | Transformation-sensitive protein IEF SSP 3521 |
| SGC35223 | | EST | GDB:4582598 | 0.13 | AGCCACTTTATTGTTATTTTGATGC (SEQ. ID NO.: 131) | AAGAGTGAACAAAAGCAAACATACC (SEQ. ID NO.: 132) | ZNF162 - splicing factor 1 |
| WI-16754 | | EST | GDB:4578377 | 0.15 | GTGGAGTGTGGGATTGGG (SEQ. ID NO.: 133) | TACTGTTCTTGATAAGTATGTCGGC (SEQ. ID NO.: 134) | |
| WI-6315 | D11S4418 | EST | GDB:678804 | 0.224 | ATGCTTTTGCATGATTCTAATTATT (SEQ. ID NO.: 135) | TCCCCAAAAGAATGTAAAGG (SEQ. ID NO.: 136) | |
| WI-16915 | | EST | GDB:4584055 | 0.125 | CTGGTCTTCCTTGTGTGCTG (SEQ. ID NO.: 137) | ATCACCCAGGCCAGGGAT (SEQ. ID NO.: 138) | Mitogen inducible gens (MIG-2) |
| SGC30608 | | EST | | 0.128 | TCAGAAGCAGAACTGTTTTTAACA (SEQ. ID NO.: 139) | CCTGCTTGAAAGTTCTAGAGCC (SEQ. ID NO.: 140) | |
| WI-17663 | | EST | GDB:4583346 | 0.126 | CAAGCCGGGTTTTATTGAAA (SEQ. ID NO.: 141) | GATGCCAGGACCATGGAC (SEQ. ID NO.: 142) | |
| WI-6383 | | Gene | GDB:1222237 | 0.199 | GCATATAGAAACAATTTATTGCCG (SEQ. ID NO.: 143) | CTCTGAAGCAGGGACCAGAG (SEQ. ID NO.: 144) | Human tat interactive protein (TIP60) |
| SGC31567 | | Gene | GDB:4578432 | 0.207 | CTACCACACCACACCAGGC (SEQ. ID NO.: 145) | CAAGCGAAAGCTGCCTTC (SEQ. ID NO.: 146) | Calcium activated neutral protease large subunit, muCANP, calpain |
| SGC30658 | | EST | GDB:4584037 | 0.15 | GTTGTCTTGACTTCAGGTCTGTC (SEQ. ID NO.: 147) | TTTTCCTTCAACAATCACTACTCC (SEQ. ID NO.: 148) | |
| SGC34590 | | EST | | 0.13 | GCGTGGGGATATAGAGGTCA (SEQ. ID NO.: 149) | TACGTGGCCAAGAAGCTAG (SEQ. ID NO.: 150) | |
| SGC33927 | | EST | GDB:4582382 | 0.15 | TAATATATACCCCAGTCTAAGGCAT (SEQ. ID NO.: 151) | AGCTTGCAGATGGAGCCC (SEQ. ID NO.: 152) | |
| WI-8671 | | EST | GDB:1222235 | 0.124 | TGGTTTTAAACCTTTAATGAGAAAA (SEQ. ID NO.: 153) | TGTTGATCTATACCCTGTTTCCG (SEQ. ID NO.: 154) | |
| WI-12334 | | EST | GDB:1222257 | 0.127 | AATTATTTAAAAGAGAGGAAAGGCA (SEQ. ID NO.: 155) | TGGCTGTGAACTTCCTCTGA (SEQ. ID NO.: 156) | |
| WI-18402 | | EST | GDB:4581874 | 0.113 | GGTTACAGAAAAACATTTGAGAGAT (SEQ. ID NO.: 157) | TGAGCTTTAGTTCCCTTCTCTG (SEQ. ID NO.: 158) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| WI-18671 | | EST | GDB:4584947 | 0.131 | TTGAAAAACCATTTATTTCACCG (SEQ. ID NO.: 159) | TCTGCGGCTGTTGGATTT (SEQ. ID NO.: 160) | Hlark |
| WI-12856 | | EST | GDB:4576606 | 0.209 | TTGAAAAACCATTTATTTCACCG (SEQ. ID NO.: 161) | TGTTCTCTTCTCCCAGCAGG (SEQ. ID NO.: 162) | Hlark |
| SGC33767 | | EST | GDB:4581106 | 0.15 | CTTTATTGAAAACATTGAGTGCA (SEQ. ID NO.: 163) | TTGTCAAATTCCCCCCAAAA (SEQ. ID NO.: 164) | |
| AFM343YB5 | | MSAT | GDB:1222332 | 0.181 | AAACCACGACCNCCAA (SEQ. ID NO.: 165) | CCCTGGAAAGGTAAGATGCT (SEQ. ID NO.: 166) | |
| SCG33744 | | EST | GDB:4575826 | 0.15 | CTTTTGGTAGAGACAAGGTCTCA (SEQ. ID NO.: 167) | TATCTGTCTGTAGTGCTTCAAATGT (SEQ. ID NO.: 168) | |
| SGC32272 | | EST | GDS:4581592 | 0.135 | GACGAAGGTGATTCAGGGC (SEQ. ID NO.: 169) | ACTGAAGAACTCTTGTCCT (SEQ. ID NO.: 170) | |
| SGC34148 | | EST | GDB:4583084 | 0.1 | CAGATAAAAGAGTCACTATGGCTCA (SEQ. ID NO.: 171) | CACTTCTCCCACTTTGTCCC (SEQ. ID NO.: 172) | |
| WI-18546 | | EST | GDB:4574598 | 0.133 | TTATTGATAAGCATTAGTCAACCCC (SEQ. ID NO.: 173) | TGGCAAGTTAGGCACAGTCA (SEQ. ID NO.: 174) | Human 1.1 kb mRNA upregulated in retinoic acid treated HL-60 neutrophilic cells |
| SGC31103 | | EST | GDB:4567265 | 0.1 | CTATGCCCAGAGATGAACAGG (SEQ. ID NO.: 175) | TCCACTAAGGGCTATGTCGC (SEQ. ID NO.: 176) | |
| SGC30028 | | Gene | GDB:4580505 | 0.128 | GCCAGCTTTATTGAGTAAACTTCC (SEQ. ID NO.: 177) | CACTGGAGACTACAAGTGGTGG (SEQ. ID NO.: 178) | Human pyruvate carboxylase precuror |
| WI-2875 | D11S4407 | STS | GDB:678546 | 0.125 | CATCCCAACCATCACTCAGT (SEQ. ID NO.: 179) | GGGGACTAGCTTACAGATTTGA (SEQ. ID NO.: 180) | |
| SGC36985 | | Gene | GDB:4577182 | 0.223 | AGACTACATTTTGGAACCAGTGG (SEQ. ID NO.: 181) | TGAAAGGATATTTATAGCCTGGA (SEQ. ID NO.: 182) | LAR-interacting protein lb |
| GCT16B07 | D11S4270 | STS | GDB:626245 | 0.137 | GAAGGTTTTGTCCCTCGATC (SEQ. ID NO.: 183) | TGAGGGTTGGGAAGATCATA (SEQ. ID NO.: 184) | |
| WI-6504 | D11S3974 | EST | GDB:588142 | 0.174 | CCTTCATAGCCACACCCG (SEQ. ID NO.: 185) | CAGCTAACTGTTGACATGCCA (SEQ. ID NO.: 186) | |
| SGC31049 | | EST | GDB:4580093 | 0.15 | TCTTTACTGTGCTTACAACTTTCCT (SEQ. ID NO.: 187) | CAACAGTGCAGTCGGTATCG (SEQ. ID NO.: 188) | |
| TIGR-A002J17 | | EST | GDB:1222193 | 0.199 | AGATCAGCAAGCAGATAG (SEQ. ID NO.: 189) | CATTCCACATGGATAGAC (SEQ. ID NO.: 190) | NDUFV1 |
| WI-5996 | D11S2382 | EST | GDB:458683 | 0.1 | CATACCTATGAGGTGTGCTACAGG (SEQ. ID NO.: 191) | GCATTTTCTCATCATCCTTGC (SEQ. ID NO.: 192) | amplaxin (EMS1) |
| WI-16987 | | EST | GDB:4575848 | 0.15 | TTACAGCCACCAAGGTTTCC (SEQ. ID NO.: 193) | AGGTGTGTGTGCCAGGTTGA (SEQ. ID NO.: 194) | Nuclear mitotic apparatus protein 1, NUMA |
| SGC31912 | | EST | GDB:4567868 | 0.101 | CACTGTTATCTCATTAACTGTGAGG (SEQ. ID NO.: 195) | TTTGATTTTGTGTCTCCCAAA (SEQ. ID NO.: 196) | |
| WI-13500 | | EST | GDB:4577893 | 0.15 | CCCCACTCCCACTTTTATTT (SEQ. ID NO.: 197) | CCAGTCACCTTTACTAGTCCTTTG (SEQ. ID NO.: 198) | |
| CHLC.GAAT1B01.P7933 | D11S971 | MSAT | GDB:684255 | 0.103 | AGGACACAGCCTGCATCTAG (SEQ. ID NO.: 199) | ACCAGGCATTGCACTAAAAG (SEQ. ID NO.: 200) | |
| SGC35519 | | Gene | GBD:4577180 | 0.134 | GATGGGTCACACTAACCTGTCA (SEQ. ID NO.: 201) | ACATTTATATTTGGACATGCAACC (SEQ. ID NO.: 202) | LAR-interacting protein in mRNA |
| WI-11974 | | EST | GDB:1222255 | 0.108 | AGCATCTTTAATGTGTCAGGCA (SEQ. ID NO.: 203) | ATGTGCTGGGCTGGAAAG (SEQ. ID NO.: 204) | Carnitine palmitoyl transferase I |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| WI-15244 | | Gene | GDB:4574740 | 0.108 | TCACATTCAAAAATCGGCAA (SEQ. ID NO.: 205) | CTGCCTGTGTGGTGTCGC (SEQ. ID NO.: 206) | Beta-adrenergic receptor kinase 1, ADRB1 |
| WI-17496 | | EST | GDB:4583336 | 0.131 | TGTTTTATTTCTCAGTACAAAGCCA (SEQ. ID NO.: 207) | GACCTCCTGTGACACCACG (SEQ. ID NO.: 208) | |
| WI-9159 | D11S4381 | EST | GDB:678144 | 0.111 | CCACCAAATTATTTATAGTTCTGCG (SEQ. ID NO.: 209) | GTAAGATTCTCCACTGTTGCACC (SEQ. ID NO.: 210) | FGP4 |
| WI-4232 | | STS | GDB:1222250 | 0.175 | CCTATAATGGGCTGGACCAA (SEQ. ID NO.: 211) | ACTCCTCATGTGAAGTCACCG (SEQ. ID NO.: 212) | |
| SHGC-4167 | | EST | GDb:4566789 | 0.161 | CAGTGTGCACGTTTTCATTT (SEQ. ID NO.: 213) | CAGCATCTTCAGCACTTACC (SEQ. ID NO.: 214) | Human DNA helicase gen (SMBP2) |
| WI-14303 | | EST | GDB:4576938 | 0.15 | CTGCATTTATTATGAGAATCAACAG (SEQ. ID NO.: 215) | TGCTGCTGGGAGTCAGAGTC (SEQ. ID NO.: 216) | |
| WI-16597 | | EST | GDB:4585666 | 0.13 | CAGGGCACTGAGATACACTTACC (SEQ. ID NO.: 217) | AAGGATCAAGCAGGCATTTG (SEQ. ID NO.: 218) | |
| RC29S1CATTFOR/ RC29S1CATTREV | D11S970 | MSAT | GDB:191084 | 0.15 | ACACATCTCTTCTGTGCCCC (SEQ. ID NO.: 219) | TGAACCCTGGAGGCAGAG (SEQ. ID NO.: 220) | |
| UT979 | D11S1296 | MSAT | GDB:198525 | 0.362 | CATTCCCCAGTTTGCAGAC (SEQ. ID NO.: 221) | GTGCTGGGATTACAGGTGT (SEQ. ID NO.: 222) | |
| 1281/1282 | D11S1959E | EST | GDB:335216 | 0.07 | GCAGAGAAGTCCTGTTAGCC (SEQ. ID NO.: 223) | CCATGCTAGAGAAGCACAAC (SEQ. ID NO.: 224) | |
| D11S468 | D11S468 | STS | | 0.096 | AGTGTCCCCCAGGACCTCTG (SEQ. ID NO.: 225) | CAGACAGATAGCCCTGGGTCC (SEQ. ID NO.: 226) | |
| D11S668 | D11S668 | STS | GDB:179349 | 0.143 | TCCCTCATCCCCTTGTCTGT (SEQ. ID NO.: 227) | AGCCCCCCTGGGGATAATC (SEQ. ID NO.: 228) | |
| RM18048 | | Gene | GDB:4572853 | 0.188 | GATGCTTACCTACCACGGC (SEQ. ID NO.: 229) | AGGATTCCTATCTGGGCTATG (SEQ. ID NO.: 230) | Aldehyde dehydrogenase (ALDHS) |
| IGHMBP2 | | Gene | GDB:4590087 | 0.699 | TGGCAGACCATGCTCCGCCT (SEQ. ID NO.: 231) | GAGAAGGCCGGGAGGCTCTG (SEQ. ID NO.: 232) | Human DNA helicase gen (SMBP2) |
| NUMA | | Gene | GDB:4590244 | 0.277 | CTCCATCACAACCAGATTTGAGGCT (SEQ. ID NO.: 233) | GGGTGTGAGCTGCTGCTGAAGG (SEQ. ID NO.: 234) | Nuclear mitotic apparatus protein 1, NUMA |
| KRN1 | | Gene | GDB:4590232 | 0.228 | AGTGGGAAACCTCAGGTAGCTCCCGA (SEQ. ID NO.: 235) | CAGTTTGGCTCAGACATATGGGGGCA (SEQ. ID NO.: 236) | High sulphur keratin, KRN |
| Cda1ff06 | D11S2302E | EST | GDB:445587 | 0.091 | CATTAAGTAGTGGGGGGACAG (SEQ. ID NO.: 237) | CAAAGCGACAGTGAGTTAGGG (SEQ. ID NO.: 238) | |
| RH10753 | | Gene | GDB:4563588 | 0.194 | GGAGTAGACCATGATTACTG (SEQ. ID NO.: 239) | CATGGTCTATTTATTCTCG (SEQ. ID NO.: 240) | protein posphatase 2A, PP2A |
| EMS1 | | Gene | GDB:459016 | 0.64 | CGCCCTGGATCCTCACACTACA (SEQ. ID NO.: 241) | GGGCATCAGGGGATGGGTAGA (SEQ. ID NO.: 242) | Amplaxin |
| SHGC-11098 | DXS9736 | Gene | GDB:737674 | 0.137 | GCTCCTATCTGTGTTTTGAATGG (SEQ. ID NO.: 243) | CCGTGGCATAAGATAAGTAAACG (SEQ. ID NO.: 244) | Androgen Receptor |
| INPPL1 | | Gene | GDB:4590093 | 0.382 | CTTGGAGCGCTATGAGGAGGGC (SEQ. ID NO.: 245) | ATGGCAACTGACCTTCCGTCCTG (SEQ. ID NO.: 246) | 51C protein, inositol polyphosphate phosphatase-like 1 |
| RH18051 | | EST | GDB:4572859 | 0.195 | TTGGAGTCACAGGGGC (SEQ. ID NO.: 247) | CAGCACTATCCTTGGGG (SEQ. ID NO.: 248) | NOF1 |
| Cda1cc11 | D11S2297E | EST | GDB:445869 | 0.1 | AACAAAGCTGCTTAGCACCTG (SEQ. ID NO.: 249) | GATGAGGACCAACTGGTGAC (SEQ. ID NO.: 250) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| 1249/1250 | D11S1957E | EST | GDB:335210 | 0.247 | TTTTCCAATAATGTGACTTC (SEQ. ID NO.: 251) | CAATCCCAACCGTAACAGGC (SEQ. ID NO.: 252) | |
| NDUFV1 | D11S2245E | EST | GDB:445695 | | CTTGATCTCGCCCAGGAAC (SEQ. ID NO.: 253) | GCTCGCTGAAGGATGAAGAC (SEQ. ID NO.: 254) | NDUFV1 |
| AFMb032zg5 | D11S4136 | MSAT | GDB:609546 | 0.19 | GAATCGCTTGAACCCAG (SEQ. ID NO.: 255) | CCAGGTGGTCTTAACGG (SEG. ID NO.: 256) | |
| AFMa059xg9 | D11S4196 | MSAT | GDB:614025 | 0.2 | GAACGTTNTTCATGTAGGCGT (SEQ. ID NO.: 257) | TAATGGTCGCTGTCCC (SEQ. ID NO.: 258) | |
| Cda17c12 | D11S2268E | EST | GDB:445842 | 0.158 | AGGGAAAATGGTATGTGGGGAG (SEQ. ID NO.: 259) | GCAGTGTGTGAAGGCAGG (SEQ. ID NO.: 260) | |
| SHGC-1364 | D11S95IE | EST | GDB:4562765 | 0.137 | AGTGGACAAAATGAGGAAAACAGG (SEQ. ID NO.: 261) | CCAACACAGTTTGCTCACATGCC (SEQ. ID NO.: 262) | |
| RH17410 | | EST | GDB:4571587 | 0.126 | TGACATCTTTGCATTATGGC (SEQ. ID NO.: 263) | AGTTATCCCACCTGATACCG (SEQ. ID NO.: 264) | |
| RH17414 | | EST | GDB:4571595 | 0.121 | AGCTCTTGCTTCTCAGTCCA (SEQ. ID NO.: 265) | CAAAAGTTGTTTCTGTGTTTGTTC (SEQ. ID NO.: 266) | |
| RH17770 | | EST | GDB:4572301 | 0.267 | GCCTCTCAAAGTAGTTGGAACC (SEQ. ID NO.: 267) | TGTGTATCCATAGTGCAAAACAG (SEQ. ID NO.: 268) | |
| SEA | | EST | GDB:4590169 | 0.13 | CTCAAGGCCAGGCATCACT (SEQ. ID NO.: 269) | GGACTCTTCCATGCCAGTG (SEQ. ID NO.: 270) | S13 avian erythroblastosis oncogene homolog |
| RH10689 | | EST | GDB:4563460 | 0.107 | AATGATGATCTCAACTCTG (SEQ. ID NO.: 271) | ACTGAAGAACTCTTGTCCT (SEQ. ID NO.: 272) | |
| TIGR-A006P20 | | EST | GDB:4587692 | 0.236 | GACATCTGTTAGTCTCATAATTC (SEQ. ID NO.: 273) | GGTAACAGTGTCTTGCTT (SEQ. ID NO.: 274) | |
| TIGR-A007D15 | | Gene | GDB:4588398 | 0.24 | CTATGTACAAAACAGGAAGAG (SEQ. ID NO.: 275) | ATCCTAGTTTCCTCTCCTT (SEQ. ID NO.: 276) | Menin gene (MEN1) |
| TIGR-A008B14 | | EST | GDB:4588882 | 0.141 | GTAAATGAGAAACAGACAAATGA (SEQ. ID NO.: 277) | CTATTGGATGTGATATGTTATGG (SEQ. ID NO.: 278) | |
| TIGR-A008K11 | | EST | GDB:4589094 | 0.203 | AAGTAGAAACAAAATGAGGGAC (SEQ. ID NO.: 279) | CCTACCCCAAGGTAACAG (SEQ. ID NO.: 280) | |
| TIGR-A008P15 | | EST | GDB:4589662 | 0.182 | ACTTCCTATAAATGGAGGTGAG (SEQ. ID NO.: 281) | GAGGAGCTTCAAGAGGAA (SEQ. ID NO.: 282) | |
| TIGR-A008T11 | | EST | GDB:4589278 | 0.138 | CATACTCCTAGACTCAAGGAATC (SEG. ID NO.: 283) | GAATGATGTACATGAATTCTTTG (SEQ. ID NO.: 284) | |
| TIGR-A008U48 | | EST | GDB:4589364 | 0.107 | GTGTTGAGGAGAAAAGCACT (SEQ. ID NO.: 285) | CTCCCAGTAGTCACATTCC (SEQ. ID NO.: 286) | |
| TIGR-A008X45 | | EST | GDB:4589838 | 0.242 | CAAGTTACAAATAACTTAAGCCG (SEQ. ID NO.: 287) | CAAGACCCTATCTCTACAAAAAC (SEQ. ID NO.: 288) | |
| SHGC-11839 | D11S4611 | Gene | GDB:740339 | 0.151 | TTTATTAGAAGTGACTCTTGGCCC (SEQ. ID NO.: 289) | GACTACCTGCCCTCAGCTTG (SEQ. ID NO.: 290) | Folate receptor 2 (FBP2) |
| NTB1242 | D11S4929E | EST | GDB:3888276 | 0.149 | TTCTCATGTACAAAGCGGTC (SEQ. ID NO.: 291) | CCACTGGCTTCTCTCTTTTT (SEQ. ID NO.: 292) | cGMP-stimulated 3',5'-cyclic nucleotide phosphodiesterase PDE2A3 (PDE2A) |
| SHGC-13599 | D22S1553 | Gene | GDB:737558 | 0.147 | CACCAGAAGGTTGGGGTG (SEQ. ID NO.: 293) | ACTATTACGACATGAACGCGG (SEQ. ID NO.: 294) | Macrophage Migration Inhibitory factor |
| SHGC-11867 | D11S4331 | Gene | GDB:674684 | 0.14 | CTCATGCTGGATGACCCC (SEQ. ID NO.: 295) | TTGCCTTTCTTGAAACTTAATTCC (SEQ. ID NO.: 296) | P2U Purinoceptor |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| SHGC-15349 | D12S2124 | EST | GDB:740819 | 0.141 | TCACAGCCTTCAGTCAGGG (SEQ. ID NO.: 297) | ACATGCTGTGGCACCATG (SEQ. ID NO.: 298) | |
| Bda84a05 | D11S2235E | EST | GDB:445662 | 0.095 | CCTGAGCTACTGCCACAG (SEQ. ID NO.: 299) | CCCTGACTTGGACAGTGTCC (SEQ. ID NO.: 300) | |
| Bda99d07 | D11S2238E | EST | GDB:445674 | 0.09 | TCAGAGTCACTCCTGCCC (SEQ. ID NO.: 301) | CAAATTCAAGCTCATCCAGACC (SEQ. ID NO.: 302) | |
| folr1 | | Gene | GDB:197840 | 0.3 | CGGCATTTCATCCAGGAC (SEQ. ID NO.: 303) | GGTGTAGGAGGTGCGACAAT (SEQ. ID NO.: 304) | Folate receptor2 (FBP2) |
| NIB1738 | D11S4284 | EST | GDB:626260 | 0.173 | TTCCATTTATTGAGCACCTG (SEQ. ID NO.: 305) | CTTAAGCCACTGTGTTTTGG (SEQ. ID NO.: 306) | |
| WI-7351 | D11S4433 | Gene | GDB:679143 | 0.324 | CCTCCTACACCTGCAAAAGC (SEQ. ID NO.: 307) | TGGAAGAACCCCAGAGGAC (SEQ. ID NO.: 308) | Folate receptor3 (FBP3) |
| WI-14325 | | EST | GDB:4578507 | 0.132 | AAAGCACAAAAGTAACAGCAACA (SEQ. ID NO.: 309) | GTGTGTGGGCCACAATATTG (SEQ. ID NO.: 310) | |
| WI-15192 | | EST | GDB:4575806 | 0.15 | AGAGCACCTTTCCTCAGCAC (SEQ. ID NO.: 311) | AGAATCTCATCACAGGGGCG (SEQ. ID NO.: 312) | |
| WI-17872 | | EST | GDB:4577492 | 0.141 | AAAAAGGACAGTGTCTAAAATTTGA (SEQ. ID NO.: 313) | AATTGTTTTTGTTTGTTTTTTGAGT (SEQ. ID NO.: 314) | |
| SHGC-30732 | | EST | GDB:4567830 | 0.105 | GATTTAGGGAGTACAAGTGCGG (SEQ. ID NO.: 315) | GGGGACAAATTATACTTTATTCAGG (SEQ.ID NO.: 316) | |
| stSG4288 | | EST | GDB:4566057 | 0.123 | CCATCATCATATTGGTGTGACC (SEQ. ID NO.: 317) | TGGCTGCCCAAGAAGAAG (SEQ. ID NO.: 318) | |
| WI-13814 | | EST | GDB:4579290 | 0.15 | TTAAGATGCCATTAAACTCATGAC (SEQ. ID NO.: 319) | CCAAGGAGATGACCAAGTGG (SEQ. ID NO.: 320) | (DRES9 |
| WI-14122 | | Gene | GDB:4576114 | 0.126 | CCATCTCTTTTATCAGGGTTGG (SEQ. ID NO.: 321) | CTCTGTGCAAGTAAGCATCTTACA (SEQ. ID NO.: 322) | Human VEGF related factor isoform VRF186 precursor (VRF) |
| 2729/2730 | D11S4057 | EST | GDB:596509 | 0.118 | CGACTGTGTATTTTCCACAG (SEQ. ID NO.: 323) | AGAAGCCCATATCAATGCAC (SEQ. ID NO.: 324) | |
| SHGC-31329 | | EST | GDB:4567386 | 0.15 | AGCTTAAAGTAGGACAACCATGG (SEQ. ID NO.: 325) | GGATGCTTCACTCCAGAAAG (SEQ. ID NO.: 326) | |
| SGC33858 | | EST | GDB:4578600 | 0.127 | TGTTGTTTATTTCCACCTGCC (SEQ. ID NO.: 327) | AGAGTGGCTGCAGGCCAG (SEQ. ID NO.: 328) | |
| WI-12191 | | EST | GDB:1222208 | 0.15 | TTTTTTTTTTTACACGAATTTGAGG (SEQ. ID NO.: 329) | TGAGGAAGTAAAAACAGGTCATC (SEQ. ID NO.: 330) | |
| WI-13701 | | EST | GDB:4574892 | 0.15 | ATGAAATCTTAAGCAGAATCCCCA (SEQ. ID NO.: 331) | CACAGAGTCCCAGGGTCTGT (SEQ. ID NO.: 332) | |
| WI-14069 | | EST | GDB:4584373 | 0.15 | AAACCCCTTTATTTATCTCTCTCTG (SEQ. ID NO.: 333) | CCCTCAGAGCTGGTGGGT (SEQ. ID NO.: 334) | |
| WI-14272 | | EST | GDB:4578525 | 0.125 | GCTTCTAAGTCTTAGAGTCAGCTGG (SEQ. ID NO.: 335) | AGCCCACAGTCAGCCTACC (SEQ. ID NO.: 336) | |
| WI-17347 | | EST | GDB:4578523 | 0.127 | TTGGTTAAATGATGCCCAGA (SEQ. ID NO.: 337) | TGGTCCCACTCACATCCC (SEQ. ID NO.: 338) | |
| stSG1561 | | EST | GDB:4564515 | 0.215 | ACACAGCATGCAGGGAGAG (SEQ. ID NO.: 339) | ATCCCTGGTGCTTAGGTGG (SEQ. ID NO.: 340) | |
| stSG1938 | | EST | GDB:4564568 | 0.137 | GATGGAAGTAGCTCCTCTCGG (SEQ. ID NO.: 341) | GGAAGGCCAGCAAGTACTACC (SEQ. ID NO.: 342) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| stSG2759 | | EST | GDB:4565137 | 0.141 | CCGGTGCTTGGAAAGATG (SEQ. ID NO.: 343) | GAAGTGTCTCTGTTGGGGGA (SEQ. ID NO.: 344) | |
| RH97 | | EST | GDB:4559690 | 0.17 | TTACAGGCATGAGTCACTACGC (SEQ. ID NO.: 345) | ACCACTCTCACAGCCCCTTACA (SEQ. ID NO.: 346) | |
| stSG4794 | | EST | GDB:4573113 | 0.141 | CCCTCCCTCCACACACAC (SEQ. ID NO.: 347) | GCTCACTGAACTTTCAGGGC (SEQ. ID NO.: 348) | |
| stSG4957 | | EST | GDB:4569051 | 0.171 | AGATACGGGCAAAACACTGG (SEQ. ID NO.: 349) | GTTGAATATAGAGCAGGGCCC (SEQ. ID NO: 350) | |
| stSG4974 | | EST | GDB:4569063 | 0.166 | TTCTGAGGTCAGGGCTGTCT (SEQ. ID NO.: 351) | AGCTTGGAAAATCTCGTGTCA (SEQ. ID NO.: 352) | |
| stSG8144 | | EST | GDB:4573137 | 0.17 | ACTCAGTCCCTCCCACC (SEQ. ID NO.: 353) | TCCTCTCACTCCTTCCCAGA (SEQ. ID NO.: 354) | |
| stSG9275 | | EST | GDB:4569999 | 0.19 | GTGATCACGGCTCAACCTG (SEQ. ID NO.: 355) | TGGAGGACTGCTTGAGCC (SEQ. ID NO.: 356) | |
| SHGC-10667 | D11S4583 | Gene | GDB:740246 | 0.277 | CTGCAGCTGCCTCAGTTTC (SEQ. ID NO.: 357) | TCAAAAGTGCTGGTGACAGC (SEQ. ID NO.: 358) | Human protein kinase (MLK-3) |
| SHGC-11930 | | Gene | GDB:1231223 | 0.21 | ATTTCCAGAGCCAGCTCAAA (SEQ. ID NO.: 359) | CTTTAATGTTGTGATGACACAAAGC (SEQ. ID NO.: 360) | FGP3 |
| SHGC-32786 | | EST | GDB:4567878 | 0.125 | GATCATGCACTGTTGACCAC (SEQ. ID NO.: 361) | TACATTTGAAACATTTAAAACCTGA (SEQ. ID NO.: 362) | |
| FKBP2 | | Gene | | 0.064 | AACTGAGCTGTAACCAGACTGGGA (SEQ. ID NO.: 363) | TCCAACAGTCTGGTCCTGATGG (SEQ. ID NO.: 364) | FK506-Binding Protein Precursor (FKBP-13) |
| WI-13116 | | EST | GDB:4585099 | 0.202 | TTATCCCTTTATTGTTTCTCCTTTG (SEQ. ID NO.: 365) | TGGTCACCTGTATTTATTGCTAGG (SEQ. ID NO.: 366) | |
| MDU1 | | Gene | GDB:4590064 | 0.859 | TCTTCAAAGCCTCTGCAGTACC (SEQ. ID NO.: 367) | CTCATCTCCAACCTGTCTAACC (SEQ. ID NO.: 368) | 4F2 CellL-Surface Antigen Heavy Chain (4F2HC) |
| S453 | D11S579 | STS | GDB:196276 | 0.108 | GTGGCTGCAGCTAATGTAAGACAC (SEQ. ID NO.: 369) | CACCACAGACAATGGCGTAAGTCC (SEQ. ID NO.: 370) | |
| STS1-cSRL-112e11 | D11S3866 | STS | GDB:547681 | 0.135 | CTGATTGAGAACCAGAACAG (SEQ. ID NO.: 371) | TAAAGCCCTATAACCTCTCC (SEQ. ID NO.: 372) | |
| STS1-cSRL-44a3 | D11S3830 | STS | GTC:547609 | 0.118 | TAGTAAGGGACCTTCACCAG (SEQ. ID NO.: 373) | AGATGTTTGGTATGACTTGG (SEQ. ID NO.: 374) | |
| STS1-cSRL-31b12 | D11S2439 | STS | GDB:459728 | 0.123 | GATGATTAAACTCTCCTGGC (SEQ. ID NO.: 375) | GAGACAGCTAAGCACTCATG (SEQ. ID NO.: 376) | |
| cSRl-4f9 | D11S1137 | STS | GDB:197824 | 0.196 | GAGGTGGTGGGCACCTGTA (SEQ. ID NO.: 377) | AGAGGGGAGGAACACCTT (SEQ. ID NO.: 378) | Folate receptor2 (FBP2) |
| SHGC-10323 | D11S4351 | Gene | GDB:676135 | 0.141 | GACCAGAGTCTGCCCAGAAG (SEQ. ID NO.: 379) | TCCCCAGCTCTATCCCAAC (SEQ. ID NO.: 380) | Collagen binding protein 2, colligin-2 gene (CBP2) |
| WI-9219 | | Gene | GDB:678179 | 0.1 | GGAGGGATGGACAAGTCTGA (SEQ. ID NO.: 381) | GTCCAGCTCGCTGACTATCC (SEQ. ID NO.: 382) | Retinal outer segment membrane protein 1, ROM1 |
| GTC_ZNP | | Gene | | 0.172 | TCAAAACACAGTCATCTCCA (SEQ. ID NO.: 383) | GCAAAGGCTTTACCATATTG (SEQ. ID NO.: 384) | ZNF126 |
| AFMA152yh1 | D11S4087 | MSAT | GDB:603797 | 0.158 | GCTCAGCACCCCCATT (SEQ. ID NO.: 385) | TCCCTGCTCGGGAAAC (SEQ. ID NO.: 386) | |
| AFMb331xh5 | D11S4162 | MSAT | GDB:611241 | 0.263 | GTTCTCCAGAGAGACAGCAC (SEQ. ID NO.: 387) | GAGAGCAACACTATTGCCC (SEQ. ID NO.: 388) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| AFMb038yb9 | D11S4139 | MSAT | GDB:609621 | 0.151 | TATAGACTTCAGCCCTGCTGC (SEQ. ID NO.: 389) | CCTCTGTAGGATGCAGTTGG (SEQ. ID NO.: 390) | |
| AFM212xe3 | D11S1314 | MSAT | GDB:199292 | 0.209 | TTGCTACGCACTCCTCTACT (SEQ. ID NO.: 391) | GTGAAGGCAGGAAATGTGAC (SEQ. ID NO.: 392) | |
| WI-18813 | | EST | | 0.13 | ATCCTAGACCAGAGGAGCCC (SEQ. ID NO.: 393) | CTCCCCCTGGTCCAGTTATT (SEQ. ID NO.: 394) | Serine/threonine kinase |
| WI-19549 | | EST | | 0.252 | AACTTTCATTTGCCAAGGGA (SEQ. ID NO.: 395) | AGCAGATCTGCTCTTGCGAT (SEQ. ID NO.: 396) | |
| WI-20154 | | EST | | 0.25 | ACAGTTGTCATCGGTAGGCA (SEQ. ID NO.: 397) | AAAAGTATGAATGGGATGGAGC (SEQ. ID NO.: 398) | |
| WI-22393 | | EST | GDB:4583084 | 0.142 | GTGCAGGTGGCGTTTATTTT (SEQ. ID NO.: 399) | CCCTATATCTCCGTGTGCTCC (SEQ. ID NO.: 400) | DRES9 |
| WI-7587 | | EST | GDB:1223732 | 0.274 | GCTCTAGTGGGAAACCTCAGG (SEQ. ID NO.: 401) | GAATTCCAGGCTCTTGCTTG (SEQ. ID NO.: 402) | Ultra high-sulphur keratin protein (KRN1) |
| EST455579 | | EST | | 0.273 | GGTTTGGTCTCAAAGGCAAA (SEQ. ID NO.: 403) | CCAGTACATGGTGGTCACCA (SEQ. ID NO.: 404) | |
| WI-21134 | | EST | | 0.293 | GCTGCCTTGGAATTTCTGTT (SEQ. ID NO.: 405) | GTGCTGTGGTGGGGAAAG (SEQ. ID NO.: 406) | Pas-associating death domain-containing protein. FADD |
| WI-21698 | | EST | | 0.25 | ATTCAAGCTCATCCAGACCC (SEQ. ID NO.: 407) | GGACTGGCCCTTTGAAACTC (SEQ. ID NO.: 408) | |
| SHGC-7373 | D11S4567 | STS | GDB:740192 | 0.225 | ATATTGACCGTGCACAAATACG (SEQ. ID NO.: 409) | AGACCTGGGAAAAGTGGAGAA (SEQ. ID NO.: 410) | |
| SHGC-36533 | | STS | | 0.125 | ATTGGCAGTGGAAAATGCTT (SEQ. ID NO.: 411) | TTAATCTTTTGTCAACTTCCTGATT (SEQ. ID NO.: 412) | |
| ARIX | | Gene | | 0.242 | tctgtcctcctttcaccggaagc (SEQ. ID NO.: 413) | ggataaagaaactccgctctgctggtaga (SEQ. ID NO.: 414) | Arix homeodomain protein, neuroendocrine specific, tx factor |
| CLCI.PCR | | Gene | GDB:6262613 | | TCAGGGCCTGTGTTGCCGCACTCTG (SEQ. ID NO.: 415) | AGCGATGTAAAGGGTACCAGTGCCGAGG (SEQ. ID NO.: 416) | Chloride channel current inducer, ICLN gene |
| B188N21-HL | | STS | | | AGGCATGCAAGCTTCTTA (SEQ. ID NO.: 417) | CCGGGAGGAGACATCTAT (SEQ. ID NO.: 418) | |
| B234C17-HR | | STS | | | TGGTAAGCACAGAAAATGC (SEQ. ID NO.: 419) | AATGGATGGGGGATTATT (SEQ. ID NO.: 420) | |
| B235G10-HR | | STS | | | CTGGACGTTATGTCTGCC (SEQ. ID NO.: 421) | AGAGGCCCAGTCACAGAT (SEQ. ID NO.: 422) | |
| B247F23-HR | | STS | | | ATCACTCTGAACTGCCACT (SEQ. ID NO.: 423) | CCCTTCTGTTTTTCTGTTTT (SEQ. ID NO.: 424) | |
| B337H24-HL | | STS | | | CAAGCTTTGAAGGAAGAG (SEQ. ID NO.: 425) | TAGGACGTTAAGTGAGGAC (SEQ. ID NO.: 426) | |
| B137L5-HL | | STS | | | GCTCTGCAGTGGGTAAAA (SEQ. ID NO.: 427) | ACTCTCCAAGACTGTGCG (SEQ. ID NO.: 428) | |
| B382N10-HR | | STS | | | CCCTTTCTGAGGCAAGAT (SEQ. ID NO.: 429) | GACCACCTGGGAGAGAAC (SEQ. ID NO.: 430) | |
| B12I1-HR | | STS | | | CGCTATGAGTCCCATCTG (SEQ. ID NO.: 431) | GATCAGCTGCAATGAAGG (SEQ. ID NO.: 432) | |
| B180D17-HR | | STS | | | TTGAGTACACGGGGTGAC (SEQ. ID NO.: 433) | CGCAGGACTGAAAGATGA (SEQ. ID NO.: 434) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B236E6-HR | | STS | | | ACCTGTCTCCTCTCCTGG (SEQ. ID NO.: 435) | TGCTTTTCTTCTGTGGGA (SEQ. ID NO.: 436) | |
| B278E22-HR | | STS | | | ATGACCAGCAAGCATTGT (SEQ. ID NO.: 437) | GTACTGGGATTACAGGCG (SEQ. ID NO.: 438) | |
| B312P21-HR | | STS | | | GCAGAAGGTCCTTTGGAT (SEQ. ID NO.: 439) | TTTGCAGGATTCATGCTT (SEQ. ID NO.: 440) | |
| B337H24-HR | | STS | | | CGACATTCTTTTCTGGAGG (SEQ. ID NO.: 441) | ACCTTTGCATGTTGGTTTT (SEQ. ID NO.: 442) | |
| B358H9-HR | | STS | | | GCACTTTTCCTTCCTTCC (SEQ. ID NO.: 443) | TGCTTTGCTTTCTTCTGG (SEQ. ID NO.: 444) | |
| B148N18-HL | | STS | | | ACAGCTCCAGAGAGAAGGA (SEQ. ID NO.: 445) | GCAGTCACTTGAAACCAGA (SEQ. ID NO.: 446) | |
| B172N12-HL | | STS | | | AGGCATCAAGCTTTCCTT (SEQ. ID NO.: 447) | GGTTTAGAGAACCGAGCC (SEQ. ID NO.: 448) | |
| B172N12-HR | | STS | | | GTGGTGCTGCAAGTTACC (SEQ. ID NO.: 449) | GGAATCCCTTTCTTTCCA (SEQ. ID NO.: 450) | |
| B215J11-HR | | STS | | | GACCATTTGTTACGCAGC (SEQ. ID NO.: 451) | GATGGGTGTGAATGAACAA (SEQ. ID NO.: 452) | |
| B223E5-HR | | STS | | | CTCAAGCTTCTGTTCATGC (SEQ. ID NO.: 453) | GCTGTGAGTGTCTTGGCT (SEQ. ID NO.: 454) | |
| B312B3-HR | | STS | | | TACAGAAAACCGCAGCTC (SEQ. ID NO.: 455) | GCCACCAAAGGAAAGATT (SEQ. ID NO.: 456) | |
| B328G19-HL | | STS | | | AAAAGGAGGGAATCATGG (SEQ. ID NO.: 457) | TCACTTAGCAGGAGGCAG (SEQ. ID NO.: 458) | |
| B328G19-HR | | STS | | | CTGAGCATCCGATGAGAC (SEQ. ID NO.: 459) | GTGCAAAATGAGCAGCTT (SEQ. ID NO.: 460) | |
| B329I10-HL | | STS | | | TCTAACCCCTTACTGGGC (SEQ. ID NO.: 461) | TCCTCAAACTGGGAATGA (SEQ. ID NO.: 462) | |
| B329I10-HR | | STS | | | TTTACACAGGACCAGGGA (SEQ. ID NO.: 463) | ATCTCCCCCACTCAGAAG (SEQ. ID NO.: 464) | |
| B368G19-HL | | STS | | | GTCCACGGGCTTTATTCT (SEQ. ID NO.: 465) | TGAGCATAAATTTCATTAGCTG (SEQ. ID NO.: 466) | |
| B368G19-HR | | STS | | | GGAAGAGCAAAATAAATCCA (SEQ. ID NO.: 467) | GGTGCACAGAATTGTTCAT (SEQ. ID NO.: 468) | |
| B36F16-HL | | STS | | | AGCACGCTTATTTCATGG (SEQ. ID NO.: 469) | GTAACACCAGCAGGGACA (SEQ. ID NO.: 470) | |
| B250K11-HR | | STS | | | TCCTGCTGCATTATGGAT (SEQ. ID NO.: 471) | GGGGGTGAGAAGTAGGAA (SEQ. ID NO.: 472) | |
| 8338D17-HR | | STS | | | ATGGGGATTAAATACGGG (SEQ. ID NO.: 473) | AGCTAGCATTGGGCTCTT (SEQ. ID NO.: 474) | |
| B268I23-HL | | STS | | | CTGAGGAGAAGAGGCTGG (SEQ. ID NO.: 475) | CGCCTTACAAGGCAAGTA (SEQ. ID NO.: 476) | |
| B268I23-HR | | STS | | | AGGATGCTTGCTAGGGTT (SEQ. ID NO.: 477) | CACAAGTGTCTGGAAGGC (SEQ. ID NO.: 478) | |
| B371E15-HR | | STS | | | GGTCTCAGGAGCCCTTTA (SEQ. ID NO.: 479) | ACATGCCACTCTTCTCACTAA (SEQ. ID NO.: 480) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B312F21-HL | | STS | | | ACTTAACCAAGGATGGGG (SEQ. ID NO.: 481) | CAACCCACGAGCATAAGA (SEQ. ID NO.: 482) | |
| B338D17-HL | | STS | | | TAGGCTCTGCACTCTTGG (SEQ. ID NO.: 483) | ACCCACGGAGTCTCTCTC (SEQ. ID NO.: 484) | |
| B369H19-HL | | STS | | | TAAAGGCGGTGAAGTGAG (SEQ. ID NO.: 485) | CTACCGCTCTCCTAGGCT (SEQ. ID NO.: 486) | |
| B369H19-HR | | STS | | | TGGGGCCAGATAATTCTT (SEQ. ID NO.: 487) | CTGGTGTTTGGTGGTGTT (SEQ. ID NO.: 488) | |
| B444M11-HR | | STS | | | AAGGAAGAGGTCACCAGG (SEQ. ID NO.: 489) | CACAAATTCCATTTCCCA (SEQ. ID NO.: 490) | |
| B269L23-HL | | STS | | | TCAATAGGTGATCCAACATTT (SEQ. ID NO.: 491) | AAAGTCCCACAAAGGGTC (SEQ. ID NO.: 492) | |
| B250K11-HL | | STS | | | GGGTAGGGGGATCTTTTT (SEQ. ID NO.: 493) | TGTGGAACATTCATTGGC (SEQ. ID NO.: 494) | |
| B269L23-HR | | STS | | | GTCCTGGGAAAGATGGAA (SEQ. ID NO.: 495) | TCAAAGCGTCTCCCATAA (SEQ. ID NO.: 496) | |
| B364H4-HL | | STS | | | TCTTTCGCTGTACTTGGC (SEQ. ID NO.: 497) | TGGGAGGTCAGAGTGATG (SEQ. ID NO.: 498) | |
| B364H4-HR | | STS | | | GGACAGTGTATGTGTTGGG (SEQ. ID NO.: 499) | AGGCAGCTGTTTTTGTGA (SEQ. ID NO.: 500) | |
| B47303-HR | | STS | | | CTTCTTGAGTCCCGTGTG (SEQ. ID NO.: 501) | CAACCGAGAATCCTCTAGC (SEQ. ID NO.: 502) | |
| B180D17-HL | | STS | | | GCTGGGAGAGAATCACAA (SEQ. ID NO.: 503) | GCTTTGCAGAAGAGACCA (SEQ. ID NO.: 504) | |
| B200E21-HL | | STS | | | ACGCTGTCAGGTCACACT (SEQ. ID NO.: 505) | GGAGGATGCTCAGGTGAT (SEQ. ID NO.: 506) | |
| B200E21-HR | | STS | | | TAGGGGGATCTTTTTCCA (SEQ. ID NO.: 507) | GAGCAATTTGAAAAGCCA (SEQ. ID NO.: 508) | |
| B14L15-HR | | STS | | | ATGGTCCAGCTCCTCTGT (SEQ. ID NO.: 509) | ATAGAGCACCCCATCTCC (SEQ. ID NO.: 510) | |
| B442P6-HR | | STS | | | AACATTGCTGTTAGCCCA (SEQ. ID NO.: 511) | GCAATCGAAACAGCATTC (SEQ. ID NO.: 512) | |
| B188N21-HR | | STS | | | ATGAGTTGGCAGCTGAAG (SEQ. ID NO.: 513) | AATGAAGGTCTTGCCTCC (SEQ. ID NO.: 514) | |
| GTC-ARRB1 | | Gene | | 0.067 | GAGGAGAAGATCCACAAGCG (SEQ. ID NO.: 515) | TCTCTGGGGCATACTGAACC (SEQ. ID NO.: 516) | Beta-arrestin-1 |
| B508A5-HL | | STS | | | CTGAGCTTTTGGCACTGT (SEQ. ID NO.: 517) | CTGCTAGGTGACAGCAGG (SEQ. ID NO.: 518) | |
| B36F16-HR | | STS | | | TGTATGAGTCTGGAGGGTGT (SEQ. ID NO.: 519) | ACACCTGGCTGAGGAAAT (SEQ. ID NO.: 520) | |
| B117N18-HL | | STS | | | GCAGGGGACGTGATAATA (SEQ. ID NO.: 521) | TTTTGCTTCCTTACCATGC (SEQ. ID NO.: 522) | |
| B14l15-HL | | STS | | | AAAATTGTGAGCACCTCC (SEQ. ID NO.: 523) | TTTATATTTAAAGTGGCTTTGTT (SEQ. ID NO.: 524) | |
| B21K22-HL | | STS | | | GTGCAAAGCCCACAGTAT (SEQ. ID NO.: 525) | AGGAAAATGCAAGAGCAG (SEQ. ID NO.: 526) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B21K22-HR | | STS | | | CCACTGAATTGCATACTTTG (SEQ. ID NO.: 527) | TCTGGGTCCAGTCTGCTA (SEQ. ID NO.: 528) | |
| B223E5-HL | | STS | | | AGATTTTGGGGAGTCAGG (SEQ. ID NO.: 529) | GCGCTCAAGCAATTCTC (SEQ. ID NO.: 530) | |
| B278E22-HL | | STS | | | CAAGCCCCAAAGTAGTCA (SEQ. ID NO.: 531) | GAATCATCCAATCCACGA (SEQ. ID NO.: 532) | |
| B444M11-HL | | STS | | | AGCCTCCAGGTGACTACC (SEQ. ID NO.: 533) | GAAGGACATGGTCAGCAG (SEQ. ID NO.: 534) | |
| B543O19-HR | | STS | | | ATGCTTTCAGCATTTTCG (SEQ. ID NO.: 535) | TGATCCGTGGTAGGGTTA (SEQ. ID NO.: 536) | |
| B117N18-HR | | STS | | | GTCGGATTGGTTTCACAA (SEQ. ID NO.: 537) | TTTTATCCGAATTCAGCC (SEQ. ID NO.: 538) | |
| B543019-HL | | STS | | | TTTGGAAAAGAACAGAAATGT (SEQ. ID NO.: 539) | GGCTAGTCTTTCCTGAACC (SEQ. ID NO.: 540) | |
| B442P6-HL | | STS | | | CCTTAATGCCCCTGATTC (SEQ. ID NO.: 541) | GCGTTTACAAGCTGAGGA (SEQ. ID NO.: 542) | |
| B367H4-HR | | STS | | | TCAAGCTTGCTTTCTCAA (SEQ. ID NO.: 543) | GTAGCCCAGCAAGTGTCT (SEQ. ID NO.: 544) | |
| B250E21-HR | | STS | | | CCTGGCTGGAGATAGGAT (SEQ. ID NO.: 545) | CTTCCCCTCTGCCTATGT (SEQ. ID NO.: 546) | |
| B250E21-HL | | STS | | | GGCACGTACTTCCTACCA (SEQ. ID NO.: 547) | GGTGCTTCTTACAGGCAA (SEQ. ID NO.: 548) | |
| B248C16-HR | | STS | | | ACCCAGGCTGGTGTGT (SEQ. ID NO.: 549) | ACTGAGTTAATTATCACTCCCCT (SEQ. ID NO.: 550) | |
| B248C16-HL | | STS | | | GATGCATTTTGCTTCACC (SEQ. ID NO.: 551) | TCTGCTTTTAGAGCTGTTAGC (SSQ. ID NO.: 552) | |
| B160D8-HR | | STS | | | TCAAGCTTCAAAGAGCAGA (SEQ. ID NO.: 553) | GGAGTACATCCCAGGACC (SEQ. ID NO.: 554) | |
| B539L7-HR | | STS | | | TGGTGCTTTTAAATCCAGA (SEQ. ID NO.: 555) | CTCCCTTACTTACTTGCATTG (SEQ. ID NO.: 556) | |
| B473O3-HL | | STS | | | TCTTCTCCCAGGGAATCT (SEQ. ID NO.: 557) | TTTATGTCCCCTGAGCAC (SEQ. ID NO.: 558) | |
| APMa190xd9 | D11S4095 | STS | GDB:606064 | 0.193 | TCCCTGGCTATCTTGAATC (SEQ. ID NO.: 559) | CTTGACTGGGTCCACG (SEQ. ID NO.: 560) | |
| ARRB1(2) | | STS | | | CGAGACGCCAGTAGATACCA (SEQ. ID NO.: 561) | CATCCTCCATCCCTTTCAGT (SEQ. ID NO.: 562) | |
| ARRB1(1) | | STS | | | AGTTCCAGAGAACGAGACGC (SEQ. ID NO.: 563) | CTTGTCATCCTCCATGCCTT (SEQ. ID NO.: 564) | |
| P102P3S | | STS | GDB:6054145 | | GAGCGTGAGAGGTTGAGGAG (SEQ. ID NO.: 565) | AAACAAACTCCAGACGCACC (SEQ. ID NO.: 566) | |
| N172A | | STS | GDB:6054146 | 0.208 | CTGAACCACTACCTGTATGACCTG (SEQ. ID NO.: 567) | CTAACTACTTACTCCTACAGGGCCC (SEQ. ID NO.: 568) | |
| N60A | | STS | GDB:6054147 | 0.23 | GAAGCATTTCAATACTTTAACTG (SEQ. ID NO.: 569) | CCACTCCAGTGCACCCAATC (SEQ. ID NO.: 570) | |
| cCI11-44A | | STS | GDB:6054148 | 0.239 | CTTCTCCTGGCCCTCTGC (SEQ. ID NO.: 571) | GGTTTACCTTTGAATCCCAGC (SEQ. ID NO.: 572) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| CN1677-2A | | STS | GDB:6054149 | 0.271 | TGAGGATGAATGAGCACATAGG (SEQ. ID NO.: 573) | TTTGTGGTCCATTGAGTAGGC (SEQ. ID NO.: 574) | |
| cCI11-524B | | STS | GDB:6054150 | 0.221 | AGGGGAAGGAATGTGCTTGG (SEQ. ID NO.: 575) | TTCGGCTGAGCGGGCAGTGT (SEQ. ID NO.: 576) | |
| P117F3T | | STS | GDB:6054151 | 0.168 | ATTGAAGGTCCTCCAAAAGAATGCTGCAGC (SEQ. ID NO.: 577) | AGAACGTCAACATATCTTTTTGGGGGACAC (SEQ. ID NO.: 578) | |
| ARRB1(3) | | Gene | | | TTGTATTTGAGGACTTTGCTCG (SEQ. ID NO.: 579) | CGGTACCATCCTCCTCTTCC (SEQ. ID NO.: 580) | |
| B215J11-HL | | STS | | 0.122 | TTTTTGCCTCATCTATGCCC (SEQ. ID NO.: 581) | GGGTGACAGAGCAAGACTCC (SEQ. ID NO.: 582) | |
| B317G1-HR | | STS | | | TTGCTCAAGTTCTCCTGG (SEQ. ID NO.: 583) | ACCTTGTTTTGAGGGGAG (SEQ. ID NO.: 584) | |
| B317G1-HL | | STS | | | CTTGGCTATTTGGACAGC (SEQ. ID NO.: 585) | GGGCATTTACTCACTTGC (SEQ. ID NO.: 586) | |
| B292J18-HR | | STS | | | CTTGTGTCAGTTGTCAGGG (SEQ. ID NO.: 587) | TGGAATTGTTGTGTCTTGG (SEQ. ID NO.: 588) | |
| B10A1B-HL | | STS | | | CCAGTTCCACTGGATGTT (SEQ. ID NO.: 589) | ATGGGCTGTGTTTCTCAA (SEQ. ID NO.: 590) | |
| B10A18-HR | | STS | | | CTGCCTATCCCTGGACTT (SEQ. ID NO.: 591) | AGTTTGTCCCTAGTGCCC (SEQ. ID NO.: 592) | |
| B527D12-HL | | STS | | | CAACACGTCTGACATCCAT (SEQ. ID NO.: 593) | GGATAGTGCACACCCA (SEQ. ID NO.: 594) | |
| B372J11-HR | | STS | | | TGGGTGGTACTATTGTTCCCAT (SEQ. ID NO.: 595) | AGTTCCAGCCCCCTTACCAG (SEQ. ID NO.: 596) | |
| B372J11-HL | | STS | | | GGCCACTATCATCCCTGTGT (SEQ. ID NO.: 597) | TTTCACATGGGAAGAACACG (SEQ. ID NO.: 598) | |
| B37E17-HR(GS) | | STS | | | ACAGTGACACTAGGGACGGG (SEQ. ID NO.: 599) | TGCCAGGATGGAGATAACAA (SEQ. ID NO.: 600) | |
| B37E17-HL(GS) | | STS | | | CCTGTGGCACACATATCACC (SEQ. ID NO.: 601) | ACAACCAAGAATGGAGCCAC (SEQ. ID NO.: 602) | |
| B34F22-HR(GS) | | STS | | | TGCTGTGTAACAAGTCCCCA (SEQ. ID NO.: 603) | TGAACGGAGGACCTACCAAG (SEQ. ID NO.: 604) | |
| B34F22-HL(GS) | | STS | | | GCAGGGTCCGACTCACTAAG (SEQ. ID NO.: 605) | GCTGTGAGTTCCCTTTACGC (SEQ. ID NO.: 606) | |
| B648P22-HR1 | | STS | | | ACAGTGGGGACAAAGACAGG (SEQ. ID NO.: 607) | TACAGGGCACCTCCCAGTAC (SEQ. ID NO.: 608) | |
| B82A4-HR2 | | STS | | | TCTTCTGTTAAGGTTTCCCCC (SEQ. ID NO.: 609) | TGTCTCAAACCTCCCTCTGC (SEQ. ID NO.: 610) | |
| B648P22-HL | | STS | | | AACATATTTCCTCCCCAGCC (SEQ. ID NO.: 611) | CAGTCCCAGCCAATGAGAAC (SEQ. ID NO.: 612) | |
| BB2L11-HL (GS) | | STS | | | CTCCTCTGCATGGGAGAATC (SEQ. ID NO.: 613) | AGACCTGGGACCAGTCTGTG (SEQ. ID NO.: 614) | |
| B86J13-HL | | STS | | | GGGAGACGACGTCACAAGAT (SEQ. ID NO.: 615) | TGATGTTGGGAAGATGGTGA (SEQ. ID NO.: 616) | |
| 144A24-HL | | STS | | | CAGGCATCTTCTATGTGCCA (SEQ. ID NO.: 617) | GGGAGGCACAAGTTCTTTCA (SEQ. ID NO.: 618) | |

TABLE 3-continued

HBM STS Table

| STS Name | Locus Name | Type | GDB Access. # | Size (kb) | Forward Primer | Reverse Primer | Gene Name |
|---|---|---|---|---|---|---|---|
| B82L11-HR (GS) | | STS | | | ACTTCGTCGCACTGAGTGTG (SEQ. ID NO.: 619) | CCTTTCTTACGGATGAGGCA (SEQ. ID NO.: 620) | |
| B86J13-HR (GS) | | STS | | | GGCTGCTGAGCTCTTCTGAT (SEQ. ID NO.: 621) | TGGGTCTCTCTGCCTGACTT (SEQ. ID NO.: 622) | |
| B82L11-HL2(GS) | | STS | | | TCACCTACTTCCAGCTTCCG (SEQ. ID NO.: 623) | AGACCTGGGACCAGTCTGTG (SEQ. ID NO.: 624) | |
| B82L11-HL3(GS) | | STS | | | CTCCTCTGCATGGGAGAATC (SEQ. ID NO.: 625) | AATTCAGGAGACCTGGGACC (SEQ. ID NO.: 626) | |
| B648P22-HR1 | | STS | | | ACAGTGGGGACAAAGACAGG (SEQ. ID NO.: 607) | TACAGGGCACCTCCCAGTAG (SEQ. ID NO.: 608) | |
| B82A4-HR2 | | STS | | | TCTTCTGTTAAGGTTTCCCCC (SEQ. ID NO.: 609) | TGTCTCAAACCTCCCTCTGC (SEQ. ID NO.: 610) | |
| B648P22-HL | | STS | | | AACATATTTCCTCCCCAGCC (SEQ. ID NO.: 611) | CAGTCCCAGCCAATGAGAAC (SEQ. ID NO.: 612) | |
| B82L11-HL (GS) | | STS | | | CTCCTCTGCATGGGAGAATC (SEQ. ID NO.: 613) | AGACCTGGGACCAGTCTGTG (SEQ. ID NO.: 614) | |
| B86J13-HL (GS) | | STS | | | GGGAGACGACGTCACAAGAT (SEQ. ID NO.: 615) | TGATGTTGGGAAGATGGTGA (SEQ. ID NO.: 616) | |
| 144A24-HL | | STS | | | CAGGCATCTTCTATGTGCCA (SEQ. ID NO.: 617) | GGGAGGCACAAGTTCTTTCA (SEQ. ID NO.: 618) | |
| B82L11-HR (GS) | | STS | | | ACTTCGTGGCACTGAGTGTG (SEQ. ID NO.: 619) | CCTTTCTTACGGATGAGGCA (SEQ. ID NO.: 620) | |
| B86J13-HR (GS) | | STS | | | GGCTGCTGAGCTCTTCTGAT (SEQ. ID NO.: 621) | TGGGTCTCTCTGCCTGACTT (SEQ. ID NO.: 622) | |
| B82L11-HL2(GS) | | STS | | | TCACCTACTTCCAGCTTCCG (SEQ. ID NO.: 623) | AGACCTGGGACCAGTCTGTG (SEQ. ID NO.: 624) | |
| B82L11-HL3(GS) | | STS | | | CTCCTCTGCATGGGAGAATC (SEQ. ID NO.: 625) | AATTCAGGAGACCTGGGACC (SEQ. ID NO.: 626) | |

Novel STSs were developed either from publicly available genomic sequence or from sequence-derived BAC insert ends. Primers were chosen using a script which automatically performs vector and repetitive sequence masking using Cross_match (P. Green, U. of Washington) and subsequent primer picking using Primer3 (Rozen, Skaletsky (1996, 1997). Primer3 is available at www.genome.wi.mit.edu/genome_software/other/primer3.html.

Polymerase chain reaction (PCR) conditions for each primer pair were initially optimized with respect to $MgCl_2$ concentration. The standard buffer was 10 mM Tris-HCl (pH 8.3), 50 mM KCl, $MgCl_2$, 0.2 mM each dNTP, 0.2 μM each primer, 2.7 ng/μl human DNA, 0.25 units of AmpliTaq (Perkin Elmer) and $MgCl_2$ concentrations of 1.0 mM, 1.5 mM, 2.0 mM or 2.4 mM. Cycling conditions included an initial denaturation at 94° C. for 2 minutes followed by 40 cycles at 94° C. for 15 seconds, 55° C. for 25 seconds, and 72° C. for 25 seconds followed by a final extension at 72° C. for 3 minutes. Depending on the results from the initial round of optimization the conditions were further optimized if necessary. Variables included increasing the annealing temperature to 58° C. or 60° C., increasing the cycle number to 42 and the annealing and extension times to 30 seconds, and using AmpliTaqGold (Perkin Elmer).

BAC clones (Kim et al, *Genomics*, 32:213–218 (1996), Shizuya et al, *Proc. Natl. Acad. Sci. USA*, 89:8794–8797 (1992)) containing STS markers of interest were obtained by PCR-based screening of DNA pools from a total human BAC library purchased from Research Genetics. DNA pools derived from library plates 1–596 were used corresponding to nine genomic equivalents of human DNA. The initial screening process involved PCR reactions of individual markers against superpools, i.e., a mixture of DNA derived from all BAC clones from eight 384-well library plates. For each positive superpool, plate (8), row (16) and column (24) pools were screened to identify a unique library address. PCR products were electrophoresed in 2% agarose gels (Sigma) containing 0.5 μg/ml ethidium bromide in 1×TBE at 150 volts for 45 min. The electrophoresis units used were the Model A3-1 systems from Owl Scientific Products. Typically, gels contained 10 tiers of lanes with 50 wells/tier. Molecular weight markers (100 bp ladder, Life Technologies, Bethesda, Md.) were loaded at both ends of the gel. Images of the gels were captured with a Kodak DC40 CCD camera and processed with Kodak ID software. The gel data were exported as tab delimited text files; names of the files included information about the library screened, the gel image files and the marker screened. These data were automatically imported using a customized Perl script into Filemaker™ PRO (Claris Corp.) databases for data storage and analysis. In cases where incomplete or ambiguous clone address information was obtained, additional experiments were performed to recover a unique, complete library address.

Recovery of clonal BAC cultures from the library involved streaking out a sample from the library well onto LB agar (Maniatis et al, *Molecular Cloning: A Laboratory Manual.*, Cold Spring Harbor Laboratory, Cold Spring Harbor, N.Y. (1982)) containing 12.5 μg/ml chloramphenicol (Sigma). Two individual colonies and a portion of the initial streak quadrant were tested with appropriate STS markers by colony PCR for verification. Positive clones were stored in LB broth containing 12.5 μg/ml chloramphenicol and 15% glycerol at −70° C.

Several different types of DNA preparation methods were used for isolation of BAC DNA. The manual alkaline lysis miniprep protocol listed below (Maniatis et al, *Molecular Cloning: A Laboratory Manual*, Cold Spring Harbor Laboratory, Cold Spring Harbor, N.Y. (1982)) was successfully used for most applications, i.e., restriction mapping, CHEF gel analysis, FISH mapping, but was not successfully reproducible in endsequencing. The Autogen and Qiagen protocols were used specifically for BAC DNA preparation for endsequencing purposes.

Bacteria were grown in 15 ml Terrific Broth containing 12.5 μg/ml chloramphenicol in a 50 ml conical tube at 37° C. for 20 hrs with shaking at 300 rpm. The cultures were centrifuged in a Sorvall RT 6000 D at 3000 rpm (~1800 g) at 4° C. for 15 min. The supernatant was then aspirated as completely as possible. In some cases cell pellets were frozen at −20° C. at this step for up to 2 weeks. The pellet was then vortexed to homogenize the cells and minimize clumping. 250 μl of P1 solution (50 mM glucose, 15 mM Tris-HCl, pH 8; 10 mM EDTA, and 100 μg/ml RNase A) was added and the mixture pipetted up and down to mix. The mixture was then transferred to a 2 ml Eppendorf tube. 350 μl of P2 solution (0.2 N NaOH, 1% SDS) was then added, the mixture mixed gently and incubated for 5 min. at room temperature. 350 μl of P3 solution (3M KOAc, pH 5.5) was added and the mixture mixed gently until a white precipitate formed. The solution was incubated on ice for 5 min. and then centrifuged at 4° C. in a microfuge for 10 min. The supernatant was transferred carefully (avoiding the white precipitate) to a fresh 2 ml Eppendorf tube, and 0.9 ml of isopropanol was added, the solution mixed and left on ice for 5 min. The samples were centrifuged for 10 min., and the supernatant removed carefully. Pellets were washed in 70% ethanol and air dried for 5 min. Pellets were resuspended in 200 μl of TE8 (10 mM Tris-HCl, pH 8.0, 1.0 M EDTA), and RNase A (Boehringer Mannheim) added to100 μg/ml. Samples were incubated at 37° C. for 30 min., then precipitated by addition of $C_2H_3O_2Na.3H_2O$ to 0.5 M and 2 volumes of ethanol. Samples were centrifuged for 10 min., and the pellets washed with 70% ethanol followed by air drying and dissolving in 50 μl TE8. Typical yields for this DNA prep were 3–5 μg/15 ml bacterial culture. Ten to 15 μl were used for HindIII restriction analysis; 5 μl was used for NotI digestion and clone insert sizing by CHEF gel electrophoresis.

BACs were inoculated into 15 ml of 2×LB Broth containing 12.5 μg/ml chloramphenicol in a 50 ml conical tube. 4 tubes were inoculated for each clone. Cultures were grown overnight (~16 hr) at 37° C. with vigorous shaking (>300 rpm). Standard conditions for BAC DNA isolation were followed as recommended by the Autogen 740 manufacturer. 3 ml samples of culture were placed into Autogen tubes for a total of 60 ml or 20 tubes per clone. Samples were dissolved finally in 100 μl TE8 with 15 seconds of shaking as part of the Autogen protocol. After the Autogen protocol was finished DNA solutions were transferred from each individual tube and pooled into a 2 ml Eppendorf tube. Tubes with large amounts of debris (carry over from the pelleting debris step) were avoided. The tubes were then rinsed with 0.5 ml of TE8 successively and this solution added to the pooled material. DNA solutions were stored at 4° C.; clumping tended to occur upon freezing at −20° C. This DNA was either used directly for restriction mapping, CHEF gel analysis or FISH mapping or was further purified as described below for use in endsequencing reactions.

The volume of DNA solutions was adjusted to 2 ml with TE8, samples were then mixed gently and heated at 65° C. for 10 min. The DNA solutions were then centrifuged at 4° C. for 5 min. and the supernatants transferred to a 15 ml conical tube. The NaCl concentration was then adjusted to 0.75 M (~0.3 ml of 5 M NaCl to the 2 ml sample). The total volume was then adjusted to 6 ml with Qiagen column equilibration buffer (Buffer QBT). The supernatant containing the DNA was then applied to the column and allowed to enter by gravity flow. Columns were washed twice with 10 ml of Qiagen Buffer QC. Bound DNA was then eluted with four separate 1 ml aliquots of Buffer QF kept at 65° C. DNA was precipitated with 0.7 volumes of isopropanol (~2.8 ml). Each sample was then transferred to 4 individual 2.2 ml Eppendorf tubes and incubated at room temperature for 2 hr or overnight. Samples were centrifuged in a microfuge for 10 min. at 4° C. The supernatant was removed carefully and 1 ml of 70% ethanol was added. Samples were centrifuged again and because the DNA pellets were often loose at this stage, the supernatant removed carefully. Samples were centrifuged again to concentrate remaining liquid which was removed with a micropipet tip. DNA pellets were then dried in a desiccator for 10 min. 20 μl of sterile distilled and deionized $H_2O$ was added to each tube which was then placed at 4° C. overnight. The four 20 μl samples for each clone were pooled and the tubes rinsed with another 20 μl of sterile distilled and deionized $H_2O$ for a final volume of 100 μl. Samples were then heated at 65° C. for 5 min. and then mixed gently. Typical yields were 2–5 μg/60 ml culture as assessed by NotI digestion and comparison with uncut lambda DNA.

3 ml of LB Broth containing 12.5 μg/ml of chloramphenicol was dispensed into autoclaved Autogen tubes. A single tube was used for each clone. For inoculation, glycerol stocks were removed from −70° C. storage and placed on dry ice. A small portion of the glycerol stock was removed from the original tube with a sterile toothpick and transferred into the Autogen tube; the toothpick was left in the Autogen tube for at least two minutes before discarding. After inoculation the tubes were covered with tape making sure the seal was tight. When all samples were inoculated, the tube units were transferred into an Autogen rack holder and placed into a rotary shaker at 37° C. for 16–17 hours at 250 rpm. Following growth, standard conditions for BAC DNA preparation, as defined by the manufacturer, were used to program the Autogen. Samples were not dissolved in TE8 as part of the program and DNA pellets were left dry. When the program was complete, the tubes were removed from the output tray and 30 μl of sterile distilled and deionized $H_2O$ was added directly to the bottom of the tube. The tubes were then gently shaken for 2–5 seconds and then covered with parafilm and incubated at room temperature for 1–3 hours. DNA samples were then transferred to an Eppendorf tube and used either directly for sequencing or stored at 4° C. for later use.

V. BAC Clone Characterization for Physical Mapping

DNA samples prepared either by manual alkaline lysis or the Autogen protocol were digested with HindIII for analysis of restriction fragment sizes. This data were used to compare the extent of overlap among clones. Typically 1–2 μg were used for each reaction. Reaction mixtures included: 1×Buffer 2 (New England Biolabs), 0.1 mg/ml bovine serum albumin (New England Biolabs), 50 μg/ml RNase A (Boehringer Mannheim), and 20 units of HindIII (New England Biolabs) in a final volume of 25 μl. Digestions were incubated at 37° C. for 4–6 hours. BAC DNA was also digested with NotI for estimation of insert size by CHEF gel analysis (see below). Reaction conditions were identical to those for HindIII except that 20 units of NotI were used. Six μl of 6×Ficoll loading buffer containing bromphenol blue and xylene cyanol was added prior to electrophoresis.

HindIII digests were analyzed on 0.6% agarose (Seakem, FMC Bioproducts) in 1×TBE containing 0.5 μg/ml ethidium bromide. Gels (20 cm×25 cm) were electrophoresed in a Model A4 electrophoresis unit (Owl Scientific) at 50 volts for 20–24 hrs. Molecular weight size markers included undigested lambda DNA, HindIII digested lambda DNA, and HaeIII digested_X174 DNA. Molecular weight markers were heated at 65° C. for 2 min. prior to loading the gel. Images were captured with a Kodak DC40 CCD camera and analyzed with Kodak 1D software.

NotI digests were analyzed on a CHEF DRII (BioRad) electrophoresis unit according to the manufacturer's recommendations. Briefly, 1% agarose gels (BioRad pulsed field grade) were prepared in 0.5×TBE, equilibrated for 30 minutes in the electrophoresis unit at 14° C., and electrophoresed at 6 volts/cm for 14 hrs with circulation. Switching times were ramped from 10 sec to 20 sec. Gels were stained after electrophoresis in 0.5 μg/ml ethidium bromide. Molecular weight markers included undigested lambda DNA, HindIII digested lambda DNA, lambda ladder PFG ladder, and low range PFG marker (all from New England Biolabs).

BAC DNA prepared either by the manual alkaline lysis or Autogen protocols were labeled for FISH analysis using a Bioprime labeling kit (BioRad) according to the manufacturer's recommendation with minor modifications. Approximately 200 ng of DNA was used for each 50 μl reaction. 3 μl were analyzed on a 2% agarose gel to determine the extent of labeling. Reactions were purified using a Sephadex G50 spin column prior to in situ hybridization. Metaphase FISH was performed as described (Ma et al, *Cytogenet. Cell Genet.*, 74:266–271 (1996)).

VI. BAC Endsequencing

The sequencing of BAC insert ends utilized DNA prepared by either of the two methods described above. The DYEnamic energy transfer primers and Dynamic Direct cycle sequencing kits from Amersham were used for sequencing reactions. Ready made sequencing mix including the M13-40 forward sequencing primer was used (Catalog # US79730) for the T7 BAC vector terminus; ready made sequencing mix (Catalog # US79530) was mixed with the M13-28 reverse sequencing primer (Catalog # US79339) for the SP6 BAC vector terminus. The sequencing reaction mixes included one of the four fluorescently labeled dye-primers, one of the four dideoxy termination mixes, dNTPs, reaction buffer, and Thermosequenase. For each BAC DNA sample, 3 μl of the BAC DNA sample was aliquoted to 4 PCR strip tubes. 2 μl of one of the four dye primer/termination mix combinations was then added to each of the four tubes. The tubes were then sealed and centrifuged briefly prior to PCR. Thermocycling conditions involved a 1 minute denaturation at 95° C., 15 second annealing at 45° C., and extension for 1 minute at 70° C. for 35 total cycles. After cycling the plates were centrifuged briefly to collect all the liquid to the bottom of the tubes. 5 μl of sterile distilled and deionized $H_2O$ was then added into each tube, the plates sealed and centrifuged briefly again. The four samples for each BAC were then pooled together. DNA was then precipitated by adding 1.5 μl of 7.5 M $NH_4OAc$ and 100 μl of −20° C. 100% ethanol to each tube. Samples were mixed by pipetting up and down once. The plates were then sealed and incubated on ice for 10 minutes. Plates were centrifuged in a table top Haraeus centrifuge at 4000 rpm (3,290 g) for 30 minutes at 4° C. to recover the DNA. The supernatant was removed and excess liquid blotted onto paper towels. Pellets were washed by adding 100 μl of −20° C. 70% ethanol into each tube and recentrifuging at 4000 rpm (3,290 g) for 10 minutes at 4° C. The supernatant was removed and excess liquid again removed by blotting on a paper towel. Remaining traces of liquid were removed by placing the plates upside down over a paper towel and centrifuging only until the centrifuge reached 800 rpm. Samples were then air dried at room temperature for 30 min. Tubes were capped and stored dry at −20° C. until electrophoresis. Immediately prior to electrophoresis the DNA was dissolved in 1.5 $\mu$l of Amersham loading dye. Plates were then sealed and centrifuged at 2000 rpm (825 g). The plates were then vortexed on a plate shaker for 1–2 minutes. Samples were then recentrifuged at 2000 rpm (825 g) briefly. Samples were then heated at 65° C. for 2 min. and immediately placed on ice. Standard gel electrophoresis was performed on ABI 377 fluorescent sequencers according to the manufacturer's recommendation.

VII. Sub-cloning and Sequencing of HBM BAC DNA

The physical map of the Zmax1 gene region provides a set of BAC clones that contain within them the Zmax1 gene and the HBM gene. DNA sequencing of several of the BACs from the region has been completed. The DNA sequence data is a unique reagent that includes data that one skilled in the art can use to identify the Zmax1 gene and the HBM gene, or to prepare probes to identify the gene(s), or to identify DNA sequence polymorphisms that identify the gene(s).

BAC DNA was isolated according to one of two protocols, either a Qiagen purification of BAC DNA (Qiagen, Inc. as described in the product literature) or a manual purification which is a modification of the standard alkaline lysis/Cesium Chloride preparation of plasmid DNA (see e.g., Ausubel et al, *Current Protocols in Molecular Biology*, John Wiley & Sons (1997)). Briefly for the manual protocol, cells were pelleted, resuspended in GTE (50 mM glucose, 25 mM Tris-Cl (pH 8), 10 mM EDTA) and lysozyme (50 mg/ml solution), followed by NaOH/SDS (1% SDS/0.2N NaOH) and then an ice-cold solution of 3M KOAc (pH 4.5–4.8). RnaseA was added to the filtered supernatant, followed by Proteinase K and 20% SDS. The DNA was then precipitated with isopropanol, dried and resuspended in TE (10 mM Tris, 1 mM EDTA (pH 8.0)). The BAC DNA was further purified by Cesium Chloride density gradient centrifugation (Ausubel et al, *Current Protocols in Molecular Biology*, John Wiley & Sons (1997)).

Following isolation, the BAC DNA was sheared hydrodynamically using an HPLC (Hengen, *Trends in Biochem. Sci*., 22:273–274 (1997)) to an insert size of 2000–3000 bp. After shearing, the DNA was concentrated and separated on a standard 1% agarose gel. A single fraction, corresponding to the approximate size, was excised from the gel and purified by electroelution (Sambrook et al, *Molecular Cloning: A Laboratory Manual*, Cold Spring Harbor Laboratory, Cold Spring, N.Y. (1989)).

The purified DNA fragments were then blunt-ended using T4 DNA polymerase. The blunt-ended DNA was then ligated to unique BstXI-linker adapters (SEQ. ID. NOS.: 627–628) (5' GTCTTCACCACGGGG and 5' GTGGTGAAGAC in 100–1000 fold molar excess). These linkers were complimentary to the BstXI-cut pMPX vectors (constructed by the inventors), while the overhang was not self-complimentary. Therefore, the linkers would not concatemerize nor would the cut-vector religate itself easily. The linker-adapted inserts were separated from the unincorporated linkers on a 1% agarose gel and purified using GeneClean (BIO 101, Inc.). The linker-adapted insert was then ligated to a modified pBlueScript vector to construct a "shotgun" subclone library. The vector contained an out-of-frame lacZ gene at the cloning site which became in-frame in the event that an adapter-dimer is cloned, allowing these to be avoided by their blue-color.

All subsequent steps were based on sequencing by ABI377 automated DNA sequencing methods. Only major modifications to the protocols are highlighted. Briefly, the library was then transformed into DH5α competent cells (Life Technologies, Bethesda, Md., DH5α transformation protocol). It was assessed by plating onto antibiotic plates containing ampicillin and IPTG/Xgal. The plates were incubated overnight at 37° C. Successful transformants were then used for plating of clones and picking for sequencing. The cultures were grown overnight at 37° C. DNA was purified using a silica bead DNA preparation (Ng et al, *Nucl. Acids Res*., 24:5045–5047 (1996)) method. In this manner, 25 $\mu$g of DNA was obtained per clone.

These purified DNA samples were then sequenced using ABI dye-terminator chemistry. The ABI dye terminator sequence reads were run on ABI377 machines and the data was directly transferred to UNIX machines following lane tracking of the gels. All reads were assembled using PHRAP (P. Green, Abstracts of DOE Human Genome Program Contractor-Grantee Workshop V, Jan. 1996, p.157) with default parameters and quality scores. The initial assembly was done at 6-fold coverage and yielded an average of 8–15 contigs. Following the initial assembly, missing mates (sequences from clones that only gave one strand reads) were identified and sequenced with ABI technology to allow the identification of additional overlapping contigs. Primers for walking were selected using a Genome Therapeutics program Pick_primer near the ends of the clones to facilitate gap closure. These walks were sequenced using the selected clones and primers. Data were reassembled with PHRAP into sequence contigs.

VIII. Gene Identification by Computational Methods

Following assembly of the BAC sequences into contigs, the contigs were subjected to computational analyses to identify coding regions and regions bearing DNA sequence similarity to known genes. This protocol included the following steps.

1. Degap the contigs: the sequence contigs often contain symbols (denoted by a period symbol) that represent locations where the individual ABI sequence reads have insertions or deletions. Prior to automated computational analysis of the contigs, the periods were removed. The original data was maintained for future reference.

2. BAC vector sequences were "masked" within the sequence by using the program cross match (Phil Green, http:\\chimera.biotech.washington.edu\UWGC). Since the shotgun libraries construction detailed above leaves some BAC vector in the shotgun libraries, this program was used to compare the sequence of the BAC contigs to the BAC vector and to mask any vector sequence prior to subsequent steps. Masked sequences were marked by an "X" in the sequence files, and remained inert during subsequent analyses.

3. *E. coli* sequences contaminating the BAC sequences were masked by comparing the BAC contigs to the entire *E. coli* DNA sequence.

4. Repetitive elements known to be common in the human genome were masked using cross match. In this implementation of crossmatch, the BAC sequence was compared to a database of human repetitive elements (Jerzy Jerka, Genetic Information Research Institute, Palo Alto, Calif.). The masked repeats were marked by X and remained inert during subsequent analyses.

5. The location of exons within the sequence was predicted using the MZEF computer program (Zhang, *Proc. Natl Acad Sci.*, 94:565–568 (1997)).

6. The sequence was compared to the publicly available unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389–3402 (1997)). The parameters for this search were: E=0.05, v=50, B=50 (where E is the expected probability score cutoff, V is the number of database entries returned in the reporting of the results, and B is the number of sequence alignments returned in the reporting of the results (Altschul et al, *J. Mol. Biol.*, 215:403–410 (1990)).

7. The sequence was translated into protein for all six reading frames, and the protein sequences were compared to a non-redundant protein database compiled from Genpept Swissprot PIR (National Center for Biotechnology Information, National Library of Medicine, 38A, 8N905, 8600 Rockville Pike, Bethesda, Md. 20894; www.ncbi.nlm.nih.gov). The parameters for this search were E=0.05, V=50, B=50, where E, V, and B are defined as above.

8. The BAC DNA sequence was compared to the database of the cDNA clones derived from direct selection experiments (described below) using blastn2 (Altschul et al, *Nucl. Acids. Res.*, 25:3389–3402 (1997)). The parameters for this search were E=0.05, V=250, B=250, where E, V, and B are defined as above.

9. The BAC sequence was compared to the sequences of all other BACs from the HBM region on chromosome 11q12-13 using blastn2 (Altschul et al, *Nucl. Acids. Res.*, 25:3389–3402 (1997)). The parameters for this search were E=0.05, V=50, B=50, where E, V, and B are defined as above.

10. The BAC sequence was compared to the sequences derived from the ends of BACs from the HBM region on chromosome 11q12-13 using blastn2 (Altschul et al, *Nucl. Acids. Res.*, 25:3389–3402 (1997)). The parameters for this search were E=0.05, V=50, B=50, where E, V, and B are defined as above.

11. The BAC sequence was compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389–3402 (1997)). The parameters for this search were E=0.05, V=50, B=50, where E, V, and B are defined as above.

12. The BAC sequence was compared to the STS division of Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, 1997). The parameters for this search were E=0.05, V=50, B=50, where E, V, and B are defined as above.

13. The BAC sequence was compared to the Expressed Sequence (EST) Tag Genbank database (National Center for Biotechnology Information, National Library of Medicine, 38A, 8N905, 8600 Rockville Pike, Bethesda, Md. 20894; www.ncbi.nln.nih.gov) using blastn2 (Altschul et al, *Nucl. Acids. Res.*, 25:3389–3402 (1997)). The parameters for this search were E=0.05, V=250, B=250, where E, V, and B are defined as above.

IX. Gene Identification by Direct cDNA Selection

Primary linkered cDNA pools were prepared from bone marrow, calvarial bone, femoral bone, kidney, skeletal muscle, testis and total brain. Poly (A) +RNA was prepared from calvarial and femoral bone tissue (Chomczynski et al, *Anal. Biochem.*, 162:156–159 (1987); D'Alessio et al, *Focus,* 9:1–4 (1987)) and the remainder of the mRNA was purchased from Clontech (Palo Alto, Calif.). In order to generate oligo(dT) and random primed cDNA pools from the same tissue, 2.5 μg mRNA was mixed with oligo(dT) primer in one reaction and 2.5 μg mRNA was mixed with random hexamers in another reaction, and both were converted to first and second strand cDNA according to manufacturers recommendations (Life Technologies, Bethesda, Md.). Paired phosphorylated cDNA linkers (see sequence below) were annealed together by mixing in a 1:1 ratio (10 μg each) incubated at 65° C. for five minutes and allowed to cool to room temperature.

Paired linkers oligo1/2

OLIGO 1: 5' CTG AGC GGA ATT CGT GAG ACC 3' (SEQ ID NO: 12)

OLIGO 2: 5' TTG GTC TCA CGT ATT CCG CTC GA 3' (SEQ ID NO:13)

Paired linkers oligo3/4

OLIGO 3: 5' CTC GAG AAT TCT GGA TCC TC 3' (SEQ ID NO:14)

OLIGO 4: 5' TTG AGG ATC CAG AAT TCT CGA G 3' (SEQ ID NO:15)

Paired linkers oligo5/6

OLIGO 5: 5' TGT ATG CGA ATT CGC TGC GCG 3' (SEQ ID NO:16)

OLIGO 6: 5' TTC GCG CAG CGA ATT CGC ATA CA 3' (SEQ ID NO:17)

Paired linkers oligo7/8

OLIGO 7: 5' GTC CAC TGA ATT CTC AGT GAG 3' (SEQ ID NO:18)

OLIGO 8: 5' TTG TCA CTG AGA ATT CAG TGG AC 3' (SEQ ID NO:19)

Paired linkers oligo11/12

OLIGO 11: 5' GAA TCC GAA TTC CTG GTC AGC 3' (SEQ ID NO:20)

OLIGO 12: 5' TTG CTG ACC AGG AAT TCG GAT TC 3' (SEQ ID NO:21)

Linkers were ligated to all oligo(dT) and random primed cDNA pools (see below) according to manufacturers instructions (Life Technologies, Bethesda, Md.).

Oligo 1/2 was ligated to oligo(dT) and random primed cDNA pools prepared from bone marrow. Oligo 3/4 was ligated to oligo(dT) and random primed cDNA pools prepared from calvarial bone. Oligo 5/6 was ligated to oligo (dT) and random primed cDNA pools prepared from brain and skeletal muscle. Oligo 7/8 was ligated to oligo(dT) and random primed cDNA pools prepared from kidney. Oligo 11/12 was ligated to oligo(dT) and random primed cDNA pools prepared from femoral bone.

The cDNA pools were evaluated for length distribution by PCR amplification using 1 μl of a 1:1, 1:10, and 1:00 dilution of the ligation reaction, respectively. PCR reactions were performed in a Perkin Elmer 9600, each 25 μl volume reaction contained 1 μl of DNA, 10 mM Tris-HCl (pH 8.3), 50 mM KCl, 1.5 mM MgCl2, 0.001% gelatin, 200 mM each dNTPs, 10 $\mu$M primer and 1 unit Taq DNA polymerase (Perkin Elmer) and was amplified under the following conditions: 30 seconds at 94° C., 30 seconds at 60° C. and 2 minutes at 72° C. for 30 cycles. The length distribution of the amplified cDNA pools were evaluated by electrophoresis on a 1% agarose gel. The PCR reaction that gave the best representation of the random primed and oligo(dT) primed cDNA pools was scaled up so that ~2–3 $\mu$g of each cDNA pool was produced. The starting cDNA for the direct selection reaction comprised of 0.5 $\mu$g of random primed cDNAs mixed with 0.5 $\mu$g of oligo(dT) primed cDNAs.

The DNA from the 54 BACs that were used in the direct cDNA selection procedure was isolated using Nucleobond AX columns as described by the manufacturer (The Nest Group, Inc.).

The BACs were pooled in equimolar amounts and 1 $\mu$g of the isolated genomic DNA was labelled with biotin 16-UTP by nick translation in accordance with the manufacturers instructions (Boehringer Mannheim). The incorporation of the biotin was monitored by methods that could be practiced by one skilled in the art (Del Mastro and Lovett, *Methods in Molecular Biology*, Humana Press Inc., NJ (1996)).

Direct cDNA selection was performed using methods that could be practiced by one skilled in the art (Del Mastro and Lovett, *Methods in Molecular Biology*, Humana Press Inc., NJ (1996)). Briefly, the cDNA pools were multiplexed in two separate reactions: In one reaction cDNA pools from bone marrow, calvarial bone, brain and testis were mixed, and in the other cDNA pools from skeletal muscle, kidney and femoral bone were mixed. Suppression of the repeats, yeast sequences and plasmid in the cDNA pools was performed to a Cot of 20. 100 ng of biotinylated BAC DNA was mixed with the suppressed cDNAs and hybridized in solution to a Cot of 200. The biotinylated DNA and the cognate cDNAs was captured on streptavidin-coated paramagnetic beads. The beads were washed and the primary selected cDNAs were eluted. These cDNAs were PCR amplified and a second round of direct selection was performed. The product of the second round of direct selection is referred to as the secondary selected material. A Galanin cDNA clone, previously shown to map to 11q12-13 (Evans, *Genomics*, 18:473–477 (1993)), was used to monitor enrichment during the two rounds of selection.

The secondary selected material from bone marrow, calvarial bone, femoral bone, kidney, skeletal muscle, testis and total brain was PCR amplified using modified primers of oligos 1, 3, 5, 7 and 11, shown below, and cloned into the UDG vector pAMP10 (Life Technologies, Bethesda, Md.), in accordance with the manufacturer's recommendations.

Modified primer sequences:

Oligo1-CUA: 5' CUA CUA CUA CUA CTG AGC GGA ATT CGT GAG ACC 3' (SEQ ID NO:22)

Oligo3-CUA: 5' CUA CUA CUA CUA CTC GAG AAT TCT GGA TCC TC 3' (SEQ ID NO:23)

Oligo5-CUA: 5' CUA CUA CUA CUA TGT ATG CGA ATT CGC TGC GCG 3' (SEQ ID NO:24)

Oligo7-CUA: 5' CUA CUA CUA CUA GTC CAC TGA ATT CTC AGT GAG 3' (SEQ ID NO:25)

Oligo11-CUA: 5' CUA CUA CUA CUA GAA TCC GAA TTC CTG GTC AGC 3' (SEQ ID NO:26)

The cloned secondary selected material, from each tissue source, was transformed into MAX Efficiency DH5a Competent Cells (Life Technologies, Bethesda, Md.) as recommended by the manufacturer. 384 colonies were picked from each transformed source and arrayed into four 96 well microtiter plates.

All secondarily selected cDNA clones were sequenced using M13 dye primer terminator cycle sequencing kit (Applied Biosystems), and the data collected by the ABI 377 automated fluorescence sequencer (Applied Biosystems).

All sequences were analyzed using the BLASTN, BLASTX and FASTA programs (Altschul et al, *J. Mol. Biol.*, 215:403–410 (1990), Altschul et al, *Nucl. Acids. Res.*, 25:3389–3402 (1997)). The cDNA sequences were compared to a database containing sequences derived from human repeats, mitochondrial DNA, ribosomal RNA, *E. coli* DNA to remove background clones from the dataset using the program cross_match. A further round of comparison was also performed using the program BLASTN2 against known genes (Genbank) and the BAC sequences from the HBM region. Those cDNAs that were >90% homologous to these sequences were filed according to the result and the data stored in a database for further analysis. cDNA sequences that were identified but did not have significant similarity to the BAC sequences from the HBM region or were eliminated by cross_match were hybridized to nylon membranes which contained the BACs from the HBM region, to ascertain whether they hybridized to the target.

Hybridization analysis was used to map the cDNA clones to the BAC target that selected them. The BACs that were identified from the HBM region were arrayed and grown into a 96 well microtiter plate. LB agar containing 25 $\mu$g/ml kanamycin was poured into 96 well microtiter plate lids. Once the agar had solidified, pre-cut Hybond N+ nylon membranes (Amersham) were laid on top of the agar and the BACs were stamped onto the membranes in duplicate using a hand held 96 well replica plater (V&P Scientific, Inc.). The plates were incubated overnight at 37° C. The membranes were processed according to the manufacturers recommendations.

The cDNAs that needed to be mapped by hybridization were PCR amplified using the relevant primer (oligos 1, 3, 5, 7 and 11) that would amplify that clone. For this PCR amplification, the primers were modified to contain a linkered digoxigenin molecule at the 5' of the oligonucleotide. The PCR amplification was performed under the same conditions as described in Preparation of cDNA Pools (above). The PCR products were evaluated for quality and quantity by electrophoresis on a 1% agarose gel by loading 5 $\mu$l of the PCR reaction. The nylon membranes containing the stamped BACs were individually pre-hybridized in 50 ml conical tubes containing 10 ml of hybridization solution (5×SSPE, 0.5×Blotto, 2.5% SDS and 1 mM EDTA (pH 8.0)). The 50 ml conical tubes were placed in a rotisserie oven (Robbins Scientific) for 2 hours at 65° C. 25 ng of each cDNA probe was denatured and added into individual 50 ml conical tubes containing the nylon membrane and hybridization solution. The hybridization was performed overnight at 65° C. The filters were washed for 20 minutes at 65° C. in each of the following solutions: 3×SSPE, 0.1% SDS; 1×SSPE, 0.1% SDS and 0.1×SSPE,0.1% SDS.

The membranes were removed from the 50 ml conical tubes and placed in a dish. Acetate sheets were placed between each membrane to prevent them from sticking to each other. The incubation of the membranes with the Anti-DIG-AP and CDP-Star was performed according to manufacturers recommendations (Boehringer Mannheim). The membranes were wrapped in Saran wrap and exposed to Kodak Bio-Max X-ray film for 1 hour.

X. cDNA Cloning and Expression Analysis

To characterize the expression of the genes identified by direct cDNA selection and genomic DNA sequencing in comparison to the publicly available databases, a series of experiments were performed to further characterize the genes in the HBM region. First, oligonucleotide primers were designed for use in the polymerase chain reaction (PCR) so that portions of a cDNA, EST, or genomic DNA could be amplified from a pool of DNA molecules (a cDNA library) or RNA population (RT-PCR and RACE). The PCR primers were used in a reaction containing genomic DNA to verify that they generated a product of the size predicted based on the genomic (BAC) sequence. A number of cDNA libraries were then examined for the presence of the specific cDNA or EST. The presence of a fragment of a transcription unit in a particular cDNA library indicates a high probability that additional portions of the same transcription unit will be present as well.

A critical piece of data that is required when characterizing novel genes is the length, in nucleotides, of the processed transcript or messenger RNA (mRNA). One skilled in the art primarily determines the length of an mRNA by Northern blot hybridization (Sambrook et al, *Molecular Cloning: A Laboratory Manual*, Cold Spring Harbor Laboratory, Cold Spring Harbor N.Y. (1989)). Groups of ESTs and direct-selected cDNA clones that displayed significant sequence similarity to sequenced BACs in the critical region were grouped for convenience into approximately 30 kilobase units. Within each 30 kilobase unit there were from one up to fifty ESTs and direct-selected cDNA clones which comprised one or more independent transcription units. One or more ESTs or direct-selected cDNAs were used as hybridization probes to determine the length of the mRNA in a variety of tissues, using commercially available reagents (Multiple Tissue Northern blot; Clontech, Palo Alto, Calif.) under conditions recommended by the manufacturer.

Directionally cloned cDNA libraries from femoral bone, and calvarial bone tissue were constructed by methods familiar to one skilled in the art (for example, Soares in Automated DNA Sequencing and Analysis, Adams, Fields and Venter, Eds., Academic Press, N.Y., pages 110–114 (1994)). Bones were initially broken into fragments with a hammer, and the small pieces were frozen in liquid nitrogen and reduced to a powder in a tissue pulverizer (Spectrum Laboratory Products). RNA was extracted from the powdered bone by homogenizing the powdered bone with a standard Acid Guanidiniun Thiocyanate-Phenol-Chloroform extraction buffer (e.g. Chomczynski and Sacchi, *Anal. Biochem.*, 162:156–1 59 (1987)) using a polytron homogenizer (Brinkman Instruments). Additionally, human brain and lung total RNA was purchased from Clontech. PolyA RNA was isolated from total RNA using dynabeads-dT according to the manufacturer's recommendations (Dynal, Inc.).

First strand cDNA synthesis was initiated using an oligonucleotide primer with the sequence: 5'-AACTGGAAGAATTC <u>GCGGCCGC</u>AGGAATTTTTTTTTTTTTTTTTT-3' (SEQ ID NO:27). This primer introduces a NotI restriction site (underlined) at the 3' end of the cDNA. First and second strand synthesis were performed using the "one-tube" cDNA synthesis kit as described by the manufacturer (Life Technologies, Bethesda, Md.). Double stranded cDNAs were treated with T4 polynucleotide kinase to ensure that the ends of the molecules were blunt (Soares in *Automated DNA Sequencing and Analysis*, Adams, Fields and Venter, Eds., Academic Press, N.Y., pages 110–114 (1994)), and the blunt ended cDNAs were then size selected by a Biogel column (Huynh et al in *DNA Cloning*, Vol. 1, Glover, Ed., IRL Press, Oxford, pages 49–78 (1985)) or with a size-sep 400 sepharose column (Pharmacia, catalog # 27-5105-01). Only cDNAs of 400 base pairs or longer were used in subsequent steps. EcoRI adapters (sequence: 5' OH-AATTCGGCACGAG-OH 3' (SEQ ID NO:28), and 5' p-CTCGTGCCG-OH 3' (SEQ ID NO:29)) were then ligated to the double stranded cDNAs by methods familiar to one skilled in the art (Soares, 1994). The EcoRI adapters were then removed from the 3' end of the cDNA by digestion with NotI (Soares, 1994). The cDNA was then ligated into the plasmid vector pBluescript II KS+ (Stratagene, La Jolla, Calif.), and the ligated material was transformed into *E. coli* host DH10B or DH12S by electroporation methods familiar to one skilled in the art (Soares, 1994). After growth overnight at 37° C., DNA was recovered from the *E. coli* colonies after scraping the plates by processing as directed for the Mega-prep kit (Qiagen, Chatsworth, Calif.). The quality of the cDNA libraries was estimated by counting a portion of the total numbers of primary transformants and determining the average insert size and the percentage of plasmids with no cDNA insert. Additional cDNA libraries (human total brain, heart, kidney, leukocyte, and fetal brain) were purchased from Life Technologies, Bethesda, Md.

cDNA libraries, both oligo(dT) and random hexamer ($N_6$) primed, were used for isolating cDNA clones transcribed within the HBM region: human bone, human brain, human kidney and human skeletal muscle (all cDNA libraries were made by the inventors, except for skeletal muscle(dT) and kidney(dT) cDNA libraries). Four 10×10 arrays of each of the cDNA libraries were prepared as follows: the cDNA libraries were titered to $2.5\times10^6$ using primary transformants. The appropriate volume of frozen stock was used to inoculate 2 L of LB/ampicillin (100 mg/ml). This inoculated liquid culture was aliquotted into 400 tubes of 4 ml each. Each tube contained approximately 5000 cfu. The tubes were incubated at 30° C. overnight with gentle agitation. The cultures were grown to an OD of 0.7–0.9. Frozen stocks were prepared for each of the cultures by aliquotting 100 $\mu$l of culture and 300 $\mu$l of 80% glycerol. Stocks were frozen in a dry ice/ethanol bath and stored at −70° C. The remaining culture was DNA prepared using the Qiagen (Chatsworth, Calif.) spin miniprep kit according to the manufacturer's instructions. The DNAs from the 400 cultures were pooled to make 80 column and row pools. The cDNA libraries were determined to contain HBM cDNA clones of interest by PCR. Markers were designed to amplify putative exons. Once a standard PCR optimization was performed and specific cDNA libraries were determined to contain cDNA clones of interest, the markers were used to screen the arrayed library. Positive addresses indicating the presence of cDNA clones were confirmed by a second PCR using the same markers.

Once a cDNA library was identified as likely to contain cDNA clones corresponding to a specific transcript of interest from the HBM region, it was manipulated to isolate the clone or clones containing cDNA inserts identical to the EST or direct-selected cDNA of interest. This was accomplished by a modification of the standard "colony screening" method (Sambrook et al, *Molecular Cloning: A Laboratory Manual*, Cold Spring Harbor Laboratory, Cold Spring Harbor N.Y. (1989)). Specifically, twenty 150 mm LB+ampicillin agar plates were spread with 20,000 colony forming units (cfu) of cDNA library and the colonies allowed to grow overnight at 37° C. Colonies were transferred to nylon filters (Hybond from Amersham, or equivalent) and duplicates prepared by pressing two filters together essentially as described (Sambrook et al, *Molecular Cloning: A Laboratory Manual*, Cold Spring Harbor Laboratory, Cold Spring Harbor N.Y. (1989)). The "master" plate was then incubated an additional 6–8 hours to allow the colonies to grow back. The DNA from the bacterial colonies was then affixed to the nylon filters by treating the filters sequentially with denaturing solution (0.5 N NaOH, 1.5 M NaCl) for two minutes, neutralization solution (0.5 M Tris-Cl pH 8.0, 1.5 M NaCl) for two minutes (twice). The bacterial colonies were removed from the filters by washing in a solution of 2×SSC/0.1% SDS for one minute while rubbing with tissue paper. The filters were air dried and baked under vacuum at 80° C. for 1–2 hours.

A cDNA hybridization probe was prepared by random hexamer labeling (Fineberg and Vogelstein, *Anal. Biochem.*, 132:6–13 (1983)) or by including gene-specific primers and no random hexamers in the reaction (for small fragments). Specific activity was calculated and was >$5\times10^8$ cpm/$10^8$ $\mu$g of cDNA. The colony membranes were then prewashed in 10 mM Tris-Cl pH 8.0, 1 M NaCl, 1 mM EDTA, 0.1% SDS for 30 minutes at 55° C. Following the prewash, the filters were prehybridized in >2 ml/filter of 6×SSC, 50% deionized formamide, 2% SDS, 5×Denhardt's solution, and 100 mg/ml denatured salmon sperm DNA, at 42° C. for 30 minutes. The filters were then transferred to hybridization solution (6×SSC, 2% SDS, 5×Denhardt's, 100 mg/ml denatured salmon sperm DNA) containing denatured $\alpha^{32}$P-dCTP-labelled cDNA probe and incubated at 42° C. for 16–18 hours.

After the 16–18 hour incubation, the filters were washed under constant agitation in 2×SSC, 2% SDS at room temperature for 20 minutes, followed by two washes at 65° C. for 15 minutes each. A second wash was performed in 0.5×SSC, 0.5% SDS for 15 minutes at 65° C. Filters were then wrapped in plastic wrap and exposed to radiographic film for several hours to overnight. After film development, individual colonies on plates were aligned with the autoradiograph so that they could be picked into a 1 ml solution of LB Broth containing ampicillin. After shaking at 37° C. for 1–2 hours, aliquots of the solution were plated on 150 mm plates for secondary screening. Secondary screening was identical to primary screening (above) except that it was performed on plates containing ~250 colonies so that individual colonies could be clearly identified for picking.

After colony screening with radiolabeled probes yielded cDNA clones, the clones were characterized by restriction endonuclease cleavage, PCR, and direct sequencing to confirm the sequence identity between the original probe and the isolated clone. To obtain the full-length cDNA, the novel sequence from the end of the clone identified was used to probe the library again. This process was repeated until the length of the cDNA cloned matches that estimated to be full-length by the northern blot analysis. RT-PCR was used as another method to isolate full length clones. The cDNA was synthesized and amplified using a "Superscript One Step RT-PCR" kit (Life Technologies, Gaithersburg, Md.). The procedure involved adding 1.5 $\mu$g of RNA to the following: 25 $\mu$l of reaction mix provided which is a proprietary buffer mix with $MgSO_4$ and dNTP's, 1 $\mu$l sense primer (10 $\mu$M) and 1 $\mu$l anti-sense primer (10 $\mu$M), 1 $\mu$l reverse transcriptase and Taq DNA polymerase mix provided and autoclaved water to a total reaction mix of 50 $\mu$l. The reaction was then placed in a thermocycler for 1 cycle at 50° C. for 15 to 30 minutes, then 94° C. for 15 seconds, 55–60° C. for 30 seconds and 68–72° C. for 1 minute per kilobase of anticipated product and finally 1 cycle of 72° C. for 5–10 minutes. The sample was analyzed on an agarose gel. The product was excised from the gel and purified from the gel (GeneClean, Bio 101). The purified product was cloned in pCTNR (General Contractor DNA Cloning System, 5 Prime-3 Prime, Inc.) and sequenced to verify that the clone was specific to the gene of interest.

Rapid Amplification of cDNA ends (RACE) was performed following the manufacturer's instructions using a Marathon cDNA Amplification Kit (Clontech, Palo Alto, Calif.) as a method for cloning the 5' and 3' ends of candidate genes. cDNA pools were prepared from total RNA by performing first strand synthesis, where a sample of total RNA sample was mixed with a modified oligo(dT) primer, heated to 70° C., cooled on ice and followed by the addition of: 5× first strand buffer, 10 mM dNTP mix, and AMV Reverse Transcriptase (20 U/$\mu$l). The tube was incubated at 42° C. for one hour and then the reaction tube was placed on ice. For second strand synthesis, the following components were added directly to the reaction tube: 5× second strand buffer, 10 mM dNTP mix, sterile water, 20× second strand enzyme cocktail and the reaction tube was incubated at 16° C. for 1.5 hours. T4 DNA Polymerase was added to the reaction tube and incubated at 16° C. for 45 minutes. The second-strand synthesis was terminated with the addition of an EDTA/Glycogen mix. The sample was subjected to a phenol/chloroform extraction and an ammonium acetate precipitation. The cDNA pools were checked for quality by analyzing on an agarose gel for size distribution. Marathon cDNA adapters (Clontech) were then ligated onto the cDNA ends. The specific adapters contained priming sites that allowed for amplification of either 5' or 3' ends, depending on the orientation of the gene specific primer (GSP) that was chosen. An aliquot of the double stranded cDNA was added to the following reagents: 10 $\mu$M Marathon cDNA adapter, 5× DNA ligation buffer, T4 DNA ligase. The reaction was incubated at 16° C. overnight. The reaction was heat inactivated to terminate the reaction. PCR was performed by the addition of the following to the diluted double stranded cDNA pool: lox cDNA PCR reaction buffer, 10 $\mu$M dNTP mix, 10 $\mu$M GSP, 10 $\mu$M AP1 primer (kit), 50× Advantage cDNA Polymerase Mix. Thermal Cycling conditions were 94° C. for 30 seconds, 5 cycles of 94° C. for 5 seconds, 72° C. for 4 minutes, 5 cycles of 94° C. for 5 seconds, 70° C. for 4 minutes, 23 cycles of 94° C. for 5 seconds, 68° C. for 4 minutes. After the first round of PCR was performed using the GSP to extend to the end of the adapter to create the adapter primer binding site, exponential amplification of the specific cDNA of interest was observed. Usually a second nested PCR is performed to confirm the specific cDNA. The RACE product was analyzed on an agarose gel and then excised and purified from the gel (GeneClean, BIO 101). The RACE product was then cloned into pCTNR (General Contractor DNA Cloning System, 5'-3', Inc.) and the DNA sequence determined to verify that the clone is specific to the gene of interest.

XI. Mutation Analysis

Comparative genes were identified using the above procedures and the exons from each gene were subjected to mutation detection analysis. Comparative DNA sequencing was used to identify polymorphisms in HBM candidate genes from chromosome 11q12-13. DNA sequences for candidate genes were amplified from patient lymphoblastoid cell lines.

The inventors developed a method based on analysis of direct DNA sequencing of PCR products amplified from candidate regions to search for the causative polymorphism. The procedure consisted of three stages that used different subsets of HBM family to find segregating polymorphisms and a population panel to assess the frequency of the polymorphisms. The family resources result from a single founder leading to the assumption that all affected individuals will share the same causative polymorphism.

Candidate regions were first screened in a subset of the HBM family consisting of the proband, daughter, and her mother, father and brother. Monochromosomal reference sequences were produced concurrently and used for comparison. The mother and daughter carried the HBM polymorphism in this nuclear family, providing the ability to monitor polymorphism transmission. The net result is that two HBM chromosomes and six non-HBM chromosomes were screened. This allowed exclusion of numerous frequent alleles. Only alleles exclusively present in the affected individuals passed to the next level of analysis.

Polymorphisms that segregated exclusively with the HBM phenotype in this original family were then re-examined in an extended portion of the HBM pedigree consisting of two additional nuclear families. These families consisted of five HBM and three unaffected individuals. The HBM individuals in this group included the two critical crossover individuals, providing the centromeric and telomeric boundaries of the critical region. Tracking the heredity of polymorphisms between these individuals and their affected parents allowed for further refining of the critical region. This group brought the total of HBM chromosomes screened to seven and the total of non-HBM chromosomes to seventeen.

When a given polymorphism continued to segregate exclusively with the HBM phenotype in the extended group, a population panel was then examined. This panel of 84 persons consisted of 42 individuals known to have normal bone mineral density and 42 individuals known to be unrelated but with untyped bone mineral density. Normal bone mineral density is within two standard deviations of BMD Z score 0. The second group was from the widely used CEPH panel of individuals. Any segregating polymorphisms found to be rare in this population were subsequently examined on the entire HBM pedigree and a larger population.

Polymerase chain reaction (PCR) was used to generate sequencing templates from the HBM family's DNA and monochromosomal controls. Enzymatic amplification of genes within the HBM region on 11q12-13 was accomplished using the PCR with oligonucleotides flanking each exon as well as the putative 5' regulatory elements of each gene. The primers were chosen to amplify each exon as well as 15 or more base pairs within each intron on either side of the splice. All PCR primers were made as chimeras to facilitate dye primer sequencing. The M13-21F (5'-GTA A CGA CGG CCA GT-3') (SEQ ID NO:30) and -28REV (5'-AAC AGC TAT GAC CAT G-3') (SEQ ID NO:31) primer binding sites were built on to the 5' end of each forward and reverse PCR primer, respectively, during synthesis. 150 ng of genomic DNA was used in a 50 $\mu$l PCR with 2UAmpliTaq, 500 mM primer and 125 $\mu$M DNTP. Buffer and cycling conditions were specific to each primer set. TaqStart antibody (Clontech) was used for hot start PCR to minimize primer dimer formation. 10% of the product was examined on an agarose gel. The appropriate samples were diluted 1:25 with deionized water before sequencing.

Each PCR product was sequenced according to the standard Energy Transfer primer (Amersham) protocol. All reactions took place in 96 well trays. 4 separate reactions, one each for A, C, G and T were performed for each template. Each reaction included 2 $\mu$l of the sequencing reaction mix and 3 $\mu$l of diluted template. The plates were then heat sealed with foil tape and placed in a thermal cycler and cycled according to the manufacturer's recommendation. After cycling, the 4 reactions were pooled. 3 $\mu$l of the pooled product was transferred to a new 96 well plate and 1 $\mu$l of the manufacturer's loading dye was added to each well. All 96 well pipetting procedures occurred on a Hydra 96 pipetting station (Robbins Scientific, USA). 1 $\mu$l of pooled material was directly loaded onto a 48 lane gel running on an ABI 377 DNA sequencer for a 10 hour, 2.4 kV run. Polyphred (University of Washington) was used to assemble sequence sets for viewing with Consed (University of Washington). Sequences were assembled in groups representing all relevant family members and controls for a specified target region. This was done separately for each of the three stages. Forward and reverse reads were included for each individual along with reads from the monochromosomal templates and a color annotated reference sequence. Polyphred indicated potential polymorphic sites with a purple flag. Two readers independently viewed each assembly and assessed the validity of the purple-flagged sites.

A total of 23 exons present in the mature mRNA and several other portions of the primary transcript were evaluated for heterozygosity in the nuclear family of two HBM-affected and two unaffected individuals. 25 SNPs were identified, as shown in the table below.

TABLE 4

Single Nucleotide Polymorphisms in the Zmax1 Gene and Environs

| Exon Name | Location | Base Change |
|---|---|---|
| b200e21-h_Contig1_1.nt | 69169 (309G) | C/A |
| b200e21-h_Contig4_12.nt | 27402 (309G) | A/G |
| b200e21-h_Contig4_13.nt | 27841 (309G) | T/C |
| b200e21-h_Contig4_16.nt | 35600 (309G) | A/G |
| b200e21-h_Contig4_21.nt | 45619 (309G) | G/A |
| b200e21-h_Contig4_22.nt-a | 46018 (309G) | T/G |
| b200e21-h_Contig4_22.nt-b | 46093 (309G) | T/G |
| b200e21-h_Contig4_22.nt-c | 46190 (309G) | A/G |
| b200e21-h_Contig4_24.nt-a | 50993 (309G) | T/C |
| b200e21-h_Contig4_24.nt-b | 51124 (309G) | C/T |
| b200e21-h_Contig4_25.nt | 55461 (309G) | C/T |
| b200e21-h_Contig4_33.nt-a | 63645 (309G) | C/A |
| b200e21-h_Contig4_33.nt-b | 63646 (309G) | A/C |
| b200e21-h_Contig4_61.nt | 24809 (309G) | T/G |
| b200e21-h_Contig4_62.nt | 27837 (309G) | T/C |
| b200e21-h_Contig4_63.nt-a | 31485 (309G) | C/T |
| b200e21-h_Contig4_63.nt-b | 31683 (309G) | A/G |
| b200e21-h_Contig4_9.nt | 24808 (309G) | T/G |
| b527d12-h_Contig030g_1.nt-a | 31340 (308G) | T/C |
| b527d12-h_Contig030g_1.nt-b | 32538 (308G) | A/G |
| b527d12-h_Contig080C_2.nt | 13224 (308G) | A/G |
| b527d12-h_Contig087C_1.nt | 21119 (308G) | C/A |
| b527d12-h_Contig087C_4.nt | 30497 (308G) | G/A |
| b527d12-h_Contig088C_4.nt | 24811 (309G) | A/C |
| b527d12-h_Contig089_1HP.nt | 68280 (309G) | G/A |

In addition to the polymorphisms presented in Table 4, two additional polymorphisms can also be present in SEQ ID NO:2. These is a change at position 2002 of SEQ ID NO:2. Either a guanine or an adenine can appear at this position. This polymorphism is silent and is not associated with any change in the amino acid sequence. The second change is at position 4059 of SEQ ID NO:2 corresponding in a cytosine (C) to thymine (T) change. This polymorphism results in a corresponding amino acid change from a valine (V) to an alanine (A). Other polymorphisms were found in the candidate gene exons and adjacent intron sequences. Any one or combination of the polymorphisms listed in Table 4 or the two discussed above could also have a minor effect on bone mass when present in SEQ ID NO:2.

The present invention encompasses the nucleic acid sequences having the nucleic acid sequence of SEQ ID NO: 1 with the above-identified point mutations.

Figure 5:
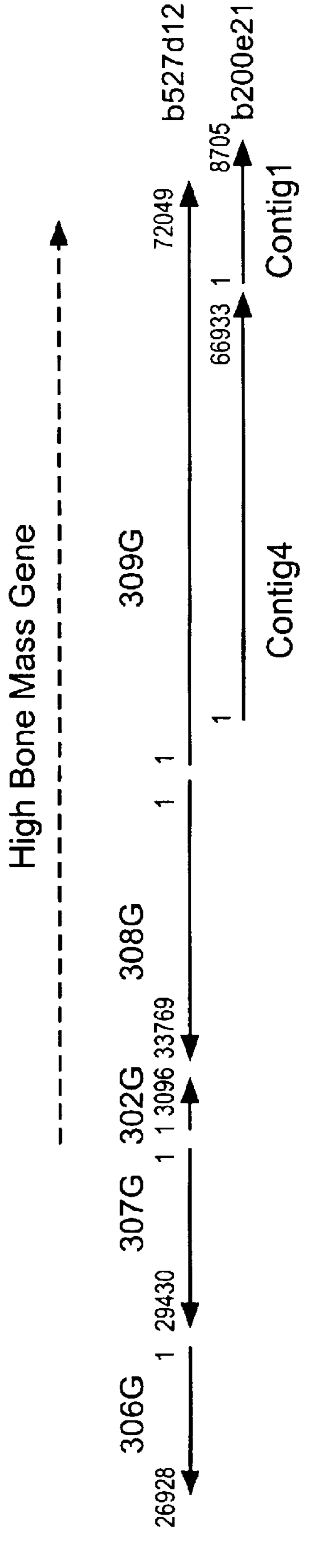
FIG. 5 is a schematic illustration of the BAC contigs B527D12 and B200E21 in relation to the HBM gene.

Preferably, the present invention encompasses the nucleic acid of SEQ ID NO: 2. Specifically, a base-pair substitution changing G to T at position 582 in the coding sequence of Zmax1 (the HBM gene) was identified as heterozygous in all HBM individuals, and not found in the unaffected individuals (i.e., b527d12-h_Contig087C_1.nt). FIG. 5 shows the order of the contigs in B527D12. The direction of transcription for the HBM gene is from left to right. The sequence of contig308G of B527D12 is the reverse complement of the coding region to the HBM gene. Therefore, the relative polymorphism in contig 308G shown in Table 4 as a base change substitution of C to A is the complement to the G to T substitution in the HBM gene. This mutation causes a substitution of glycine 171 with valine (G171V).

The HBM polymorphism was confirmed by examining the DNA sequence of different groups of individuals. In all members of the HBM pedigree (38 individuals), the HBM polymorphism was observed in the heterozygous form in affected (i.e., elevated bone mass) individuals only (N=18). In unaffected relatives (N=20) (BMDZ<2.0) the HBM polymorphism was never observed. To determine whether this gene was ever observed in individuals outside of the HBM pedigree, 297 phenotyped individuals were characterized at the site of the HBM gene. None were heterozygous at the site of the HBM polymorphism. In an unphenotyped control group, 1 of 42 individuals was observed to be heterozygous at position 582. Since this individual is deceased, their bone mineral density could not be obtained. Taken together, these data prove that the polymorphism observed in the kindred displaying the high bone mass phenotype is strongly correlated with the G®T polymorphism at position 582 of Zmax1. Taken together, these results establish that the HBM polymorphism genetically segregates with the HBM phenotype, and that both the HBM polymorphism and phenotype are rare in the general population.

XII. Allele Specific Oligonucleotide (ASO) Analysis

The amplicon containing the HBM1 polymorphism was PCR amplified using primers specific for the exon of interest. The appropriate population of individuals was PCR amplified in 96 well microtiter plates as follows. PCR reactions (20 $\mu$l) containing 1× Promega PCR buffer (Cat. # M1883 containing 1.5 mM $MgCl_2$), 100 mM dNTP, 200 mM PCR primers (SEQ. ID. NO.: 629–630) (1863F: CCAAGTTCTGAGAAGTCC and 1864R: AATACCTGAAACCATACCTG), 1 U Amplitaq, and 20 ng of genomic DNA were prepared and amplified under the following PCR conditions: 94° C.., 1 minute, (94° C., 30 sec.; 58° C., 30 sec.; 72° C., 1 min.) X35 cycles), 72° C., 5', 4° C., hold. Loading dye was then added and 10 $\mu$l of the products was electrophoresed on 1.5% agarose gels containing 1 $\mu$g/ml ethidium bromide at 100–150 V for 5–10 minutes. Gels were treated 20 minutes in denaturing solution (1.5 M NaCl, 0.5 N NaOH), and rinsed briefly with water. Gels were then neutralized in 1 M Tris-HCl, pH 7.5, 1.5 M NaCl, for 20 minutes and rinsed with water. Gels were soaked in 10×SSC for 20 minutes and blotted onto nylon transfer membrane (Hybond N+-Amersham) in 10×SSC overnight. Filters were the rinsed in 6×SSC for 10 minutes and UV crosslinked.

The allele specific oligonucleotides (ASO) were designed with the polymorphism approximately in the middle. Oligonucleotides were phosphate free at the 5' end and were purchased from Gibco BRL. Sequences of the oligonucleotides are (SEQ. ID. NOS.: 631–632):

2326 Zmax1.ASO.g: AGACTGGGGTGAGACGC

2327 Zmax1.ASO.t: CAGACTGGGTTGAGACGCC

The polymorphic nucleotides are underlined. To label the oligos, 1.5 $\mu$l of 1 $\mu$g/$\mu$l ASO oligo (2326.Zmax1.ASO.g or 2327.Zmax1.ASO.t), 11 $\mu$l dd$H_2O$, 2 $\mu$l 10× kinase forward buffer, 5 $\mu$l $\gamma$-$^{32}$P-ATP (6000 Ci/mMole), and 1 $\mu$l T4 polynucleotide kinase (10 U/$\mu$l) were mixed, and the reaction incubated at 37° C. for 30–60 minutes. Reactions were then placed at 95° C. for 2 minutes and 30 ml $H_2O$ was added. The probes were purified using a G25 microspin column (Pharmacia).

Blots were prehybridized in 10 ml 5×SSPE, 5×Denhardt's, 2% SDS, and 100 $\mu$g/ml, denatured, sonicated salmon sperm DNA at 40° C. for 2 hr. The entire reaction mix of kinased oligo was then added to 10 ml fresh hybridization buffer (5×SSPE, 5×Denhardts, 2% SDS) and hybridized at 40° C. for at least 4 hours to overnight.

All washes done in 5×SSPE, 0.1%. SDS. The first wash was at 45° C. for 15 minutes; the solution was then changed and the filters washed 50° C. for 15 minutes. Filters were then exposed to Kodak biomax film with 2 intensifying screens at −70° C. for 15 minutes to 1 hr. If necessary the filters were washed at 55° C. for 15 minutes and exposed to film again. Filters were stripped by washing in boiling 0.1×SSC, 0.1% SDS for 10 minutes at least 3 times.

Figure 9:
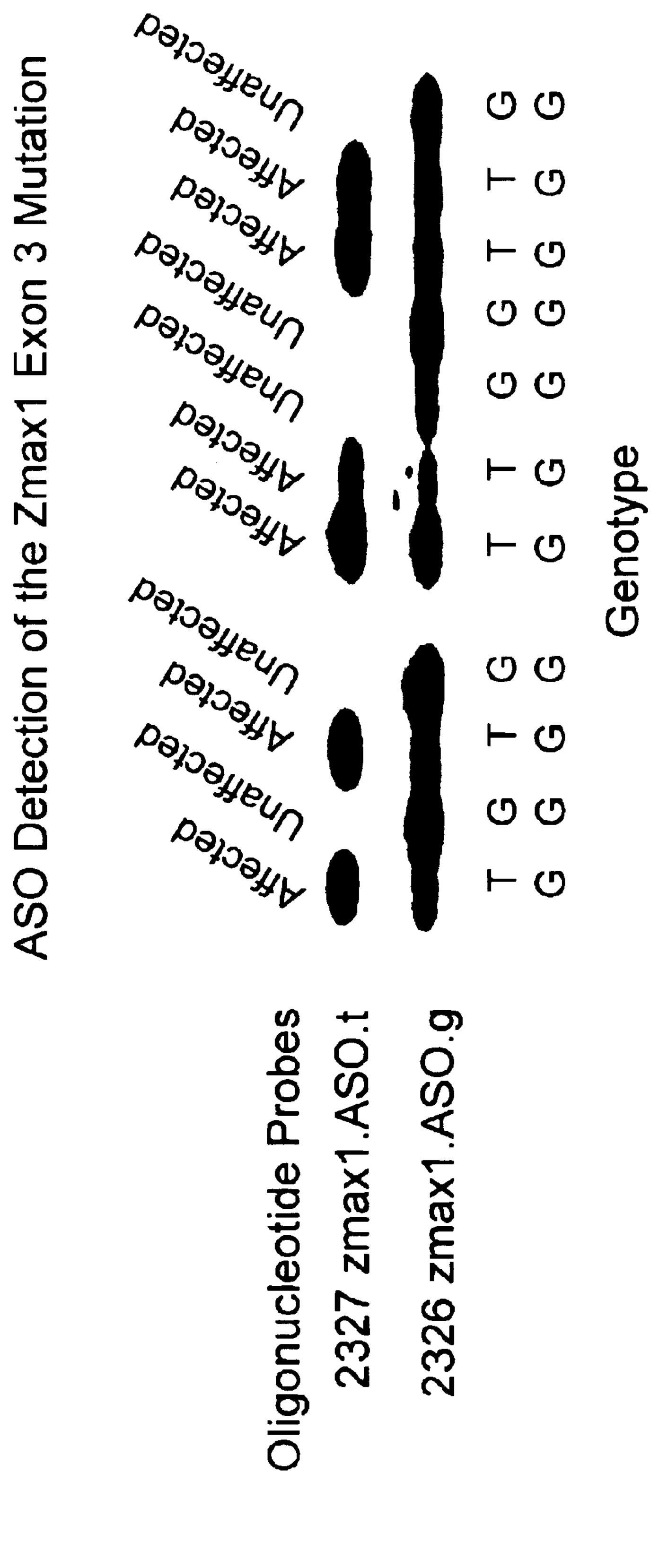
FIG. 9 is allele specific oligonucleotide detection of the Zmax1 exon 3 mutation.

The two films that best captured the allele specific assay with the 2 ASOs were converted into digital images by scanning them into Adobe PhotoShop. These images were overlaid against each other in Graphic Converter and then scored and stored in FileMaker Pro 4.0 (see FIG. 9).

XIII. Cellular Localization of Zmax1

A. Gene Expression in Rat Tiba by Non Isotopic In Situ Hybridization

In situ hybridization was conducted by Pathology Associates International (PAI), Frederick, Md. This study was undertaken to determine the specific cell types that express the Zmax1 gene in rat bone with particular emphasis on areas of bone growth and remodeling. Zmax1 probes used in this study were generated from both human (HuZmax1) and mouse (MsZmax1) cDNAs, which share an 87% sequence identity. The homology of human and mouse Zmax1 with rat Zmax1 is unknown.

For example, gene expression by non-isotopic in situ hybridization was performed as follows, but other methods would be known to the skilled artisan. Tibias were collected from two 6 to 8 week old female Sprague Dawley rats euthanized by carbon dioxide asphyxiation. Distal ends were removed and proximal tibias were snap frozen in OCT embedding medium with liquid nitrogen immediately following death. Tissues were stored in a −80° C. freezer.

Probes for amplifying PCR products from cDNA were prepared as follows. The primers to amplify PCR products from a cDNA clone were chosen using published sequences of both human LRP5 (Genbank Accession No. ABO17498) and mouse LRP5 (Genbank Accession No. ABO64984). In order to minimize cross reactivity with other genes in the LDL receptor family, the PCR products were derived from an intracellular portion of the protein coding region. PCR was performed in a 50 $\mu$l reaction volume using cDNA clone as template. PCR reactions contained 1.5 mM $MgCl_2$, 1 unit Amplitaq, 200 $\mu$M dNTPs and 2 $\mu$M each primer. PCR cycling conditions were 94° C. for 1 min., followed by 35 cycles of 94° C. for 30 seconds, 55° C. for 30 seconds, 72°

C. for 30 seconds; followed by a 5 minute extension at 72° C. The reactions were then run on a 1.5% agarose Tris-Acetate gel. DNA was eluted from the agarose, ethanol precipitated and resuspended in 10 mM Tris, pH 8.0. Gel purified PCR products were prepared for both mouse and human cDNAs and supplied to Pathology Associates International for in situ hybridizations.

The sequence of the human and mouse PCR primers and products were as follows:

Human Zmax1 sense primer (HBM1253 (SEQ. ID. NO.: 633)

CCCGTGTGCTCCGCCGCCCAGTTC

Human Zmax1 antisense primer (HBM1465) (SEQ. ID. NO.: 634)

GGCTCACGGAGCTCATCATGGACTT

Human Zmax1 PCR product (SEQ. ID. NO.: 635)

CCCGTGTGCTCCGCCGCCCAGTTCCCCT-
GCGCGCGGGGTCAGTGTGTGGACCTGC GCCT-
GCGCTGCGACGGCGAGGCAGACTGTCAG-
GACCGCTCAGACGAGGTGGACT
GTGACGCCATCTGCCTGCCCAACCAGT-
TCCGGTGTGCGAGCGGCCAGTGTGTCCT CAT-
CAAACAGCAGTGCGACTCCTTC-
CCCGACTGTATCGACGGCTCCGACGAGCTC
ATGTGTGAAATCACCAAGCCGCCCTCA-
GACGACAGCCCGGCCCACAGCAGTGCC
ATCGGGCCCGTCATTGGCATCATC-
CTCTCTCTCTTCGTCATGGGTGGTGTCTATTT
TGTGTGCCAGCGCGTGGTGTGCCAGCGC-
TATGCGGGGGCCAACGGGCCCTTCCC GCAC-
GAGTATGTCAGCGGGACCCCGCACGTGC-
CCCTCAATTTCATAGCCCCGGG
CGGTTCCCAGCATGGCCCCTTCACAG-
GCATCGCATGCGGAAAGTCCATGATGAG CTC-
CGTGAGCC

Mouse Zmax1 Sense primer (HBM1655) (SEQ. ID. NO.: 636)

AGCGAGGCCACCATCCACAGG

Mouse Zmax1 antisense primer (HBM1656) (SEQ. ID. NO.: 637)

TCGCTGGTCGGCATAATCAAT

Mouse Zmax1 PCR product (SEQ. ID. NO.: 638)

AGCAGAGCCACCATCCACAGGATCTC-
CCTGGAGACTAACAACAACGATGTGGCT ATC-
CCACTCACGGGTGTCAAAGAGGCCTCTG-
CACTGGACTTTGATGTGTCCAACA
ATCACATCTACTGGACTGATGTTAGCCT-
CAAGACGATCAGCCGAGCCTTCATGAA TGG-
GAGCTCAGTGGAGCACGTGAT-
TGAGTTTGGCCTCGACTACCCTGAAGGAAT
GGCTGTGGACTGGATGGGCAAGAACCTC-
TATTGGGCGGACACAGGGACCAACAG GAT-
TGAGGTGGCCCGGCTGGATGGGCAGTTC-
CGGCAGGTGCTTGTGTGGAGAGA
CCTTGACAACCCCAGGTCTCTGGCTCTG-
GATCCTACTAAAGGCTACATCTACTGG ACT-
GAGTGGGGTGGCAAGCCAAGGATTGT-
GCGGGCCTTCATGGATGGGACCAAT
TGTATGACACTGGTAGACAAGGTGGGC-
CGGGCCAACGACCTCACCATTGATTAT
GCCGACCAGCGA

Riboprobes were synthesized as follows. The PCR products were reamplified with chimeric primers designed to incorporate either a T3 promoter upstream, or a T7 promoter downstream of the reamplification products. The resulting PCR products were used as template to synthesize digoxigenin-labeled riboprobes by in vitro transcription (IVT). Antisense and sense riboprobes were synthesized using T7 and T3 RNA polymerases, respectively, in the presence of digoxigenin-11-UTP (Boehringer-Mannheim) using a MAXIscript IVT kit (Ambion) according to the manufacturer. The DNA was then degraded with Dnase-1, and unincorporated digoxigenin was removed by ultrafiltration. Riboprobe integrity was assessed by electrophoresis through a denaturing polyacrylamide gel. Molecular size was compared with the electrophoretic mobility of a 100–1000 base pair (bp) RNA ladder (Ambion). Probe yield and labeling was evaluated by blot immunochemistry. Riboprobes were stored in 5 μl aliquots at −80° C.

The in situ hybridization was performed as follows. Frozen rat bone was cut into 5 μM sections on a Jung CM3000 cryostat (Leica) and mounted on adhesive slides (Instrumedics). Sections were kept in the cryostat at −20° C. until all the slides were prepared in order to prevent mRNA degradation prior to post-fixation for 15 minutes in 4% paraformaldehyde. Following post-fixation, sections were incubated with 1 ng/μl of either antisense or sense riboprobe in Pathology Associates International (PAI) customized hybridization buffer for approximately 40 hours at 58° C. Following hybridization, slides were subjected to a series of post-hybridization stringency washes to reduce nonspecific probe binding. Hybridization was visualized by immunohistochemistry with an anti-digoxigenin antibody (FAB fragment) conjugated to alkaline phosphatase. Nitroblue tetrazolium chloride/bromochloroindolyl phosphate (Boehringer-Mannheim), a precipitating alkaline phosphatase substrate, was used as the chromogen to stain hybridizing cells purple to nearly black, depending on the degree of staining. Tissue sections were counter-stained with nuclear fast red. Assay controls included omission of the probe, omission of probe and anti-digoxigenin antibody.

Specific cell types were assessed for demonstration of hybridization with antisense probes by visualizing a purple to black cytoplasmic and/or peri-nuclear staining indicating a positive hybridization signal for mRNA. Each cell type was compared to the replicate sections, which were hybridized with the respective sense probe. Results were considered positive if staining was observed with the antisense probe and no staining or weak background with the sense probe.

Figure 10A:
FIGS. 10A–10B are the cellular localization of mouse Zmax1 by in situ hybridization at 100× magnification using sense and antisense probes.
Figure 10B:
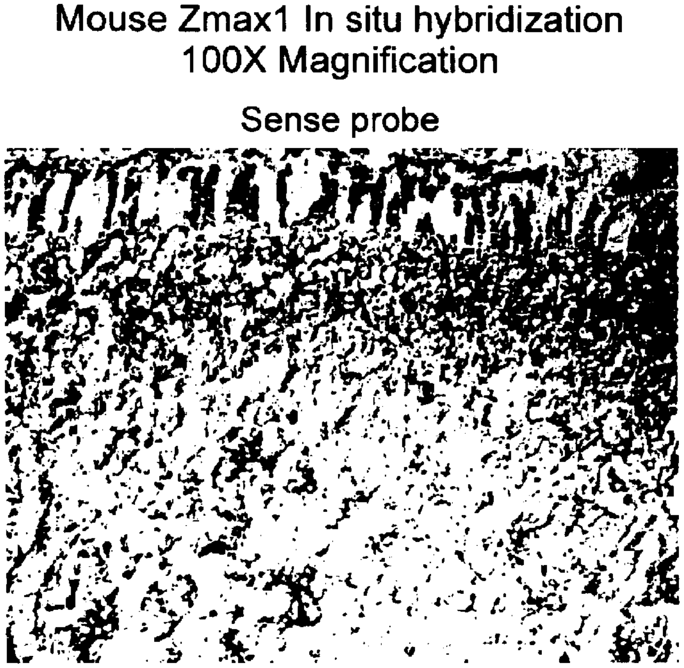
Figure 11A:
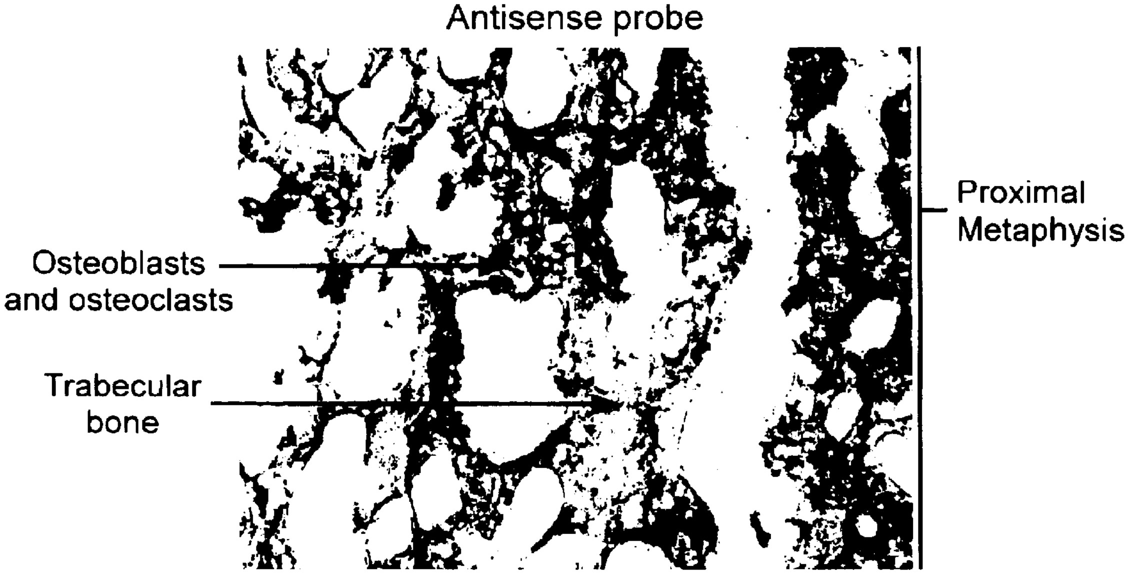
FIGS. 11A–11B are the cellular localization of mouse Zmax1 by in situ hybridization at 400× magnification using sense and antisense probes.
Figure 11B:
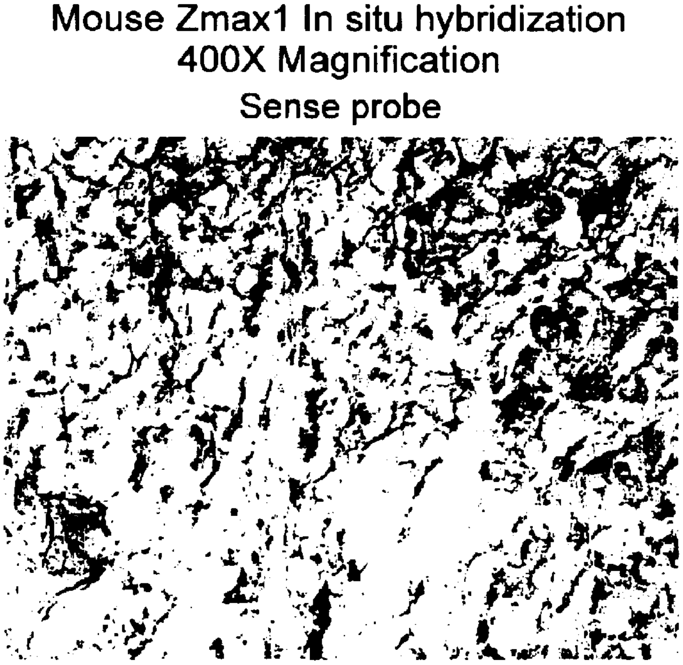
Figure 12A:
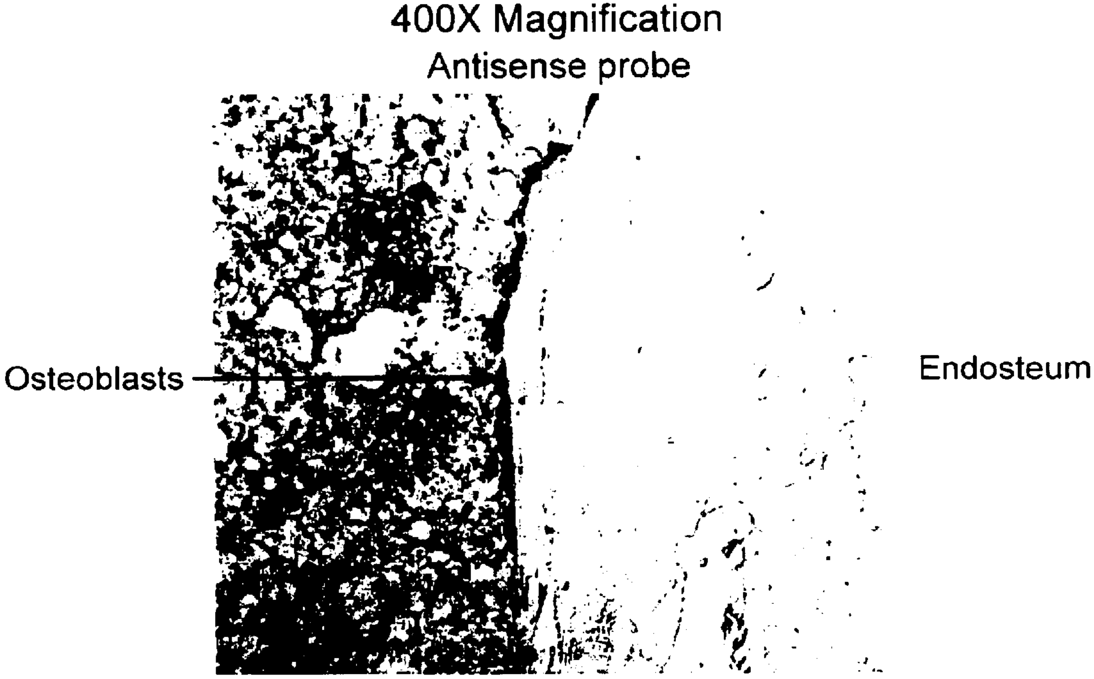
FIGS. 12A–12B are the cellular localization of mouse Zmax1 by in situ hybridization of osteoblasts in the endosteum at 400× magnification using sense and antisense probes.
Figure 12B:

The cellular localization of the hybridization signal for each of the study probes is summarized in Table 5. Hybridization for Zmax1 was primarily detected in areas of bone involved in remodeling, including the endosteum and trabecular bone within the metaphysis. Hybridization in selected bone lining cells of the periosteum and epiphysis were also observed. Positive signal was also noted in chondrocytes within the growth plate, particularly in the proliferating chondrocytes. See FIGS. 10, 11 and 12 for representative photomicrographs of in situ hybridization results.

TABLE 5

Summary of Zmax1 in situ hybridization in rat tibia

| PROBE | SITE | ISH SIGNAL |
|---|---|---|
| Hu Zmax1 | Epiphysis | |
| | Osteoblasts | + |
| | Osteoclasts | − |

TABLE 5-continued

Summary of Zmax1 in situ hybridization in rat tibia

| PROBE | SITE | ISH SIGNAL |
|---|---|---|
| | Growth Plate | |
| | resting chondrocytes | – |
| | proligferating chondrocytes | + |
| | hypertrophic chondrocytes | – |
| | Metaphysis | |
| | osteoblasts | + |
| | osteoclasts | + |
| | Diaphysis | – |
| | Endosteum | |
| | osteoblasts | + |
| | osteoclasts | + |
| | Periosteum | – |
| MsZmax1 | Epiphysis | |
| | Osteoblasts | + |
| | Osteoclasts | – |
| | Growth Plate | |
| | resting chondrocytes | – |
| | proligferating chondrocytes | + |
| | hypertrophic chondrocytes | + |
| | Metaphysis | |
| | osteoblasts | + |
| | osteoclasts | + |
| | Diaphysis | – |
| | Endosteum | |
| | osteoblasts | + |
| | osteoclasts | + |
| | Periosteum | + |

Legend:
"+" = hybridization signal detected
"–" = no hybridization signal detected
"ISH"—In situ hybridization These studies confirm the positional expression of Zmax1 in cells involved in bone remodeling and bone formation. Zmax1 expression in the zone of proliferation and in the osteoblasts and osteoclasts of the proximal metaphysis, suggests that the Zmax1 gene is involved in the process of bone growth and mineralization. The activity and differentiation of osteoblasts and osteoclasts are closely coordinated during development as bone is formed and during growth as well as in adult life as bone undergoes continuous remodeling. The formation of internal bone structures and bone remodeling result from the coupling of bone resorption by activated osteoclasts with subsequent deposition of new material by osteoblasts. Zmax1 is related to the LDL receptor gene, and thus may be a receptor involved in mechanosensation and subsequent signaling in the process of bone remodeling. Therefore, changes in the level of expression of this gene could impact on the rate of remodeling and degree of mineralization of bone.

XIV. Antisense

Antisense oligonucleotides are short synthetic nucleic acids that contain complementary base sequences to a targeted RNA. Hybridization of the RNA in living cells with the antisense oligonucleotide interferes with RNA function and ultimately blocks protein expression. Therefore, any gene for which the partial sequence is known can be targeted by an antisense oligonucleotide.

Antisense technology is becoming a widely used research tool and will play an increasingly important role in the validation and elucidation of therapeutic targets identified by genomic sequencing efforts.

Antisense technology was developed to inhibit gene expression by utilizing an oligonucleotide complementary to the mRNA that encodes the target gene. There are several possible mechanisms for the inhibitory effects of antisense oligonucleotides. Among them, degradation of mRNA by RNase H is considered to be the major mechanism of inhibition of protein function. This technique was originally used to elucidate the function of a target gene, but may also have therapeutic applications, provided it is designed carefully and properly.

An example of materials and methods for preparing antisense oligonucleotides can be performed as follows. Preliminary studies have been undertaken in collaboration with Sequiter (Natick, Mass.) using the antisense technology in the osteoblast-like murine cell line, MC3T3. These cells can be triggered to develop along the bone differentiation sequence. An initial proliferation period is characterized by minimal expression of differentiation markers and initial synthesis of collagenous extracellular matrix. Collagen matrix synthesis is required for subsequent induction of differentiation markers. Once the matrix synthesis begins, osteoblast marker genes are activated in a clear temporal sequence: alkaline phosphatase is induced at early times while bone sialoprotien and osteocalcin appear later in the differentiation process. This temporal sequence of gene expression is useful in monitoring the maturation and mineralization process. Matrix mineralization, which does not begin until several days after maturation has started, involves deposition of mineral on and within collagen fibrils deep within the matrix near the cell layer-culture plate interface. The collagen fibril-associated mineral formed by cultured osteoblasts resembles that found in woven bone in vivo and therefore is used frequently as a study reagent.

MC3T3 cells were transfected with antisense oligonucleotides for the first week of the differentiation, according to the manufacturer's specifications (U.S. Pat. No. 5,849,902).

The oligonucleotides designed for Zmax1 are given below (SEQ. ID. NOS.: 639–641):

10875: AGUACAGCUUCUUGCCAACCCAGUC

10876: UCCUCCAGGUCGAUGGUCAGCCCAU

10877: GUCUGAGUCCGAGUUCAAAUCCAGG

Figure 13:
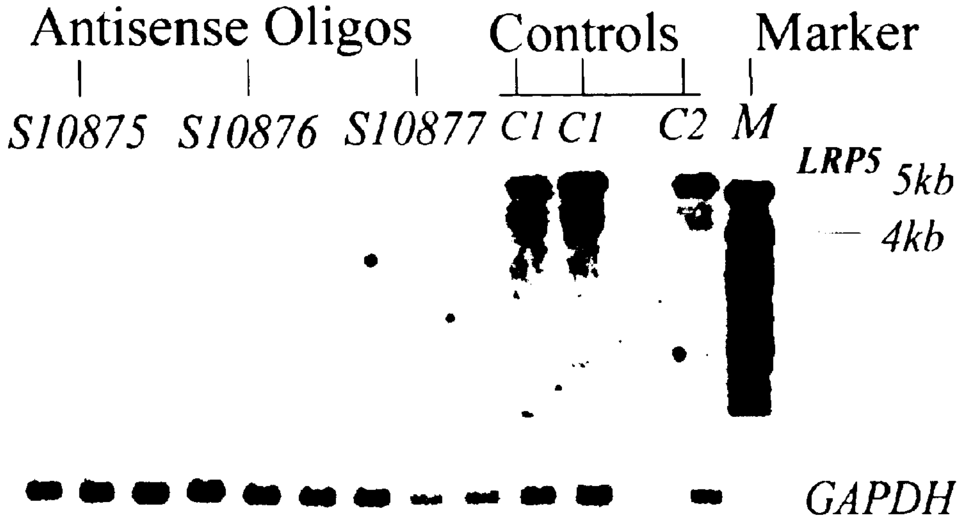
FIG. 13 shows antisense inhibition of Zmax1 expression in MC-3T3 cells.

FIG. 13 shows the results of antisense inhibition of Zmax1 in MC3T3 cells. The three oligonucleotides shown above were transfected into MC3T3 and RNA was isolated according to standard procedures. Northern analysis clearly shows markedly lower steady state levels of the Zmax1 transcript while the control gene GAPDH remained unchanged. Thus, antisense technology using the primers described above allows for the study of the role of Zmax1 expression on bone biology.

The protein encoded by Zmax1 is related to the Low Density Lipoprotein receptor (LDL receptor). See, Goldstein et al, *Ann. Rev. Cell Biology*, 1:1–39 (1985); Brown et al, *Science*, 232:34–47 (1986). The LDL receptor is responsible for uptake of low density lipoprotein, a lipid-protein aggregate that includes cholesterol. Individuals with a defect in the LDL receptor are deficient in cholesterol removal and tend to develop artherosclerosis. In addition, cells with a defective LDL receptor show increased production of cholesterol, in part because of altered feedback regulation of cholesterol synthetic enzymes and in part because of increased transcription of the genes for these enzymes. In some cell types, cholesterol is a precursor for the formation of steroid hormones.

Thus, the LDL receptor may, directly or indirectly, function as a signal transduction protein and may regulate gene expression. Because Zmax1 is related to the LDL receptor, this protein may also be involved in signaling between cells in a way that affects bone remodeling.

The glycine 171 amino acid is likely to be important for the function of Zmax1 because this amino acid is also found in the mouse homologue of Zmax1. The closely related LRP6 protein also contains glycine at the corresponding position (Brown et al, *Biochemical and Biophysical Research Comm.*, 248:879–888 (1988)). Amino acids that are important in a protein's structure or function tend to be conserved between species, because natural selection prevents mutations with altered amino acids at important positions from arising.

In addition, the extracellular domain of Zmax1 contains four repeats consisting of five YWT motifs followed by an EFG motif. This 5YWT+EGF repeat is likely to form a distinct folded protein domain, as this repeat is also found in the LDL receptor and other LDL receptor-related proteins. The first three 5YWT+EGF repeats are very similar in their structure, while the fourth is highly divergent. Glycine 171 occurs in the central YWT motif of the first 5YWT+EGF repeat in Zmax1. The other two similar 5YWT+EGF repeats of Zmax1 also contain glycine at the corresponding position, as does the 5YWT+EGF repeat in the LDL receptor protein. However, only 17.6% of the amino acids are identical among the first three 5YWT+EGF repeats in Zmax1 and the single repeat in the LDL receptor. These observations indicate that glycine 171 is essential to the function of this repeat, and mutation of glycine 171 causes a functional alteration of Zmax1. The cDNA and peptide sequences are shown in FIGS. 6A–6E. The critical base at nucleotide position 582 is indicated in bold and is underlined.

Figure 7B:
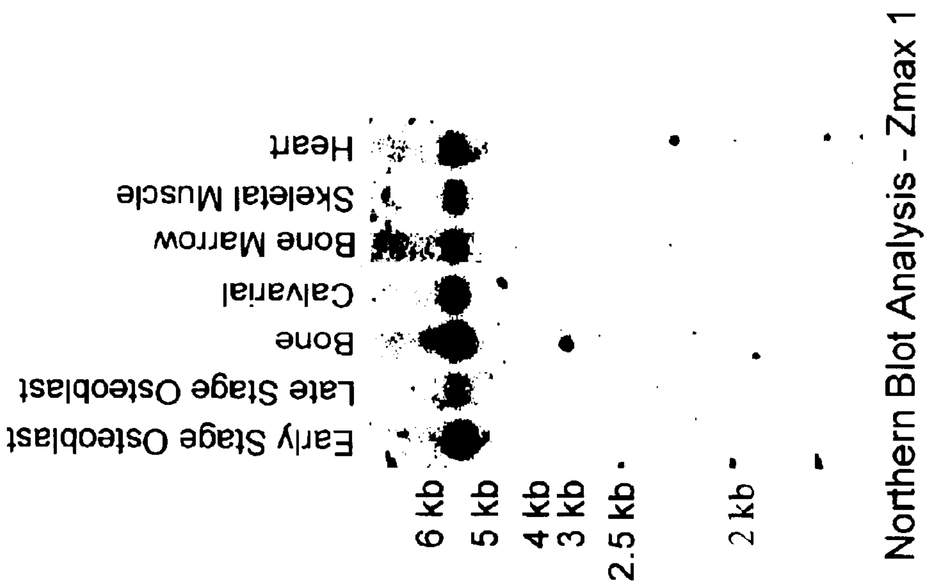
FIGS. 7A and 7B are northern blot analyses showing the expression of Zmax1 in various tissues.
Figure 7A:
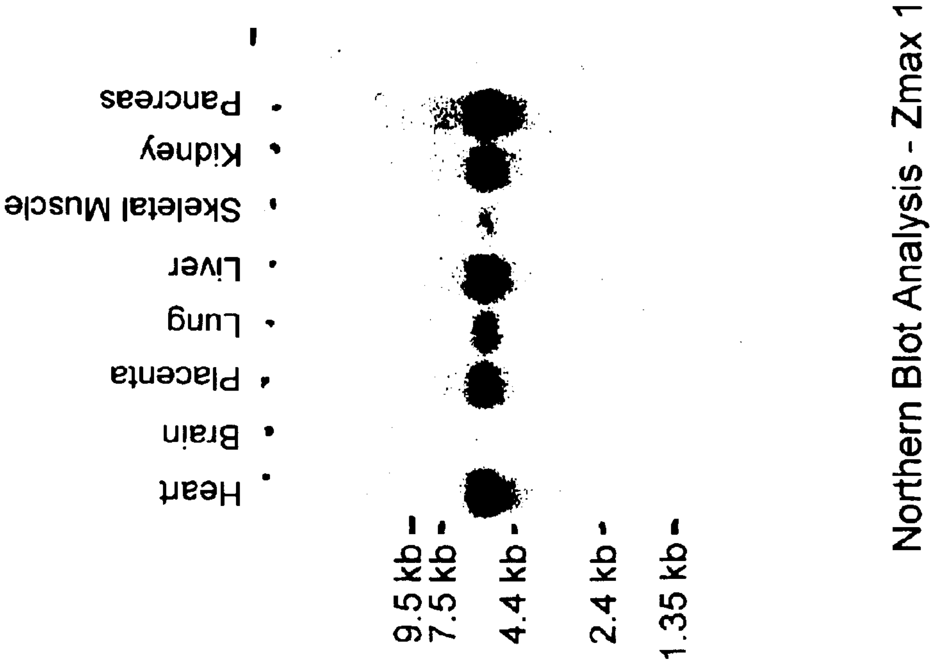
Figure 8:
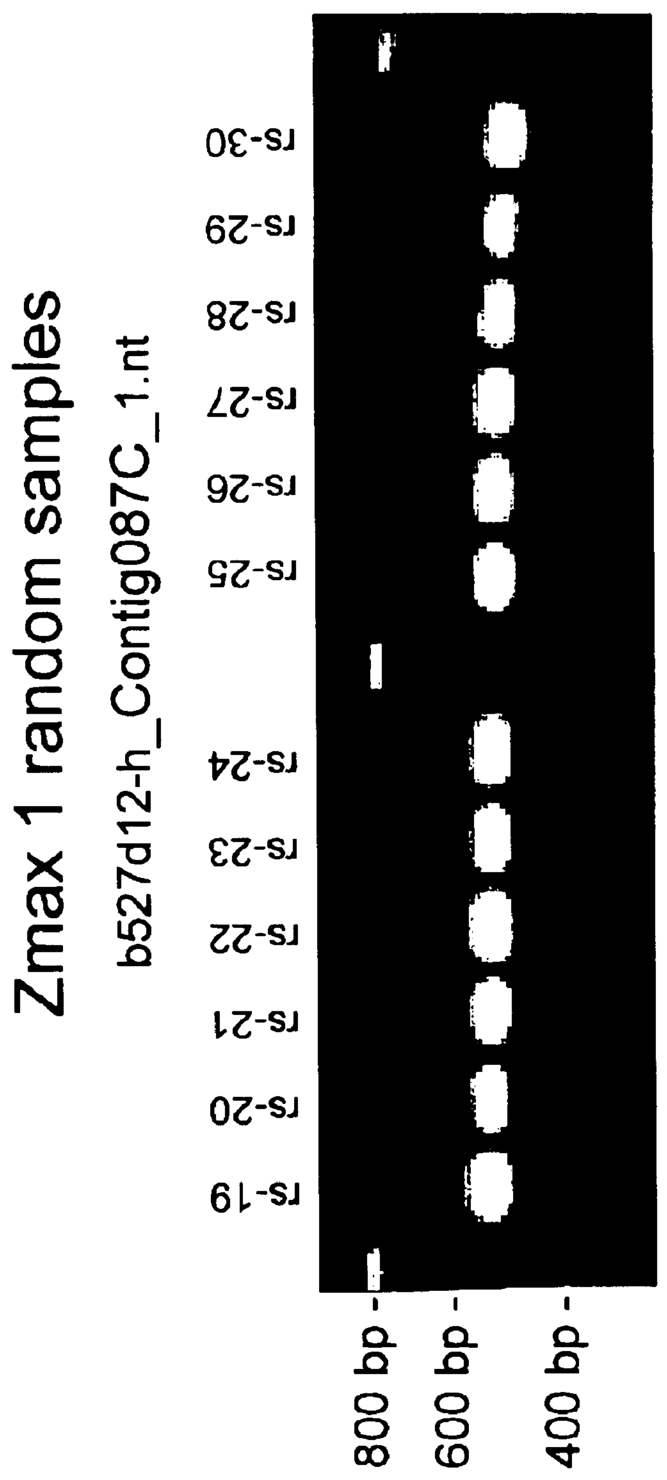
FIG. 8 is a PCR product analysis.

Northern blot analysis (FIGS. 7A–B) reveals that Zmax1 is expressed in human bone tissue as well as numerous other tissues. A multiple-tissue Northern blot (Clontech, Palo Alto, Calif.) was probed with exons from Zmax1. As shown in FIG. 7A, the 5.5 kb Zmax1 transcript was highly expressed in heart, kidney, lung, liver and pancreas and is expressed at lower levels in skeletal muscle and brain. A second northern blot, shown in FIG. 7B, confirmed the transcript size at 5.5 kb, and indicated that Zmax1 is expressed in bone, bone marrow, calvaria and human osteoblastic cell lines.

Taken together, these results indicate that the HBM polymorphism in the Zmax1 gene is responsible for the HBM phenotype, and that the Zmax1 gene is important in bone development. In addition, because mutation of Zmax1 can alter bone mineralization and development, it is likely that molecules that bind to Zmax1 may usefully alter bone development. Such molecules may include, for example, small molecules, proteins, RNA aptamers, peptide aptamers, and the like.

XV. Preparation of Nucleic Acids, Vectors, Transformations and Host Cells

Large amounts of the nucleic acids of the present invention may be produced by replication in a suitable host cell. Natural or synthetic nucleic acid fragments coding for a desired fragment will be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, N.Y. (1992).

The nucleic acids of the present invention may also be produced by chemical synthesis, e.g., by the phosphoramidite method described by Beaucage et al, *Tetra. Letts.*, 22:1859–1862 (1981) or the triester method according to Matteucci, et al, *J. Am. Chem. Soc.*, 103:3185 (1981), and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Nucleic acid constructs prepared for introduction into a prokaryotic or eukaryotic host may comprise a replication system recognized by the host, including the intended nucleic acid fragment encoding the desired protein, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HBM or Zmax1 protein or from other receptors or from secreted proteins of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, N.Y. (1992).

An appropriate promoter and other necessary vector sequences will be selected so as to be functional in the host, and may include, when appropriate, those naturally associated with Zmax1 or HBM genes. Examples of workable combinations of cell lines and expression vectors are described in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, N.Y. (1992). Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in EP 73,675A. Appropriate non-native mammalian promoters might include the early and late promoters from SV40 (Fiers et al, *Nature*, 273:113 (1978)) or promoters derived from murine Moloney leukemia virus, mouse tumor virus, avian sarcoma viruses, adenovirus II, bovine papilloma virus or polyoma In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al, *FEBS Letts*. 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the nucleic acids into the host cell by any method known in the art, including those described above, will be referred to herein as "transformation." The cells into which have been introduced nucleic acids described above are meant to also include the progeny of such cells.

Large quantities of the nucleic acids and proteins of the present invention may be prepared by expressing the Zmax1 or HBM nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), *Cell Culture. Methods in Enzymology*, volume 58, Academic Press, Inc., Harcourt Brace Jovanovich, N.Y., (1979)). Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the nucleic acids of the present invention will be useful not only for the production of the nucleic acids and proteins of the present invention, but also, for example, in studying the characteristics of Zmax1 or HBM proteins.

Antisense nucleic acid sequences arc useful in preventing or diminishing the expression of Zmax1 or HBM, as will be appreciated by one skilled in the art. For example, nucleic acid vectors containing all or a portion of the Zmax1 or HBM gene or other sequences from the Zmax1 or HBM region may be placed under the control of a promoter in an antisense orientation and introduced into a cell. Expression of such an antisense construct within a cell will interfere with Zmax1 or HBM transcription and/or translation and/or replication.

The probes and primers based on the Zmax1 and HBM gene sequences disclosed herein are used to identify homologous Zmax1 and HBM gene sequences and proteins in other species. These Zmax1 and HBM gene sequences and proteins are used in the diagnostic/prognostic, therapeutic and drug screening methods described herein for the species from which they have been isolated.

XVI. Protein Expression and Purification

Expression and purification of the HBM protein of the invention can be performed essentially as outlined below. To facilitate the cloning, expression and purification of membrane and secreted protein from the HBM gene, a gene expression system, such as the pET System (Novagen), for cloning and expression of recombinant proteins in *E. coli* was selected. Also, a DNA sequence encoding a peptide tag, the His-Tap, was fused to the 3' end of DNA sequences of interest to facilitate purification of the recombinant protein products. The 3' end was selected for fusion to avoid alteration of any 5' terminal signal sequence.

Nucleic acids chosen, for example, from the nucleic acids set forth in SEQ ID) NOS: 1,3 and 5–12 for cloning HBM were prepared by polymerase chain reaction (PCR). Synthetic oligonucleotide primers specific for the 5' and 3' ends of the HBM nucleotide sequence were designed and purchased from Life Technologies (Gaithersburg, Md.). All forward primers (specific for the 5' end of the sequence) were designed to include an NcoI cloning site at the 5' terminus. These primers were designed to permit initiation of protein translation at the methionine residue encoded within the NcoI site followed by a valine residue and the protein encoded by the HBM DNA sequence. All reverse primers (specific for the 3' end of the sequence) included an EcoRI site at the 5' terminus to permit cloning of the HBM sequence into the reading frame of the pET-28b. The pET-28b vector provided a sequence encoding an additional 20 carboxyl-terminal amino acids including six histidine residues (at the C-terminus), which comprised the histidine affinity tag.

Genomic DNA prepared from the HBM gene was used as the source of template DNA for PCR amplification (Ausubel et al, *Current Protocols in Molecular Biology*, John Wiley & Sons (1994)). To amplify a DNA sequence containing the HBM nucleotide sequence, genomic DNA (50 ng) was introduced into a reaction vial containing 2 mM $MgCl_2$, 1 $\mu$M synthetic oligonucleotide primers (forward and reverse primers) complementary to and flanking a defined HBM, 0.2 mM of each of deoxynucleotide triphosphate, DATP, dGTP, dCTP, dTTP and 2.5 units of heat stable DNA polymerase (Amplitaq, Roche Molecular Systems, Inc., Branchburg, N.J.) in a final volume of 100 microliters.

Upon completion of thermal cycling reactions, each sample of amplified DNA was purified using the Qiaquick Spin PCR purification kit (Qiagen, Gaithersburg, Md.). All amplified DNA samples were subjected to digestion with the restriction endonucleases, e.g., NcoI and EcoRI (New England BioLabs, Beverly, Mass.) (Ausubel et al, *Current Protocols in Molecular Biology*, John Wiley & Sons, Inc. (1994)). DNA samples were then subjected to electrophoresis on 1.0% NuSeive (FMC BioProducts, Rockland, Me.) agarose gels. DNA was visualized by exposure to ethidium bromide and long wave UV irradiation. DNA contained in slices isolated from the agarose gel was purified using the Bio 101 GeneClean Kit protocol (Bio 101, Vista, Calif.).

The pET-28b vector was prepared for cloning by digestion with restriction endonucleases, e.g., NcoI and EcoRI (New England BioLabs, Beverly, Mass.) (Ausubel et al, *Current Protocols in Molecular Biology*, John Wiley & Sons, Inc. (1994)). The pET-28a vector, which encodes the histidine affinity tag that can be fused to the 5' end of an inserted gene, was prepared by digestion with appropriate restriction endonucleases.

Following digestion, DNA inserts were cloned (Ausubel et al, *Current Protocols in Molecular Biology*, John Wiley & Sons, Inc. (1994)) into the previously digested pET-28b expression vector. Products of the ligation reaction were then used to transform the BL21 strain of *E. coli* (Ausubel et al, *Current Protocols in Molecular Biology*, John Wiley & Sons, Inc. (1994)) as described below.

Competent bacteria, *E. coli* strain BL21 or *E. coli* strain BL21 (DE3), were transformed with recombinant pET expression plasmids carrying the cloned HBM sequence according to standard methods (Ausubel et al, *Current Protocols in Molecular Biology*, John Wiley & Sons, Inc. (1994)). Briefly, 1 $\mu$l of ligation reaction was mixed with 50 $\mu$l of electrocompetent cells and subjected to a high voltage pulse, after which samples were incubated in 0.45 ml SOC medium (0.5% yeast extract, 2.0% tryptone, 10 mM NaCl, 2.5 mM KCl, 10 mM $MgCl_2$, 10 mM $MgSO_4$ and 20 mM glucose) at 37° C. with shaking for 1 hour. Samples were then spread on LB agar plates containing 25 $\mu$g/ml kanamycin sulfate for growth overnight. Transformed colonies of BL21 were then picked and analyzed to evaluate cloned inserts, as described below.

Individual BL21 clones transformed with recombinant pET-28b HBM nucleotide sequences were analyzed by PCR amplification of the cloned inserts using the same forward and reverse primers specific for the HBM sequences that were used in the original PCR amplification cloning reactions. Successful amplification verifies the integration of the HBM sequence in the expression vector (Ausubel et al, *Current Protocols in Molecular Biology*, John Wiley & Sons, Inc. (1994)).

Individual clones of recombinant pET-28b vectors carrying properly cloned HBM nucleotide sequences were picked and incubated in 5 ml of LB broth plus 25 $\mu$g/ml kanamycin sulfate overnight. The following day plasmid DNA was isolated and purified using the Qiagen plasmid purification protocol (Qiagen Inc., Chatsworth, Calif.).

The pET vector can be propagated in any *E. coli* K-12 strain, e.g., HMS174, HB101, JM109, DH5 and the like, for purposes of cloning or plasmid preparation. Hosts for expression include *E. coli* strains containing a chromosomal copy of the gene for T7 RNA polymerase. These hosts were lysogens of bacteriophage DE3, a lambda derivative that carries the lacI gene, the lacUV5 promoter and the gene for T7 RNA polymerase. T7 RNA polymerase was induced by addition of isopropyl-β-D-thiogalactoside (IPTG), and the T7 RNA polymerase transcribes any target plasmid containing a functional T7 promoter, such as pET-28b, carrying its gene of interest. Strains include, for example, BL21(DE3) (Studier et al, *Meth. Enzymol.*, 185:60–89 (1990)).

To express the recombinant HBM sequence, 50 ng of plasmid DNA are isolated as described above to transform competent BL21(DE3) bacteria as described above (provided by Novagen as part of the pET expression kit). The lacZ gene (β-galactosidase) is expressed in the pET-System as described for the HBM recombinant constructions. Transformed cells were cultured in SOC medium for 1 hour, and the culture was then plated on LB plates containing 25 $\mu$g/ml kanamycin sulfate. The following day, the bacterial colonies were pooled and grown in LB medium containing kanamycin sulfate (25 $\mu$g/ml) to an optical density at 600 nM of 0.5 to 1.0 O.D. units, at which point 1 mM IPTG was added to the culture for 3 hours to induce gene expression of the HBM recombinant DNA constructions.

After induction of gene expression with IPTG, bacteria were collected by centrifugation in a Sorvall RC-3B centrifuge at 3500×g for 15 minutes at 4° C. Pellets were resuspended in 50 ml of cold mM Tris-HCl, pH 8.0,0.1 M NaCl and 0. 1 mM EDTA (STE buffer). Cells were then centrifuged at 2000×g for 20 minutes at 4° C. Wet pellets were weighed and frozen at −80° C. until ready for protein purification.

A variety of methodologies known in the art can be used to purify the isolated proteins (Coligan et al, *Current Protocols in Protein Science*, John Wiley & Sons (1995)). For example, the frozen cells can be thawed, resuspended in buffer and ruptured by several passages through a small volume microfluidizer (Model M-110S, Microfluidics International Corp., Newton, Mass.). The resultant homogenate is centrifuged to yield a clear supernatant (crude extract) and, following filtration, the crude extract is fractioned over columns. Fractions are monitored by absorbance at $OD_{280}$ mn and peak fractions may be analyzed by SDS-PAGE.

The concentrations of purified protein preparations are quantified spectrophotometrically using absorbance coefficients calculated from amino acid content (Perkins, *Eur. J. Biochem.*, 157:169–180 (1986)). Protein concentrations are also measured by the method of Bradford, *Anal. Biochem.*, 72:248–254 (1976) and Lowry et al, *J. Biol. Chem.*, 193:265–275 (1951) using bovine serum albumin as a standard.

SDS-polyacrylamide gels of various concentrations were purchased from BioRad (Hercules, Calif.), and stained with Coomassie blue. Molecular weight markers may include rabbit skeletal muscle myosin (200 kDa), *E. coli* β-galactosidase (116 kDa), rabbit muscle phosphorylase B (97.4 kDa), bovine serum albumin (66.2 kDa), ovalbumin (45 kDa), bovine carbonic anyhdrase (31 kDa), soybean trypsin inhibitor (21.5 kDa), egg white lysozyme (14.4 kDa) and bovine aprotinin (6.5 kDa).

Once a sufficient quantity of the desired protein has been obtained, it may be used for various purposes. A typical use is the production of antibodies specific for binding. These antibodies may be either polyclonal or monoclonal, and may be produced by in vitro or in vivo techniques well known in the art. Monoclonal antibodies to epitopes of any of the peptides identified and isolated as described can be prepared from murine hybridomas (Kohler, *Nature*, 256:495 (1975)). In summary, a mouse is inoculated with a few micrograms of HBM protein over a period of two weeks. The mouse is then sacrificed. The cells that produce antibodies are then removed from the mouse's spleen. The spleen cells are then fused with polyethylene glycol with mouse myeloma cells. The successfully fused cells are diluted in a microtiter plate and growth of the culture is continued. The amount of antibody per well is measured by immunoassay methods such as ELISA (Engvall, *Meth. Enzymol.*, 70:419 (1980)). Clones producing antibody can be expanded and further propagated to produce HBM antibodies. Other suitable techniques involve in vitro exposure of lymphocytes to the antigenic polypeptides, or alternatively, to selection of libraries of antibodies in phage or similar vectors. See Huse et al, *Science*, 246:1275–1281 (1989). For additional information on antibody production see Davis et al, *Basic Methods in Molecular Biology*, Elsevier, N.Y., Section 21-2 (1989).

XVII. Methods of Use: Gene Therapy

In recent years, significant technological advances have been made in the area of gene therapy for both genetic and acquired diseases. (Kay et al, *Proc. Natl. Acad. Sci. USA*, 94:12744–12746 (1997)) Gene therapy can be defined as the deliberate transfer of DNA for therapeutic purposes. Improvement in gene transfer methods has allowed for development of gene therapy protocols for the treatment of diverse types of diseases. Gene therapy has also taken advantage of recent advances in the identification of new therapeutic genes, improvement in both viral and nonviral gene delivery systems, better understanding of gene regulation, and improvement in cell isolation and transplantation.

The preceding experiments identify the HBM gene as a dominant mutation conferring elevated bone mass. The fact that this mutation is dominant indicates that expression of the HBM protein causes elevated bone mass. Older individuals carrying the HBM gene, and, therefore expressing the HBM protein, do not suffer from osteoporosis. These individuals are equivalent to individuals being treated with the HBM protein. These observations are a strong experimental indication that therapeutic treatment with the HBM protein prevents osteoporosis. The bone mass elevating activity of the HBM gene is termed "HBM function." Therefore, according to the present invention, a method is also provided of supplying HBM function to mesenchymal stem cells (Onyia et al, *J. Bone Miner. Res.*, 13:20—30 (1998); Ko et al, *Cancer Res.*, 56:4614–4619 (1996)). Supplying such a function provides protection against osteoporosis. The HBM gene or a part of the gene may be introduced into the cell in a vector such that the gene remains extrachromosomal. In such a situation, the gene will be expressed by the cell from the extrachromosomal location.

Vectors for introduction of genes both for recombination and for extrachromosomal maintenance are known in the art, and any suitable vector may be used. Methods for introducing DNA into cells such as electroporation, calcium phosphate co-precipitation, and viral transduction are known in the art, and the choice of method is within the competence of one skilled in the art (Robbins, Ed., *Gene Therapy Protocols*, Human Press, NJ (1997)). Cells transformed with the HBM gene can be used as model systems to study osteoporosis and drug treatments that promote bone growth.

As generally discussed above, the HBM gene or fragment, where applicable, may be used in gene therapy methods in order to increase the amount of the expression products of such genes in mesenchymal stem cells. It may be useful also to increase the level of expression of a given HBM protein, or a fragment thereof, even in those cells in which the wild type gene is expressed normally. Gene therapy would be carried out according to generally accepted methods as described by, for example, Friedman, *Therapy for Genetic Diseases*, Friedman, Ed., Oxford University Press, pages 105–121 (1991).

A virus or plasmid vector containing a copy of the HBM gene linked to expression control elements and capable of replicating inside mesenchymal stem cells, is prepared. Suitable vectors are known and described, for example, in U.S. Pat. No. 5,252,479 and WO 93/07282, the disclosures of which are incorporated by reference herein in their entirety. The vector is then injected into the patient, either locally into the bone marrow or systemically (in order to reach any mesenchymal stem cells located at other sites, i.e., in the blood). If the transfected gene is not permanently incorporated into the genome of each of the targeted cells, the treatment may have to be repeated periodically.

Gene transfer systems known in the art may be useful in the practice of the gene therapy methods of the present invention. These include viral and non-viral transfer methods. A number of viruses have been used as gene transfer vectors, including polyoma, i.e., SV40 (Madzak et al, *J. Gen. Virol.*, 73:1533–1536 (1992)), adenovirus (Berkner, *Curr. Top. Microbiol. Immunol.*, 158:39–61 (1992); Berkner et al, *Bio Techniques,* 6:616–629 (1988); Gorziglia et al, *J. Virol.*, 66:4407–4412 (1992); Quantin et al, *Proc. Natl. Acad Sci. USA*, 89:2581–2584 (1992); Rosenfeld et al, *Cell*, 68:143–155 (1992); Wilkinson et al, *Nucl. Acids Res.*, 20:2233–2239 (1992); Stratford-Perricaudet et al, *Hum. Gene Ther.*, 1:241–256 (1990)), vaccinia virus (Mackett et al, *Biotechnology*, 24:495–499 (1992)), adeno-associated virus (Muzyczka, *Curr. Top. Microbiol. Immunol.*, 158:91–123 (1992); Ohi et al, *Gene*, 89:279–282 (1990)), herpes viruses including HSV and EBV (Margolskee, *Curr. Top. Microbiol. Immunol.*, 158:67–90 (1992); Johnson et al, *J. Virol.*, 66:2952–2965 (1992); Fink et al, *Hum. Gene Ther.*, 3:11–19 (1992); Breakfield et al, *Mol. Neurobiol.*, 1:337–371 (1987; ) Fresse et al, *Biochem. Pharmacol.*, 40:2189–2199 (1990)), and retroviruses of avian (Brandyopadhyay et al, *Mol. Cell Biol.*, 4:749–754 (1984); Petropouplos et al, *J. Virol.*, 66:3391–3397 (1992)), murine (Miller, *Curr. Top. Microbiol. Immunol.*, 158:1–24 (1992); Miller et al, *Mol. Cell Biol.*, 5:431–437 (1985); Sorge et al, *Mol. Cell Biol.*, 4:1730–1737 (I984); Mann et al, *J. Virol.*, 54:401407 (1985)), and human origin (Page et al, *J. Virol.*, 64:5370–5276 (1990); Buchschalcher et al, *J. Virol.*, 66:2731–2739 (1992)). Most human gene therapy protocols have been based on disabled murine retroviruses.

Non-viral gene transfer methods known in the art include chemical techniques such as calcium phosphate coprecipitation (Graham et al, *Virology*, 52:456–467 (1973); Pellicer et al, *Science*, 209:1414–1422 (1980)), mechanical techniques, for example microinjection (Anderson et al, *Proc. Natl. Acad. Sci. USA*, 77:5399–5403 (1980); Gordon et al, *Proc. Natl. Acad. Sci. USA*, 77:7380–7384 (1980); Brinster et al, *Cell*, 27:223–231 (1981); Constantini et al, *Nature*, 294:92–94 (1981)), membrane fusion-mediated transfer via liposomes (Felgner et al, *Proc. Natl. Acad. Sci. USA*, 84:7413–7417 (1987); Wang et al, *Biochemistry*, 28:9508–9514 (1989); Kaneda et al, *J. Biol. Chem.*, 264:12126–12129 (1989); Stewart et al, *Hum. Gene Ther.*, 3:267–275 (1992); Nabel et al, *Science*, 249:1285–1288 (1990); Lim et al, *Circulation*, 83:2007–2011 (1992)), and direct DNA uptake and receptor-mediated DNA transfer (Wolffet al, *Science*, 247:1465–1468 (1990); Wu et al, *BioTechniques*, 11:474–485 (1991); Zenke et al, *Proc. Natl.*

*Acad. Sci. USA*, 87:3655–3659 (1990); Wu et al, *J. Biol. Chem.*, 264:16985–16987 (1989); Wolff et al, *BioTechniques*, 11:474–485 (1991); Wagner et al, 1990; Wagner et al, *Proc. Natl. Acad. Sci. USA*, 88:42554259 (1991); Cotten et al, *Proc. Natl. Acad. Sci. USA*, 87:4033–4037 (1990); Curiel et al, *Proc. Natl. Acad Sci. USA*, 88:8850–8854 (1991); Curiel et al, *Hum. Gene Ther.*, 3:147–154 (1991)). Viral-mediated gene transfer can be combined with direct in vivo vectors to the mesenchymal stem cells and not into the surrounding cells (Romano et al, *In Vivo*, 12(1):59–67 (1998); Gonez et al, *Hum. Mol. Genetics*, 7(12):1913–9 (1998)). Alternatively, the retroviral vector producer cell line can be injected into the bone marrow (Culver et al, *Science*, 256:1550–1552 (1992)). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is non-specific, localized in vivo uptake and expression have been reported in tumor deposits, for example, following direct in situ administration (Nabel, *Hum. Gene Ther.*, 3:399–410 (1992)).

XVIII. Methods of Use: Transformed Hosts, Development of Pharmaceuticals and Research Tools Cells and animals that carry the HBM gene can be used as model systems to study and test for substances that have potential as therapeutic agents (Onyia et al, *J. Bone Miner. Res.*, 13:20–30 (1998); Broder et al, *Bone*, 21:225–235 (1997)). The cells are typically cultured mesenchymal stem cells. These may be isolated from individuals with somatic or germline HBM genes. Alternatively, the cell line can be engineered to carry the HBM gene, as described above. After a test substance is applied to the cells, the transformed phenotype of the cell is determined. Any trait of transformed cells can be assessed, including formation of bone matrix in culture (Broder et al, *Bone*, 21:225–235 (1997)), mechanical properties (Kizer et al, *Proc. Natl. Acad Sci. USA*, 94:1013–1018 (1997)), and response to application of putative therapeutic agents.

Animals for testing therapeutic agents can be selected after treatment of germline cells or zygotes. Such treatments include insertion of the Zmax1 gene, as well as insertion of the HBM gene and disrupted homologous genes. Alternatively, the inserted Zmax1 gene(s) and/or HBM gene(s) of the animals may be disrupted by insertion or deletion mutation of other genetic alterations using conventional techniques, such as those described by, for example, Capechi, *Science*, 244:1288 (1989); Valancuis et al, *Mol. Cell Biol.*, 11:1402 (1991); Hasty et al, *Nature*, 350:243 (1991); Shinkai et al, *Cell*, 68:855 (1992); Mombaerts et al, *Cell*, 68:869 (1992); Philpott et al, *Science*, 256:1448 (1992); Snouwaert et al, *Science*, 257:1083 (1992); Donehower et al, *Nature*, 356:215 (1992). After test substances have been administered to the animals, the growth of bone must be assessed. If the test substance enhances the growth of bone, then the test substance is a candidate therapeutic agent. These animal models provide an extremely important vehicle for potential therapeutic products.

Individuals carrying the HBM gene have elevated bone mass. The HBM gene causes this phenotype by altering the activities, levels, expression patterns, and modification states of other molecules involved in bone development. Using a variety of established techniques, it is possible to identify molecules, preferably proteins or mRNAs, whose activities, levels, expression patterns, and modification states are different between systems containing the Zmax1 gene and systems containing the HBM gene. Such systems can be, for example, cell-free extracts, cells, tissues or living organisms, such as mice or humans. For a mutant form of Zmax1, a complete deletion of Zmax1, mutations lacking the extracellular or intracellular portion of the protein, or any other mutation in the Zmax1 gene may be used. It is also possible to use expression of antisense Zmax1 RNA or oligonucleotides to inhibit production of the Zmax1 protein. For a mutant form of HBM, a complete deletion of HBM, mutations lacking the extracellular or intracellular portion of the HBM protein, or any other mutation in the HBM gene may be used. It is also possible to use expression of antisense HBM RNA or oligonucleotides to inhibit production of the HBM protein.

Molecules identified by comparison of Zmax1 systems and HBM systems can be used as surrogate markers in pharmaceutical development or in diagnosis of human or animal bone disease. Alternatively, such molecules may be used in treatment of bone disease. See, Schena et al, *Science*, 270:467–470 (1995).

For example, a transgenic mouse carrying the HBM gene in the mouse homologue is constructed. A mouse of the genotype HBM/+ is viable, healthy and has elevated bone mass. To identify surrogate markers for elevated bone mass, HBM/+ (i.e., heterozygous) and isogenic +/+ (i.e., wild-type) mice are sacrificed. Bone tissue mRNA is extracted from each animal, and a "gene chip" corresponding to mRNAs expressed in the +/+ individual is constructed. mRNA from different tissues is isolated from animals of each genotype, reverse-transcribed, fluorescently labeled, and then hybridized to gene fragments affixed to a solid support. The ratio of fluorescent intensity between the two populations is indicative of the relative abundance of the specific mRNAs in the +/+ and HBM/+ animals. Genes encoding mRNAs over- and under-expressed relative to the wild-type control are candidates for genes coordinately regulated by the HBM gene.

One standard procedure for identification of new proteins that are part of the same signaling cascade as an already-discovered protein is as follows. Cells are treated with radioactive phosphorous, and the already-discovered protein is manipulated to be more ore less active. The phosphorylation state of other proteins in the cell is then monitored by polyacrylamide gel electropboresis and autoradiography, or similar techniques. Levels of activity of the known protein may be manipulated by many methods, including, for example, comparing wild-type mutant proteins using specific inhibitors such as drugs or antibodies, simply adding or not adding a known extracellular protein, or using antisense inhibition of the expression of the known protein (Tamura et al, *Science*, 280(5369):1614–7 (1998); Meng, *EMBO J.*, 17(15):4391–403 (1998); Cooper et al, *Cell*, 1:263–73 (1982)).

In another example, proteins with different levels of phosphorylation are identified in TE85 osteosarcoma cells expressing either a sense or antisense cDNA for Zmax1. TE85 cells normally express high levels of Zmax1 (Dong et al, *Biochem. & Biophys. Res. Comm.*, 251:784–790 (1998)). Cells containing the sense construct express even higher levels of Zmax1, while cells expressing the antisense construct express lower levels. Cells are grown in the presence of $^{32}P$, harvested, lysed, and the lysates run on SDS polyacrylamide gels to separate proteins, and the gels subjected to autoradiography (Ausubel et al, *Current Protocols in Molecular Biology*, John Wiley & Sons (1997)). Bands that differ in intensity between the sense and antisense cell lines represent phosphoproteins whose phosphorylation state or absolute level varies in response to levels of Zmax1. As an alternative to the 32P-labeling, unlabeled proteins may be separated by SDS-PAGE and subjected to immunoblotting, using the commercially available anti-phosphotyrosine antibody as a probe (Thomas et al, *Nature*, 376(6537):267–71 (1995)). As an alternative to the expression of antisense RNA, transfection with chemically modified antisense oligonucleotides can be used (Woolf et al, *Nucleic Acids Res.*, 18(7):1763–9 (1990)).

Many bone disorders, such as osteoporosis, have a slow onset and a slow response to treatment. It is therefore useful to develop surrogate markers for bone development and mineralization. Such markers can be useful in developing treatments for bone disorders, and for diagnosing patients who may be at risk for later development of bone disorders. Examples of preferred markers are N- and C-terminal telopeptide markers described, for example, in U.S. Pat. Nos. 5,455,179, 5,641,837 and 5,652,112, the disclosures of which are incorporated by reference herein in their entirety. In the area of HIV disease, CD4 counts and viral load are useful surrogate markers for disease progression (Vlahov et al, *JAMA*, 279(1):35–40 (1998)). There is a need for analogous surrogate markers in the area of bone disease.

A surrogate marker can be any characteristic that is easily tested and relatively insensitive to non-specific influences. For example, a surrogate marker can be a molecule such as a protein or mRNA in a tissue or in blood serum. Alternatively, a surrogate marker may be a diagnostic sign such as sensitivity to pain, a reflex response or the like.

In yet another example, surrogate markers for elevated bone mass are identified using a pedigree of humans carrying the HBM gene. Blood samples are withdrawn from three individuals that carry the HBM gene, and from three closely related individuals that do not. Proteins in the serum from these individuals are electrophoresed on a two dimensional gel system, in which one dimension separates proteins by size, and another dimension separates proteins by isoelectric point (Epstein et al, *Electrophoresis*, 17(11): 1655–70 (1996)). Spots corresponding to proteins are identified. A few spots are expected to be present in different amounts or in slightly different positions for the HBM individuals compared to their normal relatives. These spots correspond to proteins that are candidate surrogate markers. The identities of the proteins are determined by microsequencing, and antibodies to the proteins can be produced by standard methods for use in diagnostic testing procedures. Diagnostic assays for HBM proteins or other candidate surrogate markers include using antibodies described in this invention and a reporter molecule to detect HBM in human body fluids, membranes, bones, cells, tissues or extracts thereof. The antibodies can be labeled by joining them covalently or noncovalently with a substance that provides a detectable signal. In many scientific and patent literature, a variety of reporter molecules or labels are described including radionuclides, enzymes, fluorescent, chemi-luminescent or chromogenic agents (U.S. Pat. Nos. 3,817,837; 3,850,752; 3,939,350; 3,996,345; 4,277,437; 4,275,149; and 4,366, 241).

Using these antibodies, the levels of candidate surrogate markers are measured in normal individuals and in patients suffering from a bone disorder, such as osteoporosis, osteoporosis pseudoglioma, Engelmann's disease, Ribbing's disease, hyperphosphatasernia, Van Buchem's disease, melorheostosis, osteopetrosis, pychodysostosis, sclerosteosis, osteopoikilosis, acromegaly, Paget's disease, fibrous dysplasia, tubular stenosis, osteogenesis imperfecta, hypoparathyroidism, pseudohypoparathyroidism, pseudopseudohypoparathyroidism, primary and secondary hyperparathyroidism and associated syndromes, hypercalciuria, medullary carcinoma of the thyroid gland, osteomalacia and other diseases. Techniques for measuring levels of protein in serum in a clinical setting using antibodies are well established. A protein that is consistently present in higher or lower levels in individuals carrying a particular disease or type of disease is a useful surrogate marker.

A surrogate marker can be used in diagnosis of a bone disorder. For example, consider a child that present to a physician with a high frequency of bone fracture. The underlying cause may be child abuse, inappropriate behavior by the child, or a bone disorder. To rapidly test for a bone disorder, the levels of the surrogate marker protein are measured using the antibody described above.

Levels of modification states of surrogate markers can be measured as indicators of the likely effectiveness of a drug that is being developed. It is especially convenient to use surrogate markers in creating treatments for bone disorders, because alterations in bone development or mineralization may require a long time to be observed. For example, a set of bone mRNAs, termed the "HBM-inducible mRNA set" is found to be overexpressed in HBM/+ mice as compared to +/+ mice, as described above. Expression of this set can be used as a surrogate marker. Specifically, if treatment of +/+ mice with a compound results in overexpression of the HBM-inducible mRNA set, then that compound is considered a promising candidate for further development.

This invention is particularly useful for screening compounds by using the Zmax1 or HBM protein or binding fragment thereof in any of a variety of drug screening techniques.

The Zmax1 or HBM protein or fragment employed in such a test may either be free in solution, affixed to a solid support, or borne on a cell surface. One method of drug screening utilizes eukaryotic or prokaryotic host cells which are stably transformed with recombinant nucleic acids expressing the protein or fragment, preferably in competitive binding assays. Such cells, either in viable or fixed form, can be used for standard binding assays. One may measure, for example, for the formation of complexes between a Zmax1 or HBM protein or fragment and the agent being tested, or examine the degree to which the formation of a complex between a Zmax1 or HBM protein or fragment and a known ligand is interfered with by the agent being tested.

Thus, the present invention provides methods of screening for drugs comprising contacting such an agent with a Zmax1 or HBM protein or fragment thereof and assaying (i) for the presence of a complex between the agent and the Zmax1 or HBM protein or fragment, or (ii) for the presence of a complex between the Zmax1 or HBM protein or fragment and a ligand, by methods well known in the art. In such competitive binding assays the Zmax1 or HBM protein or fragment is typically labeled. Free Zmax1 or HBM protein or fragment is separated from that present in a protein:protein complex, and the amount of free (i.e., uncomplexed) label is a measure of the binding of the agent being tested to Zmax1 or HBM or its interference with Zmax1 or HBM: ligand binding, respectively.

Another technique for drug screening provides high throughput screening for compounds having suitable binding affinity to the Zmax1 or HBM proteins and is described in detail in WO 84/03564. Briefly stated, large numbers of different small peptide test compounds are synthesized on a solid substrate, such as plastic pins or some other surface. The peptide test compounds are reacted with Zmax1 or HBM proteins and washed. Bound Zmax1 or HBM protein is then detected by methods well known in the art. Purified Zmax1 or HBM can be coated directly onto plates for use in the aforementioned drug screening techniques. However, non-neutralizing antibodies to the protein can be used to capture antibodies to immobilize the Zmax1 or HBM protein on the solid phase.

This invention also contemplates the use of competitive drug screening assays in which neutralizing antibodies capable of specifically binding the Zmax1 or HBM protein compete with a test compound for binding to the Zmax1 or HBM protein or fragments thereof. In this manner, the antibodies can be used to detect the presence of any peptide that shares one or more antigenic determinants of the Zmax1 or HBM protein.

A further technique for drug screening involves the use of host eukaryotic cell lines or cells (such as described above) that have a nonfunctional Zmax1 or HBM gene. These host cell lines or cells are defective at the Zmax1 or HBM protein level. The host cell lines or cells are grown in the presence of drug compound. The rate of growth of the host cells is measured to determine if the compound is capable of regulating the growth of Zmax1 or HBM defective cells.

The goal of rational drug design is to produce structural analogs of biologically active proteins of interest or of small molecules with which they interact (e.g., agonists, antagonists, inhibitors) in order to fashion drugs which are, for example, more active or stable forms of the protein, or which, e.g., enhance or interfere with the function of a protein in vivo. See, e.g., Hodgson, *Bio/Technology*, 9:19–21 (1991). In one approach, one first determines the three-dimensional structure of a protein of interest (e.g., Zmax1 or HBM protein) or, for example, of the Zmax1- or HBM-receptor or ligand complex, by x-ray crystallography, by computer modeling or most typically, by a combination of approaches. Less often, useful information regarding the structure of a protein may be gained by modeling based on the structure of homologous proteins. An example of rational drug design is the development of HIV protease inhibitors (Erickson et al, *Science*, 249:527–533 (1990)). In addition, peptides (e.g., Zmax1 or HBM protein) are analyzed by an alanine scan (Wells, *Methods in Enzymol.*, 202:390–411 (1991)). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved Zmax1 or HBM protein activity or stability or which act as inhibitors, agonists, antagonists, etc. of Zmax1 or HBM protein activity. By virtue of the availability of cloned Zmax1 or HBM sequences, sufficient amounts of the Zmax1 or HBM protein may be made available to perform such analytical studies as x-ray crystallography. In addition, the knowledge of the Zmax1 or HBM protein sequence provided herein will guide those employing computer modeling techniques in place of, or in addition to x-ray crystallography.

XIX. Methods of Use: Avian and Mammalian Animal Husbandry

The Zmax1 DNA and Zmax1 protein and/or the HBM DNA and HBM protein can be used for vertebrate and preferably human therapeutic agents and for avian and mammalian veterinary agents, including for livestock breeding. Birds, including, for example, chickens, roosters, hens, turkeys, ostriches, ducks, pheasants and quails, can benefit from the identification of the gene and pathway for high bone mass. In many examples cited in literature (for example, McCoy et al, *Res. Vet. Sci.*, 60(2):185–186 (1996)), weakened bones due to husbandry conditions cause cage layer fatigue, osteoporosis and high mortality rates. Additional therapeutic agents to treat osteoporosis or other bone disorders in birds can have considerable beneficial effects on avian welfare and the economic conditions of the livestock industry, including, for example, meat and egg production.

XX. Methods of Use: Diagnostic Assays Using Zmax1-specific Oligonucleotides for Detection of Genetic Alterations Affecting Bone Development.

In cases where an alteration or disease of bone development is suspected to involve an alteration of the Zmax1 gene or the HBM gene, specific oligonucleotides may be constructed and used to assess the level of Zmax1 mRNA or HBM mRNA, respectively, in bone tissue or in another tissue that affects bone development.

For example, to test whether a person has the HBM gene, which affects bone density, polymerase chain reaction can be used. Two oligonucleotides are synthesized by standard methods or are obtained from a commercial supplier of custom-made oligonucleotides. The length and base composition are determined by standard criteria using the Oligo 4.0 primer Picking program (Wojchich Rychlik, 1992). One of the oligonucleotides is designed so that it will hybridize only to HBM DNA under the PCR conditions used. The other oligonucleotide is designed to hybridize a segment of Zmax1 genomic DNA such that amplification of DNA using these oligonucleotide primers produces a conveniently identified DNA fragment. For example, the pair of primers CCAAGTTCTGAGAAGTCC (SEQ ID NO:32) and AATACCTGAAACCA TACCTG (SEQ ID NO:33) will amplify a 530 base pair DNA fragment from a DNA sample when the following conditions are used: step 1 at 95° C. for 120 seconds; step 2 at 95° C. for 30 seconds; step 3 at 58° C. for 30 seconds; step 4 at 72° C. for 120 seconds; where steps 2–4 are repeated 35 times. Tissue samples may be obtained from hair follicles, whole blood, or the buccal cavity.

The fragment generated by the above procedure is sequenced by standard techniques.

Individuals heterozygous for the HBM gene will show an equal amount of G and T at the second position in the codon for glycine 171. Normal or homozygous wild-type individuals will show only G at this position.

Other amplification techniques besides PCR may be used as alternatives, such as ligation-mediated PCR or techniques involving Q-beta replicase (Cahill et al, *Clin. Chem.*, 37(9):1482–5 (1991)). For example, the oligonucleotides AGCTGCTCGTAGCT G TCTCTCCCTGGATCACGGGTACATGTACTGGACAGACTGGGT (SEQ ID NO:34) and TGAGACGCCCCGGATTGAGCGGGCAGGGATAGCTTATTCCCTGT GCCGCATTACGGC (SEQ ID NO:35) can be hybridized to a denatured human DNA sample, treated with a DNA ligase, and then subjected to PCR amplification using the primer oligonucleotides AGCTGCTCGTAG CTGTCTCTCCCTGGA (SEQ ID NO:36) and GCCGTAATGCGGCACAGGGAATAAGCT (SEQ ID NO:37). In the first two oligonucleotides, the outer 27 bases are random sequence corresponding to primer binding sites, and the inner 30 bases correspond to sequences in the Zmax1 gene. The T at the end of the first oligonucleotide corresponds to the HBM gene. The first two oligonucleotides are ligated only when hybridized to human DNA carrying the HBM gene, which results in the formation of an amplifiable 114 bp DNA fragment.

Products of amplification can be detected by agarose gel electrophoresis, quantitative hybridization, or equivalent techniques for nucleic acid detection known to one skilled in the art of molecular biology (Sambrook et al, *Molecular Cloning: A Laboratory Manual*, Cold Spring Harbor Laboratory, Cold Spring, N.Y. (1989)).

Other alterations in the Zmax1 gene or the HBM gene may be diagnosed by the same type of amplification-detection procedures, by using oligonucleotides designed to identify those alterations. These procedures can be used in animals as well as humans to identify alterations in Zmax1 or HBM that affect bone development.

Expression of Zmax1 or HBM in bone tissue may be accomplished by fusing the cDNA of Zmax1or HBM, respectively, to a bone-specific promoter in the context of a vector for genetically engineering vertebrate cells. DNA constructs are introduced into cells by packaging the DNA into virus capsids, by the use of cationic liposomes, electroporation, or by calcium phosphate transfection. Transfected cells, preferably osteoblasts, may be studied in culture or may be introduced into bone tissue in animals by direct injection into bone or by intravenous injection of osteoblasts, followed by incorporation into bone tissue (Ko et al, *Cancer Research*, 56(20):4614–9 (1996)). For example, the osteocalcin promoter, which is specifically active in osteoblasts, may be used to direct transcription of the Zmax1 gene or the HBM gene. Any of several vectors and transfection methods may be used, such as retroviral vectors, adenovirus vectors, or vectors that are maintained after transfection using cationic liposomes, or other methods and vectors described herein.

Alteration of the level of functional Zmax1 protein or HBM protein affects the level of bone mineralization. By manipulating levels of functional Zmax1 protein or HBM protein, it is possible to affect bone development and to increase or decrease levels of bone mineralization. For example, it may be useful to increase bone mineralization in patients with osteoporosis. Alternatively, it may be useful to decrease bone mineralization in patients with osteopetrosis or Paget's disease. Alteration of Zmax1 levels or HBM levels can also be used as a research tool. Specifically, it is possible to identify proteins, mRNA and other molecules whose level or modification status is altered in response to changes in functional levels of Zmax1 or HBM. The pathology and pathogenesis of bone disorders is known and described, for example, in Rubin and Farber (Eds.), *Pathology*, 2nd Ed., S.B. Lippincott Co., Philadelphia, Pa. (1994).

A variety of techniques can be used to alter the levels of functional Zmax1 or HBM. For example, intravenous or intraosseous injection of the extracellular portion of Zmax1 or mutations thereof, or HBM or mutations thereof, will alter the level of Zmax1 activity or HBM activity, respectively, in the body of the treated human, animal or bird. Truncated versions of the Zmax1 protein or HBM protein can also be injected to alter the levels of functional Zmax1 protein or HBM protein, respectively. Certain forms of Zmax1 or HBM enhance the activity of endogenous protein, while other forms are inhibitory.

In a preferred embodiment, the HBM protein is used to treat osteoporosis. In a further preferred embodiment, the extracellular portion of the HBM protein is used. This HBM protein may be optionally modified by the addition of a moiety that causes the protein to adhere to the surface of cells. The protein is prepared in a pharmaceutically acceptable solution and is administered by injection or another method that achieves acceptable pharmacokinetics and distribution.

In a second embodiment of this method, Zmax1 or HBM levels are increased or decreased by gene therapy techniques. To increase Zmax1 or HBM levels, osteoblasts or another useful cell type are genetically engineered to express high levels of Zmax1 or HBM as described above. Alternatively, to decrease Zmax1 or HBM levels, antisense constructs that specifically reduce the level of translatable Zmax1 or HBM mRNA can be used. In general, a tissue-nonspecific promoter may be used, such as the CMV promoter or another commercially available promoter found in expression vectors (Wu et al, *Toxicol. Appl. Pharmacol.*, 141(1):330–9 (1996)). In a preferred embodiment, a Zmax1 cDNA or its antisense is transcribed by a bone-specific promoter, such as the osteocalcin or another promoter, to achieve specific expression in bone tissue. In this way, if a Zmax1-expressing DNA construct or HBM-expressing construct is introduced into non-bone tissue, it will not be expressed.

In a third embodiment of this method, antibodies against Zmax1 or HBM are used to inhibit its function. Such antibodies are identified herein.

In a fourth embodiment of this method, drugs that inhibit Zmax1 function or HBM function are used. Such drugs are described herein and optimized according to techniques of medicinal chemistry well known to one skilled in the art of pharmaceutical development.

Zmax1 and HBM interact with several proteins, such as ApoE. Molecules that inhibit the interaction between Zmax1 or HBM and ApoE or another binding partner are expected to alter bone development and mineralization. Such inhibitors may be useful as drugs in the treatment of osteoporosis, osteopetrosis, or other diseases of bone mineralization. Such inhibitors may be low molecular weight compounds, proteins or other types of molecules. See, Kim et al, *J. Biochem.* (Tokyo), 124(6):1072–1076 (1998).

Inhibitors of the interaction between Zmax1 or HBM and interacting proteins may be isolated by standard drug-screening techniques. For example, Zmax1 protein, (or a fragment thereof) or HBM protein (or a fragment thereof) can be immobilized on a solid support such as the base of microtiter well. A second protein or protein fragment, such as ApoE is derivatized to aid in detection, for example with fluorescein. Iodine, or biotin, then added to the Zmax1 or HBM in the presence of candidate compounds that may specifically inhibit this protein-protein domain of Zmax1 or HBM, respectively, and thus avoid problems associated with its transmembrane segment. Drug screens of this type are well known to one skilled in the art of pharmaceutical development.

Because Zmax1 and HBM are involved in bone development, proteins that bind to Zmax1 and HBM are also expected to be involved in bone development. Such binding proteins can be identified by standard methods, such as co-immunoprecipitation, co-fractionation, or the two-hybrid screen (Ausubel et al, *Current Protocols in Molecular Biology*, John Wiley & Sons (1997)). For example, to identify Zmax1-interacting proteins or HBM-interacting proteins using the two-hybrid system, the extracellular domain of Zmax1 or HBM is fused to LexA and expressed for the yeast vector pEG202 (the "bait") and expressed in the yeast strain EGY48. The yeast strain is transformed with a "prey" library in the appropriate vector, which encodes a galactose-inducible transcription-activation sequence fused to candidate interacting proteins. The techniques for initially selecting and subsequently verifying interacting proteins by this method are well known to one skilled in the art of molecular biology (Ausubel et al, *Current Protocols in Molecular Biology*, John Wiley & Sons (1997)).

In a preferred embodiment, proteins that interact with HBM, but not Zmax1, are identified using a variation of the above procedure (Xu et al, *Proc. Natl. Acad. Sci. USA*, 94(23):12473–8 (November 1997)). This variation of the two-hybrid system uses two baits, and Zmax1 and HBM are each fused to LexA and TetR, respectively. Alternatively, proteins that interact with the HBM but not Zmax1 are also isolated. These procedures are well known to one skilled in the art of molecular biology, and are a simple variation of standard two-hybrid procedures.

As an alternative method of isolating Zmax1 or HBM interacting proteins, a biochemical approach is used. The Zmax1 protein or a fragment thereof, such as the extracellular domain, or the HBM protein or a fragment thereof, such as the extracellular domain, is chemically coupled to Sepharose beads. The Zmax1- or HBM-coupled beads are poured into a column. An extract of proteins, such as serum proteins, proteins in the supernatant of a bone biopsy, or intracellular proteins from gently lysed TE85 osteoblastic cells, is added to the column. Non-specifically bound proteins are eluted, the column is washed several times with a low-salt buffer, and then tightly binding proteins are eluted with a high-salt buffer. These are candidate proteins that bind to Zmax1 or HBM, and can be tested for specific binding by standard tests and control experiments. Sepharose beads used for coupling proteins and the methods for performing the coupling are commercially available (Sigma), and the procedures described here are well known to one skilled in the art of protein biochemistry.

As a variation of the above procedure, proteins that are eluted by high salt from the Zmax1- or HBM-Sepharose column are then added to an HBM-Zmax1-sepharose column. Proteins that flow through without sticking are proteins that bind to Zmax1 but not to HBM. Alternatively, proteins that bind to the HBM protein and not to the Zmax1 protein can be isolated by reversing the order in which the columns are used.

XXI. Method of Use: Transformation-Associated Recombination (TAR) Cloning

Essential for the identification of novel allelic variants of Zmax1 is the ability to examine the sequence of both copies of the gene in an individual. To accomplish this, two "hooks," or regions of significant similarity, are identified within the genomic sequence such that they flank the portion of DNA that is to be cloned. Most preferably, the first of these hooks is derived from sequences 5' to the first exon of interest and the second is derived from sequences 3' to the last exon of interest. These two "hooks" are cloned into a bacterial/yeast shuttle vector such as that described by Larionov et al, *Proc. Natl. Acad. Sci. USA*, 94:7384–7387 (1997). Other similar vector systems may also be used. To recover the entire genomic copy of the Zmax1 gene, the plasmid containing the two "hooks" is linearized with a restriction endonuclease or is produced by another method such as PCR. This linear DNA fragment is introduced into yeast cells along with human genomic DNA. Typically, the yeast *Saccharomyces cerevisiae* is used as a host cell, although Larionov et al (in press) have reported using chicken host cells as well. During and after the process of transformation, the endogenous host cell converts the linear plasmid to a circle by a recombination event whereby the region of the human genomic DNA homologous to the "hooks" is inserted into the plasmid. This plasmid can be recovered and analyzed by methods well known to one skilled in the art. Obviously, the specificity for this reaction requires the host cell machinery to recognize sequences similar to the "hooks" present in the linear fragment. However, 100% sequence identity is not required, as shown by Kouprina et al, *Genomics*, 53(1):21–28 (October 1998), where the author describes using degenerate repeated sequences common in the human genome to recover fragments of human DNA from a rodent/human hybrid cell line.

In another example, only one "hook" is required, as described by Larionov et al, *Proc. Natl. Acad. Sci. USA*, 95(8):4469–74 (April 1998). For this type of experiment, termed "radial TAR cloning," the other region of sequence similarity to drive the recombination is derived from a repeated sequence from the genome. In this way, regions of DNA adjacent to the Zmax1 gene coding region can be recovered and examined for alterations that may affect function.

XXII. Methods of Use: Genomic Screening

The use of polymorphic genetic markers linked to the HBM gene or to Zmax1 is very useful in predicting susceptibility to osteoporosis or other bone diseases. Koller et al, *Amer. J. Bone Min. Res.*, 13:1903–1908 (1998) have demonstrated that the use of polymorphic genetic markers is useful for linkage analysis. Similarly, the identification of polymorphic genetic markers within the high bone mass gene will allow the identification of specific allelic variants that are in linkage disequilibrium with other genetic lesions that affect bone development. Using the DNA sequence from the BACs, a dinucleotide CAn repeat was identified and two unique PCR primers that will amplify the genomic DNA containing this repeat were designed, as shown below:

B200E21C16_L: GAGAGGCTATATCCCTGGGC (SEQ ID NO:38)

B200E21C16_R: ACAGCACGTGTTTAAAGGGG (SEQ ID NO:39)

and used in the genetic mapping study.

This method has been used successfully by others skilled in the art (e.g., Sheffield et al, *Genet.*, 4:1837–1844 (1995); LeBlanc-Straceski et al, *Genomics*, 19:341–9 (1994); Chen et al, *Genomics*, 25:1–8 (1995)). Use of these reagents with populations or individuals will predict their risk for osteoporosis. Similarly, single nucleotide polymorphisms (SNPs), such as those shown in Table 4 above, can be used as well to predict risk for developing bone diseases or resistance to osteoporosis in the case of the HBM gene.

XXIII. Methods of Use: Modulators of Tissue Calcification

The calcification of tissues in the human body is well documented. Towler et al, *J. Biol. Chem.*, 273:30427–34 (1998) demonstrated that several proteins known to regulate calcification of the developing skull in a model system are expressed in calcified aorta. The expression of Msx2, a gene transcribed in osteoprogenitor cells, in calcified vascular tissue indicates that genes which are important in bone development are involved in calcification of other tissues. Treatment with HBM protein, agonists or antagonists is likely to ameliorate calcification (such as the vasculature, dentin and bone of the skull visera) due to its demonstrated effect on bone mineral density. In experimental systems where tissue calcification is demonstrated, the over-expression or repression of Zmax1 activity permits the identification of molecules that are directly regulated by the Zmax1 gene. These genes are potential targets for therapeutics aimed at modulating tissue calcification. For example, an animal, such as the LDLR −/−, mouse is fed a high fat diet and is observed to demonstrate expression of markers of tissue calcification, including Zmax1. These animals are then treated with antibodies to Zmax1 or HBM protein, antisense oligonucleotides directed against Zmax1 or HBM cDNA, or with compounds known to bind the Zmax1 or HBM protein or its binding partner or ligand. RNA or proteins are extracted from the vascular tissue and the relative expression levels of the genes expressed in the tissue are determined by methods well known in the art. Genes that are regulated in the tissue are potential therapeutic targets for pharmaceutical development as modulators of tissue calcification.

The nucleic acids, proteins, peptides, amino acids, small molecules or other pharmaceutically useful compounds of the present invention that are to be given to an individual may be administered in the form of a composition with a pharmaceutically acceptable carrier, excipient or diluent, which are well known in the art. The individual may be a mammal or a bird, preferably a human, a rat, a mouse or bird. Such compositions may be administered to an individual in a pharmaceutically effective amount. The amount administered will vary depending on the condition being treated and the patient being treated. The compositions may be administered alone or in combination with other treatments.

EXAMPLES

The present invention is described by reference to the following Examples, which are offered by way of illustration and are not intended to limit the invention in any manner. Standard techniques well known in the art or the techniques specifically described below were utilized.

Example 1

The propositus was referred by her physicians to the Creighton Osteoporosis Center for evaluation of what appeared to be unusually dense bones. She was 18 years old and came to medical attention two years previous because of back pain, which was precipitated by an auto accident in which the car in which she was riding as a passenger was struck from behind. Her only injury was soft tissue injury to her lower back that was manifested by pain and muscle tenderness. There was no evidence of fracture or subluxation on radiographs. The pain lasted for two years, although she was able to attend school fill time. By the time she was seen in the Center, the pain was nearly resolved and she was back to her usual activities as a high school student. Physical exam revealed a normal healthy young woman standing 66 inches and weighing 128 pounds. Radiographs of the entire skeleton revealed dense looking bones with thick cortices. All bones of the skeleton were involved. Most importantly, the shapes of all the bones were entirely normal. The spinal BMC was 94.48 grams in L1–4, and the spinal BMD was 1.667 gm/cm$^2$ in L1–4. BMD was 5.62 standard deviations (SD) above peak skeletal mass for women. These were measured by DXA using a Hologic 2000~. Her mother was then scanned and a lumbar spinal BMC of 58.05 grams and BMD of 1.500 gm/cm$^2$ were found. Her mother's values place her 4.12 SD above peak mass and 4.98 SD above her peers. Her mother was 51 years old, stood 65 inches and weighed 140 pounds. Her mother was in excellent health with no history of musculoskeletal or other symptoms. Her father's lumbar BMC was 75.33 grams and his BMD was 1.118 gm/cm$^2$. These values place him 0.25 SD above peak bone mass for males. He was in good health, stood 72 inches tall, and weighed 187 pounds.

These clinical data suggested that the propositus inherited a trait from her mother, which resulted in very high bone mass, but an otherwise normal skeleton, and attention was focused on the maternal kindred. In U.S. Pat. No. 5,691,153, twenty-two of these members had measurement of bone mass by DXA. In one case, the maternal grandfather of the propositus, was deceased, however, medical records, ante-mortem skeletal radiographs and a gall bladder specimen embedded in paraffin for DNA genotyping were obtained. His radiographs showed obvious extreme density of all of the bones available for examination including the femur and the spine, and he was included among the affected members. In this invention, the pedigree has been expanded to include 37 informative individuals. These additions are a significant improvement over the original kinship (Johnson et al, *Am. J. Hum. Genet.*, 60:1326–1332 (1997)) because, among the fourteen individuals added since the original study, two individuals harbor key crossovers. X-linkage is ruled out by the presence of male-to-male transmission from individual 12 to 14 and 15.

Example 2

The present invention describes DNA sequences derived from two BAC clones from the HBM gene region, as evident in Table 6 below, which is an assembly of these clones. Clone b200e21-h (ATCC No. 98628; SEQ ID NOS: 10–11) was deposited at the American Type Culture Collection (ATCC), 10801 University Blvd., Manassas, Va. 20110-2209 U.S.A., on Dec. 30, 1997. Clone b527d12-h (ATCC No. 98907; SEQ ID NOS: 5–9) was deposited at the American Type Culture Collection (ATCC), 10801 University Blvd., Manassas, Va. 20110-2209 U.S.A., on Oct. 2, 1998. These sequences are unique reagents that can be used by one skilled in the art to identify DNA probes for the Zmax1 gene, PCR primers to amplify the gene, nucleotide polymorphisms in the Zmax1 gene, or regulatory elements of the Zmax1 gene.

TABLE 6

| Contig | ATCC No. | SEQ ID NO. | Length (base pairs) |
|---|---|---|---|
| b527d12-h_contig302G | 98907 | 5 | 3096 |
| b527d12-h_contig306G | 98907 | 6 | 26928 |
| b527d12-h_contig307G | 98907 | 7 | 29430 |
| b527d12-h_contig308G | 98907 | 8 | 33769 |
| b527d12-h_contig309G | 98907 | 9 | 72049 |
| b200e21-h_contig1 | 98907 | 10 | 8705 |
| b200e21-h_contig4 | 98907 | 11 | 66933 |

The disclosure of each of the patents, patent applications and publications cited in the specification is hereby incorporated by reference herein in its entirety.

Although the invention has been set forth in detail, one skilled in the art will recognize that numerous changes and modifications can be made, and that such changes and modifications may be without departing from the spirit and scope of the invention.

What is claimed is:

1. An isolated amino acid sequence of SEQ ID NO: 4.

2. An isolated amino acid sequence consisting of: the amino acid sequence of SEQ ID NO: 4.

3. The isolated amino acid sequence of claim 2, wherein said amino acid amino contains a glycine to valine substitution at position 171.

4. An isolated amino acid sequence consisting of the extracellular domain of the amino acid of SEQ ID NO: 4, wherein said extracellular domain corresponds to amino acids 23–1385 of SEQ ID NO: 4.

5. The isolated amino acid sequence of claim 4, wherein said amino acid amino contains a glycine to valine substitution at position 171.

6. An isolated amino acid sequence comprising the amino acid sequence of SEQ ID NO: 4.

7. An isolated amino acid sequence comprising the extracellular domain of the amino acid of SEQ ID NO: 4, wherein said extracellular domain corresponds to amino acids 23–1385 of SEQ ID NO: 4.

8. The isolated amino acid sequence of claim 7, wherein said amino acid amino contains a glycine to valine substitution at position 171.

* * * * *

UNITED STATES PATENT AND TRADEMARK OFFICE

CERTIFICATE OF CORRECTION

PATENT NO. : 6,780,609 B1
DATED : August 24, 2004
INVENTOR(S) : John P. Carulli et al.

It is certified that error appears in the above-identified patent and that said Letters Patent is hereby corrected as shown below:

Title page,
Item [73], should read as follows:
-- [73] Assignee: Genome Therapeutics Corporation, Waltham, MA (US)
Creighton University School of Medicine, Omaha NE (US). --

Signed and Sealed this

Twenty-third Day of November, 2004

JON W. DUDAS
*Director of the United States Patent and Trademark Office*

SEQUENCE LISTING

<160> NUMBER OF SEQ ID NOS: 641

<210> SEQ ID NO 1
<211> LENGTH: 5120
<212> TYPE: DNA
<213> ORGANISM: Homo sapiens

<400> SEQUENCE: 1

```
actaaagcgc cgccgccgcg ccatggagcc cgagtgagcg cggcgcgggc ccgtccggcc      60

gccggacaac  atg gag gca gcg ccg ccc ggg ccg ccg tgg ccg ctg ctg      109
            Met Glu Ala Ala Pro Pro Gly Pro Pro Trp Pro Leu Leu
            1               5                   10

ctg ctg ctg ctg ctg ctg ctg gcg ctg tgc ggc tgc ccg gcc ccc gcc      157
Leu Leu Leu Leu Leu Leu Leu Ala Leu Cys Gly Cys Pro Ala Pro Ala
    15                  20                  25

gcg gcc tcg ccg ctc ctg cta ttt gcc aac cgc cgg gac gta cgg ctg      205
Ala Ala Ser Pro Leu Leu Leu Phe Ala Asn Arg Arg Asp Val Arg Leu
30                  35                  40                  45

gtg gac gcc ggc gga gtc aag ctg gag tcc acc atc gtg gtc agc ggc      253
Val Asp Ala Gly Gly Val Lys Leu Glu Ser Thr Ile Val Val Ser Gly
                50                  55                  60

ctg gag gat gcg gcc gca gtg gac ttc cag ttt tcc aag gga gcc gtg      301
Leu Glu Asp Ala Ala Ala Val Asp Phe Gln Phe Ser Lys Gly Ala Val
            65                  70                  75

tac tgg aca gac gtg agc gag gag gcc atc aag cag acc tac ctg aac      349
Tyr Trp Thr Asp Val Ser Glu Glu Ala Ile Lys Gln Thr Tyr Leu Asn
        80                  85                  90

cag acg ggg gcc gcc gtg cag aac gtg gtc atc tcc ggc ctg gtc tct      397
Gln Thr Gly Ala Ala Val Gln Asn Val Val Ile Ser Gly Leu Val Ser
    95                  100                 105

ccc gac ggc ctc gcc tgc gac tgg gtg ggc aag aag ctg tac tgg acg      445
Pro Asp Gly Leu Ala Cys Asp Trp Val Gly Lys Lys Leu Tyr Trp Thr
110                 115                 120                 125

gac tca gag acc aac cgc atc gag gtg gcc aac ctc aat ggc aca tcc      493
Asp Ser Glu Thr Asn Arg Ile Glu Val Ala Asn Leu Asn Gly Thr Ser
                130                 135                 140

cgg aag gtg ctc ttc tgg cag gac ctt gac cag ccg agg gcc atc gcc      541
Arg Lys Val Leu Phe Trp Gln Asp Leu Asp Gln Pro Arg Ala Ile Ala
            145                 150                 155

ttg gac ccc gct cac ggg tac atg tac tgg aca gac tgg ggt gag acg      589
Leu Asp Pro Ala His Gly Tyr Met Tyr Trp Thr Asp Trp Gly Glu Thr
        160                 165                 170

ccc cgg att gag cgg gca ggg atg gat ggc agc acc cgg aag atc att      637
Pro Arg Ile Glu Arg Ala Gly Met Asp Gly Ser Thr Arg Lys Ile Ile
    175                 180                 185

gtg gac tcg gac att tac tgg ccc aat gga ctg acc atc gac ctg gag      685
Val Asp Ser Asp Ile Tyr Trp Pro Asn Gly Leu Thr Ile Asp Leu Glu
190                 195                 200                 205

gag cag aag ctc tac tgg gct gac gcc aag ctc agc ttc atc cac cgt      733
Glu Gln Lys Leu Tyr Trp Ala Asp Ala Lys Leu Ser Phe Ile His Arg
                210                 215                 220

gcc aac ctg gac ggc tcg ttc cgg cag aag gtg gtg gag ggc agc ctg      781
Ala Asn Leu Asp Gly Ser Phe Arg Gln Lys Val Val Glu Gly Ser Leu
            225                 230                 235

acg cac ccc ttc gcc ctg acg ctc tcc ggg gac act ctg tac tgg aca      829
Thr His Pro Phe Ala Leu Thr Leu Ser Gly Asp Thr Leu Tyr Trp Thr
        240                 245                 250

gac tgg cag acc cgc tcc atc cat gcc tgc aac aag cgc act ggg ggg      877
```

-continued

```
Asp Trp Gln Thr Arg Ser Ile His Ala Cys Asn Lys Arg Thr Gly Gly
    255                 260                 265

aag agg aag gag atc ctg agt gcc ctc tac tca ccc atg gac atc cag      925
Lys Arg Lys Glu Ile Leu Ser Ala Leu Tyr Ser Pro Met Asp Ile Gln
270                 275                 280                 285

gtg ctg agc cag gag cgg cag cct ttc ttc cac act cgc tgt gag gag      973
Val Leu Ser Gln Glu Arg Gln Pro Phe Phe His Thr Arg Cys Glu Glu
                290                 295                 300

gac aat ggc ggc tgc tcc cac ctg tgc ctg ctg tcc cca agc gag cct     1021
Asp Asn Gly Gly Cys Ser His Leu Cys Leu Leu Ser Pro Ser Glu Pro
            305                 310                 315

ttc tac aca tgc gcc tgc ccc acg ggt gtg cag ctg cag gac aac ggc     1069
Phe Tyr Thr Cys Ala Cys Pro Thr Gly Val Gln Leu Gln Asp Asn Gly
        320                 325                 330

agg acg tgt aag gca gga gcc gag gag gtg ctg ctg ctg gcc cgg cgg     1117
Arg Thr Cys Lys Ala Gly Ala Glu Glu Val Leu Leu Leu Ala Arg Arg
    335                 340                 345

acg gac cta cgg agg atc tcg ctg gac acg ccg gac ttc acc gac atc     1165
Thr Asp Leu Arg Arg Ile Ser Leu Asp Thr Pro Asp Phe Thr Asp Ile
350                 355                 360                 365

gtg ctg cag gtg gac gac atc cgg cac gcc att gcc atc gac tac gac     1213
Val Leu Gln Val Asp Asp Ile Arg His Ala Ile Ala Ile Asp Tyr Asp
                370                 375                 380

ccg cta gag ggc tat gtc tac tgg aca gat gac gag gtg cgg gcc atc     1261
Pro Leu Glu Gly Tyr Val Tyr Trp Thr Asp Asp Glu Val Arg Ala Ile
            385                 390                 395

cgc agg gcg tac ctg gac ggg tct ggg gcg cag acg ctg gtc aac acc     1309
Arg Arg Ala Tyr Leu Asp Gly Ser Gly Ala Gln Thr Leu Val Asn Thr
        400                 405                 410

gag atc aac gac ccc gat ggc atc gcg gtc gac tgg gtg gcc cga aac     1357
Glu Ile Asn Asp Pro Asp Gly Ile Ala Val Asp Trp Val Ala Arg Asn
    415                 420                 425

ctc tac tgg acc gac acg ggc acg gac cgc atc gag gtg acg cgc ctc     1405
Leu Tyr Trp Thr Asp Thr Gly Thr Asp Arg Ile Glu Val Thr Arg Leu
430                 435                 440                 445

aac ggc acc tcc cgc aag atc ctg gtg tcg gag gac ctg gac gag ccc     1453
Asn Gly Thr Ser Arg Lys Ile Leu Val Ser Glu Asp Leu Asp Glu Pro
                450                 455                 460

cga gcc atc gca ctg cac ccc gtg atg ggc ctc atg tac tgg aca gac     1501
Arg Ala Ile Ala Leu His Pro Val Met Gly Leu Met Tyr Trp Thr Asp
            465                 470                 475

tgg gga gag aac cct aaa atc gag tgt gcc aac ttg gat ggg cag gag     1549
Trp Gly Glu Asn Pro Lys Ile Glu Cys Ala Asn Leu Asp Gly Gln Glu
        480                 485                 490

cgg cgt gtg ctg gtc aat gcc tcc ctc ggg tgg ccc aac ggc ctg gcc     1597
Arg Arg Val Leu Val Asn Ala Ser Leu Gly Trp Pro Asn Gly Leu Ala
    495                 500                 505

ctg gac ctg cag gag ggg aag ctc tac tgg gga gac gcc aag aca gac     1645
Leu Asp Leu Gln Glu Gly Lys Leu Tyr Trp Gly Asp Ala Lys Thr Asp
510                 515                 520                 525

aag atc gag gtg atc aat gtt gat ggg acg aag agg cgg acc ctc ctg     1693
Lys Ile Glu Val Ile Asn Val Asp Gly Thr Lys Arg Arg Thr Leu Leu
                530                 535                 540

gag gac aag ctc ccg cac att ttc ggg ttc acg ctg ctg ggg gac ttc     1741
Glu Asp Lys Leu Pro His Ile Phe Gly Phe Thr Leu Leu Gly Asp Phe
            545                 550                 555

atc tac tgg act gac tgg cag cgc cgc agc atc gag cgg gtg cac aag     1789
Ile Tyr Trp Thr Asp Trp Gln Arg Arg Ser Ile Glu Arg Val His Lys
        560                 565                 570
```

-continued

```
gtc aag gcc agc cgg gac gtc atc att gac cag ctg ccc gac ctg atg      1837
Val Lys Ala Ser Arg Asp Val Ile Ile Asp Gln Leu Pro Asp Leu Met
    575                 580                 585

ggg ctc aaa gct gtg aat gtg gcc aag gtc gtc gga acc aac ccg tgt      1885
Gly Leu Lys Ala Val Asn Val Ala Lys Val Val Gly Thr Asn Pro Cys
590                 595                 600                 605

gcg gac agg aac ggg ggg tgc agc cac ctg tgc ttc ttc aca ccc cac      1933
Ala Asp Arg Asn Gly Gly Cys Ser His Leu Cys Phe Phe Thr Pro His
                610                 615                 620

gca acc cgg tgt ggc tgc ccc atc ggc ctg gag ctg ctg agt gac atg      1981
Ala Thr Arg Cys Gly Cys Pro Ile Gly Leu Glu Leu Leu Ser Asp Met
            625                 630                 635

aag acc tgc atc gtg cct gag gcc ttc ttg gtc ttc acc agc aga gcc      2029
Lys Thr Cys Ile Val Pro Glu Ala Phe Leu Val Phe Thr Ser Arg Ala
        640                 645                 650

gcc atc cac agg atc tcc ctc gag acc aat aac aac gac gtg gcc atc      2077
Ala Ile His Arg Ile Ser Leu Glu Thr Asn Asn Asn Asp Val Ala Ile
    655                 660                 665

ccg ctc acg ggc gtc aag gag gcc tca gcc ctg gac ttt gat gtg tcc      2125
Pro Leu Thr Gly Val Lys Glu Ala Ser Ala Leu Asp Phe Asp Val Ser
670                 675                 680                 685

aac aac cac atc tac tgg aca gac gtc agc ctg aag acc atc agc cgc      2173
Asn Asn His Ile Tyr Trp Thr Asp Val Ser Leu Lys Thr Ile Ser Arg
                690                 695                 700

gcc ttc atg aac ggg agc tcg gtg gag cac gtg gtg gag ttt ggc ctt      2221
Ala Phe Met Asn Gly Ser Ser Val Glu His Val Val Glu Phe Gly Leu
            705                 710                 715

gac tac ccc gag ggc atg gcc gtt gac tgg atg ggc aag aac ctc tac      2269
Asp Tyr Pro Glu Gly Met Ala Val Asp Trp Met Gly Lys Asn Leu Tyr
        720                 725                 730

tgg gcc gac act ggg acc aac aga atc gaa gtg gcg cgg ctg gac ggg      2317
Trp Ala Asp Thr Gly Thr Asn Arg Ile Glu Val Ala Arg Leu Asp Gly
    735                 740                 745

cag ttc cgg caa gtc ctc gtg tgg agg gac ttg gac aac ccg agg tcg      2365
Gln Phe Arg Gln Val Leu Val Trp Arg Asp Leu Asp Asn Pro Arg Ser
750                 755                 760                 765

ctg gcc ctg gat ccc acc aag ggc tac atc tac tgg acc gag tgg ggc      2413
Leu Ala Leu Asp Pro Thr Lys Gly Tyr Ile Tyr Trp Thr Glu Trp Gly
                770                 775                 780

ggc aag ccg agg atc gtg cgg gcc ttc atg gac ggg acc aac tgc atg      2461
Gly Lys Pro Arg Ile Val Arg Ala Phe Met Asp Gly Thr Asn Cys Met
            785                 790                 795

acg ctg gtg gac aag gtg ggc cgg gcc aac gac ctc acc att gac tac      2509
Thr Leu Val Asp Lys Val Gly Arg Ala Asn Asp Leu Thr Ile Asp Tyr
        800                 805                 810

gct gac cag cgc ctc tac tgg acc gac ctg gac acc aac atg atc gag      2557
Ala Asp Gln Arg Leu Tyr Trp Thr Asp Leu Asp Thr Asn Met Ile Glu
    815                 820                 825

tcg tcc aac atg ctg ggt cag gag cgg gtc gtg att gcc gac gat ctc      2605
Ser Ser Asn Met Leu Gly Gln Glu Arg Val Val Ile Ala Asp Asp Leu
830                 835                 840                 845

ccg cac ccg ttc ggt ctg acg cag tac agc gat tat atc tac tgg aca      2653
Pro His Pro Phe Gly Leu Thr Gln Tyr Ser Asp Tyr Ile Tyr Trp Thr
                850                 855                 860

gac tgg aat ctg cac agc att gag cgg gcc gac aag act agc ggc cgg      2701
Asp Trp Asn Leu His Ser Ile Glu Arg Ala Asp Lys Thr Ser Gly Arg
            865                 870                 875

aac cgc acc ctc atc cag ggc cac ctg gac ttc gtg atg gac atc ctg      2749
Asn Arg Thr Leu Ile Gln Gly His Leu Asp Phe Val Met Asp Ile Leu
        880                 885                 890
```

-continued

```
gtg ttc cac tcc tcc cgc cag gat ggc ctc aat gac tgt atg cac aac     2797
Val Phe His Ser Ser Arg Gln Asp Gly Leu Asn Asp Cys Met His Asn
    895                 900                 905

aac ggg cag tgt ggg cag ctg tgc ctt gcc atc ccc ggc ggc cac cgc     2845
Asn Gly Gln Cys Gly Gln Leu Cys Leu Ala Ile Pro Gly Gly His Arg
910                 915                 920                 925

tgc ggc tgc gcc tca cac tac acc ctg gac ccc agc agc cgc aac tgc     2893
Cys Gly Cys Ala Ser His Tyr Thr Leu Asp Pro Ser Ser Arg Asn Cys
                930                 935                 940

agc ccg ccc acc acc ttc ttg ctg ttc agc cag aaa tct gcc atc agt     2941
Ser Pro Pro Thr Thr Phe Leu Leu Phe Ser Gln Lys Ser Ala Ile Ser
            945                 950                 955

cgg atg atc ccg gac gac cag cac agc ccg gat ctc atc ctg ccc ctg     2989
Arg Met Ile Pro Asp Asp Gln His Ser Pro Asp Leu Ile Leu Pro Leu
        960                 965                 970

cat gga ctg agg aac gtc aaa gcc atc gac tat gac cca ctg gac aag     3037
His Gly Leu Arg Asn Val Lys Ala Ile Asp Tyr Asp Pro Leu Asp Lys
    975                 980                 985

ttc atc tac tgg gtg gat ggg cgc cag aac atc aag cga gcc aag gac     3085
Phe Ile Tyr Trp Val Asp Gly Arg Gln Asn Ile Lys Arg Ala Lys Asp
990                 995                 1000                1005

gac ggg acc cag ccc ttt gtt ttg acc tct ctg agc caa ggc caa aac     3133
Asp Gly Thr Gln Pro Phe Val Leu Thr Ser Leu Ser Gln Gly Gln Asn
                1010                1015                1020

cca gac agg cag ccc cac gac ctc agc atc gac atc tac agc cgg aca     3181
Pro Asp Arg Gln Pro His Asp Leu Ser Ile Asp Ile Tyr Ser Arg Thr
            1025                1030                1035

ctg ttc tgg acg tgc gag gcc acc aat acc atc aac gtc cac agg ctg     3229
Leu Phe Trp Thr Cys Glu Ala Thr Asn Thr Ile Asn Val His Arg Leu
        1040                1045                1050

agc ggg gaa gcc atg ggg gtg gtg ctg cgt ggg gac cgc gac aag ccc     3277
Ser Gly Glu Ala Met Gly Val Val Leu Arg Gly Asp Arg Asp Lys Pro
    1055                1060                1065

agg gcc atc gtc gtc aac gcg gag cga ggg tac ctg tac ttc acc aac     3325
Arg Ala Ile Val Val Asn Ala Glu Arg Gly Tyr Leu Tyr Phe Thr Asn
1070                1075                1080                1085

atg cag gac cgg gca gcc aag atc gaa cgc gca gcc ctg gac ggc acc     3373
Met Gln Asp Arg Ala Ala Lys Ile Glu Arg Ala Ala Leu Asp Gly Thr
                1090                1095                1100

gag cgc gag gtc ctc ttc acc acc ggc ctc atc cgc cct gtg gcc ctg     3421
Glu Arg Glu Val Leu Phe Thr Thr Gly Leu Ile Arg Pro Val Ala Leu
            1105                1110                1115

gtg gtg gac aac aca ctg ggc aag ctg ttc tgg gtg gac gcg gac ctg     3469
Val Val Asp Asn Thr Leu Gly Lys Leu Phe Trp Val Asp Ala Asp Leu
        1120                1125                1130

aag cgc att gag agc tgt gac ctg tca ggg gcc aac cgc ctg acc ctg     3517
Lys Arg Ile Glu Ser Cys Asp Leu Ser Gly Ala Asn Arg Leu Thr Leu
    1135                1140                1145

gag gac gcc aac atc gtg cag cct ctg ggc ctg acc atc ctt ggc aag     3565
Glu Asp Ala Asn Ile Val Gln Pro Leu Gly Leu Thr Ile Leu Gly Lys
1150                1155                1160                1165

cat ctc tac tgg atc gac cgc cag cag cag atg atc gag cgt gtg gag     3613
His Leu Tyr Trp Ile Asp Arg Gln Gln Gln Met Ile Glu Arg Val Glu
                1170                1175                1180

aag acc acc ggg gac aag cgg act cgc atc cag ggc cgt gtc gcc cac     3661
Lys Thr Thr Gly Asp Lys Arg Thr Arg Ile Gln Gly Arg Val Ala His
            1185                1190                1195

ctc act ggc atc cat gca gtg gag gaa gtc agc ctg gag gag ttc tca     3709
Leu Thr Gly Ile His Ala Val Glu Glu Val Ser Leu Glu Glu Phe Ser
```

-continued

```
        1200                1205                1210

gcc cac cca tgt gcc cgt gac aat ggt ggc tgc tcc cac atc tgt att     3757
Ala His Pro Cys Ala Arg Asp Asn Gly Gly Cys Ser His Ile Cys Ile
    1215                1220                1225

gcc aag ggt gat ggg aca cca cgg tgc tca tgc cca gtc cac ctc gtg     3805
Ala Lys Gly Asp Gly Thr Pro Arg Cys Ser Cys Pro Val His Leu Val
1230                1235                1240                1245

ctc ctg cag aac ctg ctg acc tgt gga gag ccg ccc acc tgc tcc ccg     3853
Leu Leu Gln Asn Leu Leu Thr Cys Gly Glu Pro Pro Thr Cys Ser Pro
                1250                1255                1260

gac cag ttt gca tgt gcc aca ggg gag atc gac tgt atc ccc ggg gcc     3901
Asp Gln Phe Ala Cys Ala Thr Gly Glu Ile Asp Cys Ile Pro Gly Ala
            1265                1270                1275

tgg cgc tgt gac ggc ttt ccc gag tgc gat gac cag agc gac gag gag     3949
Trp Arg Cys Asp Gly Phe Pro Glu Cys Asp Asp Gln Ser Asp Glu Glu
        1280                1285                1290

ggc tgc ccc gtg tgc tcc gcc gcc cag ttc ccc tgc gcg cgg ggt cag     3997
Gly Cys Pro Val Cys Ser Ala Ala Gln Phe Pro Cys Ala Arg Gly Gln
    1295                1300                1305

tgt gtg gac ctg cgc ctg cgc tgc gac ggc gag gca gac tgt cag gac     4045
Cys Val Asp Leu Arg Leu Arg Cys Asp Gly Glu Ala Asp Cys Gln Asp
1310                1315                1320                1325

cgc tca gac gag gtg gac tgt gac gcc atc tgc ctg ccc aac cag ttc     4093
Arg Ser Asp Glu Val Asp Cys Asp Ala Ile Cys Leu Pro Asn Gln Phe
                1330                1335                1340

cgg tgt gcg agc ggc cag tgt gtc ctc atc aaa cag cag tgc gac tcc     4141
Arg Cys Ala Ser Gly Gln Cys Val Leu Ile Lys Gln Gln Cys Asp Ser
            1345                1350                1355

ttc ccc gac tgt atc gac ggc tcc gac gag ctc atg tgt gaa atc acc     4189
Phe Pro Asp Cys Ile Asp Gly Ser Asp Glu Leu Met Cys Glu Ile Thr
        1360                1365                1370

aag ccg ccc tca gac gac agc ccg gcc cac agc agt gcc atc ggg ccc     4237
Lys Pro Pro Ser Asp Asp Ser Pro Ala His Ser Ser Ala Ile Gly Pro
    1375                1380                1385

gtc att ggc atc atc ctc tct ctc ttc gtc atg ggt ggt gtc tat ttt     4285
Val Ile Gly Ile Ile Leu Ser Leu Phe Val Met Gly Gly Val Tyr Phe
1390                1395                1400                1405

gtg tgc cag cgc gtg gtg tgc cag cgc tat gcg ggg gcc aac ggg ccc     4333
Val Cys Gln Arg Val Val Cys Gln Arg Tyr Ala Gly Ala Asn Gly Pro
                1410                1415                1420

ttc ccg cac gag tat gtc agc ggg acc ccg cac gtg ccc ctc aat ttc     4381
Phe Pro His Glu Tyr Val Ser Gly Thr Pro His Val Pro Leu Asn Phe
            1425                1430                1435

ata gcc ccg ggc ggt tcc cag cat ggc ccc ttc aca ggc atc gca tgc     4429
Ile Ala Pro Gly Gly Ser Gln His Gly Pro Phe Thr Gly Ile Ala Cys
        1440                1445                1450

gga aag tcc atg atg agc tcc gtg agc ctg atg ggg ggc cgg ggc ggg     4477
Gly Lys Ser Met Met Ser Ser Val Ser Leu Met Gly Gly Arg Gly Gly
    1455                1460                1465

gtg ccc ctc tac gac cgg aac cac gtc aca ggg gcc tcg tcc agc agc     4525
Val Pro Leu Tyr Asp Arg Asn His Val Thr Gly Ala Ser Ser Ser Ser
1470                1475                1480                1485

tcg tcc agc acg aag gcc acg ctg tac ccg ccg atc ctg aac ccg ccg     4573
Ser Ser Ser Thr Lys Ala Thr Leu Tyr Pro Pro Ile Leu Asn Pro Pro
                1490                1495                1500

ccc tcc ccg gcc acg gac ccc tcc ctg tac aac atg gac atg ttc tac     4621
Pro Ser Pro Ala Thr Asp Pro Ser Leu Tyr Asn Met Asp Met Phe Tyr
            1505                1510                1515

tct tca aac att ccg gcc act gcg aga ccg tac agg ccc tac atc att     4669
```

-continued

```
Ser Ser Asn Ile Pro Ala Thr Ala Arg Pro Tyr Arg Pro Tyr Ile Ile
        1520                1525                1530

cga gga atg gcg ccc ccg acg acg ccc tgc agc acc gac gtg tgt gac      4717
Arg Gly Met Ala Pro Pro Thr Thr Pro Cys Ser Thr Asp Val Cys Asp
    1535                1540                1545

agc gac tac agc gcc agc cgc tgg aag gcc agc aag tac tac ctg gat      4765
Ser Asp Tyr Ser Ala Ser Arg Trp Lys Ala Ser Lys Tyr Tyr Leu Asp
1550                1555                1560                1565

ttg aac tcg gac tca gac ccc tat cca ccc cca ccc acg ccc cac agc      4813
Leu Asn Ser Asp Ser Asp Pro Tyr Pro Pro Pro Pro Thr Pro His Ser
                1570                1575                1580

cag tac ctg tcg gcg gag gac agc tgc ccg ccc tcg ccc gcc acc gag      4861
Gln Tyr Leu Ser Ala Glu Asp Ser Cys Pro Pro Ser Pro Ala Thr Glu
            1585                1590                1595

agg agc tac ttc cat ctc ttc ccg ccc cct ccg tcc ccc tgc acg gac      4909
Arg Ser Tyr Phe His Leu Phe Pro Pro Pro Pro Ser Pro Cys Thr Asp
        1600                1605                1610

tca tcc tgacctcggc cgggccactc tggcttctct gtgcccctgt aaatagtttt      4965
Ser Ser
    1615

aaatatgaac aaagaaaaaa atatatttta tgatttaaaa aataaatata attgggattt   5025

taaaaacatg agaaatgtga actgtgatgg ggtgggcagg gctgggagaa ctttgtacag   5085

tggagaaata tttataaact taattttgta aaaca                              5120


<210> SEQ ID NO 2
<211> LENGTH: 5120
<212> TYPE: DNA
<213> ORGANISM: Homo sapiens

<400> SEQUENCE: 2

actaaagcgc cgccgccgcg ccatggagcc cgagtgagcg cggcgcgggc ccgtccggcc     60

gccggacaac  atg gag gca gcg ccg ccc ggg ccg ccg tgg ccg ctg ctg      109
            Met Glu Ala Ala Pro Pro Gly Pro Pro Trp Pro Leu Leu
            1               5                   10

ctg ctg ctg ctg ctg ctg ctg gcg ctg tgc ggc tgc ccg gcc ccc gcc      157
Leu Leu Leu Leu Leu Leu Leu Ala Leu Cys Gly Cys Pro Ala Pro Ala
    15                  20                  25

gcg gcc tcg ccg ctc ctg cta ttt gcc aac cgc cgg gac gta cgg ctg      205
Ala Ala Ser Pro Leu Leu Leu Phe Ala Asn Arg Arg Asp Val Arg Leu
30                  35                  40                  45

gtg gac gcc ggc gga gtc aag ctg gag tcc acc atc gtg gtc agc ggc      253
Val Asp Ala Gly Gly Val Lys Leu Glu Ser Thr Ile Val Val Ser Gly
                50                  55                  60

ctg gag gat gcg gcc gca gtg gac ttc cag ttt tcc aag gga gcc gtg      301
Leu Glu Asp Ala Ala Ala Val Asp Phe Gln Phe Ser Lys Gly Ala Val
            65                  70                  75

tac tgg aca gac gtg agc gag gag gcc atc aag cag acc tac ctg aac      349
Tyr Trp Thr Asp Val Ser Glu Glu Ala Ile Lys Gln Thr Tyr Leu Asn
        80                  85                  90

cag acg ggg gcc gcc gtg cag aac gtg gtc atc tcc ggc ctg gtc tct      397
Gln Thr Gly Ala Ala Val Gln Asn Val Val Ile Ser Gly Leu Val Ser
    95                  100                 105

ccc gac ggc ctc gcc tgc gac tgg gtg ggc aag aag ctg tac tgg acg      445
Pro Asp Gly Leu Ala Cys Asp Trp Val Gly Lys Lys Leu Tyr Trp Thr
110                 115                 120                 125

gac tca gag acc aac cgc atc gag gtg gcc aac ctc aat ggc aca tcc      493
Asp Ser Glu Thr Asn Arg Ile Glu Val Ala Asn Leu Asn Gly Thr Ser
                130                 135                 140
```

-continued

```
cgg aag gtg ctc ttc tgg cag gac ctt gac cag ccg agg gcc atc gcc      541
Arg Lys Val Leu Phe Trp Gln Asp Leu Asp Gln Pro Arg Ala Ile Ala
            145                 150                 155

ttg gac ccc gct cac ggg tac atg tac tgg aca gac tgg gtt gag acg      589
Leu Asp Pro Ala His Gly Tyr Met Tyr Trp Thr Asp Trp Val Glu Thr
        160                 165                 170

ccc cgg att gag cgg gca ggg atg gat ggc agc acc cgg aag atc att      637
Pro Arg Ile Glu Arg Ala Gly Met Asp Gly Ser Thr Arg Lys Ile Ile
    175                 180                 185

gtg gac tcg gac att tac tgg ccc aat gga ctg acc atc gac ctg gag      685
Val Asp Ser Asp Ile Tyr Trp Pro Asn Gly Leu Thr Ile Asp Leu Glu
190                 195                 200                 205

gag cag aag ctc tac tgg gct gac gcc aag ctc agc ttc atc cac cgt      733
Glu Gln Lys Leu Tyr Trp Ala Asp Ala Lys Leu Ser Phe Ile His Arg
                210                 215                 220

gcc aac ctg gac ggc tcg ttc cgg cag aag gtg gtg gag ggc agc ctg      781
Ala Asn Leu Asp Gly Ser Phe Arg Gln Lys Val Val Glu Gly Ser Leu
            225                 230                 235

acg cac ccc ttc gcc ctg acg ctc tcc ggg gac act ctg tac tgg aca      829
Thr His Pro Phe Ala Leu Thr Leu Ser Gly Asp Thr Leu Tyr Trp Thr
        240                 245                 250

gac tgg cag acc cgc tcc atc cat gcc tgc aac aag cgc act ggg ggg      877
Asp Trp Gln Thr Arg Ser Ile His Ala Cys Asn Lys Arg Thr Gly Gly
    255                 260                 265

aag agg aag gag atc ctg agt gcc ctc tac tca ccc atg gac atc cag      925
Lys Arg Lys Glu Ile Leu Ser Ala Leu Tyr Ser Pro Met Asp Ile Gln
270                 275                 280                 285

gtg ctg agc cag gag cgg cag cct ttc ttc cac act cgc tgt gag gag      973
Val Leu Ser Gln Glu Arg Gln Pro Phe Phe His Thr Arg Cys Glu Glu
                290                 295                 300

gac aat ggc ggc tgc tcc cac ctg tgc ctg ctg tcc cca agc gag cct     1021
Asp Asn Gly Gly Cys Ser His Leu Cys Leu Leu Ser Pro Ser Glu Pro
            305                 310                 315

ttc tac aca tgc gcc tgc ccc acg ggt gtg cag ctg cag gac aac ggc     1069
Phe Tyr Thr Cys Ala Cys Pro Thr Gly Val Gln Leu Gln Asp Asn Gly
        320                 325                 330

agg acg tgt aag gca gga gcc gag gag gtg ctg ctg ctg gcc cgg cgg     1117
Arg Thr Cys Lys Ala Gly Ala Glu Glu Val Leu Leu Leu Ala Arg Arg
    335                 340                 345

acg gac cta cgg agg atc tcg ctg gac acg ccg gac ttc acc gac atc     1165
Thr Asp Leu Arg Arg Ile Ser Leu Asp Thr Pro Asp Phe Thr Asp Ile
350                 355                 360                 365

gtg ctg cag gtg gac gac atc cgg cac gcc att gcc atc gac tac gac     1213
Val Leu Gln Val Asp Asp Ile Arg His Ala Ile Ala Ile Asp Tyr Asp
                370                 375                 380

ccg cta gag ggc tat gtc tac tgg aca gat gac gag gtg cgg gcc atc     1261
Pro Leu Glu Gly Tyr Val Tyr Trp Thr Asp Asp Glu Val Arg Ala Ile
            385                 390                 395

cgc agg gcg tac ctg gac ggg tct ggg gcg cag acg ctg gtc aac acc     1309
Arg Arg Ala Tyr Leu Asp Gly Ser Gly Ala Gln Thr Leu Val Asn Thr
        400                 405                 410

gag atc aac gac ccc gat ggc atc gcg gtc gac tgg gtg gcc cga aac     1357
Glu Ile Asn Asp Pro Asp Gly Ile Ala Val Asp Trp Val Ala Arg Asn
    415                 420                 425

ctc tac tgg acc gac acg ggc acg gac cgc atc gag gtg acg cgc ctc     1405
Leu Tyr Trp Thr Asp Thr Gly Thr Asp Arg Ile Glu Val Thr Arg Leu
430                 435                 440                 445

aac ggc acc tcc cgc aag atc ctg gtg tcg gag gac ctg gac gag ccc     1453
Asn Gly Thr Ser Arg Lys Ile Leu Val Ser Glu Asp Leu Asp Glu Pro
                450                 455                 460
```

-continued

```
cga gcc atc gca ctg cac ccc gtg atg ggc ctc atg tac tgg aca gac      1501
Arg Ala Ile Ala Leu His Pro Val Met Gly Leu Met Tyr Trp Thr Asp
            465                 470                 475

tgg gga gag aac cct aaa atc gag tgt gcc aac ttg gat ggg cag gag      1549
Trp Gly Glu Asn Pro Lys Ile Glu Cys Ala Asn Leu Asp Gly Gln Glu
        480                 485                 490

cgg cgt gtg ctg gtc aat gcc tcc ctc ggg tgg ccc aac ggc ctg gcc      1597
Arg Arg Val Leu Val Asn Ala Ser Leu Gly Trp Pro Asn Gly Leu Ala
    495                 500                 505

ctg gac ctg cag gag ggg aag ctc tac tgg gga gac gcc aag aca gac      1645
Leu Asp Leu Gln Glu Gly Lys Leu Tyr Trp Gly Asp Ala Lys Thr Asp
510                 515                 520                 525

aag atc gag gtg atc aat gtt gat ggg acg aag agg cgg acc ctc ctg      1693
Lys Ile Glu Val Ile Asn Val Asp Gly Thr Lys Arg Arg Thr Leu Leu
                530                 535                 540

gag gac aag ctc ccg cac att ttc ggg ttc acg ctg ctg ggg gac ttc      1741
Glu Asp Lys Leu Pro His Ile Phe Gly Phe Thr Leu Leu Gly Asp Phe
            545                 550                 555

atc tac tgg act gac tgg cag cgc cgc agc atc gag cgg gtg cac aag      1789
Ile Tyr Trp Thr Asp Trp Gln Arg Arg Ser Ile Glu Arg Val His Lys
        560                 565                 570

gtc aag gcc agc cgg gac gtc atc att gac cag ctg ccc gac ctg atg      1837
Val Lys Ala Ser Arg Asp Val Ile Ile Asp Gln Leu Pro Asp Leu Met
    575                 580                 585

ggg ctc aaa gct gtg aat gtg gcc aag gtc gtc gga acc aac ccg tgt      1885
Gly Leu Lys Ala Val Asn Val Ala Lys Val Val Gly Thr Asn Pro Cys
590                 595                 600                 605

gcg gac agg aac ggg ggg tgc agc cac ctg tgc ttc ttc aca ccc cac      1933
Ala Asp Arg Asn Gly Gly Cys Ser His Leu Cys Phe Phe Thr Pro His
                610                 615                 620

gca acc cgg tgt ggc tgc ccc atc ggc ctg gag ctg ctg agt gac atg      1981
Ala Thr Arg Cys Gly Cys Pro Ile Gly Leu Glu Leu Leu Ser Asp Met
            625                 630                 635

aag acc tgc atc gtg cct gag gcc ttc ttg gtc ttc acc agc aga gcc      2029
Lys Thr Cys Ile Val Pro Glu Ala Phe Leu Val Phe Thr Ser Arg Ala
        640                 645                 650

gcc atc cac agg atc tcc ctc gag acc aat aac aac gac gtg gcc atc      2077
Ala Ile His Arg Ile Ser Leu Glu Thr Asn Asn Asn Asp Val Ala Ile
    655                 660                 665

ccg ctc acg ggc gtc aag gag gcc tca gcc ctg gac ttt gat gtg tcc      2125
Pro Leu Thr Gly Val Lys Glu Ala Ser Ala Leu Asp Phe Asp Val Ser
670                 675                 680                 685

aac aac cac atc tac tgg aca gac gtc agc ctg aag acc atc agc cgc      2173
Asn Asn His Ile Tyr Trp Thr Asp Val Ser Leu Lys Thr Ile Ser Arg
                690                 695                 700

gcc ttc atg aac ggg agc tcg gtg gag cac gtg gtg gag ttt ggc ctt      2221
Ala Phe Met Asn Gly Ser Ser Val Glu His Val Val Glu Phe Gly Leu
            705                 710                 715

gac tac ccc gag ggc atg gcc gtt gac tgg atg ggc aag aac ctc tac      2269
Asp Tyr Pro Glu Gly Met Ala Val Asp Trp Met Gly Lys Asn Leu Tyr
        720                 725                 730

tgg gcc gac act ggg acc aac aga atc gaa gtg gcg cgg ctg gac ggg      2317
Trp Ala Asp Thr Gly Thr Asn Arg Ile Glu Val Ala Arg Leu Asp Gly
    735                 740                 745

cag ttc cgg caa gtc ctc gtg tgg agg gac ttg gac aac ccg agg tcg      2365
Gln Phe Arg Gln Val Leu Val Trp Arg Asp Leu Asp Asn Pro Arg Ser
750                 755                 760                 765

ctg gcc ctg gat ccc acc aag ggc tac atc tac tgg acc gag tgg ggc      2413
Leu Ala Leu Asp Pro Thr Lys Gly Tyr Ile Tyr Trp Thr Glu Trp Gly
```

-continued

```
                770                 775                 780

ggc aag ccg agg atc gtg cgg gcc ttc atg gac ggg acc aac tgc atg     2461
Gly Lys Pro Arg Ile Val Arg Ala Phe Met Asp Gly Thr Asn Cys Met
            785                 790                 795

acg ctg gtg gac aag gtg ggc cgg gcc aac gac ctc acc att gac tac     2509
Thr Leu Val Asp Lys Val Gly Arg Ala Asn Asp Leu Thr Ile Asp Tyr
        800                 805                 810

gct gac cag cgc ctc tac tgg acc gac ctg gac acc aac atg atc gag     2557
Ala Asp Gln Arg Leu Tyr Trp Thr Asp Leu Asp Thr Asn Met Ile Glu
    815                 820                 825

tcg tcc aac atg ctg ggt cag gag cgg gtc gtg att gcc gac gat ctc     2605
Ser Ser Asn Met Leu Gly Gln Glu Arg Val Val Ile Ala Asp Asp Leu
830                 835                 840                 845

ccg cac ccg ttc ggt ctg acg cag tac agc gat tat atc tac tgg aca     2653
Pro His Pro Phe Gly Leu Thr Gln Tyr Ser Asp Tyr Ile Tyr Trp Thr
                850                 855                 860

gac tgg aat ctg cac agc att gag cgg gcc gac aag act agc ggc cgg     2701
Asp Trp Asn Leu His Ser Ile Glu Arg Ala Asp Lys Thr Ser Gly Arg
            865                 870                 875

aac cgc acc ctc atc cag ggc cac ctg gac ttc gtg atg gac atc ctg     2749
Asn Arg Thr Leu Ile Gln Gly His Leu Asp Phe Val Met Asp Ile Leu
        880                 885                 890

gtg ttc cac tcc tcc cgc cag gat ggc ctc aat gac tgt atg cac aac     2797
Val Phe His Ser Ser Arg Gln Asp Gly Leu Asn Asp Cys Met His Asn
    895                 900                 905

aac ggg cag tgt ggg cag ctg tgc ctt gcc atc ccc ggc ggc cac cgc     2845
Asn Gly Gln Cys Gly Gln Leu Cys Leu Ala Ile Pro Gly Gly His Arg
910                 915                 920                 925

tgc ggc tgc gcc tca cac tac acc ctg gac ccc agc agc cgc aac tgc     2893
Cys Gly Cys Ala Ser His Tyr Thr Leu Asp Pro Ser Ser Arg Asn Cys
                930                 935                 940

agc ccg ccc acc acc ttc ttg ctg ttc agc cag aaa tct gcc atc agt     2941
Ser Pro Pro Thr Thr Phe Leu Leu Phe Ser Gln Lys Ser Ala Ile Ser
            945                 950                 955

cgg atg atc ccg gac gac cag cac agc ccg gat ctc atc ctg ccc ctg     2989
Arg Met Ile Pro Asp Asp Gln His Ser Pro Asp Leu Ile Leu Pro Leu
        960                 965                 970

cat gga ctg agg aac gtc aaa gcc atc gac tat gac cca ctg gac aag     3037
His Gly Leu Arg Asn Val Lys Ala Ile Asp Tyr Asp Pro Leu Asp Lys
    975                 980                 985

ttc atc tac tgg gtg gat ggg cgc cag aac atc aag cga gcc aag gac     3085
Phe Ile Tyr Trp Val Asp Gly Arg Gln Asn Ile Lys Arg Ala Lys Asp
990                 995                 1000                1005

gac ggg acc cag ccc ttt gtt ttg acc tct ctg agc caa ggc caa aac     3133
Asp Gly Thr Gln Pro Phe Val Leu Thr Ser Leu Ser Gln Gly Gln Asn
                1010                1015                1020

cca gac agg cag ccc cac gac ctc agc atc gac atc tac agc cgg aca     3181
Pro Asp Arg Gln Pro His Asp Leu Ser Ile Asp Ile Tyr Ser Arg Thr
            1025                1030                1035

ctg ttc tgg acg tgc gag gcc acc aat acc atc aac gtc cac agg ctg     3229
Leu Phe Trp Thr Cys Glu Ala Thr Asn Thr Ile Asn Val His Arg Leu
        1040                1045                1050

agc ggg gaa gcc atg ggg gtg gtg ctg cgt ggg gac cgc gac aag ccc     3277
Ser Gly Glu Ala Met Gly Val Val Leu Arg Gly Asp Arg Asp Lys Pro
    1055                1060                1065

agg gcc atc gtc gtc aac gcg gag cga ggg tac ctg tac ttc acc aac     3325
Arg Ala Ile Val Val Asn Ala Glu Arg Gly Tyr Leu Tyr Phe Thr Asn
1070                1075                1080                1085

atg cag gac cgg gca gcc aag atc gaa cgc gca gcc ctg gac ggc acc     3373
```

-continued

```
Met Gln Asp Arg Ala Ala Lys Ile Glu Arg Ala Ala Leu Asp Gly Thr
                1090                1095                1100

gag cgc gag gtc ctc ttc acc acc ggc ctc atc cgc cct gtg gcc ctg      3421
Glu Arg Glu Val Leu Phe Thr Thr Gly Leu Ile Arg Pro Val Ala Leu
            1105                1110                1115

gtg gtg gac aac aca ctg ggc aag ctg ttc tgg gtg gac gcg gac ctg      3469
Val Val Asp Asn Thr Leu Gly Lys Leu Phe Trp Val Asp Ala Asp Leu
        1120                1125                1130

aag cgc att gag agc tgt gac ctg tca ggg gcc aac cgc ctg acc ctg      3517
Lys Arg Ile Glu Ser Cys Asp Leu Ser Gly Ala Asn Arg Leu Thr Leu
    1135                1140                1145

gag gac gcc aac atc gtg cag cct ctg ggc ctg acc atc ctt ggc aag      3565
Glu Asp Ala Asn Ile Val Gln Pro Leu Gly Leu Thr Ile Leu Gly Lys
1150                1155                1160                1165

cat ctc tac tgg atc gac cgc cag cag cag atg atc gag cgt gtg gag      3613
His Leu Tyr Trp Ile Asp Arg Gln Gln Gln Met Ile Glu Arg Val Glu
                1170                1175                1180

aag acc acc ggg gac aag cgg act cgc atc cag ggc cgt gtc gcc cac      3661
Lys Thr Thr Gly Asp Lys Arg Thr Arg Ile Gln Gly Arg Val Ala His
            1185                1190                1195

ctc act ggc atc cat gca gtg gag gaa gtc agc ctg gag gag ttc tca      3709
Leu Thr Gly Ile His Ala Val Glu Glu Val Ser Leu Glu Glu Phe Ser
        1200                1205                1210

gcc cac cca tgt gcc cgt gac aat ggt ggc tgc tcc cac atc tgt att      3757
Ala His Pro Cys Ala Arg Asp Asn Gly Gly Cys Ser His Ile Cys Ile
    1215                1220                1225

gcc aag ggt gat ggg aca cca cgg tgc tca tgc cca gtc cac ctc gtg      3805
Ala Lys Gly Asp Gly Thr Pro Arg Cys Ser Cys Pro Val His Leu Val
1230                1235                1240                1245

ctc ctg cag aac ctg ctg acc tgt gga gag ccg ccc acc tgc tcc ccg      3853
Leu Leu Gln Asn Leu Leu Thr Cys Gly Glu Pro Pro Thr Cys Ser Pro
                1250                1255                1260

gac cag ttt gca tgt gcc aca ggg gag atc gac tgt atc ccc ggg gcc      3901
Asp Gln Phe Ala Cys Ala Thr Gly Glu Ile Asp Cys Ile Pro Gly Ala
            1265                1270                1275

tgg cgc tgt gac ggc ttt ccc gag tgc gat gac cag agc gac gag gag      3949
Trp Arg Cys Asp Gly Phe Pro Glu Cys Asp Asp Gln Ser Asp Glu Glu
        1280                1285                1290

ggc tgc ccc gtg tgc tcc gcc gcc cag ttc ccc tgc gcg cgg ggt cag      3997
Gly Cys Pro Val Cys Ser Ala Ala Gln Phe Pro Cys Ala Arg Gly Gln
    1295                1300                1305

tgt gtg gac ctg cgc ctg cgc tgc gac ggc gag gca gac tgt cag gac      4045
Cys Val Asp Leu Arg Leu Arg Cys Asp Gly Glu Ala Asp Cys Gln Asp
1310                1315                1320                1325

cgc tca gac gag gtg gac tgt gac gcc atc tgc ctg ccc aac cag ttc      4093
Arg Ser Asp Glu Val Asp Cys Asp Ala Ile Cys Leu Pro Asn Gln Phe
                1330                1335                1340

cgg tgt gcg agc ggc cag tgt gtc ctc atc aaa cag cag tgc gac tcc      4141
Arg Cys Ala Ser Gly Gln Cys Val Leu Ile Lys Gln Gln Cys Asp Ser
            1345                1350                1355

ttc ccc gac tgt atc gac ggc tcc gac gag ctc atg tgt gaa atc acc      4189
Phe Pro Asp Cys Ile Asp Gly Ser Asp Glu Leu Met Cys Glu Ile Thr
        1360                1365                1370

aag ccg ccc tca gac gac agc ccg gcc cac agc agt gcc atc ggg ccc      4237
Lys Pro Pro Ser Asp Asp Ser Pro Ala His Ser Ser Ala Ile Gly Pro
    1375                1380                1385

gtc att ggc atc atc ctc tct ctc ttc gtc atg ggt ggt gtc tat ttt      4285
Val Ile Gly Ile Ile Leu Ser Leu Phe Val Met Gly Gly Val Tyr Phe
1390                1395                1400                1405
```

-continued

```
gtg tgc cag cgc gtg gtg tgc cag cgc tat gcg ggg gcc aac ggg ccc      4333
Val Cys Gln Arg Val Val Cys Gln Arg Tyr Ala Gly Ala Asn Gly Pro
                1410                1415                1420

ttc ccg cac gag tat gtc agc ggg acc ccg cac gtg ccc ctc aat ttc      4381
Phe Pro His Glu Tyr Val Ser Gly Thr Pro His Val Pro Leu Asn Phe
            1425                1430                1435

ata gcc ccg ggc ggt tcc cag cat ggc ccc ttc aca ggc atc gca tgc      4429
Ile Ala Pro Gly Gly Ser Gln His Gly Pro Phe Thr Gly Ile Ala Cys
        1440                1445                1450

gga aag tcc atg atg agc tcc gtg agc ctg atg ggg ggc cgg ggc ggg      4477
Gly Lys Ser Met Met Ser Ser Val Ser Leu Met Gly Gly Arg Gly Gly
    1455                1460                1465

gtg ccc ctc tac gac cgg aac cac gtc aca ggg gcc tcg tcc agc agc      4525
Val Pro Leu Tyr Asp Arg Asn His Val Thr Gly Ala Ser Ser Ser Ser
1470                1475                1480                1485

tcg tcc agc acg aag gcc acg ctg tac ccg ccg atc ctg aac ccg ccg      4573
Ser Ser Ser Thr Lys Ala Thr Leu Tyr Pro Pro Ile Leu Asn Pro Pro
                1490                1495                1500

ccc tcc ccg gcc acg gac ccc tcc ctg tac aac atg gac atg ttc tac      4621
Pro Ser Pro Ala Thr Asp Pro Ser Leu Tyr Asn Met Asp Met Phe Tyr
            1505                1510                1515

tct tca aac att ccg gcc act gcg aga ccg tac agg ccc tac atc att      4669
Ser Ser Asn Ile Pro Ala Thr Ala Arg Pro Tyr Arg Pro Tyr Ile Ile
        1520                1525                1530

cga gga atg gcg ccc ccg acg acg ccc tgc agc acc gac gtg tgt gac      4717
Arg Gly Met Ala Pro Pro Thr Thr Pro Cys Ser Thr Asp Val Cys Asp
    1535                1540                1545

agc gac tac agc gcc agc cgc tgg aag gcc agc aag tac tac ctg gat      4765
Ser Asp Tyr Ser Ala Ser Arg Trp Lys Ala Ser Lys Tyr Tyr Leu Asp
1550                1555                1560                1565

ttg aac tcg gac tca gac ccc tat cca ccc cca ccc acg ccc cac agc      4813
Leu Asn Ser Asp Ser Asp Pro Tyr Pro Pro Pro Pro Thr Pro His Ser
                1570                1575                1580

cag tac ctg tcg gcg gag gac agc tgc ccg ccc tcg ccc gcc acc gag      4861
Gln Tyr Leu Ser Ala Glu Asp Ser Cys Pro Pro Ser Pro Ala Thr Glu
            1585                1590                1595

agg agc tac ttc cat ctc ttc ccg ccc cct ccg tcc ccc tgc acg gac      4909
Arg Ser Tyr Phe His Leu Phe Pro Pro Pro Pro Ser Pro Cys Thr Asp
        1600                1605                1610

tca tcc tgacctcggc cgggccactc tggcttctct gtgcccctgt aaatagtttt      4965
Ser Ser
    1615

aaatatgaac aaagaaaaaa atatatttta tgatttaaaa aataaatata attgggattt   5025

taaaaacatg agaaatgtga actgtgatgg ggtgggcagg gctgggagaa ctttgtacag   5085

tggagaaata tttataaact taattttgta aaaca                              5120


<210> SEQ ID NO 3
<211> LENGTH: 1615
<212> TYPE: PRT
<213> ORGANISM: Homo sapiens

<400> SEQUENCE: 3

Met Glu Ala Ala Pro Pro Gly Pro Pro Trp Pro Leu Leu Leu Leu Leu
 1               5                  10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45
```

-continued

```
Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Lys Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Trp Ser His Leu Cys Leu Leu Ser Pro Ser Glu Pro Phe Tyr Thr
305                 310                 315                 320

Cys Ala Cys Pro Thr Gly Val Gln Met Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
```

-continued

```
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
        595                 600                 605

Asn Gly Gly Cys Ser His Leu Cys Phe Phe Thr Pro His Ala Thr Arg
    610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
        675                 680                 685

Ile Tyr Trp Thr Asp Val Ser Leu Lys Asn Ile Ser Arg Ala Phe Met
    690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
        755                 760                 765

Asp Pro Thr Lys Gly Tyr Ile Tyr Trp Thr Glu Trp Gly Gly Lys Pro
    770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
        835                 840                 845

Phe Gly Leu Thr Gln Tyr Ser Asp Tyr Ile Tyr Trp Thr Asp Trp Asn
    850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895
```

-continued

```
Ser Ser Arg Gln Asp Gly Leu Asn Asp Cys Met His Asn Asn Gly Gln
            900                 905                 910

Cys Gly Gln Leu Cys Leu Ala Ile Pro Gly Gly His Arg Cys Gly Cys
        915                 920                 925

Ala Ser His Tyr Thr Leu Asp Pro Ser Ser Arg Asn Cys Ser Pro Pro
    930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
        995                 1000                1005

Gln Pro Phe Val Leu Thr Ser Leu Ser Gln Gly Gln Asn Pro Asp Arg
    1010                1015                1020

Gln Pro His Asp Leu Ser Ile Asp Ile Tyr Ser Arg Thr Leu Phe Trp
1025                1030                1035                1040

Thr Cys Glu Ala Thr Asn Thr Ile Asn Val His Arg Leu Ser Gly Glu
                1045                1050                1055

Ala Met Gly Val Val Leu Arg Gly Asp Arg Asp Lys Pro Arg Ala Ile
            1060                1065                1070

Val Val Asn Ala Glu Arg Gly Tyr Leu Tyr Phe Thr Asn Met Gln Asp
        1075                1080                1085

Arg Ala Ala Lys Ile Glu Arg Ala Ala Leu Asp Gly Thr Glu Arg Glu
    1090                1095                1100

Val Leu Phe Thr Thr Gly Leu Ile Arg Pro Val Ala Leu Val Val Asp
1105                1110                1115                1120

Asn Thr Leu Gly Lys Leu Phe Trp Val Asp Ala Asp Leu Lys Arg Ile
                1125                1130                1135

Glu Ser Cys Asp Leu Ser Gly Ala Asn Arg Leu Thr Leu Glu Asp Ala
            1140                1145                1150

Asn Ile Val Gln Pro Leu Gly Leu Thr Ile Leu Gly Lys His Leu Tyr
        1155                1160                1165

Trp Ile Asp Arg Gln Gln Gln Met Ile Glu Arg Val Glu Lys Thr Thr
    1170                1175                1180

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
                1205                1210                1215

Cys Ala Arg Asp Asn Gly Gly Cys Ser His Ile Cys Ile Ala Lys Gly
            1220                1225                1230

Asp Gly Thr Pro Arg Cys Ser Cys Pro Val His Leu Val Leu Leu Gln
        1235                1240                1245

Asn Leu Leu Thr Cys Gly Glu Pro Pro Thr Cys Ser Pro Asp Gln Phe
    1250                1255                1260

Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
                1285                1290                1295

Val Cys Ser Ala Ala Gln Phe Pro Cys Ala Arg Gly Gln Cys Val Asp
            1300                1305                1310
```

-continued

```
Leu Arg Leu Arg Cys Asp Gly Glu Ala Asp Cys Gln Asp Arg Ser Asp
        1315                1320                1325

Glu Val Asp Cys Asp Ala Ile Cys Leu Pro Asn Gln Phe Arg Cys Ala
    1330                1335                1340

Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
                1365                1370                1375

Ser Asp Asp Ser Pro Ala His Ser Ser Ala Ile Gly Pro Val Ile Gly
            1380                1385                1390

Ile Ile Leu Ser Leu Phe Val Met Gly Gly Val Tyr Phe Val Cys Gln
        1395                1400                1405

Arg Val Val Cys Gln Arg Tyr Ala Gly Ala Asn Gly Pro Phe Pro His
    1410                1415                1420

Glu Tyr Val Ser Gly Thr Pro His Val Pro Leu Asn Phe Ile Ala Pro
1425                1430                1435                1440

Gly Gly Ser Gln His Gly Pro Phe Thr Gly Ile Ala Cys Gly Lys Ser
                1445                1450                1455

Met Met Ser Ser Val Ser Leu Met Gly Gly Arg Gly Gly Val Pro Leu
            1460                1465                1470

Tyr Asp Arg Asn His Val Thr Gly Ala Ser Ser Ser Ser Ser Ser Ser
        1475                1480                1485

Thr Lys Ala Thr Leu Tyr Pro Pro Ile Leu Asn Pro Pro Pro Ser Pro
    1490                1495                1500

Ala Thr Asp Pro Ser Leu Tyr Asn Met Asp Met Phe Tyr Ser Ser Asn
1505                1510                1515                1520

Ile Pro Ala Thr Ala Arg Pro Tyr Arg Pro Tyr Ile Ile Arg Gly Met
                1525                1530                1535

Ala Pro Pro Thr Thr Pro Cys Ser Thr Asp Val Cys Asp Ser Asp Tyr
            1540                1545                1550

Ser Ala Ser Arg Trp Lys Ala Ser Lys Tyr Tyr Leu Asp Leu Asn Ser
        1555                1560                1565

Asp Ser Asp Pro Tyr Pro Pro Pro Pro Thr Pro His Ser Gln Tyr Leu
    1570                1575                1580

Ser Ala Glu Asp Ser Cys Pro Pro Ser Pro Ala Thr Glu Arg Ser Tyr
1585                1590                1595                1600

Phe His Leu Phe Pro Pro Pro Pro Ser Pro Cys Thr Asp Ser Ser
                1605                1610                1615


<210> SEQ ID NO 4
<211> LENGTH: 1615
<212> TYPE: PRT
<213> ORGANISM: Homo sapiens

<400> SEQUENCE: 4

Met Glu Ala Ala Pro Pro Gly Pro Pro Trp Pro Leu Leu Leu Leu Leu
1               5                   10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80
```

-continued

```
Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Lys Ala Ile Ala Leu Asp Pro
145                 150                 155                 160

Ala His Gly Tyr Met Tyr Trp Thr Asp Trp Val Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Trp Ser His Leu Cys Leu Leu Ser Pro Ser Glu Pro Phe Tyr Thr
305                 310                 315                 320

Cys Ala Cys Pro Thr Gly Val Gln Met Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495
```

-continued

```
Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
        595                 600                 605

Asn Gly Gly Cys Ser His Leu Cys Phe Phe Thr Pro His Ala Thr Arg
    610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
        675                 680                 685

Ile Tyr Trp Thr Asp Val Ser Leu Lys Asn Ile Ser Arg Ala Phe Met
    690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
        755                 760                 765

Asp Pro Thr Lys Gly Tyr Ile Tyr Trp Thr Glu Trp Gly Gly Lys Pro
    770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
        835                 840                 845

Phe Gly Leu Thr Gln Tyr Ser Asp Tyr Ile Tyr Trp Thr Asp Trp Asn
    850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
            900                 905                 910

Cys Gly Gln Leu Cys Leu Ala Ile Pro Gly Gly His Arg Cys Gly Cys
```

-continued

```
        915                 920                 925

Ala Ser His Tyr Thr Leu Asp Pro Ser Ser Arg Asn Cys Ser Pro Pro
    930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
        995                 1000                1005

Gln Pro Phe Val Leu Thr Ser Leu Ser Gln Gly Gln Asn Pro Asp Arg
    1010                1015                1020

Gln Pro His Asp Leu Ser Ile Asp Ile Tyr Ser Arg Thr Leu Phe Trp
1025                1030                1035                1040

Thr Cys Glu Ala Thr Asn Thr Ile Asn Val His Arg Leu Ser Gly Glu
                1045                1050                1055

Ala Met Gly Val Val Leu Arg Gly Asp Arg Asp Lys Pro Arg Ala Ile
            1060                1065                1070

Val Val Asn Ala Glu Arg Gly Tyr Leu Tyr Phe Thr Asn Met Gln Asp
        1075                1080                1085

Arg Ala Ala Lys Ile Glu Arg Ala Ala Leu Asp Gly Thr Glu Arg Glu
    1090                1095                1100

Val Leu Phe Thr Thr Gly Leu Ile Arg Pro Val Ala Leu Val Val Asp
1105                1110                1115                1120

Asn Thr Leu Gly Lys Leu Phe Trp Val Asp Ala Asp Leu Lys Arg Ile
                1125                1130                1135

Glu Ser Cys Asp Leu Ser Gly Ala Asn Arg Leu Thr Leu Glu Asp Ala
            1140                1145                1150

Asn Ile Val Gln Pro Leu Gly Leu Thr Ile Leu Gly Lys His Leu Tyr
        1155                1160                1165

Trp Ile Asp Arg Gln Gln Gln Met Ile Glu Arg Val Glu Lys Thr Thr
    1170                1175                1180

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
                1205                1210                1215

Cys Ala Arg Asp Asn Gly Gly Cys Ser His Ile Cys Ile Ala Lys Gly
            1220                1225                1230

Asp Gly Thr Pro Arg Cys Ser Cys Pro Val His Leu Val Leu Leu Gln
        1235                1240                1245

Asn Leu Leu Thr Cys Gly Glu Pro Pro Thr Cys Ser Pro Asp Gln Phe
    1250                1255                1260

Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
                1285                1290                1295

Val Cys Ser Ala Ala Gln Phe Pro Cys Ala Arg Gly Gln Cys Val Asp
            1300                1305                1310

Leu Arg Leu Arg Cys Asp Gly Glu Ala Asp Cys Gln Asp Arg Ser Asp
        1315                1320                1325

Glu Val Asp Cys Asp Ala Ile Cys Leu Pro Asn Gln Phe Arg Cys Ala
    1330                1335                1340
```

-continued

```
Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
                1365                1370                1375

Ser Asp Asp Ser Pro Ala His Ser Ser Ala Ile Gly Pro Val Ile Gly
            1380                1385                1390

Ile Ile Leu Ser Leu Phe Val Met Gly Gly Val Tyr Phe Val Cys Gln
        1395                1400                1405

Arg Val Val Cys Gln Arg Tyr Ala Gly Ala Asn Gly Pro Phe Pro His
    1410                1415                1420

Glu Tyr Val Ser Gly Thr Pro His Val Pro Leu Asn Phe Ile Ala Pro
1425                1430                1435                1440

Gly Gly Ser Gln His Gly Pro Phe Thr Gly Ile Ala Cys Gly Lys Ser
                1445                1450                1455

Met Met Ser Ser Val Ser Leu Met Gly Gly Arg Gly Gly Val Pro Leu
            1460                1465                1470

Tyr Asp Arg Asn His Val Thr Gly Ala Ser Ser Ser Ser Ser Ser Ser
        1475                1480                1485

Thr Lys Ala Thr Leu Tyr Pro Pro Ile Leu Asn Pro Pro Pro Ser Pro
    1490                1495                1500

Ala Thr Asp Pro Ser Leu Tyr Asn Met Asp Met Phe Tyr Ser Ser Asn
1505                1510                1515                1520

Ile Pro Ala Thr Ala Arg Pro Tyr Arg Pro Tyr Ile Ile Arg Gly Met
                1525                1530                1535

Ala Pro Pro Thr Thr Pro Cys Ser Thr Asp Val Cys Asp Ser Asp Tyr
            1540                1545                1550

Ser Ala Ser Arg Trp Lys Ala Ser Lys Tyr Tyr Leu Asp Leu Asn Ser
        1555                1560                1565

Asp Ser Asp Pro Tyr Pro Pro Pro Pro Thr Pro His Ser Gln Tyr Leu
    1570                1575                1580

Ser Ala Glu Asp Ser Cys Pro Pro Ser Pro Ala Thr Glu Arg Ser Tyr
1585                1590                1595                1600

Phe His Leu Phe Pro Pro Pro Pro Ser Pro Cys Thr Asp Ser Ser
                1605                1610                1615


<210> SEQ ID NO 5
<211> LENGTH: 3096
<212> TYPE: DNA
<213> ORGANISM: Homo sapiens

<400> SEQUENCE: 5

catcttctca cacgatctct cgcttcgcac tccttccttt gattggtttt caccatttac     60

tcagacgacg gtccttcttc gatctttgca cattcttcta tcatctacta ccttcatacc    120

cagctccgtc ccctaatatt catgcgcgga tggcccattc cgtggtgaaa attcccttct    180

actctgctaa tctgctgttc tctctccctc ccgtcgggtt ctgctcctgc cacgttctcc    240

cctctcccca ccaaaggctg ggttttcttt gtcagggctc ctttcccctt tggaagaagg    300

ggggctgtat ggccttggtg cgaggccctc cagtgacagg atccccccatc acccagagtt    360

ccacaggccc tggtagggag gagggggagc agaagaggag gtgccatctt tgcctgctgg    420

ggaagggcag gggccaccca cacagagctc tcccatttgc tgtggaccct ggggccactg    480

cccagttcct tccaaaggaa agccagctcc ccaggtggtg ggagagtgat atggcttcct    540

cttaaactta gggaattgag tgtgtggttg cttctaagtg ccttagaagc cgggagcggc    600
```

-continued

```
tcctggaaag agcctgcctg ccacagcggg ccttaccctg gctgtgccca cagatgtccc    660
tggggcctgc cgctcctgcc cggctctcct ggcctccccc ggtgtgggtt gggaaaagca    720
cagcaaatta aaaaacacct ccatctctgg cctttgaaga atgcatctga acagccgaga    780
gtgtaaaccg tggtgaaatg tggtctttcc agtttgggga gaagcagggc agagctgggg    840
cttttgtacc cagggtttcc aagagctcct gcctccctcg gctgggctgg ccagggcccc    900
ccgctgggac ctccagctgt aatagggaag gttttactgg gttgctggcc actgtggact    960
gcccctaagg gcaggtatgc ctgcctttac ccgggttccc ctcctgcctg gaagatacag   1020
cccatgggag gcctgttgtc tgtgggatcc tccagcatca gagacactgg ggccagcgtc   1080
tgcctggtga ggtgcaggcc tggcaggccc ggtcccccac ctgcttgagc acccacggtg   1140
gtgggggctc gctgcctccc gagacaatct atgtcattgt tgtccaagga agctaattta   1200
gagtagaaag ttccgtgtcc agtcccactc tgtgcgtgtg ttagcagggg actctcgggc   1260
cggagctggg tccaccctgg taggggggact tcatggggcc tgggcgacag cactgtgtat   1320
ttgtgtgtgt gtgtgtttgt gtgtgtgtgt gtctgaggag gtggaccagt ttctcaaaag   1380
gcctgtgacc ccaagaacca aggaatttca gcctgggtgg atcacacctt cactggtgag   1440
tgggacaagc tgggggccct cgccacagga gcagccaggg catggggcac agttggcctc   1500
attcacaaaa tgggagtata agtgatccct gctctggcgg ccaggacgat gagtgggaac   1560
acaccgtgtg gggcgctgcct ggcctgggtg tgccgcgggt gtccttgttg gtgatggttc   1620
cacctgcttg tgccaccagt gccctctggg tctcacacac aactctcttc ccagcgaagg   1680
cccctcctgc cctcaggcct cagtgctgct tccgtctcgg aaggccccag gagctcctgc   1740
atcctgggcg tgattcctgt gtgcctgcag accccctcgc ggctgccatc tcatcctttg   1800
gtgcacctgt tggccagacc tcctggtagc gggtgctgca ctcccctgaa tgtgccgggg   1860
cctgggggca gggacctggg ctcctccctc actgagtgga gggaactcag tgtcttggag   1920
ttggggtgcc tgcaggctgg gtggtgcagg tgaaatgcag acctctcagc tggtgttcca   1980
gagcagctgc cttcccccgc ccgagggact tcacccgcag cccagtcagg ggtggcgcct   2040
gggtgcatcg cccgcaggct gggtaggggt ggagcctggg tggccctgcc tgtgagctgc   2100
atagttgtcg cctttgaccc tgagttttct tcgttatctg tttggacctg tttggggcag   2160
gcaggggatg agatctgaag ataaatgcct tagctgtgac catctccttt tgtgagaggt   2220
caatgtccag ttccgctgca gttataacat cccatttttt gatttctttt tattttttcc   2280
tttttctttt tgagatggag tctcgctctg tcacccaggc tggagtgcaa tggggtgacc   2340
tcagctcact gcaacctcca cttctcgggt tcaagtgatt ctcctgcctc agcctcctga   2400
ctagcagggg ttacaggcgt gagccaccac gcccagctaa tttttgtatt tttagtagag   2460
gcaaggtttc gtcatgttgg ccaggctggt ctcaaactcc tggccttaag tgatctgccc   2520
gcctcggcct cccaaagtgc tgagatgaca ggtgtgagcc accgtgcccg gcccagaact   2580
ctttaattcc cacctgaaac ttgccgcctt aagcaggtcc ccagtctccc tcccctagtc   2640
cctggtccca ccattctgct ttctgtctca atgaatttgc ctaccgtaag tacctcatat   2700
aaattgaatc ataaagtatt tgtcttttta tatctggctt atttcactta gcataacatt   2760
cttaagtttc atccatgttg tagcatgtgt cagaatctct ctcttttttt tttttttttt   2820
tttttttttt ttttgcagac agagtctcgc tctgtcatct agactggagt tcagtggcac   2880
gatctcggtt cactgcaaca tctgcctcct gggtccaagc aattctcctg cctcagcctc   2940
```

-continued

```
cttagcagct ggaactacag gcgcgtgcca ccatgccttg ctaatttttg tatttttatg   3000

tggaggcagg gtttcaccat cttggccagg ctggtctcga attcctggtc ttcaccacgg   3060

gggcccgaag gacccgggca aagcgtggag gggagg                             3096
```

<210> SEQ ID NO 6
<211> LENGTH: 26928
<212> TYPE: DNA
<213> ORGANISM: Homo sapiens
<220> FEATURE:
<221> NAME/KEY: unsure
<222> LOCATION: (12044),(12489),(26433),(26434),(26435),(26436),(26439),(26441)
<223> OTHER INFORMATION: Identity of nucleotide sequences at the above locations are unknown.

<400> SEQUENCE: 6

```
gaagaccaag ggcacacagc gaggcagttt cagggcgggc agcctggggc cccacggggc     60

ggccccggac acttgttctc acctgtggag ggcagagaag ggaacaggga gagaagtggc    120

cggctgggag tggaggtggg tttgaggttt tactgtaaac taaatgtgta ccctctacct    180

tagttatgaa ttatgagaca cgaagactgc gaaacagaca cactcctcta aaagtgcctc    240

taggctgaca gggagaaagt cccgccaggc tcccagacgc cacctttgag tccttcaaca    300

agcccgccag ggcctcttgc ccaccggtgt cagctcagcc actgaaccct ccaggaagaa    360

gacgtgctgg taggagaaga atctcaccca ggcacagcct ggaaggggca cagaaggggc    420

tccggaacca gcaagcccaa gttggaactc ccagtctgct actttctaga acgactgtgc    480

ccttggcggg tctaagtaga acctctccgc gcactctttc ctcctttgta aagtggggac    540

agcaatggcc accttgcagg ttcagagagg gcttgcagta cctcacagaa ctgagtgccc    600

gtgaacgtgt gtgttcctcc agatttgtga cagctttgcc aggctggagt caggctgaac    660

gcctctgccc tcatggggtt tatattctag gaagaccaac aaaaacaaga agacggaaaa    720

ttaaaacaac aaaagcccca ttgacaggcc gtgaagaatg ccatgaaaaa tgaatggcgt    780

tgtgctgcag tctttgggga aacgggctta cggaaagaag gacacttgag ctgctaccaa    840

tgagcagccg tccggtggga gggcagttca ggaagagcag acatccactg aggaggcgct    900

ggggcagagg gcagcctggt cgctggattc gggggaggaa ccacatcagg ccatgagctg    960

gagctggtgg tagaatgtac aggagaggcc agccagggcc agctcatgtc agacctcaag   1020

cggggaagat gaatcgagaa tgcaccccac gagcaatggg aagccagtct acgatttaag   1080

cagcaaaaat attttccctt cttccaccct gcatccagct ctaccagcac agcctggggt   1140

tctattttca agatagaata gacccagact cccagctctt cttacacttc tactactgcc   1200

acctgtcacc cactcatgcg tccccacttg cagcctcgac ccccttccac ctgatctcat   1260

ggcagccagg gaagctccag ggctcgtgag ggctgccatc tcaggaaaga agcaaaagcc   1320

ttcggcacct gcagggcctg ctccaaccac acttcttcct tgacctctca gcttccttag   1380

ccactccctt cccacatctc accctgctcc agccacagtg gtgtctctgt gggttctcaa   1440

acacaccagg tgcactcctg cctcagggcc tttgtgcttg ctgttctctg ctgggactct   1500

tttttttttt tttttttttg agacagggtc tcactctgtg gcccaggctg gagtgtagtg   1560

gtgtgatcgt agctcattgc aacctcaaac tcctgggctc aagcaatcct cccacctcag   1620

cctctcaagt agttagcttt tgttgttttg ttttgagatg ggatctcact ctgttgccca   1680

ggctggagtg cagtggggca atcttggctc accacaacct ctgcctccca ggctcaagca   1740

attctcctgc ctcagcctcc caagtagctg ggattacagg catgtgccac cacgcccagc   1800
```

-continued

```
ttatttttgt atttttagta gagacagggt ttcaccatgt tggtctggct ggtcttgaac   1860
tcctggcctc agatgatcca cctgcctcgg cctcccaaag tgctgggatg acaggcatga   1920
gcctgtctct agtagttagg actacagaga ggggccatca tgcctggtga tcctcccacc   1980
ttttctgctc caactctttc accccactta gcctcgtggc tcactctctt acctcttcag   2040
ctcctcagtc aggcctgagg acccctgttg aaaattgcaa accacacccc ccaccaccac   2100
cacccactat tgccagcact ttctactcca tttctctgct ttacttttct cctttgtact   2160
catcaccacc tgactcatta catgtttacg tatctttctt ctctccacta gcatggaagc   2220
tccaggagag cagagagtgt agttttattc cctgatgtgt ttcctgtgcc cgtaccaggg   2280
cctagcacac agtaggtgct cagtaaatgt gtgttggatg aacaaataca gtgaaaggat   2340
ctgatctaca tttataaaga aggcactctg gctgctgagt ggggatgaga ctgtcaggag   2400
gaaagaggcc cctgtggggg cctggccagc aggtgggtac aatggtagca gccaggagag   2460
agggcctctt ggactcaagt ggatggggcc tgctcagggc tccggccaca ggaacaaagg   2520
gaagggggcc caggatggcc tgtcatagag gacacattac aactggccca aagttcaagt   2580
caggtttcta aatttgggaa gggatacaga aaaactaaag actctactgg acagtcagtt   2640
attgaaatga ttacatagaa aatgtaccaa gaattaaaaa aaaaaaaaaa aagcattatg   2700
aaggggccac cagagactcc cagagaggaa agggactatg ggctggatgc ggtgactcac   2760
acctataatc ccagcacttt gggaggccga ggagggtgga tcacgaggtc aggagttcaa   2820
aaccagccta ggcaacatgg taaaaccccc gtttctacta aaaatacaaa aaattagctg   2880
ggcatggcag catgtgcctg taatcccagc tactcgggag gctgaggcag gagagttgct   2940
agaacccagg aggcagaggt tgcagtgagc cgagattgag ccactatgct ccagcttggg   3000
cgacagagca agactccgtc tctaaaaaaa agaaaaaaaa ggccagatga ggtggctcat   3060
gcctgtaatc ccagcacttt gggaggccga ggtgggtgga tcacgaggtc aggagatcga   3120
gaccatcctg gctaacatgg tgaaactcca tctctactta aaatacaaaa aattagccgg   3180
gcgtggtggc gggcacctgt agtcccagct acttgggagg ctgaggcagg agaatggcgt   3240
gaacctggga ggcggagctt gcagtgagcc gagattgcgc cactgcactc catccagcct   3300
gggcgacaga gttagactcc gtctcaaaaa aaaaaaaaaa aaaaaaatta gctgattagt   3360
tgggcttggt ggcgggcgcc tgtaatccca actactcggg aggctgaggc gggagaatca   3420
cttgaacccg ggaggcagag gttgcaatga gccgatatca cgccactaca ctccagcctg   3480
ggcgacagag caagactcca tctcaaaaaa gaaaaaaaaa aagaaagggg ctgtgctgtg   3540
gcctgggacc caaagcacac tactgcaagg tcccagggtg cctgactcca accggagcct   3600
tgagaacatt catttgcaaa gaatgaatta aaattcagca ctattttatt ctgcaggatt   3660
ccagcacccc aaggacagtc atttttagac ccttcagtaa cgtaataagt aaccggagga   3720
tgtgctgagc ttccacttcc ccagacggtt gcctgtcaca gctcatcagg ccaacaaact   3780
tttcttaggc ctcaaatttg gaaatgttca ctctcagttc gttccttaga tgcaagtcca   3840
tcccaatgaa gtaacagggg ctcagcacct gtccaatctc attgcttccg gggacagggg   3900
cccatgagga tgtcgtttca gcccggtgac acttgggcaa agtgcctttt ggtttccctc   3960
ccaggctgga acgtgctggc tctgtgaagt tacgctgggc acaagagccc cccccaaccc   4020
ggcaggactg actgctgtgg tcagaggcgc ccctggggct ttgggagcca cagaatcttc   4080
ctgagggcag cgccggagga ggccccagtg agagtgccca ctgccaggct cattcctcag   4140
```

-continued

```
gctgccgcag gcctctcccc aaaacaggca atgcttctca gcaacctgcc ccaggagcag   4200
gccagggaag gccgccatcg gcctacagtg ctgggctctg gagggcttgg ttggtaacag   4260
gccatggttt ctatgagcca gctggggtgt gaaggacaca ggctggattc acctctctgg   4320
gcctcagttt ctgcattcaa aaagtgggaa tcatgatatc tgctctattt cttatctctc   4380
agtgctgatg tgaacctcca ataagacttt taaaaatact ctttctacct tacttttatt   4440
tttcatttat tttaagataa tgtctagctg tctcacccag gctggagtgc agtggtgtga   4500
ttacggctca ctacagcctt aacctcccag gctcaagtga tcctcctacc acagcctccc   4560
aagtagctgg aactacaggc atgcaccacc gcacctggat aatttttttct tttgagacaa   4620
ggtttcactc tgttgcccag gctggagtgc agtggtgcac tcttggctca ctgcagcctc   4680
aacctccctg ggcttaggtg atcctcacac ttcagtctcc caagtagctg ggactacagg   4740
tatgtgccag tacacccagc taatattttt gaaggatggg gtttcactat attgcccagg   4800
ctggtcttga actccagggt ttaagcaatc taccttcctc agcctgccaa agtgctagga   4860
ttataggtat gagccacccc ccggcctata atcctaccac tttaaaaaag cctgtaattt   4920
tagcacttta aaaaattttt ctaaattttt tatagagatg ggggacagct gtggtctcac   4980
tgtgttgccc aggctggtct tgaactccta ggatcaagcc atcctcctgg cctggcctcc   5040
caaagtgttg ggattataag cataagcctt accttacctt tttttttga gttgcagttt   5100
tgttcttgtt gctcaggctg gagtgcaatg gcaagatctt ggctcactgc aacctccacc   5160
tcccgggttc aagcaattct cctgcctcag cctcccgagt agctgggatt acaggcatgc   5220
gccaccacac ccagctaatt ttgtattttt agtagagatg gggtttctct atataccta    5280
attttaaagc actgcattca tgtaaattgt gattaacatg gattcaagag agggagtgag   5340
gatgaatgag ccaggcagtc acctcggctg tcaccctcca cttctctcct ccttctgaca   5400
gtcatcgtcc atccgtttct gcagctgttt gtttgactct cctgatcatt ttgcttgcca   5460
cataacttgc ctcctgggaa agaatgccct gggcaggccc acatgagtag tgaaaaataa   5520
tctgcagtga aaaataaaac taagtagtct ggtccacaga gcagtcttat tttttcactg   5580
cagatgaagg agttgacatt caggcttcat tctcatttat aagtgtttta aagacacata   5640
cagtggattg aacagtggcc ttcaaaaaga tgtatctaca tcctaatccc tgggacctgt   5700
gaatgttaac caagttagga aaagggtctt cccgggtgtc attaagttag agatcttgag   5760
atgaggagct catcgtggat tatccaggtg gaccctgcat ccaaggacaa atggtcctta   5820
gaaaagaaaa gcagaggctg ggcacagtgg ctcaagcctg taatcccagc actttgagag   5880
gccgaggtgg gtggatcacc taaggtcatg agttcgagag cagcctggcc aacatgatga   5940
aatcccatct ctactaaaaa tacaaaaatt agcaaggcat ggtggcgggt gcctataatc   6000
ccagctactc aggaagctga ggcaggagaa tggcttgcac ctgggaggcg gaggttgcag   6060
tgagccaaga tcgcgccact gcactccagc ctgagggaga aaagtgaaac tctgtctcat   6120
aaaagaaaag aaaagcagac agagatctga gacagaagag gagagtgaag gaaaaaaggc   6180
catgtgaaga tgaggcagag gttggagcca tgcagccaca agccaaggaa tacctggagc   6240
cccagaagtt gcaagaggta ggaagaagcc tcccctagag cctccagacg gagcacagcc   6300
ctgccaacac ctccacctca gacttctggc ctccagcact gtgagataat caactgctgt   6360
tgttttaagc caccagattt gtggtaattt gttatggcag ccacaggaaa ctaatacagt   6420
acctaatctt cacaaaccca tcttacagaa aaggaaactg aagtcagaga ggtagtggct   6480
tgtgcagtgt gttaggccat tcttgtatta ctataaagaa atacctgagg ccgggcatgg   6540
```

-continued

```
tggctcacgc ctgtaatccc agcactttgg gaggccaagg tgagtggatc acttgaggtc   6600
aggagttcaa gaccagcctg gacaacatgg tgaaacccca tttctactga aaatatgaaa   6660
attagccagg catggtggcg tgcatctgta gtcccagcta ctcaggaggc tgaggcagga   6720
gaatcacttg cgcccgggag gaggaggttg tagtgagcca agattgtgcc actgcactcc   6780
agcctgggag acaagagaga aaccctgtct caaaataaat aaaaaacaaa taaacacctg   6840
agactgggta gtttataaag aaaggggtta actggctccc ggttctgcag gctgtacaag   6900
catggtgccg gcatctgctt ggttgctggg aaggcttcag ggagttttac tcatcgtgga   6960
aggcagagcc agagcaggtg catcacacag caaaagcagg agcgagagag agagagagca   7020
gggaggtgtg cacactttta aatgagcaga tctcacgaga actcaccatt gcaaggacag   7080
caccaagcca cgaggggtct gcccccatga cccaaacctc ccactaggcc ccaccccaa    7140
cattgggaat tacagttcaa catgaggttt gggggacaa atatccaaac tatatcattc    7200
cacccctggc cccccagatc tcatgttctt ctcacattgc aaaatatagt catgccttcc   7260
cagtagcccc ccaaagtctt aactcatccc agcattaact caaaaatccc attcccaagt   7320
ccaacgtctc atctgaagat gagttccttt cacctacaag actgtaaaaa tgaaaacagt   7380
tatttactgc tgagatacaa tgggggcata ggcattaggt aaacattcct gttccaaaag   7440
ggagaaatcg gtcaaaagaa aggggctata ggccccaagc aagtccaaaa cccagcagag   7500
caatcattca atcttaaagc tccaaaataa cctccttaaa ctccatgtcc catagccagg   7560
gcacactggt gcaaggggca ggctcccaag gccttgggca gctctattcc tgcggctttg   7620
cagaattcag tccccatggc tgctcttaca gattggagat gagggcctgc ggcttttcca   7680
ggtgcagggt gcaagctgct ggtgatctac cattctgggg tgtggatggt ggcggccccg   7740
tcccgcagct ccactaggca ttgtcccagt ggggactcta tgtggggcct ccaaccccac   7800
atttcccctc caatgggaag gctctgcccc tgcagcagcc ttcttcctgg gctcccaggc   7860
tttctcatac atcctctgac atctaggtgg atggtgtcaa gcttccttca ctcttgcact   7920
ctgcacacct acaggcttaa caccacatgg aagctgccaa ggtgtatggc tggaaccctc   7980
tgaagcagca gcctgagctg tgactatggc cctttgagcc aaggctggag ctggaacagt   8040
ctagatgcag gcagggagca gtgtcctgag gctgtgcaga gcagcagggc cctgtgcctg   8100
gacaatgaaa ccattctttc ctcctcatcc tctgggcctg tgatgggagg gttgtggaag   8160
atctctgaaa tgcctttgag gccttttttgc ctctgaggcc tatttcctat tgtctcagtt  8220
attggcagtc ggctcctttt tagttatgca aatcctctag caagaggtta ctccactgcc   8280
ggcttgaact cctctcctga aaaagctttt tctttctttg tcacatggcc aggctgcaaa   8340
ttttccaaac ttttatgctc tgttttacct ttaaatataa cttctaactt taattcattt   8400
atttgctcct gcatttgagc atagggaatt caaagaagct gggccacatc ttgaatgctt   8460
tgctgcttca aaatttatgg ccacgcttgg tggctcacac ctgtaatccc agcactttgg   8520
gaggcctagg tgggcagatc acgagatcag gagatcgaga ccatcctggt caacatggtg   8580
aaacccatct ctactaaaaa tacaaaaaaa ttagcttggt gtggtggcgc agacctgtag   8640
tcccagctac tggagaggct gaggcaggag aattacttga acctgggagg cagaggttgc   8700
agtgagccca gatcatgcca ctgcactcca gcctggtgac agaataagat ttgatctcga   8760
aaggaaggaa ggaaggagga agggaagaaa tgtcttcccc ccagatgtcc tgggtcatcc   8820
ctcttatgtt caaacttcaa cagatcccta gggcatgaaa ataatacagc caaattattt   8880
```

-continued

```
gctaaggcat aacgaaagtg acctttgctc cagttcccaa taagttcctc atttccatct   8940
gagactcatc accctggcct tggcttgtcc atatcactgt cagcattttg gtcacaatca   9000
tttaaccagc taatcgggag gctgaggcaa gaggatcact tgaacccagg aggttgaggc   9060
tgcagtgagc tgtgatcaca tcactgcagt ccagcttggg caacagagca agatcctgtc   9120
tcaataaata aataaataaa tacataaata acttaagttt atttaaagct gcatctttgc   9180
caccatggag aaaggccagg ccagctcctt ctctctttct gcacgtgttc ctcccacctc   9240
agctgcctct gctcctcaag gaggaacaga gggagtagga aaggccatcc caggaggccc   9300
agcaccccat gacctggctc tggggccttg tgggtttatg gattcccagt gctgagtcat   9360
ccctcacagg ctcttgtggg caccttggac attggtcaga agcatgtggt ccccgggaac   9420
acaccttttc ctgatcatct gggaagggca gcttgtgcca gcgaggccac ctgttcagcg   9480
ccacggcccg ccagacagct gcagccacag ccttgccttt gatcagagca aacaccagac   9540
atgtgtgtca tgcccccaac ccatctccag gggacacatg tcctttcttg ccaggcctga   9600
gatgaacaag agagggacaa gtccccaagc ctctctctcc ttcctgcctc acccactccg   9660
ctgttagatt ctcaaggtgg atggtgggct aactagggca accgaccatc ctggtttacc   9720
tagaactgag gggcatttt caggaataaa actgcaaaag tctggagcaa acaggagcaa   9780
gttggtcact ctggggctgg tggagtcagg tttccttctg caggcccccct ccccgcaagc   9840
atgggtggaa cccaggacag gaacacagag caggccccag gaccgggctt gtcacttaca   9900
agtctttttt tttttttttt ttttgagatg gagtcttgct ctgtcatcag ggctggagta   9960
cagtggtgcc atcttagctc actgcaacct ctgccttctg ggttcaagtg atccccctgc  10020
ctcagcctcc tgagtagctg ggactacagg tggcaccacc acgcccagct aatttttttgt  10080
atttctagta gagatgagat ggccaggctg gtcttgaact cctgacctca agtgatctgc  10140
ccgccttggc ctcccaaagt gctgggatta caggtgtgag ccactgtgcc tggccccact  10200
cacaagtctt aaaccatgcc tcagcacatc aatgccattt acaaaaaggt agagggattt  10260
tccaggcaaa aatagatgaa agacatagga tgattgatca tgtcctgctt aaacataggt  10320
ctgatgctat taagaattga gggctgggag cggtggctca cgcctgtaat cccagcactt  10380
tgggaggccg aggcgggcgg atcacgaggt caggagatcg agaccatcct ggctaacacg  10440
gtgaaacccc atctctacta aaaatacaaa aaatggccgc gcgcggtgac tcacgcctgt  10500
aatcccagca ctttgggagg ccaaggcggg cggatcacga ggtcaggaga tcgagaccat  10560
cctggctaac acagtgaagc cccgtctcta ctaaaaaata caaaaaaaat tagccaggca  10620
tggtggcggg cgcctgtagt cccagcaact tgggaggctg aggcaggaga agaatggtgt  10680
gaacctggga ggtggagctt ccagtgagcc gagatcacac cactgcactc cagcctgggc  10740
gacagagtga aactccatct caaaaaaaaa ataaataaat aaataagaat tgttagtatt  10800
ttgcaggtgt gacaaatgat tctgtttctg tggcagaatg ttctcaggag atctcttttg  10860
aactctcatg gaaagcatca tgctgttggc aacatcacat ttatttttat ttatttatta  10920
ttttttagag acagggtctt gctctgttgc ccaggctgga gtgcagtggc acaatcacag  10980
ctcactgcag cctcaacctc ctgggctcaa gcaatcctcc tgcctcagcc tcccaaagta  11040
gctgggacca caggcgtgag ccactgcact cagcccaatg taccttcaat atttacattt  11100
ctggcaaagg tagcaaaacc ttaacaaatt ttgaatctag ataataaaat tatgaggctg  11160
ggtgcagtgg ccctgacagg gatggctcac atctgtaatc tcaacatttt gggaggccaa  11220
ggtaggcgga tcacctgagg ccaggagttt gagaccagcc tggccaacat ggtgtaaccc  11280
```

-continued

```
tgtctctaac aaaaatacaa aaaaattagc cagacgtggt ggtgcacgtc tgtcatccca  11340
gctactaggg aggctgaggc aggagaattg cttgaacccg agaggcagag gttgtgatga  11400
gccgagatcg cgtcattgca ctccagcctg ggcaaaagca agagcgaaac tctctctcca  11460
aaaaataaaa aaaaaataaa ttaatgaatt aattaaaata aaataaaata atggatagtc  11520
actgtaaaga aaaaataaat gtatatatca gccaacaagt gatggaatag agcaccccat  11580
ctccctggct ggacagatac atcccacaac acctggaagg cggctccatg tagaactttc  11640
tggactgctt gaggtgctgt gctggagcac ggtgacagag gagctggacc atggacctcc  11700
cccggccccc accaagggcg aggtccccct gtggtgggtc tgagggaggc atccgtatgg  11760
cctctgcggc ttgggcaggg aatttggggt ccaagtactt ggtgcaaagc ctggaaagag  11820
ggtttgggtg ctgagggcat atcccctggg ccacatgggg gcagaagtgg ggcccccctga  11880
agcttggagt cctgggcagg ggcatctatt ttgctgtctg aggccttcag tacttgaagc  11940
aaaatggagg cagaatgtcc caccttaatg cccctgattc ctccaaacca attccagaga  12000
cagcaagggc cagaacaggg atggccctgc ccagggtcat gcancgagga agtggccagg  12060
ctgggatctg aacccaggct aatcccctcc cttgtcctcc tccaggccct cacccctgca  12120
tagagccctc cagctcactc atcctcggcc agctccatct cctcagcttg taaacccccc  12180
cgggattttc ctttcttaaa aaacaaaggc ttggccaggc acggtggctc acgcctgtac  12240
tttgggggtg gctcccagca ctttgggagg ccaaggtggg cggatcatga ggtcaagaga  12300
ttgagaccat tctggccagc atggtgaaac cctgtattta ctaaaaaaaa aaaaattaac  12360
tgggcatggt ggctagctac ttaggaggct gaggcaggag aatcgcttga acctgggaga  12420
aagaggttgc agtgagccaa gatcgcgcca ctccacttta acctggcaac agaacaagat  12480
tccgtttcna aaaacaaaca aacaaacaaa taaacaaaaa aaggcggagc gcgatggctc  12540
gcgcctgcaa tcccagcact ttgggaggct gaggcgggcg gatcacttga ggttaggagt  12600
ttgagaccag cttggccaac atggtgaaac cccatttcca ctaaaagtac aaaaatcagc  12660
caggtgtggt ggtgggtgcc tgtaatccca gctactcagg aggctgaggc aggagaatcg  12720
cttgaaccca tgacctggag gctacagtga gctgagattg cgccactgta ctccagcttg  12780
ggcaacaaga tttgtttctc taaaaaaaaa aaaaaaaaga ctggcccttc cccttcagct  12840
cttcctcagg gtccctgagc actctacacc cccgtctaca ctgagcactc caccctgctg  12900
tctacactga gcactccacc ctgccatcta cactgaggac tccaccccac tgtctacact  12960
ggctgcctcc cgccctcacc tcctgctaag gccattcccc gctgcatctg tcttctagat  13020
tctgcagcct tcagcacgct gggcccctcc tttgtcccct tgagccacct ccagcctccc  13080
cctgagctgc tactcctctc ccagcagcct ccacccaagc ccctccagtc cccaagctgt  13140
cccttgcatc cagcactgcc cttccacgtg ccccttccct ccagcttcac agcagggtgg  13200
ggcctccagg ccctgcccac tgtgcccatc cacaagttgt ggtgggagct ccgaggggag  13260
gcaggggtgt gcatggactt gggacgtcca agtctgggac caggggcagc tggttggtgg  13320
agtgtggagg gggataggga ctttcaggta gagaggctgt aggggcaaga tcgggacggc  13380
ggatgtccct aaggagggct ctgacctggg aaatattgtg cagcttcctc tttgccattc  13440
ctggagctca gacactggcc ggctctcacc ccgcccttcc tgcaggacac agctccatcc  13500
cagtgagttc ctagtgtaga catctccagc agcacggatg ggaaaggaag tcatcaaagg  13560
tgcccaggac cggaggcttt ttctggaggt ggcagaggag ggtgtgggtc tcagggctct  13620
```

-continued

```
ggctgagggc aagcgtggga ggtcttaggt ctgcaccagc cccgtgaagg cccctcctgc  13680
tccctggtgg agtcctagag ggaacagcag cccctaggct ctagcaggag tgggtagggg  13740
cttttctggc ttcctactgt gccagcagga tagctgggcc tggcactgag cccaaagatc  13800
acatgccggg gcattggcgc agtgaggaac agacccttgc caaagctggc aaagaagacc  13860
ccatggggtg cagctggtga agctgagagc tcaatgtttg ggggagcctg gcaaaagggg  13920
tcctcccctc cctctgcagg ccaggatcgc aggttttccc tacatgttgg taattctcaa  13980
acaatcccat ggccactgga gcaaagatca cagtgggcgg cggcctcggg agcagtggac  14040
agggcacgca gtgcctttga tgccagagcc ctcgccccaa agtcaacaaa ctctgcagcg  14100
gactttgcac ccggactttg ttttcaccat acaaggaaag ggacagatca caggccctct  14160
cgctgccctc gctgagccgg aagctgcagc gtgagctctc tcaagcccca tttctaggtt  14220
ccccaggcgc accccctgagc ccctactcgc ctattaagtt ctcctaatag cccttcaagg  14280
tcttaatgta tgtccattag acagagggga aaactgaggc gagggcaagt gacttgaccg  14340
aggttcctcg gcgagcaggg cgtggagctg agaacctcgt tattactgct ccccacacaa  14400
ccctctggcc gttcttggaa gaaggctgag ccccgggggg gccagagtga cccaaacacc  14460
atgggccgcc tgcggtaaca cgtgcggcca cgaaggggca gcagtttccc gcccggccgg  14520
gctctctccg gcgctcagta tccgtcccag gccaagaaga agaaactcgg ggaggagggc  14580
ggagggggct gcgtgggagg gcgtggaaga tggacgtggc caggggagtg gcagctgcac  14640
acagtggatg ctgttaagat gaagggaaag aacgtgggct ccgagatcac tggacacggt  14700
tccacctttc ttcccgctca ctgcatggcc ctgggcgggt tgttgaaccc ttggaaacct  14760
gtttttcctt ttttcctttt tttttgagac agggtcttgc tctgtggccc agactggagt  14820
gccgtggcac gatcttggct cactgctgcc tcccaggttc aagtgatcct cccagctcag  14880
cctcctgcgt agctgggacc ccaggtatgt gtcaccacag ccggctaatt tttgtatttt  14940
tttgtagaga cgggatttcg ccgtattgcc caggctggtc tcaaactcct gagttcaccg  15000
gatcttcctg cctcagcctc ccaaagtgct gggattactg gcatgagcca ccgcacccag  15060
cagagacctc agttttctaa cctgtgccag caggaataat gatagctgcc tagcttggct  15120
gtgctgggaa ttaagtaaga tgaccgggta gcaaatatga agtattactg gacacagagg  15180
gccccaggct gggttagcag cggtggtcag ggctgctgct tcctggcctg agctcgaagg  15240
agggccctca ttaccacctg ggtgagtcct cgtccaagcc tggcactgct gcgtgggaat  15300
aacttctgcc acccaagttg gcagattgtg tgcaaagtta agtcctgact ctgtggggtg  15360
gacttcgagg cctcttcatc ggacctgctt ccggtgactg cattcgcacc tcctcctgtt  15420
cctggtttaa cacagcccag ctttcctcct gctgagccct ccctgggcct gctgtcaccc  15480
tcgtgccgct gtgcctcgca gtgccactcc ctgtaccctg aatactttgc cctgcctctc  15540
cacccagctg agagtcaggg cccctgtgag gctctgccca gcccgtcctc cgggtttctg  15600
cctctgctga gcacttccct gcatgattgc ttctgagagt ccccccagcc tgtgagcttc  15660
tcaggactgg gacagcttct caggaccgag gcttcctggt ctgcttgcaa ttttacaggc  15720
gggcacattt tcccttggcc aacatcagag actggacatc tgcagatctg tgctagccac  15780
tgagcaccca ggcaccccag caggtagctc tgtaaccaac ccattctgta aagctgaggc  15840
tcagagaggt gaagcgcctg gcctggggcc acagcctgcg tcagctgcag agccaggagc  15900
tgagatatgc acctgcggct ctgctcacag ggtcctgcac agactgctgc tggagccacc  15960
tatgtagagt caagagagtt catgttaact ccctctcaca tccctcagcc agggtggggg  16020
```

-continued

```
ctgacgatag acactcaggg atggcctacc ctccccaaca acccccgtca ggtttgccgg  16080
atctccttgg aagaaaagtt ctgggcagaa ttccaccgtt ggcctggcct acactctcct  16140
tagtggctta ggaccctcag cggtggataa gttgtgggca gaagagatgc aatcaggatt  16200
ctcacccact cacccccttgc cagccccaat aagctcaata agctgggctc ggtctgagga  16260
agtgtccagg aaatgtgcaa atggcctggg acagccctgt gttcctttca gtaaggttgc  16320
tgaaggtgag gctgaaagtt ggagaaacag aagccagtgc ttatggtttt aattaagata  16380
atggaatgta tgtatgtatg tatgtatgta tgtatgtatt tatgtattta tctttagaga  16440
tagagtctca ctctgttgcc caggctggaa tgcggtgaca caatcatagc tccttgcagc  16500
ctcgacttcc tatgcccaaa tgatcctcct acctcagcct cctgagtagc tgggactaca  16560
gacacacgcc aactatgcct agctaatttt tatttctatt ttttgtggag actgggttct  16620
cactttgttg cccaggctgg tcttgaaccc ctagcttcaa gcaatcctcc tgcctcagcc  16680
tcccaaagtg gagggattac aggtgtgagc caccacacct ggcctggaat ttatttgtat  16740
tctgcttata aaattaatac attcttattg cagaaaagtt tgaaaataaa agaaaggaca  16800
aagaacaaaa agcgtatata atttcacagc tcagatctca ctgctattaa catttttatt  16860
tactttcagg ctttttttctt tctaggtaca tatgcagaga ttatttttatt ttatttattt  16920
tattttatat tttattttat atttttttatt tcattatttt attttatttt attttattat  16980
ttttagagac agggcctcac tctgtcaccc aggctggagt acaatggagt gatcatagct  17040
cactgcagcc tcaaacacct gggctcaagc aatcccccca ctcagccttc tgagtagttg  17100
ggactaaagt gtgagtctgg ctaatttttt ttactttttg tattgacaga ggtctcacta  17160
tgttgcccag gctgatctca aactcctggg ttcaagcgat cctcccacct tggactccca  17220
aagtgctggg attacaggca tgagccacca tgcctggcct aaaatgccac tttttgtcat  17280
ttactaaaat cccatggaca ctttgacatg tctgtattct atgctattga tctgactgtt  17340
ggcatctaca tcattatggc catctatcat ctatcataat ccattttaac attaaaattg  17400
tgctgctgct tagattttc tggcctgtct cctatttgta ttcttccaga taaattttag  17460
aatcatttta tcaaattccc cttgcagaaa aagccctatt ggattttggt tgaaaaatac  17520
tgaattttta cattaactta ggaaagggct gggcacggtg gctcacgcct gtaatcccta  17580
cacttttcga ggccaaggca ggtggatcac ttgaggttgg gagtttgaga ccagcctggc  17640
caacatggtg aaactcggtc tttactaaaa atacaaaaat tgccaggcgc attggctcac  17700
ctgtaatccc agcactttgg gaggccgagg tgggtggatc acgaggtcag gagatagaga  17760
ccatcctggc taacacggtg caaccccgtc tctcctaaaa atacaaaaaa ttagccaggc  17820
gtggtggtgg gcgcctgtgg tctcagctac ttaggaggct gaggcaggag aatggtgtga  17880
acccaggagg cggagcttgc agtgagccaa gatcgcgcca ctgcactcca gcctgggcga  17940
cagagtgaga ctccatctca aaaaaaaata ataataataa tacaaaaatt agccgggggt  18000
cgtggcgtgc acctataatc ccagttactt gggaggctga ggcaggagaa tcgcttgaat  18060
ccaggaggtg gaggttgcaa tgagcagaga tcgtgccact gtactccagc ctgggtgaca  18120
gagtgacact ctgtgaaaaa aaaaaaaaaa ttctgaagga ttgagactct tagactctta  18180
ggtcttccta tccaagagca caatatagct tttcatgtat tcaagccttt ttcaatgcat  18240
caacagaatt ttacagtttt tttcatgata tcctgctatt tcttataaaa tgtattccta  18300
gatattctgc atgttttccg gttgtttgtt aataaatatt tttcatttgt cattatttcc  18360
```

-continued

```
taattggctg ttatttgtat atatgacatc tgttgaattt tttgattact ttgaaaatgg  18420
ccattctttt gtgttttttt ttaactttct attttgagat aattttgact tacagaagat  18480
ttgcaaaaat agtacagaga gttcctgttt ccccttatg ttaacccagt ttctccttat  18540
gttaacatct tacataacta cagaacaatt gtcaaatcta agaatcaacc tgggcacaat  18600
gctattaact aaactgcaga agctgttcag atctcaccag ttcttctact gctccccttt  18660
tctcttccag tgttcaatcc ggaatcctac attatattta gttgtcattt ctctttggtg  18720
tcttccaatc tgtgacagtt cctcagtctt tctttgtctt tcatgacttt cattttttta  18780
tacttttgaa aaatactggc cggttgtttt gtagaacgcc ctcagtttgg gtttgcctga  18840
agttttttgt gattagatcg aggtcatgca ttattggaga gggtgccacc gcctcgatgt  18900
gcaagctcaa tgcatcatat cagagggttt gtaatgtcag tttataccgc cggagaccct  18960
aacctggagc atttcgtgaa ggtgctgtct gccaggattc tccactagaa agttactatt  19020
tttccctttt taattactga atgtctgagg ggaaatactt tgagactatg caaatatcct  19080
gtttctgctt taacttcggc tcactaagtt tagcattcat ctatggatct cgcttatagc  19140
aagtattact gtggagttct aatggtaatt ttctgtttct ctcattcctt caacctttat  19200
taatatgctt cttcctcact tattcatttt gtttcagttg tttataccaa catggatttg  19260
tggatattgg ttttattctt tgggttgcaa ttgaatccta tcattatttt gttagtcagt  19320
tgttccatcc gaccttggtc attaggagcc cttgaaattt ggctcccatg cctttttttt  19380
ttttttgag accgagtctc actctgtcac ccaggtttga gtgcagtggc atgatcttgg  19440
cttcctgcaa cctccgcctc ccaggttcaa gcaattctcc tgcctcagcc tcctgagtag  19500
ctggtattat aggcgctcca ccaccttgcc cggctaattt tttgtatttt tagtagagat  19560
ggggttttat tatgttggcc aggctggtct caaactcctg acctcaggtg atctgcccgc  19620
ctcggcctcc caaagtgctg ggactacagg cgtgagccac cacacctggc ctcctatgcc  19680
attttaacat gcccgtcttt tctttttctt tcctactttc tgtgactgta agaagctcca  19740
ggatacattt ttgctgccct agacttagcc tcaatcagtt ctcagaaaag ctctggttct  19800
ttttatggga tacttagaaa actagctctg tatggcctgg cgcggtggct cacgcctgta  19860
atcccagtac tttgggaggc cgaggtgggc agatcacaga tcacgaagtc aggagatcaa  19920
gaccatcctg gctaacatgg tgaaactctg tctctactaa acatacaaaa aattagtcca  19980
ggcgcggtgg cgggcgcctg tagtcccagc tactcaggag gctgaggcag gagaacggca  20040
tgaacccggg aggcggagct tgcagtgagc cgagatcggc agccactgca ctccagcctg  20100
ggccacagag cgagactccg tctcaaaaaa aaaaaaagga aaaagaaaaa agaaaactag  20160
ctctgtatgc tagttttttt tttaagacag ggtctctctt gccccagctg gagtgtagca  20220
gcacgatcac agctcactgt agcctcaacc ttctgggctc aagcaatcct cctgcctcag  20280
tctcctaagt agctgggtct acaggcatgc accaccgtac gtggcaattt ttaaaaactg  20340
tttgtagaga tggagtctcc ctatgttgcc tggtctggaa ctcctggcct caagtgatcc  20400
tcctgcctcg gcctcccaaa gtgctgagat tacaggcatg agccactgta cctggcctgg  20460
ccaaggtctg tcttttttta aaagaagttg ttgtatagtt gttttttttt ttattttttt  20520
ttctgagacg gagtctcgct ctgtcgccca ggctggagtg cagtggtgcg atctcggctc  20580
actgcaagct ccgcctccca ggttcacgcc attctcctgc ctcagcctcc cgagtagctg  20640
ggcctacagg cgcccgctac cacgcccggc taatttttg catttttagt agagacgggg  20700
tttcaccgtg ttagccagga tggtctcgat ctcctgacct cgtgatccgc ccgcctcggc  20760
```

-continued

```
ctcccaaagt gctgggatta caggcgtgag ccaccgcgcc cggcctgttg tatagttttt  20820
atctcgagtt ttctagcgat ttaatcatat tggttacaaa aaaggatgat tttactacct  20880
cctttccaat gtttctacat attttttcat tttatctaac tgcattttaa aataaacttt  20940
taattttaga atggtttcat atttacagaa aatgtgcaaa gatagtacag agagttcctg  21000
tgtactccac acccggtttc cttattatta tcttaacgtg atacacaatt aataaaccag  21060
taacattatt attcactgaa gtccacactt tctttttttt tttttctgag acggagtcta  21120
cttctgtcac ccaggctgga gtgcagtggc gcaatctcgg ctcactgcaa cctccacctc  21180
ctgggttcag gcaattctgt ggctcagcat cccaagtagc tgggaataca ggtgcccgcc  21240
accacgcccg gctaattttt tgtattttta gtagagatgg ggtttcacca tgttagccag  21300
gatggtcttg aactcctgac ctcgtgatct gcctgcctca gcctcccaaa gtgctgggat  21360
tacaggcgtg agccaccgcg cccggcgtcc atactttctt tagatatcct tcctttttac  21420
ctaacgtcct tcttctggtt caggatccca tccagaaagc aacattaccc ctcgccatca  21480
cgtcttcaca ggctcccctt gacgggaaga gttcctcaga ctttccttgt ttttgttgac  21540
cttgacagtt ttgaggagga ctggtatctt agtctgtttt gtgctgctat cacagactag  21600
ctgagaccga tacatgatac atgaaaaaaa atgtattctt acagttgtgg aggctgggaa  21660
gttcaagacg aagttgctgg ttggtttggt ctctggtttc aagatggcgc cttgctgctg  21720
catcctctgg agaagaagaa tgcggtgtcc tctcactgca gaagatggaa gcgctaaaag  21780
gaatgaactc cctttgccaa gccattttat aatgggcatt aatccacaaa ggatgaaacc  21840
ctgagaaaca tcaagcttta aagcactggt tctcaacctt tttggtctca ggagcccttt  21900
atactcttaa aacgttttga ggatcccaaa aaaaggcttc tacaggttcc atcttttaat  21960
atttaccata tcaaaaatta aactgaaaaa attttaaatt atttattcat ttaaaataac  22020
aaggataaac ccattacatg ctaacataaa tcatgtattt tatgaaaaat agctatattt  22080
atcaaaacaa aaattagtga gaagagtggc atgtataatt ttttttgttt attttttgtt  22140
tttagatgga atcttattct gtcgcccagg ctggagtgca gtggtgtgat ctcggctcac  22200
tgcaagctct gcctcccagg ttcacaccat tctcctgcct cagcctcctg agtagctggg  22260
actgcaggtg cctgccacca cgcccggcta attttttgta tttttagtag agatggagtt  22320
tcaccgtgtt agccaggatg gtcttgatct cctgaccttg tgatccaccc gcctcagcct  22380
cccaaagtgc tgggattaca ggcttgagcc actgcgtctg gcctaaattt ttgtgaatgt  22440
ctttaatgcc tgccttctca tatttgtttc tgcattcaag ttattgcaaa atgttgtgtt  22500
ggttgaagtt tgtaaagaaa atgtggcctc atacagttgt gtagttggaa aggcaagagt  22560
attttgattc tctcttcaaa caactatgga caacctgctg ttacaaaacc agaatgcaaa  22620
aagttgtagt aaatacaggt taggtgtagt gtggaatctg aaagcatgtg aatgaacttt  22680
ctgagttttg taacattaaa gtccagttgc gttaagctac tgtgatagca tatagcattg  22740
tcctaatact ggaattagta tcagaagtgg ggtgctactg ttaataaata aaaagaaata  22800
aataaatcat gtgatactgg ctcagaagtc aggcagtagg ctgtgtggaa cctgacatca  22860
cgccatgtaa tacattggca accatttgat ccagctgtct gtcatgatga cttggaaagt  22920
caaccacata cttacagagc ctgtagacat aggggaaaat agtataaaac agaatactaa  22980
cagtggacct tggttcttgc cagttgcatt tagccaaata ttaaacaaaa gagatattct  23040
tgggcagcaa ctggaccatc ttcaagtaaa agtgaaaggt aataaacaga gtccagacat  23100
```

-continued

```
ttgtgcccat gcgggttaag aaaaatccag ttgcttctag acaccgtata tgaaaacaac  23160
gctgaaaaca agcctttgag tggtaaaggc cgattaacac tcagcgcggt aacaaagacc  23220
aggtgggcta acccgaaatg aaatgagaag cctgtggtga tgaggaggca gagaagtaaa  23280
atcaagtttg agcatttcgt ttaggagagt ttgggctctg attacttgca catgcaaacg  23340
aactggaaac aaacagatca gatgtctacc acttcttcga gggaattgca ttgccaaaga  23400
agtcatgaaa gcagactcta tactgattag gcattaaaac aaaaacaatc tttaggcccc  23460
taaacttgca tgggcaggaa gtgggctgtc aaagctgttc atcctctaag gtggacctag  23520
ttcctagtcc ccagtataca cttcagatgt ggccctggag gacactggac atggaggacc  23580
tcccagagga tgaggctagg gcttcatttc tccaatgacc tcagctgcct ctatttcccc  23640
ttcttcctct ggaagtccta tcatcgttat tattattatt atcatcattt ttattttgag  23700
ataaggtctc gctctgttgc ccaggctgga gtgcagtgac atgatcatgg ctcactgcag  23760
ccctcccagg ctcaagtgat cctcctgcct cagcctcctg agtagctggg agtacaggca  23820
catgccacca tgcttggcta tttttttttt cagtagagat agggctctca ctatgttgcc  23880
agggctgatc tcaacctcct gggttcaaga gatcctccta cctcagctcc tgagtagctg  23940
ggattcgggt gcacaccacc atgccaacta atttttaatt tttttttgta tggacaggat  24000
gtacagtgtt agaaatggat tgcttgcaga ggcaggagga tcacttgagc ccaggagttt  24060
gatcacactg tgaaccatga tcgcacccct gcactccaat ctgggcaaca gagtgagacc  24120
ttgtctcaaa aaaaaaaaaa aagagagaga gagagagact caaagatagg caaaaaagtg  24180
ggaaagcttt atagtggaca aaaaggaacg ctctaagtct gccctattgg catggtgctg  24240
aaggtgggct aactagagat agggggtact atgtggttga ctatgggtgc atctttggct  24300
ttccctgggt gatcctaagt tggaagcagg gacaaaaatt agggaagctg ttagttattc  24360
atcacgttct ggcagtagtg gactggttgt gatagaagtt attgttttgg ccaggtgcgg  24420
tggctcatgc ctgtaatcct agccctttca gagttcaacg tgggtggatc aggaaggagg  24480
gaggatttgg gaggtcagga gttagcctgg ctaacctggc gaaatcccat ctctactaaa  24540
aatacaaaaa ttagctgggc gtggtggtgc atgcctataa tcccagctac tcgggacgct  24600
gaggcaggag aatcagttga acctggggag gcggaggttg cagtgagcca agatcgtgcc  24660
caatttcatc tcaaaaaaaa aaaaaaagtt atcgtttagc ttcctcgatt gttactggac  24720
gtagtaatct ggcttcctgc aagtctaact ttcagcagac tggctacatg ggctgtgtac  24780
tgtagataag gcagtaagta aagcaaaaat tgatagagca tcaaggataa atagaaaatc  24840
cgtaatcaag cagaagattt gaacacttca ctttcagtaa ctgataaaac aagtagacaa  24900
aaaaaatcag taaggatgta gaagatttga acaacgtaat taacaaactt gacttgattt  24960
acacgtctag aaccctgcag aacacacact ttttcaagca tactcagaac atttatataa  25020
agtgaccata tggtggacca taaagcagtt tcaacaaatc tcacaggagt aaaataacag  25080
accgtgtttt ctgaccgtaa gtacagttaa cctagaaatt gaaaacaaaa agctagaaaa  25140
accccatgta tctggaaatt ttaatataca ctttgaaata acaaatggat cagagattaa  25200
ttcaaatagg aatttagaaa taccttgaac tgaaaaataa tgagaatact ataccccaaa  25260
actgtggggt gcagctgaac agtatataga cgaaaagtat actcatatgt gcatacctta  25320
aggagcgggg aggattgaaa gttaatggga ggcaaaagca ggtggatcac ttgaggttag  25380
gagttcaaga tcagcctggc taacagggtg aaaccccatc tctactaaaa atacaaaaaa  25440
ttatccaggc gtagtgaggc tgaggcaaga gaatcgttgg aacccaggag gcagaggttg  25500
```

-continued

```
cagtgagccg cgattgcgcc actgcacccc agcctgggag acagagcgag actccatctc  25560
aagaaagaaa aaaaaaaaag aaaaggccag gcgcggtggc tcatgcctgt aatcccagca  25620
ttttgggagg ccgaggtggg cggatcacga ggtcaggaga tcgagactat cctggctagc  25680
acggtgaaac cccgcctcta ctaaaaatac aaaaaaatta gccaggcgtg gtggcgggtg  25740
cctgtagtcc cagctactca ggaggctgag gcaggagaat gtcatgaacc caggaggcag  25800
agcttgcagt gagccgagat cgcgccactg tactccagcc tgggcaacag agagagactc  25860
tgtctcaaaa aaaaaaaaaa gttaatggga taaacatcca tctcaagaag ttagaaagga  25920
atgacaaata aaccaaaaaa aaaaaaatca aaagaagaaa atcataaggt caagactata  25980
aagagagtgg ctgggtgcag tggctcaggc ctgtaatctc agcattttgg gaagcagagg  26040
tgggcagatc acttgagccc aggagttcaa gaccagcctg agtaacatag agagacctca  26100
tctttgctga aaataaaaat aaaaaattag ccaggcatgg tggtactgag gtgggaggat  26160
cacttgagcc taggaggttg aggctgcagt aagccatgat tgtgccactg cacttcagcc  26220
tgggtgacag agtgggaccc tgtctctaaa aaactaaaat aaggctgggc gcggtggctc  26280
aaatctgtaa tcccaccact ttgggaggcc aaggctgagg tcagcagttt gagaacagct  26340
tggccaacaa gatgaaacct catctctact aaaaatacaa aaaattagtt gggtgtggtg  26400
gcatgtgcct gtaatcccag ctacttagga ggnnnnctnt ngattatatt ttctccttcc  26460
tacgtcgtta ttggactgaa ttcagaatga tgactctcat tggagctctt cctgtctcct  26520
aactacagtg gcttccgacc ccactctggt tttcacttca cccctctgct gctcatacga  26580
gtagatactt ccttccttct ttctcacttg ttgctcttcc tcaacccccc ccgttggtgt  26640
cccctcctct ttatcttttt ctcgcgacac ctgcgttctc ttgccctctt atcatccctt  26700
tctcgaggcg gtcctttcct ttatccagct taaatacctt ctcctctgtt tatttggggg  26760
ttgggttttt atctctcacc ctccctctaa tttctttcct ctttccgcac ccatcaagcc  26820
tctcgtggtt tctcttcctc tactctcggg tccccccct ctccccttct ttttttcttc  26880
accccccaa gcgctttgcc tttttttct ttgcccttta ttcccccc             26928
```

<210> SEQ ID NO 7
<211> LENGTH: 29430
<212> TYPE: DNA
<213> ORGANISM: Homo sapiens
<220> FEATURE:
<221> NAME/KEY: unsure
<222> LOCATION: (4336),(4345),(4349),(4392),(4447),(4490)
<223> OTHER INFORMATION: Identity of nucleotide sequences at the above locations are unknown.

<400> SEQUENCE: 7

```
aggggaaggg ccggctccgt agctcacacc tataatccca gcactttccg aggagagagg     60
atcatctcag gccaggagtt caagaccagc ctgggcaaca cagcaagacc gcatctctac    120
aaaaacttct tttaaagctt aaaaaaaaaa aaaaaagcaa agaggacagt tcaggagaaa    180
agcctgtaga ggcagcacac taaggaggag acgcagccca ggcaccagga ggggctggcc    240
atgggcactc actcctccag caggcgagtg cccagcacca gctggcccac ccagacaccc    300
aggacacggc ctgaatggct ccgtattcac gtgggtggta ataaacaagc aatacacata    360
gccaataagg acaccttagt aatgttacat cataaacgct gcagatcagg gaaatggtgc    420
agggtgaagt gggttggggg gctgcatgct acatgagaag tgggtcgggg ggctgcatgc    480
tacctgagac agagcaggcc ttgctgggaa agaaggagcc ggcaggcctg ggcaaaggtc    540
```

-continued

```
ctggggtggg agcacactgg agcagagtgt gggggtagca tggcgggtgc tggtcctctg    600
ggcgccttcc caccacgtca tgtgcccatg tgcccaaggt ctctcgtttc acagccccct    660
gaagctcagg ggtcacagct acacagcccc cagatacctt ggcctgcccc aggtcattcc    720
atccagtgat ggacctgctg acctctagcc tgacctctgg gcagcgtaat ttgagaagga    780
ggagaaggga gggcaacaga cctggggcga tgagggatgc acagggtggc agacacctga    840
ggctgcacct tggagcctca gttctgggtg tgggtggggg atggacaggc tgagggctga    900
agcagctggg cccggccacc atcacacccc aggacccacc agatcaccat gaaaaaccga    960
atgtcaactg gcagcccaga gtgcagaaca aacctttcag aaacacggtg gtgactgccg   1020
catcatgaac ataaaataat tacgccctct ccccagggat cacccctgca ggagtttgtc   1080
ccaagaaaca ccagaaagaa ggaaaacgtc tgagtcacaa tatttgctga ggccttattt   1140
gtaatagcaa aaaaaaaaaa aaaaaaagaa caatctccag cggcaggggt aactagacta   1200
ttgtctccgt ggaaaggtag caccaattaa ctagtaacaa aatgactgcg gtaacaacaa   1260
aacgttcgac atgtcaacac caaaaaccac acacccagca taaccgtgaa ccatgatttc   1320
tactagaatg aatggcagtt atgagaaagc accagcggag acaaagattg aaaaagtaaa   1380
ggtggcctca ttagggagac aagtctctgg gtaatatatt gtaatactgg taaatatata   1440
gtttttaata tattttttaa ttccaaattc catatatgtt cctatgaagc tatttctgca   1500
aatatttttt tcaggaccgt acatcacaaa ggcaaaaggg ccaggtcagc tctccagctg   1560
agagtgacca cttcagagca gacggcagac tccagggtta gcaagcctgg ctgagacctg   1620
gcccatgaca atcactcaac ccctctgacc tcaacatcct gtctgtgaaa tggggataat   1680
tactgcacct ccacatcaca gagtgcgagg cttaaacagg atgcttcata gaaaagcgct   1740
caagaggtaa cagccgggag ggggtagtgg ttttcattaa ttaaatgttg ccttcatcca   1800
gccctgggcc agctccaaca caaagcacac accatccact cagactcagt tgcctggatt   1860
caaagcccgg cctggcctcc agctgtgaga ttccgggcag gatttcccat ctcccagagc   1920
ctcagtttcc tcattcatga aacaggaagt gatcattcct tttattttta tttttatttt   1980
tattttgaga cggagtttca ctctagttgc ccaggctgga gtatgatggc gcaatctcag   2040
ctcactgcaa cctcggcctc ccagtttcaa gcgattctcc cacctcagtc tcctgagtag   2100
ctgggattac aggcacacgc caccacgccc agctaatttt gtatttttag tagagacggg   2160
gttttgccat gttggtcagg ctggtctcga actcctgacc tcaggtgatc cgcccgcctt   2220
ggcatcccaa agtgctggga ttacaggtgt gagccaccaa gcccagttga caactgcttt   2280
taaagacacc tctggctgct gtggaaaaca gcctggtagt gcctcaaaaa gttacacata   2340
gaatgatcct atgaccagta attccactcc tacatatata cccaaaagaa ctgaacccct   2400
ctactcatgt atgtacacat acaggtacac gcatgttaac agcagtgttc acaaagccaa   2460
aacatggaaa cagctcaaat gtccataacc gatgaacgga taaatgaaac gtagtctatt   2520
caccacctga cggaggtgag aggggccata aaaaggaatg atgcataaaa acgaatatta   2580
tggccaggta tggtggctca cgcctgtaat cccaggactt tgggaggctg aggcgggcgg   2640
atcacgaggt aaggagttcg agaccagcct ggccaacacg gtgaaacccc atctctacta   2700
aaaatacaca aattagctgg gcatggtgga gggcgcctgt aataccagct actccggagg   2760
ctgaggcaag agaatccctt gaacctggga aacagaggtt gcagtgagct gagattgcac   2820
cactgcactc cagcctgggc gacagaccaa aactccgttt cggaaaaaaa agaaaaaatt   2880
```

-continued

```
agccaggtgt ggtggcgggt gggtccctgt aatcccagct ctacttggga tactgaggca   2940
ggagaaccac ttgaacccgg gaggtggagg tagcggtgag ctgagattgt gccactgcgc   3000
tccagcctgt gtgacagaag gagactctgt ctctaaaaaa caaaaacaaa aaaggcccga   3060
cgcggtgtct tacacctgta atgccaacac tttgggaagc caaggcaggc agatcatctg   3120
aggtcaggag tttgagagca gcctgggcaa cacggtgaaa ccccatctct actaaaaata   3180
cagaaattag ccaggtgtgg tggcacatgc ctgtaatccc agctactcgg gaggctgagg   3240
caggagaatc gcttgaaccc aggaagcgga ggttgcagtg agccgacatt gcaccattat   3300
actccagcct gggtgacaga gtgagattct gtctcaaaaa aaaaaaaaaa aaaaaaaaaa   3360
ctaaacaaaa gcaaaaaaac caatgagtaa tgttgtcaag tgaacttcat cccaatggga   3420
atgcagataa tttgtttaaa aggcaccatg cacactgggc aggctggctt cccctgggaa   3480
cgtcttcttt tgcctggatt cccagttggt ttaatcgggc gtagaacact ttcttcaatc   3540
cgggattcag gcacccctgc tcagcacaaa ctcagtacac cccgcactct gctgtgggtt   3600
cttggcacta ttaggagaat gtgagggggt gattcagatc tatctctagt gggtgcatgt   3660
ctgccactcc caggaacgcc cacttctggc aagtcagtgt cagagaaagg ccagctcgtg   3720
gcccctcctg ccttgagtcc caggacccgt gatcagtcct acccggagca gaatcaggag   3780
tttgaaaacc caagtgccaa caatctcatt ttaacccatg taagcatatc caatatttat   3840
atatagaatt cataacagat gtctgggctt ccattccaat agcctatatt ttacactgtt   3900
tatttacatg gttacaccaa acaagactca attcaaggta acccaatcct ttgctactat   3960
accaaaataa gcaacatttt cagtccatgc cttatatata ttcaccaagc attacactag   4020
gcctccaact gctcatcgga gcaagctgca gcctggacac aagctagaga ttaatcagtc   4080
aggaatgatc ctgcgtccag tgccagcatg atggaagaga cagagaaaca gaagacatca   4140
gggctccaga gtcaaggagc ctgcaggtta gttgggcagg atatacacac atacacacac   4200
acacgcacac acaaaaccac ccaagaagaa aaggtgggat gaatgcatgg acaggtaatg   4260
cctggagcct ggggatggat aagctgactg caggtggccc aggcaggctt cctggaggaa   4320
gaagacctgg ctgtangtgg ggtangcang ctttctaaat ggggaaaatc tggctgtggg   4380
tggagttggc angtttccga aaagaagaaa agctgactat gggtacacct ggctgttggt   4440
ggaacangca ggcttcttgg aagaagaaaa tctggctgtg ggtggatcan gcaagcttct   4500
tggaagaagt aaacctgact atgggtggac caggcaggct tcctagagga agaagaccgg   4560
ctgtgggtga accaggcagg cttcctagac agaggaagat ctggctgcgg ttagagtggg   4620
caggcttcta agaagaggaa gggctgactg tgggtagacc tggctgtggg tagactgggc   4680
aggcttcctg gaggaggaag agctggagca ttgaaaaaca aacatgactt ggtgaatgtt   4740
gagcatgccc aggcctgatc cccagaggca attacgcact caagttactt aattctactc   4800
acaatgcctc acaaacaact tctctgacac ctaacacagc tctgggcacc ttctagcttc   4860
agctcctcaa agcagttatt cacgctacta ccctgcacac ctcctcacac cccaacccca   4920
gggacaggag ttctgccaga tgccaaagct cctgatgcca aagcctgggt ctgcttccgg   4980
gctcctcttg gtctaactgt ccaccccgca tcggcatgat gtgcaaaaac aaggctttgc   5040
aatctgccct gatgcctggc ggagcgagtc cctcccgatt cgtctccttc agaaacacct   5100
gggctgccct ggtcctgtta tacccccaac acattctaca gtcagctccg caagttccac   5160
aaagatcaac gctggcgttt ttatggcatt ttatttacag tttttacaat ataaaaaagg   5220
aaggatgcca cagctcagcc agcaggacag acagagatct atgatgcttc tgctgcacca   5280
```

-continued

```
ttgtttgtgg tcaagaaagt ctgttttcaa tgatttatta aattgtggtg ggagatggat   5340
ggtggcagtg gttaccagca acatgaatgt tcttaatgcc actgaacttc acacttacaa   5400
atggttacga cgataagtgt tatatgtatt ttaccacaat taaaaacagg taaatgcagg   5460
ccgggcacgg tggctcacga ctgtaatctc agcactttgg gaggccaagg caggcagatc   5520
acctgaggtc aggggttcga gaccagtctc gccaacacgg tgaaactctg tctctattaa   5580
aaatacaaaa attagccaga tgtggtggtg catgcctgta atcccagctt ctcaggaggc   5640
tgaggcagga aaatagcttg aaaccgggag gcagaggttg ccatgagctg agattgtacc   5700
attgcactcc agcctgggtg acaaaagcaa aactctgtct caaaaaaata aaataaaata   5760
aaaataggta aatgcaaaca tatggtatag taatattatg ggctattatg agctacaaaa   5820
aagaatgact tgggactaca gttacagccc tcattcagga atttgtttta aatgtgggtt   5880
ggtcgctaag gcatgtacac aacattttga cgttcaaata ttcctagatt tggacagtga   5940
gcacccctct aagctggctc ttctgtccca gaggtcccca ccagtcctcc agaacttctt   6000
tgctttctta cacaataaga tgccccatgc tcggcttgta cctttccttg ccccagccct   6060
agaaccagct tcttcgtgga caagctctga ctcctttggg tggagaatgg tattcagaaa   6120
cccagacctg ggctctggtg tgctcactgc tacttggggt cattgcttct aggcctctct   6180
gctgatggag gtaggatata cacgtacagt cttccctctt cccagattcc gtacttgagc   6240
tcgcctactt gctaacattt atttatatcc cccaaattaa acctcacagc acttctgcaa   6300
tcactcactg acttgcagag tgtgaaaaaa ctgagtcacc atcacacgtt ccaaactgag   6360
gtcaactgag gccacaacgc cccatcttct tgctccggct gtcgagatgt aagcaagtgt   6420
ccttctctcg gtctagctag tgccatgctt tccacatcac tgtgcttttt gtgggcaatt   6480
ttgctgtata aaatgtcccc tgcacatatg ctgctgtgta gtgctcctag gtgcatgagg   6540
ctgccccacg ccttacagag agaatatgca tgagaggctt tattcaggta tgagttatag   6600
cgtagttggc catgaattca atgttaatga atcaacaata tacagtaaat aaggtgcttt   6660
ttagagacag ggtctcactc tgtcacccag gctttagagt ccagtggtgt gaccttggct   6720
cactgccgcc tcaacctcct gggctcaagt gatcctccca cctcagcctc ccaaactgtt   6780
gggattacag gcgtgagcta ctgcactcag cctaaataag gtgtcttaga aacacacata   6840
agacaaggtt atgggctgag tgcggtggct catgcctgta atcccaacac tttgggaggc   6900
caaggtggga ggttcacttg aggccagaag tttgagacta gcctgggcaa catggcaaga   6960
cctcatctgt atattttttt aaatcagaca ggtgtggtgg tgcatgccta tagtcccagc   7020
tactggagag gctgaggcag gaaaatggcc tgagcccagg aggtcaaggc tgcagtgacc   7080
catgattgta ccactgcatt ccagcctggg gtgacacagc aagacgctgt cttaaaaaaa   7140
aaaaaaaaaa aagccaggtc aggtatcgaa cagttggcaa aaacgttgtg acctgaggct   7200
cacaggaacc tagcccgatg tttcccctag gagcaatggt tcagtattca ataattcagg   7260
gttcccagtg actttatgga gcataacttt caagaataac aagaaccaac tgtacgtgtg   7320
tatgtatact cacactttta ttttatttta ttttattttt tgagacagag tctcactctg   7380
tcacccaggc tggagtaaaa tggcgtgatc tcgactcact gcaacctccg cctcccaggt   7440
tcaagtgatt ctcagcctcc caagtagctg ggattacagg tgtgccccca caaccggcta   7500
atttctgtat ttttagtaga gacggagttt cgccacattg gccacgctgg tctcaaactc   7560
ctaacctcaa gtgatccacc cacctcagcc tcccaaagtg ctggaattac aggcatgagc   7620
```

-continued

```
tgccgtgcct agcctacata cacttttata cacacatgca tctatgacta tttctctatt   7680
tctgtgcatg tgtgcgtggc agtacctaca gtttcagcta tgtgtctggg tactgtctcg   7740
tccaagtttg taagcacctt ctccaaagtg caaagcctgg cttgtgttac tatccatatg   7800
tttacttatt tgctcaatca atttacttat tagctccata accagcttcc catctgctcc   7860
agtagcctct gctgtcagtc acctctgcac cctaccccac cttgcttccg gatgctggat   7920
gccaatcacc cccgacacct ctacatagca ccaccctcga catgctgctt ctttatttct   7980
tatttatttg tttgagatgg agtcttactc tgttgcccag gctggagtgc agtggcacga   8040
tccaggctca ctgcaacgtc cgcctcctgg gttcaagtga ttctcctgcc tcagcttctc   8100
aaatagctgg gattacaggt gcccaccacc acgcccagct aatttttgta tttttagtag   8160
agatggggtt tcaccatgtt ggccaggctg gtctcgaact cctgacctca agtgatccac   8220
cttggcctct caaagtgctg ggattacagg tgtgagccac cgcgcctggt ctgcttcttt   8280
aaatgccagg caccaacatt tgtgcaatgg ggtgggagga aagaacaggg aggagagcac   8340
actgccggcc cctgcactga atccactgat caatctgggg gcaactgcca tctccatctc   8400
ctgtcttcct atccgtgaac atctactgca gtcctctcca atgtccttct gtaaagttgt   8460
attatgtttt gcatacaggc cttgcatatt agttctcaga tataatccat atactttata   8520
taaaattcaa accacattta aaaaaataaa actagcatga ctataacgga gtctgcaaca   8580
ttctcacaga ctttatgata aaacatgaaa cttcaaagat acttagggtg gggcagggac   8640
aatgtttaag gctgcctgga agcctcccca tccctgagcc agaaagtcct atctcccctt   8700
caaggggaaa tgcttgaaaa agcactgatc aggctaaaat gacagggatc agggagtaat   8760
caaagtacaa gtgagctggt ctcctccatt ctgagcacag caaagttcag tctctccaag   8820
tccaagaatc atacacctgt ttgccaagaa tgaagttcag gtgtctacaa gtggctgaaa   8880
atattcattg ctgggccatt aacaacattc ttggcaaaac cataccttag cttctcgtgg   8940
aaatttctta aggtagaaga aacaggaaac acccaggctc gcttttatgt agacagttcc   9000
atgaagccag ggaccttccc cacatccacg tttcaattac ctgcacgcag ctcacagtgt   9060
attcaacatc tacgcgtctc tcctactggg gtggcggtgg ccactcaaac cctcatgcag   9120
ctacgatgac cgcaattttg gcaacataat ttcatgtttt tccttgggct tttacccaag   9180
tcagtgacac aattctgcag ttgtctaaag attcaaaatg agggacttga catttacaac   9240
aataataaaa tcttgggttt cctttaacca agcacatgtt ctgcctttta gagaaagctc   9300
tgcaaactca agctggagtg ggatacttgc tgacatcttc aagcacccca ggaatagctc   9360
tactccccca tttccacctt ggctgaacca tctatatccc accaattccc ccaacatccc   9420
tccatccgtc catccatcca cccaaggacc tgctaagcca ggaggtctct cccatctacc   9480
ccacagcctg gcctcagccc acaagggctc tctctacatg aatcccaccg caccagagta   9540
gaccaagtct cccgtagact ccaccctgac cacctccatg cctccagcca ttcccacccc   9600
taaaaaccct ccctggtctc tacacccagc tgatgaatac ttggctgaat gtgacctggc   9660
ctcctggacc caggtgaagc ccacgtcctc cgtaagcccg ccagctcacc ctgcctctgc   9720
accttcactg gagagagccc gcacttcacc tcctcagggc aggcatggct gatgccaccc   9780
agtggaatct ggtgcaaagc agggcccggt gcagagcagg gctgcctgca gagcaaggcc   9840
ctggtgctgg ggccgagcac ctccaatgct ggccgtggaa ccatccctcc cattccaggt   9900
gctgtctcca tcaagaatga gcgagctgct gacatttgca tgacaataat gaataaatac   9960
catattttgc ttcaaatcca gaatagatgt ggccagggtt ggcatatgac tgttgggaaa  10020
```

-continued

```
ggacagtttg cctcttccca aaccaacttg gattataaaa agcttttctt aacgaccaca  10080
agagcggagg agctcagggg cagacaaaag gaaggctggc tgcagaaggc gggagagtgg  10140
ggccttcagg ggcgggtggg gagagagaaa gcctggagct gcacccccaa ggtctgtgta  10200
catcaggtgc tacagaataa caccacctct tccagcttgg cccccacctg ccctctccca  10260
gcccagtcac ccagacagca ccccactccc cacacacacc tcacatctgc ccgcctcaca  10320
ctcaccagct tcggctctca atgcaacctg gaacctgccc ttggcctctc agctcagcca  10380
cccccattcc tgttggcccc tggcccccca tcgaattctc tctaatccta atgcacacac  10440
ttgcacactc aaacacacac acacacacac acacacacag cccagaggaa aaccataatt  10500
gactgaggtc caggcaagtt tcccgagcag ggaccacatt tcaaaggtca gggaagcagg  10560
cgaacaggaa acatacaggg ggcacgtttg ggggtggagc aggaaataag aaatcacttg  10620
caaaagataa aaagaaaatg aggtagctgg tttcagacac ctcggagcac acagaacagg  10680
acaggcgcct ccgggtcttc cctcaacagg gagatgggcc aggcaggtcc ctgctgctcc  10740
accgcagagc tgggggctat ggccctgaca ccaaggccct ggggcaggcg gggaggcagc  10800
tgttctcctg cctgtgctcc cgggcagggc ctggccccac aagggaactg gccgaaggct  10860
ctgcttggct actccggaaa gtcctgggag acaagcaaag gacttgctag gtcactccaa  10920
acggcccaga tgtgacaact gtgaagaagc cacaccaaag caaggtgaca gaacaatgtt  10980
ggtgacgtca ggttatcagc ttacgctcaa ctccacttac ccggactcac ccgtaacctg  11040
ccgtctcttc ccaaccagta aaggatgcct aggtagaggg gcacaaggcc tggagcataa  11100
ttaccatttt aaaggctctg agaagtcctg cggtgaggaa gcctagttca ctttctctcc  11160
cctaggattt cccaactgcg cctgatcaca gaacattttt tcatttccac tcaggaaaca  11220
tattttgaaa aacactggcc tagaggcaga agtgaaatgg aaaacacaaa agtaaaactg  11280
aacaggaggc actgggcaga gaacggtcag aggcgccctg aatcctggac cggtggagat  11340
ccccagcttg gcatgctccc ctccctgggc ccagaccgcc tccccccatt tcctggataa  11400
gaaggctaat gcgcatcagg gtgaagggct tgcctgggct acacccccag gctcgcccca  11460
caccaatcgc gctcctgcga gagccagtga ctttcttgat ttggctactg tggaattgtt  11520
tgcaactaac caccccagat acagatacaa atgacaggat gatcagatgt aaaggaccca  11580
caggtctctg tgatacggct tcatgcagcc agcatggcta gtgccgtgca gaatgagaat  11640
gaccccaggc aagtccttgc ctcccagacc cagaacccca tggagcccac cagggctggt  11700
tcacaagcac tgtctgggtc gggcagagat tccagcaaga ggagggaaca tccatgcacc  11760
ggagccagtt accagaagca aatcgcctct tccaaaaccc aggctattaa tggagtccac  11820
tgttgagtgg agctggggtc tagctatgga atactgcaca gcagagatct tcctgagaga  11880
aagcagtttt ccctgaaagc catgtgtcct ccactaactg tgttttaatt gggcgaacgt  11940
ctgtatctca ttgcagtggc cgcgcatgtg ctgacaaggg gctgggggcg gggtggggag  12000
cagaagctca ggggcctggg agggaaggaa acaggccacc agggctcccc agaaggcatg  12060
tatctctctc acaaacacac gcatgcacac acacgtgcac acatactctg caagccctga  12120
gttagcaact gtggaatgtg accagctcag tgatcccagg acaagctgct agggaatatg  12180
acatttgatt gatgtctgca aatgtgcgtt ttcactaatt agaaggttta gggcagagca  12240
gagaaaaata tgtatttcag agtcccagtt tgacctgcca gaaaccagcc cattactaac  12300
attcttattt tcaacaaaat atagcattct gattacatac catcttggtt ccacgcctcc  12360
```

-continued

```
tgccttgcca agcccccgga agcggcccaa ggccatggca aatagtgaga gaaacagttc  12420
cagggtggag actgactcag ggtgtcagt cagtggggcg ctgatggccg gtgggaggcc  12480
agcagtcatc accctctcct tgggacagtt gagtagctct cccccagggt catgtggcca  12540
ctcaggttca tatgggaggc gagaggagtg gcagagtcca ggagagtggc tccgaagtca  12600
ctgttccctc caggcctcag tgtcttcatc cattaaatgg gtaggctgag gtctgggatg  12660
acaaggaggg cttgcactta ctgaaaccca tgggaggctg ttcgccgatt tcttttattg  12720
atggaagaaa acactcgtat aattcaagta ccaattaaaa ggcaggcact ggaaccaccg  12780
tctgccaatt cctagttttg cctataccaa atttgagcaa gttaattgac ctctcccagc  12840
ctcagtttct tcgtctgtaa aatgagggta gggatggccc ccagcccaca gggcagctgg  12900
aaggattaaa gaaatcaaac atctcttaga gcccacctgg cacactgtga tacacaacaa  12960
atgttagcta tttttgtcta tgaagtctag attttatatc ttgggtgttc taaagcagga  13020
tacatttatt taaaaacaag gattttcatt aaacacgtac cccacagaca gcaaccccat  13080
ggagactgct cttaattcag gccagtatcg aaacgactct aactacaagc tttatacagg  13140
tctcttggct gtccttcaaa tccaactaag gtggtacttc tgaagcactg tgcacatgtg  13200
tgtgtgcatg cacacgtgtg ggaagggcgg gctcacggat ccctcaggta ccccacccac  13260
gcagtctcaa gtcacaaagc gacagagcag ccgaggaagg tctgtgcccc actggaccct  13320
cgtgaagcca ccaactctac ctctgcgccg tgtcctgcag actgggctac cctttgggtg  13380
gggaccagca tttgatgcaa gaaaggcaga cagaaaagga aaagggcaag ttcgactcca  13440
gataacacag acagtaccaa gccccagggt ccataaatgc cacgcagatg gaagcattta  13500
ctgcgaggcc acacagcaaa cgcacggatc cagggacgga ggtgcagact gcggtgcccc  13560
tgagccatga ccctgcaaat taccaccatg ggaaaggagg ctgccaaacc ccccgacagt  13620
cggctgggct ggcacagact cgtggtttcc atcgaggtgg gaggaggtgg gacgtcccag  13680
cccctccccc atgcccactg cagagggaag cggccgtttc ccctgtgtgg ttacaaaggt  13740
ctcattgttc ttcctcacag ggaggaaact ggaggaccga gctcagaacg cattttagaa  13800
ctggcagaaa agaacatctg ggaaggaaa cacatttcag aaacaaacat acctttgtac  13860
cagcttttat tttctttaag tgttgaaaaa ataataataa taaagacatg ccaaatttat  13920
catcgctcta caaaatccct ttattgagca aaacgtggca gctctacttt caaatgatta  13980
ctgttcctgg aaaattgcag caacgtggat gccaaggccc gaaggccgcc atcagcagcc  14040
aaacaaaaga tgccacctcg ggctccgcga cactgtacca tgccagggaa ctggacagat  14100
ttggggaatg ccacggtttg cctttaaccc cttgcctcct ggtctcctga tgcatctcag  14160
aggctaacat tctttgagga actggcattt cttagttgta aatatgcatg tgggtttggg  14220
agctgcctgc aaagtccagt gttgacgatc agctttgatt tccttggaat caagtttacg  14280
tgtcgagtct ggaagttaag aagaatttgg agaagctgag cactatggtg ttgcaggccc  14340
tgggtgaact cttccaccaa gcattcattg tggactgaca gcgtgcgagg ggctctgcag  14400
gcaggtgcac aggacgaaac acattccgtc cgggggaaac ctgcaggaaa gctccctctt  14460
cttcctaagg tgccgggcct agcttcatgg gtccctaccc tccacgcctg tcacactttc  14520
tgagtctcat gtgggagctg cttctggttc ctgacttcac tcagtcctca taggaggtgg  14580
aactactgtc accccatttt acagatgggg agactgggca caaggggacc aagaaaccaa  14640
tgcaaagtca cacttgtggg atcagtgaca ggggagatca attcccaggt tctttctgca  14700
agagttaaat tgttttcatg ctgcctaagg gggggcaact gaaagaccac tgcatatctt  14760
```

-continued

```
tgccaaaagg gtcaagcaca ggagccgcag ccagtgggtc agatccgcag aggcgctggg  14820
gtgaccctcc ccatacctgg agggatgctt gtcccctcct ggccttcact gggtcccctc  14880
atgaccgtgg cctcccagga cctcagcaca atcccggtcc tgtgctccag gacaagccct  14940
ccgtccccaa gactgtgagg aaatggaacg aagaggggct cgctgcagcc cagcacccac  15000
actgcccctt ctcaggggca agaaccgtcc tggaggactt ggctttggag ggggagcctg  15060
ggaggccagt aagtcaacaa gcctctactg ctcatgggtg ggatcccacc gcaggccccc  15120
acctgctggg gcgggcaggg acgggcggca cagcttggcc agggcagata acccccacct  15180
tggccagggc gaaggcagga cacgtgggct ccagcctggc cccaccatcc ctgcacaaca  15240
ctgggcaaag tccacgtttt cctcaactgg gtgttgacat ctgcaggaca ggggcatgga  15300
ggtacagagc gctgaagcca cacagcaacc taggagcgag actccatgcc tccccgggga  15360
cccctcccca ccatgaggac catgaaggct tcccatgtgc cgcaaggact ctggtgtgga  15420
gacacacgtc tcctacacag ccaggcctaa cgctcttgta actgggtggt cccacctggg  15480
ctcacagctg gagggccagg agctcaaggc ttcgcagggt ctgctctcat cccagaggcg  15540
atggggagcc acagcaggct gcaggagaga gggtgggccc cctccacttc agaggcccca  15600
tctggcccac agactggaga gcacatctct cagcaaccac ggagcgccaa ctgcgcacag  15660
ggcctggtcg tcagagcggg gcaaaggcac tgaccgtcac ggccagggcg agggaagacg  15720
ggtgggcagg gaccttgggc agagggggaa gaacctggtg cccaggctgg ccctgccttc  15780
agcagtgaag ctgagtgggg aggcgctgat gcagggggcc agaaagggct gctggtcagc  15840
cgggaggagc cccccacaga ggaagcagcc agcccagacg cagatggcag ggtcccctca  15900
acaatgtcct ctgaaaagga gaggcgggga ctgctctggt gacacctaca aatagatagt  15960
cagccctcag ccccctgcca tacttctgac aaagcagagg cccccagggg aggcgcaccc  16020
gaaggtacct gcacctgtcc cccagactcc tagagcccac ctgaccccat cccaccaggg  16080
ctccagctac aaaataaatg ccgaggccag ctaggcaagg acgcacactc ggtaccgact  16140
gaataggctc cacgttgtca tgagcgcaac ccacaggcca ccaggccaca ctatgcagag  16200
ctgagatggt ttcggccaag cagcctctca gctgagctga acaagtccag agtccccggg  16260
gggtcgtcac tatggagtaa caattgcgat gcgatggtaa ccctaacagc taaccgtcac  16320
tgagccaggc cctgagctag gtacttttca acgctgcctc tctgcagcct caggacgagc  16380
ctgtgggagc ataaagatca ttccctatca cggatgggga aactgagctc tgaagcagtt  16440
aacgtgcttg tcccagaccg cagagctagg agcaggacac aacagcaggt caggcaggaa  16500
cgggtgaggg gggcctgcat gggcttctct ggaggctgcg catacacgca acccccagga  16560
ccccgaccct gcacctgcag ctcgctactg ccccctcagt gactccagca aacctcgggg  16620
taggggaagg aggctgggaa tacctcgggt gtccgaaaca gcagcttctg cttggaggcc  16680
actgctgcat aatggttgct gcccagcaca ccccaagcca cctgtgccac ctgtggtgac  16740
cttccagcat gccttggtga ccaagctggc cttaggtgct gtgggcagcc aagaatagaa  16800
cagggcccac ccctcctctt cacactaaca caaagcaaga ggcgggcact tcgactgagt  16860
gcatccctct agctcaaggg cctcacggat cacaggggtc agggcaagat cccaattctg  16920
cattcccgtc tgcctttcat cctgctctgc caacaacagc cagtgaggct ggggacatcc  16980
ctgaacctgt ttctcacctg aaacacatca taccattgga ccccagccct ccgggagagg  17040
ccctaatccc tgactgtggt gagatcagat cactggttaa gtacccagaa gggccttggt  17100
```

-continued cagggggctcc aggggtgggg ggtgatgggc gtggtggtat cccgctctgg gctatagtcc 17160
accctgatgg aggaggtctg tggtcagaac cgggctgtgc agggcacagg agcccagagg 17220
gacccccaga gctcacctgg tggtctctga gcagggctcc ctcaaccctc agagaaaagc 17280
acagcaagga ggccgcccag agcccagcgc ctagcaccca gtggcgtgcc agacctgcct 17340
ggatcctgga gatctctcat caccctccaa gtcagtcatg cccaacccag ggacccacag 17400
cccacggggc cgtgaaggtg tgctgagtcc aagaaggcct tcgacactgg gaagccaagt 17460
ggcacctcct ggtgtggagc aggcggaatc ccaccagcct ctgctctgcc agtgggcaca 17520
gctggacgat gagcagaagg ggctgttgct taataaacgt catttcctta agaggataaa 17580
acctttcaaa acagatggaa attttttttt aattaaaact ggtggccaaa gagatggaaa 17640
gcaccccttg tgcctccctc ccatcgtgac ccatcctctg cacacctcaa gctgttcgct 17700
gcccaggtgt ctcctgaggc actgggggcg ggtgagaatc cgtgagccct cggccagccg 17760
tggctctctg gagctctgcc ccaggccatc agggcacacg ccgggcaccc tgggggccac 17820
acagggcaga gcccagctgg gtcagcacac agggccacac tgggcacaca agtctctgag 17880
cctcccctgt ggacgcagct ctcactatcc caccccacta ggtcccgggg atctgtccca 17940
cagggtgata tgctgtcaca gaccactacc agagccatgg cctgctgttc cgcccgcagc 18000
caggtagtca cttgctccac agggacaggc aacgccgcac ttgggggctg ctctgcggca 18060
ggactagagc tccagcagct cagccctcct gagaaggaga actccatgct ctaagaggca 18120
gacgcagcgg acggcaccaa agccaccaca agcccacggg gccctgcatg gcaggtcagg 18180
agtccctgac cactcgctct ttgtaaccag agctgcagtg gagtctacga ggcaaggact 18240
gtgggcggca gtggccacag caaatgaatg agtgtcccaa gggagcaggc ggctgcgggg 18300
aggcacagcc gggacccagg agtcctccgg cactgcagca aactccctgg gccccctgag 18360
cagcgaccag gtggcaagtg catgaactcc cgggggcata acctgggagg gtgacactct 18420
cttcgtgttc aaattcttga gaacgcatta aaaatatcac tcagtcacct actctatagt 18480
tttaactcaa aagtaccaaa gtagccaggc gcggtggctc acgcctataa tcccagtact 18540
ttgggaagct gaggcaagag gatcacttaa gcccaggagt tccaaatgaa cctgggcaac 18600
atggagggac cccatttcta caaaaaaagt gttttaaaaa attacctggg cctggtggtg 18660
tgtgcctgta gtcccagcta ctcaggaggc tgaggcggga gaaccacatg aacccagggg 18720
aggtagaggc tgcagtaggc tgtgatggca ccactgcact ccagcctggg taacagagtc 18780
agactctatc tcaaaataaa tttaaaaagc accaagccag gcttggtggc tcacacctgt 18840
aatcccagca ctcagggagg ctgaggcaag tggatcacct gagtcagaag ttcgagacca 18900
gcccagccaa catggtgaaa ctccatctcc actaaaaata caaaaattac ccaggcgtgg 18960
tggcgggtgc ctgtaatccc agctactcag gaagctgagg caggagaact gcttgaaccc 19020
aggaggcaga ggttgcagtg agccaagact gtgctactgc actcaagcct gggagacaga 19080
acgagactcc atctcaaaaa ataaataaat caatcaaaac caccaagact ttttaatata 19140
aacatttatt attccataat tcctttttttg catgattaaa aatgtttata taaagtttcc 19200
tgaaaatggt aagaatgcca agtgaaggct gcaaatgccc aagcccccac cgtggcatct 19260
cacggagtct gggccctagg aggctggtgg gtaccacgtg gacccgagac ttcacagtca 19320
agtccctttg gggtacactg ggtttcccac accccagaaa tatgggctct tactgcagga 19380
ccatgggggt cctcacactt ggcccagaag ctgtcacata gccagacagg tgttctacaa 19440
cctaggctag agggagctca tgctccagca gaattcgagc cagaggaggt aaaagatggg 19500

-continued

```
taagatctgc tccctggaca gatgaggcct tggcctcaga acagttactg atcatctacc  19560
agacatcaca ctagaggcag aggggcgcag acgaagacag cccctgtcct caaggccctc  19620
ccaggttggg tggaccatgg aaggttccag acagatctgg caagagaagt gcccacacca  19680
ggggcagaag atgggcaggt ctgctcaggg cggcacggcc tgccaggcca aaaagttcca  19740
acttcagatg ctggagaatg ggcacgactg tctgagaaag ggaaggatgt gatgaaaact  19800
acttggagaa aaattaatct ggccagagca taagataaat gggcaaaggg gaggttccag  19860
aaagcaagga gaccaagtaa aagctgatgt cattggctct gaatctaggc tttcactgaa  19920
tatgcaccgc agggcctgta ggtaaagcct cagagcccag ggagtctgag tggaggagag  19980
ggcaggggac agagctgggg cctgtgtcta cagtgctcag gaggaatagg catggacgtc  20040
agctcggagg ctccagctga agtgaggagg cggccagggc agcacggcca cgcccggatc  20100
cagactcctt ttgggaagca agttcgctct gggggaaagt ttggagaaat ggcctttacc  20160
cgcagaagca agccccagaa catatcttgc tccaaaacta tctcgtacag tgaggacgtt  20220
aagcttcagg tcccctagag gagacagtct gctccttcct ggggcagaac ccaaggtggc  20280
cagagcctgg aaggcaccca gcacccaggc tggtgtgttc cagcccaggc cacacgctca  20340
gatagctatt aatgccccgt tgagcaattt cctgagagct ttgccaggca ggtaccgcct  20400
ccccatctga actaatacag ggtacatcc caaggaagaa atgaaaggtg cccacatttt  20460
gctctgggat taactaggga ggggagtgat aattaactca gtaattatat ttgccatcgg  20520
gctaatgcta aaattagtgt gcattagaat ttctttcctg agcagacacc ggagtgagtt  20580
gggcagcagg agtggctcgg gcaagtcggc acaaagggca cctccagagc cttccacaaa  20640
tgtcagcaaa acccacaaat gtcaaggccg gctccactgc acccagcaga tgaattcact  20700
tccacagcct gagaccgcca gctcatcgga ggccatttaa aatccagccc tctgacacct  20760
gctggatatc accatttacc gtccccagat caagagatca aagggtggaa cctgatagga  20820
cggctctgaa gttcaccaca aaagcataaa cgtgcaagca gagccaatac gtcttttgaa  20880
aaggacaatg aggtgggaat ttacataact gatcttaaaa tatgttctga tgcttcagag  20940
atggagacag cagcattccg gtacacaaag acactcacag gcagtggagc acagtgaagg  21000
gtctggaatc aggacccagg tgtctgtgga cactacacat aaaagagcag catttacaat  21060
gaatggatag gatggaccat cccaccaagg tgttggacaa ctccctattc actggccaga  21120
cccctacctc ataccatata caaaaaaaaa aaaaaaaaaa aaacccagac agaataatgt  21180
ctgaatgtaa aacataaaac agtaacagtc ctggaagaaa ataatggagg atatatttat  21240
aatctggaga tggagtaaca agggatagga aaaaagccat agggaaaaag tagagttatg  21300
attatatgaa gcttcttaat atctttatga taatgtacca ccagaaacaa ggatgaagga  21360
ctagctacag accagcagtg aaacctgaaa caaacagaac aaagaattaa agtccatacc  21420
aaataaagac ctcccacaaa tctataagaa aaagataaac aggctggcac cgtggcttat  21480
gtctgtaatc ccagcacttt gggaggcgga gatgggtagg tcacttgagg tcaggagttc  21540
gagaccagcc tggccaacat ggtgaaaccc tgtctctacc aaaaatacaa aaattagcca  21600
ggcgtggtgg cgcatgcctg tagtcccagc tacttgggag gctgagccag gagaacagct  21660
ggaacccggg aggcagaggt tgcagtgaac caagatggca atcgcgccac tgcactccag  21720
cctggaggac acagcgagac tctgtctcaa aaaaaaaaaa aaaagaagaa gaagaaaaaa  21780
gaaaagaaaa agacaacaga aaaatgggcc aaggataagt gtaggcaatt tgcagaaaag  21840
```

-continued

```
taaataccaa taaaccagaa atgagggttg tgcaaatcaa aaggtgttat aatttttaac  21900
caaactggac caaagaaaac accaaaaacc aaaatcttgt aattgccagc atcagagagg  21960
atataggaaa gtgtgtgttc tcgtagatgc ttgcaggtat gaactgctac agccttttag  22020
gagttatgta tgtatgtatg cttgtatgta tgtatttgag acagggtctc gctctgttgc  22080
ccaggctaga tctgttgcag tgctgtgatc atggcttact gcagccttga cctcctgagc  22140
tcaatagatt ttcccacctc agcctttcaa gtagctgaga ctacaggagt gtgcaatcat  22200
actcagctaa ttttttaaat tttttgtaga catggggggt ctcccaattt tgcccaggct  22260
ggtctcgaac tcctggactc aagtgatcct cctgcctcaa cctcccaaag tgctgggatt  22320
acctggatga gccactgtgc ccggcctcaa tatctttaaa aacagaaatg gacacactct  22380
ttgactagga atgtatccta taaaaacact tatacacatg cagagacaca cgagcaagca  22440
tgctttgtaa tagcaatgaa ggctggaaaa actcctcaat caggtaaatg ctgtcaagtg  22500
cacctgtgta ctatgaaatg gcacttggct tttaacaaga gcaaagacag aaaagcaaaa  22560
gtacaaagta gggtgtgatg gcacatgcct gcagtcccag ctactcagga ggctgaggca  22620
ggaagatcct ttgagcccag gagttggagg ccaggagctg ggcaatagtg agaaaaaata  22680
aaattaaata ataataataa taaaataggc tgggcacagc ggctcatgcc tgtaatccca  22740
acactttggg aggctgaggt gggaggatcg cttgatccca ggagttcaag gccagcctgg  22800
gcagcaaagc aagacaccca tctcaacgac aaattttaaa aaatcagcca ggcaggctgg  22860
gcatggtggc tcacgcctgt aatcccagca ctttgggagg ccgaggcagg cagatcactt  22920
gaggtcagga gttcgagacc agcctggcca acgtggcaaa accctgtctc tactaaaaat  22980
acaaaaatta gctgggcatg gtggcagatg cctgtagtcc cagctactga ggcacaagaa  23040
tcgcttgaac cagggtggca gaagttacag tgagccgaga tcgtgccacc gcactccatc  23100
ctgggcgtga gtgagactcc tgtctcaaaa aaaaaaaaaa aaaaaaaaca aggagccagg  23160
cacggtgggg tgagggaggg cacagaagca gcgcctcttc tgggggcacc cccaatctct  23220
agcgatccag aggcctcagg atcctgaagg gagaaaaaac gtgaagctcc gtgctagaag  23280
agaccataga gattggaatc agctggttct attttacaaa aaaaggaaac tgaggccctc  23340
agaaggtgag tgcctctcaa tgccccacag ggaggcaggg agagggctct gagccctgca  23400
gggccctgga ttcttgcaat ggggtggagt ggagcctgtg ccgcccccac caggcacctt  23460
ctcaggagag gagccgttgt catatccttg aaggggtcct tgagcccctc aaaaggctaa  23520
aaaccacttt cctccttgag tgaaccttca cctcagttta accacaagaa aaactacatt  23580
aaggcccagc gcagtggctc atgtctgtaa tcccagcact ttgggaggct gaggtgggtg  23640
gatcgcttga gcccaggagt tcaagaccag cctgggcaac atagtgaaac cctgtctcta  23700
caaaaaaacaa caaaatcagc tgggcgtggt ggtgcacacc tgaggtccca actacttgcg  23760
ggctgaggtg agaggattgc ttcagcccag gaggtagagg ctgcagtaag cggtgactga  23820
atcactgcac tccagcctca gcaacagagc aagactcaaa aaaaaaaaaa aaagcaggcc  23880
gggtgtggtg gctcacgcct gtaatcccag caccttggga ggccgagcgg gaggatcagg  23940
agatggagac catcctggct aacacggtga aaccccgtct ctactaaaaa tgcaaaaaat  24000
tagccgggcg tggtggcggg tgcctgtagt tccagctact caggaggctg aggcaggaga  24060
aaggcgtgac cctgggaggt ggagcttgca gtgagctgag atcacaccgc tgcactccag  24120
cctgggcgac agagcaagac tccatctcaa aaaaaaaaaa attaaatctc aaaaaaaatt  24180
acattaaggc aaactaaaag atgtttaaaa tatatatatt aaattaaata cactccaata  24240
```

-continued

```
gagcaaatac gaaaataccc agaaaacaca atccccgcac ccccaggaca acctcccagg  24300
gggtccacag caagagaccc caagcacgag agacagagaa cagtgtccct gtggcggaac  24360
ctctggccca tcaggctcta ttagaaaata aggctcttgc cactgagaga aagaggcaca  24420
gtcgcccagc agccacgggc tctggcacac cacgagtcag gccagcaaag tgtcaactgc  24480
cccctacaag gtgacaaact aggacaaact ggaaaccaga ggctggacct ggagcacagg  24540
gaccaccaca tggggctggg gaatgggcag ggacctcaga gcgccaccca catgcctaag  24600
agcagcgcgt atgcgcatgc ctctgcatgg cttagggaca cagggagctc cccccacccc  24660
caacccagga aggcagcccc cactacccag gtagggaacg gataggacca gcacccccgtt  24720
ctgctcgtaa ctcagggctc caggccccct cgggggcaac cagcacagag ctcagacccc  24780
aaatatcttc acccacctcc tggtccccat ctggacaagg gtgctgggga ctggctctca  24840
gtcacaccct cggggtactc ttcaaaggac agctggatgc cccagggcag gagcttttgg  24900
cccccagctc cctcacccca gacaccagct cttgggaccc caccagcatg ggcaaggtgg  24960
acaccatcgt cccgattttg cagatgagga aactgaggct gagggctggc acacggctct  25020
ccagagctga agagaatgca gagagcagcc ggagccagcc ggtgggtccc tgaggccggc  25080
tcgtagcaag ccacagctgc ctccgcccat cacacttgga cctcactggc cccaggacag  25140
ccctccaggg cggcctggca cagagcccac accctgctgc ttcctgaaca aataagtgaa  25200
caaggccacc aagccgagga cctggatgta gccccggctc ccgccagggc ctccccaaca  25260
gactccccat ttggagagcg cattaagtgt ttccaaagcc tcacaaacca cagatgtccg  25320
gctgtctcac ggcttctgta acctgaactt ggccctcact ctgccctccc agcactcctc  25380
tcagggccca ggcccctcct ctgagatgcc agcactgact ccccaacttg tccccatcac  25440
ctggctcgtt cctgaacctc ggcaggagag tctcaggcca gatcctccca ccagccacct  25500
ccaccaggat gcaggaggca tgagacctgc tcgtgccggc tgggagatgc aaccaaccaa  25560
gatcaatcca atcagcggat gaactgacaa atataatgtg gtccctccac acaatggaat  25620
attattcagc cacaaaaagg gctgaaatag gccgggcgtg atggctcaca cctgtaatcc  25680
cagcactttg ggaggccgag gccggcagct cacttgaggt caggagttca agaccagcct  25740
ggccaacatg gtgaaatccc gtctctacta aaaatacaaa aattagctgg gcgtggtggc  25800
gggcacctgt aatgcaagct acttgggagc ctgaggcagg agaatcactt aaacccagga  25860
ggcagaagtt gcagtgagcc aagatcgcac caccgcactc caacctgggc aacagagcaa  25920
gactccattt caaaaaaaaa ataaaaggct gaaacaccca tacgtggtac tacttggatg  25980
actcctgaaa acgttacagt aaccaaggaa gtcagccacg aagacgcatt gtaagattcc  26040
cttcatgcaa aatgcccaga acaggcagaa ccacagaggc agaaagtcga ctggtgttca  26100
ccaggggatc cggggagagg gaacgggaag tcaccgtgta atgggtatgg gttttatttt  26160
ggggtgatgg aaatctctta taacttgata gaagagaggg ttgtaaacac tgtgaatgta  26220
ccaaatgcct gccttctata ctttaatatt ttatattata taagtttcac ctcaatttaa  26280
aaaaaaaaca actcgacacc tttcacctag gaaagatctg gctttagctt gcatttcctg  26340
taactcctgc ctaaagcctt ccagaagctt ccgctgcctt gtggatcaca accagactcc  26400
acaccatgat ctggcctcta agggcctctc gcaggacacc ccgagggtga aggagcaccc  26460
gtgggcccac ctctgcatag ctgcaaagct tctttccctg tcctcccctc tacatgggaa  26520
gctctgcccg caggggcggg gccttatctg ccattctatc gcactcaacc ctagcacttc  26580
```

-continued

```
actcggtagc agacaccaaa gcaaaacagc aacagcatta taccgggcca ggtgcacgtt  26640
aactcactga attcatggta ggaaggattc tattcccatt ttacaggtga gaaaactgag  26700
gcacacaaag gtagcatcag cttcctaagc ctcccagcac aggaagcggc caggctggaa  26760
tcagaccctg ggcgcagggg ctctgtccac agtgctaact aactactcct gcccccgagg  26820
gctgcagcgg tgagtgagtg agtttgtcag tggactggat gtccaaggtc atacaggaaa  26880
aatccagact attgtaataa cagcctctag accggctggg gccagaaaga tcgaggacgc  26940
tgacacacaa ctgcgctcac tgcagctctg ccagggatgg ggctaaaggt ctcacacagg  27000
gcagttaggg ctccccatag cctgggagag gaacggggtg agataacaga aactaggtat  27060
ggtgcccgaa gtcaaacagc cactgagcat gtaaacccag gtgggtctga ccccaaaccc  27120
ctccaccccc atcagccctg caacccgtcg ctgcaaggga gaaagcaact cagaggcctc  27180
acctgcctac atcccccacc cgtgtgtgtg agttctacta aatgcctgag cagtgacaca  27240
gcacggctga aattaaacgg gttccaaaaa cgacaggaag cacgaagtga atctccccag  27300
gaaagtgctg aacaaatgct ggatcgggtt caccggcgaa tttcttggaa ctgaagaggg  27360
gagctaaaca cacggggccc tgctttggag gggactctct cagggtgctc cacacagcac  27420
ttggttaacc ccactcagcc cttctgggct ctcccagagg gcccggcctt ggccttgggc  27480
atctacagga ggaacctcca gggggagagg gggtgcctgg acaggccggc cctggaacaa  27540
gcacttgggc cccgaggaga gaggactagg gcttgggagc tggggaagtt ctcagcactg  27600
ggaccactag aacaaagcca tttccgtgcg ttcacagctt ccaattgcaa caggaagcaa  27660
tcaggaaaaa taattagcgg cccacttact ggcttcgctg aggtccgagg catgtatttc  27720
acacagtaaa accagggata taacatcaaa accgttctgc agaaagattc ctccctttcc  27780
ttccatttta ggcctggatc accacattca ctggggctcc caggccttgc tgcctaatgt  27840
taaaataatc aactctattt ttgcctcaca cacaactgaa ctctacagct ataattcttt  27900
ctcctcaggg gctcgaacca catggacgac aggcatttga ctccagcaac atcaccccaa  27960
aacgtgcaca aaacccaaaa ctgcaatgag gtgaaaggca acgcggtcgg cctagaaacc  28020
ccccctttaa aacaaacagt ttccccaaaa ccccttttgc ctccttgacc caggcatttc  28080
cggaaaaagg agcggcgctg gcctgtactc cccagatact gtcgctgttt tgtcttcacc  28140
ttgttttgct agctccagac aaggccccac aatgtaaaca cgctcctgaa agaggcagat  28200
ttggggtgaa actgtccata gaatctctag gcttgggtca gaggcaggag gacgtgaaac  28260
aaactccaag ctcctcctgt tccccgctgt cccccacacc tccaagcaga ggctgcagcc  28320
tgggggatct gactacaggg ccaccccgct gcaccattca cactggaaat attcagggag  28380
acagctgttt gccttaagga ggcccagaca aaggggcccg aggtcctccc cgctaaactg  28440
ccacaaacag aacaggagcc gcggcgtgca caggcacttg cggccgtgcc acttggccag  28500
ccatactcca gaaaaacaaa acacgcacat ccgaagagaa tgatttaggt agcaagaggc  28560
ttgcttgaaa aaccacatgg caatctccaa attaaaagaa catgtgtagc gtttcacgac  28620
tgcttaagtt tcctgagtcc tcctgacctc aactccaccc cctgggaaac accaaaagtt  28680
ggatgagaaa gttcccccgc cctacctctc cccacgggag tgtacaactg aggcacaagc  28740
ctgcctcccc cactgccccg cgatctggga ccacgtctcc tccgcgtagc cgacccgggg  28800
atggacacta tctggggacc cggcggccac acggggcatt cgggtcgccc gggcacctgg  28860
caggtgtcag tccgcttgga aacccacagc cacgcggctc acaggagcag cgccaccggc  28920
taggccgccc cgcgcccggg ctcagaactt tctcgctgcc acttcagccc gtcctcggag  28980
```

-continued

```
cacgcggggc ggccgcgcgg ccgctggaaa caggcttgcg aaccggctcc ccgggccagg  29040

cccgcctccg cgccccaagt ccccgctcgg tgcccggccc gggccacacg ggcccagcgc  29100

gggctcggct cggctcccgg cttcccgcgg gctcgggcag gtgaggaccc gcccgcgccg  29160

cacctggcgg agcgggcgcc ctcctcgcca gcccgggacg cagcgtcccc ggggagggcc  29220

cgggtgggga gacaaagggc ccgcgcgtgg cggggacgcc ggggacggca gggggatccc  29280

gggcgcgcgc cccaactcgc tcccaactcg ccaagtcgct tccgagacgg cggcggcgcc  29340

cgcgcacttg gccgcggggc cgcccgggcc attgtccgag caacccgcgg cccgtcttac  29400

acgccgggcg cgggaaggta tcgaatcagg                                  29430
```

```
<210> SEQ ID NO 8
<211> LENGTH: 33769
<212> TYPE: DNA
<213> ORGANISM: Homo sapiens
<220> FEATURE:
<221> NAME/KEY: unsure
<222> LOCATION: (33739),(33749),(33758)
<223> OTHER INFORMATION: Identity of nucleotide sequences at the above
      locations are unknown.

<400> SEQUENCE: 8
```

```
cttcccctta cactggtcct tcgacccgcc tcggatgaaa actgaatggg tttagcctta     60

gaggctctcg gtctctaagg gaggtgggtc aggatgccgg ggacagggtc ctcttcctgg    120

ggcaacgtgg gggaacgagc cacctacccc tccactgaat tgccctgggg tgtgggtacc    180

gacggctcat tcggtgtcca gggtctgaga tgtgttgaca ggaagaatga aaggggatgg    240

gagggatggg gcgaaagaag ccacctgcag ccccaggaac tatctggcca gcacaccgtc    300

acccagcggc ctgagccacc cctgccagag ccaggaggag accctgccaa tgggtcacca    360

gtgtgcagga actcagaagg tcatcacagt taataccctc catgccccaa tgtgggaaaa    420

caggtttttt cacaacaaac aagataattt ttgttatttt ggcaaaagga ggcagggcag    480

ccccggacac ctccatccca cctcatcacc cagccgcagg gccccggcca tccctgcaga    540

cagagtggat gtcacaacct ccctgcaccg aaccaagtgc agctcccagg ccacaggcca    600

cccaggaaag gtccagtggc ccccggaggc tcccaccgca ggcctcccac cacagccggc    660

accaacccag gatagctgtg ttctcctggc ttcttttcac acgggtagca gaaagctgag    720

atccggggaa agctgagatc cagggaaagc tgagaatcgg cctctgctgc ccggacgccc    780

acccccagct ctgctcccag ctccagggcc tccttctcag gtgcccttac aggaggcaga    840

gggcttgagc cacctcctgg gcctggggca cgcaggatga acggggtcac ggtgcaggcc    900

actgtccact gcgcagatcc caaggccata aacagcctgg ccacagtggc ttcccagctg    960

gcaggcggcc agattatttt tgttgtttag caattgatta agtttctccg ctgcccccag   1020

gggtaagtgg tggggcaaat gccgcaaccg cagcatttga cccgggatcc tgtgccaagt   1080

gaccataggg tcacaaagca caagggaagt ggctgggccc gatgctggct ctgctggaac   1140

ctgaggccgg ccactgtcac ctgcacggtg cctgggacct tccagcaagc acagagaagc   1200

tatggccctc caggagcagc tggcaggcac cttggcctgc agtcaggggc tctgtctgct   1260

cagctctaaa acaggaaagt cgctgctctg cctggggtca gggcagccag agagtgacca   1320

agtcagtgcc ggcctcagga agggacctgc aggcgggtcc cttcctctcc catccctcgg   1380

tgccagccag cccctcctgt ggccccccac tgcctgcctc tgcccccatg ccccaccaca   1440

acctcaggcc catggctgca tggccactcc ccaggcaggc agtggggatg ggatttcacc   1500
```

-continued

```
atgttggcca ggctggtctc gaactcctga cctcaggtga ggagttccta aagtgctggg   1560
attacaggcg tgagccaccg cgccagccct ccctgtggta ctaaacactc acaccccctt   1620
gctggggacc ctggtgaggg aacacagcct cacaagtgaa gtgtggtttt gttgagcaaa   1680
tgacgcctgg gcagccctct catctttgcc taaaactgaa gaatttaggg gcgtggatgt   1740
ataaaacagt tggtgactta aatgaaaaag aaggccacac tccccccttt aggcaggcgg   1800
cctaattctt taaaagccag cacagggtgc ctttctgaac ccaggcacac agtaggtgtt   1860
caatggacag cagcggttac ttgtactgct catgacaccc tgtctgtggc ctctgcagct   1920
ggctccagcc tgacgcatgg ctgcgcccct ccgcaaggcc accccggtat acatggaaac   1980
tctgtggaga aggccttggg ggccggccag gacgccaggc ccagatccca tctgcgccct   2040
tcctccatag acctcagcga gctctcggca ccatgtgcct caggcccatt taagaagtag   2100
ggccggccag gcatggtggc tcatgcctgt aatcccagca ctttgggagg cccaaggtgg   2160
gtggatcacg agatggtcag gagatcgaga ccatcctggc taacacggtg aaaccccatc   2220
tctactaaaa atacaaaaaa taagccgagt gtggtggcgg gtgcctatag tccaagctac   2280
tcgggaggct gaggcaggat aatcgcttga gctcagcagg cagaggttgc agttagcgga   2340
gatcgcgcca ttgcactcca gcctaggtga cagagagaga ctctgtctca attaaaaaaa   2400
aaaaaaataa aaaaaagaag cagggccagc cacggacgac ccctcacaca gctcccagga   2460
cgcgtgcctg ggtatagggc tcaggaccat gaccgctgca gtggccccca agaaacgtta   2520
cttttgtcac ccaccccgcc tcagtggcag tagccaaaat aacggattag aatggaacca   2580
tgtgacaatg ccactgcccc aactgacaga agatggctat cagcagttca cgcggcccca   2640
cctatcacaa gtgcagggca ctctacaact tatgcatcct tccccagaca ccgtcctttc   2700
gaccctccca ggtcagcaag gcacacaggg cctacatttc acagccacac agcagagggc   2760
tgaggctgga actcggatgc tctgatttcc gttcaatcac atccccagag gtggcacaga   2820
gacggggggc ttctcttgac aaagtcaaga aagtcactgc cagctccact gaagaccaaa   2880
gaacctcagc tctcaaaccc tcttgaaggt gttaccgaac tctcccagcc tgtttcctgg   2940
gtcccgatgt tggtcccgtg ggacacagga agaggaagaa gctccctaga gcagagcctg   3000
gtgcacctgc cacactctca gagggctgcg cacgggcgga ggagccgtgt gcaggagtgg   3060
ggtctggatg gaggggcgct gtggccgggg gcagggggca ggggaagggt gctccaggtg   3120
gtgggcacag cacgagcagg ggcagggagg tccacactca gatgtgcaca gggagaaaca   3180
aatcgtgcat ttccattgga ataggcggta aaaggtagaa aaacagagtg ggggccagga   3240
agggagtcgg agccttctag tgtctctctg caggtgagcg gcagcccgag gtgtcagctc   3300
agcagacttg ggtccagggg gccgtgtctt ctatcactga ccccagggca cacggaactg   3360
gggagggaga gcagaggcac agggcacggt cagtgaaacg aaacaaggag tcatcaccaa   3420
atgcggaaag ggcaaggagt gcccgcagcc gcacaagggt tctgtctggg caacgtgggc   3480
gtcccaccag gccccgcacc ctgcaagcgc aaagctcgcc actgaagata aagggaagct   3540
gttggagctg cggagctggt ctggggtccg catggagctg ggcttatgct gcagtcacaa   3600
gggggacatg gaagaggctg caggggacaa aaccagtgac cacagtctaa ctctgagcct   3660
gtggaaaggc gcccacagca ttcacccatc ccagagatgc cattcccccct gtgccccgc   3720
tccacggtga cagcgttctc caggaatatg atgcgcccct ctcctcttgc atcagccctg   3780
acagtgagta ttcaggccaa aaagcagaag agcacagctg cgtggttcca tttccatgta   3840
```

-continued

```
gttctggaac aggcaacgct aatccaaggt gatagaagtc aggagagtgg tggagggggc   3900
gggggttgag gatggcaaag gggcaccggg aactttccca gtggtagaaa tgttctctgt   3960
ctggaccgtg tggtagttat gcagacatat gcagctgtca aagttaatcc aaatgtacac   4020
gttaaaatgt gtgcgtttta ttgcctgcaa gttatacctc aattaaaaaa ataaagttag   4080
cactcaggct tcttccacaa cttcctgaac cgtgtgagct gattttcttg ctattaaaaa   4140
ttcacggtcc atggctgaga acagcagctg ccttctgttt gcaaagtcaa cgccaatcac   4200
tgcccggccg cggcagactc ggccccacag gacctccttt ctttttttccc tttgacctac   4260
ttccctgata agtgacaaga cagccagact ctgggaacaa acgcccgtta ttcggccccg   4320
agctgagcgg gccctgcttc ctgagctaat ccgcccggac agacggaggg acgtgagggg   4380
ctttgccgtc ggctccagct gtcagtctgc ccgtcagact cgacagtggc cccctctgtt   4440
cctcccgctg cccccactcc atccccgact tctttttgtt tcctgtccct gacagacgaa   4500
catctgttaa aactctgtct gggtgagctg tggccagcgg cccacaaatc cccaagccgc   4560
accccagcct catctgggcg ctgccgggag cactgcctgg ccaccctctg gacatagctc   4620
tgagagccac cggccagggc acgtgtggcc cgagtggcat ggtgcacgcc gctaagccca   4680
ctgcccaaag gcccccaagc aggagggatg tgcaggagac aaaagtcaaa agaacagggg   4740
cacgttccac agaggatggg gctggagggg tggcagtgag gaacagcagc ttccgaggat   4800
ggcggtggca actcccaaat aaggcctcac tcctgctgtt tttagctcat tccacataat   4860
tggaaaaaca tggcagaaac cgaagccagc tgctgccttg gtcctggggc tgtgtggagg   4920
gggtggggag gccggaggcc caggctctgc actcgactgc tggggatgag agtgactctg   4980
agctgcagag agcagcatcg cagccgccat ggtcccattg agccccggcc acgctgggcg   5040
gcagaggctc gtgggatata cctgccctgt ctcatggggg tcacttcagg aggggcgggg   5100
gagccaggac acagcccagg gctagcggtc accctgcagc tcaggggcca cgtaaatagt   5160
gccaccttga aggcacacag cagtgcgggg cccccccgc caccaacgca tccctacctc   5220
taggaggccg cctgtgtgcc cctgggaacg ctgctccctg tcccttgggg tcctggtgtg   5280
accaccctct cagccccttc cttggggaag gcacctgact ccctacaccc agctggcttt   5340
catttgctca aaatcaggaa aaagcagaat tcaagacatc acagaaatgt cttcgcctgt   5400
aactccatga aagataaacg gtcagacacc caggagggag tcccagggac ccttgagtct   5460
cacctgaggc tctggcttca aacctcgaga tgtttccagc catgctagcg ccgcccccca   5520
caacctgccc cacacagtcc tcccttggga actcacagat ttggccccca cctgccccgt   5580
ttcttctggt ggagtgggtg cgttgggttg gggtggggct ggggactctg gatgtgtctt   5640
aagagtctga gtgattctga cacagccagg ccctgccccc ctcctgacct tcgccccaca   5700
ggaaagggag ccacacgcct gaagcgccca gcacaccccc ctccgtcctc cccaggtcac   5760
ccgctggccg tgtgagccgt gctcccccact gcccccttcac ccaccccagc tcctcctggc   5820
agcacccagc cttggaagct acttctgatt acaaccgccg aaggaagact cgctccctcg   5880
gcactgaccc agacagcctg caccatcacg ctgctcagca caacccacac agccttcctc   5940
caaaccccat ggagcgggga gtataatcac cccctttcta ccaacggaca aactgaagca   6000
cagagaggtt aagtcacttt cctaagctcc caacacgatg acaaaaaata gaaggtcagc   6060
ccgcaagtgg aactaggtgc tccaagtccc cggtctgcct gacactgcac ctcctcgccg   6120
ccacggtccc gggtccgcct gacactgcac ctcctcgccg ccacggtccc gggtccgcct   6180
gacactgcac ctcctcgccg ccacggtccc gggtccgcct gacactgcac ctcctcgccg   6240
```

-continued

```
ccacggtccc gggtccgcct gacactgcac ctcctcgccg ccacggtccc gggtccgcct   6300
gacactgcac ctcctcgccg ccacggtccc gggtccgcct gacactgcac ctcctcgccg   6360
ccacggtccc gggtctgcct gacactgcac ctcctcaaca ccaccacggt cccgggtctg   6420
cctgacactg cacctcctca ccaccaccac agtcccgggt ctgcctgaca ctgcatttcc   6480
tcatcaccac agtcccgggt ctgcctgaca ctgcatttcc tcatcaccac ggtcccgggt   6540
ctgcctgaca ctgcacctcc tcaccgccac ggtcccgggt ctgcctgaca ctgcactttc   6600
tcaacaccac tccttggccg gctcccaact acaaaccaag ccatgtcttc catcctgaat   6660
cctcttggcc taaacatcac tcacaatgcc tccctcggga acaggcacaa gtcccaccag   6720
cacagcctcc ttcgttacct gcgtttccgc tagcccaggg ccagctccag agccctcacc   6780
acagagcctc tatccttcac ccccggacac tggacctcac caacccatag cctggaggag   6840
atccctgtgt gaccccaggg cctcctctgc ccgactctga atttcactgc ccaacgtgac   6900
acctcggaag gctctctggg cactggcagc cctccatggg caccgctcct tctggccagc   6960
tctgacatcc cggctggtga ggtgccctgc acgaggcctc tgcccactgg gacctcacag   7020
ccgtgctgtc agctgcaaca agcgacagaa tttcacgttt tcttcacgtt gcccctgggt   7080
gagcagctcc aggtagtttt cagtcgaggc gaggcgtccc gtcagcagcc aggcggcaca   7140
gctaattcat gcccgccggg cgcacggccg caataccaat gggcacctgc agcctggaaa   7200
gccacagagg aaccgagaac agcgactgtg ctcaggtgac aggactgtgg tcttttaaca   7260
aaacattttc ctttaacgtg atattttacg gcaaggaatg aaacctggag ggcaggacat   7320
ttggatacta aagccccagg ctgccgcgtg gtctgctttg tgaagtctga agcccgcgcc   7380
ccattctggc cccgctcaca ggtccggctc tgactcacca gcttcaatgc taggccgtgc   7440
ctgtcctcca accagaacat gacttcctta aggacaaagc cgtttctcgc ccatccccat   7500
ctccctctgg attaagaaat atgggaagat cttctagaac cacctcaaat ttgcagagag   7560
ccatcctggt gacaaaccct tgaaatgctt ctaagaagag tttaggtttc ttctcaactc   7620
taaaacctct agaaaactct atttccacac cagctgcccc tggaacactt cagcttcaaa   7680
agggcccagg gcagggagac ggaggagcca gcatccacac cgagcaccag cctgttaatt   7740
aacgggaagc gggtggggcc catctccagg cagctctgag gtcagactgg ggaaccatgc   7800
ttacaaaaaa aagtgaactg aaacgctcac gtcctcatgc aaaaccagac tcccagttgc   7860
atctttctgt ctcattgagg agctttttcc tccctttgac agaacaccct acacacggca   7920
tctggaacca aagcagaaag attcaggctc agagtaaaac agtccccaca ctggctgcat   7980
gtggacgttc ccggcccaga gtctcgccca agcagggcct ataaatgaca caaaatgttt   8040
ttctcctgcg tgccagtcat gctccaactg agttatgtgt aaaagtgcct ctcacggctg   8100
agggcaaaaa cagttcccac aagactagag aaaggtgacc cctgacggct gagtctctag   8160
ggagcgtgga gctgcgtgct cagccctgcg gccctgacgg ctctggaatg gaaaagctat   8220
ccaactggaa gggcagggct cgctgctagt ccagcggtcc aaccccacag gtgtctgtgg   8280
tgtcagctcc atgccacaga gcccagggct ggggccagag ccaccaggcc ccctgccagc   8340
ctgcaggggc ctcctcctct gggtagccta accaccccct gtgagcgcag gcagcctcct   8400
ctaatcacca cagggcctgt cccccccctct cccccgcttg caggaaaatg agccctgagg   8460
actccccagg gctgctctgg gcctggacat ggagactggg aattacattt gcagaaggag   8520
cgcaatgccc ttgaagggct cagccacgag cagccagtcc ccagggctca gaaggcccag   8580
```

-continued

```
ctgttagaac cctgggagcc agcaaagagc caggggctcc acctaagtct atagcccctg   8640
cctcttctgg ttgggaaaga aatcaacgcc cctttactgg ctcccactga cagcccactc   8700
ccccaggtat gggaggattc tgggacgatg caggcaaacc tggaccctga gtgaacctgc   8760
cccagctctc acgggcctgg caccagccac agcacctaag gcgccggtca tggtgacaac   8820
atgaaggtga taagggcatg gacagtggac atggcagctg gacactgggc acccactgga   8880
tgccaggcac ccagcacggc tccgtcaccc ctggatgagc agtggccctt tgcaagccag   8940
ggtagcctgg gcaagttatt tgggggtctc caagcttgtc cagctgtgcg acttcactga   9000
gccatgagtc tgggatttta tcagggccca cacccgttcc tggaactctg atacgtgagg   9060
gagccacaca gggaccctta acaaaagctc ccagggcaac atgttctctt gcctcagtct   9120
cccaaatagc tgggattaca ggcgcacgac taccgcccgg ctaatttttg tatttttagt   9180
agagacaggg tttcaccatg ttggccaggc tggtcttgaa cccctgacct caaatgatcc   9240
ttccactgtt agggcaaggc acctgacagg cacgactgca cgatctgctt gttgggggct   9300
gtgtccattc cccactcctt cgacaaatgt ccacacccag ccttgctttg acaccccaag   9360
aacagagatg gtgacacctg cttcctacat gcccattgct ctcccaaggc agacatcccc   9420
agcagatgca acacagtgtt taggcagaca tcaccaatcg atggtggcaa cagacaccag   9480
gccctgctcc ctctaactcc agtggccagg ccccaagcca gctctcacct gcccactccc   9540
aacccacagc agcaagactc agaaatggca aaaacacaaa gagaacagaa acgccccata   9600
gcgggaggat gactaaaaga catgtcttga taagatattg ttcaggcata ggccaggcac   9660
agtggctcat gcctgtgatc ctagaacttt aggaggctga ggtaggtgga tcacctgagg   9720
ttaggagttc aagaccagcc tagccaacat ggtgaaaccc catctctact aaacatacaa   9780
aaattagcca gacatagtag cgggcgcctg taatcccagc tgcttgggag gctgaggcag   9840
gagaattgct tgaacctggg aggtggaagc tgctgtgagc cactgtactc caacctggac   9900
aacagagcaa gactctgtct caaaaaaaaa aaaaaaaaaa gatatccttc actaaaactc   9960
atgtctttga tacatattta cctcctgcaa tcgcaaatgc ttctgcagtg cataaagtga  10020
aataaatagc aggaagcctt acggttcgat cacccacaca gacacacagt cacatacagg  10080
aaaaacgcag ggagggctgg ggaacaaaaa aacagaagat aaaatgtgga gacagacaca  10140
ccaagagagt aagagaccac ctccagacct ccccttcagct tctcaaacac acgagccggg  10200
cccgttacag aatttgcggg gaccgctgca aaatggaagt gcagacagcc ccttactcaa  10260
aaggtaggaa tttcaggtca acaacagagc tcacctcata tgactacaca ggtcacacag  10320
cccgtgaagt cggtcccaac accagcatgc tcctgcctca aagccgctgc acgtgctgtt  10380
ccttctcgcc tttccctctt ttagtccttc agatctcagg cctcctgaga gagacctctg  10440
acctgccggc tcaggcggcc acacccccag tacaggagtc tccggctcag cccctgctgt  10500
gttccgtacc cgatccaggt ctgtcctatg tccatctgtg tgccggcttg cttcctgaca  10560
tggcccccac cacacgtgtg cctcggggca ggggaacagg cccgtctcat taactgcttt  10620
cttctcagat attttctgga atatttgtgg atattgggca acatatatgc tccacctttt  10680
tcagactagc caggacgagc tgcatttttt tttttttttt tttgagacag ggtctcactc  10740
tgttgcccag gctggagtat agcggcatga tcttggctca gtgcaacctc cgcctcctag  10800
gctcaagcaa ttctcctgcc tcagtctccc aagtagctgg gattacaggc ccgtgccact  10860
actgcccagc taatttttat atttttagta gagatggagt ttcaccatgt tggccaggct  10920
ggtcttgaac tcctgacctc aaatgatcca cctgccttgg actcccaaat tgttgggatt  10980
```

-continued acaggcgtga gccactgcgc ccggcccgag ctgcctgttt tacacctttg ccatattccg 11040
gtgattctct ctcccctccg tcccccggcc ctgactgtgg tggccactcc ctgccgtcat 11100
gagcccgtat gtcctcactc tttccctttc cgccaggact tcaaccaaca ctgcagagcg 11160
cagggtccag ctccagcact gagttcagcc tcttctcacc aacagacagg caggaaagaa 11220
aacaaactct gagaaggcca aggttcccgg gcagccagca agccaagcat ccttctccgc 11280
tgaggcttgt gcagccgagg cacccccctcc tccagggagc aggcagcgtc ctggggcagt 11340
ctgcgaggga gaccagggcc cttgctccac cagggcccca ggtatggggg cagcagcaaa 11400
ctcatggctc tgggagccag accccacctg ctagaaccta ctatgccacc tgctgtgggc 11460
aaccccaggc tggtgacttg ccctggcctc ctctgtaaac aaagggctca tccaacctgg 11520
tcaaaccact cctccccttc aagggtctat aatcctccct taacctgctt ggtccaaacc 11580
cctggtgtcg ccaggtcact caggaggcag ctcatctgga ctccttccct gggtccagtt 11640
tctctctcaa cattgccttt gaggccgagg tgaacggtca acagcgaagg gccccagagg 11700
tgatggagga gcgggtgtcc aagacactca ccctttctaa tgcactgact ccctcgtgga 11760
ctcacttgtg ccgtctcccc cacccaccca gccccagagc ccagagtgcg agcgccagag 11820
gcccgggatt ctgtctgcac cgcggggtcc ccagtgcctc ggagcaatgc cagcacccgg 11880
caagtgttcg acaaatgcct gctgaatgag caaatggatg gatgaacgaa tgaatgagca 11940
agcagatgaa tgaatggggt gctgtccaga gccgtgagga ctaggccgcc caagtcccca 12000
tttctcaaat tctccttctc ccgacttggg aaacaagatg cttggtcggg gaggctctcc 12060
aaccatcccc tgcagcagcc ggcacagcgg acagaccctt tgatgtaaca gccatgtctt 12120
cattaaagat gccctgctct cagaaagaga aagacaaata caaacctgga aaatcctcac 12180
caaacgcagg accccctgcca gggagcagag aaaagaccca cacgccacgg gcgccacgac 12240
cacacacaca ccccagccgc tgcacacaaa cacagaccct agccagcaag aacaggggga 12300
ccaggaaact gttcctaaag tcaggacccc catgtgctca gacagcagtg agagcaagga 12360
cacttctcca tccaccggat gccaggagag tccttttagg gggccccaca ccgagactct 12420
gcccttagga ctgttcctga gtgtggaagc cagcccactt ggaagccccc tgccctcccg 12480
agtgggacac cggcacagga agcaggccct gtccccccacc actttctgca agctgggccc 12540
catcacgcta cagaaacggg gaggactggt cccagggatg gcgctttcct gacacctctc 12600
gttacccccct cgcttgccag gccccagggt cagccccaga ggccagactg gctatcccag 12660
gcccgggagc atccccgaag gcgagctgca tcctgaacgt gtgtgatttc ccgaagggcc 12720
cgccccgaac cgacacctgg aaagaaagat cctcagccgg tgccccagag gagaagagcc 12780
atgcctcact gcaacacagt cccaggaagc accaagtgcc tgaggaccaa ggcggagagt 12840
aaaaaagtgg aaaatatctg gggcaaaaat aaaacaaaac aaaacaggat tgacctcctg 12900
ggctcaagca atcctcccaa ctcagcttcc cgagtagctg ggaccacaga cttgaatcac 12960
cacacccgcc aagtggatca tttcgaacgg gtttgccgag gttccttctg gggcaccccc 13020
ggcggccgca acccattccc gccaggcccc gccccgcccg cccgccccgt cccgtcccac 13080
cgcctcacct gccttacacg tcctgccgtt gtcctgcagc tgcacacccg tggggcaggc 13140
gcatgtgtag aaaggctcgc ttggggacag caggcacagg tgggagcagc cgccattgtc 13200
ctcctcacag cgagtgtgga ctgagaaaac caggacagac tgagagaagg ttccagaaga 13260
ggaccgtcac ttgtttctga atgagtcaca tcctgcctcg tcccccgtga cagcctccag 13320

-continued

```
tgtgtccctc tgcccaaaca tcggcctcaa gtggcatcag ggacctcccc gcgggcacca  13380
ttccacctgc ctcatcgctg gccccgtcca catggggccc tcagcctggc cagacggcct  13440
gcaatttccc caaaaccagc cgtgaccttc ctggccaccc tcacacccag atgtgacctg  13500
cccatggagt gacatcctcc ccatctgctt cctcccacca agctcctatg actagaacac  13560
cctccccagc tcctcggagc ccccaaagga cacccctctg caaaggctgc cccccacgct  13620
ccaatggccg gggtcaggac ctgcctgtgt ggtagtgacg ggaaccccag agacaatggg  13680
ctcctgggca aaaggcttgt cttgtctttg tgctatgtgt ggacccagca gcttccatag  13740
gaacactgtc cttcttgctg ggatggccaa gcttgtcact ctcccaagcc ctcctatgac  13800
caacagcaat tgaacggaac tcgataaatg cttccagcac ctcattcaaa ccaggggaaa  13860
gctgggtgta gcagccccaa aatacggata taactggaac aacaaactca tcaaaatgaa  13920
cctctccctc cctcatgctg ccccaagtgt agatgggttt tgtgaccacg actttctcac  13980
caggaaacag ctccagagag ccccaccctc ctgtgtcctg ctctgggaac agctggcacc  14040
cctaggcccc acatttcaat tcaaagtcca aaccttccat aatggcctgg ccagaaatct  14100
ccatccctgg tccctgtggg agtgggccac tgtccccaga gccgcagccc cactgtcaca  14160
gaagctggtg catttcccca tcagggacct ctgtcacaac ccagcgtggc ccccaggctg  14220
agaactgctg attctgggca gattattcat tgataaatac gcgacttgca gggccaagca  14280
tggtggctca tacctgtgac cccagcactt tgggaagtca aggtgtgagg atcactggag  14340
cccacgagtt tgagacaagc ctgggcaacg tggcaaaatc tctcatctct attaaaaata  14400
catacacaca cacacacaca cacacacaca cacatatata tgtatatata aataaccata  14460
tatatatata cacacatacg tgtatgtgta tataaataca tatacacaca cacacagaca  14520
acttcttctg ggccttgaaa acgaggcaac cttccttgga aatccccttg ccactgctga  14580
gcctgaaata gcccccatga gctctgcaga ggggtcctct gcaggcccgt gtcccccagc  14640
cagccacaca cctccctcca ttgcagcagg taccccttta gagaggggc cccccagagc  14700
atgggcttct gcagggaggg gtcacctgcc cccccaccc acccacgccc gcgcaccccc  14760
acgcccccgc atcctcccac tcccctgccc cgcgccccg ctccccccag cccccctcacc  14820
ctctccccg tgccccaacc ggcactcaca aaaaggctgc cgctcctggc tcagcacctg  14880
gatgtccatg ggtgagtata gggcactcag gatctccttc ctcttccccc cagtgcgctt  14940
gttgcaggca tggatggagc gggtctgcca gtctgtccag tacagagtgt ccccggagag  15000
cgtcagggcg aaggggtgcg tcaggctgcc ctccaccacc ttctgcctgc agtcagggaa  15060
gcggggtgga ggagccatca ggagggtccc ccgacagtca ttgctgctga cccaattaat  15120
ttcttttttt ttttttgaga tggagtctcg gtctgtcgcc caggctggag tgcagtgatg  15180
taatctcagc tcactgcaac ctccgcctcc cgggttcaag caattatcct gcctcagcct  15240
cccgagtagc tgggatcact gatgcccacc actacgccca gatgattttt gtatttttag  15300
tagagacagg gtttcatcat gttggcaagg ctggtctcga actcctgacc tcaggtgatc  15360
cacccacctc agcctctcaa agcgctggga ttacaggcgt gcgccaccat gccaggcttc  15420
ccatttgctt tcaaccagac aagtgaggcc aggtcaagag ccccaggagc tggcgccctc  15480
gtacatttct cccggcgtgc acagggcacc tcccaaacac agcctgtgat ggtgacacac  15540
gggctccccc aggtcaagtg gcaaagtctc ccccagggaa gaaaggagga agccatgcct  15600
ggcaaaaagc acacctctcc tgcccaacgc tttaacctct gtatacaaat caggccatgt  15660
gcactcgctc cttcttacaa tgctcataat ttatactttc agagtaaatg aaacttggca  15720
```

-continued

```
tcaacccgag aaacagctat tcttttctag atgcttacag tgcccagcaa atgaggactc  15780
gggtgtaatg agattatgga cactggaaac aggatcataa tgtgacgtgg tcggtaatgt  15840
gcagttttat ttgcttaatg accctcgccc cgtgacaggc tccctgaggg tgggcctggg  15900
ggcagaggtc cccgccacgt ccccagccct cagcacagtt gccaggagag ggtgacactc  15960
atgaagtggc acagggaaga tgggagctgt gggctctgca gatccaccac ctcttctgtt  16020
catttttgtt gatgctgttt tttaagaaaa ttattgaagt aaaattcaca ggacatacgt  16080
ttactttttt tttttttttt ggagatgggg tctcactctg tcacccaggt tggagtgcag  16140
tggtgtgatc tcagctcact gcaacctctg cctcccaggt tcaagcgatt ctcccacctc  16200
cgcctccaga gtagctggga ccacaggcgt gcaccaccac acccagctaa tttttggggg  16260
gtatcttttt ggtagagaca gggtttcgcc atgttgccca aggctggtct tgaagccctg  16320
agctcaggcg atccacccgc cttggcctct caaagtgctg ggattacagg cataagccac  16380
tgcacccagc ctaaatttac cactttaaag tgaatagtgt tacctagtgc attcgcaagg  16440
cggtgcagcc tccacttctg tctagttcca aagcacttcc attgccccac aggcaaaccc  16500
cacacccggc agcagtcatg ccccagtccc cgcccccagc cccggcaaac acttttgatg  16560
gacttaacta cacacattct caacatctca tataaacgga atcacaatat acagcctctg  16620
atgtctgtct tctttgactt ggcaccatgt tttcgaggtt catccaggct gtagcatgtc  16680
agtgcttcat cccgttttag gggtgaacca tattccagtg tgcagacaga aaccaatctg  16740
tgcatccatt cacccactgg gggacctttg tgtcatttcc accctcggct gttgtgcaca  16800
gtgctgctac ggacattact gtccattcac attttgtgtg aagacctgtt ttcgattctt  16860
aagagtatac agctaggagc ggaattgctg ggtcatacgt aaatcaatgt ttacgtctca  16920
aggaatcaac aaactgtttt ccacaatgtt gtcttttttg tttgttttct gagacagggt  16980
cttgctctgt cacccaggct ggagtgcggt ggtgtgatca tggctcactg cagcctcaat  17040
ctcctaagct caatccatcc tcctgcctca gcctcctgag tagctgggaa cacaggtatg  17100
taccaccatg gccagctaat tttctaattt tatttttttt tgtttttgtt tttttgagac  17160
agagtctcgc tctgtcgccc aggctggagt gcagtggtgc catctcagct cactgcaagc  17220
tctgcctccc gggttcacac cattctcctg cctcagcctc ccgagtggct gggactatag  17280
tcaccggcca ccacgcctgg ctaatttttt tgtattttta gtagagatgg ggtttcaccg  17340
tgttacccag gatggtctcg atctcctaac ttcatgatcc acctgccttg gcctcccaaa  17400
gttctgggat tacaggcgtg agccaccacg cccgacctta cttttaattt tttaatttta  17460
ttattttatt ttattttttt tttttttgag acagagtctc gctctgtagc ccaggctgga  17520
gtgcagtggc gggatctcag ctcactgcaa gctccacctc ccaggttcac gccattctcc  17580
tgcctcagcc tcccgagtag ctgggactac aggtgcccac cacgatgccc ggctaatttt  17640
ttgtattttt agtagagaca gggtttcact gtgttagcca ggatgatctc aatctcctga  17700
cctcgtgatc cgcccgtctc agcctcccaa agtgctggga ttacaggcgt gagccaccgc  17760
gcccagcctt tttttttttt tttttttttt ttttgagata gagtcttgct ctgtcgccca  17820
ggctggagtg cagtggcggg atctcagctc actgcaagct ccgcctccca ggttcacgcc  17880
attctcctgc ctcagcctcc cgagtagctg ggactacagg cacccaccac cacacctggc  17940
taatgttttg tatttttagt agagacgagg tttcaccgtg ttagccagga tggtctcgat  18000
ctcctgacct cgtaatccgc ccgcctcggc ctcccaaagt gctgggatta cacgcgtaag  18060
```

-continued

```
ccatggcgcc cagcccatgt ggccattttt cagtgagaga agccagaggc ccatcactct  18120
cggttgctcc ctgggccatg ctctgcctca gccagaagca ctgagggaag gtcagcctcg  18180
gcccttgccc cagccacagt cacagataaa ggggcctgca caggtctgtg tggctccaga  18240
gctcgtcacc caacacacga cgcttccatg tgaatagccc caggtgcatc atgaagagcg  18300
atggccgctg cagaggcaga agaatcccgc ggggaagcag gtgggagaga ggctgagaac  18360
agaccagacc ctggagctac agaccctatg ttccaaccct ggctgggact agctgtgtgg  18420
ctctgggcaa attcacatgc ttctctgtgc acaggggatc aaaatagcaa acacaggcta  18480
ggcacagtgg ttcacaccta taatcccagt gctttgagag gccgaggtgg acacatggct  18540
taagctcagg agtttgagac cagcctgggc aacatggtga aacctcgtct ctacaaaaaa  18600
aataccaaat aaattagcca ggcgtggtgg tacgtgcctg tggtctcagc tacttggaag  18660
gctgaggcgg gaggaacact tgagcccaag aagtcaaggc tgtggccgcg tgtggtggct  18720
cacgcctgta atcccagcac tttgagaggc tcaggtgggt ggatcacttg tgatcaggag  18780
ttcaagacca gcctggccaa catggtgaaa ccccgtccct actaaaaaaa tacaacaatt  18840
tgccaggcgt ggtggcgggc acctgtaatc ccagctactt gggaggctga ggcaggagaa  18900
tagttagaac ttgggaggtg gaggttgtag ttagccaaga tggtgccgct gcactccagc  18960
caggggggaca gagcaagact ccatcccaaa aaaaaaaaaa acaaacaaac aaacaaaaaa  19020
agaggtcaag gctgcagtga accatgattg tgccaatgca ctccagcctg ggtgacaaag  19080
tgagaccctg cctcaaaaca ataaaaatat aaataaaaat aaaacataat agcaaacgtt  19140
tcatagaggt ggtatgagca ttaaatgaac tgataaacgt ccctggaaaa cagtaagtgc  19200
tatggaagga ttcgctgccg ccaccgccac caccattagc atgtttcaac ctccatcacc  19260
ctcactgtcc cctgtcacca tcctttgacc agggcactcc cagctgcagc ctttctatcc  19320
tcttgtccac ccttcataac tgtaagatca ctcagctccc aagaaccaca gtctacaggg  19380
taaccacatt tccaaatctc aaaccagacc cgctggtctg cacttccagg gacaacagga  19440
tattttcaaa ccagcccaaa agagatgtgt ggctcagcat aagaggaaca ggagaaactg  19500
aggcctcttg ccctgagaat gagcttggaa gtggatgtcc cggcctcact caaaccttca  19560
gatgactgag gcccagccag gagcttgagt gtaccctcag gtcataccct gagccagaag  19620
cacccagcta atccactcct catcactgac tccctcccca taaaaaacct gtttgctgtt  19680
tcaggctgtt aagttgtggg ctgttttgtt acacagcaat ggataactaa cacacgaggc  19740
ctggcaagtg tggagcaaag ctgcccaagc cctcaagtct gttcatgtgg gtgttggcct  19800
gtgtttgcag aaatccagcc actgagtcct cccatgcagt cactactgcc ctctgcacag  19860
acacctgcca catccctgcc tgggccagga gctccactag tgcaggaatg gggtctgccg  19920
tcccaggagg atccctgaca cctagcacag ggctagcagc aggcagcact tggttagtga  19980
ataaactgcc cttcacctgt acacagaagg gatgtttcta taaggggtaa ttaagtacag  20040
agctgggaag ctatgctgac cagaaggctc taaaagcaat taaccaacga ggggaaaacc  20100
cttcctactc attctcggcc cattttattg agcactgacc atgtggaagg ccccctggtg  20160
agactgggga atgcaccaat aactgagaca gcttccggct gttgccctca ggatgcctga  20220
gctgggatag ggccagggtg ggggtggtgc gtgtgacagg gttactgttc acaaccctgc  20280
cgggccataa gccctcccca acaattccaa aatccaaaac gctctgaaga tggaaagctt  20340
ttgttgctca tctggtgaca aaacctcatt tggtgcatgg gccgggtgcg gtggctcacg  20400
cctgtaatcc cagcactctg ggagccgagg ggaaggatcc cttgagctta ggagtttgag  20460
```

-continued

```
accagcctga gcaacatgtg agaccccgtc tctaccaaaa atacaaaaat tagccaggtg  20520
tggtggcgca ctcctgtagt cccagctact cgggaggctg aggcgggagg atcgcttgag  20580
cctgggaggt gggggctgca gtgagctgag attatgacat tgcactccag cctgggtgaa  20640
agagtgagac tctgtctcaa aaaaacaaag ttaaaaaaaa aaaaactgtg catgggtgtg  20700
ggctacagat agtcttttct gccctactta gaatgaacgt gccacatttg ctatagaaat  20760
attcaagggc tggtggcaaa tgccacacag accctgacgc tgttccaagt tctgagaagt  20820
cctgcattcc tcagggcccc agagtttcag agaagagtct gtaggcctga gttaagaagg  20880
aacgccttca aaagccctgg ggacaaaggg gaaaggggtg ccccaggact gcgtgggtac  20940
ctaccggaac gagccgtcca ggttggcacg gtggatgaag ctgagcttgg cgtcagccca  21000
gtagagcttc tgctcctcca ggtcgatggt cagtccattg ggccagtaaa tgtccgagtc  21060
cacaatgatc ttccgggtgc tgccatccat ccctgcccgc tcaatccggg gcgtctcacc  21120
ccagtctgtc cagtacatgt acctgtgacg ggggcagggc aagagaagca gctaacacag  21180
atctgttttt tgtttttgtc tgcatagatg cagacatgaa acaacagaca gtgaacttgc  21240
cctaaaatct cacccatcgg aaataaccaa caggtatggt ttcaggtatt cctgccttaa  21300
gctgggcaat caaaatatac tatttccaac ttgttctcag ttaacagtaa attctgggca  21360
ccttcccttc ttgtggatag aaagattcct tgttcttttg atgattgcct agtgtactct  21420
gctgtaagtt ttttaaagaa cttcaggtta tttctgattt ttttgctacc atgaaaatgc  21480
tgtaaatgaa cctctaaaag gcaattcaaa acactcagga tggaatatta tttagtggta  21540
taaagaaatg agctatcggc tgggcccagt ggctcacacc tctaatccca gcactttggg  21600
aggccaaggc gggtggatca cgaggtcggg agatcaagac catcctggct aacacagtga  21660
aaccccgtcc ctactaaaaa tacaaaacat tagccaggcg tggtagtgag cacctgtagt  21720
cccagctact taggaggctg aggcaggaga atcatttgaa cccgggaggg ggaggttgca  21780
gtgagcagaa atcgcaccat tgcactccat cctgggcgac agagcgagac tccatctcaa  21840
aaaaaaaaaa aagaaaagaa aagaaatgat ctatcaagcc atgaaaagac atggaggaaa  21900
cttaaatgca tgttagtagg tgaaagagcc aatctgtatg agtccagttc taaacactct  21960
ggaaaaagca aatacacaga gacagtaaag catcagtggt tgccaggagt tggagaggag  22020
agggatgaat gagtggagca cagaaaatca gggcagtgga actatcctgt atgacatgga  22080
atggtgggtg catgtcctta ctcatctgtc taaaccaaga atgtacaaat caagggcgaa  22140
ccctcgtgta aacgtggatt ttgggtgatg gtgcgtcagc cagctttcat cagttgtaac  22200
aaatgtacca ccctgcacag gatgctgaca gttgggaagg ctgtgtgggt gtgaggacag  22260
ggatgtatag gaactcagta cctgctgctc atcaattttg ctgtgaacct acaactgttt  22320
gaaaaaatta agtctattta aaaacaacaa aacatggcca ggcacgatgg cttgcacctg  22380
taattccagt acttcgggag gctgaggtgg gtgggtcact tgagccaccc tgggcaacat  22440
ggcaaaatcc cacctctaca aaaaataaaa attaaaaaaa agttagctgg gcatggtggc  22500
acactcttgt agtcccagct acttgggagg ctgacgtggg aggatccctt cagccctggg  22560
aggtcgaggc tgcagtgagc tgtgactgta ccactgcact ccagcctgga tgacagagtg  22620
agaccctgcc taaaaaaaaa aaaaaaaagg ctgggtgcgg tggctcatgc ctgtaattcc  22680
agcgctttgg gaggccgaga tgggcggatc acgaggtcag gagatcgaga ccatcctggc  22740
taacacggtg aaaccccgtc tctactaaaa gtacaaaaaa aaaaattagc cgggcatggt  22800
```

-continued

```
ggcggacacc tgtagtcaca gctactcggg aggctgaggc aggagaatgg cgtgaacccg  22860
ggaggcggag cttgcagtga gccaagatca caccactgca ctctcagcct gggagacagc  22920
aacactccgt ctcaaaaaaa aaagaataaa acccatggct gggatggacc ctgaacctgc  22980
agctgcagct gttcctgggt aggtctgtgg gcgacgtggc tttgcttctc catgttccca  23040
agagacaagc atcacccatc catgagaaac aagcacatcc tcagggcgcc cttacgtgat  23100
ctctggccaa tgaaccaaga caaagtgagc agacaccagg tctgggatgg caggtcccac  23160
ccccaccagt gcccagtgtg ccctgtttgg aggtgaccac agggtgtgtg cccagaggct  23220
gggcgtgact ctcagcggag accagagggg aaccacacca gcttggagga ctcagttccc  23280
atcccagcca gctgggatga gccacaggac acaagggctg gcagacctat tgtgttttgt  23340
ccacccttca cagcagagaa aggggacagt gcccagaatg tcctctgagg agcctcctcc  23400
cactcttggt ccttgtaaaa tggtgctgac tcccttgctc ccttcttcct ggggtgggcg  23460
gcaaacccca ttcccctcag ccttagcaag tgatttagaa acaggcagct cgcccaagcc  23520
aggcatgaga gtgatcccgg gacacaggga gaacaagccc cgctttgccc tctgggggtc  23580
tccattcagc agaagaggca aatgacagac acacagccgc ctcctccccc accatggtgc  23640
tctgcagcct caggagcctc aggtgcacca agggccaccc catccagggg gccatgcttc  23700
cttgagtggt atcgttcctg agcgagtacc atctccacct tccagagggg ctgtgacaag  23760
atcaacaaga atgagggcat aggagcctcg aaccaaacat gccctcttcc ctgcagaggc  23820
tgactgcgcc cagctgctat caccaagccc ctgctcctcc ggccccgtgg ggacagggta  23880
agaggggtgt cacatggaac agctctccaa acagtccctc tcaagctgct gtctcctgtg  23940
catctagtga gaacccaacc aacaaaggga aggtgggaat tgctattccc attaggcaga  24000
tgagaaaact gaggccccga aaggctggcc tgttccaggt tacaggcgct gagcggctgc  24060
tctgggaaca cacttggtgt ctgctgaggg cccgagcccg gccatcatat gactcaccct  24120
tcgccagcaa agcccgggtg tgggtgaact tttcctggca gcctgggact ccaaggtgct  24180
ggcagccagc ccagggaagg ctcccgcgtg cctgcggcag acgccttgct ttacctgcac  24240
gtccccaccc ctaggagcct ggacagagcc cagaccctcc gccacctcct gagaaggtat  24300
caggggcatc agtctggact tggggggggaa tccacacagg ccttccccaa atgctccacc  24360
gtggcccatg gaaaaggctg gaaaacgtgc aggagcagga gcctccgcat ggagcataat  24420
tcacattcct tccccgagtt tcataacaga ggcctgctgg tttccttaaa tggggaattt  24480
gcgagccagt cggtgaccag agactggttg gcgtggacgt gctcttgcag agtctcaaac  24540
gctaccacaa gcccagccaa attccacgga ggaaaatcga cttccgaaga aaagagctgc  24600
agcatggcct tcgtgcagag ccagctgcgg ttgtggttgt gtgttatttt agggaagggc  24660
cattttgcat tttaaagagg gggttgggtt tcaccctggc tttaatttga gacccggggg  24720
ccactgcagc cccttgtcag gctggtacag gccggggact cctcccatgc taagccagtg  24780
tctttctggc cccagatcct caggggccag agggtcatcc ccagagcccg ctctgccacc  24840
cacatgggta ccctgggcct gggagggatg tgccttccct caaccctgcc tggatgtccg  24900
cacggggcca cctgcattgc tgaaactgca acgaagtcga gtctcaggag gggccccccct  24960
ggctgcaggg ctcttgatcc ttttggccac gtgcacactg aggtggacgc tcggacccag  25020
agaccccctt catgatgatg gccggggcag gaaccccctc ctctgaggaa ggaccctggt  25080
gggggacagc actgcaggag ggcacaggag atgacggggg ctctagcagg gccgggagga  25140
aggccaagat gctcctcgca accgtgtgcc tgtggccagg acagaggaca aacccaccct  25200
```

-continued

```
ccactgtccc cactctcagg acagcagtcc tgccccagga ctcagcgccc acacttatgc  25260
ctgaggacca ctattcaagt cagtatttgg cgagcagggg ttgctgccgc gggcgctgtg  25320
acaggctgga atcctctccc tctccctctc cctctccgga gacatggagc ctacagggac  25380
agagtcagca cctcagggta ggaccatggc tggcgtcatc agcatcactg gatctgatga  25440
gtgggagccg gcatctcact gttttcactc tctcattcaa atgactggag caaagggaag  25500
gtgtggggag aggcccagga atcaacacta aggtcaactt tgccccccagg ggcaggggtg  25560
ggagtgaaca gccacaggtg tgatcctggg gagggcttct gggagagaat tcagaggcaa  25620
gcatgtagag gaaccatttc aaatagttaa gaaaagccag agccaaacag ggacagttgg  25680
ctcgcagaga tgatgcaggc aaagccagct cagatctgag catgggaaag actactccca  25740
accaagggcc cagcatctcc caaccaagca ccaagtacct cccaaccaaa tgccaagcac  25800
ctcccaatca aatacctccc aaccaagcac ctagcacctc tcaactggac accaactact  25860
cccaaccagg caccaagtac ctcccaacca agtgccaagc acctcccaac caagtaccaa  25920
ttacctccca accaagcgcc tagcacctcc caactgagca tcatgcacct cccaacagag  25980
catctagcac ctcccaactg atcacctccc aacctagcac cgagcacctc ccaaccaagt  26040
gcagagcacc tcccaaccaa gtgccaagca cctcccaatc aaatacctcc caaccaagca  26100
cctagcacct ctcaactgga caccaacaac tcccaaccaa gcgccaagca cctcctaaca  26160
aagtaccaat caccttccaa ccgagcacct agcacctccc aactgagcat catgcacctc  26220
ccaacaaatc acctagcacc tcccgactga tcacctccca acctagcact gagcacttcc  26280
caaccaacat agcaaaagcc ataaagaagt aaaaagacaa aaccacgtag gcatggagac  26340
tggacttctg gtggcgagga aagggcattt ttattataac gacagctaac atttgttgaa  26400
ctcacaaact gttcttggtg ttttcctcat gacatgcagc atggtcacgc ctctgtacag  26460
acaaggatac tgaggcacag agtggcaccg tgccaacctt gtctcatctt tttatcgaac  26520
ctacatgcag agtgccagca aatccagctg tcttttctct tcagaacaga tcccaaatct  26580
cgccactcct tacccccaca agtgaggtgt ccccgctgct gctttctgtc gccaggatcc  26640
cggtaataac cgtggagagg gctcctgccc ccacgccacc caccccacag ctcactctcg  26700
ctccagccac caggggatgc cttccagcac gagtcagagc tggcacctcc tctgctcgag  26760
acctcatgtg tcctctcctc acaccttggg ccctgtttcc ctacattctg ctacagcccc  26820
tcaaacaggc cccgccccaa accagcccag ggcctttgca ctggctgatc cctctgcctg  26880
gaccgcgctg cccccagaca gccacacggt tctcagcctc atctgcttcc agtctcgact  26940
caaaagtcac caagaggcct tcccagcacc tgagctccga cggaagcccc tcgccacagc  27000
acccaagcac tgctttatcc ccctacgcac acgtcccttt caaatactat tcatttacca  27060
tctcctccca ctcactgaaa gggccagaga ctgggctata cccgctgcgt ggggagcagg  27120
accaggcgca agggctcaca aatgcagtgg atgcctggtt gggaggtgag ggagctgcag  27180
cgacccacgc tgggagggaa cgcaatgaca ggaggagcgc aggtcctggc gacacgatgg  27240
ccatggcagc cgctggtgag caaccgcagg ccggccctgg gagagggctt ctagcaagct  27300
gctatcttca gcctctccga ctactgcaga tgccccctcc tagccagaga cactgctaca  27360
ccagccgacc cttccaaaaa gaaggtcagt aaccccgcga ctcctggagc cacagtgcag  27420
ggggagaggg ctgagagggc aacagttcac caagcggaac agaggctgcc ccggaggtca  27480
gctggctccc cggcagctgc aggggtggct agcccactcg gagggcagcg agggcatacg  27540
```

-continued

```
aggggctcca gggatgagtg gttgcccagc acagcacccc tgggaggccg ggggcacttc  27600
tcaggtagtg ggggcacgag gctgctctgg cctgacctca gggactcaaa atactttggc  27660
gataaattcc accgtgtccc acccctgctg gtaccccata cttacacaca gactggttca  27720
gatgcagaca ctctcgcgca catactcgct cacacgggca catacacgtg cacacacagt  27780
cacatgcgca cactcataca cacacaaata tccactcaca cgcatgcatg cacacacacg  27840
gacacacaca ggctcacacg tatgcacgca tatgcgtgca cacgcacaca cacacacaca  27900
cgctcacatc ctcccactcc cacactcagt tgctcagaca cacacacgcc tggctctcac  27960
acaaacctgt tgggctctga aaggctccag cccttcccat gctcgtcaga agccagtcaa  28020
tggcttccta agtcaccaca cagatcaaag aggtgaactt ggccacatgg cactctgctt  28080
cctgagctcc caaacaccag ccttggtgag gacagaccct caccccacac cctcattccc  28140
actaccctgg gcaggcccag aggaggggca tctgcaggat ctggcaacca gcccctcccg  28200
cccggctcct gcagccggca ccatgggagt caggggggagg tcactgcaaa gggcaacagc  28260
aagttggtgg ccccaggact agagcccagg ggtcttcagt cctactccag agcttggaca  28320
ctgtcccaca gggcatggcc aagggaaggg cttccagagc cctgacttca gggaggaggg  28380
caggcgggct cctgtggcag gcctggatgc atggccgccc actcctggga ctttctaacc  28440
tagaatatct aggtcaggct gggtgcagtg gctcacgcct gcaatcccaa cactttggga  28500
ggccgaggag ggtggatcac ttgaggttag gagtttgaga ccagcctggc caacatggcg  28560
aaaccctgtg tctactaaaa atacaaaacc tagccaggtg tggtagtgca cgcctgtaat  28620
cacagctact caggaggctg aggcaggaga atcacttgaa ctcgggaggt ggaggttgca  28680
gtgagctgag atcgtgccat tgcgcaaaga agatctaggc cggcccctca accggtgagg  28740
tccaggctgg gagtgctgag agactgtggt gacactgaat gaactaacag gcaaagggct  28800
tccaactgag cctgggggtg gtgggaaatg gctcttgtgt tctagtcaag acctctgcca  28860
accagttctg acactgaccc agcacagaac ctgacaggtc agcaagggcc agggcttagc  28920
acagcccagg taagggtgtg tgtacggccc ccagagtcac tcccaggctg caagaaaagg  28980
gacaaaggag ggacaagggg tggccaagca aactgttccc tctgctcggg agtctggggt  29040
gacctggcct agctggccag tggagctggg ccacctcccc ttaaactctc caccccggac  29100
ttcgactcca aagctttcct gccacccacg ctctccccac ctgggatcac ggccaggccc  29160
tgagccttca agggcccagg tgaactcagc cagactagga gctgaggagg acacagggca  29220
gcttccagaa cggacccgag aaccactccc agcaggttct gcttccagac aaggagctgc  29280
actttttcag ccaatgcaat tagaaagcca ggagaaggtg caaattccac ctgcctgagc  29340
gtccgcactt cccaggccgc ccaccataca cacagcaaag atgtgtttaa ccattcaaac  29400
ccatggccaa ccacatcggt tgcctcagac atgcaagttt taaaaaggaa cataactatg  29460
ggccaggcac ggtggttcac gtctgtaatc ccagcacttt gggaggccga ggtgggtgga  29520
tcacctgagg tcaggagttc gagaccagcc tagacaccat ggtgaaaccc catctgtacc  29580
aaaactacaa aaattagctg ggcgtggtgg tgggcgcctg taatcccagc tacttgggaa  29640
gctgaggcag gagaatcact tgaacccggg aggcgaaggt tgcagtgagc cgagattgtg  29700
ccactgcact ccagcctggg caacaaggga gactccatct caattaaaaa aaaaaaaaaa  29760
aaaaaggaac ataactatgg agtctcaagg ggaagtaatt ccttcaacaa taacaaatct  29820
tgaaagctga gctctttttt ttttttgaga caggatctcc tcactttgtc gcccaggctg  29880
gagtgcagtg gtgggatcac agctcactgc agcctcgatc tcccaggctc aaatgatcct  29940
```

-continued

```
cctacctcag cctcccaaga agctgggatt acaggtgcat accatcacac ccgattcatt  30000
tttgtatact ttgaagagat ggggtctcac catgttgccc agtgtggtct tgaattcctg  30060
gactcaggtg atctgcccgc cttggcctcc cagagtgctg ggattacagg cctgagccaa  30120
cacccccacg ggttcatttt cagagtcgca ccgagtgctg ggttacagg cctgagccaa  30180
cccccccacg ggttcatttt aagagtgaca ccgagtgctg gggttacagg cctgaaccaa  30240
cccccccacg agttcatttt cagagtcgca ccgagtgctg gggttacagg cctgagccaa  30300
cccccccacg ggttcatttt aagagtgaca ccgagtgctg gggttacagg cctgagccaa  30360
cacccccacg ggttcatttt cagagtcaca ccgagtgctg gggttacagg cctgagccaa  30420
cccccccacg ggttcatttt cagagtcaca ccctttttct gaaaaacaac ttgggctcat  30480
gcaaattcga gagagagatg gtgacactcc ccgccccctg gacccaggtg gagtcgcagc  30540
agggtttacc cgtgagcggg gtccaaggcg atggccctcg gctggtcaag gtcctgccag  30600
aagagcacct tccgggatgt gccattgagg ttggccacct cgatgcggtt ggtctctgag  30660
tccgtccagt acagcttctt gcccacccag tcgcaggcga ggccgtcggg agagaccagg  30720
ccggagatga ccacgttctg cacggcggcc cccgtctggt tcaggtaggt ctgcttgatg  30780
gcctcctcgc tcacgtctgt ccagtacacg gctcccttgg aaaactggaa gtccactgcg  30840
gccgcatcct ccaggccgct gaccacgatg gtggactcca gcttgactcc gccggcgtcc  30900
accagccgta cgtcccggcg gttggcaaat agcaggagcg gcgaggctgt ggggcagaag  30960
caaaccgtga gggccactgg ctaagccagc aagatacaca gccctgggat ggagcactat  31020
gcccagagca ctcctggtac tgccctgccc atgcccaaga cctccagttc cttcctccca  31080
cccctaaggc gttgtcagga agttgcctgg gcagccccgg cccgcatcat tcagaggctc  31140
ctgcagcgca gcaaacagcc ttcttcccac attcggtgac agcacctgtt tgtttaccaa  31200
ctgttacgtc tgttccccca gatatgggtg acccttcctg ccatgcccaa aacctcccac  31260
atcgtcctcc agaggctaca ggggccctgt cctgttctgc agagaagcca catccccttt  31320
gttggcctga cacaggggat ggggacatgc aggcacagca ctggccatgc tgctcgctac  31380
agacccagcc acagggccac attttttgag gggttcagag cccaggccag acagagcctc  31440
aagattccct tacaagtctt tgaccactgt ccaagctcag gcccgtttcc ttggccgtgg  31500
catcagcttc ccatccaccc ctgtattcca tgtttctccc accctgcttc tggacattcc  31560
tacatttaaa gggtcactct ggaatgccac cccttggctc agacaccttc cacagctccc  31620
tgtgccagtg ccatgcagaa caaggtcaga ccccctagcc tggcctccaa ggccttggcc  31680
tctggcctca cctacacttc tctccaccac cccaccccaa gcattcctga tctgcctgcg  31740
gccaggctgg ctccctcacc tccctgtgca ccgcagccct cagccccttc tgcctgtgca  31800
agaagcctca tctcacagac aacggtctca ttcccacaac gggctcaatg agaaatcagg  31860
agaggccttc agaccatcac cccaccagac acctcagacg tcggaccagg agggtccagc  31920
aacccccaac acagactcag agggactaag aagccacatg aggagtgaac acaagatgtg  31980
gacaggagga ggttaagggc ctccagggag ctccatcagt ccgtgttctg ctgtcagcag  32040
ggttaggctg ggctggccac aaacaccccc aaaaaacatc tgaagccttg gcttgaaaca  32100
gctgacattc ctcatgaaaa ctgcagaccc ctgggtcctc ctgcgcagat gggggagccc  32160
agccaacccc acactcccac cttcaccaag aaagagaaag ccaaaacaaa ctcaactcag  32220
ccaatgacaa tcacagaact gaatcctgta gttagttcag ttggtttcat ttcagcaggg  32280
```

-continued gaaagatttg cagcctctat gagggtagct gggaacacaa agggccagag catggcccag 32340
gagaccccag cgcagtgggg tagatggttc cgagcacagg cctccctgcc aagacaagca 32400
ctggctcaaa tcctggcccc tcccattccc aggagacatg ctccacagga tgggaggaca 32460
cacagaggac ctgaggccag gaaaatgaca gcggcgcctc cgccgcccca cccgtgctgt 32520
catcatctta ggtctacagt tctttgtggc aacgagggac actgtgaaag tcaaacaaca 32580
ggaaggcata ggccacaaat aaagacaaac gggacttcat gggaagctaa agattttgtg 32640
catcaaaaga cactatcgag agagtaaaaa ggcaacccac agaatgagag aaaatatttc 32700
caaatcatag atctactaag agattaatat ccatgaaata cagagaactc ctaaaactca 32760
acaatgagaa aacaactaag ccaactcaaa aatgggcaaa caacttgaac agacatttct 32820
ccaaagatga catataaatg gccaataaac acatcaaaac aggcttaata tatccctaat 32880
catcagggaa atgcaaatca aaactacaat aagataccat cttgcaccaa ttaggacggc 32940
tactatcaaa aaaacaaaat agcaagtgtt ggtgaggatc tggagcaact ggaacccttg 33000
tgcaccactg gcaaaaatgt gaaatggtgc agctactatg gaaaacagca tggcagttcc 33060
ccaaaaactt aaacacagaa ttaccatatg acccagcaat ttcgctttgg gttatatacc 33120
caaaagaact gaaaacaggg acacaatcag atatgcatac accttggatc acagcagcat 33180
ccttcccaac agctaaaaca tggaggcagc caggcatggt ggctcacgcc tgtaatccca 33240
gcactttggg aggctgaggc gggtggatca cctgaggtca ggagttcgag accagcctgg 33300
ccaacatggt gaaaccccgt ctctactaaa atacaaaaat tagctgggcg tagtgacggg 33360
cacctgtaat cccagctact cacaagtctg aggcaggaga atcacttgaa ccctggaagt 33420
ggacgttgca gtgagccaag attgcgccac tgcattccag cctgggtgac acagcgagac 33480
tctgtctcaa aaaacagcaa aacaaaaaca aaaaaacaaa caaacatgga agcaacccaa 33540
gcgtccctct actgagggat gaatagcggg gcaaaatctg ctccatccac acaatggagt 33600
actattcagt ctcaaaaagg aaaaagattc tggtcaggca cggtggctca tgcctgtaat 33660
cccagcactt ggggaggctg aggcgggtgg atcacctgaa gtcaggaatt caaggcccgc 33720
ctggccaaga ctggcaccna gctacacana aagtatangg ccccggaaa 33769

<210> SEQ ID NO 9
<211> LENGTH: 72049
<212> TYPE: DNA
<213> ORGANISM: Homo sapiens
<220> FEATURE:
<221> NAME/KEY: unsure
<222> LOCATION: (8356),(8385),(38585)
<223> OTHER INFORMATION: Identity of nucleotide sequences at the above locations are unknown.

<400> SEQUENCE: 9
tataccttgc gcggaccttc ggctcctgtg gtgaagacaa tatgaagaaa atagaaatta 60
cccataattt tgccacacag acttagttgt gtccatgtat cttgtgcacc ttttttctgt 120
ttacggatca aaatcgactt ttagggtcag gcgcggtggc tcacacctgt aatcccaaca 180
ctttgggagg ctggagttgg ggttgggggg tggatcactg aagatcagga gtttgagacc 240
agcctggcca acatggcgaa actccatctc tactaaaaat aaaagattag ccaggcgtgg 300
tggtgggtgc ctctaatccc agctactccg gaggctgagg caggagaatc gcttgaaccc 360
aggagacaga ggttgcagtg agccaggatc acgccactgc actccagcct ggcaacagag 420
cgagactctg tctcaaaaaa aaaaataaaa ataaaataaa taaatacata aattgacttt 480

-continued

```
taggagattg gttcaaacaa tgtgtgtaat gttgtgtctg agtgtttttc atttatcgtt    540
catgcaaatt ccgacatcat tcactcttct ccagagtgtg ctgttttcct gcctgtgtca    600
tcacccgtca ccttgaatgc cctcgtttag gtaaaataag tacattttat tcaaaaatat    660
ttgaggacat ttgggttgtc tccaggttct tggtcttgag ttttgctgtt cttgtggagc    720
catggtggtg tctggttgca ggaacctcca tgcgttccag ctgctgcttc tgcctgtgtt    780
cttagagagg aaatgctggg gtccgcggtt cccgggctgc tgaccaggaa gcctgcggtg    840
ctttacggcc cttccagaag cgggagatgc ccccacttaa gtgtcagaca ggcctttcca    900
cctcactggc agctctgagc ggctcccttc tatttgcaga tgactgagaa gttaccaatt    960
tccacgttta ctgactgctg tttctcctgt taatttgtat ttatagtctt cgctaattta   1020
ttgctagggt tttggtgttg tccctattga cttgtatgcc ttttaatttt ttaaacaaca   1080
ttaatatact tcattttttt agagcagttt taagtttaca ggaaaattaa gggacaagta   1140
cagagagttc cttccacctg ctgtcctcct ctcctcctcc ccaccttccc tccttcccct   1200
attgtaactt tctttctgat attataaaag tcactcatgg ctgggcgtgg tggctcacgc   1260
ctgtaatccc agcacgttgg gaggcagagg caggcagatc acctgaggtc aggagttcca   1320
gaccagcctg gccaacatgg tgaaaccccg tctctactaa aaacacaaaa agttagccag   1380
gcgtggtggc gggcacctgt aatcccagct actcaggagg ctgaggcagg agaatggcgt   1440
gaacctggga ggcagaggtt acagtgagtc gagatcgcgc cactgcactc cagcctgggc   1500
aataagagtg aagcttcgtc tcaaaaacaa agtcacacac gcttcttgta cgagggtcat   1560
ttggccgagg ggccagatgg ctcaccatct agttgggaca ggccatgagc tcggaatgct   1620
ttttacatat ttacatggtt gagaagaaaa tcaggagaat aatgttttgg gacatgggaa   1680
aatgacatgg aatttgcatt ttagtgtcca taaatgaagt tttgtttgct cccagctgtg   1740
ttgactgagg caggctggct tcctacagct gcggcagagc tgaggaggcg ggaaggagac   1800
cgtgcaggcc gcagcaccga aaatatttgc tctctggccc ttcccagagt gcttgccgac   1860
ctctgtccga cagctagaag gaaggatagg acccgtccga cgataaccac tgttgacatt   1920
tgagcgcgtt tccttcccgg cttttgtgtg agagtggcag tctgtttgct tttgtggtcg   1980
ggatctgctg cacgcacggc gggctgtttg catgaggctt cctggaggat agggctgggc   2040
tcggagctgc acgcagtggg gcgtgtcctg catgcagtgg ggcctcagaa gagagctgtg   2100
gtgggcgggg cagtgccaac gctggtgggt gccaggcctc cacgctcaga tcagccccgg   2160
cgacaggttt gggccaccct ctctctggcc tctgtgcagt ggcccaggcc gtctgctctg   2220
cctggcacac ttgcctctgt ccttccactg aagcgctcct cttaccctct gctcccggct   2280
gggtacgttg aattgtgtcc ctcaaggaga tatgctaaag gtctaacccc aggaacctgt   2340
gtatgtgatc taatttggaa acagggtctt ggctgatgta atcaagcgag gatgaggtca   2400
ccctagagta gggggcctat atccacggtg ctggtgtcct catgagagca ggtgagcaga   2460
cactgacact caggggtgaa ggctgcatgg agtcagaaca gggcttagtg cgatggcggc   2520
cacaagccaa ggaactccaa gtatttcctg caacaccaga agctggaaga tgccaggaag   2580
gatcctgccc tggagccttc ggagggagtc tgtccctgca gacgtcttga cttttgattg   2640
cagggatgca tgtcttaggg tgtgtggggg ggtgcatttc tgatgttaga agccacctgg   2700
ttggtggcga tgtgtcacgg gagccctctg caggttctgc gtgtccatgt ggtcggggac   2760
agaggtgggc agggacggac ggtgtcgagc tggacatgtc catgacgtcg gccatcccctt  2820
gggatggctt ttttgttttg aggataaggc tgcctgccag gaagctgtgc cctgcctggc   2880
```

-continued

```
ccttgcccca agcccctggc ctgtgcttgg cctcgcggaa gggatgtcgc ccttctctcc   2940
tgcatgcgtg cagggaggaa ggggagaggt cagcagcccg cctggaggag gctcgggcga   3000
ggggaaggtt tcactttcag gcaatgttgt ggggctgttt aaacaacccc aaagaaaacc   3060
atttggccaa actgttagtt tccaaacatt ttacttcctt ggtgtttaaa taaattccta   3120
ccaagactct gtagctggtc ccagggaagg agttggcctc tcttctttat agcccggcac   3180
agtcagtccc ctgcacctgc cctcccaac cccaggcctg cttccccgtg gccatggctg   3240
ctgcccggac ctctctacac acagaacctc ctggaggcca gctgtgggca ccagccttgg   3300
cagggctgtg gcggagccca ggctgctggt actctctctg cagctgctcc ctgctggcct   3360
ggctggacag cgtccccacc accactgggg tcacctctgt gctggtcaca gctcactcag   3420
accttcaggc aaatgggttg gatcctgcct ctctcccagg tgtctcagtc tctgcaaaac   3480
tcaaaaacct cagaggcctt gcagcctgag ggtgtcaga gacacctcct tcgaatcagt   3540
aaacacctac agattcaccc cagcagtgaa aggactgctt cgccacagag gtttgattta   3600
ctcctaagta attggaaggg atgccgagaa taggttcctc atggtgggac tagaggccct   3660
ctgctgacct agttaacaga gggctagggc tgggtgtgct cagcccctga aggttctagg   3720
cccatttggg acaccccgcc agaacctgcc acaacctgcc atgtggtgac agctacctaa   3780
atcccagagg ctcttgagct ggagagcaga cctctcaatc tcagcaggcc ccccacacag   3840
accccataac cctagtctgc cttcacagta cagttcgtgg ctatgtgttc acggatggtg   3900
ttgttcacct aaggtctctg ccctgtgacc ccaagggcgt cctgagggca gattccaagt   3960
ctgtttcgtc cacccctcct tccctagcag cgggtccagg gcctggcctg aactagcttc   4020
ccacagagat actggtggga tgatgaaggc agccaggcgg caagtgaaaa acgcacttcc   4080
tgcatgtgct ggctcctggg attgaagtgt ttgaggaagc aaagtgaagt gagctttcct   4140
cttgcggctg tgtgtccttg ggccgggagc ctaccctctc tgagcgttgg ggtccttgtc   4200
agtagaatgg ggcatcctca tagctcaagg ggtggtgtgt gaaaattgtg ctattgtgtt   4260
actttaatga tttttttttt ttcgagacaa agtctcaccc caacgcgcag gctggagtgc   4320
agtggcgcga tctcagctca ttgcaacctc tgcctcctgg gttcaagtga ttctcctgcc   4380
tcagcctccc aagtagctgg aattacagga gtgcgccacc aggcccggca tatttttcta   4440
tttttagtag agaggggttt ttaccatgtt ggctaggctg gtcttgaact cctgacctca   4500
ggtgatccac ctgcctcggc ctcccaaagt gctgggatta caagcatgag ccaccgcgcc   4560
cggcctactt tagtgatttc ttaggaggac agagggaacg ggctggcaag acaggcttgg   4620
aatgtgtttt gggatcaagt gccggtttct gtctggcact ggcgttctct gtggggccat   4680
gatggacaca ctgctgaggt caagcgtgat tcgtcttgcg ctgtgcctgg cagtctcatt   4740
ggaaagttct gtagacatcg tgtggatggg gctcttcccg gccaagccct tggggacctt   4800
ccaggactgt gatctcccca cagtggctgt taagcaggga cctttcgtga agtggagtct   4860
ctggtcccct ccaagtcata gctagacagg gactcgggca tcgccaagcc tggctgatta   4920
ttcactggat gaggagacag gcccagagag gggcaggaac ctgcccgagg tcacccagca   4980
ggccccagag gtttcggtct cggattctcc ctgctcatcc ctggatgtag tgctgctgtg   5040
gatgtggttc tgtgctgggg gctgtggaga gcagggggct tgtgccagga ccccagtgag   5100
ggtggcgccc tcgccatgag gccgactgtt ggtatggggc ggccatccac tggggtgtgg   5160
ggaggaacag ctttcctgag gaggaggtgg cgggaggaac agcttccctg aggaggaggt   5220
```

-continued

```
ggcggtgctg tgtgacctgg gccttgaagg acaggtccat tgtcaacaga acattttggg   5280
agtggagcct agagggagaa aatttgttga aattcagatt cccctccccc taccaataca   5340
caccaaatca gatgcccctg accagatcta aatttggctc tcagagattt ccattgtagc   5400
tgggcacttg gggaaccttc taagtgctgc ctctgcctct ccccagcctg cctgcctcag   5460
tttccccagc cctgggcccg tgtcgctgtt gccatcacgt gggcgccctc tagtggagga   5520
atcagattat gcactccggg gcttggagca ggagtcagga ggggctcctg tctttccttg   5580
aaacgttgga tgccgggatc ctggaacagt ctctgcattc ctcctggcga gaaccagagc   5640
ctgggcacag gggaccatct gttgtttgaa ggctgcagcc tggcagggca ctcaggagat   5700
ctggcagttg gctgcagggc caggtctagg ggccagggca tcagggaggc tctgggctgg   5760
ttcagccccg ggcccctttg cagattgtga cctgggcccc tgtgcagggg catggccaca   5820
ggatgctggg aggggtctct gaccctgacc ttcttggctc tgtgcatcct tgagaccaga   5880
aaggtctgga acaaatgagt agacgatgcc ctaacctggg gagggagcca catcctgatc   5940
ccagcaacct cgggaaggat ctgtcaggat tatggggcac cctgggggcc ccaagtctgc   6000
atgggtctcc acttgcaatt tctgtaggaa gctctgataa atccaaactg gggtcctag    6060
gacacagtca gaaatgctga taccgttgtg tgtggagcct cgggccctgg gggtcaggag   6120
catgtggagg gtgggccacg gggggttcaga agagaatcct gtaacccccc accccccaaa   6180
ctgaagccca cttgagggcc atggctgaaa ggttgggggg tctccgtgcg tcctgtggag   6240
tgggtggtga ggagtccttg ggtttgcacg cctctgggcc tgagcggcgg gaccccgtcc   6300
acagcggatc cctgggccct gttgctcaga tgctctcaga gtgttgctgt ggccacggag   6360
ggagcctgag ttaagcttct cttgtgccgg ttgtacgctg tcaggtcaca ctggtgagtt   6420
aggcagggca cagatgccca gagcagaggg aactttcctt ggggattcaa cacgtgcaag   6480
tcttaggggc tggcaaatcc tgccctcagc tagagagggg gcttttattt gagaccagaa   6540
tcacctgagc atcctcctgt ccccagctgt gtccagcctg tctgcaggga catcctgaga   6600
ggaccaggct ctcccctcat ccacctgcct aagtgccact ctgaaccctg tccacctgtg   6660
ccgtggaggg gcgtgacctc aagctgctca gccagcagca ggcttggccc tggggggcag   6720
cagagaccca ggtggctgtg gggtgggtgc ttcgtggcgt ggttctgaaa cttcgttgga   6780
agtgtgtgga cagtgccttg cctgttctct gtgggaccct atttagaaac gaggtctgag   6840
ttactggggg tcatcactgt gttctgatgg cccagctgtg tggaggccgc ggtgcagccc   6900
catccaagga gccagggccc tgggtctagc cgtgaccaga atgcatgccc cggaggtgtt   6960
tctcatctcg cacctgtgtt gcctggtgtg tcaagtggtc gtgaaactct gtgttagctc   7020
ttggtgttcc tgaaagtgcc cccgggtctc aggcctcaga accagggttt cccttcatct   7080
cggtggcctg ggagcatctg ggcagttgag caaagagggc gattcacttg aaggatgtgt   7140
ctggccctgc ctaggagccc cccggcacgg tgctggggcc tgaagctgcc ctcgggtggt   7200
ggagaggagg gagcgatgaa gtggcgtcga gctgggcagg aagggtgagc ccctgcaagg   7260
tgggcatgct ggggacgctg agcagcatgg ccagcagctg ggtctgcagc ctggtacccg   7320
gcgggacttg tggttggggc tggtttgtgg ccaggagagg ggctggcagg agacaagggg   7380
gactgtgagg cagctcccac ccagcagctg aagcccaatg gcctggctgt gtggctctca   7440
gctgcgtgca taacctctca gtgcttcagt tctctcattt gtaaaatgag gaaacaaaca   7500
gtgccagcct cccagaggtg tcatgaggat gaacgagtga ccatgtagca tgggctgggt   7560
gcgtgtcacc taacatcacc agcctttgca aggagagccc tgggggcctg gctgagtatt   7620
```

-continued

```
tcccttgccc ggcccacccc aggcctagac ttgtgcctgc tgcaggccct tgacccctga   7680
ccccattgca cctgtctcca caggagccga ggaggtgctg ctgctggccc ggcggacgga   7740
cctacggagg atctcgctgg acacgccgga cttcaccgac atcgtgctgc aggtggacga   7800
catccggcac gccattgcca tcgactacga cccgctagag ggctatgtct actggacaga   7860
tgacgaggtg cgggccatcc gcagggcgta cctggacggg tctggggcgc agacgctggt   7920
caacaccgag atcaacgacc ccgatggcat cgcggtcgac tgggtggccc gaaacctcta   7980
ctggaccgac acgggcacgg accgcatcga ggtgacgcgc ctcaacggca cctcccgcaa   8040
gatcctggtg tcggaggacc tggacgagcc ccgagccatc gcactgcacc ccgtgatggg   8100
gtaagacggg cgggggctgg ggcctggagc cagggccagg ccaagcacag gcgagaggga   8160
gattgacctg gacctgtcat tctgggacac tgtcttgcat cagaacccgg aggagggctt   8220
gttaaaacac cggcagctgg gccccacccc cagagcggtg attcaggagc tccagggcgg   8280
ggctgaagac ttgggtttct aacaagcacc ccagtggtcc ggtgctgctg ctgggtccat   8340
gcgtagaaag ccctgnaaac tggagggagc cctttgtccc cctgncttca gtttcctcat   8400
ctgtagaatg gaacggtcca tctgggtgat ttccaggatg acagtagtga cagtaagggc   8460
agcctctgtg acactgacca cagtacaggc caggcctctt tttttctttt tttttttgag   8520
atggagtctc actctgtcgc ccaggctgga gtgcagtggt gtgatctcag ctcactacaa   8580
cctctgcctc ctgggctcaa gtgattctcc tgcctcagcc tcctgagtag ctgggattac   8640
aggtgcctgc cactgtgctt ggctaatgtt tgtatttttg gtagagatgg ggtttcaccg   8700
tcttggccag gctggtcgca aactcctgac ctcaggtgat ccacctgcct cagcctccca   8760
aagtgctggg attacaggca tgagccacca cgcccggtca ggccaggcct cttttgaaca   8820
ctttgcacac catgggtctt ttcatccagg ggggtaggta cagttgtaca gttgaggaca   8880
ctgaagccca gagaggctca gggacttgcc cagggtcaca cagcaggatg tggcaggtgt   8940
ggggctgggc ctggcagcgt ggctccagct ttccagcata gaaatctgtg aaagcagata   9000
gtttgtcggt cggtagggga gactttctga gacccgcccc agcggctcag agggtagtag   9060
ccaggggcct tcctgggggc tcataaccca gaacactgaa tgggaaaacc ctgatggagg   9120
aggcgcagtg gagctgtggg tgccgatggg aagtcccaga ggagctggga ggtcagtagc   9180
ggtgctgccc tctgtggagc acttagtggg caccaggtgt gtttccaggt tcatggccct   9240
gggacctgaa gctcagaagg tgaagtaact tgcccagggc acccgtcggg cagcggcggg   9300
cagaggattt gtgggctgtg gagcctgtgc tcgtggccca gccctggggg ttgtgagtgt   9360
gctggccggg gagcttttcc tgcaagtgga ctggtgtcta ggagccagca tgtcaggcag   9420
caggcagcgg gagtgcagca ggcagcggga gcacagcagg cagagggcgg ggctcgagca   9480
gccatccgtg gaccctgggg cacggaggca tgtgggagag ggctgctcca tggcagtggc   9540
tgaagggctg ggttgtgccc cgaggagggt ggatgagggt aagaagtggg gtccccaggg   9600
gctttagcaa gaggaggccc aggaactggt tgccagctac agtgaaggga acacggccct   9660
gaggtcagga gcttggtcaa gtcactgtct acatgggcct cggtgtcctc atctgtgaaa   9720
aaggaaggga tggggaagct gactccaagg cccctcctag ccctggtttc atgagtctga   9780
ggatcccagg gacatgggct tggcagtctg acctgtgagg tcgtggggtc cagggagggg   9840
caccgagctg gaagcgggag gcagaggggc tggccggctg ggtcagacac agctgaagca   9900
gaggctgtga cttggggcct cagaaccttc accccctgagc tgccacccca ggatctgggt   9960
```

-continued

```
tccctccttg gggggcccca gggaacaagt cacctgtcct ttgcataggg gagcccttca  10020
gctatgtgca gaaggttctg ctctgcccct tcctccctct aggtgctcag ctcctccagc  10080
ccactagtca gatgtgaggc tgccccagac cctgggcagg gtcatttctg tccactgacc  10140
tttgggatgg gagatgagct cttggcccct gagagtccaa gggctggtgt ggtgaaaccc  10200
gcacagggtg gaagtgggca tccctgtccc aggggagccc ccagggactc tggtcactgg  10260
gcttgccgct ggcatgctca gtcctccagc acttactgac accagcatct actgacacca  10320
acatttacaa acaccgacat tgaccgacac cgacatttac cgacactgac atttaccaac  10380
actgtttacc aacactgaca tctactgaca ctggcatcta ccaacactga catttaccga  10440
cactgacatt taccaacact atttaccaac actgacatct actgacattg gcatctacca  10500
acaccaacat ttaccgacac caacatttac caacactgaa atttaccgac accgacattt  10560
accgacaccg tttaccaaca ccgacgttta ccgacaccga catttaccga cactgatatt  10620
taccaacact gacatctact gacgctggca tctactgaca ccgatgccag catctaccaa  10680
caccgacatt taccaacact gacatttacc aacactgaca tttaccgaca ttgacattta  10740
ctgacactga catctactga cactggcatc tactgacact gacgtttacc gacactagca  10800
tctactgaca ctgacattta ccaacaccag catctaccaa caccgacatt taccaacact  10860
gacatttact gacactgata tctactgaca ctggcatcta ctgacaccaa catttaccaa  10920
caccagcatc taccaacacc gacatttacc aacaccagca tttaccaaca ccgatgttta  10980
ccaacgccga cgtttaccga cgccagcatc taccaacact gacatttacc gacaccgaca  11040
tttaccgaca ctgacattta ctgacactga catctactga tactggcatc taccgacact  11100
gatatttacc aacgccagca tctactgaca ctgatgttta ccaacaccga catttacgag  11160
caccgacatt tactgacacc aatatttact gacatcaaca tttagccatg tgatgggggc  11220
cggcttgggg gcaggccttg ctcttggcac tggggatgct gcagagacca gacagactca  11280
tggggtcatg gacttctgct tcttctccag cctcatgtac tggacagact ggggagagaa  11340
ccctaaaatc gagtgtgcca acttggatgg gcaggagcgg cgtgtgctgg tcaatgcctc  11400
cctcgggtgg cccaacggcc tggccctgga cctgcaggag gggaagctct actggggaga  11460
cgccaagaca gacaagatcg aggtgaggct cctgtggaca tgtttgatcc aggaggccag  11520
gcccagccac cccctgcagc cagatgtacg tattggcgag gcaccgatgg gtgcctgtgc  11580
tctgctattt ggccacatgg aatgcttgag aaaatagtta caatactttc tgacaaaaac  11640
gccttgagag ggtagcgcta tacaacgtcc tgtggttacg taagatgtta tcattcggcc  11700
aggtgcctgt agacacagct acttggagac tgaggtggga ggatcgctgg agtccaagag  11760
tttgaggcca gcccgggcaa aggggacaca ggaatcctct gcactgcttt tgccacttac  11820
tgtgagattt aaattatttc acaatacaaa attaagacaa aaagttaatc acatatccac  11880
tgccctgctt aagacagaaa acatgggtgt tgttgaagcc agaggcagct gctggcctga  11940
gtttggtgat tggttcctaa gcagttgaag gcagttttgt ttttccatag atgtctgttc  12000
tccctttgct gggtgcagcc tcgccctgct gctgtggtcg ggtttcagtg gcctcgtccc  12060
gtggacgcag cctcgccctg ccgctgtggt cgggtttcag tggcctcgtc ccgtggacgc  12120
agcctcgccc tgccgctgtg gtcgggtttc agtggcctcg tcccgtggac gcagcctcgc  12180
cctgccgctg tggtcgggtt tcagtggcct cgtcccgtgg acgcagcctc gccctgccgc  12240
tgtggtcggg tttcagtggc ctcgtcctgt ggacgcagcc tcgccctgcc gctgtggtcg  12300
ggtttcagtg gcctcgtccc atgggcgtgc tttggcagct tttgctcac ctgtggagcc  12360
```

-continued

```
tctcttgagc ttttttgttt gttgtttgtt tttgtttgat tttgtttgat tgtttgtttt  12420
tgttgtcgtt gttgttgccc aggctggagt gcagtggcgc gatctcagct cactgaaacc  12480
tctgcctcct tgggttcatg ccattctcct gcctcagcct cccacatagc tgggattaca  12540
agtgcccgcc accacgcctg gctaaatttt gtatttttag tagacagggg gtttcaccat  12600
gttggtcagg ctggtctgga actcctggtc tcacatgatc cacctgcctc ggcctcccaa  12660
agtgttggga ttacaggcgt gagccaccgc gcccagccct ctgttgagca tattttgagg  12720
ttctcttggt gccagtgata tgtacatgtg tccccatcgc accatcgtca cccattgagg  12780
tgacattggt gcctctcctc ggggtggatg cctccctctg tttccagcaa cttctgaagg  12840
attttcctga gctgcatcag tccttgttga cgtcaccatc ggggtcacct ttgctctcct  12900
cagggctccc aggggaggcc cgaatcaggc agcttgcagg gcagggcagg atggagaaca  12960
cgagtgtgtg tctgtgttgc aggatttcag accctgcttc tgagcgggag gagtttcagc  13020
accttcaggg tggggaaccc agggatgggg gaggctgagt ggacgccctt cccacgaaaa  13080
ccctaggagc tgcaggtgtg gccatttcct gctggagctc cttgtaaatg ttttgttttt  13140
ggcaaggccc atgtttgcgg gccgctgagg atgatttgcc ttcacgcatc cccgctaccc  13200
gtgggagcag gtcagggact cgcgtgtctg tggcacacca ggcctgtgac aggcgttgtt  13260
ccatgtactg tctcagcagt ggttttcttg agacagggtc tcgctcgctc acccaggcga  13320
gagtgcagtg gcgcaatcac ggctcgctgt agcctcaatc tccctgggct caggtgatcc  13380
tcctgcctca ccctctgagt agctgggact acagacacat accaccacac ccagctagtt  13440
tttgtgtatt ttttgtgggg ggagatgggg tttcgctgtg gtgcccaagc tgatctcaaa  13500
ctcctgaggc acaagcgatc cacctgcctc ggcctcccaa agtgctggga tgacaggcat  13560
cagccgtcac acgcagctca atgattttat tgtggtaaaa taaacatagc acaaaattga  13620
tgattttaac cattttaaag tgaacagttc aggctgggcg tggtggctta tgcttgtaat  13680
cccagtactt tgagaggctg aggtgggcag atcacctgag gtcaggagtt tgagaccagc  13740
ctggccaaca tgatgaaatc cagtctctac taaaaataca aaaattagcc gggcatggtg  13800
gcaggtgcct gtaatcccag ctactcggga ggctgaggca ggagaatcgc ttgagcccgg  13860
gaggtggagg ttgcagtgat ctgagatcat gccactgcac tccaatctgt gtgacagagc  13920
aagactctgt cttgaaaaat aaataaataa aaaaaatttt aaaaagtgaa caattcaggg  13980
catttagtat gaggacaatg tggtgcaggt atctctgcta ctatctactt ctagaacact  14040
ttcttctgcc ctgaaggaaa ccccatgccc accggcactc acgcccattc tcccctctct  14100
cccagcctct gtcaaccact aatctacttt ctgtctctgg gggttcactt cttctggacg  14160
ttttgtgtga ctggaatcct gcaatatgtg gtccctgcgt gtggcttctt tccatagcat  14220
tgtgttttcc agattcaccc acacattgtc gcacgttatc agaatctcat tcctgactgg  14280
gtgcagtggg ttaggcctgt aatcctaaca ttctgggagg ccaaggcggg acgatcactt  14340
gaggcaggag tttgagacca gcctggccag cctagcaaga ccccagctac caaaaaattt  14400
taaaagttaa ctgaacgtgg tggtggtggg cacttgtggt tcccagctac ctgggaggct  14460
gaggttggag gatcgcttaa gcccaggagg tcaaggctgc agtgagctat gatcgcacca  14520
ctgcactcca gcctggacaa cagagcaaga ccctgtctga aaaaaaaaac aaaaaaaaaa  14580
gttcctttct ttttgtggct ggatgacatc ccattgtatg gccacagcac attttgtttg  14640
tctgtttatc gggtggtggg cagtggtttc caccttttgt ctcctgtgaa taatgctgct  14700
```

-continued

```
gtgaacattt gaattcaagt ttttgtttga acacctgttg tgaattattt ggatatatgt  14760
gtaggggtag gattgctgag tcctatggta atgttaggtt tgacttactg aggaaccatt  14820
aaactgtttt caacagtggc tgcgccgttc tgcatcccca ccggcagtgt gtgagggttc  14880
tgactttacc tcctcacaaa cgcttctttt ccatttaaaa aaatattcag ccaggtgctc  14940
tggctcacgc ctgtaatccc agcactttgg gaggccgtgg cgggcggatc acctgaggtc  15000
aggagttcga gacgagcctg gccaacatgg tgtaacccca tctctaccaa aaatataaaa  15060
attagccggg tgtggcagcg ggcgcctgta atcccagcta cttgggaggc tgaggcagga  15120
gaatcacttg aacccgggag gcagaggttg cagtgagcca agatcgcgcc actacactcc  15180
agcctgggtg acaagagtga aactccatct aaaataaaac aaaaataaaa ataaataaaa  15240
atttattaaa acattcatca cagccagcct agtgggtgtc ccatgtggct ttgcctcgca  15300
tttccctgat aactaggatg ctgagcgtct tgtcccaggc ttgccacacc tcagcacttt  15360
gagatacgtc gcacagtccc catttgcgaa cgagaaatga ggtttaggga acagcagctg  15420
tgtcatgtca cacagcgagc agggggtctc tgagccgtct gaccccacag ccgaccaagc  15480
tccaatcctt accgcctcct agtgttgtgg atgtagccca gggtgctccc acatttttca  15540
gatgagaaca ccgaagctca aaacaggagc gttttgtcca cattggatac acgatgtctg  15600
tggtttggtc ctgaagtcac tttatatctc agtggtccag actggagtag gacagggggt  15660
tctggggaat ggggaaggtg tctcaggtga aaggaaggaa ttccagattc tccatactgt  15720
ccttgggaag ttagaagact cagagggtct ggcaaagtca gacaaagcaa gagaaatgca  15780
gtcaggagga agcggagctg tccaggaaca gggggtcgc aggagctcac ccccaggaac  15840
tacacttgct ggggccttcg tgtcacaatg acgtgagcac tgcgtgttga ttacccactt  15900
tttttttttt tttgaggtgg agtctcgctc tcttgcccag tctggagtgc agtggcacga  15960
tctcggctca ctgcaagctc tgcctcccgg gttcatgcca ttctcctgcc tcagcctccc  16020
gcgtagctgg gactacaggc gcctgccacc gcgcccggct aatttttgta tttttagtag  16080
agatgggatt tcactacatt agccaggatg gtctcgatct cctgacctca tgatccgccc  16140
gtctcggcct cccaaagtgc tgggattaca ggcgtgagcc accgcgcccg gcccgatttc  16200
ccactttaag aatctgtctg tacatcctca aagccctata cacagtgctg ggttgctata  16260
gggaatatga ggcttacagg ccatggtgct ggacacacag aagggacgga ggtcaggagg  16320
tagaagggcg gagagaggga acaggcggag gtcacatcct tggctttcaa aatgggccag  16380
ggagagacac cctctgagca tggtaggaca ggaaagcaag attggaacac attgagagca  16440
accgaggtgg ctgggcgtgg tggcttacgc ctgtaatccc aacactttgg aaagctgagg  16500
tgggtggatt gcttgaggcc aggagttcaa gaccagcctg gccaacatgg tgagaccccg  16560
tctctactaa atatacaaaa attagccagg cgtgatggtg catacctgta atcccagctg  16620
cttgggaggc tgaggcagga gaattgctta aacctgggag gcggaggttg cagtgagccg  16680
agatcccgcc actgcactcc agcctgggcc acagagtgag actccatctc aaaaaaaaaa  16740
aaaaaaaaga taaaaagacc aaccgaggaa ttgaagtggg ggggcgtcac agtagcagaa  16800
gggggatcgt ggagcaggcc accctgtggt catgcactgg aagctcatta cctgacgatt  16860
tggagctcat cactgggggc ctaaggagaa tagatactga aggatgagga gtgatggcgc  16920
ggggcacggg tgtctttggt ggccagaact tggggactgc tggggtgcct cactgcaggc  16980
cttctcagcg ccctttatat gcttacacag gctgtttcta agagggggat acattgcata  17040
agcgttttca gactacctca tcatgggtcc ctttctttac cctctgtggc cctggtggcg  17100
```

-continued

```
cactctctgg gaaggtgcag gtggatgccc agacccgccc tgccatccac ctgcacgtcc  17160
agagctgact tagcctcgag attgctgctg gcacctcctg ccccgggaca cctcggatgt  17220
gcccgtggag atgctggctc tgtgttttct gctggagttt ggtgcgtctt ttcctcctgc  17280
aagtggccac cgctcttggg tatgtcctca ggcttctgcg agtcatggct gcttctcagg  17340
tccttgccca gcgccaggag caaaccctcc tggcactttg ttcaggggtg gatgcgccag  17400
tgttcctgct gtggaccgcc atctcacatg agggtcttgg gcctgcaggc tcgttcagga  17460
aacacccgct gagtatgcag tgtgtgccag ctgtgtccca ggcaatggcg gggacagtgg  17520
ctgctgctgg ggttgtggtg gcttctgggg actctgggga cagctgaggt gcaaggagcc  17580
acggctcctt gaggatgcag ttggactcca ggtggaaggg atggttgggg gaggtataaa  17640
tggggtcagg gaggagacac atttggaaca atgggaacat ttttaagatg ctatgtcggg  17700
aggcaacaag gtggccaacc caggtgctga ggagcccaca ccagccctgg acgtgttttg  17760
ccgctcacct ttgctgggga gtggtgggag agaggattcc gttccacgtg gtggtgtgcg  17820
cagctgggct gtgtggagct gggcgctagg aggaaggtgc tttctgcggg gctagccggg  17880
ctctgccttt gaacacaatc aggctccagg ttttcagcat ccagtgcatg agaggacttc  17940
acgggcagct gtggctgatc ccttgatgaa ttgggagaag aacaaaggtc tatgaaatga  18000
ggtttcatgt agatggcatt agagacgccc acaacagatt tacagagtgg agcggagacg  18060
gcggatgggt ctgggaggcc cctcctgctg gccttgactg tgacagctgt cctgggaatc  18120
agcttccagg ccgccccagc agcctgactg acacacacag ggttttagc  cccatcctgc  18180
gaccagctgt tgccatcatc agtgacagct gggagtggcg gtggttccag ccctgggcac  18240
cctccccacc tgctggggcc cacccagggc agtcctgaca cctacaggtt gcttggagcc  18300
gcatccgagt cctgccccac cacgtgtgaa gcccgagtgg tcgtgggctg aggtcccctg  18360
attgcatccc cacttccctt ctgcttcaca tagctgcctc ttctcaccgt ttttccagcc  18420
tcctgggcta ggaattccag tgttgtgctg gctttgcccc aggacacctc cttagccctc  18480
ttcctgagtc tagagccccg ggggttggaa gtcctggccc ctgggacacc tgcagccaca  18540
ctcagcttct cctgtgagcc tccagcatgt cccctcagga ccaagccctc acgttcttgc  18600
ctccccgccc acctgggctc agccagggga aggcctggct gggagcgtct cccctctgcc  18660
ctgcccttct cccctcctac cctgcccttc tctcctctgc cccgccatgg cttttatatc  18720
ctgtgccaca agacatggct gtgtgtgaaa gtggcagggt ctggcatctc tgtgggtctc  18780
tgaggcccac gctccagtgc cactcttccc acccgctggc cgtgccctca tgctggaggg  18840
acagcccagc cctctcccga accccagccc catgtgccca gctgccccg  gccctctccc  18900
ctggaagccg gggtcactcc agccgtatgc catggtgggg acatcctgct tccttggcct  18960
tccagggaag gtcctctttc caaatggcga cacctggtcc ctgcctggag gctggaagct  19020
gtggcccttg tatgcccctc cagggtctgt gcgctcggtt ggcccgagtt cccatcaccg  19080
tcatcatcac catcatcatt gtcatttcgc ttgtctgtga gccggcctgg tctcccagag  19140
cagagaccct ctgaggtcca gcctgagttg gggtctccgt gctgacccct gacggggact  19200
caggacgtac caggtctggg tcaggagtga cccccaaacc tcgtgccctt tgacaggcac  19260
ccctgacttt tgctaagtgg gtggaggtga catcacttac agcgggagtg atgggacagg  19320
gtctgttggc tgcactgtgc tcccagggat ctggggagag gctatatccc tgggctttgg  19380
cactgcagag ctgtgtgtgt ttgtgtgtgt gtgtgtgtgt gtgtgtgtgt gtgtgtgtgt  19440
```

-continued gtgtgtgttt gcgtgcgcgc acatgtgtat aagatctttt tttattacat gaagcaagat 19500
aactgttgct gtttcctttt gggttttgtg ttcaacagag tggggtactt cttccctcag 19560
acaacagaac tctccccttt aaacacgtgc tgtcagaggg tgggtcttgg gctcatgtct 19620
gtttgcacag ccgagtcaga ggaaacacag ggttcttcat aaaaacactg cacagcaggc 19680
gactgtccag agtcagcctg caggacggca gcagccctgc ccctcagagc acagctaggg 19740
tgggctgctt tgggatctcc cgtcattccc tcccagctgg cagccggcgg ccggcccatt 19800
ccttggtgtg ctggtcaggg gggcgtgcgc ctgctctgct caccctggga atgggacaga 19860
agctggcagc tcggagagga cagggctgga cccttgggtg gcctctggct ggaccatctc 19920
attgtcctca gacacagcct ctcgggtcta gtttcatttc ctgaaaaaca agtgcacaga 19980
actagagcag gagtcgagag ctacggcccc cgggccagat ccagccctgc cacctgtttt 20040
cacaccatgc tcaagctgag tgggttttac attttttaat tacttgaaaa aaaaaaagcc 20100
aaaggaggtt tcatgaccca tgaaaattat atggaattca aaaaaaaaaa attatatgga 20160
attcaaattt cagtgtccat aaataatttc ttgagacagg gtctcgctct gtcacccagg 20220
ctggagtgca gtgctatggc atggctcgct gtacccttga cctcccaggc tcaagcgatc 20280
ctcctgtctc agcctcctga gtagctggga ctacgggtgt gtgccaccaa gcccggctaa 20340
ttttttttta attttagtaa agacagggtc tttctatgtt gcccaggctt ttctggaact 20400
ccatcttggc ctcccaaagt gctgggatta caggctcgag ccacggagcc cagcctgttt 20460 ttgtttttttc actgataaag ttttgccggg tgtggtagtg tgtgcctcta gcgatttggg 20520
aggctgaggt gggaggatcg cttaagccca ggagtttgag gctgggctca agtgatcagg 20580
aggtgaacta tgatcatgtc attgcattcc agcctgggtg acagagcaag aacctatctc 20640
ttaaaaatat atatttaaaa agtattgggt gtggtggctc acgcctgtgg tcccagctac 20700
ttaggcatct gaggtgggag gatggcttga gcccaggagt ttgaggttgc agcgagccaa 20760
gatcgtgtca ctacactcta gcctgggtga cagagcccag accctgcctc tttaaaaaaa 20820
aaaaccaaaa aacatgtatt ggaacacagc catgcctgtt cagtcacgtg ctctccatgc 20880
tgctttctgc tccagagacc cttatggcct gaaagctgaa aatattttct atcctttaca 20940
aaaaagtttg ctgacctctg tcctggaaaa ttcatctccc aagttctctt ccggcactgg 21000
cgttcctggg tgtcctaaat ttggcccctg ttatttctga actctgtttt ggctctgttc 21060
cctcccagga gccaggacag gcacgttctc tgcatcttgt cccctgacgc ccagaggctt 21120
ggctcggctc aggcattctt ggaaatatct ggctccagga aaggcagagg cctcctgagt 21180
cggcccagag ggaacctgcc ccaggtctgg gggaggcctg acccagcaga gtggcttttg 21240
ccgatgggtt gggccggtca agatgtgctg aaagttgtcc tcagaaggcc actttgggat 21300
tccttcctcc agtattagag caactgagag ctgctcattg caagcctgat gttttcccag 21360
ttggccgggt ccaccgggtg ccctgggatt ctgggatctg ggtggaaagt agggggcttg 21420
ggggagtgtc ctgggttctg gaatccaggt ggcaagtggt gaggttcagg gagtggcttc 21480
tgagccacca taggggtctc tgtgggaggc tctgcccatc caggagattc cgcaggccct 21540
gccggcccag agccagcgtc ttgcgcttgc cgaggctaca gccagcccca gccgggtgga 21600
acagcccgtc gcctcctctc actttgtttt ggggccacct gggagtgtgg agcaagggta 21660
gagagggagg aagtggctgc cggccgctgc ccagcaccct tgtttgcctt gggccctctg 21720
tgggctcctt tttattgctc ttcaatgaag ccagggaaat ggacttcctt gcctcacttc 21780
agttcaacat gtctggaagt ttggtattaa aattaagaaa gtgtggaaat agagcaagaa 21840

-continued gagaaaaatc tctccaagag ataatagtga cctctgagct gggcgcggtg gctcacgcct 21900
gtaaatccca gtactttggg aggctgaggc gggcagatca cctgaggtcg ggagtttgtg 21960
accggcctga ccaagatgga gaaaccccgt ctctactaaa aataaataaa taaataaata 22020
aataaataca aaattagcca ggcatggtgg cgcctgccta taatcccagc taaggcagga 22080
gaatcgcttg aacctgggag gcaaaggttg cagtgagcca agatcacgcc attgcactct 22140
agtctgggca acaagagtga aactccgtct caaaaaaaat aaataaataa aaaataaaaa 22200
tagtgacctc tggccaggtg tggcagctca tacccgtaat cccagcactt tggaaggaag 22260
gccgagatgg gcagattgct ttagcacagg agtttgagac cagcctggcc aacatggtgg 22320
aaccccatct ctacaaaaat agaataaaat ttaagaggta atagtgacct tttggtagat 22380
cgaaacctgg attgctttct ttttctaaat gctgattctt ttctttgtgg tgtttgtgtt 22440
ctgtgccgat gtccctcccc cagccctgtt attgtgagtg gaagaagggg aaagggttcg 22500
cccgctactg tgagcccctc ctctcacgct gggtgtcctt ggagaagcct gcacttcttc 22560
attgtacgcc agggctgggt ccctccctgg agtggttctg tgctgctggg atggggccaa 22620
cccctcagat gttttctgag tgtcacacac aggtgtgtgc attcatggcc tttgcgtgtc 22680
ttcctgttgt ggaggcaaaa atgtgaagaa ccctagatga ttttgggacc agggctccat 22740
cacctgctgt tcattgcaca ccggagcatc caggcatggg tggagagctc agacttccag 22800
gcacggtcgc aggggctggt ctaaccatgt tcccgcccgc ctgctcgtca gaaccgcctg 22860
ttgggagctg ttatcatgat accatacctg ggccctgggc tatccgattc tgacttaatt 22920
gctccaggtt ggggccaggc cgttgtttgc tgttttgttg tttcttctgt gacgttagcc 22980
actgggctaa tctgagcccc tcagttacag gtggagaaac tgagacccat gggggtgcaa 23040
ggacttgccg aggacccaga gccccttggg ggcagagctg aggcggggcc tggctttggg 23100
tcccagagct tccagtcccc ttcccgctct cctaacagct tttttttttg agacaagatc 23160
tcaccctgtc acccaggctg gagtgcaatg gcatgatctc ggctcactgc aatcttcgct 23220
agctgcgttc cagcgattct cctgcctcag cctcccgagc agctgggatt acaggtgtgt 23280
gccgccatgc ccagctcgtt ttttttgta cttttagtag agatagggtt tcaccatgtt 23340
ggccaggctg atctcgaact cctgacctca aatgatccgc ctgcctcggc ctcccaaagt 23400
gctaggatta caggctggga tcacactgtg cctggcccta gcagctttgt cctgtgccat 23460
ccaacaacag atgaccgaag tctttgtttc ttaacatgca ttccatctgc cttacagttt 23520
tgccacctgc aaaacagagg acttgtcgct tttctggtaa gctggaaatg taatctggta 23580
gcaggaggcc tgtggaagct tgcctttaat ggccttgtgt ctctttcatc ctgtcctgag 23640
agccggagaa cttggatgtt gcacctaact caaccttcct gttaacatac agttctgcag 23700
gctcatggat catcagaacc acgtcctatc tcacgcggct gtatgcttcc gttggttcag 23760
gtgtttttac cttgacagta ttttctcctc ggtggctttt gcggtggttg cttttaatca 23820
gcattgactc ttcaagaaaa atatttagct gctacatctc agaggagaca gggtggaaag 23880
catctgagac ctgcaggctc agacttagaa ccagaagtgc cctcagagtt catccggccc 23940
tgacccagcg ggaaatgagt tcacagagaa gcgggagaac tttgccccag gccctgccgt 24000
tgctcataac tgccccaggt ccttacattt gctccaggtc ctgccccagg ccctgcagtt 24060
gctcataact gccccaggtc cttatatttg ctccaggtcc tgccccaggt cctgcagttg 24120
ctctgtgtgg tgggtgtgat ctggagccct ccgcccattg ctgcacctgg ggcaggcatt 24180

-continued

```
gctaattgat cccaggactc cttcctgcgg agcacgccct ggttctccag gcagccgctg  24240
cctgtcagcc tgcagtggtt cgggagagga cacctgcttg cctggtctgt tccaaatctt  24300
gcttctcatc ccagcacagg taggggtgc tatgggaaag ggatcctcag ttggccctgt  24360
cactgctcta tcagctgggg acgtggcatc ctagtgaaaa catcatggcc gggcgcggtg  24420
gctcacgcct ggaatcccag cactttggga ggctgaggag ggtggatcac ttgaggtcag  24480
aagttcgaga ccagcctggt caacatggtg aaacccatct ctactaaaaa tacaaaaatt  24540
cgccaggtgt ggtggcgggt acctgtaatc cgagctactc gggaggctga ggcaggagaa  24600
tcgcttgaac ctgggaggtg gagcttgcag tgagccgaga tcttgccact gcactccagc  24660
ctgggcaaca gagtgagacg ctgtctcaaa atctcaaaca aacaaacaaa caaaaaacaa  24720
acaaacaaag cgtcatttat ccagcacccc tggggaacca tgctacctgg tgttttatgg  24780
tacctggcaa ggtgcaggtg aagttgctgc tcttgggcat tgaacccgtc ttgtttgggg  24840
cagctcaggc cccaggcagg gtccgggttg gctctcgttg gtgtggccct ggcccatcca  24900
gacctatatt tctgccgtcc tgcaggtgat caatgttgat gggacgaaga ggcggaccct  24960
cctggaggac aagctcccgc acattttcgg gttcacgctg ctgggggact tcatctactg  25020
gactgactgg cagcgccgca gcatcgagcg ggtgcacaag gtcaaggcca gccgggacgt  25080
catcattgac cagctgcccg acctgatggg gctcaaagct gtgaatgtgg ccaaggtcgt  25140
cggtgagtcc ggggggtccc aagccatggc tcagccatgc agacttgcat gaggaggaag  25200
tgacgggtcc atgcctgggc ataagtgttg agctcaggtg ccccgacctg gggaagggca  25260
ggacaggaaa ggtgacagta tctggccaag gacagatggg aagggaccaa gggagctgat  25320
tagggagtgg ttatggacta ggaatgtcgg taacaatggt tagaaagtga ctaacatttg  25380
ttgagcacct gctgtgtgcc cggccctggc cgggagcctt cgtgcccaca gtgaccccgt  25440
ctgcaaatgt agttccttgc cctactcgca ctggggagca ggacgcagag ccgtgcaact  25500
cacaggtgcc aagctcagga ctccctcctg ggtctgcctg ggctgggctg tgcttgttgc  25560
ccctgtggcc cacgcatgtg caccttccac ctgaaagcca ggatcttcag gacgctcccc  25620
gaggaggtcg ttgtctggca caatgatttg tctcttcctg aaaaggtgac agagttacac  25680
tggagagagc agcatccagg tgcggcaggg acaggcctgg ggctcgcggg cagggactct  25740
gtgtcctgcc ggggtcccac actgcacctg cttgtcagag gcactcagtc aatctttgct  25800
gatgaaggat gagaggacag aggacgtgat gcttgctgct gcattgcctg cagtcctggg  25860
tgagatgccc gggttgactc tgctgcccgt cgggtggatg tgatgtcaga tccccggctt  25920
taaaatacga gggagctggg aattgaggga gcaggttggg gcagaaagca cagccccgtg  25980
gaagcctgga gctgaggcag tgtgggcgac ccctggagca gtgagtgctt ccttcatggc  26040
cttcatcgca ccctgcagtc ctcatgtagg ggatgccatc catgaattta gttttcccag  26100
cctcctttaa aaacgcgttc atgctggggc cggggcagtg cagtggctca catctgaaat  26160
cccaccactt tgggaggccg aggcgggtgg atcatgaggt caggagatcg agaccatcct  26220
ggctaacaag gtgaaacccc gtctctacta aaaatacaaa aaattagccg ggtgcggtgg  26280
cgggcgcctg tagtcccagc tactcgggag gctgaggcag gagaatggcg tgaacccggg  26340
aagcggagct tgcagtgagc cgagattgcg ccactgcagt ccgcagtccg gcctgggcga  26400
cagagcgaga ctccgtctca aaaaaaaaaa aaaaagtaca aaaaaaaaaa aattagtctg  26460
ggtgtggtat cacgcgccta taatctcact actcgagagg ctgaggcgga gaattgcttg  26520
aacccaggag gtagaggttg tagtgagccc gtatcgtacc actgccctcc acctgggcaa  26580
```

-continued

```
tagagcgaga ctctgtctca aaaagaaaaa aaaaaaaaga acatttatgc caggtgtggt  26640
ggctcatgcc tgaaatccca gaactttgga agactgaggc aggaggatca cttgagccca  26700
gaaatttgag agtgtcttcc ctgggcaaca tagagagacc tcatctctac cagaaaaaaa  26760
aaaattagcc cggcatggtg gcatatccct gtggtcccag ctacttaggg ggctgacgtg  26820
gcaggatcac ctgagtctgg aggcagaggt tgaagtgagc tgagatcatg ccactgcact  26880
ccagcctggg tgacagacag agaccctgtc tcaaaaaaaa aaaaaaaaaa aagcatttac  26940
tatccaccat ggaaggtgag actgacctgt gagtgattgt tcaaagaaca aaaaataaac  27000
cccagagata agacaaaagg gtgcctccat gggggtgtga tttaaagctg agaaattggg  27060
cttcttcccc ctcccctctc accccgtggt ttgctaaagg agatgggaaa aaggattctt  27120
tttttggctg aaatatttaa cactaaatta aagccaattt taacagcact ttggttgatg  27180
agtgaaatta acagactggc caaaaataaa cgaacggtct gtactatgtg aaaaagaggc  27240
agctttggcc atgctgggcc aatgtgagtt ttcagggttg ctgggaatgt ctgtgaatcg  27300
gaggaagggc ctagctggga ctctcaggag ccaaggccct gaggggcaac ttgcctggtc  27360
cctgccctga ggcgttcact gctttcttcc tgggccagat cacaggcccg gaggctggac  27420
cactgggctg gcactcttgc cgagctgctc cctgacttcc tgaccatgct cctttcagca  27480
gccttgctgc actttagttt ccttgaatga aaaatgggga tgagaatagc tcctacctcc  27540
aaggtgaatg gagtgagttc ggacaggtga ctccctggga ccagtgcctg gcgcctgaca  27600
aggtccagtc agagcccgca ctgctgttac tgataccctt ggctgtacca ggggagaact  27660
tggttgccat tgccaggtgt tctcccacca cccccactac tgtccctgtt tgatgtgtgg  27720
cgggaataaa gctgtgcaca ttggagcttt tggcacatcc tggctttcag gtgaaaggtg  27780
cgtgtgtgtt tgagggttta gcctggccaa cccagccatg aggtcggacc tgacctgggg  27840
gtgagtcctg agctcggcac ccctgagctg tgtggctcac ggcagcattc attgtgtggc  27900
ttgggccgca cccctttccc tgctgggctg ttgatgttta gactggagcc tctgtgttcg  27960
cttccaggaa ccaacccgtg tgcggacagg aacggggggt gcagccacct gtgcttctgc  28020
acaccccacg caacccggtg tggctgcccc atcggcctgg agctgctgag tgacatgaag  28080
acctgcatcg tgcctgaggc cttcttggtc ttcaccagca gagccgccat ccacaggatc  28140
tccctcgaga ccaataacaa cgacgtggcc atcccgctca cgggcgtcaa ggaggcctca  28200
gccctggact ttgatgtgtc caacaaccac atctactgga cagacgtcag cctgaaggta  28260
gcgtgggcca gaacgtgcac acaggcagcc tttatgggaa aaccttgcct ctgttcctgc  28320
ctcaaaggct tcagacactt ttcttaaagc actatcgtat ttattgtaac gcagttcaag  28380
ctaatcaaat atgagcaagc ctatttaaaa aaaaaaaaga tgattataat gagcaagtcc  28440
ggtagacaca cataagggct tttgtgaaat gcttgtgtga atgtgaaata tttgttgtcc  28500
gttgagcttg acttcagaca ccccacccac tcccttgtcg gtgcccgttt gctcagcaga  28560
ctctttcttc atttatagtg caaatgtaaa catccaggac aaatacagga agactttttt  28620
tttttttttt tgagacagag tcttactctg ttgcccaggc tggagtaccg tagcgtgagc  28680
tcagctcact gcaacctccg cctcccaggt tcaagcgatt cttctgcctc agcctcctga  28740
gtagctggga ctacagacat gcaccaccac acccagctaa ttttttttat atttttagta  28800
gagacagggt ttcatcatgt tggccaggct ggtcttgaac tcctgacctc aggggaacag  28860
acggggttgg cctcccaaag ggcggaaata acaggggtga gccaccgttc ccggcctagg  28920
```

-continued

```
aaaacttttt gccttctaaa gaagagttta gcaaactagt ctgtgggctg gccttctgat  28980
tctgtaaaga aagtttgatt ggtggctggg tgcggtggct cacacctgta atcccagcac  29040
tttgggaggc cgaggtgggc agatcacctg aggtcgggag ttcgagacca gcctcaccaa  29100
cgtggagaaa ccccgtctct actaaaaata caaaaaaaaa attaaccggg catggcggcg  29160
cctgcctgta atcgcagcta ctcaggaggc tgaagcagga gaattgcttg aacctgggag  29220
gcggaggttg tggtgagctg agatggcacc attgcactcc agcctgggca acaaaagtga  29280
aactccgtct cagaaaaaaa aaagtttgat tggtgtaacc aaagcgcatt tgtttatgga  29340
ttgtctgtgg cagcttttgt tctgccgaga tgagttgtga cagatctgta tgggctctaa  29400
agcctaaaac atgtgccatc cgcccctta cagaaaaagt gtgctgacct ctgttctaaa  29460
gtattggaca actacaatgt ttgctcattt attattctat gatttgtttt ctgctttttg  29520
ttgttgttgt tgttgttgag atagggtttc cctctgtcac tcaggctgga gtgcagtggt  29580
gtaatttcag ctcactgcag cctcgacctc ctgggctcta gtgatcctct catctcagcc  29640
tccctagtag ctgggactac aggcacacac caccactcct ggctgatttt tttttttttt  29700
tttttttttt gtggagacag ggtttccgca tgttgcccag gctggtttca aactcctagg  29760
ctcaaacacc cacctcagcc tcccaaagtg ctgggattac aggcgtgagc caccatgccc  29820
agcctattct actgtttgta ttacatagct ttaaaagatt ttttatgact ttaagtcaca  29880
agggttcttt gtagaaaaaa atatatatat aggaaagtat aaaaagaaag taaaaattgt  29940
ccataacctc tccagccaga gacgaccgtt gctgacacct cagcatattg cctttaagtc  30000
tttttctct aagatagcat ttctcttcat cacagtcata tgctacgcag aattctgtat  30060
cctgattttt tcacttgaca ttacaacagg tatttgatgg cgctgtgaca aactctttgg  30120
cacaatcttt taaatgtatg aaatactcca ctgcacagat gtttgctttt aggcttaact  30180
gttcttttat tttgcgtgtg ctggttacag ccgggcacag tggctcatgc ctgtaatcac  30240
aacactttga gagggtgagg caggaggatc acttgagccc agaagtttga gaccggcctg  30300
ggcaacatag tgagacccca tctctacaaa aaactttttt aataagtcgg gcgtagtggt  30360
gcatagctgt agtcccagcc accaaggagg ctgagttggg aggattgctt gagccccagg  30420
aggttgatgc tgcagtgacc tgagattact ccactgtact ccaacctgag cgacagagca  30480
agacttgtct ggggaaaaaa aaaaaaaaaa tatatatata tatatatata tatatacata  30540
tatacataca cgcacacaca cataatataa aaatatatat ttataaatat ataatatata  30600
atataaaaat atatatttat aaataaaatt tataaattat atttataagt aaatatataa  30660
tatataatat aaaaatatat attatataat atataataaa atatataata taaaaatata  30720
tatttataaa taatatataa tacatactta taagtatata tttaaaatat atgtaatgta  30780
tattttttaa tgtatgatat ataatataca tttataaata cacatttata ttattttata  30840
taaaatatat ataaaatctc caagttgctt tttccaaaaa ggtgtcttgc tgcatttcaa  30900
acattcattt aaaaacttga atgctggtga tctggtccag aatgtgttca gtagctgctg  30960
ccagtggcca agcatctcgg gagatgtcta caaaacacgc tggttctggc ctggcgtggt  31020
ggctcacgcc tgtaatctca gcactttggg aggctgaggc aggtggatca actgaggtct  31080
ggatttcgag accagccttg ccagcttggt gaaaccccat ctctactaat aatacaaaaa  31140
aattagccag gcgtggtggc atgtgcctgt aatcccacct acttgggagg ctaaggctgg  31200
agaatcgctt gaacccaggg ggcagaggtt gcagtgagcc gagatcgcac cattgcactc  31260
caggctgggc aagaagagcg aaactccgtc tcaaaaaaaa aaaaaaagat gctggttcct  31320
```

-continued aaaatgtggc ccttttcctc ctcacctgct gccagaccat cagccgcgcc ttcatgaacg 31380
ggagctcggt ggagcacgtg gtggagtttg gccttgacta ccccgagggc atggccgttg 31440
actggatggg caagaacctc tactgggccg acactgggac caacagaatc gaagtggcgc 31500
ggctggacgg gcagttccgg caagtcctcg tgtggaggga cttggacaac ccgaggtcgc 31560
tggccctgga tcccaccaag ggtaagtgt ttgcctgtcc cgtgcgtcct tgtgttcacc 31620
tcgtatgaga cagtgcgggg gtgccaactg ggcaaggtgg caggctgtcc gtgtggccct 31680
cagtgattag agctgtactg atgtcattag ccttgatggt ggccaggact ggtagggccc 31740
tcagaggtca tggagttcct tcgtggagcg ggtgctgagg ctgtatcagg cacagtgctg 31800
gctgctttca cctgggccgt ctcaccgaag tgtccatgga gcctgcgtag ggtgggtatc 31860
tgtgtcgatt ttacagatgc agaaacaggc tcagagaaac cgagtgactt ccctaaggtc 31920
acatacccag ttagagcaga gctgggccag gaagtgctgt ctcaggctcc tgaccaggtc 31980
tccttgcttt gcactcttgc caaaaccatg atccagaact gactttgagg tccccggacc 32040
tcaggctcct ccgaaatggc ctcttggagg ctgctgagcc acagcttagg acccacctcg 32100
agaggcaaat gtgctttgag ctgccaggcg tcctgggggc cctgccttgg gcacggggtt 32160
cagacaggcc ccagatgtgt ggggcgtctt tctggacttg agttttcttt tctgtgtggt 32220
ggacacagtg ctcacccctt aaagcacctg tgatgtgtgc agcagcccaa tccctgcctg 32280
tcgcctgttc tgctagggaa ggaaggaata cttcaggatg gcaggacaac agaaagaggt 32340
ccaggtttta gagcaagggc aggtcaaact tagaaaattc tggaatgagg atgtgcattt 32400
cctcttctgg atctgctaaa agaagaggga aggaggggct gctgggggag gagcccagag 32460
ccgagtttac atccggatcc cgcaaggcct cccctgccct gaggtcttgt tttgtgatgt 32520
gcttgtgtcc atcctggttt ctgccgtgtc cccaacatcc ggccaagctt aggtggatgt 32580
tccagcacac actcaccctg tctgtgcacc tgtttttgtg tccgtaagtg ggtatttact 32640
caccttacga gtgagccact gtgggaattc agggaggtgg cgcagtgacc accccctggag 32700
ggatatgtgt gtggcagggg tcgagggtct cgcccttccc tgcttcctgc gcgtggcttt 32760
ctccaggacg gggagggctg agctgaagag gtggggacag ttgcgtcccc ccgccaccca 32820
ctgtcctgcg gtgagagcag actcactgag cctgcccttc tcccttgtgc cttccagcta 32880
catctactgg accgagtggg gcggcaagcc gaggatcgtg cgggccttca tggacgggac 32940
caactgcatg acgctggtgg acaaggtggg ccgggccaac gacctcacca ttgactacgc 33000
tgaccagcgc ctctactgga ccgacctgga caccaacatg atcgagtcgt ccaacatgct 33060
gggtgagggc cgggctgggg ccttctggtc atggagggcg gggcagccgg gcgttggcca 33120
cctcccagcc tcgccgcacg taccctgtgg cctgcaagtt ccccaacctg gcaggagctg 33180
tggccacacc cacgactgcc cagcagcctc accctctgct gtgggagttg tccccgtcca 33240
cccctgggtg cctttgctgc agttatgtcg ggagaggctc tggtgacagc tgtttcctgt 33300
gcacctgctg ggcactaggt cccagctaat ccctgtgcca ggactctaat ttcaccctaa 33360
cacacatggt ggttttcatt gctggggaag ctgaggcctg agcacatgac ttgccttagg 33420
tcacatagct ggtgagttca ggatccccca gagataccag ggccagcact cgatccccac 33480
ccagccctga accccaccat gtgctgggat tgtgctggga gtgtccacac gcctgggacc 33540
ccagggctgg tgctctcatc tcctttttcc agatcatgag aatgaggctc agggaagttt 33600
gaaaaaaacc tatcccaagt cacacagcaa caggagcagg atttgaaccc agaaaagggg 33660

-continued accgcacact ctgttctgct agagtagtta gctgtcctgg gtgatatggc aggtgacagg 33720
ggcaactgtg cttaacaaag gaacccccat ccccctgcc aagttgggag actagaaggt 33780
caggggcaga agctctgaag ggccaggtgc agtggctgac acctctaatc ccagcacttt 33840
gtgaggccaa ggcgggcaga tgatttgagc ccaggagttc aagatcagcc tgggtaatgt 33900
agtgagacgc catctctaca aaaaaatttt ttaaaaatta gctgggcatg gtggttcatg 33960
cctgtagtcc aagctacttg ggaggctcag gtgggaggat tgcttgagcc caggaggttg 34020
aggttgtggt gagctgtgat catgccactg cactccagcc tgggcaatag agtgagaccg 34080
tctccaaaaa aaaaaaaaga agaagaaaaa gaagctctga ggctccaagt ccccaggcac 34140
cccttggctt gagggcagac aagggaggag agggtcacct gggcagccct gacttttgtc 34200
ccctggcaaa gggaccttca gtgaccttgg ccctaggaga gcctctgagc acgtcagcca 34260
tgtcgaaccg ctcaggaagg gcagcaagaa tttggcttct gacctctgcc tctcctactc 34320
gccatctgca ctgggtgtgg ttgtgcccat tttacagatg aggaggctgg ggcatcgacc 34380
agctgaatgc cttgtcccag gtactgcgta ggcagagctg gcagttgaac cccgtgtcct 34440
ggttgtcgct gggggtgggc tgcaccctga cttgtgaggc cagtagcaag gtttgcacgt 34500
gacttcgtga ccgtcaccca gctctgcagc acatcccgtg acccagctca tccaggccgc 34560
atgcaaacct gttgccaggc gagaaaccag tcaccgcaca gctgtggttg cctgaaatga 34620
ttaagctcat taatcacccc ggagtgagga cagactcaga tgaaaaccag caaaagccct 34680
ggaaactcat gtgaccctgc caatgagggc ggccatgtgc attgcagcct ggccgtcact 34740
cctcggtacg tgttttggac ttaaacgctc cggatgttta ctgagtgctt gattaataac 34800
atggaaggcc tggtctcatt gctgtgggag tgaaggatgc acagccaggc ctgacatgat 34860
gagaacaaga acctggagtc tcgctgcctg ggtggtaatc ctggccctgc cacttagcaa 34920
ctgtgtgact gtagccaggt cacttaattt tgctagatcc tgcctgcgct tcagtggatc 34980
ttgctggttt tccaaggtgg ccaaacactt taaggcattc atgtggtcgc taggctgcag 35040
ggttgaaccc tggctcaccc cgcagggcgc cgtgtgctct gtggcctggc tgtgcctttg 35100
ctgacaccgt gcccgtgtgt gttcatgcag gtcaggagcg ggtcgtgatt gccgacgatc 35160
tcccgcaccc gttcggtctg acgcagtaca gcgattatat ctactggaca gactggaatc 35220
tgcacagcat tgagcgggcc gacaagacta gcggccggaa ccgcaccctc atccagggcc 35280
acctggactt cgtgatggac atcctggtgt tccactcctc ccgccaggat ggcctcaatg 35340
actgtatgca caacaacggg cagtgtgggc agctgtgcct tgccatcccc ggcggccacc 35400
gctgcggctg cgcctcacac tacaccctgg accccagcag ccgcaactgc agccgtaagt 35460
gcctcatggt cccccgcacc tcactccctc gttagatcag gctggttctg ggagctgacg 35520
ctgaaaggag cttctcatct ggggttcctg ggtgtacata gatggttggg taggttgtgc 35580
actgcacaag ctgcatgatg ctacctgggg gtccaggtcc aggctggatg gacttgttgc 35640
ttcatcagga catagataaa tggccaaaac tcctcagctg gaaggtcctg ggcaggatct 35700
ttgggtgtga aaaccagtca caggggaagg gtgcttgctc atactgccag cacagtgctg 35760
agtgctttcc atagcgctcg tttactcctc aagcctggag ggtggggagt agcatggtcc 35820
catttcacgt acaaggaacc cgatgcacag agaggtgtgg caacccatcc aaggccatac 35880
aactggggtg ggttgagccg gggttgactg tggcaggctg gctcaagagt ccctgctcct 35940
gaacccttgc caggcagcct ggcatcagct cggggaattt ttgccctgac ccttggaagc 36000
aagtgggcct ctttgttctc atgtcagtga tgagaagagt gactttccta tggcccctct 36060

-continued ggagtacagg tgtttcctgt tggcgggctc ttcccccatg acatcagcag cgagctggtt 36120
atgattccct acgcagaact tgatagttta taaagctctt tgtcatccag gccccgttgg 36180
agtctcacgc agacctggtc gcaggcgggg ctggtcttgc ctgtcccagc tgcatggatg 36240
gggaacttga ggcttgcaaa ggttaagggg ctgttcgagg cccacgctgg caggagatgg 36300
gcctgggcca gagtctggga cttcccatgc ctgggctgtc tttggtcctg ttgctcacca 36360
tccctccctg ggccatgac cttagagagc caaatggagg tgcaggtaac ccacggcaag 36420
gaggggttgc catgactcag agtccccgtc ctgtggccgg cagtacctgg tgcaacgact 36480
tggatttcag accagccact gtagcccgct gacggtgcgc tcgaagtgcc acagcttctg 36540
aagccaggca ggactcaggc caggagactc tgttagctgt tgagagggag aggccaacgg 36600
atgttctggt tctgctagag agctggttct tcggatcctg gtaccagtgc actgagagga 36660
ggcccagctt gattctgggg ctgccttgtg gtggcatgtg ctgctcactg acaccctcga 36720
ggagtgtctt ctctcgggct tgttgactgt gcccggtttt ccgcagttca ctggtgcaca 36780
cataggcaca tagcaaaccg cacacacagt cgtgggtatg agtttcacta cattccacca 36840
ccagtgttca ctaccattac ctgccttccg tcttaagtgt tcatcattta aaaataaatt 36900
tattgggctg gacgcggtgg ctcatgactg ttatcccagc actttgggag gctgaggcgg 36960
gcagatcacc tgaggtcagg agttcaagac cagcctggcc aatatggtga aactccatct 37020
ctactaaaaa tacaaaatta gctgggcatg gtggggcatg cctataatcc cagctactca 37080
ggaggctgag gcaggagaat ggcgtgaacc cgagaggcag agcttacagt gagcccagat 37140
agcaccactg cagtccagcg tgggcaacag tgcgagactc catctcaaaa aaaaaataaa 37200
taaataaaag aaaaataaat ttatgatcta tttcaaaaat aacacatgta ctttgaaaca 37260
gcagagacac atatgacacg gagaatgaaa ttccccatag cgcacccccca agagacagcc 37320
ctggtccccc cgtctttccc gtggacctcc agcggggcag atgctgagcc gcctgttgtc 37380
gagtggcatg ctatcccgtc ctccagctcc tctgtggctt acagacaccc acctgcagcc 37440
ctgtctttgc ctcctctagc gcccaccacc ttcttgctgt tcagccagaa atctgccatc 37500
agtcggatga tcccggacga ccagcacagc ccggatctca tcctgcccct gcatggactg 37560
aggaacgtca aagccatcga ctatgaccca ctggacaagt tcatctactg ggtggatggg 37620
cgccagaaca tcaagcgagc caaggacgac gggacccagg caggtgccct gtgggaaggg 37680
tgcggggtgt gcttcccaag gcgctcctct tgctggtttc caggctgctg cccctgtcct 37740
tagcagaggg aggaaacaga ggatggctct gggtgaatga tgacttgggc ttcgattatg 37800
tagtcacagg gtatgaccct gagatgcgtg gaaccccgag actgtgatta tatgtagaaa 37860
ctgggtttcc ccgttgttta agtagtcatg gtggggtcag accccacagg acttttgtct 37920
tttcaagaaa gaaaatggtc gtgtgtcatg caggggtagt tggtactggt taatccaggt 37980
ttatccttta ttttgtggga actgtacagt catttctgct acaatgctgt atatgctctt 38040
ctgaaagaca cctatgcaaa atcgcacagt aaaaatgaca caactcatag ggaaagcggg 38100
gccagggcac agccctcaaa atctccatca atgacatgta agaaaagaga ggaacctggg 38160
aaatagcaaa gtgccttttg cacattaaat ggttagctat atcccacaat actgtgcatt 38220
cgtaaacgtt aatgctgcaa taaatacggc acttcacctt gggaagatct ggagttggct 38280
tatgagtgtg gaagggtgta gcgcatgagt ttttgtgaaa cactggaagg aggattgtgg 38340
gaaatcaaat ggaaagttct caccccaggc gtggagaaga gtgggtcatg gccccagcag 38400

-continued tgagcccagg gaggtcagag acggaggtgt gtgtgtgggt gtgaccctgc gcagttccct 38460
gccggctgta gttttttgca ttcgcttaat gtttctcgtg gaggaaattg tgcatgagca 38520
aatgtgaaac cgtgctgtgc tcaaattgtc ctaatacatc attgcattgg aacagattgg 38580
ctttnttttt tttttttttt tttttttttt tttgaaatgg agtctcactc tgtcaccagc 38640
ctggagtgca gtggcatgat cttggctcac tgcaaccttt gcctcctatg ttcaagtgat 38700
tttcctgcct cagcctcctg agtaactggg attacagggc atgagccacc gcggccggcc 38760
agatttgcat ttttgaaaca actgctaggc tgggcgcggt ggctcacacc tgtaatccca 38820
gcactgtggg aggccgaggc aggtggatca cctgaggtca ggggttcgag accagcctgg 38880
ccaacatggt gaaaccccgt ctctactgaa tatacaaaaa tcagctgggt gtggtggcgg 38940
gtgcctgtaa tcccagctac tcaggaggct gaggcaggag aattgcttga acccaggagg 39000
cagaggttgc ggtgagccga gatcacacca ttgcactcca gcctgggcaa caagagcaaa 39060
actccatctc aaaaaataaa aaatagaaaa acaagtgctg tagcggaagt gagcactttg 39120
cggagtcagg cttgtgtggc ctgttccaca aatgatgtgc tcacggtggc ctcaggccca 39180
cctggagtct gcagcatggg gcacaacagg ttcattagtg tagaattcca ggacaggcct 39240
ggctcctaag cagccttctt ttacaaaaac tgcagagccc gcctgtatcg tagcactttg 39300
ggaggccgaa gtgggtggat cacgaggtca ggagttcaag accagcctgg ccaacatggt 39360
gaaaccccat ctctactaaa tatacgaaaa ttagctgggt gtggtggcac gcgcctgtag 39420
tcccagctac tcgggaggct gaggcagaat tgcttgaacc tgggaggtgg aggttgcagg 39480
gatctgagac catgtcattg cactccagcc tgggcaacag agcgagacgc catctcaaaa 39540
aaaaaaaacc tacagagcca cacggcctct ttctccaccg agtgttggtg tgggagcttg 39600
tgttattgtg gtgaaatctt ggtactttct tgaggcagag agaggctgag cgcctggaga 39660
gactttcaca tgggtcgcca tgtccgccgt cggtttcgct gttgtgctcc ccatctgaag 39720
gctggtgccg tccagacagg ctggacgccc ctttccacca gatccttcct cccgcagcag 39780
tttctagtta cgttgtactg tgaggtctgt gtccttggtt gatggcaaaa gtcagccgaa 39840
ttgaaattca gagccatgcc tggctccctg gagcttctct cctgggcagc tgtgatcatt 39900
gcctctgctg tggtgtgggt ggtggaaatg gattcctttc atcttgcttg ctacaggtga 39960
ctgtcacgtg gagtcctttg gagagaggga cgtgttaatt gatggatgtg gctcccatgc 40020
tgagaaagct cctgggcgta cattgcctta gagtttcatt ggagctgcgt tcttttatgg 40080
tgtctgctag gcagaagtga tgaagacttg gaagaaaacc cagaaggttt tccacttaat 40140
ttggaaaatg tgcttttccc ctcctgtgtc ttttgctaag gtccagcctc ctgcagcctc 40200
cccgctctgt ggactctggc tttgattctt tattaggagt ccccctgctc ccccaaaaga 40260
tggtgtctaa attatcatcc aattggccga ggttttgttt tctattaatt gtttttattt 40320
tttattgtgg taaatttata taacataaaa tttgccattt taattgtttt gttattgttg 40380
tttttgagac agggtctcac cccagtgccc aggctggagt gcagtggtgc gatcatggct 40440
cactgcagcc tcagcctcca gggctccagt gatcctctca cctcagcctc tctagtagcc 40500
gggactacag gcatacacta ccacatctgg ctgatttttt gtattttttt tttattgtag 40560
agacccgcta tgttgcccag gctggtctca actcctggac tcaagccatc ctcccacctc 40620
accctcccaa agtgctggga ttacaggcat gagccacaac acccagccat tttaattttt 40680
tttttttttt ttgagatgga gtctcactct atcgcccagg ctggagtgca gtggcgtggt 40740
atcaactcac tgcaacctct gcctcccagg ttcaagcgac tctcctgcct cagcctcctc 40800

-continued ccgagtagct gggattacag gtgcccatca ctatgcctgg ctaatttttg tattttttag 40860
cagagacggg gtttcaccat gttggccagg ctggtcttga actcctaacc tggtgatccg 40920
cccgcctcgg cctcccaaaa tgctgagatt acaggtgtga gccaccgtgc ccggcctttt 40980
tttgtttttg agacagggtc ttgccctgtc acccagactg gagtgcaatg gtgggctctt 41040
ggctcactgc agcctccgcc tcccaggctc aagttgtgca cctccacacc tggctaactg 41100
tattttatgt agagacagat ttcaccatgt tgcccaggct gggcttgaaa tggactcaag 41160
cagtccaccc acctcagcct cccaaagtgc tgagattaca ggcgcgagcc accgcaccca 41220
gcccatttta cctattctgc agttgacagt tcagtggcat tcagtcagtt cacgaggtaa 41280
ccatcactgc cattcatctc cagactactt caccttctcg gcagatgtcc gaaactgtcc 41340
gcattgaaca cactcctcat ctccctctga cagccaccat tctactttgt atctctctct 41400
gccttctcta ggtacctcat gtaagtggaa ttataccaat atttgccctt gtgtgactgg 41460
cttctttcat gtgacatggt gtcctcaagg ttcatctgtg ttatagcctg tgtcagaatt 41520
tccttcctta aagcctgaat aataacccgt tgtaaaggct gggcgcggtg gctcacaccc 41580
tctaatccca gcattttggg agtccgaggt gggcagatca cttgaggtca ggagtttgag 41640
accagcctgg ccaacatagt gaaaccctgg ctctactaaa agtacaaaat tagctgggtg 41700
tggtggcgcg cacctgtaat cccagttact caggaggctg aggcaggaga atcgcttgta 41760
cccgggaggc agaggttgca atgaaccaag attgtgcctc tgcagtccag cctgggtaac 41820
agagtgagac ttcctgtctc aaaaaaaaaa aaaatcatcg gatggatgga cggaccactt 41880
cttgttattt atccatccac gggtgctagg tttcttccac ctttggttgt cgtgaataag 41940
gccactatga acatttcctt ccgtggtgaa ggttttgtac tagtgaggaa aaggcgtgtt 42000
tgtggtgttg cataggattc tggtaagaaa gtttgcacta accataagta tttgtactac 42060
attaaaatga aagctcaggg gccgggcgcg gtggctcacg cctgtaatcc cagcactttg 42120
ggaggccagg gcgggcggat catgaggtca ggagatcaag accatcctgg ccaacatggt 42180
gaaaccccgt ctctactaaa aataccaaaa aactagccag gtgtggtggc gggcacctgt 42240
agtcccagct acttgggagg ctgaggcagg agaatggcgt gaacccggga ggcggagctt 42300
gcggtgagcc gagatcgctt cactgcactc gagcctgggc aacagagcaa gactccgtct 42360
cacgcaaaac tctgtctcac gcaagactcc gtctcaaaaa aaaaaagagt tcagggttta 42420
tgaaactggc cagccgcgta aagtttgctg tgttgttttt gtgcccggga ggagtgtggc 42480
cagggtgtca cgtcacacag tacacgtttc tcagatggtg gttctccaga ctgctgtccc 42540
aaagtctgtt tttgcatctg gttcccacag acccaccctc cacggtgagc ctgattttgg 42600
ccagggtagc tggaatcttg cttgtctttc agcccggcag ctgtaccagt ccagggtcca 42660
cagctagtgg cttttaggaa ggaatttgtt cagttggctt tgacacatgg ccccctaggg 42720
tccacagctc tgtagtgatg tggatgttgt tatctacaaa gacacatgat ccttcgtgtc 42780
cagatgaaag tgatgatgtc tttgcagctg cccagcaagg ctgtgtgtgt gtgtgtgtgt 42840
gtgtgtgtgt gtgtgtgtgg tgtgtgtgtg gtgtgtgtgt gtgtatgggg gagggaggca 42900
ccctttccat ctgggggtgt gtgtgtgtgg ggtgtgtgtg tgtgtgtgcg cgtgtgtgtg 42960
gtgtgtggtg tgtgtgtgtg tatgggggag gcaccctttc catctgggtc caagagactg 43020
ggcctgggga agacgcttct ttttatctac ttagagactt tgttttattt gtattttttt 43080
gagacagggt ctcactctgt cacccaggct ggggtatggt gatatgagca tagctcactg 43140

-continued

```
cagcctcggc ctcccaggct gaagcgatcc tcccacctca gccttctgaa tagctgggac  43200
tgtaggcgtg cgtcaccata ctgagctatt gttttttttg tttggttggt ttaatttttt  43260
ttgatacaga tggagtcttg ctatgttgcc cagactagtc tcaaactcct gaactcaagt  43320
gattctccca cctcagtttc ccgacattct gggatcacag gtgtgagcca ctgctgtctc  43380
cctgttttat taactgctga aagacctaga taaagaaagt ctgaaaagac ttactatcag  43440
agcaccatcc taagatgatt ccctctgact caatggagag ggaggggagc ttttccttca  43500
ggcctgggtg gcaggagccc aggtgctcca ggccccattt gccccaggcc aaatcactcg  43560
ggaacttgga tgcagctgtc tttcagggta acccaaagga accagatccc cgcaggcagt  43620
aggcttctgg gctgtcctct cctcctacgt cagctcagta agagcccttc gaagggatgc  43680
tgtgtcggag gccccaaaag cccaggctca tccctgagat gcacagggtg ggctgggctt  43740
aggcagcgct cgagcatctc ctggacggtg accccagaga gtgtggagac ggagagtcct  43800
tgagagtcac tgagagacgt ggctgccctg ccttcccaag aggggctctg agtcattccc  43860
cacactcacc tgcccctacc caccctcacc tggcccccag cctcacctac ccccacatct  43920
gtaccgatcc ctttacccgc accttcccta cccaccctca cctcccctgt accttcacct  43980
cccccactca cccgcccctg caccctcacc tgtcccccac cttcacctaa cccccaccct  44040
cacctgccct cccctcacct ggcctccttc cgttggggaa ggggttgtaa ggggcggccc  44100
ccaaactgtc tgtcctggtg ccctgcagag aaaacagtac gtgagggccg cagtccaaaa  44160
gcttgagtcc tggaaggtgg aggagacagg gatgtgttgg gaagggcccc atggtcttgg  44220
atcccttctc gactgtcaat ggggccttca tgggagcgcc agtctagtga tgcacagctg  44280
ggtgcccggc gggtggctga ggaggcctaa agtccgaggc ggcaagagct cttccagagg  44340
ctgttgtcct aatcgctctg gcatactcag gcgggcacgt agttaggagc tgattggaga  44400
ggagagaccc ccacaccaat actgggattt gactttcagg ctaaacttga gaagtgtggc  44460
ctctgctgtc ctgccagagc tctccagcca gtgcccaggg ctctccagcc agtgcccggg  44520
ggtctccacc agtgcccggg ggtctccgcc agtgccaggg gtctccgcca gtgcccaggg  44580
gtctccgcca gtgctcagga gtcttggttt ctttgtctta cagccctttg ttttgacctc  44640
tctgagccaa ggccaaaacc cagacaggca gccccacgac ctcagcatcg acatctacag  44700
ccggacactg ttctggacgt gcgaggccac caataccatc aacgtccaca ggctgagcgg  44760
ggaagccatg gggtggtgc tgcgtgggga ccgcgacaag cccagggcca tcgtcgtcaa  44820
cgcggagcga gggtaggagg ccaacgggtg ggtgggggtg ctgcccgtcc aggcgtgccc  44880
gccgtgtctt ctgccgaatg ccagcctctc acaggctggg gagactttcc accctgggga  44940
tccaatgggt ggctttccag ggtcccaaaa gcaaacacag gctctttcac agcccctcca  45000
ggaaagcaga aagccccaag ggctggaagg gaagggggag ctctgctgag aggttacaag  45060
gcagcgctgg ccgacgggag ttgcagttga taggttttgt atcatccttg ttaaacttga  45120
accctgtgca gaaatccctt ccacggcatg gggctgcct gttgactcgc tcctgttcca  45180
ccacagggag ctcctgggct tcttcctccc agaggccccc gacgctccca cctgttggtc  45240
gtcagagctt ctggttggtg ggaaggcacc caggaccttg aggtctccag agagaaaagc  45300
cagggaaaga gggagaccga aacccatgtg acatgaaact caggctccaa actgagcacg  45360
ggaacgtttg gggacaggag cgcgatggcc ttcctcagat agctgggggg ctggcatgaa  45420
gacgggagct acagccagca caggtcctgg gccgggagcc cagagattga gccctgactc  45480
tgtcacttac tggccacgtg accttgggcg ggtggcatag cctcttggag actcagtttc  45540
```

-continued

```
ctcattggta ggagtgacgg ccacagtggt gcggcctctg cagcacacgg ggggctcggt  45600
gggcggaagc cccgggtcta taaggcggct gtgcaggagc cagccgagct ggtctcccaa  45660
cagccagggc tccggggtcc ttagcagctg tggggggcct gcacctgttt cccatggctg  45720
ctgtcagaaa ttaccagaag ccaggtggct gagagtaatg gacacttgtt ctctcacagt  45780
tcctgagggc tgaagcccga gatcgaggtg tgggcagggc cctgcgccct ctgaaggctc  45840
tgagggaacc tttgggcttc tggtggctcc aggcacccct tgacttgtgg tcctgtcact  45900
ccagtctctc tgtctggctg cacatggcgt ggcctcttct gtaccattga aggacacttc  45960
agttggattt agggcctacc ctcacccatt gtggtcgtat cttgatcctt catgacattt  46020
gtaaagaccc tgcttccaaa taagctcaca ttctgaggtt ctggggtgag cgggaatttg  46080
gagagcattg ttcaactagt atagaatgtg acctgtcagc ctcgggcagc cctgagaggc  46140
aggggctttc cacagcccag ctgggtgccc tgggctccgt gctgtccgag gagacgccat  46200
ccccacaccc gtccttcacc cgccaccctc ccgcaggtac ctgtacttca ccaacatgca  46260
ggaccgggca gccaagatcg aacgcgcagc cctggacggc accgagcgcg aggtcctctt  46320
caccaccggc ctcatccgcc ctgtggccct ggtggtggac aacacactgg gcaagctgtt  46380
ctgggtggac gcggacctga agcgcattga gagctgtgac ctgtcaggta cgcgccccgg  46440
ggcctgccct aaccgcagac acccggcctt cattgtcagt aatggcagca gctgccacat  46500
tgtccgagac ctgccgtgag cccagtgccg cgccaggggc tttgtgtgta gcgtgttttg  46560
tcctcacact gacagctgta ggctggggtt ctgagtgagc cccacagggc agaggcagaa  46620
aatgagtctc agagagggtg agcgagctgc ttgggggccc acagcaggag atggagcagg  46680
actgcagcct agcctctgcc cccagcacct gcgcaagaag ctgctctgct ctggactgtg  46740
ttaggctgcg agggctggag agaaatgaga gttggtgctt agagaggggg cgcaggtccc  46800
catggctttt cctcttatga tgaggtagat gggtgaaggg aggggccatg cttgcagggg  46860
ccagtgaccg aggcccgccg ttggaactga tggccttcat cccgagccca gcccaggtgg  46920
gagcagggct ttccgagggc ttgtcttggg tcggcctgct tccagggact ctgctgcagc  46980
tcccacccct gtccaaagca tggaatcccc caggctccct ggcagtcctg tcaacctctg  47040
tcctcccaag ctgagtgtgg ggcaagttct ggaggtcagc actgctcagg ggggcccacg  47100
ggctgcttgc aggggccaac cgcctgaccc tggaggacgc caacatcgtg cagcctctgg  47160
gcctgaccat ccttggcaag catctctact ggatcgaccg ccagcagcag atgatcgagc  47220
gtgtggagaa gaccaccggg gacaagcgga ctcgcatcca gggccgtgtc gcccacctca  47280
ctggcatcca tgcagtggag gaagtcagcc tggaggagtt ctgtacgtgg gggctggcag  47340
tggggtgggc agggtggcct ctaaacccga cccctggagg aggctggagg ccagtgcaag  47400
atcctgtgtg gcctcagcca ggcggtggtc tctgccagat gccaactgtt gcccgctggg  47460
gttcagcgac atgtccgaat gtcccgaggc ctctgaggtt gttttctttt gccgcagaac  47520
aaatcaccac gaacagcgtt ttaagacaac accaactctt tttttttttt ttttttttga  47580
gtcaggatct tgctctgttg cccaggctgg ggtgccctgg tgcaaacaca gttcactgca  47640
gcctcgacct ctgggcttaa ttaagtgaac accttgcctc agcctcccag gtagctggga  47700
ctacaggtgg gcaccaccac acctggctaa tttttttttg tagagacggg gtttccccat  47760
gttgcccagg ctggtctgca actcctgggc acaagctatc tgcctgctgt ggcctcccaa  47820
agtgctagga ttataggtgt gagccactgg cctgacaaca cccacggatt gtctctcagt  47880
```

-continued

```
tctgtaaggc aaagtccagg cacagcgtgg ctcacctggg ttctctgctc agggtctcac  47940
ggggccagaa tcaaggtgtc aggaacgctg ggccctcagc ggaggctctg tggagaaatt  48000
agcttccttg ctcactcagc aggtagcagt tgtgggatcg aggttctgtt ttctctctgg  48060
ttattggtcg gggaccactc tcagctccta gaggccaccc caggtccttg ccccgtggcc  48120
ctctctgcct cagcagtggg ggctccctgc gtcagtccct cccgcacctt gagtctctct  48180
gatttgcttc taaagggccc tgtgattcgg ctcagccacc tttagattag gttagcctcc  48240
cctttgatag actccaagtc ggctgattaa taaccttact cacatctgca gaatcccttc  48300
tgccacataa ggtcatgacg ccgtgctggg gactggggtg ggaaattacg gggtcattta  48360
ggattctgcc tgccactgcc ttgctgtgtc ccagggcttg ggggaggggc ctccacagct  48420
gggaccacag tccttcctcc cctccatggt aaccatctga ggattacttg agaccagcct  48480
gggcaacatg gtgagaaccc atccctacaa aaaatacaaa caaaaaggga ccaggctggg  48540
cttggtggct catgcctata atcccagcac tttgggagac caaggtgggc tgatcacttg  48600
aggttgggag ttcgagacca gcctgcccaa catagtgaaa tcccgtctct actaaaaata  48660
caaaaattag ctgggtgtgg tggcaggcgc ctgtattccc agctactggg gaggctgagg  48720
tgggagaatt acttgaacct gggaggcgga agttgcagtg agccaaaatt acgccactgc  48780
actccagcct aggcaataga gtgagactcc gtctcaaaaa aaaaaaaggg ccaggggtgg  48840
tagtgacaaa gagaccctat cccaaaaaaa ccgaacactg aatccttgag actgagtaag  48900
gacactgtga aatttttctg ggtggggcag ggaacagagc gtcttctgtc atttcttcca  48960
cctgggtgtg gtcagctctc cctccaagct gcctcctctt cttctcattg tccgggtgtt  49020
ggacacattt ggttaactgg atagaataac gcgagttccc agggacttgg tccatttgct  49080
attttatttt attttatttt attttatttt atttatttat ttatttattt atttatttat  49140
tgagatggag tttcgttttt gtcgcccagg ctggagtgca gtggcgcgat ctcggttcac  49200
tgcaacctct gcctcccagg ttcaagtgat tctcctacct cagccttcca agtaactggg  49260
attacaggca cccaccacca taccaggcta atttttttgt atttttagta gagacgggtt  49320
ttcgccattt tgcccaggct ggtcttcaac tcctagcctc aggtgatcca cgcacctcgg  49380
cctcccaaag tgctgggatt acaggcatga gccaccacgc ctggcaccat ttgctatttt  49440
aattcccatg tgtattagtg tcccacggct gctgtaacaa atgaccacaa actggatggc  49500
ttaaagcaac agaaatggat tcccccaatg tgctggagac cagaagcctg cgaccaaact  49560
gttgggaggg ctgtgcttcc tctgggggct ccagggagga tctatttgtt ggcccttcca  49620
gtgctgtggg tgccagcgtt ccacacttgt ggatgcgccg cctcaacctc tgcccatctt  49680
catgtgtcca tctcctttgt gtctgcgtct ttacctcttc ttcttgtctg tgttgcctct  49740
tataaggacg tttgtcattg ggtttagggc ccacccaaat catccgagat gacctcgtct  49800
tgagatcctt aacctgcaaa gaccctttttt ccaaaaaaag gttatgctca cagattctag  49860
gccttaagac atgggtgtat ctttctgggg ggcactatcc aaccccttat acaatgaaag  49920
acgggaagag ggccaggtgt ggtagttcac gcctgtaatc tcagcacttt aggaagctga  49980
agcgggagga tcacttgagc ccaggagttt acaagtagct aggcaacatg atgagacccc  50040
atttctacaa aaagtaaaaa aaaaaaaaaa aaaaaaaaag ccaggtgtgg tggctcacac  50100
ctgtaatccc agcactttgg gaggctgagg caggcagatc acgaggtcag gagattgaga  50160
ccatcctggc taacacggtg aaaccccgtc tctactaaaa atacaaaaaa ttatggccgg  50220
gcgcagtggc tcccgcctgt aatcccagca ctttgggagg ccgaggtggg tgaattacaa  50280
```

-continued ggtcaagaga tcgagaccat cttggctaac acggtgaaac cccatcaaga tcacaaggtc 50340
aagagatgga gaccatcctg gctaacacgg tgaaaccccg tctctactaa aaatacaaaa 50400
aattagccgg gcatggtagc gggcgcctgt agtcccagct gctcgggagg ctgaggcagg 50460
agaatggcgt gaacccggga ggcggagctt gcggtgagcc gagatcgctc catgccattg 50520
cactccagcc tgggtgacag agtgagactc cgtctcaaaa aaaaaaaaaa aaagaaaatt 50580
agccaggcac agtggcaggt gcctattgtc ccagctactt gggaggctaa ggcaggagaa 50640
tggcatgaac ccgggaggtg gagtttgcag tgagccgaga tcatgccact gcgctccagc 50700
ctgggcgata gagcaagact ctgtctcaaa aaaaaaagcc aggcatggtg gtgcatgcct 50760
gtagtcccag ctactcaaga ggctgaggca ggagggttgt tcgacccacg gagatcaagg 50820
ctacagtgag ccatgatcgc accactgccc tccagcctgg gtgacagagt gtgaccctgt 50880
ctcaaagtaa gtaaatagga ggagagacaa gtgggcagtt cagactgatg gtatgggcac 50940
agtagagact ggtgcagaca ggctggcctg tgatgtcaag caacttctgt aactgtttcc 51000
ggcatccatt tgtgtgtcaa tttccgtgtc agtaggaaga ctctgtaggc tgccaagagg 51060
aataagtggg aggatcctcc cagagaggcc gggcctgcag gagggccagt tctcatgagt 51120
tcttatttgg cccctaccct ccaggctgtg gttctgaggt gggagacaga gcctgacctc 51180
tgtttgtctt gttttgtctt tgcagcagcc cacccatgtg cccgtgacaa tggtggctgc 51240
tcccacatct gtattgccaa gggtgatggg acaccacggt gctcatgccc agtccacctc 51300
gtgctcctgc agaacctgct gacctgtgga ggtaggtgtg acctaggtgc tcctttgggg 51360
tgatggacag gtacctgatt ctctgcctgc taggctgctg cctggcatcc ttttaaaatc 51420
acagtccctg tggcatccag tttccaaagc tgattgtgtc ttcctttgcc ctcctttctt 51480
ttctactatg tgcattcggt gctatgaatt ttcctctaag tactgcgttt cctgcatctc 51540
acaaattttg ttacattttc attttcaggt agtttgaata tttttacact tctcctgaga 51600
tgacatcttt ggctcatgtg ttatttagaa gtgttgctta gtttctaaag agttggggct 51660
tttccagctg tctctctgca actgatttct aatttaattc tactgtagtc tgagagctta 51720
ttttatatga tttctgttat tttaaatgtg ttgggtgtgg tgtttttgtt gttattgttt 51780
ttgtgtcttt ttgttttgtt ttgcttcgtt tgttttgttt ttgagacagt gtcttgctct 51840
gtcactcagg ctggagtgca atggcgcgat ctcagctcac cgcaacctct gcctcccggg 51900
ttcaagtgat cctcttgcct cagcctcctg agtagctggg attacaggtg cacgccacca 51960
tacccagcta atttttgtat ttttagtaga gacggggttt caccatgttg gtcaggctgg 52020
tctcgaactc ctgacctcgt gatccgccca cctcggcctc ccaaagtgct gggattatag 52080
gcgtgagcca ctgtgcctgg ccattaggtg tgttttatca cccagcatca tgcagtttat 52140
cttggtgaat gttctgtgta ctcttgaaaa gaatgtggat tctgctgttg ttgggtggag 52200
tgttccagaa acatcaatta gatccagttg gttaatagtg ctcatcaggt tgtctctatc 52260
cttccttcct gactgcctgc ttgagctgtc agttattgac aggggtgtgg agtctccaac 52320
tctaatggtg gatttgttta tttctcctag tagttctatc tttttctctc cttctaccct 52380
tgatcctctt ctccccctag ggcttcctgg tgttggtggt gggagagtgg ggtagtgaag 52440
aacctggact ttagggccaa agaggccagg gttcaaatcc tggctctgtc acttcccagt 52500
tgagtgaccc tggctggtgc ctgaatctct gtgagcctcc acttcctcct ctgtgaaatt 52560
gagagcactt acctggcagg ctgtcatggg catcaagtaa cagggcactc cacctggacc 52620

-continued

```
ctgacacgtg atgcacagga atgccagctg ctatgccatg ggtgtggcag tagtaataaa  52680
gtgaccatct gtatcctcac cacagtgaag cctgtccagg gctttctctc ctatgccccc  52740
atgcctccag gtggccttgg atcctgttgg ttctgtgctc tgctcagcga cctttctccc  52800
gtgggagttc ctgggggttc agcttcatcc tacagacagc agcacacact ggctgtgcac  52860
cctttttttt tttttttttt ttttttttga gatggagtct cgcttttttc gcgcaggctg  52920
aagtgcagtg gtgtgatctt ggctcactgc aacctctacc tcctgggttc aagtgatttt  52980
cctgcctcac cctcccaagt agctgggatt acaggctccc accaccacgc ccggctaatt  53040
tttgtatttt cagtagagat ggtgtttcac catgttggcc aggatggtct tgaactcctg  53100
acctcaggtg atccgcccac ctcagcctcc caaagtgcag ggattacagg cgtgagccac  53160
cacacccgga gtgccggttg tttttagcag tttgtcttgt tcctggagag actggctcct  53220
gcccaggagc tcggggagta gggccgcggg gtgctgcctc acacctcgag tttggccgta  53280
agcagagggg acattttgtg actgtccccc tcctgagctt cccagcagct tttctccaag  53340
ttacagccca aaagctcagg tggatttgca acccaacggt gtctgtgcac ctcccactga  53400
tgcccgaact gccctggcca agaaacgggg ccgtcagaac gctgcactaa ctgcagcctt  53460
gggcctccat gccagaggcc atgcccttcc atccaccacc ccctggcctg ggccctggcc  53520
ctcctggctc gggaactcca ggccccttcc tcacggatcg agagacgtgt atttaccgca  53580
caggtgcttg tcattctctt gtggcctctt ctccagggag atcacagaag gacagggcct  53640
cactgaggtc tcggacatgg accctttgat agtggcagga gccaggctgg gcaagaggcg  53700
gccacagtca cctcagcagt gccatcacca ccgccattca gcccttccct gagccgggcg  53760
cgcccctggc tctggcccca gtgtcccagt tacagctcac aggagcttgt ggtgcccagc  53820
ggctgcttct gattgagagt cgaggtcgga ggctttggga ggctgagagg ctgctcggtt  53880
tcacaactgc tgagggagac ttgggctcca tctcaggtct gccccatgtc gccctcaacc  53940
tccagccacc ggtcctccgt gtcccccatg gccaggcacg gcttgcagac atctgtcgtt  54000
ggctcctctc agccgtcgtg ggctgaccct ggcacgtcct cctgtggctg agcccagtgg  54060
ggacagctgc ttccttttat taccctagaa ctctcgtctt tgatcaggcc ccctccccta  54120
tgccacacag tccctgtcac tcgggtgagc ccagtagtca tggggaaggc ctgcgggttc  54180
caaacatcca aaggcttgcg tgcagcatga cagcttgaaa ccgatgtttt ttaccttgat  54240
cagatttcag cttggcgggg gctttgctca gctttcagtg aggcctgggc cgatttccca  54300
gcatcccctc ctgaggccag cctctgtttc ctgtgatttt ctgcacaaag tgggagggag  54360
gagtcttagg aaatgggggg ccacctcgaa acctaggcct cctctggctt ctctgtgcca  54420
gtgcccccac gctttgtgtc tgtgtcccca gcccatggga ctgtgttatt ccctgagtgc  54480
tgccgcatgc ccagcccgca ctgaggacgt ggagccccga ggggcaggat ggcctccatg  54540
gtcacacgta ggaagtggcc tccaccctcc gatgatcctc tcccccccctc cctttcagcg  54600
ccttccccgg gggtgtcatc agccctcctg cctgtgcttt gtcccgtctt ctgcaggcgc  54660
atgggacgtg ctgacaggtc ctctgccggg ttcctgcctt gctatgcgca cgctggtcac  54720
cacagaggcc tggcccttct tctgtagcag tcccacaccc gcaacaggtg tggctgctga  54780
ccacctgctt tctgcccctc tggtcctgag gagggcgcag tgggcactca ggcgtggctg  54840
agcagatgtg tgttgccggg aggaggaagg actgctccag tcagggctga atttcccacc  54900
cggagcattt ctgctgtatt tggtgtagcg cctgctgctt aaagctctga ttcccagttg  54960
gcaccctttc ccttctgcat tgaaaaacat acggatgcat gtcttcttgc agtgaatgtg  55020
```

-continued

```
tattctccca gcctctcttc tgggttgggg ctggaggtgg agcggcacac aggagccgca  55080
gcgatggagg atgtgcgggt gcagcacccc gtacagcagg gatgccaaac ccgcgctgag  55140
tccctctcaa cttctgcttt gaagcccagt cacgccattg cctgggtttt gctgggcggg  55200
gctgcatgtg atgttctcct ctgtccctcc cccagagccg cccacctgct ccccggacca  55260
gtttgcatgt gccacagggg agatcgactg tatccccggg gcctggcgct gtgacggctt  55320
tcccgagtgc gatgaccaga gcgacgagga gggctgcccc gtgtgctccg ccgcccagtt  55380
cccctgcgcg cggggtcagt gtgtggacct gcgcctgcgc tgcgacggcg aggcagactg  55440
tcaggaccgc tcagacgagg tggactgtga cggtgaggcc ctccccgtca aggctctgcc  55500
aagaccctgg ccctgccctc cgggatacga gcttggggct gcctccggcc tcacaggagt  55560
aggggctctg aaaacctttg cttgcaggga gattgccaag tctgtctttt aggcccaaca  55620
aggaaaactc tgcagttcca cccatcctgt cccaccaggt agtgtggctt gaaggcagac  55680
tgtgagggtc tatctcacct tcctgcatta ggtcaggagt ttcacagaaa cctgaggcac  55740
attcaggggt gggctgcaga ggtccatggc tcacaccctg gaaaatccgc ccccaaaaga  55800
cagtgctgtc tccactgacc agtctgtggg atagtgctta agcctgagtg gtttctatca  55860
acatgtagaa tcaggaggta taaagagatt tgctcaggca tcctgggccc tctctgacca  55920
gcaggatctt cctttagatc ttgacagtga aacacatctc ttctgtgccc cctgtgagtt  55980
ttctttcatt cattcattca ttcattcatt cattcattca ttcgagacag agtcttgctc  56040
tgtcacccag gctggagtgc cctggtgtaa tctcggctca ctgcaacctc tgcctccagg  56100
gttcaatcga ttctcctgcc tcagcctccc gagtagctgg gatgacaggt gcgcaccacc  56160
atgcctggct aatttttgta tttttagtag agacagggtt tcaccatgtt ggccaggctg  56220
gtctcgaact cctgacctca ggtgatccgc ccgcctcagc ctcccaaagt gctgggatta  56280
caggcatgag ccaccgcgcc cggcctgagt tttcctttta tgaaggacct gcttggttgg  56340
ttgcctgcca catgttgtca gcaccatggg cccaggactg ctgaggagct gttgatgccc  56400
tcgctctccc agagccaccg gctctgttag ataattcaca tgcagtctgg ccactgtcct  56460
acgtcctcat tcacaaagag cagacatttc gtagaagatg agggcctggg agtaacctcc  56520
ctgcatgttt ttctataaag gcatagtggt taagtccttc cagctcattg accattggag  56580
aattttatgg aggctgtaga ctaggggctg gtaaactaag ggcccagggg ccaaatccag  56640
cctgccacct actttgtaa ataaagtttt cttggtgcac agccatgccc attcattcat  56700
ttgcacaatg tctgtggctg ctttcatgcc aaaagcagga gaactgagtg gttatgctgg  56760
agacctacgg ccttcaaagc cccagacctc acgtctggcc cttgacagac agagcttccc  56820
cagccctgct gcgcatcctg gcccagcatg tgctgtgtgt gtgatttcag cttgcaggag  56880
ccgtggttag gaattgtccc tgtgttggtc cattttgcat tgctatgaag gagcacctga  56940
ggccgggtag attatgaagg aaagaggtct gtctggctca tggttctgta ggcagcacca  57000
gtatggcacc cgcatctgct cagcttctag tgaggtctca ggaagctttg actcatggtg  57060
gaagtcgaag cgggagcagg tgcatcacat ggtgagagag ggagcaacgg agagagagag  57120
agagagagag agagcgcctc tccctcttgc cctcaccttg agaggagatg ccaggctcct  57180
ttaagtaacc agctcccatg tgaactcaca gtgagagccc atttgctact gcggagaggg  57240
caccaggcat ctgctcccat gacccaaaca ctgcccacca ggccctacct ccaaccttgg  57300
ggtcatattt tattctgttc tatgctatgc tatgctatgc catgccatgc catgccatgc  57360
```

-continued

```
tattcctatt ctattatttg agacagaatc tcgctctgtt gcccaggctg gagtgcagtg  57420
gcatgatctt ggctcactgc aacctccacc tcccaggttc aagcgattct cctgcctcag  57480
cctcccgagt agctgggatt acaggcacac accaccacac ccgggtaatt tttgtatttt  57540
caatagagat ggggtttcac catgttggcc aggctggtct caaactcctg gcctcaagtg  57600
atccacttac ctcggcctcc caaagtgcca tgattacaga tgtgagtcac tgcgcccagt  57660
gagggtcaca tttccgttga gatttggagg ggcagacgtt ggagccatct gagccccctc  57720
gtcccgctct agcttctcct cccgtgtgcc ccgcggtgct ggtggcaggc ccttacgccg  57780
gttctggctg cacgctctgt tccagaagct ttcttccctg cttggttacc agaaaatcat  57840
cccatccatt acaaggacag ggtcccctta tctcccattc ccagggcagg acaccggggg  57900
cagggcaggt ggggaactga gcaagttctc tgggggcagg cgtggctatg gctccctctg  57960
ggtgggcgtc tggggagggg tggaggcagc cgtcagcgcc ctggcttgct cttcctccct  58020
ggccagagac tgtggccttg tgctgctccc gtgtgggctg cctgcacctc cagtgggttg  58080
tgctccctcc cctcccctcc cctcaagctc tgctgagcac cactgccttc cacagccccc  58140
actctcggga ggcgaggctc ctcgtggcca ttcctgtcct tggcacccac ccccccacca  58200
acctggtaga gccttgggcg gggtctgtta ctccttgcat ggcgtagacc tccccacagt  58260
aggcacctga cacatacctc ctggggggca ggcaggaggt gcgttgaggt ctcagccctg  58320
gcagtccctc ccctgcgtgg cataggcctc gccacagggt catcgagggt gggtggagac  58380
tgtactagac cactccccgc tggtcctaga aagggtccca tctgtctgct ctctgtttgg  58440
agtccagacc ttggttgctg tgccctgcat ggtgggctgg ggggcaccct ccagcctctc  58500
tgagtgcatg gcctctcctt gcagccatct gcctgcccaa ccagttccgg tgtgcgagcg  58560
gccagtgtgt cctcatcaaa cagcagtgcg actccttccc cgactgtatc gacggctccg  58620
acgagctcat gtgtggtgag ccagcttctg gcacggggaa ggggcgtccg ggctgggttc  58680
ccccaggaac gtggagttta ggggaggaga cgtgcctttc cagcggggct gggggctgtg  58740
tgggagactc aggcggctgg gaggctcctt gcgggaggca gggaagcctt tcccagggca  58800
gcggccagga ggacagactg tgagctgtgg gctcggcggc tacagagtct gcctcagtgg  58860
gcggggctga tggtgtccag gtgcctgcag cacgcaccca cccacgggac cttgctgagc  58920
agcgtctgtc aggcagcaag attacccgag ggctgcagtg gtcctgttcc ctggcagctt  58980
actgtctggc tgaggaggag tgatgttcac atatgcacac atgtcatgtg cacacacatg  59040
tacatgacaa catcccacat gctcctcaaa tagcatgacc tgtacagtca cggatatagg  59100
gcctagggga taggaggcca agacagtcag ggaagacttt ccagaggcag tggctcctga  59160
aaggctgtct gattcaggca ggaagggagc tgagttcaga taggaagtag caatgagtca  59220
ttgtgtctgg ggacatggcc actccttcgc tgcagaggga cctgggctga gagctcctct  59280
cttatggctg cagtcgggag agaagtctgt tggggggaga agggggcttc ctcaagggac  59340
tccctgtgcc ctttggcacc ttcgtgccag gtcaggcttg aggcctgaag gcagtggtgg  59400
gggccaccaa gggtcgcctc ctctgctggg caagttccca gtctgacggg cctgtgccgt  59460
gggccccagc tgtgggggcg ctgttgatgc gcagccaggc ctcgccgcca gagcccgcac  59520
gcttccattc cgctgacttc atcgacgccc tcaggatcgc tgggccggcc ctgtgggaga  59580
gtgaatgtgg cttttgccaa agttgagtct ggagcctgga aacttcccta tgggcagcct  59640
tgatagtgga gtggcccaag gagcccaccc agccgaccct gcccctcccg tggctggtgg  59700
gcggcaccag ggctgcctgg gctttgctcg ttcaccaaca tcacccgggc tggccagggc  59760
```

-continued

```
gcgctcactt ctgccaccac cgagggccct gggcgaagga gtgaatacca ggctgccttg  59820
gcagggatgt gttgagggct gtggggagtc ggacagcggc gggggtcaga ggaggaggag  59880
ggtgcaccgt gcaggctgaa gggccacgtt accctgaggt tggccaggct ccccaggcct  59940
agcctcccag ctcccccact ttctccccac cctccaccag tggcaaagcc agccccttca  60000
gggcgcacgg tgtctgcccc caaggagggc ccattccgtt ggggttaatg ttggccacct  60060
ctttctgttt gtctctggca gaaatcacca agccgccctc agacgacagc ccggcccaca  60120
gcagtgccat cgggcccgtc attggcatca tcctctctct cttcgtcatg ggtggtgtct  60180
attttgtgtg ccagcgcgtg gtgtgccagc gctatgcggg ggccaacggg cccttcccgc  60240
acgagtatgt cagcgggacc ccgcacgtgc ccctcaattt catagccccg ggcggttccc  60300
agcatggccc cttcacaggt aaggagcctg agatatggaa tgatctggag gaggcaggag  60360
agtagtctgg gcagctttgg ggagtggagc agggatgtgc taccccaggc cctcttgcac  60420
atgtggcaga cattgctaat cgatcacagc attcagcctt tcccactgag cctgtgcttg  60480
gcatcagaat ccttcaacac agaggcctgc atggctgtag caacccaccc tttggcactg  60540
taggtgtgga gaaagctcct tggacttgac cttcatattc tagtaggaca tgtgctgtgt  60600
tgtccacaaa tcctcatgta ccctagaaat gaatgtgggg gcggctgggc tctctccaga  60660
gctgaaggaa tcactctgta ccatacagca gctttgtctt gagtgcagct gggatttgtg  60720
gctgagcagt tacaattcct acgtggccca ggcaccagga acgcaggctg tgtttgtaga  60780
tggctgggca gccgcaccgc agagctgcac catgctggtt tgtatcacat gggtgaccat  60840
ggtatgtcta agaaggtgga gtccctgtga ggtctgcagg tgcccccaca gctccaggcc  60900
accttgagga ttgcctctgc ctgcccagcc ctgagttccc tctcccctgt cctgtcccac  60960
tgtcacccca agccggcctc attgggagcc tgttggatgg cagggtatag atgtaacctg  61020
attctctctg gggagcgggg ttatctggct tctcaagagc tcctaggagc ccacagtggt  61080
ggcaccatca cagtcgcagc agcccccaga gaacgcggcc ctgtctgttc ctggcgtgct  61140
ctgtgctgcc ccgcctgggt tccctgcccc agtcgcaggc cccttggagg aggtaccatg  61200
tgtctcccgt ttcacagatg agccccgggg agctcactct agtagtggcc agagaggcct  61260
gcggctcagg gagcggggca catttccaac aggacacacc gccctggtct gagtctcgtg  61320
ggtagtggga gcagaggaga gcgccctatg tctgtggggc ggcttggctg agcctggaag  61380
ccacctgacc tcccccgtcc cttccctgcc aggcatcgca tgcggaaagt ccatgatgag  61440
ctccgtgagc ctgatggggg gccggggcgg ggtgcccctc tacgaccgga accacgtcac  61500
aggggcctcg tccagcagct cgtccagcac gaaggccacg ctgtacccgc cggtgagggg  61560
cggggccggg gaggggcggg gcgggatggg gctgtgggcc cctcccaccg tcagtgctgg  61620
ccaccggagg cttcccgggt tcctggggc tgtgccaccg cctctgaggc atgcttgctt  61680
tcttcccttt tcaaaccctt ctgcttcctt ctttaatgac attgttgatt gtggataatc  61740
tgaaaactac acaaaaatat aaagagccaa aatctcaccc aaatccacct cctagagtgg  61800
ctgttgggct ccgtcagcat ccaggcggcc gtctgtgttc cgcacggccc agcccatcga  61860
tagccgcctg caccaggcct gtctgccctc tgtgagcctc cccacagggt tccctccaca  61920
aacaccctgt tctcccaccc agggctggct gcttcctgga aaacagctgg atggttttgt  61980
gcatgacaga caaacacagg gtgattttcg tggctaaaat actccctgga gcttttggca  62040
gggtgagggg ctggctccag ctgagccacg ccttgagtga aatgactgtg aggagaataa  62100
```

-continued

```
actgccgctg ccctccagga tcactggggc tggctgggga gaacccccgt ttctgggagc  62160
acagtcccag gatgccaagg cgagcttggt gccgagatgt gaactcctga gtgtaaacag  62220
cgggggctga cttgacatgc tttgtatgct tttcatttgt tcctgcagct gtatgcccct  62280
aaggtgagtc cagcccctt ctgcttcctc tggggcctcg ccagtgagcc ccaccttgct  62340
ggggctggtt cctcctgccc ttctgggtat ccctcacatc tggggtcttg tcttcttgtt  62400
ttatttttct tttttttttg agacggagtt tcacttttgt tgcccaggct tcagtgcaat  62460
ggtgtgatct ctaggctcac cgcaacctct gcctcccagg ttcaagcagt tctcctgcct  62520
cagcctccct agtagctggg attacaggca tgtgccacca cgcccagcta attttgtatt  62580
tttagtagag atggggtttc tccatgttgg tcaggctgat cttgaactcc ctacctcagg  62640
tgatccgccc accttggcct cccaaagtgc tgggattaca ggcgtgagcc accgcacctg  62700
gccttttctt tttcttttct tttctttttt ctgagacagg gtctcgctct gtcacccagg  62760
ctggagtgca atggtgtcat catggctaac tgcagcctct accttctagg ctcaagcaat  62820
cctcccatct cagcccctaa gtagctagga ctgcacgcat gcatccccat gcccagctaa  62880
tatttacatt ttttgtagag atgaagtttc actatattgc ccaggctggt ctccaactcc  62940
tggactcgag cgatcctcct gcctcggcct ccccaggtgc tgggattaca ggcgtgagcc  63000
accgtgcctg gcctggggta ttgtcttctt atggcacctg actgtggtgg gccctgggaa  63060
ggaagtagca gaagagggtt cttcttggtt tcctggacag taactgagtg ttctggaggc  63120
cccagggcct ggctttgttt agggacaaag ggaactggta accagaagcc gagagtttaa  63180
acacccactg cccttcttcc ctgctcctgc tgctgcaacc cagcttaacc agccaggagt  63240
gctaggaacc caagcagggc ccccgagcac acagcaggca gctcacgaat tctcttttcc  63300
tgttctccct tgggagctgg gaggatctta atcaggcaat aagagatggc actgagcagc  63360
cagctaattt tttaaatcac tttattgttt aaccatatga ctcacccact taaaaaaggg  63420
tacagttcag tgggttttag tgtattcaca gatgtgtgca accctcacca cagttaattt  63480
tagaacattt tcctgcccct aaaagaaact ctgcatgaag ccagctgttt ttaaattagc  63540
aaagttattt tgcatccttt aaatatatgt tcatggtaca aaattcaaaa gatacagaag  63600
agtctgcagt ccaaagagac tccgccccca tgacgccaag caggactccc tgggaggcat  63660
ggcctcctgc agtgtgtttc ttctatgtcc ccccaggggt catctgtaca tatgcaagca  63720
tacaagagcg tggactttgt tttccaagcc agaagataat tgtagattta tgtgcagttg  63780
tgagaaagag cacagaccca tttatcctct gcctggtttc ccccagtgct gcctgccatc  63840
ttgcatgact tccattccta tcataagcaa gacactgata acgattcttt caccttattc  63900
agattgacat aagtgttttt tgtttgttct tgagacaaac ttcctctgtc acccagtggg  63960
agtgcagtgg cacaatcaca gctcactgca gcctcaaact cctgggctca agcgattctc  64020
ctgcctcagt cccctcaagt agctcagatg gcaggtgtgc accatcatgc caggctaatt  64080
tttaaatttt ttgtggaggt gaggcctcac taaatttcct gggctagtct tgaactcctg  64140
agctaaagtg atcctcctgc ctcagcctcc caaagtggta ggattacagg catgagccac  64200
tgcgcctggg ctgacatatg tgttttcgta agcccgaaag atagcatctg aagagtcaac  64260
attgagcctt gccttttgct gctaatgatg tataaaagct gctgttctga gcatttcgga  64320
ggctcccagc tgccgtgtgc accctgccta gagctctacc gtaacccatc tccgggagga  64380
ggtgctattg ttttcctcat tttgcaacaa ggaggctgaa gaactgagca tgaaccactg  64440
gcctgggtcg ttcggttggt aggcagtggg gccaggccat ccaactcaca accaccttct  64500
```

-continued

```
actctgcttc ccccgcaccc tgaagtttgt tctgttttga ggacacagcc gtcacattct  64560
tggtggctga acagcactcc ttgtcaggtg tggctgggcc cccactggag ggcatcatgg  64620
tcctctctcc tgctgcggtt gaaccttggc tgtttcaacc actcctgcca agtggccctc  64680
tgaaagggac agtccatctt ttctcagcag agggccacac tggcaaaacg gtccctggca  64740
ccctttctct ccacctgtct aatatagagt aaaaatggta tcatgttaag atcttcattt  64800
atatttattt tatcatgaat gatgtaagca tcattttgtg tgtttaagaa cctttgggcc  64860
cagcgtgatg gcttgcagct gtaatctcag cactttagga ggctgagatg agcggatcac  64920
ttgaggccgg gagtttgaga ccagcctggc caacatggag aaaccccgtc tctagtaaaa  64980
atttaaaaat tagccgggta tggtgatccc agctacttgg gagtctgaag catgagaatt  65040
gcttgaacat gggaggcgga ggttgcagtg agccgagatc gcgccattgc actccagcct  65100
gggcgacaga gcgagactct gtctcacaaa aaaaaaaaaa aaagaaaaga aaagaaatta  65160
tcaatctcct cttttatggc atatatatat atatatatat atatatatat ttatttccct  65220
ttcttggtta tgttcataaa ggcctcccct gctctgatca taaaaaacaa cttattttca  65280
cactctctct cttttttttt tgagacagag ttttgctcct gttgcccagg ctggagtgca  65340
gtggcgcaat ctcagctcac tgtaacctcc gcctcccggg ttggagtgat tctcctgcct  65400
taccttcccg agtagctggg attataggca tgcaccacca tgcctggcta attttgtact  65460
tttagtagag acggggggttt ctccatgttg gtcaggctgg tctcgaactc gcgacctcag  65520
gtgatccacc cacctcggcc tcccaaagtg ctgggattac agacgtgagc caccatgccc  65580
agcccacact ctctttctta acgtcctcct cctttcgttt tacgttcaca tctttaattc  65640
ttctgggatg taattagatt tgatgagcaa ggtgggcatc cagcttgttt cttggctgat  65700
ggcttatggg tggcgtgaat tagtcggggt ctatcaggag gcagaaactc tatgagaatt  65760
tgaacagaga aagttccgtc tacaggctta ttaccaggga ctggaatagc agaaattgaa  65820
cagtgagatg tacagagaac tctaagaatg caggaatagg ccaggcatgg tggctcacac  65880
ctgtcatccc agcactttgg gagaccaagg cgggtggatc acctgaggtc aggagttcga  65940
gaccagcctg gccaacatag tgaaacccca tctctactaa aaatacaaaa aaattagctg  66000
ggtgtggtgg cgcatgcctg taatcccagc ttctcgggag tctgaggctg gagaatcact  66060
tgaacctggg aggcagaggt tgtagtgagc cgagatcatg ccattgtact ccagcctggg  66120
caacaagagc gagactcagt caaaacaaca acaacgcagg aatagcagat gagccgaggt  66180
ggggcctccc cagcccccac cccccacccc gcaccctggg ccgagatcca gtcctctttg  66240
aatagggcct gggcgtggtt cacgggacat ctgagacatt gccgaggcgc tgcactggtg  66300
gatcttgcca gaagtctgcc cagtgcagat ttgggcagaa tctcaaactg ccttgggatg  66360
taggagagaa accaggcctg gtcaagttca tgggaagagg tggaaacaga ccccataggc  66420
tggggcttgg gcagctgtag gaagccctct ctgctgcctc cctgcctgct ctctgctttg  66480
aagcatcttc cccagtgccc ccagtctcat gccctctcaa cgttggggtc aaatcctgag  66540
gaatacccag actggctctc tgggccaaag aggaccctct ccagaaagag cagggcccag  66600
tgcggcttcc taaagggcag gggaagggcc tggccactcc ccagaggcta ctcaccagcc  66660
atcaggatag ccccaggaag caggccttct cgagcccatt ttattacttt attttattat  66720
tttatttaat tttaaattta ttttttgaga cagagtctca ctctgttgcc caggctggag  66780
tgcagtggtg cgatctcaac ccactgcagc ctctgcctcc agggttcaag ggattctccc  66840
```

-continued

```
acctcagcct cccaagtagc tgggattaca ggtgcccgcc accacacccg gctaattttc  66900
atatttttag tagagacgag gtttcaccat gttggccagg ctggtctcga actcctgacc  66960
tcaagtgatc cgcccgcctc ggcctcccaa agtgctaggt caagcccatt ttaaagttga  67020
agaaactgag gctgaggtaa attccctccc cagggatcct gctgcagcca gaaggtggta  67080
aaacaggact tcacccgggt ctgtctggcg tgaaaggcag tgttcttgta ccaccctagg  67140
gggcctgaga gaactgagtc cctcgggcat aactgacagt tctgttccca ttattccgca  67200
ggggctcgga tctggctgta tgctttccag gatggccttg gagacccaca taagccctac  67260
accctttggg aagctgcatg ttgggttggg gtgccgtcag tggcacttgt ggaaggtgca  67320
gacctgtgtg ggtgtgtggg cccagggccc ctggtccctt cctccctttg tagggctggt  67380
tgtgtgctgc ctggacctgg ggggcacgtt cacgtggtga atttgtctat ttactatccc  67440
cgctttgggg ctggtgccag cacaggccct tgtgaagggg gtgcctttgt ctggagtggg  67500
actgtggccc ctccctcagc gtggtgactt ctgtgtcagg gcttcagcag ggacgcagag  67560
cccctgagtg ttcggaacaa gggcgtcatt gcaggagtta gactgtgtgt gatggaggga  67620
ggaggggcag gaggaaaggt cagaaggaga gttcctggga aggtccctga ggagcctggt  67680
gaggtgctaa ctggtgtgga ggacactcag ggcctgtggg gacatctcct actgctgggg  67740
gccagccaca aagggaactg gccgaagtcc tgtccccgcc ttcacagccc agcatctggt  67800
cacaaggcag gtacttggaa gggcgcgggc acctgggcca aaagtgcctg ggttcccttt  67860
gcctttcact gagatgacct tcggggcagg tggctgctgc ctcccctcct gtccccaggt  67920
tttgccaact ggccagagga aggggtcctg ggaagcaggg gggccagaag ccctctctgc  67980
aaggaaagcc cgaggggtgt gggaggaagg aaggaatgcc caggctggcg aggctctaag  68040
tcaccctggc ttggctctcc tcagatcctg aacccgccgc cctccccggc cacggacccc  68100
tccctgtaca acatggacat gttctactct tcaaacattc cggccactgc gagaccgtac  68160
aggtaggaca tcccctgcag ccctccatgg ccattgggtt cccgccagcc cgtggtggag  68220
gggcctaatc cccatgccac tgatgagggg aggtattctg ggtgctagtg ggcaggtgcc  68280
gggcccagcc ctgcctccct ctgctctgcc aaccacacta ggctgcctcc ccagacaagc  68340
tcagcgggca ctgcatgttg ggttcagaaa tcagcagaac tccacgttct gagctgctct  68400
tcaagttgct cctatggggg ttacttttaa gctgggaaat ggctgtggcg tcgaggggcc  68460
gggggcttgg gctccaaact ctgactgtgt gtttgagtcc ggctgtggaa acctagccat  68520
tgagatgccc cctcttggtg gctctgtcct cttaggatgg gacaagtctg tgaaggctgc  68580
tgcagcaccc accgtagacc cctaatcgtg tgacgtcacc aggatggtcc gggctgctca  68640
cttgccacag tggcctgttt gagcccggga agccaacggg gctgctcagc tggacaccag  68700
ccccccgagc tgcccatgtt ggggtcacag gccccacctc cctggttggg gaggggcaac  68760
tgagagtgtg gagaggtggg acccaggtgt gctggtctcc gcaggggctg gatcagagcc  68820
tgggatgggc agggtgagcc tcctgacctt taacccagtg gtgtcaggca acgtggccca  68880
cccgccagcc gcaccaggcc ccaccccgc aggtgaaggg gtgggatagg ctgggcctgg  68940
gccaggacac ctctggacca cgcattcctc attgcttggg tccctggagc agcagggcct  69000
cccgagtgtg gtgccgcctg ccacctagtg gccatttcca cgaactccca ggcctggctg  69060
gggagccgga actgcagcct ccatttccac cccactccgg gtcgggccac ctccctgatg  69120
cctcagtatt atatcaaact gtcacagtct gtcccacagc cttacagacc actgtctcca  69180
gaatggtcac atccacactg ggcagcccag tctcgctagt tcctcgtccc acctcctgcc  69240
```

-continued

```
tttgctcatg cccgtcctgc tctgggccca ccgcggacac atcttccccc cgcccgccgt  69300
ctgacctcac agcagctggg ccccaagagg agtatcctgt cctgctgcac ttttctcaac  69360
acccggtgtt ggctgcacct tcccacccat tgcaggcccc tctgtgacag gacgggggct  69420
cctaaacaca ccacagttcc gagtctgaac tcacacagtg ggatgcggcg tttctgggcc  69480
acagttgggt gcaggtagcc tctgggagga tgggaggtca ggagccatct tgcgagtcag  69540
gttgcttgaa ctcaggatgg aagtgttccg ggcccattgg ttgctgtatt agcctgttct  69600
cacgctgcta ataaagacat acccaagact gggtaattgt aaaggaaaga ggtttaacgg  69660
actcacagtt ccacctgcct ggggtggcct cacaatcatg gtagaagaca aggaggagca  69720
agtcacatct tacatggctt cagggaacag acagcatgag aaccaagcga aaggggtttc  69780
cccttgtaaa accatcaagt ctagtgagat ttattcacta ccacgagaac agtatggggg  69840
gaaccacccc catgattcaa tcatctccca ctgggtccct cccacagcac gtgggaatta  69900
tgggagtaca attcaagatg agatttgggt ggggacacag ccaaacccta tcggttgcca  69960
acatttacag taacagtgtt aggtgaacag ttgtccagtc tcctgttttg tcggacactg  70020
tttctagcac cttccaggca gaatctcatg tatccttcac tttcgaaatg ggtactattt  70080
catccccact tttatcaatg agaaactaaa gctcgaagag gtcaagtaag ttcctggcca  70140
aggtcagcta gcaggctcta gaggcctcgt tctccttaga ggcagccttg ccagggccca  70200
ggcttggcag gctgcagggc aggtgcgggc atgcccatgg tagaggtggg accattgagg  70260
ctcagagagg gtaagtgatg agccctggcg acacagcggg gtgggtccag agtccggcct  70320
gcatcttctg gagctggcca gtggacaggc ctttcccgtt cacagccccg gggctgctgt  70380
gcccaccagg gcggatgtgc ctaccgaatc ccactcctct gtgtgtgtcc ctttcaggcc  70440
ctacatcatt cgaggaatgg cgccccccgac gacgccctgc agcaccgacg tgtgtgacag  70500
cgactacagc gccagccgct ggaaggccag caagtactac ctggatttga actcggactc  70560
agacccctat ccaccccccac ccacgcccca cagccagtac ctgtcggcgg aggacagctg  70620
cccgccctcg cccgccaccg agaggagcta cttccatctc ttcccgcccc ctccgtcccc  70680
ctgcacggac tcatcctgac ctcggccggg ccactctggc ttctctgtgc ccctgtaaat  70740
agttttaaat atgaacaaag aaaaaaatat attttatgat ttaaaaaaata aatataattg  70800
ggattttaaa aacatgagaa atgtgaactg tgatggggtg ggcagggctg ggagaacttt  70860
gtacagtgga gaaatattta taaacttaat tttgtaaaac agaactgcca ttcttttgtg  70920
ccctgtgtgc atttgagttg tgtgtccccg tggagggaat gccgaccccc ggaccaccat  70980
gagagtcctc ctgcacccgg gcgtccctct gtccggctcc tgcagggaag ggctggggcc  71040
ttgggcagag gtggatatct cccctgggat gcatccctga gctgcaggcc gggccggctt  71100
tatgtgcgtg tggcctgtgc cgtcagaaag ggccctgggc ttcatcacgc tgttgctgtt  71160
cgtcttcctc agattcttag tctttttttt tttttttttt ttttgagacg gagtctttct  71220
ctgtcatcca ggctggagtg cagtggtaca atctcagctc actgcaagct ccgactccca  71280
ggttcaagtg agtctcctgc ctcagcctcc cgagtagctg ggactacagg tgcgcgccac  71340
cacacccgcc cagctaattt ttgtattttt agtagagatg gggtttcacc atgttggcca  71400
ggatgatctc gatctcttga cctcgtgatc cgcccacctc ggcctcccaa agtgctggga  71460
ttataggcat gagccactgt acccagctga ctcttagtca cttttaagaa ggggactgtg  71520
ccttcatttt tcactgggcc ctgcagaata tatgcctggg ctctgggctc ttctgaacct  71580
```

-continued

```
gtgttggctt ccatctgacc tctctgtgcc agcccaaggc tgctgctctt cctgagggca  71640
aggagcccca tgactgcgtg ttgactcgct ggatggggct gctgagccca ctctgccaca  71700
ccacgtgccc ctggcaggga gggaatccct gggtcctcac aggaacagtc agcaagccac  71760
acctgacgcc tgctgtgggc ccatccctgc ggtgctggag aagacagaca aggcctggtc  71820
actgcctctg cagggtcccc agtccgtgga aggagacagt aatctaggca ttttcggtgg  71880
ggaagctgag ctgttctcgt gtcctgaagg ccaggcggga acagccgtct tcagagggaa  71940
gggagaaaat gcacatcgca tcagtggaga agggcctgac ttccctcagc atggtggagg  72000
gaggtcagaa aacagtcaag cttgagtatt ctatagtgtc acctaaata              72049
```

<210> SEQ ID NO 10
<211> LENGTH: 8705
<212> TYPE: DNA
<213> ORGANISM: Homo sapiens

<400> SEQUENCE: 10

```
ggactcaggg gcagcaggga ggtacaccca tggttagtgg gcggaccata gggggtaatg     60
agagggtgaa tcgatggaac ctgggggaca caatcgaagt ggttccagag tcgggctgta    120
ctaattaaag agacggggca gtggacaggc attttcagtt gactgcccag ggagtgttct    180
gcccaacagg gaggatatgc gtacagaatc atactcgatc agcatgagtc caattcagac    240
cgtacatcag tggagatatg ggtcccccga tgactccgtg gaacactgat gtttgtgaca    300
ggggagtaca gcaccagcca tcagcaggcc agtaaatcat accggcctgc gaaattggac    360
tcagacccgg atccaccctg accgacgtcc caagccccca ccccccaccc cccaccatgg    420
gccgagatcc agtcctcttt gaatagggcc tggccgtggt tcacgggaca tctgagacat    480
tgccgaggcg ctgcattggt ggatcttgcc agaagtttgc ccagtgcaga tttgggcaga    540
atctcaaact gccttgggat gtaggagaga aaccaggcct ggtcaagttc atgggaagag    600
gtggaaacag accccatagg ctggggcttg ggcagctgta ggaagccctc tctgctgcct    660
ccctgcctgc tctctgcttt gaagcatctt ccccagtgcc cccagtctca tgccctctca    720
acgttggggt caaatcctga ggaataccca gactggctct ctgggccaaa gaggaccctc    780
tccagaaaga gcagggccca gtgcggcttc ctaaagggca ggggaagggc ctggccactc    840
cccagaggct actcaccagc catcaggata gccccaggaa gcaggccttc tcgagcccat    900
tttattactt tattttatta ttttatttaa ttttaaattt attttttgag acagagtctc    960
actctgttgc ccaggctgga gtgcagtggt gcgatctcaa cccactgcag cctctgcctc   1020
cagggttcaa gggattctcc cacctcagcc tcccaagtag ctgggattac aggtgcccgc   1080
caccacaccc ggctaatttt catattttta gtagagatga ggtttcacca tgttggccag   1140
gctggtctcg aactcctgac ctcaagtgat ccgcccgcct cggcctccca aagtgctagg   1200
tcaagcccat tttaaagttg aagaaactga ggctgaggta aattccctcc ccagggatcc   1260
tgctgcagcc agaaggtggt aaaacaggac ttcacccggg tctgtctggc gtgaaaggca   1320
gtgttcttgt accaccctag ggggcctgag agaactgagt ccctcgggca taactgacag   1380
ttctgttccc attattccgc aggggctcgg atctggctgt atgctttcca ggatggcctt   1440
ggagacccac ataagcccta caccctttgg gaagctgcat gttgggttgg ggtgccgtca   1500
gtggcacttg tggaaggtgc agacctgtgt gggtgtgtgg gcccagggcc cctggtccct   1560
tcctcccttt gtagggctgg ttgtgtgctg cctggacctg gggggcacgt tcacgtggtg   1620
aatttgtcta tttactatcc ccgctttggg gctggtgcca gcacaggccc ttgtgaaggg   1680
```

-continued

```
ggtgcctttg tctggagtgg gactgtggcc cctccctcag cgtggtgact tctgtgtcag   1740
ggcttcagca gggacgcaga gcccctgagt gttcggaaca agggcgtcat tgcaggagtt   1800
agactgtgtg tgatggaggg aggaggggca ggaggaaagg tcagaaggag agttcctggg   1860
aaggtccctg aggagcctgg tgaggtgcta actggtgtgg aggacactca gggcctgtgg   1920
ggacatctcc tactgctggg ggccagccac aaagggaact ggccgaagtc ctgtccccgc   1980
cttcacagcc cagcatctgg tcacaaggca ggtacttgga agggcgcggg cacctgggcc   2040
aaaagtgcct gggttccctt tgcctttcac tgagatgacc ttcggggcag gtggctgctg   2100
cctcccctcc tgtccccagg ttttgccaac tggccagagg aaggggtcct gggaagcagg   2160
ggggccagaa gccctctctg caaggaaagc ccgaggggtg tgggaggaag gaaggaatgc   2220
ccaggctggc gaggctctaa gtcaccctgg cttggctctc ctcagatcct gaacccgccg   2280
ccctccccgg ccacggaccc ctccctgtac aacatggaca tgttctactc ttcaaacatt   2340
ccggccactg cgagaccgta caggtaggac atcccctgca gccctccatg gccattgggt   2400
tcccgccagc ccgtggtgga ggggcctaat ccccatgcca ctgatgaggg gaggtattct   2460
gggtgctaat gggcaggtgc cgggcccagc cctgcctccc tctgctctgc caaccacact   2520
aggctgcctc cccagacaag ctcagcgggc actgcatgtt gggttcagaa atcagcagaa   2580
ctccacgttc tgagctgctc ttcaagttgc tcctatgggg gttactttta agctgggaaa   2640
tggctgtggc gtcgaggggc cgggggcttg ggctccagag tctgactgtg tgtttgagtc   2700
cggctgtgga aacctagcca ttgagatgcc ccctcttggt ggctctgtcc tcttaggatg   2760
ggacaagtct gtgaaggctg ctgcagcacc caccgtagac ccctaatcgt gtgacgtcac   2820
caggatggtc cgggctgctc acttgccaca gtggcctgtt tgagcccggg aagccaacgg   2880
ggctgctcag ctggacacca gccccccgag ctgcccatgt tggggtcaca ggccccacct   2940
ccctggttgg ggaggggcaa ctgagagtgt ggagaggtgg gacccaggtg tgctggtctc   3000
cgcaggggct ggatcagagc ctgggatggg cagggtgagc ctcctgacct ttaacccagt   3060
ggtgtcaggc aacgtggccc acccgccagc cgcaccaggc cccacccccg caggtgaagg   3120
ggtgggatag gctgggcctg ggccaggaca cctctggacc acgcattcct cattgcttgg   3180
gtccctggag cagcagggcc tcccgagtgt ggtgccgcct gccacctagt ggccatttcc   3240
acgaactccc aggcctggct ggggagccgg aactgcagcc tccatttcca ccccactccg   3300
ggtcgggcca cctccctgat gcctcagtat tatatcaaac tgtcacagtc tgtcccacag   3360
ccttacagac cactgtctcc agaatggtca catccacact gggcagccca gtctcgctag   3420
ttcctcgtcc cacctcctgc ctttgctcat gcccgtcctg ctctgggccc accgcggaca   3480
catcttcccc ccgcccgccg tctgacctca cagcagctgg gccccaagag gagtatcctg   3540
tcctgctgca cttttctcaa cacccggtgt tggctgcacc ttcccaccca ttgcaggccc   3600
ctctgtgaca ggacgggggc tcctaaacac accacagttc cgagtctgaa ctcacacagt   3660
gggatgcggc gtttctgggc cacagttggg tgcaggtagc ctctgggagg atgggaggtc   3720
aggagccatc ttgcgagtca ggttgcttga actcaggatg gaagtgttcc gggcccattg   3780
gttgctgtat tagcctgttc tcacgctgct aataaagaca tacccaagac tgggtaattg   3840
taaaggaaag aggtttaacg gactcacagt tccacctgcc tggggtggcc tcacaatcat   3900
ggtagaagac aaggaggagc aagtcacatc ttacatggct tcagggaaca gacagcatga   3960
gaaccaagcg aaaggggttt ccccttgtaa aaccatcaag tctagtgaga tttattcact   4020
```

-continued

```
accacgagaa cagtatgggg ggaaccaccc ccatgattca atcatctccc actgggtccc   4080
tcccacagca cgtgggaatt atgggagtac aattcaagat gagatttggg tggggacaca   4140
gccaaaccct atcggttgcc aacatttaca gtaacagtgt taggtgaaca gttgtccagt   4200
ctcctgtttt gtcggacact gtttctagca ccttccaggc agaatctcat gtatccttca   4260
ctttcgaaat gggtactatt tcatccccac ttttatcaat gagaaactaa agctcgaaga   4320
ggtcaagtaa gttcctggcc aaggtcagct agcaggctct agaggcctcg ttctccttag   4380
aggcagcctt gccagggccc aggcttggca ggctgcaggg caggtgcggg catgcccatg   4440
gtagaggtgg gaccattgag gctcagagag ggtaagtgat gagccctggc gacacagcgg   4500
ggtgggtcca gagtccggcc tgcatcttct ggagctggcc agtggacagg cctttcccgt   4560
tcacagcccc ggggctgctg tgcccaccag ggcggatgtg cctaccgaat cccactcctc   4620
tgtgtgtgtc cctttcaggc cctacatcat tcgaggaatg gcgcccccga cgacgccctg   4680
cagcaccgac gtgtgtgaca gcgactacag cgccagccgc tggaaggcca gcaagtacta   4740
cctggatttg aactcggact cagaccccta tccaccccca cccacgcccc acagccagta   4800
cctgtcggcg gaggacagct gcccgccctc gcccgccacc gagaggagct acttccatct   4860
cttcccgccc cctccgtccc cctgcacgga ctcatcctga cctcggccgg gccactctgg   4920
cttctctgtg cccctgtaaa tagttttaaa tatgaacaaa gaaaaaaata tattttatga   4980
tttaaaaaat aaatataatt gggattttaa aaacatgaga aatgtgaact gtgatggggt   5040
gggcagggct gggagaactt tgtacagtgg agaaatattt ataaacttaa ttttgtaaaa   5100
cagaactgcc attctttcgt gccctgtgtg catttgagtt gtgtgtcccc gtggagggaa   5160
tgccgacccc cggaccacca tgagagtcct cctgcacccg ggcgtccctc tgtccggctc   5220
ctgcagggaa gggctggggc cttgggcaga ggtggatatc tcccctggga tgcatccctg   5280
agctgcaggc cgggccggct ttatgtgcgt gtggcctgtg ccgtcagaaa gggccctggg   5340
cttcatcacg ctgttgctgt tcgtcttcct cagattctta gtcttttttt tttttttttt   5400
ttttttgaga cggagtcttt ctctgtcatc caggctggag tgcagtggta caatctcagc   5460
tcactgcaag ctccgactcc caggttcaag tgagtctcct gcctcagcct cccgagtagc   5520
tgggactaca ggtgcgcgcc accacacccg cccagctaat ttttgtattt ttagtagaga   5580
tggggtttca ccatgttggc caggatgatc tcgatctctt gacctcgtga tccgcccacc   5640
tcggcctccc aaagtgctgg gattataggc atgagccact gtacccagct gactcttagt   5700
cacttttaag aaggggactg tgccttcatt tttcactggg ccctgcagaa tatatgcctg   5760
ggctctgggc tcttctgaac ctgtgttggc ttccatctga cctctctgtg ccagcccaag   5820
gctgctgctc ttcctgaggg caaggagccc catgactgcg tgttgactcg ctggatgggg   5880
ctgctgagcc cactctgcca caccacgtgc ccctggcagg gagggaatcc ctgggtcctc   5940
acaggaacag tcagcaagcc acacctgacg cctgctgtgg gcccatccct gcggtgctgg   6000
agaagacaga caaggcctgg tcactgcctc tgcagggtcc ccagtccgtg gaaggagaca   6060
gtaatctagg catttttcggt ggggaagctg agctgttctc gtgtcctgaa ggccaggcgg   6120
gaacagccgt cttcagaggg aagggagaaa atgcacatcg catcagtgga gaagggcctg   6180
acttccctca gcatggtgga gggaggtcag aaaacagtca agcttgttgc tgggtgacag   6240
tgcatttaat aatcaaaata taggctgggt acggtggctc atgcctgtaa tcccagcact   6300
ttgggaggct gaggcaggtg gatcacttga ggccaggagt ttgagaccgg cctggccaac   6360
atggcaaaac ctcaactact aaaatacaaa aactagccgg gcgtggtggt gcacgcctgt   6420
```

-continued

```
aatcccagct acttgggagg ctgaggcagg agaattgctt gaacctggga ggcggaggct   6480
gcagtgagcc gagattgtgc cactgcactc cagcctgggc aacagagcaa gactctgtct   6540
caaaaaaaaa aaaaaaaaaa gcaatacaaa atacaaatat cactttcact aaaagaaggg   6600
atggaagacc caaaacaaac agaaaacaac aaaatggcag gagtaagtcc ccacttatca   6660
ataataacat tgactgtaaa taggctaagc tctgcaatca aaagagtggg ccaggagcgg   6720
tggctcacgc ctgtaattcc aacgctttgg gaggctgagg cggatggatc atttgatgtc   6780
acgagtttta agaccagcct ggccaacaag gtgaaacccc atctgtacta aaaatacaaa   6840
aattagccag gcggtagtgg cacgcacctg taatcccagc tacttgtgag gctgaggcag   6900
gagaatcact ggaggctggg aagcggaggt tgctgtgagc caagatggag ccactgcact   6960
cccacctggg cgacagagtg agatcctgtc ttaagaaaaa aaagagtgga tgaatggatc   7020
aaaaaacaag acccaaccat ctcttgcata caagaaacac actttaccta taaaaacaca   7080
ctaggccagg tgtggtggct cacacctgta atcccagccc tttgggaggc ctgactggca   7140
gatcacctga ggccaggagt ttcagaccag cttgaccgac atggcaaaac cccatctctc   7200
ctaaaaatac aaaaaaacaa aaaaaagaaa aaggctggaa gtagtgatgt gtgcctgtag   7260
ccccagctac ttgggaggct gaggcaggag aattgcttga atccgggaag tggaggttgc   7320
agtgagccag gatggtgcca ctgcactcca gcctgggtga cagagcgaga ccctgtcata   7380
aaaaaaaaaa gaaaagaaaa gaaaaacgag aaaaacaaac acaaaattag tagaagaaaa   7440
gaaataataa agatcagaac aggccaggct catgggcaca gtggctcaac tcctacctgc   7500
tcaggagttt gagaccagtc tggccaacat ggcaaaaccc catctctcct aaaaatatga   7560
aaaaaaaaaa ataggctgga tgtggtgatg tgtgtgtgcc tgtagcccca gctacttggg   7620
aggctgaggt gggagaatca cttgagccca ggaagtggag gctgcagcga gtcatgaatg   7680
caccctgcac tctagctggg taactggagt gagattctgt ctcaaaaaag caaagaccag   7740
agcagaaata aatgaaatgg aaatgaagga aacaatgcaa aatgatacaa aaagtttttt   7800
cgaaaagata aacaaaatca acaaaccttt agccagatta agaaaaaaag agagaagacc   7860
caaataaata aaatccgaga ttaaaaagga gacattacca ctgataccac agaaattcaa   7920
aggatcatta gaggcaacta tgtgcaacta tatgctaatg aactggaaaa cctagaagaa   7980
ctgggtaaat ttctagacac atacaaccta tcaagattga accatgaaga aatccaaaac   8040
ctgaacaggc cgggcacggt ggcttacgcc tgtaatccca gcactttgga aggcctgaga   8100
tcaggagttc gagaccagcc tggccaacat ggtgaaaccc catctctact gaaaaaatat   8160
aaaaattagc cgggcgtggt ggcgggtgcc tctaatgtca gccactcggg aggctgaggc   8220
aggaaaatca cttgaacctg ggaggcatag gttgcagcga gccgaggttg caccactgca   8280
ctccagcctt ggcgacagag ccagactcca tctcaaaaaa attaaaataa caaaaacctg   8340
aacagaccaa taacaagtaa tgcgatgaaa actgtaataa aatgtttccc aacaaagaaa   8400
gcccaggaac aaatggcttc actgctgaat tttaccaaac attttttttt ttttgagacg   8460
gagtctcgct ctgtcgccca ggctggagtg cagtggtgta acctcggttc gctggtaact   8520
tatgcctctc aggctgcaag tgattttcct gcttcaggcc ccccgagtgg ctggaaatta   8580
gatggtactt gtcaaacaag gcctggctaa atttctatat ttccttcaag tagaagatgt   8640
gcttccaaca aaggttgggt tacggctggc ttctgaaaat cttggatttc aaggctcccc   8700
aaaag                                                               8705
```

-continued

<210> SEQ ID NO 11
<211> LENGTH: 66933
<212> TYPE: DNA
<213> ORGANISM: Homo sapiens

<400> SEQUENCE: 11
tataatcaag cgcgttccgt ccagtccggt gggaagattt tcgatatgct tcgtgatctg 60
ctcaagaacg ttgatcttaa agggttcgag cctgatgtac gtattttgct taccaaatac 120
agcaatagta atggctctca gtccccgtgg atggaggagc aaattcggga tgcctgggga 180
agcatggttc taaaaaatgt tgtacgtgaa acggatgaag ttggtaaagg tcagatccgg 240
atgagaactg tttttgaaca ggccattgat caacgctctt caactggtgc ctggagaaat 300
gctctttcta tttgggaacc tgtctgcaat gaaattttcg atcgtctgat taaaccacgc 360
tgggagatta gataatgaag cgtgcgcctg ttattccaaa acatacgctc aatactcaac 420
cggttgaaga tacttcgtta tcgacaccag ctgccccgat ggtggattcg ttaattgcgc 480
gcgtaggagt aatggctcgc ggtaatgcca ttactttgcc tgtatgtggt cgggatgtga 540
agtttactct tgaagtgctc cggggtgata gtgttgagaa gacctctcgg gtatggtcag 600
gtaatgaacg tgaccaggag ctgcttactg aggacgcact ggatgatctc atcccttctt 660
ttctactgac tggtcaacag acaccggcgt tcggtcgaag agtatctggt gtcatagaaa 720
ttgccgatgg gagtcgccgt cgtaaagctg ctgcacttac cgaaagtgat tatcgtgttc 780
tggttggcga gctggatgat gagcagatgg ctgcattatc cagattgggt aacgattatc 840
gcccaacaag tgcttatgaa cgtggtcagc gttatgcaag ccgattgcag aatgaatttg 900
ctggaaatat ttctgcgctg gctgatgcgg aaaatatttc acgtaagatt attacccgct 960
gtatcaacac cgccaaattg cctaaatcag ttgttgctct tttttctcac cccggtgaac 1020
tatctgcccg gtcaggtgat gcacttcaaa aagcctttac agataaagag gaattactta 1080
agcagcaggc atctaacctt catgagcaga aaaaagctgg ggtgatattt gaagctgaag 1140
aagttatcac tcttttaact tctgtgctta aaacgtcatc tgcatcaaga actagtttaa 1200
gctcacgaca tcagtttgct cctggagcga cagtattgta taagggcgat aaaatggtgc 1260
ttaacctgga caggtctcgt gttccaactg agtgtataga gaaaattgag gccattctta 1320
aggaacttga aaagccagca ccctgatgcg accacgtttt agtctacgtt tatctgtctt 1380
tacttaatgt cctttgttac aggccagaaa gcataactgg cctgaatatt ctctctgggc 1440
ccactgttcc acttgtatcg tcggtctgat aatcagactg ggaccacggt cccactcgta 1500
tcgtcggtct gattattagt ctgggaccac ggtcccactc gtatcgtcgg tctgattatt 1560
agtctgggac cacggtccca ctcgtatcgt cggtctgata atcagactgg gaccacggtc 1620
ccactcgtat cgtcggtctg attattagtc tgggaccatg gtcccactcg tatcgtcggt 1680
ctgattatta gtctgggacc acggtcccac tcgtatcgtc ggtctgatta ttagtctgga 1740
accacggtcc cactcgtatc gtcggtctga ttattagtct gggaccacgg tcccactcgt 1800
atcgtcggtc tgattattag tctgggacca cgatcccact cgtgttgtcg gtctgattat 1860
cggtctggga ccacggtccc acttgtattg tcgatcagac tatcagcgtg agactacgat 1920
tccatcaatg cctgtcaagg gcaagtattg acatgtcgtc gtaacctgta gaacggagta 1980
acctcggtgt gcggttgtat gcctgctgtg gattgctgct gtgtcctgct tatccacaac 2040
attttgcgca cggttatgtg gacaaaatac ctggttaccc aggccgtgcc ggcacgttaa 2100
ccgggctgca tccgatgcaa gtgtgtcgct gtcgacgagc tcgcgagctc ggacatgagg 2160

-continued

```
ttgccccgta ttcagtgtcg ctgatttgta ttgtctgaag ttgtttttac gttaagttga   2220
tgcagatcaa ttaatacgat acctgcgtca taattgatta tttgacgtgg tttgatggcc   2280
tccacgcacg ttgtgatatg tagatgataa tcattatcac tttacgggtc ctttccggtg   2340
atccgacagg ttacggggcg gcgacctcgc gggttttcgc tatttatgaa aattttccgg   2400
tttaaggcgt ttccgttctt cttcgtcata acttaatgtt tttatttaaa ataccctctg   2460
aaaagaaagg aaacgacagg tgctgaaagc gagctttttg gcctctgtcg tttcctttct   2520
ctgtttttgt ccgtggaatg aacaatggaa gtccgagctc atcgctaata acttcgtata   2580
gcatacatta tacgaagtta tattcgatgc ggccgcaagg ggttcgcgtc agcgggtgtt   2640
ggcgggtgtc ggggctggct taactatgcg gcatcagagc agattgtact gagagtgcac   2700
catatgcggt gtgaaatacc gcacagatgc gtaaggagaa aataccgcat caggcgccat   2760
tcgccattca ggctgcgcaa ctgttgggaa gggcgatcgg tgcgggcctc ttcgctatta   2820
cgccagctgg cgaaaggggg atgtgctgca aggcgattaa gttgggtaac gccagggttt   2880
tcccagtcac gacgttgtaa aacgacggcc agtgaattgt aatacgactc actatagggc   2940
gaattcgagc tcggtacccg gggatcctct agagtcgacc tgcaggcatg caagcttctc   3000
ttgtgccggt tgtacgctgt caggtcacac tggtgagtta ggcagggcac agatgcccag   3060
agcagaggga actttccttg ggattcaac acgtgcaagt cttaggggct ggcaaatcct   3120
gccctcagct agagaggggg cttttatttg agaccagaat cacctgagca tcctcctgtc   3180
cccagctgtg tccagcctgt ctgcagggac atcctgagag gaccaggctc tcccctcatc   3240
cacctgccta agtgccactc tgaaccctgt ccacctgtgc cgtggagggg cgtgacctca   3300
agctgctcag ccagcagcag gcttggccct gggggcagc agagacccag gtggctgtgg   3360
ggtgggtgct tcgtggcgtg gttctgaaac ttcgttggaa gtgtgtggac agtgccttgc   3420
ctgttctctg tgggacccta tttagaaacg aggtctgagt tactgggggt catcactgtg   3480
ttctgatggc ccagctgtgt ggaggccgcg gtgcagcccc atccaaggag ccagggccct   3540
gggtctagcc gtgaccagaa tgcatgcccc ggaggtgttt ctcatctcgc acctgtgttg   3600
cctggtgtgt caagtggtcg tgaaactctg tgttagctct tggtgttcct gaaagtgccc   3660
ccgggtctca ggcctcagaa ccagggtttc ccttcatctc ggtggcctgg gagcatctgg   3720
gcagttgagc aaagagggcg attcacttga aggatgtgtc tggccctgcc taggagcccc   3780
ccggcacggt gctggggcct gaagctgccc tcgggtggtg gagaggaggg agcgatgaag   3840
tggcgtcgag ctgggcagga agggtgagcc cctgcaaggt gggcatgctg gggacgctga   3900
gcagcatggc cagcagctgg gtctgcagcc tggtacccgg cgggacttgt ggttggggct   3960
ggtttgtggc caggagaggg gctggcagga gacaaggggg actgtgaggc agctcccacc   4020
cagcagctga agcccaatgg cctggctgtg tggctctcag ctgcgtgcat aacctctcag   4080
tgcttcagtt ctctcatttg taaaatgagg aaacaaacag tgccagcctc ccagaggtgt   4140
catgaggatg aacgagtgac catgtagcat gggctgggtg cgtgtcacct aacatcacca   4200
gcctttgcaa ggagagccct gggggcctgg ctgagtattt cccttgcccg gcccacccca   4260
ggcctagact tgtgcctgct gcaggccctt gacccctgac cccattgcac ctgtctccac   4320
aggagccgag gaggtgctgc tgctggcccg gcggacggac ctacggagga tctcgctgga   4380
cacgccggac ttcaccgaca tcgtgctgca ggtggacgac atccggcacg ccattgccat   4440
cgactacgac ccgctagagg gctatgtcta ctggacagat gacgaggtgc gggccatccg   4500
```

-continued

```
cagggcgtac ctggacgggt ctggggcgca gacgctggtc aacaccgaga tcaacgaccc   4560
cgatggcatc gcggtcgact gggtggcccg aaacctctac tggaccgaca cgggcacgga   4620
ccgcatcgag gtgacgcgcc tcaacggcac ctcccgcaag atcctggtgt cggaggacct   4680
ggacgagccc cgagccatcg cactgcaccc cgtgatgggg taagacgggc gggggctggg   4740
gcctggagcc agggccaggc caagcacagg cgagagggag attgacctgg acctgtcatt   4800
ctgggacact gtcttgcatc agaacccgga ggagggcttg ttaaaacacc ggcagctggg   4860
ccccaccccc agagcggtga ttcaggagct ccagggcggg gctgaagact tgggtttcta   4920
acaagcaccc cagtggtccg gtgctgctgc tgggtccatg cgtagaaagc cctggagacc   4980
tggagggagc cctttgttcc cctggcttca gtttcctcat ctgtagaatg gaacggtcca   5040
tctgggtgat ttccaggatg acagtagtga cagtaagggc agcctctgtg acactgacca   5100
cagtacaggc caggcctctt tttttctttt tttttttttg agatggagtc tcactctgtc   5160
gcccaggctg gagtgcagtg gtgtgatctc agctcactac aacctctgcc tcctgggctc   5220
aagtgattct cctgcctcag cctcctgagt agctgggatt acaggtgcct gccactgtgc   5280
ttggctaatg tttgtatttt tggtagagat ggggtttcac cgtcttggcc aggctggtcg   5340
caaactcctg acctcaggtg atccacctgc ctcagcctcc caaagtgctg ggattacagg   5400
catgagccac cacgcccggt caggccaggc ctcttttgaa cactttgcac accatgggtc   5460
ttttcatcca ggggggtagg tacagttgta cagttgagga cactgaagcc cagagaggct   5520
cagggacttg cccagggtca cacagcagga tgtggcaggt gtggggctgg gcctggcagc   5580
gtggctccag ctttccagca tagaaatctg tgaaagcaga tagtttgtcg gtcggtaggg   5640
gagactttct gagacccgcc ccagcggctc agagggtagt agccaggggc cttcctgggg   5700
gctcataacc cagaacactg aatgggaaaa ccctgatgga ggaggcgcag tggagctgtg   5760
ggtgccgatg ggaagtccca gaggagctgg gaggtcagta gcggtgctgc cctctgtgga   5820
gcacttagtg ggcaccaggt gtgtttccag gttcatggcc ctgggacctg aagctcagaa   5880
ggtgaagtaa cttgcccagg gcacccgtcg ggcagcggcg ggcagaggat ttgtgggctg   5940
tggagcctgt gctcgtggcc cagccctggg ggttgtgagt gtgctggccg gggagctttt   6000
cctgcaagtg gactggtgtc taggagccag catgtcaggc agcaggcagc gggagtgcag   6060
caggcagcgg gagcacagca ggcagagggc ggggctcgag cagccatccg tggaccctgg   6120
ggcacggagg catgtgggag agggctgctc catggcagtg gctgaagggc tgggttgtgc   6180
cccgaggagg gtggatgagg gtaagaagtg gggtccccag gggctttagc aagaggaggc   6240
ccaggaactg gttgccagct acagtgaagg gaacacggcc ctgaggtcag gagcttggtc   6300
aagtcactgt ctacatgggc ctcggtgtcc tcatctgtga aaaaggaagg gatggggaag   6360
ctgactccaa ggcccctcct agccctggtt tcatgagtct gaggatccca gggacatggg   6420
cttggcagtc tgacctgtga ggtcgtgggg tccagggagg ggcaccgagc tggaagcggg   6480
aggcagaggg gctggccggc tgggtcagac acagctgaag cagaggctgt gacttggggc   6540
ctcagaacct tcacccctga gctgccaccc caggatctgg gttccctcct tgggggggccc  6600
cagggaacaa gtcacctgtc ctttgcatag gggagccctt cagctatgtg cagaaggttc   6660
tgctctgccc cttcctccct ctaggtgctc agctcctcca gcccactagt cagatgtgag   6720
gctgccccag accctgggca gggtcatttc tgtccactga cctttgggat gggagatgag   6780
ctcttggccc ctgagagtcc aagggctggt gtggtgaaac ccgcacaggg tggaagtggg   6840
catccctgtc ccaggggagc cccagggac tctggtcact gggcttgccg ctggcatgct   6900
```

-continued

```
cagtcctcca gcacttactg acaccagcat ctactgacac caacatttac aaacaccgac   6960
attgaccgac accgacattt accgacactg acatttacca acactgttta ccaacactga   7020
catctactga cactggcatc taccaacact gacatttacc gacactgaca tttaccaaca   7080
ctatttacca acactgacat ctactgacat tggcatctac caacaccaac atttaccgac   7140
accaacattt accaacactg aaatttaccg acaccgacat ttaccgacac cgtttaccaa   7200
caccgacgtt taccgacacc gacatttacc gacactgata tttaccaaca ctgacatcta   7260
ctgacgctgg catctactga caccgatgcc agcatctacc aacaccgaca tttaccaaca   7320
ctgacattta ctgacactga tatctactga cactggcatc tactgacacc aacatttacc   7380
aacaccagca tctaccaaca ccgacattta ccaacaccag catttaccaa caccgatgtt   7440
taccaacgcc gacgtttacc gacgccagca tctaccaaca ctgacattta ccgacaccga   7500
catttaccga cactgacatt tactgacact gacatctact gatactggca tctaccgaca   7560
ctgatattta ccaacgccag catctactga cactgatgtt taccaacacc gacatttacg   7620
agcaccgaca tttactgaca ccaatattta ctgacatcaa catttagcca tgtgatgggg   7680
gccggcttgg gggcaggcct tgctcttggc actggggatg ctgcagagac cagacagact   7740
catggggtca tggacttctg cttcttctcc agcctcatgt actggacaga ctggggagag   7800
aaccctaaaa tcgagtgtgc caacttggat gggcaggagc ggcgtgtgct ggtcaatgcc   7860
tccctcgggt ggcccaacgg cctggccctg gacctgcagg aggggaagct ctactgggga   7920
gacgccaaga cagacaagat cgaggtgagg ctcctgtgga catgtttgat ccaggaggcc   7980
aggcccagcc accccctgca gccagatgta cgtattggcg aggcaccgat gggtgcctgt   8040
gctctgctat ttggccacat ggaatgcttg agaaaatagt tacaatactt tctgacaaaa   8100
acgccttgag agggtagcgc tatacaacgt cctgtggtta cgtaagatgt tatcattcgg   8160
ccaggtgcct gtagacacag ctacttggag actgaggtgg gaggatcgct ggagtccaag   8220
agtttgaggc cagcccgggc aaaggggaca caggaatcct ctgcactgct tttgccactt   8280
actgtgagat ttaaattatt tcacaataca aaattaagac aaaaagttaa tcacatatcc   8340
actgccctgc ttaagacaga aaacatgggt gttgttgaag ccagaggcag ctgctggcct   8400
gagtttggtg attggttcct aagcagttga aggcagtttt gtttttccat agatgtctgt   8460
tctccctttg ctgggtgcag cctcgccctg ctgctgtggt cgggtttcag tggcctcgtc   8520
ccgtggacgc agcctcgccc tgccgctgtg gtcgggtttc agtggcctcg tcccgtggac   8580
gcagcctcgc cctgctgctg tggtcgggtt tcagtggcct cgtcccgtgg acgcagcctc   8640
gccctgccgc tgtggtcggg tttcagtggc ctcgtcccgt ggacgcagcc tcgccctgcc   8700
gctgtggtcg ggtttcagtg gcctcgtccc atgggcgtgc tttggcagct ttttgctcac   8760
ctgtggagcc tctcttgagc ttttttgttt gttgtttgtt tttgtttgat tttgtttgat   8820
tgtttgtttt tgttgtcgtt gttgttgccc aggctggagt gcagtggcgc gatctcagct   8880
cactgaaacc tctgcctcct tgggttcatg ccattctcct gcctcagcct cccacatagc   8940
tgggattaca agtgcccgcc accacgcctg gctaaatttt gtatttttag tagacagggg   9000
gtttcaccat gttggtcagg ctggtctgga actcctggtc tcacatgatc cacctgcctc   9060
ggcctcccaa agtgttggga ttacaggcgt gagccaccgc gcccagcctc tgttgagcat   9120
attttgaggt tctcttggtg ccagtgatat gtacatgtgt ccccatcgca ccatcgtcac   9180
ccattgaggt gacattggtg cctctcctcg gggtggatgc ctccctctgt ttccagcaac   9240
```

-continued

```
ttctgaagga ttttcctgag ctgcatcagt ccttgttgac gtcaccatcg gggtcacctt   9300
tgctctcctc agggctccca ggggaggccc gaatcaggca gcttgcaggg cagggcagga   9360
tggagaacac gagtgtgtgt ctgtgttgca ggatttcaga ccctgcttct gagcgggagg   9420
agtctcagca ccttcagggt ggggaaccca gggatggggg aggctgagtg gacgcccttc   9480
ccacgaaaac cctaggagct gcaggtgtgg ccatttcctg ctggagctcc ttgtaaatgt   9540
tttgtttttg gcaaggccca tgtttgcggg ccgctgagga tgatttgcct tcacgcatcc   9600
ccgctacccg tgggagcagg tcagggactc gcgtgtctgt ggcacaccag gcctgtgaca   9660
ggcgttgttc catgtactgt ctcagcagtg gttttcttga gacagggtct cgctcgctca   9720
cccaggcgag agtgcagtgg cgcaatcacg gctcgctgta gcctcaatct ccctgggctc   9780
aggtgatcct cctgcctcac cctctgagta gctgggacta cagacacata ccaccacacc   9840
cagctagttt ttgtgtattt tttgtggggg gagatggggt ttcgctgtgg tgcccaagct   9900
gatctcaaac tcctgaggca caagcgatcc acctgcctcg gcctcccaaa gtgctgggat   9960
gacaggcatc agccgtcaca cgcagctcaa tgattttatt gtggtaaaat aaacatagca  10020
caaaattgat gattttaacc attttaaagt gaacagttca ggctgggcgt ggtggcttat  10080
gcttgtaatc ccagtacttt gagaggctga ggtgggcaga tcacctgagg tcaggagttt  10140
gagaccagcc tggccaacat gatgaaatcc agtctctact aaaaatacaa aaattagccg  10200
ggcatggtgg caggtgcctg taatcccagc tactcgggag gctgaggcag gagaatcgct  10260
tgagcccggg aggtggaggt tgcagtgatc tgagatcatg ccactgcact ccaatctgtg  10320
tgacagagca agactctgtc ttgaaaaata aataaataaa aaaaatttta aaaagtgaac  10380
aattcagggc atttagtatg aggacaatgt ggtgcaggta tctctgctac tatctacttc  10440
tagaacactt tcttctgccc tgaaggaaac cccatgccca ccggcactca cgcccattct  10500
cccctctctc ccagcctctg tcaaccacta atctactttc tgtctctggg ggttcacttc  10560
ttctggacgt tttgtgtgac tggaatcctg caatatgtgg tccctgcgtg tggcttcttt  10620
ccatagcatt gtgttttcca gattcaccca cacattgtcg cacgttatca gaatctcatt  10680
cctgactggg tgcagtgggt taggcctgta atcctaacat tctgggaggc caaggcggga  10740
cgatcacttg aggcaggagt ttgagaccag cctggccagc ctagcaagac cccagctacc  10800
aaaaaatttt aaaagttaac tgaacgtggt ggtggtgggc acttgtggtt cccagctacc  10860
tgggaggctg aggtgggagg atcgcttaag cccaggaggt caaggctgca gtgagctatg  10920
atcgcaccac tgcactccag cctggacaac agagcaagac cctgtctgaa aaaaaaaaca  10980
aaaaaaaaag ttcctttctt tttgtggctg gatgacatcc cattgtatgg ccacagcaca  11040
ttttgtttgt ctgtttatcg ggtggtgggc agtggtttcc accttttgtc tcctgtgaat  11100
aatgctgctg tgaacatttg aattcaagtt tttgtttgaa cacctgttgt gaattatttg  11160
gatatatgtg taggggtagg attgctgagt cctatggtaa tgttaggttt gacttactga  11220
ggaaccatta aactgttttc aacagtggct gcgccgttct gcatccccac cggcagtgtg  11280
tgagggttct gactttacct cctcacaaac gcttcttttc catttaaaaa aatattcagc  11340
caggtgctct ggctcacgcc tgtaatccca gcactttggg aggccgtggc gggcggatca  11400
cctgaggtca ggagttcgag acgagcctgg ccaacatggt gtaaccccat ctctaccaaa  11460
aatataaaaa ttagccgggt gtggcagcgg gcgcctgtaa tcccagctac ttgggaggct  11520
gaggcaggag aatcacttga acccgggagg cagaggttgc agtgagccaa gatcgcgcca  11580
ctacactcca gcctgggtga caagagtgaa actccatcta aaataaaaca aaaataaaaa  11640
```

-continued

```
taaataaaaa tttattaaaa cattcatcac agccagccta gtgggtgtcc catgtggctt  11700
tgcctcgcat ttccctgata actaggatgc tgagcgtctt gtcccaggct tgccacacct  11760
cagcactttg agatacgtcg cacagtcccc atttgcgaac gagaaatgag gtttagggaa  11820
cagcagctgt gtcatgtcac acagcgagca gggggtctct gagccgtctg accccacagc  11880
cgaccaagct ccaatcctta ccgcctccta gtgttgtgga tgtagcccag ggtgctccca  11940
catttttcag atgagaacac cgaagctcaa aacaggagcg ttttgtccac attggataca  12000
cgatgtctgt ggtttggtcc tgaagtcact ttatatctca gtggtccaga ctggagtagg  12060
acaggggtt ctggggaatg gggaaggtgt ctcaggtgaa aggaaggaat tccagattct  12120
ccatactgtc cttgggaagt tagaagactc agagggtctg gcaaagtcag acaaagcaag  12180
agaaatgcag tcaggaggaa gcggagctgt ccaggaacag gggggtcgca ggagctcacc  12240
cccaggaact acacttgctg gggccttcgt gtcacaatga cgtgagcact gcgtgttgat  12300
tacccacttt tttttttttt ttgaggtgga gtctcgctct cttgcccagt ctggagtgca  12360
gtggcacgat ctcggctcac tgcaagctct gcctcccggg ttcatgccat tctcctgcct  12420
cagcctcccg cgtagctggg actacaggcg cctgccaccg cgcccggcta atttttgtat  12480
ttttagtaga gatgggattt cactacatta gccaggatgg tctcgatctc ctgacctcat  12540
gatccgcccg tctcggcctc ccaaagtgct gggattacag gcgtgagcca ccgcgcccgg  12600
cccgatttcc cactttaaga atctgtctgt acatcctcaa agccctatac acagtgctgg  12660
gttgctatag ggaatatgag gcttacaggc catggtgctg gacacacaga agggacggag  12720
gtcaggaggt agaagggcgg agagagggaa caggcggagg tcacatcctt ggctttcaaa  12780
atgggccagg gagagacacc ctctgagcat ggtaggacag gaaagcaaga ttggaacaca  12840
ttgagagcaa ccgaggtggc tgggcgtggt ggcttacgcc tgtaatccca acactttgga  12900
aagctgaggt gggtggattg cttgaggcca ggagttcaag accagcctgg ccaacatggt  12960
gagaccccgt ctctactaaa tatacaaaaa ttagccaggc gtgatggtgc atacctgtaa  13020
tcccagctgc ttgggaggct gaggcaggag aattgcttaa acctgggagg cggaggttgc  13080
agtgagccga gatcccgcca ctgcactcca gcctgggcca cagagtgaga ctccatctca  13140
aaaaaaaaaa aaaaaaaaga taaaaagacc aaccgaggaa ttgaagtggg ggggcgtcac  13200
agtagcagaa gggggatcgt ggagcaggcc accctgtggt catgcactgg aagctcatta  13260
cctgacgatt tggagctcat cactgggggc ctaaggagaa tagatactga aggatgagga  13320
gtgatggcgc ggggcacggg tgtctttggt ggccagaact tggggactgc tggggtgcct  13380
cactgcaggc cttctcagcg ccctttatat gcttacacag gctgtttcta agagggggat  13440
acattgcata agcgttttca gactacctca tcatgggtcc ctttctttac cctctgtggc  13500
cctggtggcg cactctctgg gaaggtgcag gtggatgccc agacccgccc tgccatccac  13560
ctgcacgtcc agagctgact tagcctcgag attgctgctg gcacctcctg ccccgggaca  13620
cctcggatgt gcccgtggag atgctggctc tgtgttttct gctggagttt ggtgcgtctt  13680
ttcctcctgc aagtggccac cgctcttggg tatgtcctca ggcttctgcg agtcatggct  13740
gcttctcagg tccttgccca gcgccaggag caaaccctcc tggcactttg ttcaggggtg  13800
gatgcgccag tgttcctgct gtggaccccc atctcacatg agggtcttgg gcctgcaggc  13860
tcgttcagga aacacccgct gagtacgcag tgtgtgccag ctgtgtccca ggcaatggcg  13920
gggacagtgg ctgctgctgg ggttgtggtg gcttctgggg actctgggga cagctgaggt  13980
```

-continued

```
gcaaggagcc acggctcctt gaggatgcag ttggactcca ggtggaaggg atggttgggg  14040
gaggtataaa tggggtcagg gaggagacac atttggaaca atgggaacat ttttaagatg  14100
ctatgtcggg aggcaacaag gtggccaacc caggtgctga ggagcccaca ccagccctgg  14160
acgtgttttg ccgctcacct ttgctgggga gtggtgggag agaggattcc gttccacgtg  14220
gtggtgtgcg cagctgggct gtgtggagct gggcgctagg aggaaggtgc tttctgcggg  14280
gctagccggg ctctgccttt gaacacaatc aggctccagg ttttcagcat ccagtgcatg  14340
agaggacttc acgggcagct gtggctgatc ccttgatgaa ttgggagaag aacaaaggtc  14400
tatgaaatga ggtttcatgt agatggcatt agagacgccc acaacagatt tacagagtgg  14460
agcggagacg gcggatgggt ctgggaggcc cctcctgctg gccttgactg tgacagctgt  14520
cctgggaatc agcttccagg ccgccccagc agcctgactg acacacacag gggttttagc  14580
cccatcctgc gaccagctgt tgccatcatc agtgacagct gggagtggcg gtggttccag  14640
ccctgggcac cctccccacc tgctggggcc cacccagggc agtcctgaca cctacaggtt  14700
gcttggagcc gcatccgagt cctgccccac cacgtgtgaa gcccgagtgg tcgtgggctg  14760
aggtcccctg attgcatccc cacttccctt ctgcttcaca tagctgcctc ttctcaccgt  14820
ttttccagcc tcctgggcta ggaattccag tgttgtgctg gctttgcccc aggacacctc  14880
cttagccctc ttcctgagtc tagagccccg gggttggaa gttctggccc ctgggacacc  14940
tgcagccaca ctcagcttct cctgtgagcc tccagcatgt cccctcagga ccaagccctc  15000
acgttcttgc ctccccgccc acctgggctc agccagggga aggcctggct gggagcgtct  15060
cccctctgcc ctgcccttct cccctctacc ctgcccttct ctcctctgcc ccgccatggc  15120
ttttatatcc tgtgccacaa gacatggctg tgtgtgaaag tggcagggtc tggcatctct  15180
gtgggtctct gaggcccacg ctccagtgcc actcttccca cccgctggcc gtgccctcat  15240
gctggaggga cagcccagcc ctctcccgaa ccccagcccc atgtgcccag ctgccccccgg  15300
ccctctcccc tggaagccgg ggtcactcca gccgtatgcc atggtgggga catcctgctt  15360
ccttggcctt ccagggaagg tcctctttcc aaatggcgac acctggtccc tgcctggagg  15420
ctggaagctg tggcccttgt atgcccctcc agggtctgtg cgctcggttg gcccgagttc  15480
ccatcaccgt catcatcacc atcatcattg tcatttcgct tgtctgtgag ccggcctggt  15540
ctcccagagc agagaccctc tgaggtccag cctgagttgg ggtctccgtg ctgacccctg  15600
acggggactc aggacgtacc aggtctgggt caggagtgac ccccaaacct cgtgcccttt  15660
gacaggcacc cctgactttt gctaagtggg tggaggtgac atcacttaca gcgggagtga  15720
tgggacaggg tctgttggct gcactgtgct cccagggatc tggggagagg ctatatccct  15780
gggctttggc actgcagagc tgtgtgtgtt tgtgtgtgtg tgtgtgtgtg tgtgtgtgtg  15840
tgtgtgtgtg tgtgtgtgtg tttgcgtgcg cgcacatgtg tataagatct ttttttatta  15900
catgaagcaa gataactgtt gctgtttcct tttgggtttt gtgttcaaca gagtggggta  15960
cttcttccct cagacaacag aactctcccc tttaaacacg tgctgtcaga gggtgggtct  16020
tgggctcatg tctgtttgca cagccgagtc agaggaaaca cagggttctt cataaaaaca  16080
ctgcacagca ggcgactgtc cagagtcagc ctgcaggacg gcagcagccc tgcccctcag  16140
agcacagcta gggtgggctg ctttgggatc tcccgtcatt ccctcccagc tggcagccgg  16200
cggccggccc attccttggt gtgctggtca ggggggcgtg cgcctgctct gctcaccctg  16260
ggaatgggac agaagctggc agctcggaga ggacagggct ggacccttgg gtggcctctg  16320
gctggaccat ctcattgtcc tcagacacag cctctcgggt ctagtttcat ttcctgaaaa  16380
```

-continued

```
acaagtgcac agaactagag caggagtcga gagctacggc ccccgggcca gatccagccc  16440
tgccacctgt tttcacacca tgctcaagct gagtgggttt tacatttttt aattacttga  16500
aaaaaaaaaa gccaaaggag gtttcatgac ccatgaaaat tatatggaat tcaaaaaaaa  16560
aaaattatat ggaattcaaa tttcagtgtc cataaataat ttcttgagac agggtctcgc  16620
tctgtcaccc aggctggagt gcagtgctat ggcatggctc gctgtaccct tgacctccca  16680
ggctcaagcg atcctcctgt ctcagcctcc tgagtagctg ggactacggg tgtgtgccac  16740
caagcccggc taattttttt ttaattttag taaagacagg gtctttctat gttgcccagg  16800
cttttctgga actccatctt ggcctcccaa agtgctggga ttacaggctc gagccacgga  16860
gcccagcctg tttttgtttt ttcactgata aagttttgcc gggtgtggta gtgtgtgcct  16920
ctagcgattt gggaggctga ggtgggagga tcgcttaagc ccaggagttt gaggctgggc  16980
tcaagtgatc aggaggtgaa ctatgatcat gtcattgcat tccagcctgg gtgacagagc  17040
aagaacctat ctcttaaaaa tatatattta aaaagtattg ggtgtggtgg ctcacgcctg  17100
tggtcccagc tacttaggca tctgaggtgg gaggatggct tgagcccagg agtttgaggt  17160
tgcagcgagc caagatcgtg tcactacact ctagcctggg tgacagagcc cagaccctgc  17220
ctctttaaaa aaaaaaacca aaaaacatgt attggaacac agccatgcct gttcagtcac  17280
gtgctctcca tgctgctttc tgctccagag acccttatgg cctgaaagct gaaaatattt  17340
tctatccttt acaaaaaagt ttgctgacct ctgtcctgga aaattcatct cccaagttct  17400
cttccggcac tggcgttcct gggtgtccta aatttggccc ctgttatttc tgaactctgt  17460
tttggctctg ttccctccca ggagccagga caggcacgtt ctctgcatct tgtcccctga  17520
cgcccagagg cttggctcgg ctcaggcatt cttggaaata tctggctcca ggaaaggcag  17580
aggcctcctg agtcagccca gagggaacct gccccaggtc tgggggaggc ctgacccagc  17640
agagtggctt ttgccgatgg gttgggccgg tcaagatgtg ctgaaagttg tcctcagaag  17700
gccactttgg gattccttcc tccagtatta gagcaactga gagctgctca ttgcaagcct  17760
gatgttttcc cagttggccg ggtccaccgg gtgccctggg attctgggat ctgggtggaa  17820
agtagggggc ttgggggagt gtcctgggtt ctggaatcca ggtggcaagt ggtgaggttc  17880
agggagtggc ttctgagcca ccataggggt ctctgtggga ggctctgccc atccaggaga  17940
ttccgcaggc cctgccggcc cagagccagc gtcttgcgct tgccgaggct acagccagcc  18000
ccagccgggt ggaacagccc gtcgcctcct ctcactttgt tttggggcca cctgggagtg  18060
tggagcaagg gtagagaggg aggaagtggc tgccggccgc tgcccagcac ccttgtttgc  18120
cttgggccct ctgtgggctc ctttttattg ctcttcaatg aagccaggga aatggacttc  18180
cttgcctcac ttcagttcaa catgtctgga agtttggtat taaaattaag aaagtgtgga  18240
aatagagcaa gaagagaaaa atctctccaa gagataatag tgacctctga gctgggcgcg  18300
gtggctcacg cctgtaaatc ccagtacttt gggaggctga ggcgggcaga tcacctgagg  18360
tcgggagttt gtgaccggcc tgaccaagat ggagaaaccc cgtctctact aaaaataaat  18420
aaataaataa ataaataaat acaaaattag ccaggcatgg tggcgcctgc ctataatccc  18480
agctaaggca ggagaatcgc ttgaacctgg gaggcaaagg ttgcagtgag ccaagatcac  18540
gccattgcac tctagtctgg gcaacaagag tgaaactccg tctcaaaaaa aataaataaa  18600
taaaaaataa aaatagtgac ctctggccag gtgtggcagc tcatacccgt aatcccagca  18660
ctttggaagg aaggccgaga tgggcagatt gctttagcac aggagtttga gaccagcctg  18720
```

-continued

```
gccaacatgg tggaacccca tctctacaaa aatagaataa aatttaagag gtaatagtga  18780
ccttttggta gatcgaaacc tggattgctt tctttttcta aatgctgatt cttttctttg  18840
tggtgtttgt gttctgtgcc gatgtccctc ccccagccct gttattgtga gtggaagaag  18900
gggaaagggt tcgcccgcta ctgtgagccc ctcctctcac gctgggtgtc cttggagaag  18960
cctgcacttc ttcattgtac gccagggctg ggtccctccc tggagtggtt ctgtgctgct  19020
gggatggggc caacccctca gatgttttct gagtgtcaca cacaggtgtg tgcattcatg  19080
gcctttgcgt gtcttcctgt tgtggaggca aaaatgtgaa gaaccctaga tgattttggg  19140
accagggctc catcacctgc tgttcattgc acaccggagc atccaggcat gggtggagag  19200
ctcagacttc caggcacggt cgcaggggct ggtctaacca tgttcccgcc cgcctgctcg  19260
tcagaaccgc ctgttgggag ctgttatcat gataccatac ctgggccctg ggctatccga  19320
ttctgactta attgctccag gttggggcca ggccgttgtt tgctgttttg ttgtttcttc  19380
tgtgacgtta gccactgggc taatctgagc ccctcagtta caggtggaga aactgagacc  19440
catgggggtg caaggacttg ccgaggaccc agagcccctt gggggcagag ctgaggcggg  19500
gcctggcttt gggtcccaga gcttccagtc cccttcccgc tctcctaaca gcttttttttt  19560
ttgagacaag atctcaccct gtcacccagg ctggagtgca atggcatgat ctcggctcac  19620
tgcaatcttc gctagctgcg ttccagcgat tctcctgcct cagcctcccg agcagctggg  19680
attacaggtg tgtgccgcca tgcccagctc gtttttttttt gtacttttag tagagatagg  19740
gtttcaccat gttggccagg ctgatctcga actcctgacc tcaaatgatc cgcctgcctc  19800
ggcctcccaa agtgctagga ttacaggctg ggatcacact gtgcctggcc ctagcagctt  19860
tgtcctgtgc catccaacaa cagatgaccg aagtctttgt ttcttaacat gcattccatc  19920
tgccttacag ttttgccacc tgcaaaacag aggacttgtc gcttttctgg taagctggaa  19980
atgtaatctg gtagcaggag gcctgtggaa gcttgccttt aatggccttg tgtctctttc  20040
atcctgtcct gagagccgga gaacttggat gttgcaccta actcaacctt cctgttaaca  20100
tacagttctg caggctcatg gatcatcaga accacgtcct atctcacgcg gctgtatgct  20160
tccgttggtt caggtgtttt taccttgaca gtattttctc ctcggtggct tttgcggtgg  20220
ttgcttttaa tcagcattga ctcttcaaga aaaatattta gctgctacat ctcagaggag  20280
acagggtgga aagcatctga gacctgcagg ctcagactta gaaccagaag tgccctcaga  20340
gttcatccgg ccctgaccca gcgggaaatg agttcacaga gaagcgggag aactttgccc  20400
caggccctgc cgttgctcat aactgcccca ggtccttaca tttgctccag gtcctgcccc  20460
aggccctgca gttgctcata actgccccag gtccttatat ttgctccagg tcctgcccca  20520
ggtcctgcag ttgctctgtg tggtgggtgt gatctggagc cctccgccca ttgctgcacc  20580
tggggcaggc attgctaatt gatcccagga ctccttcctg cggagcacgc cctggttctc  20640
caggcagccg ctgcctgtca gcctgcagtg gttcgggaga ggacacctgc ttgcctggtc  20700
tgttccaaat cttgcttctc atcccagcac aggtaggggg tgctatggga aagggatcct  20760
cagttggccc tgtcactgct ctatcagctg gggacgtggc atcctagtga aaacatcatg  20820
gccgggcgcg gtggctcacg cctggaatcc cagcactttg ggaggctgag gagggtggat  20880
cacttgaggt cagaagttcg agaccagcct ggtcaacatg gtgaaaccca tctctactaa  20940
aaatacaaaa attcgccagg tgtggtggcg ggtacctgta atccgagcta ctcgggaggc  21000
tgaggcagga gaatcgcttg aacctgggag gtggagcttg cagtgagccg agatcttgcc  21060
actgcactcc agcctgggca acagagtgag acgctgtctc aaaatctcaa acaaacaaac  21120
```

-continued

```
aaacaaaaaa caaacaaaca aagcgtcatt tatccagcac ccctggggaa ccatgctacc  21180
tggtgtttta tggtacctgg caaggtgcag gtgaagttgc tgctcttggg cattgaaccc  21240
gtcttgtttg gggcagctca ggccccaggc agggtccggg ttggctctcg ttggtgtggc  21300
cctggcccat ccagacctat atttctgccg tcctgcaggt gatcaatgtt gatgggacga  21360
agaggcggac cctcctggag gacaagctcc cgcacatttt cgggttcacg ctgctggggg  21420
acttcatcta ctggactgac tggcagcgcc gcagcatcga gcgggtgcac aaggtcaagg  21480
ccagccggga cgtcatcatt gaccagctgc ccgacctgat ggggctcaaa gctgtgaatg  21540
tggccaaggt cgtcggtgag tccgggggt cccaagccat ggctcagcca tgcagacttg  21600
catgaggagg aagtgacggg tccatgcctg ggcataagtg ttgagctcag gtgccccgac  21660
ctggggaagg gcaggacagg aaaggtgaca gtatctggcc aaggacagat gggaagggac  21720
caagggagct gattagggag tggttatgga ctaggaatgt cggtaacaat ggttagaaag  21780
tgactaacat ttgttgagca cctgctgtgt gcccggccct ggccgggagc cttcgtgccc  21840
acagtgaccc cgtctgcaaa tgtagttcct tgccctactc gcactgggga gcaggacgca  21900
gagccgtgca tctcacaggt gccaagctca ggactccctc ctgggtctgc ctgggctggg  21960
ctgtgcttgt tgcccctgtg gcccacgcat gtgcaccttc cacctgaaag ccaggatctt  22020
caggacgctc cccgaggagg tcgttgtctg gcacaatgat ttgtctcttc ctgaaaaggt  22080
gacagagtta cactggagag agcagcatcc aggtgcggca gggacaggcc tggggctcgc  22140
gggcagggac tctgtgtcct gccggggtcc cacactgcac ctgcttgtca gaggcactca  22200
gtcaatcttt gctgatgaag gatgagagga cagaggacgt gatgcttgct gctgcattgc  22260
ctgcagtcct gggtgagatg cccgggttga ctctgctgcc cgtcgggtgg atgtgatgtc  22320
agatccccgg ctttaaaata cgagggagct gggaattgag ggagcaggtt ggggcagaaa  22380
gcacagcccc gtggaagcct ggagctgagg cagtgtgggc gacccctgga gcagtgagtg  22440
cttccttcat ggccttcatc gcaccctgca gtcctcatgt aggggatgcc atccatgaat  22500
ttagttttcc cagcctcctt taaaaacgcg ttcatgctgg ggccggggca gtgcagtggc  22560
tcacatctga aatcccacca ctttgggagg ccgaggcggg tggatcatga ggtcaggaga  22620
tcgagaccat cctggctaac aaggtgaaac cccgtctcta ctaaaaatac aaaaaattag  22680
ccgggtgcgg tggcgggcgc ctgtagtccc agctactcgg gaggctgagg caggagaatg  22740
gcgtgaaccc gggaagcgga gcttgcagtg agccgagatt gcgccactgc agtccgcagt  22800
ccggcctggg cgacagagcg agactccgtc tcaaaaaaaa aaaaaaaagt acaaaaaaaa  22860
aaaaattagt ctgggtgtgg tatcacgcgc ctataatctc actactcgag aggctgaggc  22920
ggagaattgc ttgaacccag gaggtagagg ttgtagtgag cccgtatcgt accactgccc  22980
tccacctggg caatagagcg agactctgtc tcaaaaagaa aaaaaaaaaa agaacattta  23040
tgccaggtgt ggtggctcat gcctgaaatc ccagaacttt ggaagactga ggcaggagga  23100
tcacttgagc ccagaaattt gagagtgtct tccctgggca acatagagag acctcatctc  23160
taccagaaaa aaaaaaatta gcccggcatg gtggcatatc cctgtggtcc cagctactta  23220
gggggctgac gtggcaggat cacctgagtc tggaggcaga ggttgaagtg agctgagatc  23280
atgccactgc actccagcct gggtgacaga cagagaccct gtctcaaaaa aaaaaaaaaa  23340
aaaaagcatt tactatccac catggaaggt gagactgacc tgtgagtgat tgttcaaaga  23400
acaaaaaata aaccccagag ataagacaaa agggtgcctc catgggggtg tgatttaaag  23460
```

-continued

```
ctgagaaatt gggcttcttc cccctcccct ctcaccccgt ggtttgctaa aggagatggg  23520
aaaaaggatt cttttttttgg ctgaaatatt taacactaaa ttaaagccaa ttttaacagc  23580
actttggttg atgagtgaaa ttaacagact ggccaaaaat aaacgaacgg tctgtactat  23640
gtgaaaaaga ggcagctttg gccatgctgg gccaatgtga gttttcaggg ttgctgggaa  23700
tgtctgtgaa tcggaggaag ggcctagctg ggactctcag gagccaaggc cctgaggggc  23760
aacttgcctg gtccctgccc tgaggcgttc actgctttct tcctgggcca gatcacaggc  23820
ccggaggctg gaccactggg ctggcactct tgccgagctg ctccctgact tcctgaccat  23880
gctcctttca gcagccttgc tgcactttag tttccttgaa tgaaaaatgg ggatgagaat  23940
agctcctacc tccaaggtga atggagtgag ttcggacagg tgactccctg ggaccagtgc  24000
ctggcgcctg acaaggtcca gtcagagccc gcactgctgt tactgatacc cttggctgta  24060
ccaggggaga acttggttgc cattgccagg tgttctccca ccaccccccac tactgtccct  24120
gtttgatgtg tggcgggaat aaagctgtgc acattggagc ttttggcaca tcctggcttt  24180
caggtgaaag gtgcgtgtgt gtttgagggt ttagcctggc caacccagcc atgaggtcgg  24240
acctgacctg gggtgagtc ctgagctcgg cacccctgag ctgtgtggct cacggcagca  24300
ttcattgtgt ggcttggccg caccccttc cctgctgggc tgttgatgtt tagactggag  24360
cctctgtgtt cgcttccagg aaccaacccg tgtgcggaca ggaacggggg gtgcagccac  24420
ctgtgcttct tcacacccca cgcaacccgg tgtggctgcc ccatcggcct ggagctgctg  24480
agtgacatga agacctgcat cgtgcctgag gccttcttgg tcttcaccag cagagccgcc  24540
atccacagga tctccctcga gaccaataac aacgacgtgg ccatcccgct cacgggcgtc  24600
aaggaggcct cagccctgga ctttgatgtg tccaacaacc acatctactg gacagacgtc  24660
agcctgaagg tagcgtgggc cagaacgtgc acacaggcag cctttatggg aaaaccttgc  24720
ctctgttcct gcctcaaagg cttcagacac ttttcttaaa gcactatcgt atttattgta  24780
acgcagttca agctaatcaa atatgagcaa gcctatttaa aaaaaaaaaa gatgattata  24840
atgagcaagt ccggtagaca cacataaggg cttttgtgaa atgcttgtgt gaatgtgaaa  24900
tatttgttgt ccgttgagct tgacttcaga caccccaccc actcccttgt cggtgcccgt  24960
ttgctcagca gactctttct tcatttatag tgcaaatgta aacatccagg acaaatacag  25020
gaagactttt tttttttttt tttgagacag agtcttactc tgttgcccag gctggagtac  25080
cgtagcgtga gctcagctca ctgcaacctc cgcctcccag gttcaagcga ttcttctgcc  25140
tcagcctcct gagtagctgg gactacagac atgcaccacc acacccagct aattttttttt  25200
atatttttag tagagacagg gtttcatcat gttggccagg ctggtcttga actcctgacc  25260
tcaggtgatc tgcccgcctc ggcctcccaa agtgctgaga taacaggtgt gagccaccgt  25320
tcccggcata ggaaaacttt ttgccttcta aagaagagtt tagcaaacta gtctgtgggc  25380
tggccttctg attctgtaaa gaaagtttga ttggtggctg ggtgcggtgg ctcacacctg  25440
taatcccatc actttgggag gccgacgtgg gcatatcacc tgatgtcggg acttcgagac  25500
cagcctcacc aacgtggaga aaccccgtct ctactaaaaa tacaaaaaaa aaattaaccg  25560
ggcatggcgg cgcctgcctg taatcgcagc tactcaggag gctgaagcag gagaattgct  25620
tgaacctggg aggcggaggt tgtggtgagc tgagatggca ccattgcact ccagcctggg  25680
caacaaaagt gaaactccgt ctcagaaaaa aaaaagtttg attggtgtaa ccaaagcgca  25740
tttgtttatg gattgtctgt ggcagctttt gttctgccga gatgagttgt gacagatctg  25800
tatgggctct aaagcctaaa acatgtgcca tccgcccctt tacagaaaaa gtgtgctgac  25860
```

-continued

```
ctctgttcta aagtattgga caactacaat gtttgctcat ttattattct atgatttgtt  25920
ttctgctttt tgttgttgtt gttgttgttg agatagggtt tccctctgtc actcaggctg  25980
gagtgcagtg gtgtaatctc agctcactgc agcctcgacc tcctgggctc tagtgatcct  26040
ctcatctcag cctccctagt agctgggact acaggcacac accaccactc ctggctgatt  26100
tttttttttt tttttttttt ttgtggagac agggtttccg catgttgccc aggctggttt  26160
caaactccta ggctcaaaca cccacctcag cctcccaaag tgctgggatt acaggcgtga  26220
gccaccatgc ccagcctatt ctactgtttg tattacatag ctttaaaaga ttttttatga  26280
ctttaagtca caagggttct ttgtagaaaa aaatatatat ataggaaagt ataaaaagaa  26340
agtaaaaatt gtccataacc tctccagcca gagacgaccg ttgctgacac ctcagcatat  26400
tgcctttaag tcttttttct ctaagatagc atttctcttc atcacagtca tatgctacgc  26460
agaattctgt atcctgattt tttcacttga cattacaaca ggtatttgat ggcgctgtga  26520
caaactcttt ggcacaatct tttaaatgta tgaaatactc cactgcacag atgtttgctt  26580
ttaggcttaa ctgttctttt attttgcgtg tgctggttac agccgggcac agtggctcat  26640
gcctgtaatc acaacacttt gagagggtga ggcaggagga tcacttgagc ccagaagttt  26700
gagaccggcc tgggcaacat agtgagaccc catctctaca aaaaactttt ttaataagtc  26760
gggcgtagtg gtgcatagct gtagtcccag ccaccaagga ggctgagttg ggaggattgc  26820
ttgagcccca ggaggttgat gctgcagtga cctgagatta ctccactgta ctccaacctg  26880
agcgacagag caagacttgt ctggggaaaa aaaaaaaaaa aatatatata tatatatata  26940
tatatataca tatatacata cacgcacaca cacataatat aaaaatatat atttataaat  27000
atataatata taatataaaa atatatattt ataaataaaa tttataaatt atatttataa  27060
gtaaatatat aatatataat ataaaaatat atattatata atatataata aaatatataa  27120
tataaaaata tatatttata aataatatat aatacatact tataagtata tatttaaaat  27180
atatgtaatg tatatttttt aatgtatgat atataatata catttataaa tacacattta  27240
tattatttta tataaaatat atataaaatc tccaagttgc tttttccaaa aaggtgtctt  27300
gctgcatttc aaacattcat ttaaaaactt gaatgctggt gatctggtcc agaatgtgtt  27360
cagtagctgc tgccagtggc caagcatctc gggagatgtc tacaaaacac gctggttctg  27420
gcctggcgtg gtggctcacg cctgtaatct cagcactttg ggaggctgag gcaggtggat  27480
caactgaggt ctggatttcg agaccagcct tgccagcttg gtgaaacccc atctctacta  27540
agaatacaaa aaaattagcc aggcgtggtg gcatgtgcct gtaatcccac ctacttggga  27600
ggctaaggct ggagaatcgc ttgaacccag ggggcagagg ttgcagtgag ccgagatcgc  27660
accattgcac tccaggctgg gcaagaagag cgaaactccg tctcaaaaaa aaaaaaaaag  27720
atgctggttc ctaaaatgtg gcccttttcc tcctcacctg ctgccagacc atcagccgcg  27780
ccttcatgaa cgggagctcg gtggagcacg tggtggagtt tggccttgac taccccgagg  27840
gcatggccgt tgactggatg ggcaagaacc tctactgggc cgacactggg accaacagaa  27900
tcgaagtggc gcggctggac gggcagttcc ggcaagtcct cgtgtggagg gacttggaca  27960
acccgaggtc gctggccctg gatcccacca aggggtaagt gtttgcctgt cccgtgcgtc  28020
cttgtgttca cctcgtatga gacagtgcgg gggtgccaac tgggcaaggt ggcaggctgt  28080
ccgtgtggcc ctcagtgatt agagctgtac tgatgtcatt agccttgatg gtggccagga  28140
ctggtagggc cctcagaggt catggagttc cttcgtggag cgggtgctga ggctgtatca  28200
```

-continued

```
ggcacagtgc tggctgcttt cacctgggcc gtctcaccga agtgtccatg gagcctgcgt  28260
agggtgggta tctgtgtcga ttttacagat gcagaaacag gctcagagaa accgagtgac  28320
ttccctaagg tcacataccc agttagagca gagctgggcc aggaagtgct gtctcaggct  28380
cctgaccagg tctccttgct ttgcactctt gccaaaacca tgatccagaa ctgactttga  28440
ggtccccgga cctcaggctc ctccgaaatg gcctcttgga ggctgctgag ccacagctta  28500
ggacccacct cgagaggcaa atgtgctttg agctgccagg cgtcctgggg gccctgcctt  28560
gggcacgggg ttcagacagg ccccagatgt gtggggcgtc tttctggact tgagttttct  28620
tttctgtgtg gtggacacag tgctcacccc ttaaagcacc tgtgatgtgt gcagcagccc  28680
aatccctgcc tgtcgcctgt tctgctaggg aaggaaggaa gacttcagga tggcaggaca  28740
acagaaagag gtccaggttt tagagcaagg gcaggtcaaa cttagaaaat tctggaatga  28800
ggatgtgcat ttcctcttct ggatctgcta aaagaagagg gaaggagggg ctgctggggg  28860
aggagcccag agccgagttt acatccggat cccgcaaggc ctcccctgcc ctgaggtctt  28920
gttttgtgat gtgcttgtgt ccatcctggt ttctgccgtg tccccaacat ccggccaagc  28980
ttaggtggat gttccagcac acactcaccc tgtctgtgca cctgtttttg tgtccgtaag  29040
tgggtattta ctcaccttac gagtgagcca ctgtgggaat tcagggaggt ggcgcagtga  29100
ccacccctgg agggatatgt gtgtggcagg ggtcgagggt ctcgcccttc cctgcttcct  29160
gcgcgtggct ttctccagga cggggagggc tgagctgaag aggtggggac agttgcgtcc  29220
ccccgccacc cactgtcctg cggtgagagc agactcactg agcctgccct tctcccttgt  29280
gccttccagc tacatctact ggaccgagtg gggcggcaag ccgaggatcg tgcgggcctt  29340
catggacggg accaactgca tgacgctggt ggacaaggtg ggccgggcca acgacctcac  29400
cattgactac gctgaccagc gcctctactg gaccgacctg gacaccaaca tgatcgagtc  29460
gtccaacatg ctgggtgagg gccgggctgg ggccttctgg tcatggaggg cggggcagcc  29520
gggcgttggc cacctcccag cctcgccgca cgtaccctgt ggcctgcaag ttccccaacc  29580
tggcaggagc tgtggccaca cccacgactg cccagcagcc tcaccctctg ctgtgggagt  29640
tgtccccgtc cacccctggg tgcctttgct gcagttatgt cgggagaggc tctggtgaca  29700
gctgtttcct gtgcacctgc tgggcactag gtcccagcta atccctgtgc caggactcta  29760
atttcaccct aacacacatg gtggttttca ttgctgggga agctgaggcc tgagcacatg  29820
acttgcctta ggtcacatag ctggtgagtt caggatcccc cagagatacc agggccagca  29880
ctcgatcccc acccagccct gaaccccacc atgtgctggg attgtgctgg gagtgtccac  29940
acgcctggga ccccagggct ggtgctctca tctccttttt ccagatcatg agaatgaggc  30000
tcagggaagt ttgaaaaaaa cctatcccaa gtcacacagc aacaggagca ggatttgaac  30060
ccagaaaagg ggaccgcaca ctctgttctg ctagagtagt tagctgtcct gggtgatatg  30120
gcaggtgaca ggggcaactg tgcttaacaa aggaaccccc atcccccctg ccaagttggg  30180
agactagaag gtcaggggca gaagctctga agggccaggt gcagtggctg acacctctaa  30240
tcccagcact ttgtgaggcc aaggcgggca gatgatttga gcccaggagt tcaagatcag  30300
cctgggtaat gtagtgagac gccatctcta caaaaaaatt ttttaaaaat tagctgggca  30360
tggtggttca tgcctgtagt ccaagctact tgggaggctc aggtgggagg attgcttgag  30420
cccaggaggt tgaggttgtg gtgagctgtg atcatgccac tgcactccag cctgggcaat  30480
agagtgagac cgtctccaaa aaaaaaaaaa gaagaagaaa aagaagctct gaggctccaa  30540
gtccccaggc accccttggc ttgagggcag acaagggagg agagggtcac ctgggcagcc  30600
```

-continued

```
ctgacttttg tcccctggca aagggacctt cagtgacctt ggccctagga gagcctctga  30660
gcacgtcagc catgtcgaac cgctcaggaa gggcagcaag aatttggctt ctgacctctg  30720
cctctcctac tcgccatctg cactgggtgt ggttgtgccc attttacaga tgaggaggct  30780
ggggcatcga ccagctgaat gccttgtccc aggtactgcg taggcagagc tggcagttga  30840
accccgtgtc ctggttgtcg ctgggggtgg gctgcaccct gacttgtgag gccagtagca  30900
aggtttgcac gtgacttcgt gaccgtcacc cagctctgca gcacatcccg tgacccagct  30960
catccaggcc gcatgcaaac ctgttgccag gcgagaaacc agtcaccgca cagctgtggt  31020
tgcctgaaat gattaagctc attaatcacc ccggagtgag gacagactca gatgaaaacc  31080
agcaaaagcc ctggaaactc atgtgaccct gccaatgagg gcggccatgt gcattgcagc  31140
ctggccgtca ctcctcggta cgtgttttgg acttaaacgc tccggatgtt tactgagtgc  31200
ttgattaata acatggaagg cctggtctca ttgctgtggg agtgaaggat gcacagccag  31260
gcctgacatg atgagaacaa gaacctggag tctcgctgcc tgggtggtaa tcctggccct  31320
gccacttagc aactgtgtga ctgtagccag gtcacttaat tttgctagat cctgcctgcg  31380
cttcagtgga tcttgctggt tttccaaggt ggccaaacac tttaaggcat tcatgtggtc  31440
gctaggctgc agggttgaac cctggctcac cccgcagggc gccgtgtgct ctgtggcctg  31500
gctgtgcctt tgctgacacc gtgcccgtgt gtgttcatgc aggtcaggag cgggtcgtga  31560
ttgccgacga tctcccgcac ccgttcggtc tgacgcagta cagcgattat atctactgga  31620
cagactggaa tctgcacagc attgagcggg ccgacaagac tagcggccgg aaccgcaccc  31680
tcatccaggg ccacctggac ttcgtgatgg acatcctggt gttccactcc tcccgccagg  31740
atggcctcaa tgactgtatg cacaacaacg ggcagtgtgg gcagctgtgc cttgccatcc  31800
ccggcggcca ccgctgcggc tgcgcctcac actacaccct ggaccccagc agccgcaact  31860
gcagccgtaa gtgcctcatg gtcccccgca cctcactccc tcgttagatc aggctggttc  31920
tgggagctga cgctgaaagg agcttctcat ctggggttcc tgggtgtaca tagatggttg  31980
ggtaggttgt gcactgcaca agctgcatga tgctacctgg gggtccaggt ccaggctgga  32040
tggacttgtt gcttcatcag gacatagata aatggccaaa actcctcagc tggaaggtcc  32100
tgggcaggat ctttgggtgt gaaaaccagt cacaggggaa gggtgcttgc tcatactgcc  32160
agcacagtgc tgagtgcttt ccatagcgct cgtttactcc tcaagcctgg agggtgggga  32220
gtagcatggt cccatttcac gtacaaggaa cccgatgcac agagaggtgt ggcaacccat  32280
ccaaggccat acaactgggg tgggttgagc cggggttgac tgtggcaggc tggctcaaga  32340
gtccctgctc ctgaaccctt gccaggcagc ctggcatcag ctcggggaat ttttgccctg  32400
acccttggaa gcaagtgggc ctctttgttc tcatgtcagt gatgagaaga gtgactttcc  32460
tatggcccct ctggagtaca ggtgtttcct gttggcgggc tcttccccca tgacatcagc  32520
agcgagctgg ttatgattcc ctacgcagaa cttgatagtt tataaagctc tttgtcatcc  32580
aggccccgtt ggagtctcac gcagacctgg tcgcaggcgg ggctggtctt gcctgtccca  32640
gctgcatgga tggggaactt gaggcttgca aaggttaagg ggctgttcga ggcccaggct  32700
ggcaggagat gggcctgggc cagagtctgg gacttcccat gcctgggctg tctttggtcc  32760
tgttgctcac catccctccc tggggccatg accttagaga gccaaatgga ggtgcaggta  32820
acccacggca aggaggggtt gccatgactc agagtccccg tcctgtggcc ggcagtacct  32880
ggtgcaacga cttggatttc agaccagcca ctgtagcccg ctgacggtgc gctcgaagtg  32940
```

-continued

```
ccacagcttc tgaagccagg caggactcag gccaggagac tctgttagct gttgagaggg  33000
agaggccaac ggatgttctg gttctgctag agagctggtt cttcggatcc tggtaccagt  33060
gcactgagag gaggcccagc ttgattctgg ggctgccttg tggtggcatg tgctgctcac  33120
tgacaccctc gaggagtgtc ttctctcggg cttgttgact gtgcccggtt ttccgcagtt  33180
cactggtgca cacataggca catagcaaac cgcacacaca gtcgtgggta tgagtttcac  33240
tacattccac caccagtgtt cactaccatt acctgccttc cgtcttaagt gttcatcatt  33300
taaaaataaa tttattgggc tggacgcggt ggctcatgac tgttatccca gcactttggg  33360
aggctgaggc gggcagatca cctgaggtca ggagttcaag accagcctgg ccaatatggt  33420
gaaactccat ctctactaaa aatacaaaat tagctgggca tggtggggca tgcctataat  33480
cccagctact caggaggctg aggcaggaga atggcgtgaa cccgagaggc agagcttaca  33540
gtgagcccag atagcaccac tgcagtccag cgtgggcaac agtgcgagac tccatctcaa  33600
aaaaaaaata aataaataaa agaaaaataa atttatgatc tatttcaaaa ataacacatg  33660
tactttgaaa cagcagagac acatatgaca cggagaatga aattccccat agcgcacccc  33720
caagagacag ccctggtccc cccgtctttc ccgtggacct ccagcggggc agatgctgag  33780
ccgcctgttg tcgagtggcg tgctatcccg tcctccagct cctctgtggc ttacagacac  33840
ccacctgcag ccctgtcttt gcctcctcta gcgcccacca ccttcttgct gttcagccag  33900
aaatctgcca tcagtcggat gatcccggac gaccagcaca gcccggatct catcctgccc  33960
ctgcatggac tgaggaacgt caaagccatc gactatgacc cactggacaa gttcatctac  34020
tgggtggatg ggcgccagaa catcaagcga gccaaggacg acgggaccca ggcaggtgcc  34080
ctgtgggaag ggtgcggggt gtgcttccca aggcgctcct cttgctggtt tccaggctgc  34140
tgcccctgtc cttagcagag ggaggaaaca gaggatggct ctgggtgaat gatgacttgg  34200
gcttcgatta tgtagtcaca gggtatgacc ctgagatgcg tggaaccccg agactgtgat  34260
tatatgtaga aactgggttt ccccgttgtt taagtagtca tggtggggtc agaccccaca  34320
ggacttttgt cttttcaaga aagaaaatgg tcgtgtgtca tgcaggggta gttggtactg  34380
gttaatccag gtttatcctt tattttgtgg gaactgtaca gtcatttctg ctacaatgct  34440
gtatatgctc ttctgaaaga cacctatgca aaatcgcaca gtaaaaatga cacaactcat  34500
agggaaagcg gggccagggc acagccctca aaatctccat caatgacatg taagaaaaga  34560
gaggaacctg ggaaatagca aagtgccttt tgcacattaa atggttagct atatcccaca  34620
atactgtgca ttcgtaaacg ttaatgctgc aataaatacg gcacttcacc ttgggaagat  34680
ctggagttgg cttatgagtg tggaagggtg tagcgcatga gtttttgtga aacactggaa  34740
ggaggattgt gggaaatcaa atggaaagtt ctcaccccag gcgtggagaa gagtgggtca  34800
tggccccagc agtgagccca gggaggtcag agacggaggt gtgtgtgtgg gtgtgaccct  34860
gcgcagttcc ctgccggctg tagttttttg cattcgctta atgtttctcg tggaggaaat  34920
tgtgcatgag caaatgtgaa accgtgctgt gctcaaattg tcctaataca tcattgcatt  34980
ggaacagatt ggcttttttt tttttttttt tttttttttt tttttgagat ggagtctcac  35040
tctgtcacca gcctggagtg cagtggcatg atcttggctc actgcaacct ttgcctccta  35100
tgttcaagtg attttcctgc ctcagcctcc tgagtaactg ggattacagg catgagccac  35160
cgcggccggc cagatttgca tttttgaaac aactgctagg ctgggcgcgg tggctcacac  35220
ctgtaatccc agcactgtgg gaggccgagg caggtggatc acctgaggtc aggggttcga  35280
gaccagcctg gccaacatgg tgaaaccccg tctctactga atatacaaaa atcagctggg  35340
```

-continued

```
tgtggtggcg ggtgcctgta atcccagcta ctcaggaggc tgaggcagga gaattgcttg  35400
aacccaggag gcagaggttg cggtgagccg agatcacacc attgcactcc agcctgggca  35460
acaagagcaa aactccatct caaaaaataa aaaatagaaa aacaagtgct gtagcggaag  35520
tgagcacttt gcggagtcag gcttgtgtgg cctgttccac aaatgatgtg ctcacggtgg  35580
cctcaggccc acctggagtc tgcagcatgg ggcacaacag gttcattagt gtagaattcc  35640
aggacaggcc tggctcctaa gcagccttct tttacaaaaa ctgcagagcc cgcctgtatc  35700
ctagcacttt gggaggccga agtgggtgga tcacgaggtc aggagttcaa gaccagcctg  35760
gccaacatgg tgaaacccca tctctactaa atatacgaaa attagctggg tgtggtggca  35820
cgcgcctgta gtcccagcta ctcgggaggc tgaggcagaa ttgcttgaac ctgggaggtg  35880
gaggttgcag ggatctgaga ccatgtcatt gcactccagc ctgggcaaca gagcgagacg  35940
ccatctcaaa aaaaaaaaac ctacagagcc acacggcctc tttctccacc gagtgttggt  36000
gtgggagctt gtgttattgt ggtgaaatct tggtactttc ttgaggcaga gagaggctga  36060
gcgcctggag agactttcac atgggtcgcc atgtccgccg tcggtttcgc tgttgtgctc  36120
cccatctgaa ggctggtgcc gtccagacag gctggacgcc cctttccacc agatccttcc  36180
tcccgcagca gtttctagtt acgttgtact gtgaggtctg tgtccttggt tgatggcaaa  36240
agtcagccga attgaaattc agagccatgc ctggctccct ggagcttctc tcctgggcag  36300
ctgtgatcat tgcctctgct gtggtgtggg tggtggaaat ggattccttt catcttgctt  36360
gctacaggtg actgtcacgt ggagtccttt ggagagaggg acgtgttaat tgatggatgt  36420
ggctcccatg ctgagaaagc tcctgggcgt acattgcctt agagtttcat tggagctgcg  36480
ttcttttatg gtgtctgcta ggcagaagtg atgaagactt ggaagaaaac ccagaaggtt  36540
ttccacttaa tttggaaaat gtgcttttcc cctcctgtgt cttttgctaa ggtccagcct  36600
cctgcagcct ccccgctctg tggactctgg ctttgattct ttattaggag tccccctgct  36660
cccccaaaag atggtgtcta aattatcatc caattggccg aggttttgtt ttctattaat  36720
tgtttttatt ttttattgtg gtaaatttat ataacataaa atttgccatt ttaattgttt  36780
tgttattgtt gtttttgaga cagggtctca ccccagtgcc caggctggag tgcagtggtg  36840
cgatcatggc tcactgcagc ctcagcctcc agggctccag tgatcctctc acctcagcct  36900
ctctagtagc cgggactaca ggcatacact accacatctg gctgattttt tgtatttttt  36960
ttttattgta gagacccgct atgttgccca ggctggtctc aactcctgga ctcaagccat  37020
cctcccacct caccctccca aagtgctggg attacaggca tgagccacaa cacccagcca  37080
ttttaatttt tttttttttt tttgagatgg agtctcactc tatcgcccag gctggagtgc  37140
agtggcgtgg tatcaactca ctgcaacctc tgcctcccag gttcaagcga ctctcctgcc  37200
tcagcctcct cccgagtagc tgggattaca ggtgcccatc actatgcctg gctaattttt  37260
gtatttttta gcagagacgg ggtttcacca tgttggccag gctggtcttg aactcctaac  37320
ctggtgatcc gcccgcctcg gcctcccaaa atgctgagat tacaggtgtg agccaccgtg  37380
cccggccttt ttttgttttt gagacagggt cttgccctgt cacccagact ggagtgcaat  37440
ggtgggctct tggctcactg cagcctccgc ctcccaggct caagttgtgc acctccacac  37500
ctggctaact gtattttatg tagagacaga tttcaccatg ttgcccaggc tgggcttgaa  37560
atggactcaa gcagtccacc cacctcagcc tcccaaagtg ctgagattac aggcgcgagc  37620
caccgcaccc agcccatttt acctattctg cagttgacag ttcagtggca ttcagtcagt  37680
```

-continued

```
tcacgaggta accatcactg ccattcatct ccagactact tcaccttctc ggcagatgtc  37740
cgaaactgtc cgcattgaac acactcctca tctccctctg acagccacca ttctactttg  37800
tatctctctc tgccttctct aggtacctca tgtaagtgga attataccaa tatttgccct  37860
tgtgtgactg gcttctttca tgtgacatgg tgtcctcaag gttcatctgt gttatagcct  37920
gtgtcagaat ttccttcctt aaagcctgaa taataacccg ttgtaaaggc tgggcgcggt  37980
ggctcacacc ctctaatccc agcattttgg gagtccgagg tgggcagatc acttgaggtc  38040
aggagtttga gaccagcctg gccaacatag tgaaaccctg gctctactaa aagtacaaaa  38100
ttagctgggt gtggtggcgc gcacctgtaa tcccagttac tcaggaggct gaggcaggag  38160
aatcgcttgt acccgggagg cagaggttgc agtgaaccaa gattgtgcct ctgcagtcca  38220
gcctgggtaa cagagtgaga cttcctgtct caaaaaaaaa aaaaatcatc ggatggatgg  38280
acggaccact tcttgttatt tatccatcca cgggtgctag gtttcttcca cctttggttg  38340
tcgtgaataa ggccactatg aacatttcct tccgtggtga aggttttgta ctagtgagga  38400
aaaggcgtgt ttgtggtgtt gcataggatt ctggtaagaa agtttgcact aaccataagt  38460
atttgtacta cattaaaatg aaagctcagg ggccgggcgc ggtggctcac gcctgtaatc  38520
ccagcacttt gggaggccag ggcgggcgga tcatgaggtc aggagatcaa gaccatcctg  38580
gccaacatgg tgaaaccccg tctctactaa aaataccaaa aaactagcca ggtgtggtgg  38640
cgggcacctg tagtcccagc tacttgggag gctgaggcag gagaatggcg tgaacccggg  38700
aggcggagct tgcggtgagc cgagatcgct tcactgcact cgagcctggg caacagagca  38760
agactccgtc tcacgcaaaa ctctgtctca cgcaagactc cgtctcaaaa aaaaaaaagag  38820
ttcagggttt atgaaactgg ccagccgcgt aaagtttgct gtgttgtttt tgtgcccggg  38880
aggagtgtgg ccagggtgtc acgtcacaca gtacacgttt ctcagatggt ggttctccag  38940
actgctgtcc caaagtctgt ttttgcatct ggttcccaca gacccaccct ccacggtgag  39000
cctgattttg gccagggtag ctggaatctt gcttgtcttt cagcccggca gctgtaccag  39060
tccagggtcc acagctagtg gcttttagga aggaatttgt tcagttggct ttgacacatg  39120
gccccctagg gtccacagct ctgtagtgat gtggatgttg ttatctacaa agacacatga  39180
tccttcgtgt ccagatgaaa gtgatgatgt ctttgcagct gcccagcaag gctgtgtgtg  39240
tgtgtgtgtg tgtgtgtgtg tgtgtgtgtg tggtgtgtgt gtggtgtgtg tgtgtgtatg  39300
ggggagggag gcaccctttc catctggggg tgtgtgtgtg tggggtgtgt gtgtgtgtgt  39360
gcgcgtgtgt gtggtgtgtg gtgtgtgtgt gtgtatgggg gaggcaccct ttccatctgg  39420
gtccaagaga ctgggcctgg ggaagacgct tctttttatc tacttagaga ctttgtttta  39480
tttgtatttt tttgagacag ggtctcactc tgtcacccag gctggggtat ggtgatatga  39540
gcatagctca ctgcagcctc ggcctcccag gctgaagcga tcctcccacc tcagccttct  39600
gaatagctgg gactgtaggc gtgcgtcacc atactgagct attgtttttt ttgtttggtt  39660
ggtttaattt tttttgatac agatggagtc ttgctatgtt gcccagacta gtctcaaact  39720
cctgaactca agtgattctc ccacctcagt ttcccgacat tctgggatca caggtgtgag  39780
ccactgctgt ctccctgttt tattaactgc tgaaagacct agataaagaa agtctgaaaa  39840
gacttactat cagagcacca tcctaagatg attccctctg actcaatgga gagggagggg  39900
agcttttcct tcaggcctgg gtggcaggag cccaggtgct ccaggcccca tttgccccag  39960
gccaaatcac tcgggaactt ggatgcagct gtctttcagg gtaacccaaa ggaaccagat  40020
ccccgcaggc agtaggcttc tgggctgtcc tctcctccta cgtcagctca gtaagagccc  40080
```

-continued ttcgaaggga tgctgtgtcg gaggccccaa aagcccaggc tcatccctga gatgcacagg 40140
gtgggctggg cttaggcagc gctcgagcat ctcctggacg gtgaccccag agagtgtgga 40200
gacggagagt ccttgagagt cactgagaga cgtggctgcc ctgccttccc aagaggggct 40260
ctgagtcatt ccccacactc acctgcccct acccaccctc acctggcccc cagcctcacc 40320
tacccccaca tctgtaccga tccctttacc cgcaccttcc ctacccaccc tcacctcccc 40380
tgtaccttca cctcccccac tcacccgccc ctgcaccctc acctgtcccc caccttcacc 40440
taacccccac cctcacctgc cctcccctca cctggcctcc ttccgttggg gaaggggttg 40500
taaggggcgg cccccaaact gtctgtcctg gtgccctgca gagaaaacag tacgtgaggg 40560
ccgcagtcca aaagcttgag tcctggaagg tggaggagac agggatgtgt tgggaagggc 40620
cccatggtct tggatccctt ctcgactgtc aatggggcct tcatgggagc gccagtctag 40680
tgatgcacag ctgggtgccc ggcgggtggc tgaggaggcc taaagtccga ggcggcaaga 40740
gctcttccag aggctgttgt cctaatcgct ctggcatact caggcgggca cgtagttagg 40800
agctgattgg agaggagaga cccccacacc aatactggga tttgactttc aggctaaact 40860
tgagaagtgt ggcctctgct gtcctgccag agctctccag ccagtgccca gggctctcca 40920
gccagtgccc gggggtctcc accagtgccc gggggtctcc gccagtgcca ggggtctccg 40980
ccagtgccca ggggtctccg ccagtgctca ggagtcttgg tttctttgtc ttacagccct 41040
ttgttttgac ctctctgagc caaggccaaa acccagacag gcagccccac gacctcagca 41100
tcgacatcta cagccggaca ctgttctgga cgtgcgaggc caccaatacc atcaacgtcc 41160
acaggctgag cggggaagcc atgggggtgg tgctgcgtgg ggaccgcgac aagcccaggg 41220
ccatcgtcgt caacgcggag cgagggtagg aggccaacgg gtgggtgggg gtgctgcccg 41280
tccaggcgtg cccgccgtgt cttatgccga atgccagcct ctcacaggct ggggagactt 41340
tccacctggg gatccaatgg gtggctttcc agggtcccaa aagcaaacac aggtttttca 41400
cagcccgtcc gggaaagcag aaagccccaa ggggctggaa ggggaaaggg ggagctctgc 41460
tgagaggtta caaggcagcg ctggccgacg ggagttgcag ttgataggtt ttgtatcatc 41520
cttgttaaac ttgaaccctg tgcagaaatc ccttccacgg catgggggct gcctgttgac 41580
tcgctcctgt tccaccacag ggagctcctg ggcttcttcc tcccagaggc ccccgacgct 41640
cccacctgtt ggtcgtcaga gcttctggtt ggtgggaagg cacccaggac cttgaggtct 41700
ccagagagaa aagccaggga aagagggaga ccgaaaccca tgtgacatga aactcaggct 41760
ccaaactgag cacgggaacg tttggggaca ggagcgcgat ggccttcctc agatagctgg 41820
ggggctggca tgaagacggg agctacagcc agcacaggtc ctgggccggg agcccagaga 41880
ttgagccctg actctgtcac ttactggcca cgtgaccttg ggcgggtggc atagcctctt 41940
ggagactcag tttcctcatt ggtaggagtg acggccacag tggtgcggcc tctgcagcac 42000
acggggggct cggtgggcgg aagccccggg tctataaggc ggctgtgcag gagccagccg 42060
agctggtctc ccaacagcca gggctccggg gtccttagca gctgtggggg gcctgcacct 42120
gtttcccatg gctgctgtca gaaattacca gaagccaggt ggctgagagt aatggacact 42180
tgttctctca cagttcctga gggctgaagc ccgagatcga ggtgtgggca gggccctgcg 42240
ccctctgaag gctctgaggg aacctttggg cttctggtgg ctccaggcac cccttgactt 42300
gtggtcctgt cactccagtc tctctgtctg gctgcacatg gcgtggcctc ttctgtacca 42360
ttgaaggaca cttcagttgg atttagggcc taccctcacc cattgtggtc gtatcttgat 42420

-continued

```
ccttcatgac atttgtaaag accctgcttc caaataagct cacattctga ggttctgggg  42480
tgagcgggaa tttggagagc attgttcaac tagtatagaa tgtgacctgt cagcctcggg  42540
cagccctgag aggcaggggc tttccacagc ccagctgggt gccctgggct ccgtgctgtc  42600
cgaggagacg ccatccccac acccgtcctt cacccgccac cctcccgcag gtacctgtac  42660
ttcaccaaca tgcaggaccg ggcagccaag atcgaacgcg cagccctgga cggcaccgag  42720
cgcgaggtcc tcttcaccac cggcctcatc cgccctgtgg ccctggtggt agacaacaca  42780
ctgggcaagc tgttctgggt ggacgcggac ctgaagcgca ttgagagctg tgacctgtca  42840
ggtacgcgcc ccggggcctg ccctaaccgc agacacccgg ccttcattgt cagtaatggc  42900
agcagctgcc acattgtccg agacctgccg tgagcccagt gccgcgccag gggctttgtg  42960
tgtagcgtgt tttgtcctca cactgacagc tgtaggctgg ggttctgagt gagccccaca  43020
gggcagaggc agaaaatgag tctcagagag ggtgagcgag ctgcttgggg ccccacagca  43080
ggagatggag caggactgca gcctagcctc tgccccccagc acctgcgcaa gaagctgctc  43140
tgctctggac tgtgttaggc tgcgagggct ggagagaaat gagagttggt gcttagagag  43200
ggggcgcagg tccccatggc ttttcctctt atgatgaggt agatgggtga agggaggggc  43260
catgcttgca ggggccagtg accgaggccc gccgttggaa ctgatggcct tcatcccgag  43320
cccagcccag gtgggagcag ggctttccga gggcttgtct tgggtcggcc tgcttccagg  43380
gactctgctg cagctcccac ccctgtccaa agcatggaat cccccaggct ccctggcagt  43440
cctgtcaacc tctgtcctcc caagctgagt gtggggcaag ttctggaggt cagcactgct  43500
cagggggccc cacgggctgc ttgcaggggc caaccgcctg accctggagg acgccaacat  43560
cgtgcagcct ctgggcctga ccatccttgg caagcatctc tactggatcg accgccagca  43620
gcagatgatc gagcgtgtgg agaagaccac cggggacaag cggactcgca tccagggccg  43680
tgtcgcccac ctcactggca tccatgcagt ggaggaagtc agcctggagg agttctgtac  43740
gtgggggctg gcagtggggt gggcagggtg gcctctaaac ccgacccctg gaggaggctg  43800
gaggccagtg caagatcctg tgtggcctca gccaggcggt ggtctctgcc agatgccaac  43860
tgttgcccgc tggggttcag cgacatgtcc gaatgtcccg aggcctctga ggttgttttc  43920
ttttgccgca gaacaaatca ccacgaacag cgttttaaga caacaccaac tcttttttttt  43980
tttttttttt tgagtcagga tcttgctctg ttgcccaggc tggggtgccc tggtgcaaac  44040
acagttcact gcagcctcga cctctgggct taattaagtg aacaccttgc ctcagcctcc  44100
caggtagctg ggactacagg tgggcaccac cacacctggc taattttttt ttgtagagac  44160
ggggtttccc catgttgccc aggctggtct gcaactcctg ggcacaagct atctgcctgc  44220
tgtggcctcc caaagtgcta ggattatagg tgtgagccac tggcctgaca acacccacgg  44280
attgtctctc agttctgtaa ggcaaagtcc aggcacagcg tggctcacct gggttctctg  44340
ctcagggtct cacggggcca gaatcaaggt gtcaggaacg ctgggccctc agcggaggct  44400
ctgtggagaa attagcttcc ttgctcactc agcaggtagc agttgtggga tcgaggttct  44460
gttttctctc tggttattgg tcggggacca ctctcagctc ctagaggcca ccacaggtcc  44520
ttgccccgtg gccctctctg cctcagcagt gggggctccc tgcgtcagtc cctcccacac  44580
cttgagtctc tctgatttgc ttctaaaggg ccctgtgatt cggctcagcc acctttagat  44640
taggttagcc tccccttga tagactccaa gtcggctgat taataacctt aatcacatct  44700
gcagaatccc ttctgccaca taaggtcatg acgccgtgct ggggactggg gtgggaaatt  44760
acggggtcat ttaggattct gcctgccact gccttgctgt gtcccagggc ttgggggagg  44820
```

-continued

```
ggcctccaca gctgggacca cagtccttcc tcccctccat ggtaaccatc tgaggattac  44880
ttgagaccag cctgggcaac atggtgagaa cccatcccta caaaaaatac aaacaaaaag  44940
ggaccaggct gggcttggtg gctcatgcct ataatcccag cactttggga gaccaaggtg  45000
ggctgatcac ttgaggttgg gagttcgaga ccagcctgcc caacatagtg aaatcccgtc  45060
tctactaaaa atacaaaaat tagctgggtg tggtggcagg cgcctgtatt cccagctact  45120
ggggaggctg aggtgggaga attacttgaa cctgggaggc ggaagttgca gtgagccaaa  45180
attacgccac tgcactccag cctaggcaat agagtgagac tccgtctcaa aaaaaaaaaa  45240
gggccagggg tggtagtgac aaagagaccc tatcccaaaa aaaccgaaca ctgaatcctt  45300
gagactgagt aaggacactg tgaaattttt ctgggtgggg cagggaacag agcgtcttct  45360
gtcatttctt ccacctgggt gtggtcagct ctccctccaa gctgcctcct cttcttctca  45420
ttgtccgggt gttggacaca tttggttaac tggatagaat aacgcgagtt cccagggact  45480
tggtccattt gctattttat tttattttat tttattttat tttatttatt tatttattta  45540
tttatttatt tattgagatg gagtttcgtt tttgtcgccc aggctggagt gcagtggcgc  45600
gatctcggtt cactgcaacc tctgcctccc aggttcaagt gattctccta cctcagcctt  45660
ccaagtaact gggattacag gcacccacca ccataccagg ctaatttttt tgtattttta  45720
gtagagacgg gttttcgcca ttttgcccag gctggtcttc aactcctagc ctcaggtgat  45780
ccacgcacct cggcctccca aagtgctggg attacaggca tgagccacca cgcctggcac  45840
catttgctat tttaattccc atgtgtatta gtgtcccacg gctgctgtaa caaatgacca  45900
caaactggat ggcttaaagc aacagaaatg gattccccca atgtgctgga gaccagaagc  45960
ctgcgaccaa actgttggga gggctgtgct tcctctgggg gctccaggga ggatctattt  46020
gttggccctt ccagtgctgt gggtgccagc gttccacact tgtggatgcg ccgcctcaac  46080
ctctgcccat cttcatgtgt ccatctcctt tgtgtctgcg tctttacctc ttcttcttgt  46140
ctgtgttgcc tcttataagg acgtttgtca ttgggtttag ggcccaccca aatcatccga  46200
gatgacctcg tcttgagatc cttaacctgc aaagaccctt tttccaaaaa aaggttatgc  46260
tcacagattc taggccttaa gacatgggtg tatctttctg gggggcacta tccaacccct  46320
tatacaatga aagacgggaa gagggccagg tgtggtagtt cacgcctgta atctcagcac  46380
tttaggaagc tgaagcggga ggatcacttg agcccaggag tttacaagta gctaggcaac  46440
atgatgagac cccatttcta caaaaagtga aaaaaaaaaa aaaaaaaaaa aagccaggtg  46500
tggtggctca cacctgtaat cccagcactt tgggaggctg aggcaggcag atcacgaggt  46560
caggagattg agaccatcct ggctaacacg gtgaaacccc gtctctacta aaaatacaaa  46620
aaattatggc cgggcgcagt ggctcccgcc tgtaatccca gcactttggg aggccgaggt  46680
gggtgaatta caaggtcaag agatcgagac catcttggct aacacggtga aaccccatca  46740
agatcacaag gtcaagagat ggagaccatc ctggctaaca cggtgaaacc ccgtctctac  46800
taaaaataca aaaaattagc cgggcatggt agcgggcgcc tgtagtccca gctgctcggg  46860
aggctgaggc aggagaatgg cgtgaacccg ggaggcggag cttgcggtga gccgagatcg  46920
ctccatgcca ctgcactcca gcctgggtga cagagtgaga ctccgtctca aaaaaaaaaa  46980
aaaaaaaaaa aaaaaaagaa aattagccag gcacagtggc aggtgcctat tgtcccagct  47040
acttgggagg ctaaggcagg agaatggcat gaacccggga ggtggagttt gcagtgagcc  47100
gagatcatgc cactgcgctc cagcctgggc gatagagcaa gactctgtct caaaaaaaaa  47160
```

-continued agccaggcat ggtggtgcat gcctgtagtc ccagctactc aagaggctga ggcaggaggg 47220
ttgttcgacc cacggagatc aaggctacag tgagccatga tcgcaccact gccctccagc 47280
ctgggtgaca gagtgtgacc ctgtctcaaa gtaagtaaat aggaggagag acaagtgggc 47340
agttcagact gatggtatgg gcacagtaga gactggtgca gacaggctgg cctgtgatgt 47400
caagcaactt ctgtaattgt ttccggcatc catttgtgtg tcaatttccg tgtcagtagg 47460
aagactctgt aggctgccaa gaggaataag tgggaggatc ctcccagaga ggccgggcct 47520
gcaggagggc cagttctcat gagttctcat ttggccccta ccctccaggc tgtggttctg 47580
aggtgggaga cagagcctga cctctgtttg tcttgttttg tctttgcagc agcccaccca 47640
tgtgcccgtg acaatggtgg ctgctcccac atctgtattg ccaagggtga tgggacacca 47700
cggtgctcat gcccagtcca cctcgtgctc ctgcagaacc tgctgacctg tggaggtagg 47760
tgtgacctag gtgctccttt ggggtgatgg acaggtacct gattctctgc ctgctaggct 47820
gctgcctggc atccttttaa aatcacagtc cctgtggcat ccagtttcca aagctgattg 47880
tgtcttcctt tgccctcctt tcttttctac tatgtgcatt cggtgctatg aattttcctc 47940
taagtactgc gtttcctgca tctcacaaat tttgttacat tttcattttc aggtagtttg 48000
aatattttta cacttctcct gagatgacat ctttggctca tgtgttattt agaagtgttg 48060
cttagtttct aaagagttgg ggcttttcca gctgtctctc tgcaactgat ttctaattta 48120
attctactgt agtctgagag cttattttat atgatttctg ttattttaaa tgtgttgggt 48180
gtggtgtttt tgttgttatt gtttttgtgt ctttttgttt tgttttgctt cgtttgtttt 48240
gtttttgaga cagtgtcttg ctctgtcact caggctggag tgcaatggcg cgatctcagc 48300
tcaccgcaac ctctgcctcc cgggttcaag tgatcctctt gcctcagcct cctgagtagc 48360
tgggattaca ggtgcacgcc accataccca gctaattttt gtatttttag tagagacggg 48420
gtttcaccat gttggtcagg ctggtctcga actcctgacc tcgtgatccg cccacctcgg 48480
cctcccaaag tgctgggatt ataggcgtga gccactgtgc ctggccatta ggtgtgtttt 48540
atcacccagc atcatgcagt ttatcttggt gaatgttctg tgtactcttg aaaagaatgt 48600
ggattctgct gttgttgggt ggagtgttcc agaaacatca attagatcca gttggttaat 48660
agtgctcatc aggttgtctc tatccttcct tcctgactgc ctgcttgagc tgtcagttat 48720
tgacaggggt gtggagtctc caactctaat ggtggatttg tttatttctc ctagtagttc 48780
tatctttttc tctccttcta cccttgatcc tcttctcccc ctagggcttc ctggtgttag 48840
tggtgggaga gtggggtagt gaagaacctg gactttaggg ccaaagaggc cagggttcaa 48900
atcctggctc tgtcacttcc cagttgagtg accctggctg gtgcctgaat ctctgtgagc 48960
ctccacttcc tcctctgtga aattgagagc acttacctgg caggctgtca tgggcatcaa 49020
gtaacagggc actccacctg gaccctgaca cgtgatgcac aggaatgcca gctgctatgc 49080
catgggtgtg gcagtagtaa taaagtgacc atctgtatcc tcaccacagt gaagcctgtc 49140
cagggctttc tctcctatgc ccccatgcct ccaggtggcc ttggatcctg ttggttctgt 49200
gctctgctca gcgacctttc tcccgtggga gttcctgggg gttcagcttc atcctacaga 49260
cagcagcaca cactggctgt gcaccctttt tttttttttt tttttttttt tgagatggag 49320
tctcgctttt ttcgcgcagg ctgaagtgca gtggtgtgat cttggctcac tgcaacctct 49380
acctcctggg ttcaagtgat tttcctgcct caccctccca agtagctggg attacaggct 49440
cccaccacca cgcccggcta atttttgtat tttcagtaga gatggtgttt caccatgttg 49500
gccaggatgg tcttgaactc ctgacctcag gtgatccgcc cacctcagcc tcccaaagtg 49560

-continued

```
cagggattac aggcgtgagc caccacaccc ggagtgccgg ttgtttttag cagtttgtct  49620
tgttcctgga gagactggct cctgcccagg agctcgggga gtagggccgc ggggtgctgc  49680
ctcacacctc gagtttggcc gtaagcagag gggacatttt gtgactgtcc ccctcctgag  49740
cttcccagca gcttttctcc aagttacagc ccaaaagctc aggtggattt gcaacccaac  49800
ggtgtctgtg cacctcccac tgatgcccga actgccctgg ccaagaaacg gggccgtcag  49860
aacgctgcac taactgcagc cttgggcctc catgccagag gccatgccct tccatccacc  49920
accccctggc ctgggccctg ggccctcctg gctcgggaac tccaggcccc ttcctcacgg  49980
ctcgagagac gtgtatttac cgcacaggtg cttgtcattc tcttgtggcc tcttctccag  50040
ggagatcaca gaaggacagg gcctcactga ggtctcggac atggaccctt tgatagtggc  50100
aggagccagg ctgggcaaga ggcggccaca gtcacctcag cagtgccatc accaccgcca  50160
ttcagccctt ccctgagccg ggcgcgcccc tggctctggc cccagtgtcc cagttacagc  50220
tcacaggagc ttgtggtgcc cagcggctgc ttctgattga gagtcgaggt cggaggcttt  50280
gggaggctga gaggctgctc ggtttcacaa ctgctgaggg agacttgggc tccatctcag  50340
gtatgcccca tgtcgccctc aacctccagc caccggtcct ccgtgtcccc catggccagg  50400
cacggcttgc agacatctgt cgttggctcc tctcagccgt cgtgggctga ccctggcacg  50460
tcctcctgtg gctgagccca gtggggacag ctgcttcctt ttattaccct agaactctcg  50520
tctttgatca ggccccctcc cctatgccac acagtccctg tcactcgggt gagcccagta  50580
gtcatgggga aggcctgcgg gttccaaaca tccaaaggct tgcgtgcagc atgacagctt  50640
gaaaccgatg tttttttacct tgatcagatt tcagcttggc gggggctttg ctcagctttc  50700
agtgaggcct gggccgattt cccagcatcc cctcctgagg ccagcctctg tttcctgtga  50760
ttttctgcac aaagtgggag ggaggagtcc taggaaatgg ggggccacct cgaagcctag  50820
gcctcctctg gcttctctgt gccagtgccc ccacgctttg tgtctgtgtc cccagcccat  50880
gggactctgc tattccctga gtgctgccgc atgcccagcc cgcactgagg acgtggagcc  50940
ccgaggggca ggatggcctc catggtcaca cgtaggaagt ggcctccacc ctccgatgat  51000
cctctccctc ctccctttca gcgccctccc cgggggtgtc ctcagccctc ctgcctgtgc  51060
tttgtcccgt cttctgcagg cgcctgggac gtgctgacag gtcctctgcc ggctcctgcc  51120
ttgctatgcg cacgctggtc accacagagg cctggccctt cttctgtagc agtcccacac  51180
ccgcaacagg tgtggctgct gaccacctgc tttctgcccc tctggtcctg aggagggcgc  51240
agtgggcact caggcgtggc tgagcagatg tgtgttgccg ggaggaggaa ggactgctcc  51300
agtcagggct gaatttccca cccggagcat ttctgctgta tttggtgtag cgcctgctgc  51360
ttaaagctct gattcccagt tggcaccctt tcccttctgc attgaaaaac atacggatgc  51420
atgtcttctt gcagtgaatg tgtattctcc cagcctctct tctgggttgg ggctggaggt  51480
ggagcggcac acaggagccg cagcgatgga ggatgtgcgg gtgcagcacc ccgtacagca  51540
gggatgccaa acccgcgctg agtccctctc aacttctgct ttgaagccca gtcacgccat  51600
tgcctgggtt ttgctgggcg gggctgcgtg tgatgttctc ctctgtccct cccccagagc  51660
cgcccacctg ctccccggac cagtttgcat gtgccacagg ggagatcgac tgtatccccg  51720
gggcctggcg ctgtgacggc tttcccgagt gcgatgacca gagcgacgag gagggctgcc  51780
ccgtgtgctc cgccgcccag ttcccctgcg cgcggggtca gtgtgtggac ctgcgcctgc  51840
gctgcgacgg cgaggcagac tgtcaggacc gctcagacga ggcggactgt gacggtgagg  51900
```

-continued

```
ccctccccgt caaggctctg ccaagaccct ggccctgccc tccgggatac gagcttgggg  51960
ctgcctccgg cctcacagga gtaggggctc tgaaaacctt tgcttgcagg gagattgcca  52020
agtctgtctt ttaggcccaa caaggaaaac tctgcagttc cacccatcct gtcccaccag  52080
gtagtgtggc ttgaaggcag actgtgaggg tctatctcac cttcctgcat taggtcagga  52140
gtttcacaga aacctgaggc acattcaggg gtgggctgca gaggtccatg gctcacaccc  52200
tggaaaatcc gcccccaaaa gacagtgctg tctccactga ccagtctgtg ggatagtgct  52260
taagcctgag tggtttctat caacatgtag aatcaggagg tataaagaga tttgctcagg  52320
catcctgggc cctctctgac cagcaggatc ttcctttaga tcttgacagt gaaacacatc  52380
tcttctgtgc cccctgtgag ttttctttca ttcattcatt cattcattca ttcattcatt  52440
cattcattcg agacagagtc ttgctctgtc acccaggctg gagtgccctg gtgtaatctc  52500
ggctcactgc aacctctgcc tccagggttc aatcgattct cctgcctcag cctcccgagt  52560
agctgggatg acaggtgcgc accaccatgc ctggctaatt tttgtatttt tagtagagac  52620
agggtttcac catgttggcc aggctggtct cgaactcctg acctcaggtg atccgcccgc  52680
ctcagcctcc caaagtgctg ggattacagg catgagccac cgcgcccggc ctgagttttc  52740
cttttatgaa ggacctgctt ggttggttgc ctgccacatg ttgtcagcac catgggccca  52800
ggactgctga ggagctgttg atgccctcgc tctcccagag ccaccggctc tgttagataa  52860
ttcacatgca gtctggccac tgtcctacgt cctcattcac aaagagcaga catttcgtag  52920
aagatgaggg cctgggagta acctccctgc atgtttttct ataaaggcat agtggttaag  52980
tccttccagc tcattgacca ttggagaatt tttatggaggc tgtagactag gggctggtaa  53040
actaagggcc caggggccaa atccagcctg ccacctactt ttgtaaataa agttttcttg  53100
gtgcacagcc atgcccattc attcatttgc acaatgtctg tggctgcttt catgccaaaa  53160
gcaagagaac tgagtggtta tgctggagac ctacggcctt caaagcccca gacctcacgt  53220
ctggcccttg acagacagag cttccccagc cctgctgcgc atcctggccc agcatgtgct  53280
gtgtgtgtga tttcagcttg caggagccgt ggttaggaat tgtccctgtg ttggtccatt  53340
ttgcattgct atgaaggagc acctgaggcc gggtagatta tgaaggaaag aggtctgtct  53400
ggctcatggt tctgtaggca gcaccagtat ggcacccgca tctgctcagc ttctagtgag  53460
gtctcaggaa gctttgactc atggtgaaag tcgaagcggg agcaggtgca tcacatggtg  53520
agagagggag caacggagag agagagagag cgcctctccc tcttgccctc accttgagag  53580
gagatgccag gctcctttaa gtaaccagct cccatgtgaa ctcacagtga gagcccattt  53640
gctactgcgg agagggcacc aggcatctgc tcccatgacc caaacactgc ccaccaggcc  53700
ctacctccaa ccttggggtc atattttatt ctgttctatg ctatgctatg ctatgccatg  53760
ccatgccatg ccatgctatt cctattctat tatttgagac agaatctcgc tctgttgccc  53820
aggctggagt gcagtggcat gatcttggct cactgcaacc tccacctccc aggttcaagc  53880
gattctcctg tatcagcctc ccgagtagct gggattacag gcacacacca ccacacccgg  53940
ctaatttttg tattttcaat agagatgggg tttcaccatg ttggccaggc tggtctcaaa  54000
ctcctggcct caagtgatcc acctacctcg gcctcccaaa gtgccatgat tacagatgtg  54060
agtcactgcg cccagtgagg gtcacatttc cgttgagatt tggaggggca gacgttggag  54120
ccatctgagc cccctcgtcc cgctctagct tctcctcccg tgtgccccgc ggtgctggtg  54180
gcaggccctt acgccggttc tggctgcatg ctctgttcca gaagctttct tccctgcttg  54240
gttaccagaa aatcatccca tccattacaa ggacagggtc cccttatctc ccattcccag  54300
```

-continued ggcaggacac cgggggcagg gcaggtgggg aactgagcaa gttctctggg ggcaggcgtg 54360
gctatggctc cctctgggtg ggcgtctggg gaggggtgga ggcagccgtc agcgccctgg 54420
cttgctcttc ctccctggcc agagactgtg gccttgtgct gctcccgtgt gggctgcctg 54480
cacctccagt gggttgtgct ccctccccctc ccctcccctc aagctctgct gagcaccact 54540
gccttccaca gcccccactc tcgggaggcg aggctcctcg tggccattcc tgtccttggc 54600
acccaccccc ccaccaacct ggtagagcct tgggcggggt ctgttactcc ttgcatggcg 54660
tagacctccc cacagtaggc acctgacaca tacctcctgg ggggcaggca ggaggtgcgt 54720
tgaggtctca gccctggcag tccctcccct gcgtggcata ggcctcgcca cagggtcatc 54780
gagggtgggt ggagactgta ctagaccact ccccgctggt cctagaaagg gtcccatctg 54840
tctgctctct gtttggagtc cagaccttgg ttgctgtgcc ctgcatggtg ggctgggggg 54900
caccctccag cctctctgag tgcatggcct ctccttgcag ccatctgcct gcccaaccag 54960
ttccggtgtg cgagcggcca gtgtgtcctc atcaaacagc agtgcgactc cttccccgac 55020
tgtatcgacg gctccgacga gctcatgtgt ggtgagccag cttctggcac ggggaagggg 55080
cgtccgggct gggttccccc aggaacgtgg agtttagggg aggagacgtg cctttccagc 55140
ggggctgggg gctgtgtggg agactcaggc ggctgggagg ctccttgcgg gaggcaggga 55200
agcctttccc agggcagcgg ccaggaggac agactgtgag ctgtgggctc ggcggctaca 55260
gagtctgcct cagtgggcgg ggctgatggt gtccaggtgc ctgcagcacg cacccaccca 55320
cgggaccttg ctgagcagcg tctgtcaggc agcaagatta cccgagggct gcagtggtcc 55380
tgttccctgg cagcttactg tctggctgag gaggagtgat gttcacatat gcacacatgt 55440
catgtgcaca cacatgtaca tgacaacatc ccacatgctc ctcaaatagc atgacctgta 55500
cagtcacgga tatagggcct aggggatagg aggccaagac agtcagggaa gactttccag 55560
aggcagtggc tcctgaaagg ctgtctgatt caggcaggaa gggagctgag ttcagatagg 55620
aagtagcaat gagtcattgt gtctggggac atggccactc cttcgctgca gagggacctg 55680
ggctgagagc tcctctctta tggctgcagt cgggagagaa gtctgttggg gggagaaggg 55740
ggcttcctca agggactccc tgtgcccttt ggcaccttcg tgccaggtca ggcttgaggc 55800
ctgaaggcag tggtgggggc caccaagggt cgcctcctct gctgggcaag ttcccagtct 55860
gacgggcctg tgccgtgggc cccagctgtg ggggcgctgt tgatgcgcag ccaggcctcg 55920
ccgccagagc ccgcacgctt ccattccgct gacttcatcg acgccctcag gatcgctggg 55980
ccggccctgt gggagagtga atgtggcttt tgccaaagtt gagtctggag cctggaaact 56040
tccctatggg cagccttgat agtggagtgg cccaaggagc ccacccagcc gaccctgccc 56100
ctcccgtggc tggtgggcgg caccaggggc tgcctggctt tgctcgttca ccaacatcac 56160
ctgggctggc cagggcgcgc tcacttctgc caccaccgag ggccctgggc gaaggagtga 56220
ataccaggct gccttggcag ggatgtgttg agggctgtgg ggagtcggac agcggcgggg 56280
gtcagaggag gaggagggtg caccgtgcag gctgaagggc cacgttaccc tgaggttggc 56340
caggctcccc aggcctagcc tcccagctcc cccactttct ccccaccctc caccagtggc 56400
aaagccagcc ccttcagggc gcacggtgtc tgcccccaag gagggcccat tccgttgggg 56460
ttaatgttgg ccacctcttt ctgtttgtct ctggcagaaa tcaccaagcc gccctcagac 56520
gacagcccgg cccacagcag tgccatcggg cccgtcattg gcatcatcct ctctctcttc 56580
gtcatgggtg gtgtctattt tgtgtgccag cgcgtggtgt gccagcgcta tgcgggggcc 56640

-continued

```
aacgggccct tcccgcacga gtatgtcagc gggaccccgc acgtgcccct caatttcata  56700
gccccgggcg gttcccagca tggccccttc acaggtaagg agcctgagat atggaatgat  56760
ctggaggagg caggagagta gtctgggcag ctttggggag tggagcaggg atgtgctacc  56820
ccaggccctc ttgcacatgt ggcagacatt gctaatcgat cacagcattc agcctttccc  56880
actgagcctg tgcttggcat cagaatcctt caacacagag gcctgcatgg ctgtagcaac  56940
ccaccctttg gcactgtagg tgtggagaaa gctccttgga cttgaccttc atattctagt  57000
aggacatgtg ctgtgttgtc cacaaatcct catgtaccct agaaatgaat gtgggggcgg  57060
ctgggctctc tccagagctg aaggaatcac tctgtaccat acagcagctt tgtcttgagt  57120
gcagctggga tttgtggctg agcagttaca attcctacgt ggcccaggca ccaggaacgc  57180
aggctgtgtt tgtagatggc tgggcagccg caccgcagag ctgcaccatg ctggtttgta  57240
tcacatgggt gaccatggta tgtctaagaa ggtggagtcc ctgtgaggtc tgcaggtgcc  57300
cccacagctc caggccacct tgaggattgc ctctgcctgc ccagccctga gttccctctc  57360
ccctgtcctg tcccactgtc accccaagcc ggcctcattg ggagcctgtt ggatggcagg  57420
gtatagatgt aacctgattc tctctgggga gcggggttat ctggcttctc aagagctcct  57480
aggagcccac agtggtggca ccatcacagt cgcagcagcc cccagagaac gcggccctgt  57540
ctgttcctgg cgtgctctgt gctgccccgc ctgggttccc tgccccagtc gcaggcccct  57600
tggaggaggt accatgtgtc tcccgtttca cagatgagcc ccggggagct cactctagta  57660
gtggccagag aggcctgcgg ctcagggagc ggggcacatt tccaacagga cacaccgccc  57720
tggtctgagt ctcgtgggta gtgggagcag aggagagcgc cctatgtctg tggggcggct  57780
tggctgagcc tggaagccac ctgacctccc ccgtcccttc cctgccaggc atcgcatgcg  57840
gaaagtccat gatgagctcc gtgagcctga tggggggccg gggcggggtg cccctctacg  57900
accggaacca cgtcacaggg gcctcgtcca gcagctcgtc cagcacgaag gccacgctgt  57960
acccgccggt gaggggcggg gccggggagg ggcggggcgg gatggggctg tgggcccctc  58020
ccaccgtcag tgctggccac cggaggcttc ccgggttcct gggggctgtg ccaccgcctc  58080
tgaggcatgc ttgctttctt cccttttcaa acccttctgc ttccttcttt aatgacattg  58140
ttgattgtgg ataatctgaa aactacacaa aaatataaag agccaaaatc tcacccaaat  58200
ccacctccta gagtggctgt tgggctccgt cagcatccag gcggccgtct gtgttccgca  58260
cggcccagcc catcgatagc cgcctgcacc aggcctgtct gccctctgtg agcctcccca  58320
cagggttccc tccacaaaca ccctgttctc ccacccaggg ctggctgctt cctggaaaac  58380
agctggatgg ttttgtgcat gacagacaaa cacagggtga ttttcgtggc taaaatactc  58440
cctggagctt ttggcagggt gaggggctgg ctccagctga gccacgcctt gagtgaaatg  58500
actgtgagga gaataaactg ccgctgccct ccaggatcac tggggctggc tggggagaac  58560
ccccgtttct gggagcacag tcccaggatg ccaaggcgag cttggtgccg agatgtgaac  58620
tcctgagtgt aaacagcggg ggctgacttg acatgctttg tatgcttttc atttgttcct  58680
gcagctgtat gcccctaagg tgagtccagc cccccttctgc ttcctctggg gcctcgccag  58740
tgagccccac cttgctgggg ctggttcctc ctgcccttct gggtatccct cacatctggg  58800
gtcttgtctt cttgttttct ttttcttttt tttttgagac ggagtttcac ttttgttgcc  58860
caggcttcag tgcaatggtg tgatctctag gctcaccgca acctctgcct cccaggttca  58920
agcagttccc ctgcctcagc ctccctagta gctgggatta caggcatgtg ccaccacgcc  58980
cagctaattt tgtattttta gtagagatgg ggtttctcca tgttggtcag gctgatcttg  59040
```

-continued

```
aactccctac ctcaggtgat ccgcccacct tggcctccca aagtgctggg attacaggcg  59100
tgagccaccg cacctggcct ttttcttttc ttttcttttc ttttttctga gacagggtct  59160
cgctctgtca cccaggctgg agtgcaatgg tgtcatcatg gctaactgca gcctctacct  59220
tctaggctca agcaatcctc ccatctcagc ccctaagtag ctaggactgc acgcatgcat  59280
ccccatgccc agctaatatt tacatttttt gtagagatga agtttcacta tattgcccag  59340
gctggtctcc aactcctgga ctcgagcgat cctcctgcct cggcctcccc aggtgctggg  59400
attacaggcg tgagccaccg tgcctggcct ggggtattgt cttcttatgg cacctgactg  59460
tggtgggccc tgggaaggaa gtagcagaag agggttcttc ttggtttcct ggacagtaac  59520
tgagtgttct ggaggcccca gggcctggct ttgtttaggg acaaagggaa ctggtaacca  59580
gaagccgaga gtttaaacac ccactgccct tcttccctgc tcctgctgct gcaacccagc  59640
ttaaccagcc aggagtgcta ggaacccaag cagggccccc gagcacacag caggcagctc  59700
acgaattctc ttttcctgtt ctcccttggg agctgggagg atcttaatca ggcaataaga  59760
gatggcactg agcagccagc taattttta aatcacttta ttgtttaacc atatgactca  59820
cccacttaaa aaagggtaca gttcagtggg ttttagtgta ttcacagatg tgtgcaaccc  59880
tcaccacagt taattttaga acattttcct gcccctaaaa gaaactctgc atgaagccag  59940
ctgtttttaa attagcaaag ttattttgca tcctttaaat atatgttcat ggtacaaaat  60000
tcaaaagata cagaagagtc tgcagtccaa agagactccg cccccatgac gccaagcagg  60060
catccctggg aggcatggcc tcctgcagtg tgtttcttct atgtcccccc aggggtcatc  60120
tgtacatatg caagcataca agagcgtgga ctttgttttc caagccagaa gataattgta  60180
gatttatgtg cagttgtgag aaagagcaca gacccattta tcctctgcct ggtttccccc  60240
agtgctgcct gccatcttgc atgacttcca ttcctatcat aagcaagaca ctgataacga  60300
ttctttcacc ttattcagat tgacataagt gttttttgtt tgttcttgag acaaacttcc  60360
tctgtcaccc agtgggagtg cagtggcaca atcacagctc actgcagcct caaactcctg  60420
ggctcaagcg attctcctgc ctcagtcccc tcaagtagct cagatggcag gtgtgcacca  60480
tcatgccagg ctaattttta aatttttttgt ggaggtgagg cctcactaaa tttcctgggc  60540
tagtcttgaa ctcctgagct aaagtgatcc tcctgcctca gcctcccaaa gtggtaggat  60600
tacaggcatg agccactgcg cctgggctga catatgtgtt ttcgtaagcc cgaaagatag  60660
catctgaaga gtcaacattg agccttgcct tttgctgcta acgatgtata aaagctgctg  60720
ttctgagcat ttcggaggct cccagctgcc gtgtgcaccc tgcctagagc tctaccgtaa  60780
cccatctccg ggaggaggtg ctattgtttt cctcattttg caacaaggag gctgaagaac  60840
tgagcatgaa ccactggcct gggtcgttcg gttggtaggc agtggggcca ggccatccaa  60900
ctcacaacca ccttctactc tgcttccccc gcaccctgaa gtttgttctg ttttgaggac  60960
acagccgtca cattcttggt ggctgaacag cactccttgt caggcgtggc tgggccccca  61020
ctggagggca tcatggtcct ctctcctgct gcggttgaac cttggctgtt tcaaccactc  61080
ctgccaagtg gccctctgaa agggacagtc catcttttct cagcagaggg ccacactggc  61140
aaaacggtcc ctggcaccct ttctctccac ctgtctaata tagagtaaaa atggtatcat  61200
gttaagatct tcatttatat ttattttatc atgaatgatg taagcatcat tttgtgtgtt  61260
taagaacctt tgggcccagc gtgatggctt gcagctgtaa tctcagcact ttaggaggct  61320
gagatgagcg gatcacttga ggccgggagt ttgagaccag cctggccaac atggagaaac  61380
```

-continued

```
cccgtctcta gtaaaaattt aaaaattagc cgggtatggt gatcccagct acttgggagt  61440
ctgaagcatg agaattgctt gaacatggga ggcggaggtt gcagtgagcc gagatcgcgc  61500
cattgcactc cagcctgggc gacagagcga gactctgtct caaaaaaaaa aaaaaaaaag  61560
aaaagaaaag aaattatcaa tctcctcttt tatggcatat atatatatat atatatatat  61620
atatatatat atatatattt tttttttttg gttatgttca gaaaggcctt ccctgctctg  61680
atcataaaaa acaacttatt ttcacactct ctctcttttt tttttgagac agagttttgc  61740
tcctgttgcc caggctggag tgcagtggcg caatctcagc tcactgtaac ctccgcctcc  61800
cgggttggag tgattctcct gccttacctt cccgagtagc tgggattata ggcatgcacc  61860
accatgcctg gctaattttg tacttttagt agagacgggg gtttctccat gttggtcagg  61920
ctggtctcga actcgcgacc tcaggtgatc cacccacctc ggcctcccaa agtgctggga  61980
ttacagacgt gagccaccat gcccagccca cactctcttt cttaacgtcc tcctcctttc  62040
gttttacgtt cacatcttta attcttctgg gatgtaatta gatttgatga gcaaggtggg  62100
catccagctt gtttcttggc tgatggctta tgggtggcgt gaattagtcg gggtctatca  62160
ggaggcagaa actctatgag aatttgaaca gagaaagttc cgtctacagg cttattacca  62220
gggactggaa tagcagaaat tgaacagtga gatgtacaga gaactctaag aatgcaggaa  62280
taggccaggc atggtggctc acacctgtca tcccagcact ttgggagacc aaggcgggtg  62340
gatcacctga ggtcaggagt tcgagaccag cctggccaac atagtgaaac cccatctcta  62400
ctaaaaatac aaaaaaatta gctgggtgtg gtggcgcatg cctgtaatcc cagctactcg  62460
ggaggctgag gcaggagaat cacttgaacc tgggaggcag aggttgcagt gagccgagat  62520
catgccactg tactccagcc tgggtggaag agcggaactc tgtctgaaaa aaaaaaaaaa  62580
aacaagaagt tcaacttgaa gggaaaaatg ccgtattgtc tttccctttg ttatgtcacc  62640
agggcacagt ccatcccagg ctggcgctga tccacgggct ggagaggggc tgccccagaa  62700
gaggacatgc caggaagggc ttggctggtg ttcaggagcc caggccaggt caggtcaaga  62760
ggtgttgagg ctggacggga gaggccagct aggggctcat gtaggatatg aggggtcggc  62820
ccatttcaac gtggaaactg agctcttctg cttctctttc ttcttcactg cattaagatt  62880
caataccgct tgggaagcag gtatttccct tcctataaag gatggttggg agcctgagtg  62940
ttgggagaaa gtgtagccgc tgagttacta acaactaggg ctgccgtcaa gcctatgggg  63000
aaagagagaa gaggacattt ggaaggagag agatcaagct gtggcaccct gggagaggac  63060
cacagaaaag aggccagtga gggggttccc cggtggcatc tgaaggtgtg gcccaaccag  63120
gaggtccaga ggctgccagc cgagtggccc aggagaggga acctcacagg ggctgagtgg  63180
gacccaagcc ctatccaccg tcctaaccac ccacatttct cgggaacaag acctcccaca  63240
gtggcctccc cggcagtgga aatagccaaa ctggcaacat ggactttctt caactgcccg  63300
ggcgatgctg cctcagtgcc ccagggcagg caggaagctc ccacacccat tctggaatga  63360
ggggttggag gaaggctgag ctgagcaaag gacccatctc tgctctggtt ggtggggagg  63420
gagcccatta tacaagagac ccctcagggc tcagtgaggg gtgacagaga cttggggagt  63480
agtggctgtc actgcagagg tgagagggtt tggagagaag gtacatgcct ttttggccac  63540
attgagtagc acctggtagc cagttagtaa cgtgtattgg ataaacaaaa gattaaacgg  63600
atgcaaaaaa aaatgttggc tttgcttctt tttacccaaa cctcagttcc ctcaagtaga  63660
ttctgggaac accccctacc tggctggact gttgtgaagt ttaaataagc caggttaact  63720
tcacctcctc ctttaagaca cagctcagac actgcctcct ccaagaagcc ccctctggct  63780
```

-continued

```
tcctgtgtga atatgacggc cctctgggct ctagggtatc ttagaacaat gcttccttat  63840
ggctttggaa ccccgctgtc tcctggattg ggagcaaatg caggggagga gccacacctg  63900
actaatctct gggtctccca gcacataagt ggcataaggg cagggctgtg cccgcttcag  63960
gcacttactg aaggatgtac ttggcagagg gtaggcagcc ggcggatgag cccctcactc  64020
tccccagctg actgcgtggg cgggaaaggc gggttcagga gacccagcct ccctgggctg  64080
tcaccacctc tgcacatcca gccccattga tcaagggttc aatttttggg gtcctgttgg  64140
gaggccagga gactctctcc aggcacttct tccaggtctt tgtgttaggg tgtgtgtgtg  64200
tgtgtgtgtg tgtgtgtgtg tgtgttgttt gttttatttt atttatttat ttatttattt  64260
atttatttat ttatttattt tgagacgcag tctcgctctg ttgcccaggt tggagggtgg  64320
tggcatgatc tcggctcact gcaagctccg cctcccgggt tcacgccatt ctcctgcctc  64380
actcttcctg agtagccgga ttacaggcgc acgcaccatg cctggctaat tattttgttt  64440
ttttagtaga gacagggttt cgccacgttg cccaggctgg tcttgaatcc ctggcctcaa  64500
gcgatccgcc cgcctcagcc tcccaaagtg ctgggattac aggcgtgagc caccgtgccc  64560
gcccagccta ggggtacatg aaactttttt tttttttttt ttgagacaga gtttcactct  64620
gtcctcaggc tggagtgcag tggcgtgatc tcggcgtact gcaatctccg cctcccggtt  64680
caagcgattc tcctgcctca gcctcccgag tagctgggat tgcaggcacg cgccaccaca  64740
cccagctaat ttttgtattt ttagtagaga cgggctttca ccatgtggga caggatggtc  64800
tcgatctcct gacctcgtga tccgcccgcc tcagcctccg aaagtgctgg gattacaggc  64860
ctgagccacc gtgcccagcc atgatgtttt gatacaggca tataacgtat aataatcaca  64920
tcagggtaaa tgatgtaacc atcacatcaa gcatttatcc tttgtgttac aaaaaaaaat  64980
ctaattatac tttcctactt attctttttt tttttttttt ttgagacgga gtctccctca  65040
gtcgcccagg ctggagtgca gtggcatgat ctcagttcac tgcaagctct gcctcctagc  65100
tctgcctcct gggttcatgc cattctcctg tctcagcctc gcgagtagct gggactacag  65160
gcgcctgcca ccgtgcccgg ctaatttttt tttttgtatt tttggtagag acagggtttc  65220
accgtgttag ccaggatggt ctcgatctcc tgacctcata atccgcccgt ctcggcctcc  65280
caaagtgctg ggattacagg catgagccac cgcccccagc ctatttattc ttaaatgtac  65340
aataaattat tgttgactcc agtcaccctg ctgtgctacc aaatacggat cttcttcatt  65400
ctatctaact gtatttctgt acctgttaac catctctcct ccacctcacc ccccaaaccc  65460
actacccttc tcagcctctg gtaaccatcc ttctactctc tatctctatg agttcaattg  65520
tattaatttt tagctccccg gccgggcacg gtggctcacg cctgtaatcc cagcacttca  65580
ggaggctgag gcaggtggat cacgaggtca ggagtttgag accagcctgg ccaacatggt  65640
ggaaccccat ctctactaaa aacacaaaaa ttagctgggc gtggtggtgg gcgcttgtag  65700
tcccagctac ttgggaggct gaggcaggag aatcgcttga aactgggagg cagaggttgc  65760
agtgagccaa gattgcgcca ctgcactcca gtctgggtga cagagtaaga ttccatcccg  65820
aaaaaaaaaa agtttagctc ccacaaataa gtgagaacac gtgaagtttc tctttctgtg  65880
cctcgcttgt ttcacttaac ataatgacct ccagttccat ccacgttgtt gctttgttat  65940
aaatgacagg atcttggtca ggcgcagtgg ctcatgcctg taatcccagc actttgggag  66000
gctgaggtgg actgatcatg aggtcaagag atcgagacca tcctggctaa cacagtgaaa  66060
ccccgtctct actaaaaata caagaaatta gccgggcgtg gtggtgggca cccatttccg  66120
```

-continued

```
ccccttctcg ggacgctgat gcacgacata ttacccatcc ccggaagact aatcctcccc  66180

cactctatat tgtacctctt cctttctcct ccacgcgatt ccccgagtaa cccgtcttcc  66240

ctccctcctc ggattacgct cacctttccg cttcaatcac gttgctccgt ccccttcccc  66300

attcgtacca ctcctcactt tcgtcttcct acccccacta tccctttttcg tcctctctat  66360

tccttactta ctcctccccc ttctcttcat acttcattcc ctccgctctt cccactcgcg  66420

ctcccacttt cacctagttg ccctcaccta cgttgccatc tcgccccttc ttcagctctc  66480

ggcctctcac ccatctgtcc tctctcttac ctctctcctc atctcgctca gacatctctc  66540

tagactatcc ctcactttac cttctcagtc gtcttcttcc tatccttcgt tctccatgat  66600

cttcacgtcg ccatctcttt tcgccccttt catatgtctc tcttcatgtt ctcactatca  66660

ttctcatgat cactatcgtt ctcactactt atcactcccc tctttcttca tcaattcctc  66720

tccgtcattc tcgtctctct cttacaaccg ccttccttgt gctatctaac tcaaccatgc  66780

ctctcctact ctctctctat cgcccctcca tcgcttatgc atcctcttct attgcacacc  66840

cgcccctcca tcgcttatgc atcctcttct attgcacacc gcccctccat cgcttatgca  66900

tcctcttcta ttgcacatcc tcttctattg cac                                66933


<210> SEQ ID NO 12
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 12

ctgagcggaa ttcgtgagac c                                                21


<210> SEQ ID NO 13
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 13

ttggtctcac gtattccgct cga                                              23


<210> SEQ ID NO 14
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 14

ctcgagaatt ctggatcctc                                                  20


<210> SEQ ID NO 15
<211> LENGTH: 22
<212> TYPE: DNA
<213> ORGANISM: Artificial Sequence
<220> FEATURE:
<223> OTHER INFORMATION: Artificial sequence is a primer.

<400> SEQUENCE: 15

ttgaggatcc agaattctcg ag                                               22


<210> SEQ ID NO 16
<211> LENGTH: 21
```

-continued

<212> TYPE: DNA
<213> ORGANISM: Artificial Sequence
<220> FEATURE:
<223> OTHER INFORMATION: Artificial sequence is a primer.

<400> SEQUENCE: 16
tgtatgcgaa ttcgctgcgc g 21

<210> SEQ ID NO 17
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 17
ttcgcgcagc gaattcgcat aca 23

<210> SEQ ID NO 18
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 18
gtccactgaa ttctcagtga g 21

<210> SEQ ID NO 19
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 19
ttgtcactga gaattcagtg gac 23

<210> SEQ ID NO 20
<211> LENGTH: 21
<212> TYPE: DNA
<213> ORGANISM: Artificial Sequence
<220> FEATURE:
<223> OTHER INFORMATION: Artificial sequence is a primer.

<400> SEQUENCE: 20
gaatccgaat tcctggtcag c 21

<210> SEQ ID NO 21
<211> LENGTH: 23
<212> TYPE: DNA
<213> ORGANISM: Artificial Sequence
<220> FEATURE:
<223> OTHER INFORMATION: Artificial sequence is a primer.

<400> SEQUENCE: 21
ttgctgacca ggaattcgga ttc 23

<210> SEQ ID NO 22
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 22

-continued cuacuacuac uactgagcgg aattcgtgag acc 33

<210> SEQ ID NO 23
<211> LENGTH: 32
<212> TYPE: DNA
<213> ORGANISM: Artificial Sequence
<220> FEATURE:
<223> OTHER INFORMATION: Artificial sequence is a primer.

<400> SEQUENCE: 23
cuacuacuac uactcgagaa ttctggatcc tc 32

<210> SEQ ID NO 24
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 24
cuacuacuac uatgtatgcg aattcgctgc gcg 33

<210> SEQ ID NO 25
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 25
cuacuacuac uagtccactg aattctcagt gag 33

<210> SEQ ID NO 26
<211> LENGTH: 33
<212> TYPE: DNA
<213> ORGANISM: Artificial Sequence
<220> FEATURE:
<223> OTHER INFORMATION: Artificial sequence is a primer.

<400> SEQUENCE: 26
cuacuacuac uagaatccga attcctggtc agc 33

<210> SEQ ID NO 27
<211> LENGTH: 45
<212> TYPE: DNA
<213> ORGANISM: Artificial Sequence
<220> FEATURE:
<223> OTHER INFORMATION: Artificial sequence is a primer.

<400> SEQUENCE: 27
aactggaaga attcgcggcc gcaggaattt tttttttttt ttttt 45

<210> SEQ ID NO 28
<211> LENGTH: 13
<212> TYPE: DNA
<213> ORGANISM: Artificial Sequence
<220> FEATURE:
<223> OTHER INFORMATION: Artificial sequence is a primer.

<400> SEQUENCE: 28
aattcggcac gag 13

<210> SEQ ID NO 29
<211> LENGTH: 9
<212> TYPE: DNA
<213> ORGANISM: Artificial Sequence -continued
<220> FEATURE:
<223> OTHER INFORMATION: Artificial sequence is a primer.

<400> SEQUENCE: 29 ctcgtgccg 9

<210> SEQ ID NO 30
<211> LENGTH: 14
<212> TYPE: DNA
<213> ORGANISM: Artificial Sequence
<220> FEATURE:
<223> OTHER INFORMATION: Artificial sequence is a primer.

<400> SEQUENCE: 30
gtacgacggc cagt 14

<210> SEQ ID NO 31
<211> LENGTH: 16
<212> TYPE: DNA
<213> ORGANISM: Artificial Sequence
<220> FEATURE:
<223> OTHER INFORMATION: Artificial sequence is a primer.

<400> SEQUENCE: 31
aacagctatg accatg 16

<210> SEQ ID NO 32
<211> LENGTH: 18
<212> TYPE: DNA
<213> ORGANISM: Artificial Sequence
<220> FEATURE:
<223> OTHER INFORMATION: Artificial sequence is a primer.

<400> SEQUENCE: 32
ccaagttctg agaagtcc 18

<210> SEQ ID NO 33
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 33
aatacctgaa accatacctg 20

<210> SEQ ID NO 34
<211> LENGTH: 57
<212> TYPE: DNA
<213> ORGANISM: Artificial Sequence
<220> FEATURE:
<223> OTHER INFORMATION: Artificial sequence is a primer.

<400> SEQUENCE: 34
agctgctcgt agctgtctct ccctggatca cgggtacatg tactggacag actgggt 57

<210> SEQ ID NO 35
<211> LENGTH: 56
<212> TYPE: DNA
<213> ORGANISM: Artificial Sequence
<220> FEATURE:
<223> OTHER INFORMATION: Artificial sequence is a primer.

<400> SEQUENCE: 35
tgagacgccc ggattgagcg ggcagggata gcttattccc tgtgccgcat tacggc 56

-continued

<210> SEQ ID NO 36
<211> LENGTH: 27
<212> TYPE: DNA
<213> ORGANISM: Artificial Sequence
<220> FEATURE:
<223> OTHER INFORMATION: Artificial sequence is a primer.

<400> SEQUENCE: 36
agctgctcgt agctgtctct ccctgga 27

<210> SEQ ID NO 37
<211> LENGTH: 27
<212> TYPE: DNA
<213> ORGANISM: Artificial Sequence
<220> FEATURE:
<223> OTHER INFORMATION: Artificial sequence is a primer.

<400> SEQUENCE: 37
gccgtaatgc ggcacaggga ataagct 27

<210> SEQ ID NO 38
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 38
gagaggctat atccctgggc 20

<210> SEQ ID NO 39
<211> LENGTH: 20
<212> TYPE: DNA
<213> ORGANISM: Artificial Sequence
<220> FEATURE:
<223> OTHER INFORMATION: Artificial sequence is a primer.

<400> SEQUENCE: 39
acagcacgtg tttaaagggg 20

<210> SEQ ID NO 40
<211> LENGTH: 163
<212> TYPE: DNA
<213> ORGANISM: Homo sapiens

<400> SEQUENCE: 40
actaaagcgc cgccgccgcg ccatggagcc cgagtgagct cggcgcgggc ccgtccggcc 60
gccggacaac atggaggcag ctccgcccgg gccgccgtgg ccgctgctgc tgctgctgct 120
gctgctgctg gcgctgtgcg gctgcccggc ccccgccgcg gcc 163

<210> SEQ ID NO 41
<211> LENGTH: 419
<212> TYPE: DNA
<213> ORGANISM: Homo sapiens

<400> SEQUENCE: 41
gccccacagc ctcgccgctc ctgctatttg ccaaccgccg ggacgtacgg ctggtggacg 60
ccggcggagt caagctggag tccaccatcg tggtcagcgg cctggaggat gcggccgcag 120
tggacttcca gttttccaag ggagccgtgt actggacaga cgtgagcgag gaggccatca 180
agcagaccta cctgaaccag acgggggccg ccgtgcagaa cgtggtcatc tccggcctgg 240
tctctcccga cggcctcgcc tgcgactggg tgggcaagaa gctgtactgg acggactcag 300

-continued

```
agaccaaccg catcgaggtg gccaacctca atggcacatc ccggaaggtg ctcttctggc    360

aggaccttga ccagccgagg gccatcgcct tggaccccgc tcacgggtaa accctgctg     419


<210> SEQ ID NO 42
<211> LENGTH: 221
<212> TYPE: DNA
<213> ORGANISM: Homo sapiens

<400> SEQUENCE: 42

ccccgtcaca ggtacatgta ctggacagac tggggtgaga cgccccggat tgagcgggca     60

gggatggatg gcagcacccg gaagatcatt gtggactcgg acatttactg gcccaatgga    120

ctgaccatcg acctggagga gcagaagctc tactgggctg acgccaagct cagcttcatc    180

caccgtgcca acctggacgg ctcgttccgg taggtaccca c                        221


<210> SEQ ID NO 43
<211> LENGTH: 221
<212> TYPE: DNA
<213> ORGANISM: Homo sapiens

<400> SEQUENCE: 43

tccctgactg caggcagaag gtggtggagg gcagcctgac gcaccccttc gccctgacgc     60

tctccgggga cactctgtac tggacagact ggcagacccg ctccatccat gcctgcaaca    120

agcgcactgg ggggaagagg aaggagatcc tgagtgccct atactcaccc atggacatcc    180

aggtgctgag ccaggagcgg cagccttttt gtgagtgccg g                        221


<210> SEQ ID NO 44
<211> LENGTH: 156
<212> TYPE: DNA
<213> ORGANISM: Homo sapiens

<400> SEQUENCE: 44

tttctcagtc cacactcgct gtgaggagga caatggcggc tggtcccacc tgtgcctgct     60

gtccccaagc gagccttttt acacatgcgc ctgccccacg ggtgtgcaga tgcaggacaa    120

cggcaggacg tgtaaggcag gtgaggcggt gggacg                              156


<210> SEQ ID NO 45
<211> LENGTH: 416
<212> TYPE: DNA
<213> ORGANISM: Homo sapiens

<400> SEQUENCE: 45

ctccacagga gccgaggagg tgctgctgct ggcccggcgg acggacctac ggaggatctc     60

gctggacacg ccggacttca ccgacatcgt gctgcaggtg gacgacatcc ggcacgccat    120

tgccatcgac tacgacccgc tagagggcta tgtctactgg acagatgacg aggtgcgggc    180

catccgcagg gcgtacctgg acgggtctgg ggcgcagacg ctggtcaaca ccgagatcaa    240

cgaccccgat ggcatcgcgg tcgactgggt ggcccgaaac ctctactgga ccgacacggg    300

cacggaccgc atcgaggtga cgcgcctcaa cggcacctcc cgcaagatcc tggtgtcgga    360

ggacctggac gagccccgag ccatcgcact gcaccccgtg atggggtaag acgggc        416


<210> SEQ ID NO 46
<211> LENGTH: 198
<212> TYPE: DNA
<213> ORGANISM: Homo sapiens
```

-continued

<400> SEQUENCE: 46
ttcttctcca gcctcatgta ctggacagac tggggagaga accctaaaat cgagtgtgcc 60
aacttggatg ggcaggagcg gcgtgtgctg gtcaatgcct ccctcgggtg gcccaacggc 120
ctggccctgg acctgcagga ggggaagctc tactggggag acgccaagac agacaagatc 180
gaggtgaggc tcctgtgg 198

<210> SEQ ID NO 47
<211> LENGTH: 244
<212> TYPE: DNA
<213> ORGANISM: Homo sapiens

<400> SEQUENCE: 47
ccgtcctgca ggtgatcaat gttgatggga cgaagaggcg gaccctcctg gaggacaagc 60
tcccgcacat tttcgggttc acgctgctgg gggacttcat ctactggact gactggcagc 120
gccgcagcat cgagcgggtg cacaaggtca aggccagccg ggacgtcatc attgaccagc 180
tgcccgacct gatggggctc aaagctgtga atgtggccaa ggtcgtcggt gagtccgggg 240
ggtc 244

<210> SEQ ID NO 48
<211> LENGTH: 313
<212> TYPE: DNA
<213> ORGANISM: Homo sapiens

<400> SEQUENCE: 48
gttcgcttcc aggaaccaac ccgtgtgcgg acaggaacgg ggggtgcagc cacctgtgct 60
tctgcacacc ccacgcaacc cggtgtggct gccccatcgg cctggagctg ctgagtgaca 120
tgaagacctg catcgtgcct gaggcctttt tggtcttcac cagcagagcc gccatccaca 180
ggatctccct cgagaccaat aacaacgacg tggccatccc gctcacgggc gtcaaggagg 240
cctcagccct ggactttgat gtgtccaaca accacatcta ctggacagac gtcagcctga 300
aggtagcgtg ggc 313

<210> SEQ ID NO 49
<211> LENGTH: 255
<212> TYPE: DNA
<213> ORGANISM: Homo sapiens

<400> SEQUENCE: 49
cctgctgcca gaccatcagc cgcgccttca tgaacgggag ctcggtggag cacgtggtgg 60
agtttggcct tgactacccc gagggcatgg ccgttgactg gatgggcaag aacctctact 120
gggccgacac tgggaccaac agaatcgaag tggcgcggct ggacgggcag ttccggcaag 180
tcctcgtgtg gagggacttg gacaacccga ggtcgctggc cctggatccc accaaggggt 240
aagtgtttgc ctgtc 255

<210> SEQ ID NO 50
<211> LENGTH: 210
<212> TYPE: DNA
<213> ORGANISM: Homo sapiens

<400> SEQUENCE: 50
gtgccttcca gctacatcta ctggaccgag tggggcggca agccgaggat cgtgcgggcc 60
ttcatggacg ggaccaactg catgacgctg gtggacaagg tgggccgggc caacgacctc 120
accattgact acgctgacca gcgcctctac tggaccgacc tggacaccaa catgatcgag 180

-continued

```
tcgtccaaca tgctgggtga gggccgggct                                      210


<210> SEQ ID NO 51
<211> LENGTH: 352
<212> TYPE: DNA
<213> ORGANISM: Homo sapiens

<400> SEQUENCE: 51

gtgttcatgc aggtcaggag cgggtcgtga ttgccgacga tctcccgcac ccgttcggtc      60

tgacgcagta cagcgattat atctactgga cagactggaa tctgcacagc attgagcggg     120

ccgacaagac tagcggccgg aaccgcaccc tcatccaggg ccacctggac ttcgtgatgg     180

acatcctggt gttccactcc tcccgccagg atggcctcaa tgactgtatg cacaacaacg     240

ggcagtgtgg gcagctgtgc cttgccatcc ccggcggcca ccgctgcggc tgcgcctcac     300

actacaccct ggaccccagc agccgcaact gcagccgtaa gtgcctcatg gt             352


<210> SEQ ID NO 52
<211> LENGTH: 225
<212> TYPE: DNA
<213> ORGANISM: Homo sapiens

<400> SEQUENCE: 52

gcctcctcta cgcccaccac cttcttgctg ttcagccaga aatctgccat cagtcggatg      60

atcccggacg accagcacag cccggatctc atcctgcccc tgcatggact gaggaacgtc     120

aaagccatcg actatgaccc actggacaag ttcatctact gggtggatgg gcgccagaac     180

atcaagcgag ccaaggacga cgggacccag gcaggtgccc tgtgg                     225


<210> SEQ ID NO 53
<211> LENGTH: 235
<212> TYPE: DNA
<213> ORGANISM: Homo sapiens

<400> SEQUENCE: 53

ctttgtctta cagccctttg ttttgacctc tctgagccaa ggccaaaacc cagacaggca      60

gccccacgac ctcagcatcg acatctacag ccggacactg ttctggacgt gcgaggccac     120

caataccatc aacgtccaca ggctgagcgg ggaagccatg gggtggtgc tgcgtgggga      180

ccgcgacaag cccagggcca tcgtcgtcaa cgcggagcga gggtaggagg ccaac          235


<210> SEQ ID NO 54
<211> LENGTH: 218
<212> TYPE: DNA
<213> ORGANISM: Homo sapiens

<400> SEQUENCE: 54

ccaccctccc gcaggtacct gtacttcacc aacatgcagg accgggcagc caagatcgaa      60

cgcgcagccc tggacggcac cgagcgcgag gtcctcttca ccaccggcct catccgccct     120

gtggccctgg tggtggacaa cacactgggc aagctgttct gggtggacgc ggacctgaag     180

cgcattgaga gctgtgacct gtcaggtacg cgccccgg                             218


<210> SEQ ID NO 55
<211> LENGTH: 234
<212> TYPE: DNA
<213> ORGANISM: Homo sapiens

<400> SEQUENCE: 55
```

-continued ggctgcttgc aggggccaac cgcctgaccc tggaggacgc caacatcgtg cagcctctgg 60
gcctgaccat ccttggcaag catctctact ggatcgaccg ccagcagcag atgatcgagc 120
gtgtggagaa gaccaccggg gacaagcgga ctcgcatcca gggccgtgtc gcccacctca 180
ctggcatcca tgcagtggag gaagtcagcc tggaggagtt ctgtacgtgg gggc 234

<210> SEQ ID NO 56
<211> LENGTH: 157
<212> TYPE: DNA
<213> ORGANISM: Homo sapiens

<400> SEQUENCE: 56
ttgtctttgc agcagcccac ccatgtgccc gtgacaatgg tggctgctcc cacatctgta 60
ttgccaaggg tgatgggaca ccacggtgct catgcccagt ccacctcgtg ctcctgcaga 120
acctgctgac ctgtggaggt aggtgtgacc taggtgc 157

<210> SEQ ID NO 57
<211> LENGTH: 272
<212> TYPE: DNA
<213> ORGANISM: Homo sapiens

<400> SEQUENCE: 57
gttctcctct gtccctcccc cagagccgcc cacctgctcc ccggaccagt ttgcatgtgc 60
cacaggggag atcgactgta tccccggggc ctggcgctgt gacggctttc ccgagtgcga 120
tgaccagagc gacgaggagg gctgccccgt gtgctccgcc gcccagttcc cctgcgcgcg 180
gggtcagtgt gtggacctgc gcctgcgctg cgacggcgag gcagactgtc aggaccgctc 240
agacgaggtg gactgtgacg gtgaggccct cc 272

<210> SEQ ID NO 58
<211> LENGTH: 134
<212> TYPE: DNA
<213> ORGANISM: Homo sapiens

<400> SEQUENCE: 58
tctccttgca gccatctgcc tgcccaacca gttccggtgt gcgagcggcc agtgtgtcct 60
catcaaacag cagtgcgact ccttccccga ctgtatcgac ggctccgacg agctcatgtg 120
tggtgagcca gctt 134

<210> SEQ ID NO 59
<211> LENGTH: 274
<212> TYPE: DNA
<213> ORGANISM: Homo sapiens

<400> SEQUENCE: 59
gtttgtctct ggcagaaatc accaagccgc cctcagacga cagcccggcc cacagcagtg 60
ccatcgggcc cgtcattggc atcatcctct ctctcttcgt catgggtggt gtctattttg 120
tgtgccagcg cgtggtgtgc cagcgctatg cgggggccaa cgggcccttc ccgcacgagt 180
atgtcagcgg gaccccgcac gtgcccctca atttcatagc cccgggcggt tcccagcatg 240
gccccttcac aggtaaggag cctgagatat ggaa 274

<210> SEQ ID NO 60
<211> LENGTH: 164
<212> TYPE: DNA
<213> ORGANISM: Homo sapiens

<400> SEQUENCE: 60

-continued

```
cttccctgcc aggcatcgca tgcggaaagt ccatgatgag ctccgtgagc ctgatggggg     60

gccggggcgg ggtgcccctc tacgaccgga accacgtcac aggggcctcg tccagcagct    120

cgtccagcac gaaggccacg ctgtacccgc cggtgagggg cggg                     164


<210> SEQ ID NO 61
<211> LENGTH: 130
<212> TYPE: DNA
<213> ORGANISM: Homo sapiens

<400> SEQUENCE: 61

ttggctctcc tcagatcctg aacccgccgc cctccccggc cacggacccc tccctgtaca     60

acatggacat gttctactct tcaaacattc cggccactgc gagaccgtac aggtaggaca    120

tcccctgcag                                                           130


<210> SEQ ID NO 62
<211> LENGTH: 496
<212> TYPE: DNA
<213> ORGANISM: Homo sapiens

<400> SEQUENCE: 62

tcaaacattc cggccactgc gagaccgtac aggccctaca tcattcgagg aatggcgccc     60

ccgacgacgc cctgcagcac cgacgtgtgt gacagcgact acagcgccag ccgctggaag    120

gccagcaagt actacctgga tttgaactcg gactcagacc cctatccacc cccacccacg    180

ccccacagcc agtacctgtc ggcggaggac agctgcccgc cctcgcccgc caccgagagg    240

agctacttcc atctcttccc gccccctccg tccccctgca cggactcatc ctgacctcgg    300

ccgggccact ctggcttctc tgtgcccctg taaatagttt taaatatgaa caaagaaaaa    360

aatatatttt atgatttaaa aaataaatat aattgggatt ttaaaaacat gagaaatgtg    420

aactgtgatg gggtgggcag ggctgggaga actttgtaca gtggagaaat atttataaac    480

ttaattttgt aaaaca                                                    496


<210> SEQ ID NO 63
<211> LENGTH: 22
<212> TYPE: DNA
<213> ORGANISM: Artificial Sequence
<220> FEATURE:
<223> OTHER INFORMATION: Artificial Sequence is a primer.

<400> SEQUENCE: 63

ttttgggtac acaattcagt cg                                              22


<210> SEQ ID NO 64
<211> LENGTH: 20
<212> TYPE: DNA
<213> ORGANISM: Artificial Sequence
<220> FEATURE:
<223> OTHER INFORMATION: Artificial Sequence is a primer.

<400> SEQUENCE: 64

aaaactgtgg gtgcttctgg                                                 20


<210> SEQ ID NO 65
<211> LENGTH: 21
<212> TYPE: DNA
<213> ORGANISM: Artificial Sequence
<220> FEATURE:
<223> OTHER INFORMATION: Artificial Sequence is a primer.
```

-continued

<400> SEQUENCE: 65
gtgattgagc caatcctgag a 21

<210> SEQ ID NO 66
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 66
tgagccaaat aaacccettc t 21

<210> SEQ ID NO 67
<211> LENGTH: 20
<212> TYPE: DNA
<213> ORGANISM: Homo sapiens

<400> SEQUENCE: 67
ctggactacg tggccttctc 20

<210> SEQ ID NO 68
<211> LENGTH: 19
<212> TYPE: DNA
<213> ORGANISM: Homo sapiens

<400> SEQUENCE: 68
ttcagaagca cttggctgg 19

<210> SEQ ID NO 69
<211> LENGTH: 20
<212> TYPE: DNA
<213> ORGANISM: Homo sapiens

<400> SEQUENCE: 69
ctcagtgcca tgaagatgga 20

<210> SEQ ID NO 70
<211> LENGTH: 21
<212> TYPE: DNA
<213> ORGANISM: Homo sapiens

<400> SEQUENCE: 70
caagatcact cgatctccag g 21

<210> SEQ ID NO 71
<211> LENGTH: 20
<212> TYPE: DNA
<213> ORGANISM: Homo sapiens

<400> SEQUENCE: 71
gtttcaggag actcagagtc 20

<210> SEQ ID NO 72
<211> LENGTH: 20
<212> TYPE: DNA
<213> ORGANISM: Homo sapiens

<400> SEQUENCE: 72
ttctgcaggt tgctgttgag 20

<210> SEQ ID NO 73
<211> LENGTH: 20

-continued

<212> TYPE: DNA
<213> ORGANISM: Homo sapiens

<400> SEQUENCE: 73
ttattgtgat ttcccgtggc 20

<210> SEQ ID NO 74
<211> LENGTH: 21
<212> TYPE: DNA
<213> ORGANISM: Homo sapiens

<400> SEQUENCE: 74
gccctctgtc ctgacttcag g 21

<210> SEQ ID NO 75
<211> LENGTH: 20
<212> TYPE: DNA
<213> ORGANISM: Homo sapiens

<400> SEQUENCE: 75
gagaaagaaa taaggggacc 20

<210> SEQ ID NO 76
<211> LENGTH: 20
<212> TYPE: DNA
<213> ORGANISM: Homo sapiens

<400> SEQUENCE: 76
tgctttgtaa agcactgaga 20

<210> SEQ ID NO 77
<211> LENGTH: 24
<212> TYPE: DNA
<213> ORGANISM: Homo sapiens

<400> SEQUENCE: 77
gaagtacggg cagttcagtg gcct 24

<210> SEQ ID NO 78
<211> LENGTH: 25
<212> TYPE: DNA
<213> ORGANISM: Homo sapiens

<400> SEQUENCE: 78
atacaccaag gtccatgttc cccgt 25

<210> SEQ ID NO 79
<211> LENGTH: 25
<212> TYPE: DNA
<213> ORGANISM: Homo sapiens

<400> SEQUENCE: 79
agcctgggcc acagcgtgag actac 25

<210> SEQ ID NO 80
<211> LENGTH: 25
<212> TYPE: DNA
<213> ORGANISM: Homo sapiens

<400> SEQUENCE: 80
tcccggagct tgcacacccg cttca 25

<210> SEQ ID NO 81

-continued

<211> LENGTH: 20
<212> TYPE: DNA
<213> ORGANISM: Homo sapiens

<400> SEQUENCE: 81
catgtgccca cctcattcat 20

<210> SEQ ID NO 82
<211> LENGTH: 20
<212> TYPE: DNA
<213> ORGANISM: Homo sapiens

<400> SEQUENCE: 82
caagattctg tagcttctgg 20

<210> SEQ ID NO 83
<211> LENGTH: 20
<212> TYPE: DNA
<213> ORGANISM: Homo sapiens

<400> SEQUENCE: 83
cagagaagtc aagggacttg 20

<210> SEQ ID NO 84
<211> LENGTH: 20
<212> TYPE: DNA
<213> ORGANISM: Homo sapiens

<400> SEQUENCE: 84
atcctctcac atcccacact 20

<210> SEQ ID NO 85
<211> LENGTH: 20
<212> TYPE: DNA
<213> ORGANISM: Homo sapiens

<400> SEQUENCE: 85
caaggctaaa agacgaaaaa 20

<210> SEQ ID NO 86
<211> LENGTH: 20
<212> TYPE: DNA
<213> ORGANISM: Homo sapiens

<400> SEQUENCE: 86
tcaggagcat ttcatctttt 20

<210> SEQ ID NO 87
<211> LENGTH: 19
<212> TYPE: DNA
<213> ORGANISM: Homo sapiens

<400> SEQUENCE: 87
aagtcgaggc tgcaaggag 19

<210> SEQ ID NO 88
<211> LENGTH: 20
<212> TYPE: DNA
<213> ORGANISM: Homo sapiens

<400> SEQUENCE: 88
gccctgtgtt cctttcagta 20

-continued

<210> SEQ ID NO 89
<211> LENGTH: 19
<212> TYPE: DNA
<213> ORGANISM: Homo sapiens

<400> SEQUENCE: 89
aaggtgtgag gatcactgg 19

<210> SEQ ID NO 90
<211> LENGTH: 17
<212> TYPE: DNA
<213> ORGANISM: Homo sapiens

<400> SEQUENCE: 90
agctcatggg ggctatt 17

<210> SEQ ID NO 91
<211> LENGTH: 20
<212> TYPE: DNA
<213> ORGANISM: Homo sapiens

<400> SEQUENCE: 91
gcttctccga gtgtatcaac 20

<210> SEQ ID NO 92
<211> LENGTH: 20
<212> TYPE: DNA
<213> ORGANISM: Homo sapiens

<400> SEQUENCE: 92
atggcagagg acttagaaca 20

<210> SEQ ID NO 93
<211> LENGTH: 24
<212> TYPE: DNA
<213> ORGANISM: Homo sapiens

<400> SEQUENCE: 93
gatcagcgaa cttcctctcg gctc 24

<210> SEQ ID NO 94
<211> LENGTH: 24
<212> TYPE: DNA
<213> ORGANISM: Homo sapiens

<400> SEQUENCE: 94
tccacattga ggactgtggg aacg 24

<210> SEQ ID NO 95
<211> LENGTH: 20
<212> TYPE: DNA
<213> ORGANISM: Homo sapiens

<400> SEQUENCE: 95
gctaatcaca gtctaaccga 20

<210> SEQ ID NO 96
<211> LENGTH: 19
<212> TYPE: DNA
<213> ORGANISM: Homo sapiens

<400> SEQUENCE: 96
ttgcactgtc ttggatgca 19

-continued

<210> SEQ ID NO 97
<211> LENGTH: 25
<212> TYPE: DNA
<213> ORGANISM: Homo sapiens

<400> SEQUENCE: 97
gcacagctgt agtggggttc taggc 25

<210> SEQ ID NO 98
<211> LENGTH: 25
<212> TYPE: DNA
<213> ORGANISM: Homo sapiens

<400> SEQUENCE: 98
caggcgcaaa ggacatgcac acggc 25

<210> SEQ ID NO 99
<211> LENGTH: 25
<212> TYPE: DNA
<213> ORGANISM: Homo sapiens

<400> SEQUENCE: 99
caccgatgag tgcacgttca aggag 25

<210> SEQ ID NO 100
<211> LENGTH: 25
<212> TYPE: DNA
<213> ORGANISM: Homo sapiens

<400> SEQUENCE: 100
cagacagaga tgctccacgc catac 25

<210> SEQ ID NO 101
<211> LENGTH: 19
<212> TYPE: DNA
<213> ORGANISM: Homo sapiens

<400> SEQUENCE: 101
tttctgggtg tgtctgaat 19

<210> SEQ ID NO 102
<211> LENGTH: 20
<212> TYPE: DNA
<213> ORGANISM: Homo sapiens

<400> SEQUENCE: 102
acacagttgc tctaaagggt 20

<210> SEQ ID NO 103
<211> LENGTH: 20
<212> TYPE: DNA
<213> ORGANISM: Homo sapiens

<400> SEQUENCE: 103
catttgggaa atccagaaga 20

<210> SEQ ID NO 104
<211> LENGTH: 25
<212> TYPE: DNA
<213> ORGANISM: Homo sapiens

<400> SEQUENCE: 104
taggtgtctt attttttgtt gcttc 25

<210> SEQ ID NO 105
<211> LENGTH: 25
<212> TYPE: DNA
<213> ORGANISM: Homo sapiens

<400> SEQUENCE: 105
gacataccat gaacactata agagg 25

<210> SEQ ID NO 106
<211> LENGTH: 20
<212> TYPE: DNA
<213> ORGANISM: Homo sapiens

<400> SEQUENCE: 106
caacccatac cagggataag 20

<210> SEQ ID NO 107
<211> LENGTH: 21
<212> TYPE: DNA
<213> ORGANISM: Homo sapiens

<400> SEQUENCE: 107
gaacaagagg ggtaagttgg c 21

<210> SEQ ID NO 108
<211> LENGTH: 22
<212> TYPE: DNA
<213> ORGANISM: Homo sapiens

<400> SEQUENCE: 108
tgaggacaca gatactgatg gg 22

<210> SEQ ID NO 109
<211> LENGTH: 25
<212> TYPE: DNA
<213> ORGANISM: Homo sapiens

<400> SEQUENCE: 109
gaagtgttcc ctcttaaatt ctttg 25

<210> SEQ ID NO 110
<211> LENGTH: 25
<212> TYPE: DNA
<213> ORGANISM: Homo sapiens

<400> SEQUENCE: 110
gaactatatt gtagttagtg aggag 25

<210> SEQ ID NO 111
<211> LENGTH: 18
<212> TYPE: DNA
<213> ORGANISM: Homo sapiens

<400> SEQUENCE: 111
cctgtaaccc ccagtccc 18

<210> SEQ ID NO 112
<211> LENGTH: 22
<212> TYPE: DNA
<213> ORGANISM: Homo sapiens

<400> SEQUENCE: 112

-continued tcttgcttcc taagtttctc gg 22

<210> SEQ ID NO 113
<211> LENGTH: 21
<212> TYPE: DNA
<213> ORGANISM: Homo sapiens

<400> SEQUENCE: 113
actccatcca cctcatcact g 21

<210> SEQ ID NO 114
<211> LENGTH: 20
<212> TYPE: DNA
<213> ORGANISM: Homo sapiens

<400> SEQUENCE: 114
tgctgtttgc ctcatctgac 20

<210> SEQ ID NO 115
<211> LENGTH: 20
<212> TYPE: DNA
<213> ORGANISM: Homo sapiens

<400> SEQUENCE: 115
gtggacaggc atagctgagg 20

<210> SEQ ID NO 116
<211> LENGTH: 21
<212> TYPE: DNA
<213> ORGANISM: Homo sapiens

<400> SEQUENCE: 116
tgttcactct tctgcctgca g 21

<210> SEQ ID NO 117
<211> LENGTH: 20
<212> TYPE: DNA
<213> ORGANISM: Homo sapiens

<400> SEQUENCE: 117
agctggactc tcacagaatg 20

<210> SEQ ID NO 118
<211> LENGTH: 20
<212> TYPE: DNA
<213> ORGANISM: Homo sapiens

<400> SEQUENCE: 118
caagaggctg gtagaaggtg 20

<210> SEQ ID NO 119
<211> LENGTH: 24
<212> TYPE: DNA
<213> ORGANISM: Homo sapiens

<400> SEQUENCE: 119
gactccagtc tgggcaataa aagc 24

<210> SEQ ID NO 120
<211> LENGTH: 22
<212> TYPE: DNA
<213> ORGANISM: Homo sapiens

<400> SEQUENCE: 120

-continued ggtggcagca tgacctctaa ag 22

<210> SEQ ID NO 121
<211> LENGTH: 16
<212> TYPE: DNA
<213> ORGANISM: Homo sapiens

<400> SEQUENCE: 121
caggcccagt ctcttg 16

<210> SEQ ID NO 122
<211> LENGTH: 18
<212> TYPE: DNA
<213> ORGANISM: Homo sapiens

<400> SEQUENCE: 122
cgtgtccaga tgaaagtg 18

<210> SEQ ID NO 123
<211> LENGTH: 18
<212> TYPE: DNA
<213> ORGANISM: Homo sapiens

<400> SEQUENCE: 123
acctcacggt gtaatccc 18

<210> SEQ ID NO 124
<211> LENGTH: 18
<212> TYPE: DNA
<213> ORGANISM: Homo sapiens

<400> SEQUENCE: 124
cttgaagccc atctttgc 18

<210> SEQ ID NO 125
<211> LENGTH: 23
<212> TYPE: DNA
<213> ORGANISM: Homo sapiens

<400> SEQUENCE: 125
tatttgcaaa gcttgagact tct 23

<210> SEQ ID NO 126
<211> LENGTH: 20
<212> TYPE: DNA
<213> ORGANISM: Homo sapiens

<400> SEQUENCE: 126
aatcactgtg ctttgttgcc 20

<210> SEQ ID NO 127
<211> LENGTH: 20
<212> TYPE: DNA
<213> ORGANISM: Homo sapiens

<400> SEQUENCE: 127
actttattgt cagcgtgggc 20

<210> SEQ ID NO 128
<211> LENGTH: 18
<212> TYPE: DNA
<213> ORGANISM: Homo sapiens -continued

<400> SEQUENCE: 128
actccctcga tggcttcc 18

<210> SEQ ID NO 129
<211> LENGTH: 18
<212> TYPE: DNA
<213> ORGANISM: Homo sapiens

<400> SEQUENCE: 129
gagcagggga gagaaggc 18

<210> SEQ ID NO 130
<211> LENGTH: 20
<212> TYPE: DNA
<213> ORGANISM: Homo sapiens

<400> SEQUENCE: 130
cccactggct tgttttattg 20

<210> SEQ ID NO 131
<211> LENGTH: 25
<212> TYPE: DNA
<213> ORGANISM: Homo sapiens

<400> SEQUENCE: 131
agccacttta ttgttatttt gatgc 25

<210> SEQ ID NO 132
<211> LENGTH: 25
<212> TYPE: DNA
<213> ORGANISM: Homo sapiens

<400> SEQUENCE: 132
aagagtgaac aaaagcaaac atacc 25

<210> SEQ ID NO 133
<211> LENGTH: 18
<212> TYPE: DNA
<213> ORGANISM: Homo sapiens

<400> SEQUENCE: 133
gtggagtgtg ggattggg 18

<210> SEQ ID NO 134
<211> LENGTH: 25
<212> TYPE: DNA
<213> ORGANISM: Homo sapiens

<400> SEQUENCE: 134
tactgttctt gataagtatg tcggc 25

<210> SEQ ID NO 135
<211> LENGTH: 25
<212> TYPE: DNA
<213> ORGANISM: Homo sapiens

<400> SEQUENCE: 135
atgcttttgc atgattctaa ttatt 25

<210> SEQ ID NO 136
<211> LENGTH: 21
<212> TYPE: DNA
<213> ORGANISM: Homo sapiens

<400> SEQUENCE: 136
tcccccaaaa gaatgtaaag g 21

<210> SEQ ID NO 137
<211> LENGTH: 20
<212> TYPE: DNA
<213> ORGANISM: Homo sapiens

<400> SEQUENCE: 137
ctggtcttcc ttgtgtgctg 20

<210> SEQ ID NO 138
<211> LENGTH: 18
<212> TYPE: DNA
<213> ORGANISM: Homo sapiens

<400> SEQUENCE: 138
atcacccagg ccagggat 18

<210> SEQ ID NO 139
<211> LENGTH: 24
<212> TYPE: DNA
<213> ORGANISM: Homo sapiens

<400> SEQUENCE: 139
tcagaagcag aactgttttt aaca 24

<210> SEQ ID NO 140
<211> LENGTH: 22
<212> TYPE: DNA
<213> ORGANISM: Homo sapiens

<400> SEQUENCE: 140
cctgcttgaa agttctagag cc 22

<210> SEQ ID NO 141
<211> LENGTH: 21
<212> TYPE: DNA
<213> ORGANISM: Homo sapiens

<400> SEQUENCE: 141
caagcccggg ttttattgaa a 21

<210> SEQ ID NO 142
<211> LENGTH: 18
<212> TYPE: DNA
<213> ORGANISM: Homo sapiens

<400> SEQUENCE: 142
gatgccagga ccatggac 18

<210> SEQ ID NO 143
<211> LENGTH: 24
<212> TYPE: DNA
<213> ORGANISM: Homo sapiens

<400> SEQUENCE: 143
gcatatagaa acaatttatt gccg 24

<210> SEQ ID NO 144
<211> LENGTH: 20
<212> TYPE: DNA

-continued

<213> ORGANISM: Homo sapiens

<400> SEQUENCE: 144
ctctgaagca gggaccagag 20

<210> SEQ ID NO 145
<211> LENGTH: 19
<212> TYPE: DNA
<213> ORGANISM: Homo sapiens

<400> SEQUENCE: 145
ctaccacacc acaccaggc 19

<210> SEQ ID NO 146
<211> LENGTH: 18
<212> TYPE: DNA
<213> ORGANISM: Homo sapiens

<400> SEQUENCE: 146
caagcgaaag ctgccttc 18

<210> SEQ ID NO 147
<211> LENGTH: 23
<212> TYPE: DNA
<213> ORGANISM: Homo sapiens

<400> SEQUENCE: 147
gttgtcttga cttcaggtct gtc 23

<210> SEQ ID NO 148
<211> LENGTH: 24
<212> TYPE: DNA
<213> ORGANISM: Homo sapiens

<400> SEQUENCE: 148
ttttccttca acaatcacta ctcc 24

<210> SEQ ID NO 149
<211> LENGTH: 20
<212> TYPE: DNA
<213> ORGANISM: Homo sapiens

<400> SEQUENCE: 149
gcgtggggat atagaggtca 20

<210> SEQ ID NO 150
<211> LENGTH: 20
<212> TYPE: DNA
<213> ORGANISM: Homo sapiens

<400> SEQUENCE: 150
tacgtggcca agaagctagg 20

<210> SEQ ID NO 151
<211> LENGTH: 24
<212> TYPE: DNA
<213> ORGANISM: Homo sapiens

<400> SEQUENCE: 151
taatatatcc ccagtctaag gcat 24

<210> SEQ ID NO 152
<211> LENGTH: 18

-continued

<212> TYPE: DNA
<213> ORGANISM: Homo sapiens

<400> SEQUENCE: 152
agcttgcaga tggagccc 18

<210> SEQ ID NO 153
<211> LENGTH: 25
<212> TYPE: DNA
<213> ORGANISM: Homo sapiens

<400> SEQUENCE: 153
tggttttaaa cctttaatga gaaaa 25

<210> SEQ ID NO 154
<211> LENGTH: 23
<212> TYPE: DNA
<213> ORGANISM: Homo sapiens

<400> SEQUENCE: 154
tgttgatcta taccctgttt ccg 23

<210> SEQ ID NO 155
<211> LENGTH: 25
<212> TYPE: DNA
<213> ORGANISM: Homo sapiens

<400> SEQUENCE: 155
aattatttaa aagagaggaa aggca 25

<210> SEQ ID NO 156
<211> LENGTH: 20
<212> TYPE: DNA
<213> ORGANISM: Homo sapiens

<400> SEQUENCE: 156
tggctgtgaa cttcctctga 20

<210> SEQ ID NO 157
<211> LENGTH: 25
<212> TYPE: DNA
<213> ORGANISM: Homo sapiens

<400> SEQUENCE: 157
ggttacagaa aaacatttga gagat 25

<210> SEQ ID NO 158
<211> LENGTH: 22
<212> TYPE: DNA
<213> ORGANISM: Homo sapiens

<400> SEQUENCE: 158
tgagctttag ttcccttctc tg 22

<210> SEQ ID NO 159
<211> LENGTH: 23
<212> TYPE: DNA
<213> ORGANISM: Homo sapiens

<400> SEQUENCE: 159
ttgaaaaacc atttatttca ccg 23

<210> SEQ ID NO 160

-continued

<211> LENGTH: 18
<212> TYPE: DNA
<213> ORGANISM: Homo sapiens

<400> SEQUENCE: 160
tctgcggctg ttggattt 18

<210> SEQ ID NO 161
<211> LENGTH: 23
<212> TYPE: DNA
<213> ORGANISM: Homo sapiens

<400> SEQUENCE: 161
ttgaaaaacc atttatttca ccg 23

<210> SEQ ID NO 162
<211> LENGTH: 20
<212> TYPE: DNA
<213> ORGANISM: Homo sapiens

<400> SEQUENCE: 162
tgttctcttc tccagcagg 20

<210> SEQ ID NO 163
<211> LENGTH: 23
<212> TYPE: DNA
<213> ORGANISM: Homo sapiens

<400> SEQUENCE: 163
ctttattgaa aacattgagt gca 23

<210> SEQ ID NO 164
<211> LENGTH: 20
<212> TYPE: DNA
<213> ORGANISM: Homo sapiens

<400> SEQUENCE: 164
ttgtcaaatt ccccccaaaa 20

<210> SEQ ID NO 165
<211> LENGTH: 16
<212> TYPE: DNA
<213> ORGANISM: Homo sapiens
<220> FEATURE:
<221> NAME/KEY: misc_feature
<222> LOCATION: 12
<223> OTHER INFORMATION: n = A,T,C or G

<400> SEQUENCE: 165
aaaccacgac cnccaa 16

<210> SEQ ID NO 166
<211> LENGTH: 20
<212> TYPE: DNA
<213> ORGANISM: Homo sapiens

<400> SEQUENCE: 166
ccctggaaag gtaagatgct 20

<210> SEQ ID NO 167
<211> LENGTH: 23
<212> TYPE: DNA
<213> ORGANISM: Homo sapiens

<400> SEQUENCE: 167
cttttggtag agacaaggtc tca 23

<210> SEQ ID NO 168
<211> LENGTH: 25
<212> TYPE: DNA
<213> ORGANISM: Homo sapiens

<400> SEQUENCE: 168
tatctgtctg tagtgcttca aatgt 25

<210> SEQ ID NO 169
<211> LENGTH: 19
<212> TYPE: DNA
<213> ORGANISM: Homo sapiens

<400> SEQUENCE: 169
gacgaaggtg attcagggc 19

<210> SEQ ID NO 170
<211> LENGTH: 19
<212> TYPE: DNA
<213> ORGANISM: Homo sapiens

<400> SEQUENCE: 170
actgaagaac tcttgtcct 19

<210> SEQ ID NO 171
<211> LENGTH: 25
<212> TYPE: DNA
<213> ORGANISM: Homo sapiens

<400> SEQUENCE: 171
cagataaaag agtcactatg gctca 25

<210> SEQ ID NO 172
<211> LENGTH: 20
<212> TYPE: DNA
<213> ORGANISM: Homo sapiens

<400> SEQUENCE: 172
cacttctccc actttgtccc 20

<210> SEQ ID NO 173
<211> LENGTH: 25
<212> TYPE: DNA
<213> ORGANISM: Homo sapiens

<400> SEQUENCE: 173
ttattgataa gcattagtga acccc 25

<210> SEQ ID NO 174
<211> LENGTH: 20
<212> TYPE: DNA
<213> ORGANISM: Homo sapiens

<400> SEQUENCE: 174
tggcaagtta ggcacagtca 20

<210> SEQ ID NO 175
<211> LENGTH: 21
<212> TYPE: DNA
<213> ORGANISM: Homo sapiens -continued

<400> SEQUENCE: 175
ctatgcccag agatgaacag g 21

<210> SEQ ID NO 176
<211> LENGTH: 20
<212> TYPE: DNA
<213> ORGANISM: Homo sapiens

<400> SEQUENCE: 176
tccactaagg gctatgtcgc 20

<210> SEQ ID NO 177
<211> LENGTH: 24
<212> TYPE: DNA
<213> ORGANISM: Homo sapiens

<400> SEQUENCE: 177
gccagcttta ttgagtaaac ttcc 24

<210> SEQ ID NO 178
<211> LENGTH: 22
<212> TYPE: DNA
<213> ORGANISM: Homo sapiens

<400> SEQUENCE: 178
cactggagac tacaagtggt gg 22

<210> SEQ ID NO 179
<211> LENGTH: 20
<212> TYPE: DNA
<213> ORGANISM: Homo sapiens

<400> SEQUENCE: 179
catcccaacc atcactcagt 20

<210> SEQ ID NO 180
<211> LENGTH: 22
<212> TYPE: DNA
<213> ORGANISM: Homo sapiens

<400> SEQUENCE: 180
ggggactagc ttacagattt ga 22

<210> SEQ ID NO 181
<211> LENGTH: 23
<212> TYPE: DNA
<213> ORGANISM: Homo sapiens

<400> SEQUENCE: 181
agactacatt ttggaaccag tgg 23

<210> SEQ ID NO 182
<211> LENGTH: 23
<212> TYPE: DNA
<213> ORGANISM: Homo sapiens

<400> SEQUENCE: 182
tgaaaggata tttatagcct gga 23

<210> SEQ ID NO 183
<211> LENGTH: 20
<212> TYPE: DNA
<213> ORGANISM: Homo sapiens -continued

<400> SEQUENCE: 183
gaaggttttg tccctcgatc 20

<210> SEQ ID NO 184
<211> LENGTH: 20
<212> TYPE: DNA
<213> ORGANISM: Homo sapiens

<400> SEQUENCE: 184
tgagggttgg gaagatcata 20

<210> SEQ ID NO 185
<211> LENGTH: 18
<212> TYPE: DNA
<213> ORGANISM: Homo sapiens

<400> SEQUENCE: 185
ccttcatagc cacacccg 18

<210> SEQ ID NO 186
<211> LENGTH: 21
<212> TYPE: DNA
<213> ORGANISM: Homo sapiens

<400> SEQUENCE: 186
cagctaactg ttgacatgcc a 21

<210> SEQ ID NO 187
<211> LENGTH: 25
<212> TYPE: DNA
<213> ORGANISM: Homo sapiens

<400> SEQUENCE: 187
tctttactgt gcttacaact ttcct 25

<210> SEQ ID NO 188
<211> LENGTH: 20
<212> TYPE: DNA
<213> ORGANISM: Homo sapiens

<400> SEQUENCE: 188
caacagtgca gtcggtatcg 20

<210> SEQ ID NO 189
<211> LENGTH: 18
<212> TYPE: DNA
<213> ORGANISM: Homo sapiens

<400> SEQUENCE: 189
agatcagcaa gcagatag 18

<210> SEQ ID NO 190
<211> LENGTH: 18
<212> TYPE: DNA
<213> ORGANISM: Homo sapiens

<400> SEQUENCE: 190
cattccacat ggatagac 18

<210> SEQ ID NO 191
<211> LENGTH: 24
<212> TYPE: DNA

<213> ORGANISM: Homo sapiens

<400> SEQUENCE: 191
catacctatg aggtgtgcta cagg 24

<210> SEQ ID NO 192
<211> LENGTH: 21
<212> TYPE: DNA
<213> ORGANISM: Homo sapiens

<400> SEQUENCE: 192
gcattttctc atcatccttg c 21

<210> SEQ ID NO 193
<211> LENGTH: 20
<212> TYPE: DNA
<213> ORGANISM: Homo sapiens

<400> SEQUENCE: 193
ttacagccac caaggtttcc 20

<210> SEQ ID NO 194
<211> LENGTH: 20
<212> TYPE: DNA
<213> ORGANISM: Homo sapiens

<400> SEQUENCE: 194
aggtgtgtgt gccaggttga 20

<210> SEQ ID NO 195
<211> LENGTH: 25
<212> TYPE: DNA
<213> ORGANISM: Homo sapiens

<400> SEQUENCE: 195
cactgttatc tcattaactg tgagg 25

<210> SEQ ID NO 196
<211> LENGTH: 21
<212> TYPE: DNA
<213> ORGANISM: Homo sapiens

<400> SEQUENCE: 196
tttgattttg tgtctcccaa a 21

<210> SEQ ID NO 197
<211> LENGTH: 20
<212> TYPE: DNA
<213> ORGANISM: Homo sapiens

<400> SEQUENCE: 197
ccccactccc acttttattt 20

<210> SEQ ID NO 198
<211> LENGTH: 24
<212> TYPE: DNA
<213> ORGANISM: Homo sapiens

<400> SEQUENCE: 198
ccagtcacct ttactagtcc tttg 24

<210> SEQ ID NO 199
<211> LENGTH: 20

-continued

<212> TYPE: DNA
<213> ORGANISM: Homo sapiens

<400> SEQUENCE: 199
aggacacagc ctgcatctag 20

<210> SEQ ID NO 200
<211> LENGTH: 20
<212> TYPE: DNA
<213> ORGANISM: Homo sapiens

<400> SEQUENCE: 200
accaggcatt gcactaaaag 20

<210> SEQ ID NO 201
<211> LENGTH: 22
<212> TYPE: DNA
<213> ORGANISM: Homo sapiens

<400> SEQUENCE: 201
gatgggtcac actaacctgt ca 22

<210> SEQ ID NO 202
<211> LENGTH: 24
<212> TYPE: DNA
<213> ORGANISM: Homo sapiens

<400> SEQUENCE: 202
acatttatat ttggacatgc aacc 24

<210> SEQ ID NO 203
<211> LENGTH: 22
<212> TYPE: DNA
<213> ORGANISM: Homo sapiens

<400> SEQUENCE: 203
agcatcttta atgtgtcagg ca 22

<210> SEQ ID NO 204
<211> LENGTH: 18
<212> TYPE: DNA
<213> ORGANISM: Homo sapiens

<400> SEQUENCE: 204
atgtgctggg ctggaaag 18

<210> SEQ ID NO 205
<211> LENGTH: 20
<212> TYPE: DNA
<213> ORGANISM: Homo sapiens

<400> SEQUENCE: 205
tcacattcaa aaatcggcaa 20

<210> SEQ ID NO 206
<211> LENGTH: 18
<212> TYPE: DNA
<213> ORGANISM: Homo sapiens

<400> SEQUENCE: 206
ctgcctgtgt ggtgtcgc 18

<210> SEQ ID NO 207

-continued

<211> LENGTH: 25
<212> TYPE: DNA
<213> ORGANISM: Homo sapiens

<400> SEQUENCE: 207
tgttttattt ctcagtacaa agcca 25

<210> SEQ ID NO 208
<211> LENGTH: 19
<212> TYPE: DNA
<213> ORGANISM: Homo sapiens

<400> SEQUENCE: 208
gacctcctgt gacaccacg 19

<210> SEQ ID NO 209
<211> LENGTH: 25
<212> TYPE: DNA
<213> ORGANISM: Homo sapiens

<400> SEQUENCE: 209
ccaccaaatt atttatagtt ctgcg 25

<210> SEQ ID NO 210
<211> LENGTH: 23
<212> TYPE: DNA
<213> ORGANISM: Homo sapiens

<400> SEQUENCE: 210
gtaagattct ccactgttgc acc 23

<210> SEQ ID NO 211
<211> LENGTH: 20
<212> TYPE: DNA
<213> ORGANISM: Homo sapiens

<400> SEQUENCE: 211
cctataatgg gctggaccaa 20

<210> SEQ ID NO 212
<211> LENGTH: 21
<212> TYPE: DNA
<213> ORGANISM: Homo sapiens

<400> SEQUENCE: 212
actcctcatg tgaagtcacc g 21

<210> SEQ ID NO 213
<211> LENGTH: 20
<212> TYPE: DNA
<213> ORGANISM: Homo sapiens

<400> SEQUENCE: 213
cagtgtgcac gttttcattt 20

<210> SEQ ID NO 214
<211> LENGTH: 20
<212> TYPE: DNA
<213> ORGANISM: Homo sapiens

<400> SEQUENCE: 214
cagcatcttc agcacttacc 20

-continued

<210> SEQ ID NO 215
<211> LENGTH: 25
<212> TYPE: DNA
<213> ORGANISM: Homo sapiens

<400> SEQUENCE: 215
ctgcatttat tatgagaatc aacag 25

<210> SEQ ID NO 216
<211> LENGTH: 20
<212> TYPE: DNA
<213> ORGANISM: Homo sapiens

<400> SEQUENCE: 216
tgctgctggg agtcagagtc 20

<210> SEQ ID NO 217
<211> LENGTH: 23
<212> TYPE: DNA
<213> ORGANISM: Homo sapiens

<400> SEQUENCE: 217
cagggcactg agatacactt acc 23

<210> SEQ ID NO 218
<211> LENGTH: 21
<212> TYPE: DNA
<213> ORGANISM: Homo sapiens

<400> SEQUENCE: 218
aaggatcaag ccaggcattt g 21

<210> SEQ ID NO 219
<211> LENGTH: 20
<212> TYPE: DNA
<213> ORGANISM: Homo sapiens

<400> SEQUENCE: 219
acacatctct tctgtgcccc 20

<210> SEQ ID NO 220
<211> LENGTH: 18
<212> TYPE: DNA
<213> ORGANISM: Homo sapiens

<400> SEQUENCE: 220
tgaaccctgg aggcagag 18

<210> SEQ ID NO 221
<211> LENGTH: 19
<212> TYPE: DNA
<213> ORGANISM: Homo sapiens

<400> SEQUENCE: 221
cattccccag tttgcagac 19

<210> SEQ ID NO 222
<211> LENGTH: 19
<212> TYPE: DNA
<213> ORGANISM: Homo sapiens

<400> SEQUENCE: 222
gtgctgggat tacaggtgt 19

-continued

<210> SEQ ID NO 223
<211> LENGTH: 20
<212> TYPE: DNA
<213> ORGANISM: Homo sapiens

<400> SEQUENCE: 223
gcagagaagt cctgttagcc 20

<210> SEQ ID NO 224
<211> LENGTH: 20
<212> TYPE: DNA
<213> ORGANISM: Homo sapiens

<400> SEQUENCE: 224
ccatgctaga gaagcacaac 20

<210> SEQ ID NO 225
<211> LENGTH: 20
<212> TYPE: DNA
<213> ORGANISM: Homo sapiens

<400> SEQUENCE: 225
agtgtggggc aggacctctg 20

<210> SEQ ID NO 226
<211> LENGTH: 21
<212> TYPE: DNA
<213> ORGANISM: Homo sapiens

<400> SEQUENCE: 226
cagacagata gccctgggtt c 21

<210> SEQ ID NO 227
<211> LENGTH: 20
<212> TYPE: DNA
<213> ORGANISM: Homo sapiens

<400> SEQUENCE: 227
tccctcatcc ccttgtctgt 20

<210> SEQ ID NO 228
<211> LENGTH: 19
<212> TYPE: DNA
<213> ORGANISM: Homo sapiens

<400> SEQUENCE: 228
agcccccctg gggataatc 19

<210> SEQ ID NO 229
<211> LENGTH: 19
<212> TYPE: DNA
<213> ORGANISM: Homo sapiens

<400> SEQUENCE: 229
gatgcttacc taccacggc 19

<210> SEQ ID NO 230
<211> LENGTH: 21
<212> TYPE: DNA
<213> ORGANISM: Homo sapiens

<400> SEQUENCE: 230
aggattccta tctgggctat g 21

<210> SEQ ID NO 231
<211> LENGTH: 20
<212> TYPE: DNA
<213> ORGANISM: Homo sapiens

<400> SEQUENCE: 231
tggcagacca tgctccgcct 20

<210> SEQ ID NO 232
<211> LENGTH: 20
<212> TYPE: DNA
<213> ORGANISM: Homo sapiens

<400> SEQUENCE: 232
gagaaggccg ggaggctctg 20

<210> SEQ ID NO 233
<211> LENGTH: 25
<212> TYPE: DNA
<213> ORGANISM: Homo sapiens

<400> SEQUENCE: 233
ctccatcaca accagatttg aggct 25

<210> SEQ ID NO 234
<211> LENGTH: 22
<212> TYPE: DNA
<213> ORGANISM: Homo sapiens

<400> SEQUENCE: 234
gggtgtgagc tgctgctgaa gg 22

<210> SEQ ID NO 235
<211> LENGTH: 25
<212> TYPE: DNA
<213> ORGANISM: Homo sapiens

<400> SEQUENCE: 235
agtgggaaac ctcaggtagc tcccg 25

<210> SEQ ID NO 236
<211> LENGTH: 25
<212> TYPE: DNA
<213> ORGANISM: Homo sapiens

<400> SEQUENCE: 236
cagtttggct cagacatatg ggggc 25

<210> SEQ ID NO 237
<211> LENGTH: 20
<212> TYPE: DNA
<213> ORGANISM: Homo sapiens

<400> SEQUENCE: 237
cattagtagt ggggggacag 20

<210> SEQ ID NO 238
<211> LENGTH: 21
<212> TYPE: DNA
<213> ORGANISM: Homo sapiens

<400> SEQUENCE: 238

-continued caaagcgaca gtgagttagg g 21

<210> SEQ ID NO 239
<211> LENGTH: 20
<212> TYPE: DNA
<213> ORGANISM: Homo sapiens

<400> SEQUENCE: 239
ggagtagacc atgattactg 20

<210> SEQ ID NO 240
<211> LENGTH: 19
<212> TYPE: DNA
<213> ORGANISM: Homo sapiens

<400> SEQUENCE: 240
catggtctat ttattctcg 19

<210> SEQ ID NO 241
<211> LENGTH: 22
<212> TYPE: DNA
<213> ORGANISM: Homo sapiens

<400> SEQUENCE: 241
cgccctggat cctcacacta ca 22

<210> SEQ ID NO 242
<211> LENGTH: 21
<212> TYPE: DNA
<213> ORGANISM: Homo sapiens

<400> SEQUENCE: 242
gggcatcagg ggatgggtag a 21

<210> SEQ ID NO 243
<211> LENGTH: 23
<212> TYPE: DNA
<213> ORGANISM: Homo sapiens

<400> SEQUENCE: 243
gctcctatct gtgttttgaa tgg 23

<210> SEQ ID NO 244
<211> LENGTH: 22
<212> TYPE: DNA
<213> ORGANISM: Homo sapiens

<400> SEQUENCE: 244
ccgtggcata gataagtaaa cg 22

<210> SEQ ID NO 245
<211> LENGTH: 22
<212> TYPE: DNA
<213> ORGANISM: Homo sapiens

<400> SEQUENCE: 245
cttggagcgc tatgaggagg gc 22

<210> SEQ ID NO 246
<211> LENGTH: 23
<212> TYPE: DNA
<213> ORGANISM: Homo sapiens

<400> SEQUENCE: 246

-continued atggcaactg accttccgtc ctg 23

<210> SEQ ID NO 247
<211> LENGTH: 16
<212> TYPE: DNA
<213> ORGANISM: Homo sapiens

<400> SEQUENCE: 247
ttggagtcac aggggc 16

<210> SEQ ID NO 248
<211> LENGTH: 17
<212> TYPE: DNA
<213> ORGANISM: Homo sapiens

<400> SEQUENCE: 248
cagcactatc cttgggg 17

<210> SEQ ID NO 249
<211> LENGTH: 21
<212> TYPE: DNA
<213> ORGANISM: Homo sapiens

<400> SEQUENCE: 249
aacaaagctg cttagcacct g 21

<210> SEQ ID NO 250
<211> LENGTH: 20
<212> TYPE: DNA
<213> ORGANISM: Homo sapiens

<400> SEQUENCE: 250
gatgaggacc aactggtgac 20

<210> SEQ ID NO 251
<211> LENGTH: 20
<212> TYPE: DNA
<213> ORGANISM: Homo sapiens

<400> SEQUENCE: 251
ttttccaata atgtgacttc 20

<210> SEQ ID NO 252
<211> LENGTH: 20
<212> TYPE: DNA
<213> ORGANISM: Homo sapiens

<400> SEQUENCE: 252
caatcccaac cgtaacaggc 20

<210> SEQ ID NO 253
<211> LENGTH: 19
<212> TYPE: DNA
<213> ORGANISM: Homo sapiens

<400> SEQUENCE: 253
cttgatctcg cccaggaac 19

<210> SEQ ID NO 254
<211> LENGTH: 20
<212> TYPE: DNA
<213> ORGANISM: Homo sapiens -continued

<400> SEQUENCE: 254
gctcgctgaa ggatgaagac 20

<210> SEQ ID NO 255
<211> LENGTH: 17
<212> TYPE: DNA
<213> ORGANISM: Homo sapiens

<400> SEQUENCE: 255
gaatcgcttg aacccag 17

<210> SEQ ID NO 256
<211> LENGTH: 17
<212> TYPE: DNA
<213> ORGANISM: Homo sapiens

<400> SEQUENCE: 256
ccaggtggtc ttaacgg 17

<210> SEQ ID NO 257
<211> LENGTH: 21
<212> TYPE: DNA
<213> ORGANISM: Homo sapiens
<220> FEATURE:
<221> NAME/KEY: misc_feature
<222> LOCATION: 8
<223> OTHER INFORMATION: n = A,T,C or G

<400> SEQUENCE: 257
gaacgttntt catgtaggcg t 21

<210> SEQ ID NO 258
<211> LENGTH: 16
<212> TYPE: DNA
<213> ORGANISM: Homo sapiens

<400> SEQUENCE: 258
taatggtcgc tgtccc 16

<210> SEQ ID NO 259
<211> LENGTH: 22
<212> TYPE: DNA
<213> ORGANISM: Homo sapiens

<400> SEQUENCE: 259
agggaaaatg gtatgtgggg ag 22

<210> SEQ ID NO 260
<211> LENGTH: 18
<212> TYPE: DNA
<213> ORGANISM: Homo sapiens

<400> SEQUENCE: 260
gcagtgtgtg aaggcagg 18

<210> SEQ ID NO 261
<211> LENGTH: 24
<212> TYPE: DNA
<213> ORGANISM: Homo sapiens

<400> SEQUENCE: 261
agtggacaaa atgaggaaaa cagg 24

-continued

<210> SEQ ID NO 262
<211> LENGTH: 23
<212> TYPE: DNA
<213> ORGANISM: Homo sapiens

<400> SEQUENCE: 262
ccaacacagt ttgctcacat gcc 23

<210> SEQ ID NO 263
<211> LENGTH: 20
<212> TYPE: DNA
<213> ORGANISM: Homo sapiens

<400> SEQUENCE: 263
tgacatcttt gcattatggc 20

<210> SEQ ID NO 264
<211> LENGTH: 20
<212> TYPE: DNA
<213> ORGANISM: Homo sapiens

<400> SEQUENCE: 264
agttatccca cctgataccg 20

<210> SEQ ID NO 265
<211> LENGTH: 20
<212> TYPE: DNA
<213> ORGANISM: Homo sapiens

<400> SEQUENCE: 265
agctcttgct tctcagtcca 20

<210> SEQ ID NO 266
<211> LENGTH: 24
<212> TYPE: DNA
<213> ORGANISM: Homo sapiens

<400> SEQUENCE: 266
caaaagttgt ttctgtgttt gttc 24

<210> SEQ ID NO 267
<211> LENGTH: 22
<212> TYPE: DNA
<213> ORGANISM: Homo sapiens

<400> SEQUENCE: 267
gcctctcaaa gtagttggaa cc 22

<210> SEQ ID NO 268
<211> LENGTH: 23
<212> TYPE: DNA
<213> ORGANISM: Homo sapiens

<400> SEQUENCE: 268
tgtgtatcca tagtgcaaaa cag 23

<210> SEQ ID NO 269
<211> LENGTH: 19
<212> TYPE: DNA
<213> ORGANISM: Homo sapiens

<400> SEQUENCE: 269
ctcaaggcca ggcatcact 19

-continued

<210> SEQ ID NO 270
<211> LENGTH: 19
<212> TYPE: DNA
<213> ORGANISM: Homo sapiens

<400> SEQUENCE: 270
ggactcttcc atgccagtg 19

<210> SEQ ID NO 271
<211> LENGTH: 19
<212> TYPE: DNA
<213> ORGANISM: Homo sapiens

<400> SEQUENCE: 271
aatgatgatc tcaactctg 19

<210> SEQ ID NO 272
<211> LENGTH: 19
<212> TYPE: DNA
<213> ORGANISM: Homo sapiens

<400> SEQUENCE: 272
actgaagaac tcttgtcct 19

<210> SEQ ID NO 273
<211> LENGTH: 23
<212> TYPE: DNA
<213> ORGANISM: Homo sapiens

<400> SEQUENCE: 273
gacatctgtt agtctcataa ttc 23

<210> SEQ ID NO 274
<211> LENGTH: 18
<212> TYPE: DNA
<213> ORGANISM: Homo sapiens

<400> SEQUENCE: 274
ggtaacagtg tcttgctt 18

<210> SEQ ID NO 275
<211> LENGTH: 21
<212> TYPE: DNA
<213> ORGANISM: Homo sapiens

<400> SEQUENCE: 275
ctatgtacaa aacaggaaga g 21

<210> SEQ ID NO 276
<211> LENGTH: 19
<212> TYPE: DNA
<213> ORGANISM: Homo sapiens

<400> SEQUENCE: 276
atcctagttt cctctcctt 19

<210> SEQ ID NO 277
<211> LENGTH: 23
<212> TYPE: DNA
<213> ORGANISM: Homo sapiens

<400> SEQUENCE: 277
gtaaatgaga aacagacaaa tga 23

-continued

<210> SEQ ID NO 278
<211> LENGTH: 23
<212> TYPE: DNA
<213> ORGANISM: Homo sapiens

<400> SEQUENCE: 278
ctattggatg tgatatgtta tgg 23

<210> SEQ ID NO 279
<211> LENGTH: 22
<212> TYPE: DNA
<213> ORGANISM: Homo sapiens

<400> SEQUENCE: 279
aagtagaaac aaaatgaggg ac 22

<210> SEQ ID NO 280
<211> LENGTH: 18
<212> TYPE: DNA
<213> ORGANISM: Homo sapiens

<400> SEQUENCE: 280
cctaccccaa ggtaacag 18

<210> SEQ ID NO 281
<211> LENGTH: 22
<212> TYPE: DNA
<213> ORGANISM: Homo sapiens

<400> SEQUENCE: 281
acttcctata aatggaggtg ag 22

<210> SEQ ID NO 282
<211> LENGTH: 18
<212> TYPE: DNA
<213> ORGANISM: Homo sapiens

<400> SEQUENCE: 282
gaggagcttc aagaggaa 18

<210> SEQ ID NO 283
<211> LENGTH: 23
<212> TYPE: DNA
<213> ORGANISM: Homo sapiens

<400> SEQUENCE: 283
catactccta gactcaagga atc 23

<210> SEQ ID NO 284
<211> LENGTH: 23
<212> TYPE: DNA
<213> ORGANISM: Homo sapiens

<400> SEQUENCE: 284
gaatgatgta catgaattct ttg 23

<210> SEQ ID NO 285
<211> LENGTH: 20
<212> TYPE: DNA
<213> ORGANISM: Homo sapiens

<400> SEQUENCE: 285

-continued gtgttgagga gaaaagcact 20

<210> SEQ ID NO 286
<211> LENGTH: 19
<212> TYPE: DNA
<213> ORGANISM: Homo sapiens

<400> SEQUENCE: 286
ctcccagtag tcacattcc 19

<210> SEQ ID NO 287
<211> LENGTH: 23
<212> TYPE: DNA
<213> ORGANISM: Homo sapiens

<400> SEQUENCE: 287
caagttacaa ataacttaag ccg 23

<210> SEQ ID NO 288
<211> LENGTH: 23
<212> TYPE: DNA
<213> ORGANISM: Homo sapiens

<400> SEQUENCE: 288
caagacccta tctctacaaa aac 23

<210> SEQ ID NO 289
<211> LENGTH: 24
<212> TYPE: DNA
<213> ORGANISM: Homo sapiens

<400> SEQUENCE: 289
tttattagaa gtgactcttg gccc 24

<210> SEQ ID NO 290
<211> LENGTH: 20
<212> TYPE: DNA
<213> ORGANISM: Homo sapiens

<400> SEQUENCE: 290
gactacctgc cctcagcttg 20

<210> SEQ ID NO 291
<211> LENGTH: 20
<212> TYPE: DNA
<213> ORGANISM: Homo sapiens

<400> SEQUENCE: 291
ttctcatgta caaagcggtc 20

<210> SEQ ID NO 292
<211> LENGTH: 20
<212> TYPE: DNA
<213> ORGANISM: Homo sapiens

<400> SEQUENCE: 292
ccactggctt ctctcttttt 20

<210> SEQ ID NO 293
<211> LENGTH: 18
<212> TYPE: DNA
<213> ORGANISM: Homo sapiens

<400> SEQUENCE: 293

-continued caccagaagg ttggggtg 18

<210> SEQ ID NO 294
<211> LENGTH: 21
<212> TYPE: DNA
<213> ORGANISM: Homo sapiens

<400> SEQUENCE: 294
actattacga catgaacgcg g 21

<210> SEQ ID NO 295
<211> LENGTH: 18
<212> TYPE: DNA
<213> ORGANISM: Homo sapiens

<400> SEQUENCE: 295
ctcatgctgg atgacccc 18

<210> SEQ ID NO 296
<211> LENGTH: 24
<212> TYPE: DNA
<213> ORGANISM: Homo sapiens

<400> SEQUENCE: 296
ttgcctttct tgaaacttaa ttcc 24

<210> SEQ ID NO 297
<211> LENGTH: 19
<212> TYPE: DNA
<213> ORGANISM: Homo sapiens

<400> SEQUENCE: 297
tcacagcctt cagtcaggg 19

<210> SEQ ID NO 298
<211> LENGTH: 18
<212> TYPE: DNA
<213> ORGANISM: Homo sapiens

<400> SEQUENCE: 298
acatgctgtg gcaccatg 18

<210> SEQ ID NO 299
<211> LENGTH: 18
<212> TYPE: DNA
<213> ORGANISM: Homo sapiens

<400> SEQUENCE: 299
cctgagctac tgccacag 18

<210> SEQ ID NO 300
<211> LENGTH: 20
<212> TYPE: DNA
<213> ORGANISM: Homo sapiens

<400> SEQUENCE: 300
ccctgacttg gacagtgtcc 20

<210> SEQ ID NO 301
<211> LENGTH: 18
<212> TYPE: DNA
<213> ORGANISM: Homo sapiens

<400> SEQUENCE: 301
tcagagtcac tcctgccc 18

<210> SEQ ID NO 302
<211> LENGTH: 22
<212> TYPE: DNA
<213> ORGANISM: Homo sapiens

<400> SEQUENCE: 302
caaattcaag ctcatccaga cc 22

<210> SEQ ID NO 303
<211> LENGTH: 18
<212> TYPE: DNA
<213> ORGANISM: Homo sapiens

<400> SEQUENCE: 303
cggcatttca tccaggac 18

<210> SEQ ID NO 304
<211> LENGTH: 20
<212> TYPE: DNA
<213> ORGANISM: Homo sapiens

<400> SEQUENCE: 304
ggtgtaggag gtgcgacaat 20

<210> SEQ ID NO 305
<211> LENGTH: 20
<212> TYPE: DNA
<213> ORGANISM: Homo sapiens

<400> SEQUENCE: 305
ttccatttat tgagcacctg 20

<210> SEQ ID NO 306
<211> LENGTH: 20
<212> TYPE: DNA
<213> ORGANISM: Homo sapiens

<400> SEQUENCE: 306
cttaagccac tgtgttttgg 20

<210> SEQ ID NO 307
<211> LENGTH: 20
<212> TYPE: DNA
<213> ORGANISM: Homo sapiens

<400> SEQUENCE: 307
cctcctacac ctgcaaaagc 20

<210> SEQ ID NO 308
<211> LENGTH: 19
<212> TYPE: DNA
<213> ORGANISM: Homo sapiens

<400> SEQUENCE: 308
tggaagaacc ccagaggac 19

<210> SEQ ID NO 309
<211> LENGTH: 23
<212> TYPE: DNA
<213> ORGANISM: Homo sapiens -continued

<400> SEQUENCE: 309
aaagcacaaa agtaacagca aca 23

<210> SEQ ID NO 310
<211> LENGTH: 20
<212> TYPE: DNA
<213> ORGANISM: Homo sapiens

<400> SEQUENCE: 310
gtgtgtgggc cacaatattg 20

<210> SEQ ID NO 311
<211> LENGTH: 20
<212> TYPE: DNA
<213> ORGANISM: Homo sapiens

<400> SEQUENCE: 311
agagcacctt tcctcagcac 20

<210> SEQ ID NO 312
<211> LENGTH: 20
<212> TYPE: DNA
<213> ORGANISM: Homo sapiens

<400> SEQUENCE: 312
agaatctcat cacaggggcg 20

<210> SEQ ID NO 313
<211> LENGTH: 25
<212> TYPE: DNA
<213> ORGANISM: Homo sapiens

<400> SEQUENCE: 313
aaaaaggaca gtgtctaaaa tttga 25

<210> SEQ ID NO 314
<211> LENGTH: 25
<212> TYPE: DNA
<213> ORGANISM: Homo sapiens

<400> SEQUENCE: 314
aattgttttt gtttgttttt tgagt 25

<210> SEQ ID NO 315
<211> LENGTH: 22
<212> TYPE: DNA
<213> ORGANISM: Homo sapiens

<400> SEQUENCE: 315
gatttaggga gtacaagtgc gg 22

<210> SEQ ID NO 316
<211> LENGTH: 25
<212> TYPE: DNA
<213> ORGANISM: Homo sapiens

<400> SEQUENCE: 316
ggggacaaat tatactttat tcagg 25

<210> SEQ ID NO 317
<211> LENGTH: 22
<212> TYPE: DNA

-continued

<213> ORGANISM: Homo sapiens

<400> SEQUENCE: 317
ccatcatcat attggtgtga cc 22

<210> SEQ ID NO 318
<211> LENGTH: 18
<212> TYPE: DNA
<213> ORGANISM: Homo sapiens

<400> SEQUENCE: 318
tggctgccca agaagaag 18

<210> SEQ ID NO 319
<211> LENGTH: 24
<212> TYPE: DNA
<213> ORGANISM: Homo sapiens

<400> SEQUENCE: 319
ttaagatgcc attaaactca tgac 24

<210> SEQ ID NO 320
<211> LENGTH: 20
<212> TYPE: DNA
<213> ORGANISM: Homo sapiens

<400> SEQUENCE: 320
ccaaggagat gaccaagtgg 20

<210> SEQ ID NO 321
<211> LENGTH: 22
<212> TYPE: DNA
<213> ORGANISM: Homo sapiens

<400> SEQUENCE: 321
ccatctcttt tatcagggtt gg 22

<210> SEQ ID NO 322
<211> LENGTH: 24
<212> TYPE: DNA
<213> ORGANISM: Homo sapiens

<400> SEQUENCE: 322
ctctgtgcaa gtaagcatct taca 24

<210> SEQ ID NO 323
<211> LENGTH: 20
<212> TYPE: DNA
<213> ORGANISM: Homo sapiens

<400> SEQUENCE: 323
cgactgtgta ttttccacag 20

<210> SEQ ID NO 324
<211> LENGTH: 20
<212> TYPE: DNA
<213> ORGANISM: Homo sapiens

<400> SEQUENCE: 324
agaagcccat atcaatgcac 20

<210> SEQ ID NO 325
<211> LENGTH: 23

<212> TYPE: DNA
<213> ORGANISM: Homo sapiens

<400> SEQUENCE: 325
agcttaaagt aggacaacca tgg 23

<210> SEQ ID NO 326
<211> LENGTH: 20
<212> TYPE: DNA
<213> ORGANISM: Homo sapiens

<400> SEQUENCE: 326
ggatgcttca ctccagaaag 20

<210> SEQ ID NO 327
<211> LENGTH: 21
<212> TYPE: DNA
<213> ORGANISM: Homo sapiens

<400> SEQUENCE: 327
tgttgtttat ttccacctgc c 21

<210> SEQ ID NO 328
<211> LENGTH: 18
<212> TYPE: DNA
<213> ORGANISM: Homo sapiens

<400> SEQUENCE: 328
agagtggctg caggccag 18

<210> SEQ ID NO 329
<211> LENGTH: 25
<212> TYPE: DNA
<213> ORGANISM: Homo sapiens

<400> SEQUENCE: 329
tttttttttt tacacgaatt tgagg 25

<210> SEQ ID NO 330
<211> LENGTH: 23
<212> TYPE: DNA
<213> ORGANISM: Homo sapiens

<400> SEQUENCE: 330
tgaggaagta aaaacaggtc atc 23

<210> SEQ ID NO 331
<211> LENGTH: 23
<212> TYPE: DNA
<213> ORGANISM: Homo sapiens

<400> SEQUENCE: 331
atgaaatctt aagcagaatc cca 23

<210> SEQ ID NO 332
<211> LENGTH: 20
<212> TYPE: DNA
<213> ORGANISM: Homo sapiens

<400> SEQUENCE: 332
cacagagtcc cagggtctgt 20

<210> SEQ ID NO 333

-continued

<211> LENGTH: 25
<212> TYPE: DNA
<213> ORGANISM: Homo sapiens

<400> SEQUENCE: 333
aaaggccttt atttatctct ctctg 25

<210> SEQ ID NO 334
<211> LENGTH: 18
<212> TYPE: DNA
<213> ORGANISM: Homo sapiens

<400> SEQUENCE: 334
gcctcagagc tggtgggt 18

<210> SEQ ID NO 335
<211> LENGTH: 25
<212> TYPE: DNA
<213> ORGANISM: Homo sapiens

<400> SEQUENCE: 335
gcttctaagt cttagagtca gctgg 25

<210> SEQ ID NO 336
<211> LENGTH: 19
<212> TYPE: DNA
<213> ORGANISM: Homo sapiens

<400> SEQUENCE: 336
agcccacagt cagcctacc 19

<210> SEQ ID NO 337
<211> LENGTH: 20
<212> TYPE: DNA
<213> ORGANISM: Homo sapiens

<400> SEQUENCE: 337
ttggttaaat gatgcccaga 20

<210> SEQ ID NO 338
<211> LENGTH: 18
<212> TYPE: DNA
<213> ORGANISM: Homo sapiens

<400> SEQUENCE: 338
tggtcccact cacatccc 18

<210> SEQ ID NO 339
<211> LENGTH: 19
<212> TYPE: DNA
<213> ORGANISM: Homo sapiens

<400> SEQUENCE: 339
acacagcatg cagggagag 19

<210> SEQ ID NO 340
<211> LENGTH: 19
<212> TYPE: DNA
<213> ORGANISM: Homo sapiens

<400> SEQUENCE: 340
atccctggtg cttaggtgg 19

-continued

<210> SEQ ID NO 341
<211> LENGTH: 21
<212> TYPE: DNA
<213> ORGANISM: Homo sapiens

<400> SEQUENCE: 341
gatggaagta gctcctctcg g 21

<210> SEQ ID NO 342
<211> LENGTH: 21
<212> TYPE: DNA
<213> ORGANISM: Homo sapiens

<400> SEQUENCE: 342
ggaaggccag caagtactac c 21

<210> SEQ ID NO 343
<211> LENGTH: 18
<212> TYPE: DNA
<213> ORGANISM: Homo sapiens

<400> SEQUENCE: 343
ccggtgcttg gaaagatg 18

<210> SEQ ID NO 344
<211> LENGTH: 20
<212> TYPE: DNA
<213> ORGANISM: Homo sapiens

<400> SEQUENCE: 344
gaagtgtctc tgttggggga 20

<210> SEQ ID NO 345
<211> LENGTH: 22
<212> TYPE: DNA
<213> ORGANISM: Homo sapiens

<400> SEQUENCE: 345
ttacaggcat gagtcactac gc 22

<210> SEQ ID NO 346
<211> LENGTH: 21
<212> TYPE: DNA
<213> ORGANISM: Homo sapiens

<400> SEQUENCE: 346
accactctca cagcccttac a 21

<210> SEQ ID NO 347
<211> LENGTH: 18
<212> TYPE: DNA
<213> ORGANISM: Homo sapiens

<400> SEQUENCE: 347
ccctccctcc acacacac 18

<210> SEQ ID NO 348
<211> LENGTH: 20
<212> TYPE: DNA
<213> ORGANISM: Homo sapiens

<400> SEQUENCE: 348
gctcactgaa ctttcagggc 20

-continued

<210> SEQ ID NO 349
<211> LENGTH: 20
<212> TYPE: DNA
<213> ORGANISM: Homo sapiens

<400> SEQUENCE: 349
agatacgggc aaaacactgg 20

<210> SEQ ID NO 350
<211> LENGTH: 21
<212> TYPE: DNA
<213> ORGANISM: Homo sapiens

<400> SEQUENCE: 350
gttgaatata gagcagggcc c 21

<210> SEQ ID NO 351
<211> LENGTH: 20
<212> TYPE: DNA
<213> ORGANISM: Homo sapiens

<400> SEQUENCE: 351
ttctgaggtc agggctgtct 20

<210> SEQ ID NO 352
<211> LENGTH: 21
<212> TYPE: DNA
<213> ORGANISM: Homo sapiens

<400> SEQUENCE: 352
agcttggaaa atctcgtgtc a 21

<210> SEQ ID NO 353
<211> LENGTH: 18
<212> TYPE: DNA
<213> ORGANISM: Homo sapiens

<400> SEQUENCE: 353
actcagtccc tcccaccc 18

<210> SEQ ID NO 354
<211> LENGTH: 20
<212> TYPE: DNA
<213> ORGANISM: Homo sapiens

<400> SEQUENCE: 354
tcctctcact ccttcccaga 20

<210> SEQ ID NO 355
<211> LENGTH: 19
<212> TYPE: DNA
<213> ORGANISM: Homo sapiens

<400> SEQUENCE: 355
gtgatcacgg ctcaacctg 19

<210> SEQ ID NO 356
<211> LENGTH: 18
<212> TYPE: DNA
<213> ORGANISM: Homo sapiens

<400> SEQUENCE: 356
tggaggactg cttgagcc 18

-continued

<210> SEQ ID NO 357
<211> LENGTH: 19
<212> TYPE: DNA
<213> ORGANISM: Homo sapiens

<400> SEQUENCE: 357
ctgcagctgc ctcagtttc 19

<210> SEQ ID NO 358
<211> LENGTH: 20
<212> TYPE: DNA
<213> ORGANISM: Homo sapiens

<400> SEQUENCE: 358
tcaaaagtgc tggtgacagc 20

<210> SEQ ID NO 359
<211> LENGTH: 20
<212> TYPE: DNA
<213> ORGANISM: Homo sapiens

<400> SEQUENCE: 359
atttccagag ccagctcaaa 20

<210> SEQ ID NO 360
<211> LENGTH: 25
<212> TYPE: DNA
<213> ORGANISM: Homo sapiens

<400> SEQUENCE: 360
ctttaatgtt gtgatgacac aaagc 25

<210> SEQ ID NO 361
<211> LENGTH: 20
<212> TYPE: DNA
<213> ORGANISM: Homo sapiens

<400> SEQUENCE: 361
gatcatgcac tgttgaccac 20

<210> SEQ ID NO 362
<211> LENGTH: 25
<212> TYPE: DNA
<213> ORGANISM: Homo sapiens

<400> SEQUENCE: 362
tacatttgaa acatttaaaa cctga 25

<210> SEQ ID NO 363
<211> LENGTH: 24
<212> TYPE: DNA
<213> ORGANISM: Homo sapiens

<400> SEQUENCE: 363
aactgagctg taaccagact ggga 24

<210> SEQ ID NO 364
<211> LENGTH: 22
<212> TYPE: DNA
<213> ORGANISM: Homo sapiens

<400> SEQUENCE: 364

-continued tggaacagtc tggtcctgat gg 22

<210> SEQ ID NO 365
<211> LENGTH: 25
<212> TYPE: DNA
<213> ORGANISM: Homo sapiens

<400> SEQUENCE: 365
ttatcccttt attgtttctc ctttg 25

<210> SEQ ID NO 366
<211> LENGTH: 24
<212> TYPE: DNA
<213> ORGANISM: Homo sapiens

<400> SEQUENCE: 366
tggtcacctg tatttattgc tagg 24

<210> SEQ ID NO 367
<211> LENGTH: 22
<212> TYPE: DNA
<213> ORGANISM: Homo sapiens

<400> SEQUENCE: 367
tcttcaaagc ctctgcagta cc 22

<210> SEQ ID NO 368
<211> LENGTH: 22
<212> TYPE: DNA
<213> ORGANISM: Homo sapiens

<400> SEQUENCE: 368
ctcatctcca acctgtctaa cc 22

<210> SEQ ID NO 369
<211> LENGTH: 24
<212> TYPE: DNA
<213> ORGANISM: Homo sapiens

<400> SEQUENCE: 369
gtggctgcag ctaatgtaag acac 24

<210> SEQ ID NO 370
<211> LENGTH: 24
<212> TYPE: DNA
<213> ORGANISM: Homo sapiens

<400> SEQUENCE: 370
cagcagagac aatggcgtaa gtcc 24

<210> SEQ ID NO 371
<211> LENGTH: 20
<212> TYPE: DNA
<213> ORGANISM: Homo sapiens

<400> SEQUENCE: 371
ctgattgaga accagaacag 20

<210> SEQ ID NO 372
<211> LENGTH: 20
<212> TYPE: DNA
<213> ORGANISM: Homo sapiens

<400> SEQUENCE: 372

-continued taaagcccta taacctctcc 20

<210> SEQ ID NO 373
<211> LENGTH: 20
<212> TYPE: DNA
<213> ORGANISM: Homo sapiens

<400> SEQUENCE: 373
tagtaaggga ccttcaccag 20

<210> SEQ ID NO 374
<211> LENGTH: 20
<212> TYPE: DNA
<213> ORGANISM: Homo sapiens

<400> SEQUENCE: 374
agatgtttgg tatgacttgg 20

<210> SEQ ID NO 375
<211> LENGTH: 20
<212> TYPE: DNA
<213> ORGANISM: Homo sapiens

<400> SEQUENCE: 375
gatgattaaa ctctcctggc 20

<210> SEQ ID NO 376
<211> LENGTH: 20
<212> TYPE: DNA
<213> ORGANISM: Homo sapiens

<400> SEQUENCE: 376
gagacagcta agcactcatg 20

<210> SEQ ID NO 377
<211> LENGTH: 19
<212> TYPE: DNA
<213> ORGANISM: Homo sapiens

<400> SEQUENCE: 377
gaggtggtgg gcacctgta 19

<210> SEQ ID NO 378
<211> LENGTH: 20
<212> TYPE: DNA
<213> ORGANISM: Homo sapiens

<400> SEQUENCE: 378
agaggggagg aacacacctt 20

<210> SEQ ID NO 379
<211> LENGTH: 20
<212> TYPE: DNA
<213> ORGANISM: Homo sapiens

<400> SEQUENCE: 379
gaccagagtc tgcccagaag 20

<210> SEQ ID NO 380
<211> LENGTH: 19
<212> TYPE: DNA
<213> ORGANISM: Homo sapiens -continued

<400> SEQUENCE: 380
tccccagctc tatcccaac 19

<210> SEQ ID NO 381
<211> LENGTH: 20
<212> TYPE: DNA
<213> ORGANISM: Homo sapiens

<400> SEQUENCE: 381
ggagggatgg acaagtctga 20

<210> SEQ ID NO 382
<211> LENGTH: 20
<212> TYPE: DNA
<213> ORGANISM: Homo sapiens

<400> SEQUENCE: 382
gtccagctcg ctgactatcc 20

<210> SEQ ID NO 383
<211> LENGTH: 20
<212> TYPE: DNA
<213> ORGANISM: Homo sapiens

<400> SEQUENCE: 383
tcaaaacaca gtcatctcca 20

<210> SEQ ID NO 384
<211> LENGTH: 20
<212> TYPE: DNA
<213> ORGANISM: Homo sapiens

<400> SEQUENCE: 384
gcaaaggctt taccatattg 20

<210> SEQ ID NO 385
<211> LENGTH: 16
<212> TYPE: DNA
<213> ORGANISM: Homo sapiens

<400> SEQUENCE: 385
gctcagcacc cccatt 16

<210> SEQ ID NO 386
<211> LENGTH: 16
<212> TYPE: DNA
<213> ORGANISM: Homo sapiens

<400> SEQUENCE: 386
tccctgctcg ggaaac 16

<210> SEQ ID NO 387
<211> LENGTH: 20
<212> TYPE: DNA
<213> ORGANISM: Homo sapiens

<400> SEQUENCE: 387
gttctccaga gagacagcac 20

<210> SEQ ID NO 388
<211> LENGTH: 19
<212> TYPE: DNA
<213> ORGANISM: Homo sapiens

<400> SEQUENCE: 388
gagagcaaca ctattgccc 19

<210> SEQ ID NO 389
<211> LENGTH: 21
<212> TYPE: DNA
<213> ORGANISM: Homo sapiens

<400> SEQUENCE: 389
tatagacttc agccctgctg c 21

<210> SEQ ID NO 390
<211> LENGTH: 20
<212> TYPE: DNA
<213> ORGANISM: Homo sapiens

<400> SEQUENCE: 390
cctctgtagg atgcagttgg 20

<210> SEQ ID NO 391
<211> LENGTH: 20
<212> TYPE: DNA
<213> ORGANISM: Homo sapiens

<400> SEQUENCE: 391
ttgctacgca ctcctctact 20

<210> SEQ ID NO 392
<211> LENGTH: 20
<212> TYPE: DNA
<213> ORGANISM: Homo sapiens

<400> SEQUENCE: 392
gtgaaggcag gaaatgtgac 20

<210> SEQ ID NO 393
<211> LENGTH: 20
<212> TYPE: DNA
<213> ORGANISM: Homo sapiens

<400> SEQUENCE: 393
atcctagacc agaggagccc 20

<210> SEQ ID NO 394
<211> LENGTH: 20
<212> TYPE: DNA
<213> ORGANISM: Homo sapiens

<400> SEQUENCE: 394
ctccccctgg tccagttatt 20

<210> SEQ ID NO 395
<211> LENGTH: 20
<212> TYPE: DNA
<213> ORGANISM: Homo sapiens

<400> SEQUENCE: 395
aactttcatt tgccaaggga 20

<210> SEQ ID NO 396
<211> LENGTH: 20
<212> TYPE: DNA

<213> ORGANISM: Homo sapiens

<400> SEQUENCE: 396
agcagatctg ctcttgcgat 20

<210> SEQ ID NO 397
<211> LENGTH: 20
<212> TYPE: DNA
<213> ORGANISM: Homo sapiens

<400> SEQUENCE: 397
acagttgtca tcggtaggca 20

<210> SEQ ID NO 398
<211> LENGTH: 22
<212> TYPE: DNA
<213> ORGANISM: Homo sapiens

<400> SEQUENCE: 398
aaaagtatga atgggatgga gc 22

<210> SEQ ID NO 399
<211> LENGTH: 20
<212> TYPE: DNA
<213> ORGANISM: Homo sapiens

<400> SEQUENCE: 399
gtgcaggtgg cgtttatttt 20

<210> SEQ ID NO 400
<211> LENGTH: 21
<212> TYPE: DNA
<213> ORGANISM: Homo sapiens

<400> SEQUENCE: 400
ccctatatct ccgtgtgctc c 21

<210> SEQ ID NO 401
<211> LENGTH: 21
<212> TYPE: DNA
<213> ORGANISM: Homo sapiens

<400> SEQUENCE: 401
gctctagtgg gaaacctcag g 21

<210> SEQ ID NO 402
<211> LENGTH: 20
<212> TYPE: DNA
<213> ORGANISM: Homo sapiens

<400> SEQUENCE: 402
gaattccagg ctcttgcttg 20

<210> SEQ ID NO 403
<211> LENGTH: 20
<212> TYPE: DNA
<213> ORGANISM: Homo sapiens

<400> SEQUENCE: 403
ggtttggtct caaaggcaaa 20

<210> SEQ ID NO 404
<211> LENGTH: 20

-continued

<212> TYPE: DNA
<213> ORGANISM: Homo sapiens

<400> SEQUENCE: 404
ccagtacatg gtggtcacca 20

<210> SEQ ID NO 405
<211> LENGTH: 20
<212> TYPE: DNA
<213> ORGANISM: Homo sapiens

<400> SEQUENCE: 405
gctgccttgg aatttctgtt 20

<210> SEQ ID NO 406
<211> LENGTH: 18
<212> TYPE: DNA
<213> ORGANISM: Homo sapiens

<400> SEQUENCE: 406
gtgctgtggt ggggaaag 18

<210> SEQ ID NO 407
<211> LENGTH: 20
<212> TYPE: DNA
<213> ORGANISM: Homo sapiens

<400> SEQUENCE: 407
attcaagctc atccagaccc 20

<210> SEQ ID NO 408
<211> LENGTH: 20
<212> TYPE: DNA
<213> ORGANISM: Homo sapiens

<400> SEQUENCE: 408
ggactggccc tttgaaactc 20

<210> SEQ ID NO 409
<211> LENGTH: 22
<212> TYPE: DNA
<213> ORGANISM: Homo sapiens

<400> SEQUENCE: 409
atattgaccg tgcacaaata cg 22

<210> SEQ ID NO 410
<211> LENGTH: 21
<212> TYPE: DNA
<213> ORGANISM: Homo sapiens

<400> SEQUENCE: 410
agacctggga aaagtggaga a 21

<210> SEQ ID NO 411
<211> LENGTH: 20
<212> TYPE: DNA
<213> ORGANISM: Homo sapiens

<400> SEQUENCE: 411
attggcagtg gaaaatgctt 20

<210> SEQ ID NO 412

-continued

<211> LENGTH: 25
<212> TYPE: DNA
<213> ORGANISM: Homo sapiens

<400> SEQUENCE: 412
ttaatctttt gtcaacttcc tgatt 25

<210> SEQ ID NO 413
<211> LENGTH: 23
<212> TYPE: DNA
<213> ORGANISM: Homo sapiens

<400> SEQUENCE: 413
tctgtcctcc tttcaccgga agc 23

<210> SEQ ID NO 414
<211> LENGTH: 29
<212> TYPE: DNA
<213> ORGANISM: Homo sapiens

<400> SEQUENCE: 414
ggataaagaa actccgctct gctggtaga 29

<210> SEQ ID NO 415
<211> LENGTH: 25
<212> TYPE: DNA
<213> ORGANISM: Homo sapiens

<400> SEQUENCE: 415
tcagggcctg tgttgccgca ctctg 25

<210> SEQ ID NO 416
<211> LENGTH: 25
<212> TYPE: DNA
<213> ORGANISM: Homo sapiens

<400> SEQUENCE: 416
agcgatgtaa agggtaccag tgccg 25

<210> SEQ ID NO 417
<211> LENGTH: 18
<212> TYPE: DNA
<213> ORGANISM: Homo sapiens

<400> SEQUENCE: 417
aggcatgcaa gcttctta 18

<210> SEQ ID NO 418
<211> LENGTH: 18
<212> TYPE: DNA
<213> ORGANISM: Homo sapiens

<400> SEQUENCE: 418
ccgggaggag acatctat 18

<210> SEQ ID NO 419
<211> LENGTH: 19
<212> TYPE: DNA
<213> ORGANISM: Homo sapiens

<400> SEQUENCE: 419
tggtaagcac agaaaatgc 19

-continued

<210> SEQ ID NO 420
<211> LENGTH: 18
<212> TYPE: DNA
<213> ORGANISM: Homo sapiens

<400> SEQUENCE: 420
aatggatggg ggattatt 18

<210> SEQ ID NO 421
<211> LENGTH: 18
<212> TYPE: DNA
<213> ORGANISM: Homo sapiens

<400> SEQUENCE: 421
ctggacgtta tgtctgcc 18

<210> SEQ ID NO 422
<211> LENGTH: 18
<212> TYPE: DNA
<213> ORGANISM: Homo sapiens

<400> SEQUENCE: 422
agaggcccag tcacagat 18

<210> SEQ ID NO 423
<211> LENGTH: 19
<212> TYPE: DNA
<213> ORGANISM: Homo sapiens

<400> SEQUENCE: 423
atcactctga actgccact 19

<210> SEQ ID NO 424
<211> LENGTH: 20
<212> TYPE: DNA
<213> ORGANISM: Homo sapiens

<400> SEQUENCE: 424
cccttctgtt tttctgtttt 20

<210> SEQ ID NO 425
<211> LENGTH: 18
<212> TYPE: DNA
<213> ORGANISM: Homo sapiens

<400> SEQUENCE: 425
caagctttga aggaagag 18

<210> SEQ ID NO 426
<211> LENGTH: 19
<212> TYPE: DNA
<213> ORGANISM: Homo sapiens

<400> SEQUENCE: 426
taggacgtta agtgaggac 19

<210> SEQ ID NO 427
<211> LENGTH: 18
<212> TYPE: DNA
<213> ORGANISM: Homo sapiens

<400> SEQUENCE: 427
gctctgcagt gggtaaaa 18

-continued

<210> SEQ ID NO 428
<211> LENGTH: 18
<212> TYPE: DNA
<213> ORGANISM: Homo sapiens

<400> SEQUENCE: 428
actctccaag actgtgcg 18

<210> SEQ ID NO 429
<211> LENGTH: 18
<212> TYPE: DNA
<213> ORGANISM: Homo sapiens

<400> SEQUENCE: 429
ccctttctga ggcaagat 18

<210> SEQ ID NO 430
<211> LENGTH: 18
<212> TYPE: DNA
<213> ORGANISM: Homo sapiens

<400> SEQUENCE: 430
gaccacctgg gagagaac 18

<210> SEQ ID NO 431
<211> LENGTH: 18
<212> TYPE: DNA
<213> ORGANISM: Homo sapiens

<400> SEQUENCE: 431
cgctatgagt cccatctg 18

<210> SEQ ID NO 432
<211> LENGTH: 18
<212> TYPE: DNA
<213> ORGANISM: Homo sapiens

<400> SEQUENCE: 432
gatcagctgc aatgaagg 18

<210> SEQ ID NO 433
<211> LENGTH: 18
<212> TYPE: DNA
<213> ORGANISM: Homo sapiens

<400> SEQUENCE: 433
ttgagtacac ggggtgac 18

<210> SEQ ID NO 434
<211> LENGTH: 18
<212> TYPE: DNA
<213> ORGANISM: Homo sapiens

<400> SEQUENCE: 434
cgcaggactg aaagatga 18

<210> SEQ ID NO 435
<211> LENGTH: 18
<212> TYPE: DNA
<213> ORGANISM: Homo sapiens

<400> SEQUENCE: 435
acctgtctcc tctcctgg 18

<210> SEQ ID NO 436
<211> LENGTH: 18
<212> TYPE: DNA
<213> ORGANISM: Homo sapiens

<400> SEQUENCE: 436
tgcttttctt ctgtggga 18

<210> SEQ ID NO 437
<211> LENGTH: 18
<212> TYPE: DNA
<213> ORGANISM: Homo sapiens

<400> SEQUENCE: 437
atgaccagca agcattgt 18

<210> SEQ ID NO 438
<211> LENGTH: 18
<212> TYPE: DNA
<213> ORGANISM: Homo sapiens

<400> SEQUENCE: 438
gtactgggat tacaggcg 18

<210> SEQ ID NO 439
<211> LENGTH: 18
<212> TYPE: DNA
<213> ORGANISM: Homo sapiens

<400> SEQUENCE: 439
gcagaaggtc ctttggat 18

<210> SEQ ID NO 440
<211> LENGTH: 18
<212> TYPE: DNA
<213> ORGANISM: Homo sapiens

<400> SEQUENCE: 440
tttgcaggat tcatgctt 18

<210> SEQ ID NO 441
<211> LENGTH: 19
<212> TYPE: DNA
<213> ORGANISM: Homo sapiens

<400> SEQUENCE: 441
cgacattctt ttctggagg 19

<210> SEQ ID NO 442
<211> LENGTH: 19
<212> TYPE: DNA
<213> ORGANISM: Homo sapiens

<400> SEQUENCE: 442
acctttgcat gttggtttt 19

<210> SEQ ID NO 443
<211> LENGTH: 18
<212> TYPE: DNA
<213> ORGANISM: Homo sapiens

<400> SEQUENCE: 443

-continued gcacttttcc ttccttcc 18

<210> SEQ ID NO 444
<211> LENGTH: 18
<212> TYPE: DNA
<213> ORGANISM: Homo sapiens

<400> SEQUENCE: 444
tgctttgctt tcttctgg 18

<210> SEQ ID NO 445
<211> LENGTH: 19
<212> TYPE: DNA
<213> ORGANISM: Homo sapiens

<400> SEQUENCE: 445
acagctccag agagaagga 19

<210> SEQ ID NO 446
<211> LENGTH: 19
<212> TYPE: DNA
<213> ORGANISM: Homo sapiens

<400> SEQUENCE: 446
gcagtcactt gaaaccaga 19

<210> SEQ ID NO 447
<211> LENGTH: 18
<212> TYPE: DNA
<213> ORGANISM: Homo sapiens

<400> SEQUENCE: 447
aggcatcaag ctttcctt 18

<210> SEQ ID NO 448
<211> LENGTH: 18
<212> TYPE: DNA
<213> ORGANISM: Homo sapiens

<400> SEQUENCE: 448
ggtttagaga accgagcc 18

<210> SEQ ID NO 449
<211> LENGTH: 18
<212> TYPE: DNA
<213> ORGANISM: Homo sapiens

<400> SEQUENCE: 449
gtggtgctgc aagttacc 18

<210> SEQ ID NO 450
<211> LENGTH: 18
<212> TYPE: DNA
<213> ORGANISM: Homo sapiens

<400> SEQUENCE: 450
ggaatccctt tctttcca 18

<210> SEQ ID NO 451
<211> LENGTH: 18
<212> TYPE: DNA
<213> ORGANISM: Homo sapiens

<400> SEQUENCE: 451

-continued gaccatttgt tacgcagc 18

<210> SEQ ID NO 452
<211> LENGTH: 19
<212> TYPE: DNA
<213> ORGANISM: Homo sapiens

<400> SEQUENCE: 452
gatgggtgtg aatgaacaa 19

<210> SEQ ID NO 453
<211> LENGTH: 19
<212> TYPE: DNA
<213> ORGANISM: Homo sapiens

<400> SEQUENCE: 453
ctcaagcttc tgttcatgc 19

<210> SEQ ID NO 454
<211> LENGTH: 18
<212> TYPE: DNA
<213> ORGANISM: Homo sapiens

<400> SEQUENCE: 454
gctgtgagtg tcttggct 18

<210> SEQ ID NO 455
<211> LENGTH: 18
<212> TYPE: DNA
<213> ORGANISM: Homo sapiens

<400> SEQUENCE: 455
tacagaaaac cgcagctc 18

<210> SEQ ID NO 456
<211> LENGTH: 18
<212> TYPE: DNA
<213> ORGANISM: Homo sapiens

<400> SEQUENCE: 456
gccaccaaag gaaagatt 18

<210> SEQ ID NO 457
<211> LENGTH: 18
<212> TYPE: DNA
<213> ORGANISM: Homo sapiens

<400> SEQUENCE: 457
aaaaggaggg aatcatgg 18

<210> SEQ ID NO 458
<211> LENGTH: 18
<212> TYPE: DNA
<213> ORGANISM: Homo sapiens

<400> SEQUENCE: 458
tcacttagca ggaggcag 18

<210> SEQ ID NO 459
<211> LENGTH: 18
<212> TYPE: DNA
<213> ORGANISM: Homo sapiens -continued

<400> SEQUENCE: 459
ctgagcatcc gatgagac 18

<210> SEQ ID NO 460
<211> LENGTH: 18
<212> TYPE: DNA
<213> ORGANISM: Homo sapiens

<400> SEQUENCE: 460
gtgcaaaatg agcagctt 18

<210> SEQ ID NO 461
<211> LENGTH: 18
<212> TYPE: DNA
<213> ORGANISM: Homo sapiens

<400> SEQUENCE: 461
tctaacccct tactgggc 18

<210> SEQ ID NO 462
<211> LENGTH: 18
<212> TYPE: DNA
<213> ORGANISM: Homo sapiens

<400> SEQUENCE: 462
tcctcaaact gggaatga 18

<210> SEQ ID NO 463
<211> LENGTH: 18
<212> TYPE: DNA
<213> ORGANISM: Homo sapiens

<400> SEQUENCE: 463
tttacacagg accaggga 18

<210> SEQ ID NO 464
<211> LENGTH: 18
<212> TYPE: DNA
<213> ORGANISM: Homo sapiens

<400> SEQUENCE: 464
atctccccca ctcagaag 18

<210> SEQ ID NO 465
<211> LENGTH: 18
<212> TYPE: DNA
<213> ORGANISM: Homo sapiens

<400> SEQUENCE: 465
gtccacgggc tttattct 18

<210> SEQ ID NO 466
<211> LENGTH: 22
<212> TYPE: DNA
<213> ORGANISM: Homo sapiens

<400> SEQUENCE: 466
tgagcataaa tttcattagc tg 22

<210> SEQ ID NO 467
<211> LENGTH: 20
<212> TYPE: DNA
<213> ORGANISM: Homo sapiens -continued

<400> SEQUENCE: 467
ggaagagcaa aataaatcca 20

<210> SEQ ID NO 468
<211> LENGTH: 19
<212> TYPE: DNA
<213> ORGANISM: Homo sapiens

<400> SEQUENCE: 468
ggtgcacaga attgttcat 19

<210> SEQ ID NO 469
<211> LENGTH: 18
<212> TYPE: DNA
<213> ORGANISM: Homo sapiens

<400> SEQUENCE: 469
agcacgctta tttcatgg 18

<210> SEQ ID NO 470
<211> LENGTH: 18
<212> TYPE: DNA
<213> ORGANISM: Homo sapiens

<400> SEQUENCE: 470
gtaacaccag cagggaca 18

<210> SEQ ID NO 471
<211> LENGTH: 18
<212> TYPE: DNA
<213> ORGANISM: Homo sapiens

<400> SEQUENCE: 471
tcctgctgca ttatggat 18

<210> SEQ ID NO 472
<211> LENGTH: 18
<212> TYPE: DNA
<213> ORGANISM: Homo sapiens

<400> SEQUENCE: 472
gggggtgaga agtaggaa 18

<210> SEQ ID NO 473
<211> LENGTH: 18
<212> TYPE: DNA
<213> ORGANISM: Homo sapiens

<400> SEQUENCE: 473
atggggatta aatacggg 18

<210> SEQ ID NO 474
<211> LENGTH: 18
<212> TYPE: DNA
<213> ORGANISM: Homo sapiens

<400> SEQUENCE: 474
agctagcatt gggctctt 18

<210> SEQ ID NO 475
<211> LENGTH: 18
<212> TYPE: DNA

-continued

<213> ORGANISM: Homo sapiens

<400> SEQUENCE: 475
ctgaggagaa gaggctgg 18

<210> SEQ ID NO 476
<211> LENGTH: 18
<212> TYPE: DNA
<213> ORGANISM: Homo sapiens

<400> SEQUENCE: 476
cgccttacaa ggcaagta 18

<210> SEQ ID NO 477
<211> LENGTH: 18
<212> TYPE: DNA
<213> ORGANISM: Homo sapiens

<400> SEQUENCE: 477
aggatgcttg ctagggtt 18

<210> SEQ ID NO 478
<211> LENGTH: 18
<212> TYPE: DNA
<213> ORGANISM: Homo sapiens

<400> SEQUENCE: 478
cacaagtgtc tggaaggc 18

<210> SEQ ID NO 479
<211> LENGTH: 18
<212> TYPE: DNA
<213> ORGANISM: Homo sapiens

<400> SEQUENCE: 479
ggtctcagga gcccttta 18

<210> SEQ ID NO 480
<211> LENGTH: 21
<212> TYPE: DNA
<213> ORGANISM: Homo sapiens

<400> SEQUENCE: 480
acatgccact cttctcacta a 21

<210> SEQ ID NO 481
<211> LENGTH: 18
<212> TYPE: DNA
<213> ORGANISM: Homo sapiens

<400> SEQUENCE: 481
acttaaccaa ggatgggg 18

<210> SEQ ID NO 482
<211> LENGTH: 18
<212> TYPE: DNA
<213> ORGANISM: Homo sapiens

<400> SEQUENCE: 482
caacccacga gcataaga 18

<210> SEQ ID NO 483
<211> LENGTH: 18

-continued

<212> TYPE: DNA
<213> ORGANISM: Homo sapiens

<400> SEQUENCE: 483
taggctctgc actcttgg 18

<210> SEQ ID NO 484
<211> LENGTH: 18
<212> TYPE: DNA
<213> ORGANISM: Homo sapiens

<400> SEQUENCE: 484
acccacggag tctctctc 18

<210> SEQ ID NO 485
<211> LENGTH: 18
<212> TYPE: DNA
<213> ORGANISM: Homo sapiens

<400> SEQUENCE: 485
taaaggcggt gaagtgag 18

<210> SEQ ID NO 486
<211> LENGTH: 18
<212> TYPE: DNA
<213> ORGANISM: Homo sapiens

<400> SEQUENCE: 486
ctaccgctct cctaggct 18

<210> SEQ ID NO 487
<211> LENGTH: 18
<212> TYPE: DNA
<213> ORGANISM: Homo sapiens

<400> SEQUENCE: 487
tggggccaga taattctt 18

<210> SEQ ID NO 488
<211> LENGTH: 18
<212> TYPE: DNA
<213> ORGANISM: Homo sapiens

<400> SEQUENCE: 488
ctggtgtttg gtggtgtt 18

<210> SEQ ID NO 489
<211> LENGTH: 18
<212> TYPE: DNA
<213> ORGANISM: Homo sapiens

<400> SEQUENCE: 489
aaggaagagg tcaccagg 18

<210> SEQ ID NO 490
<211> LENGTH: 18
<212> TYPE: DNA
<213> ORGANISM: Homo sapiens

<400> SEQUENCE: 490
cacaaattcc atttccca 18

<210> SEQ ID NO 491

-continued

<211> LENGTH: 21
<212> TYPE: DNA
<213> ORGANISM: Homo sapiens

<400> SEQUENCE: 491
tcaataggtg atccaacatt t 21

<210> SEQ ID NO 492
<211> LENGTH: 18
<212> TYPE: DNA
<213> ORGANISM: Homo sapiens

<400> SEQUENCE: 492
aaagtcccac aaagggtc 18

<210> SEQ ID NO 493
<211> LENGTH: 18
<212> TYPE: DNA
<213> ORGANISM: Homo sapiens

<400> SEQUENCE: 493
gggtaggggg atcttttt 18

<210> SEQ ID NO 494
<211> LENGTH: 18
<212> TYPE: DNA
<213> ORGANISM: Homo sapiens

<400> SEQUENCE: 494
tgtggaacat tcattggc 18

<210> SEQ ID NO 495
<211> LENGTH: 18
<212> TYPE: DNA
<213> ORGANISM: Homo sapiens

<400> SEQUENCE: 495
gtcctgggaa agatggaa 18

<210> SEQ ID NO 496
<211> LENGTH: 18
<212> TYPE: DNA
<213> ORGANISM: Homo sapiens

<400> SEQUENCE: 496
tcaaagcgtc tcccataa 18

<210> SEQ ID NO 497
<211> LENGTH: 18
<212> TYPE: DNA
<213> ORGANISM: Homo sapiens

<400> SEQUENCE: 497
tctttcgctg tacttggc 18

<210> SEQ ID NO 498
<211> LENGTH: 18
<212> TYPE: DNA
<213> ORGANISM: Homo sapiens

<400> SEQUENCE: 498
tgggaggtca gagtgatg 18

-continued

<210> SEQ ID NO 499
<211> LENGTH: 19
<212> TYPE: DNA
<213> ORGANISM: Homo sapiens

<400> SEQUENCE: 499
ggacagtgta tgtgttggg 19

<210> SEQ ID NO 500
<211> LENGTH: 18
<212> TYPE: DNA
<213> ORGANISM: Homo sapiens

<400> SEQUENCE: 500
aggcagctgt ttttgtga 18

<210> SEQ ID NO 501
<211> LENGTH: 18
<212> TYPE: DNA
<213> ORGANISM: Homo sapiens

<400> SEQUENCE: 501
cttcttgagt cccgtgtg 18

<210> SEQ ID NO 502
<211> LENGTH: 19
<212> TYPE: DNA
<213> ORGANISM: Homo sapiens

<400> SEQUENCE: 502
caaccgagaa tcctctagc 19

<210> SEQ ID NO 503
<211> LENGTH: 18
<212> TYPE: DNA
<213> ORGANISM: Homo sapiens

<400> SEQUENCE: 503
gctgggagag aatcacaa 18

<210> SEQ ID NO 504
<211> LENGTH: 18
<212> TYPE: DNA
<213> ORGANISM: Homo sapiens

<400> SEQUENCE: 504
gctttgcaga agagacca 18

<210> SEQ ID NO 505
<211> LENGTH: 18
<212> TYPE: DNA
<213> ORGANISM: Homo sapiens

<400> SEQUENCE: 505
acgctgtcag gtcacact 18

<210> SEQ ID NO 506
<211> LENGTH: 18
<212> TYPE: DNA
<213> ORGANISM: Homo sapiens

<400> SEQUENCE: 506
ggaggatgct caggtgat 18

-continued

<210> SEQ ID NO 507
<211> LENGTH: 18
<212> TYPE: DNA
<213> ORGANISM: Homo sapiens

<400> SEQUENCE: 507 taggggatc tttttcca 18

<210> SEQ ID NO 508
<211> LENGTH: 18
<212> TYPE: DNA
<213> ORGANISM: Homo sapiens

<400> SEQUENCE: 508
gagcaatttg aaaagcca 18

<210> SEQ ID NO 509
<211> LENGTH: 18
<212> TYPE: DNA
<213> ORGANISM: Homo sapiens

<400> SEQUENCE: 509
atggtccagc tcctctgt 18

<210> SEQ ID NO 510
<211> LENGTH: 18
<212> TYPE: DNA
<213> ORGANISM: Homo sapiens

<400> SEQUENCE: 510
atagagcacc ccatctcc 18

<210> SEQ ID NO 511
<211> LENGTH: 18
<212> TYPE: DNA
<213> ORGANISM: Homo sapiens

<400> SEQUENCE: 511
aacattgctg ttagccca 18

<210> SEQ ID NO 512
<211> LENGTH: 18
<212> TYPE: DNA
<213> ORGANISM: Homo sapiens

<400> SEQUENCE: 512
gcaatcgaaa cagcattc 18

<210> SEQ ID NO 513
<211> LENGTH: 18
<212> TYPE: DNA
<213> ORGANISM: Homo sapiens

<400> SEQUENCE: 513
atgagttggc agctgaag 18

<210> SEQ ID NO 514
<211> LENGTH: 18
<212> TYPE: DNA
<213> ORGANISM: Homo sapiens

<400> SEQUENCE: 514
aatgaaggtc ttgcctcc 18

-continued

<210> SEQ ID NO 515
<211> LENGTH: 20
<212> TYPE: DNA
<213> ORGANISM: Homo sapiens

<400> SEQUENCE: 515
gaggagaaga tccacaagcg 20

<210> SEQ ID NO 516
<211> LENGTH: 20
<212> TYPE: DNA
<213> ORGANISM: Homo sapiens

<400> SEQUENCE: 516
tctctggggc atactgaacc 20

<210> SEQ ID NO 517
<211> LENGTH: 18
<212> TYPE: DNA
<213> ORGANISM: Homo sapiens

<400> SEQUENCE: 517
ctgagctttt ggcactgt 18

<210> SEQ ID NO 518
<211> LENGTH: 18
<212> TYPE: DNA
<213> ORGANISM: Homo sapiens

<400> SEQUENCE: 518
ctgctaggtg acagcagg 18

<210> SEQ ID NO 519
<211> LENGTH: 20
<212> TYPE: DNA
<213> ORGANISM: Homo sapiens

<400> SEQUENCE: 519
tgtatgagtc tggagggtgt 20

<210> SEQ ID NO 520
<211> LENGTH: 18
<212> TYPE: DNA
<213> ORGANISM: Homo sapiens

<400> SEQUENCE: 520
acacctggct gaggaaat 18

<210> SEQ ID NO 521
<211> LENGTH: 18
<212> TYPE: DNA
<213> ORGANISM: Homo sapiens

<400> SEQUENCE: 521
gcaggggacg tgataata 18

<210> SEQ ID NO 522
<211> LENGTH: 18
<212> TYPE: DNA
<213> ORGANISM: Homo sapiens

<400> SEQUENCE: 522
ttttgcttcc taccatgc 18

<210> SEQ ID NO 523
<211> LENGTH: 18
<212> TYPE: DNA
<213> ORGANISM: Homo sapiens

<400> SEQUENCE: 523
aaaattgtga gcacctcc 18

<210> SEQ ID NO 524
<211> LENGTH: 23
<212> TYPE: DNA
<213> ORGANISM: Homo sapiens

<400> SEQUENCE: 524
tttatattta aagtggcttt gtt 23

<210> SEQ ID NO 525
<211> LENGTH: 18
<212> TYPE: DNA
<213> ORGANISM: Homo sapiens

<400> SEQUENCE: 525
gtgcaaagcc cacagtat 18

<210> SEQ ID NO 526
<211> LENGTH: 18
<212> TYPE: DNA
<213> ORGANISM: Homo sapiens

<400> SEQUENCE: 526
aggaaaatgc aagagcag 18

<210> SEQ ID NO 527
<211> LENGTH: 20
<212> TYPE: DNA
<213> ORGANISM: Homo sapiens

<400> SEQUENCE: 527
ccactgaatt gcatactttg 20

<210> SEQ ID NO 528
<211> LENGTH: 18
<212> TYPE: DNA
<213> ORGANISM: Homo sapiens

<400> SEQUENCE: 528
tctgggtcca gtctgcta 18

<210> SEQ ID NO 529
<211> LENGTH: 18
<212> TYPE: DNA
<213> ORGANISM: Homo sapiens

<400> SEQUENCE: 529
agattttggg gagtcagg 18

<210> SEQ ID NO 530
<211> LENGTH: 17
<212> TYPE: DNA
<213> ORGANISM: Homo sapiens

<400> SEQUENCE: 530

-continued gcgctcaagc aattctc 17

<210> SEQ ID NO 531
<211> LENGTH: 18
<212> TYPE: DNA
<213> ORGANISM: Homo sapiens

<400> SEQUENCE: 531
caagccccaa agtagtca 18

<210> SEQ ID NO 532
<211> LENGTH: 18
<212> TYPE: DNA
<213> ORGANISM: Homo sapiens

<400> SEQUENCE: 532
gaatcatcca atccacga 18

<210> SEQ ID NO 533
<211> LENGTH: 18
<212> TYPE: DNA
<213> ORGANISM: Homo sapiens

<400> SEQUENCE: 533
agcctccagg tgactacc 18

<210> SEQ ID NO 534
<211> LENGTH: 18
<212> TYPE: DNA
<213> ORGANISM: Homo sapiens

<400> SEQUENCE: 534
gaaggacatg gtcagcag 18

<210> SEQ ID NO 535
<211> LENGTH: 18
<212> TYPE: DNA
<213> ORGANISM: Homo sapiens

<400> SEQUENCE: 535
atgctttcag cattttcg 18

<210> SEQ ID NO 536
<211> LENGTH: 18
<212> TYPE: DNA
<213> ORGANISM: Homo sapiens

<400> SEQUENCE: 536
tgatccgtgg tagggtta 18

<210> SEQ ID NO 537
<211> LENGTH: 18
<212> TYPE: DNA
<213> ORGANISM: Homo sapiens

<400> SEQUENCE: 537
gtcggattgg tttcacaa 18

<210> SEQ ID NO 538
<211> LENGTH: 19
<212> TYPE: DNA
<213> ORGANISM: Homo sapiens -continued

<400> SEQUENCE: 538
ttttatggga atttcagcc 19

<210> SEQ ID NO 539
<211> LENGTH: 21
<212> TYPE: DNA
<213> ORGANISM: Homo sapiens

<400> SEQUENCE: 539
tttggaaaag aacagaaatg t 21

<210> SEQ ID NO 540
<211> LENGTH: 19
<212> TYPE: DNA
<213> ORGANISM: Homo sapiens

<400> SEQUENCE: 540
ggctagtctt tcctgaacc 19

<210> SEQ ID NO 541
<211> LENGTH: 18
<212> TYPE: DNA
<213> ORGANISM: Homo sapiens

<400> SEQUENCE: 541
ccttaatgcc cctgattc 18

<210> SEQ ID NO 542
<211> LENGTH: 18
<212> TYPE: DNA
<213> ORGANISM: Homo sapiens

<400> SEQUENCE: 542
gcgtttacaa gctgagga 18

<210> SEQ ID NO 543
<211> LENGTH: 18
<212> TYPE: DNA
<213> ORGANISM: Homo sapiens

<400> SEQUENCE: 543
tcaagcttgc tttctcaa 18

<210> SEQ ID NO 544
<211> LENGTH: 18
<212> TYPE: DNA
<213> ORGANISM: Homo sapiens

<400> SEQUENCE: 544
gtagcccagc aagtgtct 18

<210> SEQ ID NO 545
<211> LENGTH: 18
<212> TYPE: DNA
<213> ORGANISM: Homo sapiens

<400> SEQUENCE: 545
cctggctgga gataggat 18

<210> SEQ ID NO 546
<211> LENGTH: 18
<212> TYPE: DNA
<213> ORGANISM: Homo sapiens -continued

<400> SEQUENCE: 546
cttcccctct gcctatgt 18

<210> SEQ ID NO 547
<211> LENGTH: 18
<212> TYPE: DNA
<213> ORGANISM: Homo sapiens

<400> SEQUENCE: 547
ggcacgtact tcctacca 18

<210> SEQ ID NO 548
<211> LENGTH: 18
<212> TYPE: DNA
<213> ORGANISM: Homo sapiens

<400> SEQUENCE: 548
ggtgcttctt acaggcaa 18

<210> SEQ ID NO 549
<211> LENGTH: 16
<212> TYPE: DNA
<213> ORGANISM: Homo sapiens

<400> SEQUENCE: 549
acccaggctg gtgtgt 16

<210> SEQ ID NO 550
<211> LENGTH: 23
<212> TYPE: DNA
<213> ORGANISM: Homo sapiens

<400> SEQUENCE: 550
actgagttaa ttatcactcc cct 23

<210> SEQ ID NO 551
<211> LENGTH: 18
<212> TYPE: DNA
<213> ORGANISM: Homo sapiens

<400> SEQUENCE: 551
gatgcatttt gcttcacc 18

<210> SEQ ID NO 552
<211> LENGTH: 21
<212> TYPE: DNA
<213> ORGANISM: Homo sapiens

<400> SEQUENCE: 552
tctgctttta gagctgttag c 21

<210> SEQ ID NO 553
<211> LENGTH: 19
<212> TYPE: DNA
<213> ORGANISM: Homo sapiens

<400> SEQUENCE: 553
tcaagcttca aagagcaga 19

<210> SEQ ID NO 554
<211> LENGTH: 18
<212> TYPE: DNA

-continued

<213> ORGANISM: Homo sapiens

<400> SEQUENCE: 554
ggagtacatc ccaggacc 18

<210> SEQ ID NO 555
<211> LENGTH: 19
<212> TYPE: DNA
<213> ORGANISM: Homo sapiens

<400> SEQUENCE: 555
tggtgctttt aaatccaga 19

<210> SEQ ID NO 556
<211> LENGTH: 21
<212> TYPE: DNA
<213> ORGANISM: Homo sapiens

<400> SEQUENCE: 556
ctcccttact tacttgcatt g 21

<210> SEQ ID NO 557
<211> LENGTH: 18
<212> TYPE: DNA
<213> ORGANISM: Homo sapiens

<400> SEQUENCE: 557
tcttctccca gggaatct 18

<210> SEQ ID NO 558
<211> LENGTH: 18
<212> TYPE: DNA
<213> ORGANISM: Homo sapiens

<400> SEQUENCE: 558
tttatgtccc ctgagcac 18

<210> SEQ ID NO 559
<211> LENGTH: 19
<212> TYPE: DNA
<213> ORGANISM: Homo sapiens

<400> SEQUENCE: 559
tccctggcta tcttgaatc 19

<210> SEQ ID NO 560
<211> LENGTH: 16
<212> TYPE: DNA
<213> ORGANISM: Homo sapiens

<400> SEQUENCE: 560
cttgactggg tccacg 16

<210> SEQ ID NO 561
<211> LENGTH: 20
<212> TYPE: DNA
<213> ORGANISM: Homo sapiens

<400> SEQUENCE: 561
cgagacgcca gtagatacca 20

<210> SEQ ID NO 562
<211> LENGTH: 20

-continued

<212> TYPE: DNA
<213> ORGANISM: Homo sapiens

<400> SEQUENCE: 562
catcctccat gcctttcagt 20

<210> SEQ ID NO 563
<211> LENGTH: 20
<212> TYPE: DNA
<213> ORGANISM: Homo sapiens

<400> SEQUENCE: 563
agttccagag aacgagacgc 20

<210> SEQ ID NO 564
<211> LENGTH: 20
<212> TYPE: DNA
<213> ORGANISM: Homo sapiens

<400> SEQUENCE: 564
cttgtcatcc tccatgcctt 20

<210> SEQ ID NO 565
<211> LENGTH: 20
<212> TYPE: DNA
<213> ORGANISM: Homo sapiens

<400> SEQUENCE: 565
gagcgtgaga ggttgaggag 20

<210> SEQ ID NO 566
<211> LENGTH: 20
<212> TYPE: DNA
<213> ORGANISM: Homo sapiens

<400> SEQUENCE: 566
aaacaaactc cagacgcacc 20

<210> SEQ ID NO 567
<211> LENGTH: 24
<212> TYPE: DNA
<213> ORGANISM: Homo sapiens

<400> SEQUENCE: 567
ctgaaccact acctgtatga cctg 24

<210> SEQ ID NO 568
<211> LENGTH: 25
<212> TYPE: DNA
<213> ORGANISM: Homo sapiens

<400> SEQUENCE: 568
ctaactactt actcctacag ggccc 25

<210> SEQ ID NO 569
<211> LENGTH: 23
<212> TYPE: DNA
<213> ORGANISM: Homo sapiens

<400> SEQUENCE: 569
gaagcatttc aatactttaa ctg 23

<210> SEQ ID NO 570

-continued

<211> LENGTH: 20
<212> TYPE: DNA
<213> ORGANISM: Homo sapiens

<400> SEQUENCE: 570
ccactccagt gcacccaatc 20

<210> SEQ ID NO 571
<211> LENGTH: 20
<212> TYPE: DNA
<213> ORGANISM: Homo sapiens

<400> SEQUENCE: 571
cttctcctgg ccactctgac 20

<210> SEQ ID NO 572
<211> LENGTH: 21
<212> TYPE: DNA
<213> ORGANISM: Homo sapiens

<400> SEQUENCE: 572
ggtttacctt tgaatcccag c 21

<210> SEQ ID NO 573
<211> LENGTH: 22
<212> TYPE: DNA
<213> ORGANISM: Homo sapiens

<400> SEQUENCE: 573
tgaggatgaa tgagcacata gg 22

<210> SEQ ID NO 574
<211> LENGTH: 21
<212> TYPE: DNA
<213> ORGANISM: Homo sapiens

<400> SEQUENCE: 574
tttgtggtcc attgagtagg c 21

<210> SEQ ID NO 575
<211> LENGTH: 20
<212> TYPE: DNA
<213> ORGANISM: Homo sapiens

<400> SEQUENCE: 575
aggggaagga atgtgcttgg 20

<210> SEQ ID NO 576
<211> LENGTH: 20
<212> TYPE: DNA
<213> ORGANISM: Homo sapiens

<400> SEQUENCE: 576
ttcggctgag cgggcagtgt 20

<210> SEQ ID NO 577
<211> LENGTH: 26
<212> TYPE: DNA
<213> ORGANISM: Homo sapiens

<400> SEQUENCE: 577
attgaaggtc ctccaaaaga atgctg 26

-continued

<210> SEQ ID NO 578
<211> LENGTH: 30
<212> TYPE: DNA
<213> ORGANISM: Homo sapiens

<400> SEQUENCE: 578
agaacgtcaa catatctttt tgggggacac 30

<210> SEQ ID NO 579
<211> LENGTH: 22
<212> TYPE: DNA
<213> ORGANISM: Homo sapiens

<400> SEQUENCE: 579
ttgtatttga ggactttgct cg 22

<210> SEQ ID NO 580
<211> LENGTH: 20
<212> TYPE: DNA
<213> ORGANISM: Homo sapiens

<400> SEQUENCE: 580
cggtaccatc ctcctcttcc 20

<210> SEQ ID NO 581
<211> LENGTH: 20
<212> TYPE: DNA
<213> ORGANISM: Homo sapiens

<400> SEQUENCE: 581
tttttgcctc atctatgccc 20

<210> SEQ ID NO 582
<211> LENGTH: 20
<212> TYPE: DNA
<213> ORGANISM: Homo sapiens

<400> SEQUENCE: 582
gggtgacaga gcaagactcc 20

<210> SEQ ID NO 583
<211> LENGTH: 18
<212> TYPE: DNA
<213> ORGANISM: Homo sapiens

<400> SEQUENCE: 583
ttgctcaagt tctcctgg 18

<210> SEQ ID NO 584
<211> LENGTH: 18
<212> TYPE: DNA
<213> ORGANISM: Homo sapiens

<400> SEQUENCE: 584
accttgtttt gaggggag 18

<210> SEQ ID NO 585
<211> LENGTH: 18
<212> TYPE: DNA
<213> ORGANISM: Homo sapiens

<400> SEQUENCE: 585
cttggctatt tggacagc 18

-continued

<210> SEQ ID NO 586
<211> LENGTH: 18
<212> TYPE: DNA
<213> ORGANISM: Homo sapiens

<400> SEQUENCE: 586
gggcatttac tcacttgc 18

<210> SEQ ID NO 587
<211> LENGTH: 19
<212> TYPE: DNA
<213> ORGANISM: Homo sapiens

<400> SEQUENCE: 587
cttgtgtcag ttgtcaggg 19

<210> SEQ ID NO 588
<211> LENGTH: 19
<212> TYPE: DNA
<213> ORGANISM: Homo sapiens

<400> SEQUENCE: 588
tggaattgtt gtgtcttgg 19

<210> SEQ ID NO 589
<211> LENGTH: 18
<212> TYPE: DNA
<213> ORGANISM: Homo sapiens

<400> SEQUENCE: 589
ccagttccac tggatgtt 18

<210> SEQ ID NO 590
<211> LENGTH: 18
<212> TYPE: DNA
<213> ORGANISM: Homo sapiens

<400> SEQUENCE: 590
atgggctgtg tttctcaa 18

<210> SEQ ID NO 591
<211> LENGTH: 18
<212> TYPE: DNA
<213> ORGANISM: Homo sapiens

<400> SEQUENCE: 591
ctgcctatcc ctggactt 18

<210> SEQ ID NO 592
<211> LENGTH: 18
<212> TYPE: DNA
<213> ORGANISM: Homo sapiens

<400> SEQUENCE: 592
agtttgtccc tagtgccc 18

<210> SEQ ID NO 593
<211> LENGTH: 19
<212> TYPE: DNA
<213> ORGANISM: Homo sapiens

<400> SEQUENCE: 593
caacacgtct gacatccat 19

-continued

<210> SEQ ID NO 594
<211> LENGTH: 16
<212> TYPE: DNA
<213> ORGANISM: Homo sapiens

<400> SEQUENCE: 594
ggatagtgca caccca 16

<210> SEQ ID NO 595
<211> LENGTH: 22
<212> TYPE: DNA
<213> ORGANISM: Homo sapiens

<400> SEQUENCE: 595
tgggtggtac tattgttccc at 22

<210> SEQ ID NO 596
<211> LENGTH: 20
<212> TYPE: DNA
<213> ORGANISM: Homo sapiens

<400> SEQUENCE: 596
agttccagcc cccttaccag 20

<210> SEQ ID NO 597
<211> LENGTH: 20
<212> TYPE: DNA
<213> ORGANISM: Homo sapiens

<400> SEQUENCE: 597
ggccactatc atccctgtgt 20

<210> SEQ ID NO 598
<211> LENGTH: 20
<212> TYPE: DNA
<213> ORGANISM: Homo sapiens

<400> SEQUENCE: 598
tttcacatgg gaagaacacg 20

<210> SEQ ID NO 599
<211> LENGTH: 20
<212> TYPE: DNA
<213> ORGANISM: Homo sapiens

<400> SEQUENCE: 599
acagtgacac tagggacggg 20

<210> SEQ ID NO 600
<211> LENGTH: 20
<212> TYPE: DNA
<213> ORGANISM: Homo sapiens

<400> SEQUENCE: 600
tgccaggatg gagataacaa 20

<210> SEQ ID NO 601
<211> LENGTH: 20
<212> TYPE: DNA
<213> ORGANISM: Homo sapiens

<400> SEQUENCE: 601

-continued cctgtggcac acatatcacc 20

<210> SEQ ID NO 602
<211> LENGTH: 20
<212> TYPE: DNA
<213> ORGANISM: Homo sapiens

<400> SEQUENCE: 602
acaaccaaga atggagccac 20

<210> SEQ ID NO 603
<211> LENGTH: 20
<212> TYPE: DNA
<213> ORGANISM: Homo sapiens

<400> SEQUENCE: 603
tgctgtgtaa caagtcccca 20

<210> SEQ ID NO 604
<211> LENGTH: 20
<212> TYPE: DNA
<213> ORGANISM: Homo sapiens

<400> SEQUENCE: 604
tgaacggagg acctaccaag 20

<210> SEQ ID NO 605
<211> LENGTH: 20
<212> TYPE: DNA
<213> ORGANISM: Homo sapiens

<400> SEQUENCE: 605
gcagggtccg actcactaag 20

<210> SEQ ID NO 606
<211> LENGTH: 20
<212> TYPE: DNA
<213> ORGANISM: Homo sapiens

<400> SEQUENCE: 606
gctgtgagtt ccctttacgc 20

<210> SEQ ID NO 607
<211> LENGTH: 20
<212> TYPE: DNA
<213> ORGANISM: Homo sapiens

<400> SEQUENCE: 607
acagtgggga caaagacagg 20

<210> SEQ ID NO 608
<211> LENGTH: 20
<212> TYPE: DNA
<213> ORGANISM: Homo sapiens

<400> SEQUENCE: 608
tacagggcac ctcccagtag 20

<210> SEQ ID NO 609
<211> LENGTH: 21
<212> TYPE: DNA
<213> ORGANISM: Homo sapiens

<400> SEQUENCE: 609

-continued tcttctgtta aggtttcccc c 21

<210> SEQ ID NO 610
<211> LENGTH: 20
<212> TYPE: DNA
<213> ORGANISM: Homo sapiens

<400> SEQUENCE: 610
tgtctcaaac ctccctctgc 20

<210> SEQ ID NO 611
<211> LENGTH: 20
<212> TYPE: DNA
<213> ORGANISM: Homo sapiens

<400> SEQUENCE: 611
aacatatttc ctccccagcc 20

<210> SEQ ID NO 612
<211> LENGTH: 19
<212> TYPE: DNA
<213> ORGANISM: Homo sapiens

<400> SEQUENCE: 612
cagtcccagc caatgagaa 19

<210> SEQ ID NO 613
<211> LENGTH: 20
<212> TYPE: DNA
<213> ORGANISM: Homo sapiens

<400> SEQUENCE: 613
ctcctctgca tgggagaatc 20

<210> SEQ ID NO 614
<211> LENGTH: 20
<212> TYPE: DNA
<213> ORGANISM: Homo sapiens

<400> SEQUENCE: 614
agacctggga ccagtctgtg 20

<210> SEQ ID NO 615
<211> LENGTH: 20
<212> TYPE: DNA
<213> ORGANISM: Homo sapiens

<400> SEQUENCE: 615
gggagacgac gtcacaagat 20

<210> SEQ ID NO 616
<211> LENGTH: 20
<212> TYPE: DNA
<213> ORGANISM: Homo sapiens

<400> SEQUENCE: 616
tgatgttggg aagatggtga 20

<210> SEQ ID NO 617
<211> LENGTH: 20
<212> TYPE: DNA
<213> ORGANISM: Homo sapiens -continued

<400> SEQUENCE: 617
caggcatctt ctatgtgcca 20

<210> SEQ ID NO 618
<211> LENGTH: 20
<212> TYPE: DNA
<213> ORGANISM: Homo sapiens

<400> SEQUENCE: 618
gggaggcaca agttctttca 20

<210> SEQ ID NO 619
<211> LENGTH: 20
<212> TYPE: DNA
<213> ORGANISM: Homo sapiens

<400> SEQUENCE: 619
acttcgtggc actgagtgtg 20

<210> SEQ ID NO 620
<211> LENGTH: 20
<212> TYPE: DNA
<213> ORGANISM: Homo sapiens

<400> SEQUENCE: 620
cctttcttac ggatgaggca 20

<210> SEQ ID NO 621
<211> LENGTH: 20
<212> TYPE: DNA
<213> ORGANISM: Homo sapiens

<400> SEQUENCE: 621
ggctgctgag ctcttctgat 20

<210> SEQ ID NO 622
<211> LENGTH: 20
<212> TYPE: DNA
<213> ORGANISM: Homo sapiens

<400> SEQUENCE: 622
tgggtctctc tgcctgactt 20

<210> SEQ ID NO 623
<211> LENGTH: 20
<212> TYPE: DNA
<213> ORGANISM: Homo sapiens

<400> SEQUENCE: 623
tcacctactt ccagcttccg 20

<210> SEQ ID NO 624
<211> LENGTH: 20
<212> TYPE: DNA
<213> ORGANISM: Homo sapiens

<400> SEQUENCE: 624
agacctggga ccagtctgtg 20

<210> SEQ ID NO 625
<211> LENGTH: 20
<212> TYPE: DNA
<213> ORGANISM: Homo sapiens

<400> SEQUENCE: 625
ctcctctgca tgggagaatc 20

<210> SEQ ID NO 626
<211> LENGTH: 20
<212> TYPE: DNA
<213> ORGANISM: Homo sapiens

<400> SEQUENCE: 626
aattcaggag acctgggacc 20

<210> SEQ ID NO 627
<211> LENGTH: 15
<212> TYPE: DNA
<213> ORGANISM: Artificial Sequence
<220> FEATURE:
<223> OTHER INFORMATION: Artificial Sequence is a BstXI-linker adapter.

<400> SEQUENCE: 627
gtcttcacca cgggg 15

<210> SEQ ID NO 628
<211> LENGTH: 11
<212> TYPE: DNA
<213> ORGANISM: Artificial Sequence
<220> FEATURE:
<223> OTHER INFORMATION: Artificial Sequence is a BstXI-linker adapter.

<400> SEQUENCE: 628
gtggtgaaga c 11

<210> SEQ ID NO 629
<211> LENGTH: 18
<212> TYPE: DNA
<213> ORGANISM: Artificial Sequence
<220> FEATURE:
<223> OTHER INFORMATION: Artificial Sequence is a primer.

<400> SEQUENCE: 629
ccaagttctg agaagtcc 18

<210> SEQ ID NO 630
<211> LENGTH: 17
<212> TYPE: DNA
<213> ORGANISM: Artificial Sequence
<220> FEATURE:
<223> OTHER INFORMATION: Artificial Sequence is a primer.

<400> SEQUENCE: 630
aatacctgaa accatac 17

<210> SEQ ID NO 631
<211> LENGTH: 17
<212> TYPE: DNA
<213> ORGANISM: Artificial Sequence
<220> FEATURE:
<223> OTHER INFORMATION: Artificial Sequence is an allele specific
oligonucleotide.

<400> SEQUENCE: 631
agactggggt gagacgc 17

<210> SEQ ID NO 632
<211> LENGTH: 19

-continued

<212> TYPE: DNA
<213> ORGANISM: Artificial Sequence
<220> FEATURE:
<223> OTHER INFORMATION: Artificial Sequence is an allele specific oligonucleotide.

<400> SEQUENCE: 632
cagactgggt tgagacgcc 19

<210> SEQ ID NO 633
<211> LENGTH: 24
<212> TYPE: DNA
<213> ORGANISM: Artificial Sequence
<220> FEATURE:
<223> OTHER INFORMATION: Artificial Sequence is a primer.

<400> SEQUENCE: 633
cccgtgtgct ccgccgccca gttc 24

<210> SEQ ID NO 634
<211> LENGTH: 25
<212> TYPE: DNA
<213> ORGANISM: Artificial Sequence
<220> FEATURE:
<223> OTHER INFORMATION: Artificial Sequence is a primer.

<400> SEQUENCE: 634
ggctcacgga gctcatcatg gactt 25

<210> SEQ ID NO 635
<211> LENGTH: 502
<212> TYPE: DNA
<213> ORGANISM: Artificial Sequence
<220> FEATURE:
<223> OTHER INFORMATION: Artificial Sequence is a primer.

<400> SEQUENCE: 635
cccgtgtgct ccgccgccca gttcccctgc gcgcggggtc agtgtgtgga cctgcgcctg 60
cgctgcgacg gcgaggcaga ctgtcaggac cgctcagacg aggtggactg tgacgccatc 120
tgcctgccca accagttccg gtgtgcgagc ggccagtgtg tcctcatcaa acagcagtgc 180
gactccttcc ccgactgtat cgacggctcc gacgagctca tgtgtgaaat caccaagccg 240
ccctcagacg acagcccggc ccacagcagt gccatcgggc ccgtcattgg catcatcctc 300
tctctcttcg tcatgggtgg tgtctatttt gtgtgccagc gcgtggtgtg ccagcgctat 360
gcgggggcca acgggccctt cccgcacgag tatgtcagcg ggaccccgca cgtgcccctc 420
aatttcatag ccccgggcgg ttcccagcat ggccccttca caggcatcgc atgcggaaag 480
tccatgatga gctccgtgag cc 502

<210> SEQ ID NO 636
<211> LENGTH: 21
<212> TYPE: DNA
<213> ORGANISM: Artificial Sequence
<220> FEATURE:
<223> OTHER INFORMATION: Artificial Sequence is a primer.

<400> SEQUENCE: 636
agcgaggcca ccatccacag g 21

<210> SEQ ID NO 637
<211> LENGTH: 21
<212> TYPE: DNA
<213> ORGANISM: Artificial Sequence -continued
<220> FEATURE:
<223> OTHER INFORMATION: Artificial Sequence is a primer.

<400> SEQUENCE: 637
tcgctggtcg gcataatcaa t 21

<210> SEQ ID NO 638
<211> LENGTH: 501
<212> TYPE: DNA
<213> ORGANISM: Artificial Sequence
<220> FEATURE:
<223> OTHER INFORMATION: Artificial Sequence is a primer.

<400> SEQUENCE: 638
agcagagcca ccatccacag gatctccctg gagactaaca acaacgatgt ggctatccca 60
ctcacgggtg tcaaagaggc ctctgcactg gactttgatg tgtccaacaa tcacatctac 120
tggactgatg ttagcctcaa gacgatcagc cgagccttca tgaatgggag ctcagtggag 180
cacgtgattg agtttggcct cgactaccct gaaggaatgg ctgtggactg gatgggcaag 240
aacctctatt gggcggacac agggaccaac aggattgagg tggcccggct ggatgggcag 300
ttccggcagg tgcttgtgtg gagagacctt gacaacccca ggtctctggc tctggatcct 360
actaaaggct acatctactg gactgagtgg ggtggcaagc caaggattgt gcgggccttc 420
atggatggga ccaattgtat gacactggta gacaaggtgg gccgggccaa cgacctcacc 480
attgattatg ccgaccagcg a 501

<210> SEQ ID NO 639
<211> LENGTH: 26
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 639
raguacagcu ucuugccaac ccaguc 26

<210> SEQ ID NO 640
<211> LENGTH: 26
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 640
ruccuccagg ucgaugguca gcccau 26

<210> SEQ ID NO 641
<211> LENGTH: 26
<212> TYPE: RNA
<213> ORGANISM: Artificial Sequence
<220> FEATURE:
<223> OTHER INFORMATION: Artificial Sequence is a Zmax1 oligonucleotide.

<400> SEQUENCE: 641
rgucugaguc cgaguucaaa uccagg 26